US012559530B2

(12) United States Patent
Khalil et al.

(10) Patent No.: US 12,559,530 B2
(45) Date of Patent: Feb. 24, 2026

(54) REGULATED SYNTHETIC GENE EXPRESSION SYSTEMS

(71) Applicant: TRUSTEES OF BOSTON UNIVERSITY, Boston, MA (US)

(72) Inventors: Ahmad S. Khalil, Lexington, MA (US); Wilson Wai Chun Wong, Brookline, MA (US); Divya Israni, Boston, MA (US); Huishan Li, Brookline, MA (US)

(73) Assignee: Trustees of Boston University, Boston, MA (US)

( * ) Notice: Subject to any disclaimer, the term of this patent is extended or adjusted under 35 U.S.C. 154(b) by 699 days.

(21) Appl. No.: 17/938,787

(22) Filed: Oct. 7, 2022

(65) Prior Publication Data

US 2023/0159600 A1 May 25, 2023

Related U.S. Application Data

(63) Continuation of application No. 16/875,591, filed on May 15, 2020, now Pat. No. 11,530,246.

(60) Provisional application No. 62/848,850, filed on May 16, 2019.

(51) Int. Cl.
*C07K 14/47* (2006.01)

(52) U.S. Cl.
CPC ...... *C07K 14/4702* (2013.01); *C07K 2319/09* (2013.01); *C07K 2319/20* (2013.01); *C07K 2319/50* (2013.01); *C07K 2319/715* (2013.01); *C07K 2319/81* (2013.01)

(58) Field of Classification Search
None
See application file for complete search history.

(56) References Cited

U.S. PATENT DOCUMENTS

| | | | |
|---|---|---|---|
| 7,112,715 | B2 | 9/2006 | Chambon et al. |
| 8,173,792 | B2 | 5/2012 | Wandless et al. |
| 8,735,096 | B2 | 5/2014 | Zhou et al. |
| 10,137,180 | B2 | 11/2018 | Wandless et al. |
| 10,138,493 | B2 | 11/2018 | Khalil et al. |
| 10,550,379 | B2 | 2/2020 | Lin et al. |
| 10,590,182 | B2 | 3/2020 | Lim et al. |
| 2012/0178647 | A1 | 7/2012 | Joung et al. |
| 2013/0158098 | A1 | 6/2013 | Liang et al. |
| 2014/0234851 | A1 | 8/2014 | Leonard et al. |
| 2016/0046682 | A1 | 2/2016 | Neutzner et al. |
| 2016/0355797 | A1 | 12/2016 | Konermann et al. |
| 2017/0183654 | A1 | 6/2017 | Wong et al. |
| 2018/0057838 | A1 | 3/2018 | Khalil et al. |
| 2018/0163195 | A1 | 6/2018 | Wong et al. |
| 2018/0179522 | A1 | 6/2018 | Buckley et al. |
| 2020/0002710 | A1 | 1/2020 | Khalil et al. |

FOREIGN PATENT DOCUMENTS

| | | | |
|---|---|---|---|
| WO | 96/20951 | A1 | 7/1996 |
| WO | 2018/222880 | A1 | 12/2018 |
| WO | 2019/023164 | A1 | 1/2019 |

OTHER PUBLICATIONS

Banaszynski et al., A Rapid, Reversible, and Tunable Method to Regulate Protein Function in Living Cells Using Synthetic Small Molecules, Cell. Sep. 8, 2006; 126(5): 995-1004.
Beerli et al., Chemically regulated zinc finger transcription factors J Biol Chem. Oct. 20, 2000;275(42):32617-27.
Bintu et al., Dynamics of epigenetic regulation at the single-cell level, Science. Feb. 12, 2016; 351(6274): 720-724.
Bojar et al., Caffeine-inducible gene switches controlling experimental diabetes, Nature Communications vol. 9, Article No. 2318 (2018).
Chang et al., Rewiring T-cell responses to soluble factors with chimeric antigen receptors. Nat Chem Biol. Mar. 2018;14(3):317-324.
Chavez et al., Highly-efficient Cas9-mediated transcriptional programming, Nat Methods. Apr. 2015, 12(4): 326-328.
Cho et al., Universal Chimeric Antigen Receptors for Multiplexed and Logical Control of T Cell Responses, Cell. May 31, 2018;173(6):1426-1438.e11.
Chung et al., Tunable and reversible drug control of protein production via a self-excising degron, Nat Chem Biol. Sep. 2015; 11(9): 713-720.
Daniel et al., Conditional control of fluorescent protein degradation by an auxin-dependent nanobody, Nat Commun. Aug. 17, 2018;9(1):3297.
Daringer et al., Modular Extracellular Sensor Architecture for Engineering Mammalian Cell-based Devices, ACS Synth. Biol. 2014, 3, 12, 892-902.
Deans et al., A tunable genetic switch based on RNAI and repressor proteins for regulating gene expression in mammalian cells. Cell. Jul. 27, 2007;130(2):363-72.
Dunbar et al., Gene therapy comes of age, Science. Jan. 12, 2018;359(6372).
Ede et al., Quantitative Analyses of Core Promoters Enable Precise Engineering of Regulated Gene Expression in Mammalian Cells, ACS Synth Biol. May 20, 2016, 5(5): 395-404.
Feil et al., ., Regulation of Cre Recombinase Activity by Mutated Estrogen Receptor Ligand-Binding Domains, Biochemical and Biophysical Research Communications, vol. 237, Issue 3, Aug. 28, 1997, pp. 752-757.
Felker et al., In Vivo Performance and Properties of Tamoxifen Metabolites for CreERT2 Control, PLoS One. Apr. 14, 2016;11(4):e0152989.

(Continued)

*Primary Examiner* — Michael D Burkhart
(74) *Attorney, Agent, or Firm* — Nixon Peabody LLP; Ronald I. Eisenstein; Alissa R. Young

(57) ABSTRACT

The technology described herein is directed to regulated synthetic gene expression systems. In one aspect described herein are synthetic transcription factors (synTFs) comprising a DNA binding domain, a transcriptional effector domain, and a regulator protein. In other aspects described herein are gene expression systems comprising said synTFs and methods of treating diseases and disorders using said synTFs.

23 Claims, 43 Drawing Sheets

Specification includes a Sequence Listing.

(56) References Cited

OTHER PUBLICATIONS

Fischbach et al., Cell-Based Therapeutics: The Next Pillar of Medicine, Sci Transl Med. Apr. 3, 2013; 5(179): 179ps7.
Gao et al., Complex transcriptional modulation with orthogonal and inducible dCas9 regulators. Nat Methods. Dec. 2016;13(12):1043-1049.
Gao et al., Programmable protein circuits in living cells, Science Sep. 21, 2018: vol. 361, Issue 6408, pp. 1252-1258.
Hill et al., Human Antibody-Based Chemically Induced Dimerizers for Cell Therapeutic Applications, Nat Chem Biol. Feb. 2018;14(2):112-117.
Hilton et al., Epigenome editing by a CRISPR-Cas9-based acetyltransferase activates genes from promoters and enhancers, Nat Biotechnol. May 2015;33(5):510-7.
Iwamoto et al., A general chemical method to regulate protein stability in the mammalian central nervous system, Chem Biol. Sep. 24, 2010;17(9):981-8.
Israni et al., Synthetic transcription regulation for human cell therapy, Cell Therapies and Bioengineering Conference 2018, Poster, Sep. 20-22, 2018.
Israni et al., Synthetic transcription regulation for immune cell therapy, Immune Engineering Symposium, Koch Institute, Poster, Jan. 29, 2019 and Mar. 21-23, 2019.
Indra et al., Temporally-controlled site-specific mutagenesis in the basal layer of the epidermis: comparison of the recombinase activity of the tamoxifen-inducible Cre-ERT and Cre-ERT2 recombinases, Nucleic Acids Research, vol. 27, Issue 22, Nov. 1, 1999, pp. 4324-4327.
Jacobs et al., StaPLs: versatile genetically encoded modules for engineering drug-inducible proteins, Nat Methods. Jul. 2018; 15(7): 523-526.
Kang et al., COMBINES-CID: An efficient method for de novo engineering of highly specific chemically induced protein dimerization systems, J Am Chem Soc. Jul. 17, 2019; 141(28): 10948-10952.
Kennedy et al., Rapid blue-light-mediated induction of protein interactions in living cells, Nature Methods vol. 7, pp. 973-975(2010).
Khalil et al., A synthetic biology framework for programming eukaryotic transcription functions, Cell. Aug. 3, 2012;150 (3):647-58.
Kitada et al., Programming gene and engineered-cell therapies with synthetic biology. Science. Feb. 9, 2018;359 (6376).
Lambert et al., The Human Transcription Factors, Cell. Feb. 8, 2018;172(4):650-665.
Liang et al., Engineering the ABA plant stress pathway for regulation of induced proximity. Sci Signal. Mar. 15, 2011;4 (164):rs2.
Lim et al., The Principles of Engineering Immune Cells to Treat Cancer. Cell Feb. 9, 2017;168(4):724-740.
Lin et al., A drug-controllable tag for visualizing newly synthesized proteins in cells and whole animals, PNAS Jun. 3, 2008 105 (22) 7744-7749.
Maeder et al., Oligomerized pool engineering (OPEN): an 'open-source' protocol for making customized zinc-finger arrays. Nat Protoc. 2009;4(10):1471-501.
Mccauley et al., Hepatitis C virus NS3/4a protease inhibitors, Curr Opin Pharmacol. Oct. 2016;30:84-92.
Miyamoto et al., Rapid and orthogonal logic gating with a gibberellin-induced dimerization system Nature Chemical Biology vol. 8, pp. 465-470(2012).
Morsut et al., Engineering Customized Cell Sensing and Response Behaviors Using Synthetic Notch Receptors, Cell. Feb. 11, 2016;164(4):780-91.
Norman et al., Quantitative Comparison of Constitutive Promoters in Human ES cells, PLoS One. Aug. 26, 2010,5(8): e12413.
Park et al., Engineering Epigenetic Regulation Using Synthetic Read-Write Modules. Cell 176, 227-238 e20, (2019).
Qin et al., Systematic Comparison of Constitutive Promoters and the Doxycycline-Inducible Promoter, PLoS One. 2010, 5(5): e10611.
Roybal et al., Precision Tumor Recognition by T Cells With Combinatorial Antigen-Sensing Circuits, Cell. Feb. 11, 2016;164(4):770-9.
Sajwan et al., Gene activation by dCas9-CBP and the SAM system differ in target preference, Sci Rep. 2019; 9: 18104.
Sander et al., Selection-free zinc-finger-nuclease engineering by context-dependent assembly (CoDA). Nat Methods Jan. 2011;8(1):67-9.
Schrader et al., Making it easier to regulate protein stability, Chem Biol. Sep. 24, 2010, 17(9): 917-918.
Sheridan et al., Selectable one-step PCR-mediated integration of a degron for rapid depletion of endogenous human proteins, Biotechniques. 2016, 60(2): 69-74.
Somia, Gene therapy: trials and tribulations. Nat Rev Genet. Nov. 2000;1(2):91-9.
Stanton et al., Systematic transfer of prokaryotic sensors and circuits to mammalian cells. ACS Synth Biol. Dec. 19, 2014;3(12):880-91.
Stanton et al., Chemically induced proximity in biology and medicine, Science. Mar. 9, 2018; 359(6380): eaao5902.
Tague et al., Chemogenetic control of gene expression and cell signaling with antiviral drugs, Nat Methods. Jul. 2018;15(7):519-522.
Vora et al., Rational design of a compact CRISPR-Cas9 activator for AAV-mediated delivery, bioRxiv 2018 doi.org/10.1101/298620.
Weinberg et al., A single-layer platform for Boolean logic and arithmetic through DNA excision in mammalian cells, Nat Biotechnol. May 2017; 35(5): 453-462.
Wu et al.,. Remote control of therapeutic T cells through a small molecule-gated chimeric receptor, Science. Oct. 16, 2015;350(6258):aab4077.
Yeo et al., An enhanced CRISPR repressor for targeted mammalian gene regulation, Nature Methods vol. 15, pp. 611-616(2018).
Franco et al., Production and characterization of a genetically engineered anti-caffeine camelid antibody and its use in immunoaffinity chromatography, Journal of Chromatography B, vol. 878, Issue 2, Jan. 15, 2010, pp. 177-186.
Hossain et al., "Artificial zinc finger DNA binding domains: versatile tools for genome engineering and modulation of gene expression." Journal of cellular biochemistry 116.11 (2015): 2435-2444.
Beerli et al., Engineering polydactyl zinc-finger transcription factors. Nat Biotechnol. Feb. 2002;20(2):135-41.
Banaszynski et al. Characterization of the FKBP•Rapamycin•FRB Ternary Complex, J Am Chem Soc. Apr. 6, 2005;127(13):4715-21.
Schwarz et al., Rewiring human cellular input-output using modular extracellular sensors, Nat Chem Biol. Feb. 2017;13(2):202-209.
Xie et al., β-cell-mimetic designer cells provide closed-loop glycemic control, Science. Dec. 9, 2016;354 (6317):1296-1301.
Xie et al., Designing cell function: assembly of synthetic gene circuits for cell biology applications. Nat Rev Mol Cell Biol. Aug. 2018:19(8):507-525.
Rajakuberan et al., Protocol for a Mammalian Cell-Based Assay for Monitoring the HIV-1 Protease Activity, Methods Mol Biol. 2012;903:393-405.
Cunningham-Bryant et al. "A Chemically Disrupted Proximity System for Controlling Dynamic Cellular Processes", Journal of the American Chemical Society 141(8): 3352-3355 (Feb. 27, 2019).

MFEPKKKRKVFETSVPLYGFTSICGRRPEMEAA
VSTIPRFLQSSSGSMLDGRFDPQSAAHFFGVYD
GHGGSQVANYCRERMHLALAEEIAKEKPMLCD
GDTWLEKWKKALFNSFLRVDSEIESVAPETVGS
TSVVAVVFPSHIFVANCGDSRAVLCRGKTALPLS
VDHKPDREDEAARIEAAGGKVIQWNGARVFGVL
AMSRSIGDRYLKPSIIPDPEVTAVKRVKEDDCLIL
ASDGVWDVMTDEEACEMARKRILLWHKKNAVA
GDASLLADERRKEGKDPAAMSAAEYLSKLAIQR
GSKDNISVVVVDLKGGSGGSRPGERPFQCRICM
RNFSxxxxxxxHTRTHTGEKPFQCRICMRNFSxxxx
xxxHLRTHTGSQKPFQCRICMRNFSxxxxxxxHLRT
HTGEKPFQCRICMRNFSxxxxxxxHLKTHTGSQKP
FQCRICMRNFSxxxxxxxHLRTHTGEKPFQCRICM
RNFSxxxxxxxHLRTHLRGSPKKKRKVTCRGSGAT
NFSLLKQAGDVEENPGPGHHDEFPTMVFPSGQI
SQASALAPAPPQVLPQAPAPAPAPAMVSALAQA
PAPVPVLAPGPPQAVAPPAPKPTQAGEGTLSEA
LLQLQFDDEDLGALLGNSTDPAVFTDLASVDNS
EFQQLLNQGIPVAPHTTEPMLMEYPEAITRLVTG
AQRPPDPAPAPLGAPGLPNGLLSGDEDFSSIAD
MDFSALLSQISSGGGSGQLTQDEFTQLSQSIAEF
HTYQLGNGRCSSLLAQRIHAPPETVWSVVRRFD
RPQIYKHFIKSCNVSEDFEMRVGCTRDVNVISGL
PANTSRERLDLLDDDRRVTGFSITGGEHRLRNYK
SVTTVHRFEKEEEEERIWTVVLESYVVDVPEGNS
EEDTRLFADTVIRLNLQKLASITEAMN

[ABI]-[ZF]-[2A]-[p65]-[PYL] (SEQ ID NO: 4)

Fig. 19

MFEPKKKRKVFEETSVPLYGFTSICGRRPEM
EAAVSTIPRFLQSSSGSMLDGRFDPQSAAH
FFGVYDGHGGSQVANYCRERMHLALAEEI
AKEKPMLCDGDTWLEKWKKALFNSFLRVD
SEIESVAPETVGSTSVVAVVFPSHIFVANCG
DSRAVLCRGKTALPLSVDHKPDREDEAARI
EAAGGKVIQWNGARVFGVLAMSRSIGDRY
LKPSIIPDPEVTAVKRVKEDDCLILASDGVW
DVMTDEEACEMARKRILLWHKKNAVAGDA
SLLADERRKEGKDPAAMSAAEYLSKLAIQR
GSKDNISVVVVDLKGGSGGSRPGERPFQC
RICMRNFSxxxxxxxHTRTHTGEKPFQCRICM
RNFSxxxxxxxHLRTHTGSQKPFQCRICMRN
FSxxxxxxxHLRTHTGEKPFQCRICMRNFSxxx
xxxxHLKTHTGSQKPFQCRICMRNFSxxxxxxx
HLRTHTGEKPFQCRICMRNFSxxxxxxxHLRT
HLRGSTCRGSGATNFSLLKQAGDVEENPG
PGHHPKKKRKVDAKSLTAWSRTLVTFKDVF
VDFTREEWKLLDTAQQILYRNVMLENYKNL
VSLGYQLTKPDVILRLEKGEEPWLVEREIHQ
ETHPDSETAFEIKSSVGGGSGQLTQDEFTQ
LSQSIAEFHTYQLGNGRCSSLLAQRIHAPPE
TVWSVVRRFDRPQIYKHFIKSCNVSEDFEM
RVGCTRDVNVISGLPANTSRERLDLLDDDR
RVTGFSITGGEHRLRNYKSVTTVHRFEKEE
EEERIWTVVLESYVVDVPEGNSEEDTRLFA
DTVIRLNLQKLASITEAMN

[ABI]-[ZF]-[2A]-[KRAB]-[PYL] (SEQ ID NO: 5)

Fig. 20

MSRPGERPFQCRICMRNFSxxxxxxxHTRTH
TGEKPFQCRICMRNFSxxxxxxxHLRTHTGS
QKPFQCRICMRNFSxxxxxxxHLRTHTGEKPF
QCRICMRNFSxxxxxxxHLKTHTGSQKPFQC
RICMRNFSxxxxxxxHLRTHTGEKPFQCRICM
RNFSxxxxxxxHLRTHLRGSTCRDEFPTMVFP
SGQISQASALAPAPPQVLPQAPAPAPAPAM
VSALAQAPAPVPVLAPGPPQAVAPPAPKPT
QAGEGTLSEALLQLQFDDEDLGALLGNST
DPAVFTDLASVDNSEFQQLLNQGIPVAPHT
TEPMLMEYPEAITRLVTGAQRPPDPAPAPL
GAPGLPNGLLSGDEDFSSIADMDFSALLSQ
ISSQLCVRGSSAGDMRAANLWPSPLMIKRS
KKNSLALSLTADQMVSALLDAEPPILYSEYD
PTRPFSEASMMGLLTNLADRELVHMINWAK
RVPGFVDLTLHDQVHLLECAWLEILMIGLV
WRSMEHPVKLLFAPNLLLDRNQGKCVEGM
VEIFDMLLATSSRFRMMNLQGEEFVCLKSII
LLNSGVYTFLSSTLKSLEEKDHIHRVLDKIT
DTLIHLMAKAGLTLQQQHQRLAQLLLILSHI
RHMSNKGMEHLYSMKCKNVVPLYDLLLEA
ADAHRLHAPTSRGGASVEETDQSHLATAG
STSSHSLQKYYITGEAEGFPATA

[ZF]-[p65]-[ERT2] (SEQ ID NO: 6)

Fig. 21

M*DAKSLTAWSRTLVTFKDVFVDFTREEWKL*
*LDTAQQILYRNVMLENYKNLVSLGYQLTKP*
*DVILRLEKGEEPWLVEREIHQETHPDSETAF*
*EIKSSV*LEGGGGSG*TCRSR*PGERPFQCRIC
MRNFSxxxxxxxHTRTHTGEKPFQCRICMRN
FSxxxxxxxHLRTHTGSQKPFQCRICMRNFSx
xxxxxxHLRTHTGEKPFQCRICMRNFSxxxxxx
xHLKTHTGSQKPFQCRICMRNFSxxxxxxxHL
RTHTGEKPFQCRICMRNFSxxxxxxxHLRTHL
R*GSQL*CVRGSSAGDMRAANLWPSPLMIKR
SKKNSLALSLTADQMVSALLDAEPPILYSEY
DPTRPFSEASMMGLLTNLADRELVHMINWA
KRVPGFVDLTLHDQVHLLECAWLEILMIGLV
WRSMEHPVKLLFAPNLLLDRNQGKCVEGM
VEIFDMLLATSSRFRMMNLQGEEFVCLKSII
LLNSGVYTFLSSTLKSLEEKDHIHRVLDKIT
DTLIHLMAKAGLTLQQHQRLAQLLLILSHI
RHMSNKGMEHLYSMKCKNVVPLYDLLLEA
ADAHRLHAPTSRGGASVEETDQSHLATAG
STSSHSLQKYYITGEAEGFPATA

[KRAB]-[ZF]-[ERT2] (SEQ ID NO: 7)

Fig. 22

MSRPGERPFQCRICMRNFSxxxxxxxHTRTH
TGEKPFQCRICMRNFSxxxxxxxHLRTHTGS
QKPFQCRICMRNFSxxxxxxxHLRTHTGEKPF
QCRICMRNFSxxxxxxxHLKTHTGSQKPFQC
RICMRNFSxxxxxxxHLRTHTGEKPFQCRICM
RNFSxxxxxxxHLRTHLRGSTCRDYKDHDGD
YKDHDIDYKDDDDKMAPKKKRKVGIHGVP
GGLEGGGGSGGTEDVVCCHSIYGKKKGDI
DTYRYIGSSGTGCVVIVGRIVLSGSGTSAPIT
AYAQQTRGLLGCIITSLTGRDKNQVEGEVQI
VSTATQTFLATCINGVCWAVYHGAGTRTIAS
PKGPVIQMYTNVDQDLVGWPAPQGSRSLT
PCTCGSSDLYLVTRHADVIPVRRRGDSRGS
LLSPRPISYLKGSSGGPLLCPAGHAVGLFR
AAVCTRGVAKAVDFIPVENLETTMRSPVFT
DNSSPPAVTLTHPITKIDREVLYQEFDEMEE
CSQHYPYDVPDYAGGGGSGGTDEFPTMVF
PSGQISQASALAPAPPQVLPQAPAPAPAPA
MVSALAQAPAPVPVLAPGPPQAVAPPAPK
PTQAGEGTLSEALLQLQFDDEDLGALLGN
STDPAVFTDLASVDNSEFQQLLNQGIPVAP
HTTEPMLMEYPEAITRLVTGAQRPPDPAPA
PLGAPGLPNGLLSGDEDFSSIADMDFSALL
SQISSQL

[ZF]-[NS3]-[p65] (SEQ ID NO: 8)

Fig. 23

MDAKSLTAWSRTLVTFKDVFVDFTREEWKL
LDTAQQILYRNVMLENYKNLVSLGYQLTKP
DVILRLEKGEEPWLVEREIHQETHPDSETAF
EIKSSVTCRDYKDHDGDYKDHDIDYKDDDD
KMAPKKKRKVGIHGVPGGLEGGGGSGGTE
DVVCCHSIYGKKKGDIDTYRYIGSSGTGCVV
IVGRIVLSGSGTSAPITAYAQQTRGLLGCIITS
LTGRDKNQVEGEVQIVSTATQTFLATCINGV
CWAVYHGAGTRTIASPKGPVIQMYTNVDQD
LVGWPAPQGSRSLTPCTCGSSDLYLVTRHA
DVIPVRRRGDSRGSLLSPRPISYLKGSSGG
PLLCPAGHAVGLFRAAVCTRGVAKAVDFIP
VENLETTMRSPVFTDNSSPPAVTLTHPITKID
REVLYQEFDEMEECSQHYPYDVPDYAGGG
GSGGTSRPGERPFQCRICMRNFSxxxxxxxH
TRTHTGEKPFQCRICMRNFSxxxxxxxHLRTH
TGSQKPFQCRICMRNFSxxxxxxxHLRTHTG
EKPFQCRICMRNFSxxxxxxxHLKTHTGSQK
PFQCRICMRNFSxxxxxxxHLRTHTGEKPFQC
RICMRNFSxxxxxxxHLRTHLRGSQL

[KRAB]-[NS3]-[ZF] (SEQ ID NO: 9)

Fig. 24

MSRPGERPFQCRICMRNFSxxxxxxxHTRTHTGEKPFQ
CRICMRNFSxxxxxxxHLRTHTGSQKPFQCRICMRNFS
xxxxxxxHLRTHTGEKPFQCRICMRNFSxxxxxxxHLKTH
TGSQKPFQCRICMRNFSxxxxxxxHLRTHTGEKPFQCR
ICMRNFSxxxxxxxHLRTHLRGSTCRDEFPTMVFPSGQI
SQASALAPAPPQVLPQAPAPAPAPAMVSALAQAPAP
VPVLAPGPPQAVAPPAPKPTQAGEGTLSEALLQLQF
DDEDLGALLGNSTDPAVFTDLASVDNSEFQQLLNQGI
PVAPHTTEPMLMEYPEAITRLVTGAQRPPDPAPAPLG
APGLPNGLLSGDEDFSSIADMDFSALLSQISSQLCVR
GSSAGDMRAANLWPSPLMIKRSKKNSLALSLTADQ
MVSALLDAEPPILYSEYDPTRPFSEASMMGLLTNLAD
RELVHMINWAKRVPGFVDLTLHDQVHLLECAWLEILM
IGLVWRSMEHPVKLLFAPNLLLDRNQGKCVEGMVEI
FDMLLATSSRFRMMNLQGEEFVCLKSIILLNSGVYTF
LSSTLKSLEEKDHIHRVLDKITDTLIHLMAKAGLTLQQ
QHQRLAQLLLILSHIRHMSNKGMEHLYSMKCKNVVP
LYDLLLEAADAHRLHAPTSRGGASVEETDQSHLATA
GSTSSHSLQKYYITGEAEGFPATAPGDEMEECSQHL
PGAGSSGDIMDYKDDDDKGSSGTGSGSGTSAPITAY
AQQTRGLLGCIITSLTGRDKNQVEGEVQIVSTATQTFL
ATCINGVCWAVYHGAGTRTIASPKGPVIQMYTNVDQD
LVGWPAPQGSRSLTPCTCGSSDLYLVTRHADVIPVRR
RGDSRGSLLSPRPISYLKGSSGGPLLCPAGHAVGLFR
AAVCTRGVAKAVDFIPVENLETTMRSPVFTDNSSPPA
VTLTHPITKIDTKYIMTCMSADLEVVTSTWVLVGGVLA
ALAAYCLSTGCVVIVGRIVLSGKPAIIPDREVLY

[ZF]-[p65]-[ERT2]-[SMASh] (SEQ ID NO: 10)

Fig. 25

M*DYKDDDDK*GSSGTGSGSGTS*APITAYAQQTRGLLG CIITSLTGRDKNQVEGEVQIVSTATQTFLATCINGVCWA VYHGAGTRTIASPKGPVIQMYTNVDQDLVGWPAPQG SRSLTPCTCGSSDLYLVTRHADVIPVRRRGDSRGSLL SPRPISYLKGSSGGPLLCPAGHAVGLFRAAVCTRGVA KAVDFIPVENLETTMRSPVFTD*NSSPPAVTLTHPITKID TKYIMTCMSADLEVVTSTWVLVGGVLAALAAYCLSTG CVVIVGRIVLSGKPAGSSGSSIIPDREVLY*QEFEDVVP CSMGS*PGSR*PGERPFQCRICMRNFSxxxxxxxHTRTHT GEKPFQCRICMRNFSxxxxxxxHLRTHTGSQKPFQCRI CMRNFSxxxxxxxHLRTHTGEKPFQCRICMRNFSxxxxx xxHLKTHTGSQKPFQCRICMRNFSxxxxxxxHLRTHTG EKPFQCRICMRNFSxxxxxxxHLRTHLR*GSTCRDEFPT MVFPSGQISQASALAPAPPQVLPQAPAPAPAPAMVS ALAQAPAPVPVLAPGPPQAVAPPAPKPTQAGEGTLS EALLQLQFDDEDLGALLGNSTDPAVFTDLASVDNSE FQQLLNQGIPVAPHTTEPMLMEYPEAITRLVTGAQRP PDPAPAPLGAPGLPNGLLSGDEDFSSIADMDFSALL SQISSQL*CVRGSSAGDMRAANLWPSPLMIKRSKKNS LALSLTADQMVSALLDAEPPILYSEYDPTRPFSEASM MGLLTNLADRELVHMINWAKRVPGFVDLTLHDQVHL LECAWLEILMIGLVWRSMEHPVKLLFAPNLLLDRNQ GKCVEGMVEIFDMLLATSSRFRMMNLQGEEFVCLKS IILLNSGVYTFLSSTLKSLEEKDHIHRVLDKITDTLIHLM AKAGLTLQQQHQRLAQLLLILSHIRHMSNKGMEHLY SMKCKNVVPLYDLLLEAADAHRLHAPTSRGGASVEE TDQSHLATAGSTSSHSLQKYYITGEAEGFPATA

[SMASh]-[ZF]-[p65]-[ERT2] (SEQ ID NO: 11)

Fig. 26

M*DYKDHDGDYKDHDIDYKDDDDKMAPKKK*
*RKVGIHGVPGG*LEGGGGSGGT*ASSR*PGERP
FQCRICMRNFSxxxxxxxHTRTHTGEKPFQCRI
CMRNFSxxxxxxxHLRTHTGSQKPFQCRICMR
NFSxxxxxxxHLRTHTGEKPFQCRICMRNFSxx
xxxxxHLKTHTGSQKPFQCRICMRNFSxxxxxxx
HLRTHTGEKPFQCRICMRNFSxxxxxxxHLRTH
LR*GSTCR**DEFPTMVFPSGQISQASALAPAPP*
*QVLPQAPAPAPAPAMVSALAQAPAPVPVLAP*
*GPPQAVAPPAPKPTQAGEGTLSEALLQLQF*
*DDEDLGALLGNSTDPAVFTDLASVDNSEFQQ*
*LLNQGIPVAPHTTEPMLMEYPEAITRLVTGAQ*
*RPPDPAPAPLGAPGLPNGLLSGDEDFSSIAD*
*MDFSALLSQISS**PG*DEMEECSQHLPGAGSS
GDIM*DYKDDDDK*GSSGTGSGSGTS*APITAYA*
*QQTRGLLGCIITSLTGRDKNQVEGEVQIVSTAT*
*QTFLATCINGVCWAVYHGAGTRTIASPKGPVI*
*QMYTNVDQDLVGWPAPQGSRSLTPCTCGSS*
*DLYLVTRHADVIPVRRRGDSRGSLLSPRPISY*
*LKGSSGGPLLCPAGHAVGLFRAAVCTRGVAK*
*AVDFIPVENLETTMRSPVFTD*NSSPPAVTLTH
PITKIDTKYIMTCMSADLEVVT*STWVLVGGVL*
*AALAAYCLSTGCVVIVGRIVLSGKPAIIPDREVL*
*Y*

[ZF]-[p65]-[SMASh] (SEQ ID NO: 12)

Fig. 27

M*LAVSVTFEDVAVLFTRDEWKKLDLSQRSLYRE*
*VMLENYSNLASMAGFLFTKPKVISLLQQGEDP*
*W*GGSGSGSAC*SR*PGERPFQCRICMRNFSxxxxx
xxHTRTHTGEKPFQCRICMRNFSxxxxxxxHLRTH
TGSQKPFQCRICMRNFSxxxxxxxHLRTHTGEKP
FQCRICMRNFSxxxxxxxHLKTHTGSQKPFQCRIC
MRNFSxxxxxxxHLRTHTGEKPFQCRICMRNFSxx
xxxxxHLRTHLR*GSQL*CVRGSSAGDMRAANLWP
SPLMIKRSKKNSLALSLTADQMVSALLDAEPPIL
YSEYDPTRPFSEASMMGLLTNLADRELVHMIN
WAKRVPGFVDLTLHDQVHLLECAWLEILMIGLV
WRSMEHPVKLLFAPNLLLDRNQGKCVEGMVEI
FDMLLATSSRFRMMNLQGEEFVCLKSIILLNSG
VYTFLSSTLKSLEEKDHIHRVLDKITDTLIHLMAK
AGLTLQQQHQRLAQLLLILSHIRHMSNKGMEHL
YSMKCKNVVPLYDLLLEAADAHRLHAPTSRGG
ASVEETDQSHLATAGSTSSHSLQKYYITGEAEG
FPATA*PG*DEMEECSQHLPGAGSSGDIM*DYKDD*
*DDK*GSSGTGSGSGTS*APITAYAQQTRGLLGCIIT*
*SLTGRDKNQVEGEVQIVSTATQTFLATCINGVCW*
*AVYHGAGTRTIASPKGPVIQMYTNVDQDLVGWP*
*APQGSRSLTPCTCGSSDLYLVTRHADVIPVRRR*
*GDSRGSLLSPRPISYLKGSSGGPLLCPAGHAVG*
*LFRAAVCTRGVAKAVDFIPVENLETTMRSPVFTD*
NSSPPAVTLTHPITKIDTKYIMTCMSADLEVVT*ST*
*WVLVGGVLAALAAYCLSTGCVVIVGRIVLSGKPAI*
*IPDREVLY*

[KRAB]-[ZF]-[ERT2]-[SMASh] (SEQ ID NO: 13)

Fig. 28

M*GKKTKRTADSSSSEDEEEYVVEKVLDRRVVKGQV EYLLKWKGFSEEHNTWEPEKNLDCPELISEFMKKY KKMKEGENNKPREKSESNKRKSNFSNSADDIKSKK KREQSNDIARGFERGLEPEKIIGATDSCGDLMFLMK WKDTDEADLVLAKEANVKCPQIVIAFYEERLTWHAY PEDAENKEKETAKS*GGSGSGSAC*SR*PGERPFQCRI CMRNFSxxxxxxxHTRTHTGEKPFQCRICMRNFSxxxx xxxHLRTHTGSQKPFQCRICMRNFSxxxxxxxHLRTHT GEKPFQCRICMRNFSxxxxxxxHLKTHTGSQKPFQCR ICMRNFSxxxxxxxHLRTHTGEKPFQCRICMRNFSxxxx xxxHLRTHLRGSQL*CVRGSSAGDMRAANLWPSPLM IKRSKKNSLALSLTADQMVSALLDAEPPILYSEYDPT RPFSEASMMGLLTNLADRELVHMINWAKRVPGFVD LTLHDQVHLLECAWLEILMIGLVWRSMEHPVKLLFA PNLLLDRNQGKCVEGMVEIFDMLLATSSRFRMMNL QGEEFVCLKSIILLNSGVYTFLSSTLKSLEEKDHIHR VLDKITDTLIHLMAKAGLTLQQQHQRLAQLLLILSHI RHMSNKGMEHLYSMKCKNVVPLYDLLLEAADAHRL HAPTSRGGASVEETDQSHLATAGSTSSHSLQKYYIT GEAEGFPATAPG*DEMEECSQHLPGAGSSGDIM*DYK DDDDKGSSGTGSGSGT*SAPITAYAQQTRGLLGCIITS LTGRDKNQVEGEVQIVSTATQTFLATCINGVCWAVYH GAGTRTIASPKGPVIQMYTNVDQDLVGWPAPQGSR SLTPCTCGSSDLYLVTRHADVIPVRRRGDSRGSLLSP RPISYLKGSSGGPLLCPAGHAVGLFRAAVCTRGVAK AVDFIPVENLETTMRSPVFTD*NSSPPAVTLTHPITKID TKYIMTCMSADLEVVT*STWVLVGGVLAALAAYCLST GCVVIVGRIVLSGKPAIIPDREVLY*

[Hp1a]-[ZF]-[ERT2]-[SMASh] (SEQ ID NO: 14)

Fig. 29

MSEREVSTAPAGTDMPAAKKQKLSSDENSNPDLSGDEND
DAVSIESGTNTERPDTPTNTPNAPGRKSWGKGKWKSKKC
KYSFKCVNSLKEDHNQPLFGVQFNWHSKEGDPLVFATVG
SNRVTLYECHSQGEIRLLQSYVDADADENFYTCAWTYDSN
TSHPLLAVAGSRGIIRIINPITMQCIKHYVGHGNAINELKFHP
RDPNLLLSVSKDHALRLWNIQTDTLVAIFGGVEGHRDEVLS
ADYDLLGEKIMSCGMDHSLKLWRINSKRMMNAIKESYDYN
PNKTNRPFISQKIHFPDFSTRDIHRNYVDCVRWLGDLILSKS
CENAIVCWKPGKMEDDIDKIKPSESNVTILGRFDYSQCDIW
YMRFSMDFWQKMLALGNQVGKLYVWDLEVEDPHKAKCT
TLTHHKCGAAIRQTSFSRDSSILIAVCDDASIWRWDRLRGG
SGSGSACSRPGERPFQCRICMRNFSxxxxxxxHTRTHTGEKP
FQCRICMRNFSxxxxxxxHLRTHTGSQKPFQCRICMRNFSxxx
xxxxHLRTHTGEKPFQCRICMRNFSxxxxxxxHLKTHTGSQKP
FQCRICMRNFSxxxxxxxHLRTHTGEKPFQCRICMRNFSxxxx
xxxHLRTHLRGSQLCVRGSSAGDMRAANLWPSPLMIKRSK
KNSLALSLTADQMVSALLDAEPPILYSEYDPTRPFSEASMM
GLLTNLADRELVHMINWAKRVPGFVDLTLHDQVHLLECAW
LEILMIGLVWRSMEHPVKLLFAPNLLLDRNQGKCVEGMVEI
FDMLLATSSRFRMMNLQGEEFVCLKSIILLNSGVYTFLSSTL
KSLEEKDHIHRVLDKITDTLIHLMAKAGLTLQQQHQRLAQL
LLILSHIRHMSNKGMEHLYSMKCKNVVPLYDLLLEAADAHR
LHAPTSRGGASVEETDQSHLATAGSTSSHSLQKYYITGEA
EGFPATAPGDEMEECSQHLPGAGSSGDIMDYKDDDDKGS
SGTGSGSGTSAPITAYAQQTRGLLGCIITSLTGRDKNQVEGE
VQIVSTATQTFLATCINGVCWAVYHGAGTRTIASPKGPVIQM
YTNVDQDLVGWPAPQGSRSLTPCTCGSSDLYLVTRHADVIP
VRRRGDSRGSLLSPRPISYLKGSSGGPLLCPAGHAVGLFRA
AVCTRGVAKAVDFIPVENLETTMRSPVFTDNSSPPAVTLTHP
ITKIDTKYIMTCMSADLEVVTSTWVLVGGVLAALAAYCLSTG
CVVIVGRIVLSGKPAIIPDREVLY

[EED]-[ZF]-[ERT2]-[SMASh] (SEQ ID NO: 15)

Fig. 30

REGULATED SYNTHETIC GENE EXPRESSION SYSTEMS

CROSS-REFERENCE TO RELATED APPLICATIONS

This application is a continuation under 35 U.S.C. § 120 of co-pending U.S. application Ser. No. 16/875,591, filed May 15, 2020, which claims benefit under 35 U.S.C. § 119(e) of U.S. Provisional Application No. 62/848,850 filed May 16, 2019, the contents of each of which are incorporated herein by reference in their entireties.

GOVERNMENT SUPPORT

This invention was made with government support under Grant No. D16AP00142 awarded by the Defense Advanced Research Projects Agency and Grant No. CCF-1522074 awarded by the National Science Foundation. The government has certain rights in the invention.

SEQUENCE LISTING

The instant application contains a Sequence Listing which has been submitted in XML format via Patent Center and is hereby incorporated by reference in its entirety. Said XML copy, created on Oct. 7, 2022, is named 701586-095350USC1_SL.txt and is 881,623 bytes in size.

TECHNICAL FIELD

The technology described herein relates to regulated synthetic gene expression systems.

BACKGROUND

Next generation cell therapies seek to create designer immune cells that can sense and respond to disease in sophisticated ways. Achieving this goal fundamentally requires engineered regulatory elements and circuitry that can be used to program human cell functions by processing complex environmental inputs and mediating precisely regulated expression of therapeutic agents. Towards this goal, synthetic transcriptional programs can interface with sense and response modules to enable new layers of regulation in cells.

To advance immune cell therapies beyond reliance on simple constitutive expression of therapeutic agents, there is a need for programmable genetic components that offer tunable and versatile regulatory profiles. Moreover, these components must themselves have properties that are compatible with the human therapeutic context, including high specificity, low immunogenicity, and deliverability.

T cell immunotherapy has shown tremendous promise for cancer treatment, including liquid tumors such as leukemia and lymphoma. However, alongside its remarkable effectiveness, there are significant side effects, such as cytokine releasing syndrome (CRS) and neurotoxicity, which pose life-threatening risks to patients receiving immunotherapy. It is increasingly important to develop safe and effective sense-and-response strategies that can control the activity of engineered T cells post-infusion.

SUMMARY OF THE INVENTION

The technology described herein is directed to a method to control gene expression. In general, the technology described herein relates to a synthetic transcription factor (synTF) that comprises a regulator protein (RP), where the regulator protein regulates the activity of the synTF. In particular, the synTFs according to the methods, systems and compositions as disclosed herein comprise (i) a DNA binding domain (DBD) which binds to a target nucleic acid sequence (or target DNA binding motif (DBM)) located 3' of a promoter that is operatively linked to the nucleic acid of a gene of interest (GOI) to be expressed, (ii) an effector domain (ED) and a regulator protein (RP), where the regulator protein controls the coupling of the DNA binding domain (DBD) with the effector domain (ED), or controls the cellular localization of the ED, such that when the ED and DBD are attached and/or located in the nucleus, the ED can function to recruit or repress translation machinery to the promoter to regulate gene expression of a gene of interest. In some embodiments, the ED can be a transcriptional activator (TA), thereby turning on gene expression when the ED is present at the transcription start site of a gene of interest, and in some embodiments, the ED is a transcriptional repressor (TR), such that when the ED is present at the transcription start site of a gene of interest, the gene expression is inhibited or repressed.

In some embodiments of the systems, compositions and methods as disclosed herein, the regulator protein of the SynTF is selected from a protease, a pair of inducible proximity domains (IPDs) or a translocation domain (i.e., a cytosolic sequestering protein), each of which are described herein and in more detail below.

In some embodiments of the systems, compositions and methods as disclosed herein, the synTF comprises a regulator protein that is a self-cleaving protease, for example, one exemplary protease is NS3. SynTFs comprising self-cleaving proteases can also be referred to herein as "repressible proteases SynTF". In such embodiments of the systems, compositions and methods disclosed herein, the DBD is directly linked or indirectly linked (or coupled) to the effector domain, and the protease regulator protein (typically located between the DBD and ED) controls the coupling of the DBD to the ED. In such an embodiment, in the presence of an agent which inhibits the regulator protein (i.e., NS3 protein), the DBD and ED remain coupled or intact (either directly or indirectly) and the effector domain can control gene expression from the promoter (i.e., turning on gene expression of the gene of interest (GOI) if the ED is a TA, or repressing gene expression if the ED is a TR) (see e.g., FIG. 5A-5C). In such an embodiment, in the absence of an agent which inhibits the regulator protein (i.e., NS3 protein), the linkage between the DBD and ED is broken or cleaved, and therefore the ED is not brought into proximity of the transcription start site of the gene (or the ED dissociates from the start site), and therefore the TA can no longer initiate gene expression of the GOI, or alternatively a RP can no longer repress gene expression of the gene of interest.

In another embodiment of the systems, compositions and methods as disclosed herein, the synTF comprises a regulator protein that is a pair of inducer proximity domains (referred to as an "IPD pair") which is located between the DBD and ED, where each domain of the IPD come together in the presence of an inducer agent, and therefore linking the DBD and ED and controlling gene expression (see, e.g., FIGS. 3 and 7A). SynTFs comprising an IPD pair can also be referred to herein as a "heterodimerization domain SynTF". For example, in such embodiments, where the regulator protein is an IPD pair, each domain of the IPD pair is attached to either the DBD or the ED, such that in the presence of an inducer agent, each domain of the IPD bind to the inducer agent, thereby indirectly coupling the DBD with the ED, such that when the DBD binds to a promoter region, the ED can control gene expression from the promoter (i.e., turning on gene expression if the ED is a TA, or repressing gene expression if the ED is a TR) (see e.g., FIG. 7A). In alternative embodiments where the RP is an IPD pair, in the absence of the inducer agent, the DBD and ED remain uncoupled, and therefore the ED is not in a position to regulate gene transcription from the transcription start site at the GOI. Exemplary IPD pairs and their inducing agents are disclosed herein.

In some embodiments of the systems, compositions and methods as disclosed herein, the synTF comprises a regulator protein that is a translocation domain. In some embodiments, a translocation domain is a cytosolic sequestering protein, for example, one exemplary cytosolic sequestering protein is ERT2 and variants thereof. SynTFs comprising a translocation domain, e.g., a cytosolic sequestering protein can also be referred to herein as "Translocation Domain SynTF". In such embodiments of the systems, compositions and methods disclosed herein, the DBD is directly linked or indirectly linked (or coupled) to the effector domain, and the translocation domain, e.g., a cytosolic sequestering protein regulator protein (which can be attached to either to the ED, or DBD or located between the DBD and ED) controls the cellular localization of the synTF comprising the DBD-ED (see, e.g., FIG. 4). In such an embodiment, in the absence of a ligand that binds to the cytosolic sequestering protein, the cytosolic sequestering protein sequesters the ED and coupled DBD in the cytosol, and therefore the ED is not brought into proximity of the transcription start site of the gene (or the ED dissociates from the start site), and therefore the TA can no longer initiate gene expression of the GOI, or alternatively a RP can no longer repress gene expression of the gene of interest. In contrast, in the in the presence of a ligand that binds to the cytosolic sequestering protein, the cytosolic sequestering protein is inhibited, allowing the DBD-ED of the synTF can translocate from the cytosol to the nucleus where the DBD can bind to the DNA binding motif (DBM) and the effector domain (ED) can control gene expression from the promoter (i.e., turning on gene expression of the gene of interest (GOI) if the ED is a TA, or repressing gene expression if the ED is a TR) (see e.g., FIG. 4).

Another aspect of the systems, compositions and methods as disclosed herein are synTFs comprising a small-molecule assisted shutoff (SMASh) domain, which can also be referred to herein as an "induced degradation domain." In general, SMASh domains function to target the polypeptide that is attached to the SMASh domain for degradation. In some embodiments, the SMASh domain is attached to a synTF comprising a regulator protein that is an inducer proximity domain pair (IPD), or a cytosolic sequestering protein (e.g., see FIG. 6B). In alternative embodiments, the regulator protein can be a SMASh domain (i.e., the SMASh domain replaces a self-cleaving protease regulator protein in the synTF) (see, e.g., FIG. 6A).

In all aspects of the methods, systems and compositions disclosed herein, a SMASh domain comprises a self-cleaving protease and a degron domain. In some embodiments, the self-cleaving protease is a NS3 protease or variant thereof as disclosed herein. In some embodiments the SMASh domain comprises NS3 protease domain a partial NS3 helical domain and NS4A domain, and can be fused to the N-terminal or C-terminal of a synTF described herein. Without being limited to theory and by way of explanation only, when a SMASh domain is attached to a synTF as disclosed herein, and when there is an inhibitor of the SMASh domain self-cleaving protease present, both the SMASh domain and the attached synTF are targeted for degradation. This is referred to as "SynTF-degradation" and results in the synTF being "SynTF-OFF"—that is because the synTF is degraded, the synTF cannot bind to the DBM, or regulate the expression of the gene of interest, regardless of the type of effector domain present in the synTF. Conversely, when an inhibitor of the self-cleaving protease is absent, the self-cleaving protease cleaves (or uncouples) the SMASh domain from the synTF, and only the SMASh domain is targeted for degradation, and the activity of the released synTF is regulated by way of the regulator protein. As such, when a SMASh domain is attached to the synTF, in the absence of the protease inhibitor, it is referred to "SMASh-degradation" and results in the synTF being "SynTF-ON" enabling the synTF to be regulated by the regulator protein, and gene expression can occur or be repressed depending on whether the ED is a transcription activator or repressor protein, respectively. Accordingly, the presence of a SMASh domain attached to the synTF enables a second level of control for the expression of the GOI in addition to the regulator protein.

In some embodiments, the SMASh domain by itself serves as the regulator protein of a synTF (i.e., SMASh domain replaces a self-cleaving protease regulator protein), and is referred to as an Induced Degradation Domain SynTF (e.g., see FIG. 6A). In such embodiments, where the SMASh domain serves as the regulator protein, the SMASh domain can be attached to either the ED or the DBD of the synTF, and in the absence of a NS3 protease, the NS3 protease is active and the SMASh domain uncouples from the synTF, thereby resulting in only the SMASh domain being targeted for degradation, and the synTF comprising the DBD and the coupled ED enabling to control gene expression from the promoter (i.e., the DBD binds to the DBM, bringing the ED in close proximity to the promoter and turning on gene expression of the GOI if the ED is a TA, or repressing gene expression if the ED is a TR). In such an embodiment, in the absence of an agent which inhibits the regulator protein (i.e., NS3 protein), the linkage between the DBD and ED is broken or cleaved, and therefore the ED is not brought into proximity of the transcription start site of the gene (or the ED dissociates from the start site), and therefore the TA can no longer initiate gene expression of the GOI, or alternatively a RP can no longer repress gene expression of the gene of interest.

In some embodiments, where the SMASh domain is attached to translocation domain synTF (e.g., where the regulator protein is a sequestering protein), or a heterodimerization domain synTF (i.e., where the regulator protein is pair of inducible proximity domains (IPD pair)), the SMASH domain can be referred to as a "SMASh tag" and can be attached to the C-terminal or N-terminal of a synTF (see, e.g., FIG. 6B or FIG. 16A). By way of an example only, a C-terminal SMASh tag is attached to the C-terminal of an ED or regulator protein of a synTF can comprise in the following N-terminal to C-terminal order: a NS3 cleavage site, at least one linker, a NS3 domain, a NS3 partial helicase, a NS4A domain, wherein the SMASh tag is fused to the C-terminus of the effector domain of the synTF. In some embodiments and by way of an example only, where a SMASh tag is fused to the N-terminus of a synTF (referred to herein as a "N-terminal SMASh tag"), the SMASh tag comprises in a N-terminal to C-terminal order: at least one Linker, a NS3 domain, a NS3 partial helicase, a NS4 domain, and a NS3 cleavage site, wherein the SMASh tag is fused to the N-terminus of the synTF.

Another aspect of the technology disclosed herein relates to a system for controlling gene expression of a gene of interest (GOI), where the system comprises a synTF described herein and a nucleic acid construct comprising the elements that the synTF binds to regulate gene expression. In particular, in some aspects, the system comprising (i) at least one synthetic transcription factor (synTF) as disclosed herein, and (ii) at least a nucleic acid construct, where the synTF comprises at least one DNA binding domain (DBD), a transcriptional effector domain (ED), and at least one regulator protein (RP), and where the ED is directly or indirectly coupled or linked to the DBD, and where the coupling is regulated by the at least one RP, or wherein the cellular localization of the ED linked to the DBD is regulated by the at least one RP, and where the at least one RP is regulated by an RP inducer, where the DBD can bind to a target DNA binding motif (DBM) located upstream of a promoter operatively linked to a gene, and where the nucleic acid construct comprises (i) at least one target DNA binding motif (DBM) comprising a target nucleic acid for binding of the at least one DBD of the synTF, and (ii) a promoter sequence located 3' of the at least one DBM, and (iii) a gene of interest (GOI) operatively linked to the promoter sequence. In some embodiments where the regulator protein of the synTFs regulates the coupling of the ED to the DBD (e.g., protease domain synTF or induced proximity domain synTFs), in the presence of the RP inducer, the coupling of the ED to the DBD of the synTF is maintained, enabling the ED to be in proximity to the promoter sequence when the DBD binds to the DNA binding motif (DBM), where the ED controls the expression of the gene of interest ("ED-on"). In embodiments where the ED is a transcriptional activator (TA), it results in turning on gene expression ("TA-on" (expression)), whereas in embodiments where the ED is a transcriptional repressor protein (TR), it inhibits or represses gene expression ("TR-on" (no expression)). In contrast, where the RP inducer is absent, the coupling of the ED to the DBD of the synTF is severed, preventing the ED from being in proximity to the promoter sequence when the DBD binds to the DNA binding motif (DBM), preventing gene expression of the gene of interest ("ED-off"). In embodiments where the ED is a transcriptional activator (TA), it results in turning off the gene expression ("TA-off" (no expression)), whereas in embodiments there the ED is a transcriptional repressor protein (TR), it turns on gene expression ("TR-off"/Repression-off, therefore enabling gene expression).

In embodiments where the regulator protein of the synTF regulates the cellular localization of the synTF (DBD and linked ED), when an RP inducer is present, the ED coupled to the DBD of the synTF is not sequestered in the cytosol, enabling the DBD to bind to the DNA binding motif (DBM) and enabling the transcriptional effector domain (ED) to be in proximity to the promoter sequence to control the expression of the gene of interest ("ED-on"). In embodiments where the ED is a transcriptional activator (TA), it results in turning on gene expression ("TA-on" (expression)), whereas in embodiments where the ED is a transcriptional repressor protein (TR), it inhibits or represses gene expression ("TR-on" (no expression)).

Moreover, when the RP inducer is absent, the ED coupled to the DBD of the synTF is sequestered in the cytosol, preventing the DBD of the synTF from binding to the DBM, and preventing the effector domain (ED) from being in proximity to the promoter sequence, preventing expression of the gene of interest ("ED-off"). In embodiments where the ED is a transcriptional activator (TA), it results in turning off the gene expression ("TA-off" (no expression)), whereas in embodiments where the ED is a transcriptional repressor protein (TR), it turns on gene expression ("TR-off"/Repression-off, therefore enabling gene expression).

TABLE 17 table summarizing presence or absence of regulator protein inducers on ultimate expression of the gene of interest.

| SynTF | RP inducer → effect on the SynTF binding to the DBM | Effector domain | Gene expression ON or OFF |
|---|---|---|---|
| Protease domain synTF | Present → ED-On | TA → "TA-on" | ON |
| | | RP → "RP-on" | OFF |
| | Absent → ED-Off | TA → "TA-off" | OFF |
| | | RP → "RP-off" | ON |
| Induced proximity domain synTF | Present → ED-On | TA → "TA-on" | ON |
| | | RP → "RP-on" | OFF |
| | Absent → ED-Off | TA → "TA-off" | OFF |
| | | RP → "RP-off" | ON |
| Translocation domain synTF | Present → ED-On | TA → "TA-on" | ON |
| | | RP → "RP-on" | OFF |
| | Absent → ED-Off | TA → "TA-off" | OFF |
| | | RP → "RP-off" | ON |
| Induced degradation domain synTF | Present → ED-Off, Syn-degradation | TA → "TA-off" | OFF |
| | | RP → "RP-off" | ON |
| | Absent → ED-On, SMASh degradation | TA → "TA-on" | ON |
| | | RP → "RP-on" | OFF |

Accordingly, whether gene expression of the GOI occurs is dependent on 3 levels of control, including but not limited to; (i) the type of regulator protein in the synTF, (ii) the presence or absence of a regulator protein inducer (RP inducer), and (iii) the type of effector domain.

Moreover, in some embodiments, the system for controlling gene expression can be configured for an additional level of control for the gene expression, depending whether there is a SMASh domain attached to the synTF, as disclosed herein. For example, attachment of a SMASh domain to a synTF will result in the following outcomes: if an inhibitor to the SMASh protease is present, the SMASh protease activity is inhibited, resulting in the synTF being degraded ("Syn-degradation") and preventing the DBD of the synTF binding to the DBM and controlling the expression or repression of the gene of interest ("synTF-degradation"; TA-off (no expression), TR-off (yes-expression). In alternative embodiments, if an inhibitor to the SMASh protease is absent, the SMASh protease is active and self cleaves/uncouples from the synTF, resulting the SMASh domain being targeted for degradation and allowing the DBD of the synTF to bind to the DBM and the ED of synTF to control the expression of the gene of interest ("SMASh-degradation, TA-on (yes-expression), TR-on (no-expression).

Other aspects of the technology described herein relate to a cell comprising the nucleic acid sequences as disclosed herein for binding of the synTF to regulate the expression of the gene of interest, and also a nucleic acid encoding the synthetic transcription factor. In some embodiments, the nucleic acid sequences are on separate constructs, and in some embodiments, they are the same construct, as disclosed herein and referred to as a "single vector".

Other embodiments will become readily apparent from the disclosure. Aspects of the present invention teach certain benefits in construction and use which give rise to the exemplary advantages described below.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

FIG. 1A is a schematic showing the design of synTFs based on orthogonal 6-unit ZF arrays. FIG. 1B is a schematic showing a synTF and reporter system. FIG. 1C is a bar graph showing that synTFs robustly activate corresponding integrated reporters, across a library of cognate synTF/DBM pairs; note that mCherry expression occurred only in the presence of a specific ZF-p65 synTF and not in the absence of a TF or in the presence of GFP-p65. FIG. 1D is a heatmap showing the co-expression of specific synTFs and reporters; note that mCherry reporter is activated by a synthetic operator and its cognate synTF. FIG. 1E-1G is a series of scatterplots showing transcriptome profiling of human cells expressing synTFs, including ZF1-p65 (FIG. 1E), ZF3-p65 (FIG. 1F), and ZF10-p65 (FIG. 1G), which reveals highly specific, orthogonal regulation of the synTFs. FIG. 1H is a bar graph showing a transcriptome profiling of synTFs compared to Gal4 and TetR. Differentially regulated transcripts=Log 2|fold change|>1; FDR<0.1 (for all 3 independent replicates).

FIG. 5A is a schematic showing a synTF regulated by NS3. GRZ indicates grazoprevir (a small molecule inhibitor of NS3). FIG. 5B is a schematic showing the system in the absence of the small molecule. NS3 protease self-excision leads to decoupling of ZF (zinc finger binding domain or DNA binding domain (DBD)) and ED (effector domain), thus permitting no transcriptional regulatory activity. FIG. 5C is a schematic showing the system in the presence of the small molecule. NS3 protease activity inhibition allows local coupling of ZF and ED, thus permitting transcriptional regulatory activity.

FIG. 6A is a schematic showing a synTF regulated by SMASh. FIG. 6B is a schematic showing a regulated transcription factor utilizing both the ERT2 and SMASh domains. The SMASh domain was placed on the C-terminus of an ERT2-containing synTF ("C-terminal SMASh", top) and on the N-terminus of an ERT2-containing synTF ("N-terminal SMASh", bottom).

FIG. 7A shows a schematic of an induced proximity domain (IPD) that couples the DBD (or ZF1) to the ED. In this exemplary embodiment, ABA functions as an inducer ligand to maintain coupling of ZF1 to the ED. FIG. 7A also shows the output fluorescence measured as a function of several different ABA treatment concentrations as indicated (dose response). FIG. 7B shows that administration of a small molecule (ABA) led to temporal activation of a fluorescent protein output from a ZF-responsive promoter in Jurkat cell lines. This level of expression was compared to an untreated cell line which did not activate output expression. FIG. 7C shows that removal of a small molecule (ABA) after four days led to temporal de-activation of a fluorescent protein output from a ZF-responsive promoter in Jurkat cell lines. This level of expression was compared to an untreated cell line which did not activate output expression. The time points measured on the chart begin on the day of drug removal ("day 0").

FIG. 8A shows an exemplary synTF with a DBD (or ZF3) fused to the ED (i.e., p63) with the cytosolic sequestering protein ERT2. FIG. 8A also shows the output fluorescence measured as a function of several different 4OHT treatment concentrations as indicated (dose response). FIG. 8B shows that administration of a small molecule (4OHT) led to temporal activation of a fluorescent protein output from a ZF-responsive promoter in Jurkat cell lines. This level of expression was compared to an untreated cell line which did not activate output expression. FIG. 8C shows that removal of a small molecule (4OHT) after four days led to temporal de-activation of a fluorescent protein output from a ZF-responsive promoter in Jurkat cell lines. This level of expression was compared to an untreated cell line which did not activate output expression. The time points measured on the chart begin on the day of drug removal ("day 0").

FIG. 9A shows an exemplary synTF with a DBD (or ZF10) coupled to the protease which is coupled to the ED (i.e., p65). FIG. 9A also shows the output fluorescence was measured as a function of several different grazoprevir treatment concentrations as indicated (dose response). FIG. 9B shows that administration of a small molecule (grazoprevir) led to temporal activation of a fluorescent protein output from a ZF-responsive promoter in Jurkat cell lines. This level of expression was compared to an untreated cell line which did not activate output expression. FIG. 9C shows that removal of a small molecule (grazoprevir) after four days led to temporal de-activation of a fluorescent protein output from a ZF-responsive promoter in Jurkat cell lines. This level of expression was compared to an untreated cell line which did not activate output expression. The time points measured on the chart begin on the day of drug removal ("day 0").

FIG. 10A is a schematic showing three exemplary synTFs: a heterodimerization domain synTF, a cytosolic sequestering domain synTF, and a repressible protease synTF, which are regulated by ABA, 4OHT, or grazoprevir, respectively. FIG. 10B is a schematic showing the reporter system. FIG. 10C-10D shows a series of line graphs (left) showing synTF activation of the reporter in HEK293 cells (FIG. 10C) or Jurkat cells (FIG. 10D) at a varying times and doses of small molecule (does are indicated by the shade of grey, with darker grey corresponding to the highest dose indicated). FIG. 10C-10D also shows a series of bar graphs (right) showing synTF activation of the reporter in HEK293 cells (FIG. 10C) or Jurkat cells (FIG. 10D) at D4 and the highest dose of small molecule (1 mM for ABA; 4 uM for 4OHT; 4 uM for GRZ). In FIG. 10C-10D shows, the top graphs correspond to ABA-regulated synTF, middle graphs to 4OHT-regulated synTF, and bottom-graphs to grazoprevir-regulated synTF. In FIG. 10C-10D this enhanced level of expression was compared to an untreated cell line which did not activate output expression.

FIG. 11A is a schematic showing the reporter system and the inducible synTFs comprising a repressor as the effector domain. FIG. 11B is a series of graphs showing that administration of a small molecule (top graphs: ABA, middle graphs: 4OHT; bottom graphs: GRZ) led to temporal silencing of a fluorescent protein output from a ZF-responsive promoter in HEK293 cell lines. This decreased level of expression was compared to an untreated cell line which did not silence output expression. FIG. 11B shows a series of line graphs (left) showing synTF repression of the reporter in HEK293 cells at a varying times and a series of bar graphs (right) showing synTF repression of the reporter in HEK293 cells at day 8.

FIG. 12A is a schematic showing the reporter system and the inducible synTF comprising a repressor as the effector domain. FIG. 12B-12C is a series of graphs showing that administration of a small molecule (grazoprevir) led to temporal silencing of a fluorescent protein output from a ZF-responsive promoter in HEK293 (FIG. 12B) and Jurkat cell lines (FIG. 12C). This decreased level of expression was compared to an untreated cell line which did not silence output expression. FIG. 12B-12C shows a series of line graphs (left) showing synTF repression of the reporter in cells at a varying times and a series of bar graphs (right) showing synTF repression of the reporter in cells at day 8.

FIG. 13A is a schematic showing the CD19-CAR expression system and an inducible synTF. Shown is a repressible protease synTF comprising NS3; however, any synTF as discussed can be used to regulate the expression of the CD19-CAR GOI according to the methods disclosed herein. FIG. 13B shows a line graph (left) showing synTF activation of CD-19 synTF expression in CD4+ primary T cells at a varying times and several different grazoprevir treatment concentrations and a bar graphs (right) showing synTF activation of CD-19 synTF expression in CD4+ primary T cells at day 3. This enhanced level of expression was compared to an untreated cell line which did not activate output expression. FIG. 13C-13D show that subsequent co-culture of these primary cells with CD19 antigen-presenting target cells (CD19+NALM cells) resulted in T-cell activation, measured by enhanced production of cytokines. This enhanced level of cytokine production was compared to an untreated cell line which did not activate cytokine expression. FIG. 13C-13D are a series of bar graphs showing IFNγ expression (FIG. 13C) and IL-2 expression (FIG. 13D) at several different grazoprevir treatment concentrations at D1 or D2.

FIG. 14A is a schematic showing the CD19-CAR and IL-4 expression systems and the exemplary inducible synTFs: a repressible protease synTF to regulate CD19-CAR and a cytosolic sequestering synTF to regulate expression of IL4. FIG. 14B is a series of line graphs showing CD19-CAR expression (top graph) and IL-4 expression (bottom graph) in the presence or absence of GZV or 4OHT, as indicated, at varying time points.

FIG. 15A-15B are a series of schematics showing that this inducible activation can be achieved through the delivery of separate nucleic acid constructs for NS3-synTF expression which then controls IL10 production ("double lentiviral vector", FIG. 15A), or through the delivery of a single nucleic acid construct controlling the expression of the NS3-synTF, as well as regulating IL10 production ("single lentiviral vector", FIG. 15B). FIG. 15C is a bar graph showing IL-10 in the presence (dark grey) or absence (light grey) of 1 uM GZV for 2 days in the double vector or single vector system.

FIG. 16A is a schematic showing N-terminal SMASh synTF and C-terminal SMASh synTF. FIG. 16B is a line graph showing reporter expression following removal of 4OHT and the presence or absence of grazoprevir, as indicated.

FIG. 19 is a schematic showing an annotated sequence of SEQ ID NO: 4, [ABI]-[ZF]-[2A]-[p65]-[PYL] (903 aa); shown N-terminal to C-terminal; bold text indicates the Zinc Finger Domain; *bold italicized text* indicates the Nuclear Localization Sequence; zig zag underlined text indicates a Linker; *italicizeddoubleunderlinedtext* indicates the restriction sites; bold zig zag underlined text indicates the ABI1cs CO1 Domain; dot underlined text indicates 2A Ribosomal Skip Sequence; *bold italicized dot dash underlined text* indicates p65 (amino acids 361-551) Activation Domain; italicized text indicates the PYL1cs Domain; plain text "xxxxxxx" indicates six ZF helices, e.g., from N terminus to C terminus: helix 1, helix 2, helix 3, helix 4, helix 5, and helix 6. Following translation of the polypeptide, the 2A sequence, which is a self-cleaving peptide, cleaves the polypeptide into two polypeptides: [ABI]-[ZF] and [p65]-[PYL], which in the presence of ABA can form a [p65]-[PYL]·ABA·[ABI]-[ZF] complex, thus coupling the DBD (ZF) and ED (p65).

FIG. 20 is a schematic showing an annotated sequence of SEQ ID NO: 5, [ABI]-[ZF]-[2A]-[KRAB]-[PYL] (808 aa); shown N-terminal to C-terminal; bold text indicates the Zinc Finger Domain; *bold italicized text* indicates the Nuclear Localization Sequence; zig zag underlined text indicates a Linker; *italicizeddoubleunderlinedtext* indicates the restriction sites; bold zig zag underlined text indicates the ABI1cs CO1 Domain; dot underlined text indicates 2A Ribosomal Skip Sequence; *bold italicized dot dash underlined text* indicates KRAB Repression Domain; italicized text indicates the PYL1cs Domain; plain text "xxxxxxx" indicates six ZF helices, e.g., from N terminus to C terminus: helix 1, helix 2, helix 3, helix 4, helix 5, and helix 6. Following translation of the polypeptide, the 2A sequence, which is a self-cleaving peptide, cleaves the polypeptide into two polypeptides: [ABI]-[ZF] and [KRAB]-[PYL], which in the presence of ABA can form a [KRAB]-[PYL]·ABA·[ABI]-[ZF] complex, thus coupling the DBD (ZF) and ED (KRAB).

FIG. 21 is a schematic showing an annotated sequence of SEQ ID NO: 6, [ZF]-[p65]-[ERT2] (692 aa); shown N-terminal to C-terminal; bold text indicates the Zinc Finger Domain *bold italicized text* indicates the Nuclear Localization Sequence; zig zag underlined text indicates a Linker; *italicizeddoubleunderlinedtext* indicates the restriction sites; bold zig zag underlined text indicates the ERT2 Domain; *bold italicized dot dash underlined text* indicates p65 (amino acids 361-551) Activation Domain; italicized text indicates the PYL1cs Domain; plain text "xxxxxxx" indicates six ZF helices, e.g., from N terminus to C terminus: helix 1, helix 2, helix 3, helix 4, helix 5, and helix 6.

FIG. 22 is a schematic showing an annotated sequence of SEQ ID NO: 7, [KRAB]-[ZF]-[ERT2] (605 aa); shown N-terminal to C-terminal; bold text indicates the Zinc Finger Domain; *bold italicized text* indicates the Nuclear Localization Sequence; zig zag underlined text indicates a Linker; *italicizeddoubleunderlinedtext* indicates the restriction sites; bold zig zag underlined text indicates the ERT2 Domain; *bold italicized dot dash underlined text* indicates KRAB, Repression Domain; plain text "xxxxxxx" indicates six ZF helices, e.g., from N terminus to C terminus: helix 1, helix 2, helix 3, helix 4, helix 5, and helix 6.

FIG. 23 is a schematic showing an annotated sequence of SEQ ID NO: 8, [ZF]-[NS3]-[p65] (704 aa); shown N-terminal to C-terminal; italicized text indicates the restriction sites; bold text indicates the Zinc Finger Domain; *bold italicized text* indicates the 3×FLAG Tag+Nuclear Localization Sequence; zig zag underlined text indicates a Linker; *italicizeddoubleunderlinedtext* indicates NS3 Cleavage Site; bold zig zag underlined text indicates the NS3 Domain; dot underlined text indicates HA Tag; *bold italicized dot dash underlined text* indicates p65 (amino acids 361-551) Activation Domain; plain text "xxxxxxx" indicates six ZF helices, e.g., from N terminus to C terminus: helix 1, helix 2, helix 3, helix 4, helix 5, and helix 6.

FIG. 24 is a schematic showing an annotated sequence of SEQ ID NO: 9, [KRAB]-[NS3]-[ZF] (609 aa); shown N-terminal to C-terminal; italicized text indicates the restriction sites; bold text indicates the Zinc Finger Domain; *bold italicized text* indicates the 3×FLAG Tag+Nuclear Localization Sequence; zig zag underlined text indicates a Linker; *italicizeddoubleunderlinedtext* indicates NS3 Cleavage Site; bold zig zag underlined text indicates the NS3 Domain; dot underlined text indicates HA Tag; *bold italicized dot dash underlined text* indicates KRAB Repression Domain; plain text "xxxxxxx" indicates ZF six helices, e.g., from N terminus to C terminus: helix 1, helix 2, helix 3, helix 4, helix 5, and helix 6.

FIG. 25 is a schematic showing an annotated sequence of SEQ ID NO: 10, [ZF]-[p65]-[ERT2]-[SMASh] (998 aa); shown N-terminal to C-terminal; bold text indicates the Zinc Finger Domain; *bold italicized text* indicates the FLAG tag; zig zag underlined text indicates a Linker; *italicizeddoubleunderlinedtext* indicates the restriction sites; bold zig zag underlined text indicates the ERT2 Domain; dot underlined text indicates NS3 Cleavage Site; *bold italicized dot dash underlined text* indicates p65 (amino acids 361-551) Activation Domain; italicized text indicates the NS3 Protease Domain; bold dash underlined text indicates NS3 Partial Helicase; *italicized zig zag underlined text* indicates NS4A Domain; plain text "xxxxxxx" indicates six ZF helices, e.g., from N terminus to C terminus: helix 1, helix 2, helix 3, helix 4, helix 5, and helix 6.

FIG. 26 is a schematic showing an annotated sequence of SEQ ID NO: 11, [SMASh]-[ZF]-[p65]-[ERT2] (997 aa); shown N-terminal to C-terminal; bold text indicates the Zinc Finger Domain; *bold italicized text* indicates the FLAG tag; zig zag underlined text indicates a Linker; *italicizeddoubleunderlinedtext* indicates the restriction sites; bold zig zag underlined text indicates the ERT2 Domain; dot underlined text indicates NS3 Cleavage Site; *bold italicized dot dash underlined text* indicates p65 (amino acids 361-551) Activation Domain; italicized text indicates the N3 Protease Domain; bold dash underlined text indicates NS3 Partial Helicase; *italicized zig zag underlined text* indicates NS4A Domain; plain text "xxxxxxx" indicates six ZF helices, e.g., from N terminus to C terminus: helix 1, helix 2, helix 3, helix 4, helix 5, and helix 6.

FIG. 27 is a schematic showing an annotated sequence of SEQ ID NO: 12, [ZF]-[p65]-[SMASh]; (728 aa); shown N-terminal to C-terminal; bold text indicates the Zinc Finger Domain; *bold italicized text* indicates the FLAG tag; zig zag underlined text indicates a Linker; *italicizeddoubleunderlinedtext* indicates the restriction sites; dot underlined text indicates NS3 Cleavage Site; *bold italicized dot dash underlined text* indicates p65 (amino acids 361-551) Activation Domain; italicized text indicates the NS3 Protease Domain; bold dash underlined text indicates NS3 Partial Helicase; *italicized zig zag underlined text* indicates NS4A Domain; plain text "xxxxxxx" indicates six ZF helices, e.g., from N terminus to C terminus: helix 1, helix 2, helix 3, helix 4, helix 5, and helix 6.

FIG. 28 is a schematic showing an annotated sequence of SEQ ID NO: 13, [KRAB]-[ZF]-[ERT2]-[SMASh]; (878 aa); shown N-terminal to C-terminal; bold text indicates the Zinc Finger Domain; *bold italicized text* indicates the FLAG tag; zig zag underlined text indicates a Linker; *italicizeddoubleunderlinedtext* indicates the restriction sites; dot underlined text indicates NS3 Cleavage Site; *bold italicized dot dash underlined text* indicates KRAB Repressor Domain; bold zig zag underlined text indicates the ERT2 Domain; italicized text indicates the NS3 Protease Domain; bold dash underlined text indicates NS3 Partial Helicase; *italicized zig zag underlined text* indicates NS4A Domain; plain text "xxxxxxx" indicates six ZF helices, e.g., from N terminus to C terminus: helix 1, helix 2, helix 3, helix 4, helix 5, and helix 6.

FIG. 29 is a schematic showing an annotated sequence of SEQ ID NO: 14, [HP1a]-[ZF]-[ERT2]-[SMASh], (1003 aa); shown N-terminal to C-terminal; bold text indicates the Zinc Finger Domain; *bold italicized text* indicates the FLAG tag; zig zag underlined text indicates a Linker; *italicizeddoubleunderlinedtext* indicates the restriction sites; dot underlined text indicates NS3 Cleavage Site; *bold italicized dot dash underlined text* indicates HP1a Repressor Domain; bold zig zag underlined text indicates the ERT2 Domain; italicized text indicates the NS3 Protease Domain; bold dash underlined text indicates NS3 Partial Helicase; *italicized zig zag underlined text* indicates NS4A Domain; plain text text "xxxxxxx" indicates six ZF helices, e.g., from N terminus to C terminus: helix 1, helix 2, helix 3, helix 4, helix 5, and helix 6.

FIG. 30 is a schematic showing an annotated sequence of SEQ ID NO: 15, [EED]-[ZF]-[ERT2]-[SMASh], (1253 aa); shown N-terminal to C-terminal; bold text indicates the Zinc Finger Domain; *bold italicized text* indicates the FLAG tag; zig zag underlined text indicates a Linker; *italicizeddoubleunderlinedtext* indicates the restriction sites; dot underlined text indicates NS3 Cleavage Site; *bold italicized dot dash underlined text* indicates HP1a Repressor Domain; bold zig zag underlined text indicates the ERT2 Domain; italicized text indicates the NS3 Protease Domain; bold dash underlined text indicates NS3 Partial Helicase; *italicized zig zag underlined text* indicates NS4A Domain; plain text "xxxxxxx" indicates six ZF helices, e.g., from N terminus to C terminus: helix 1, helix 2, helix 3, helix 4, helix 5, and helix 6.

Figure 1A:
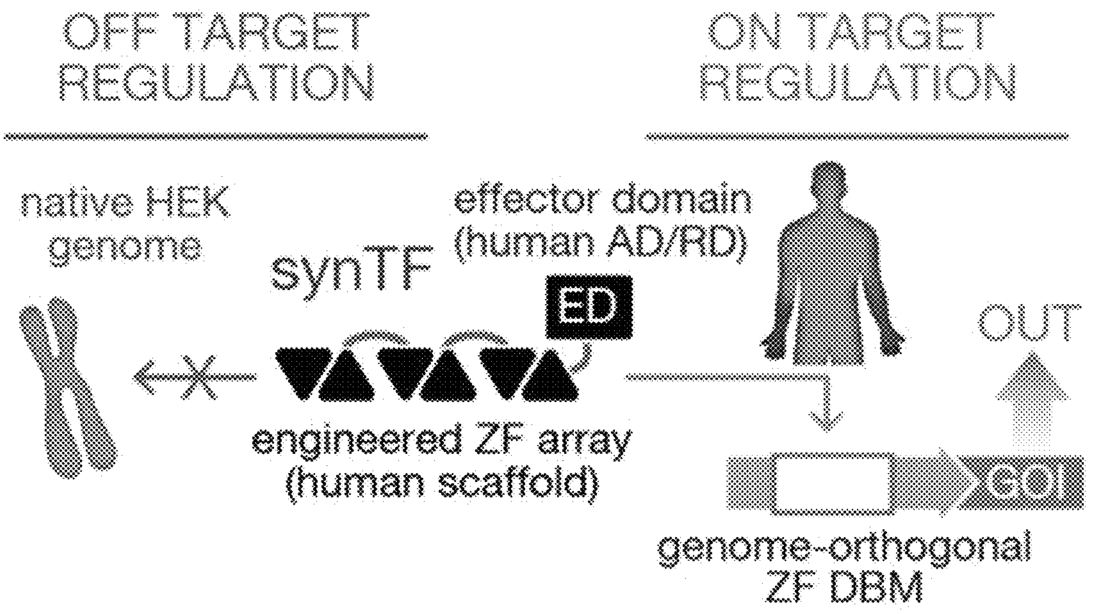
FIG. 1A-1H is a series of schematics and graphs showing the design and characterization of mammalian synTFs based on orthogonal ZF arrays.
Figure 1B:
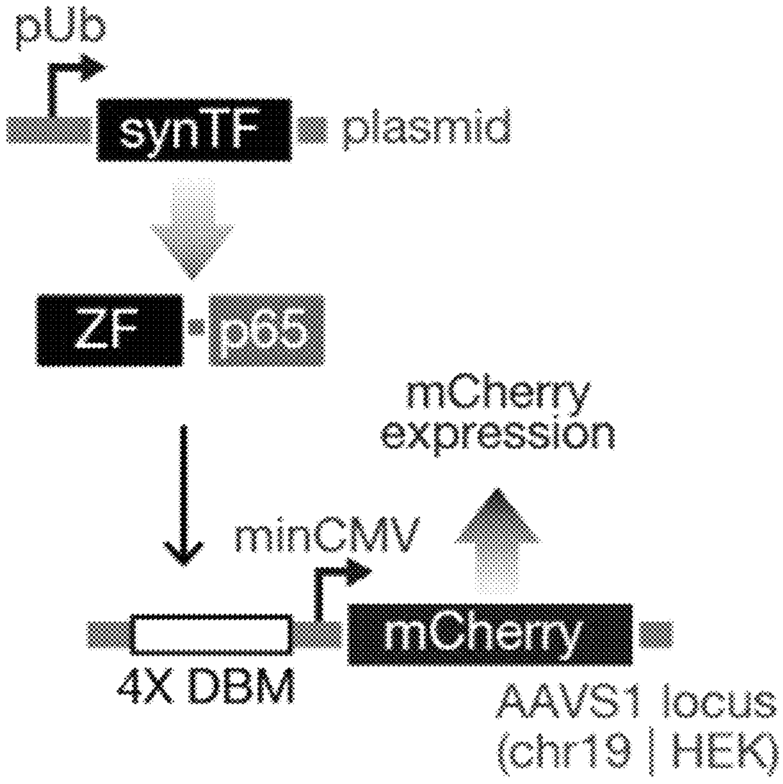
Figure 1C:
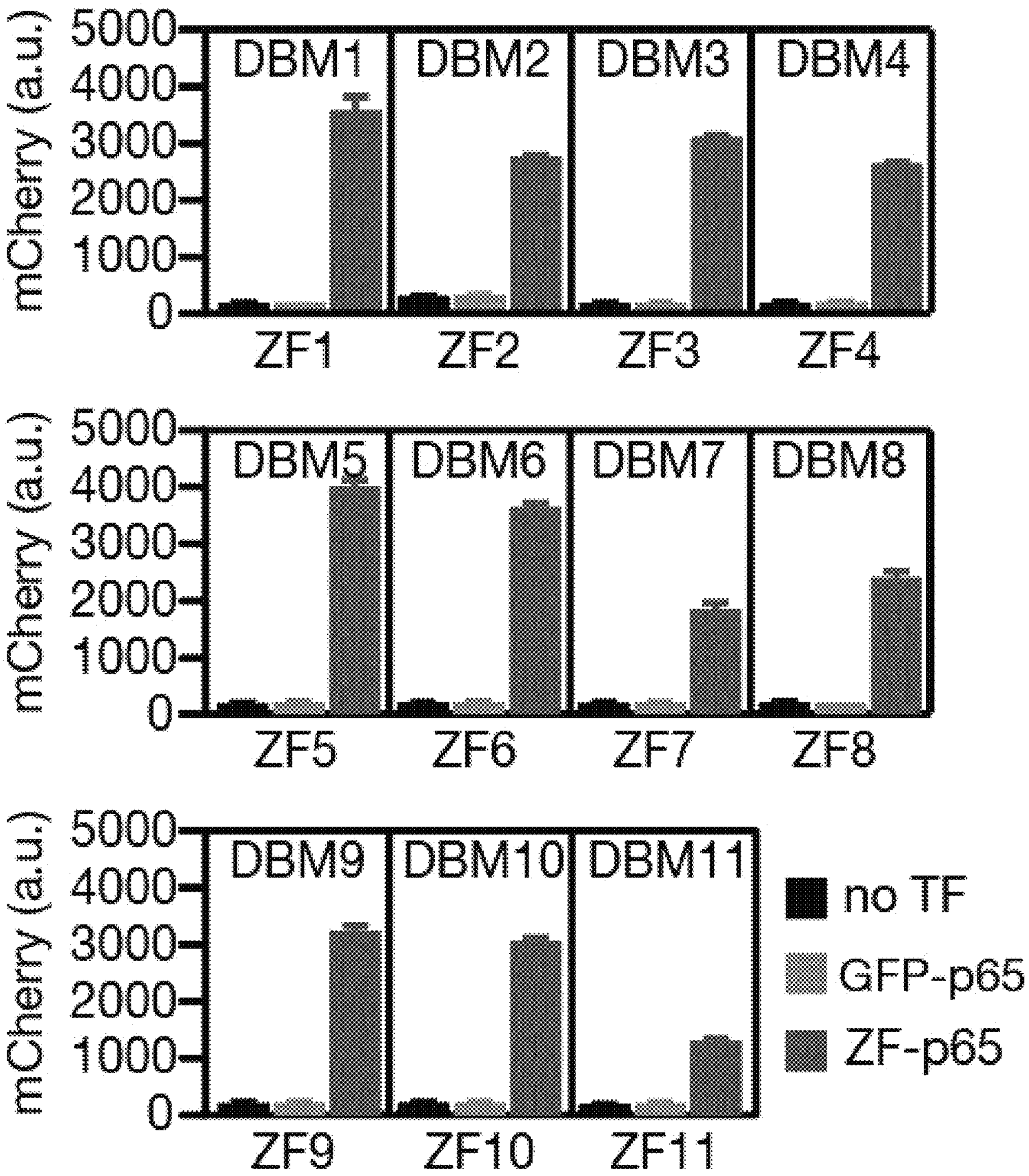
Figure 1D:
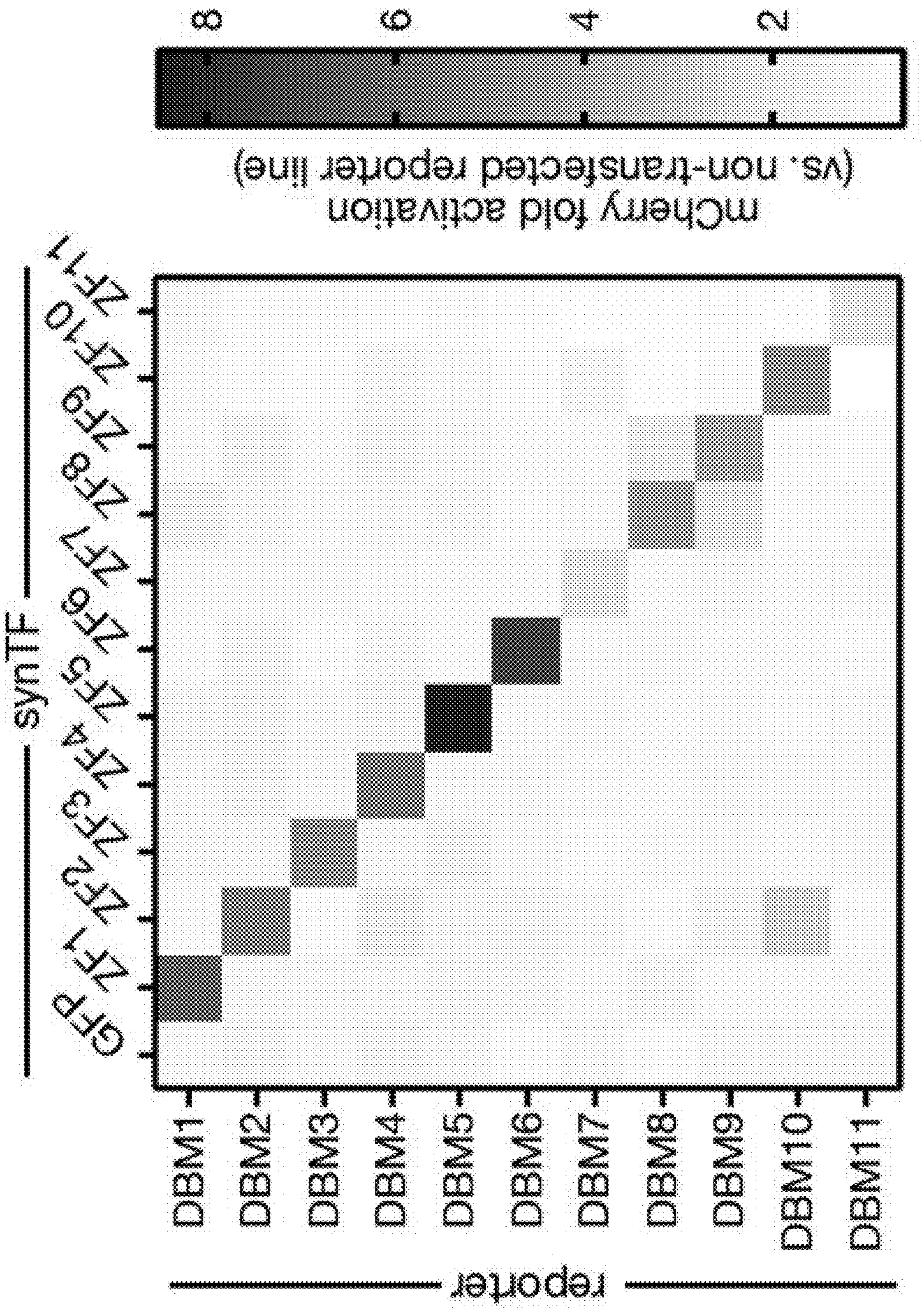
Figure 1E:
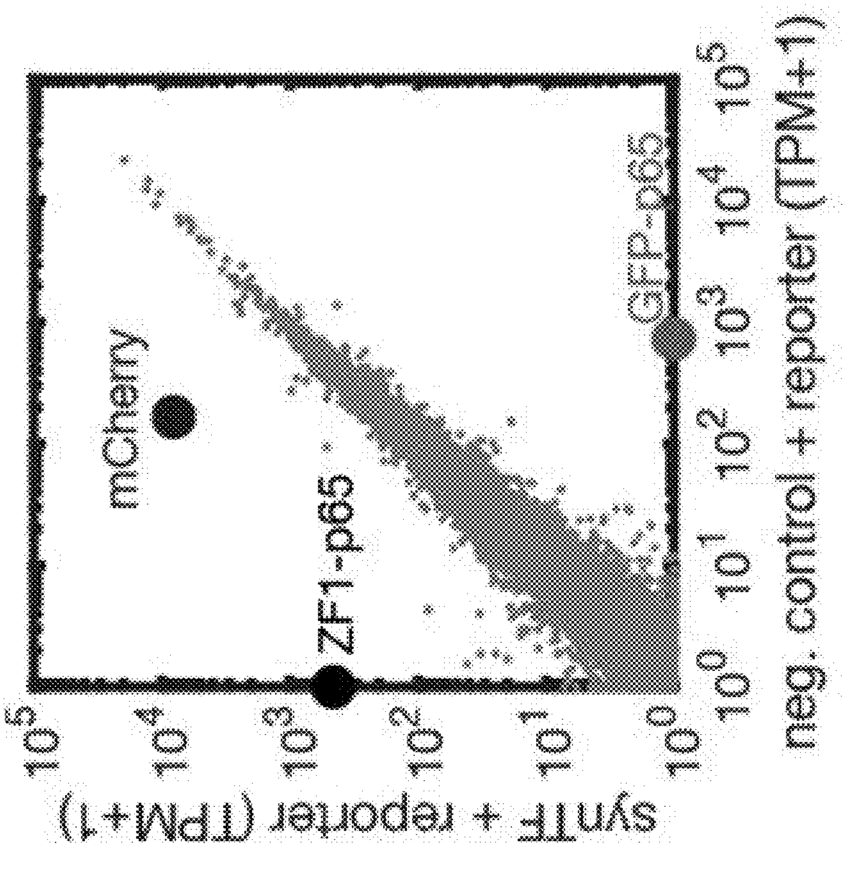
Figure 1F:
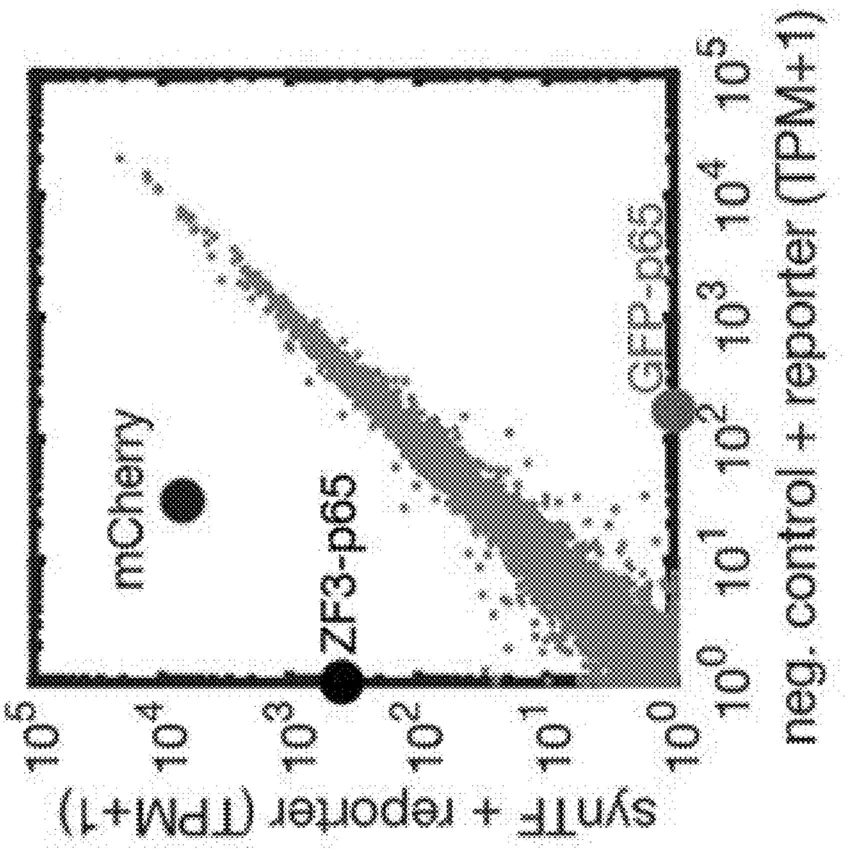
Figure 1G:
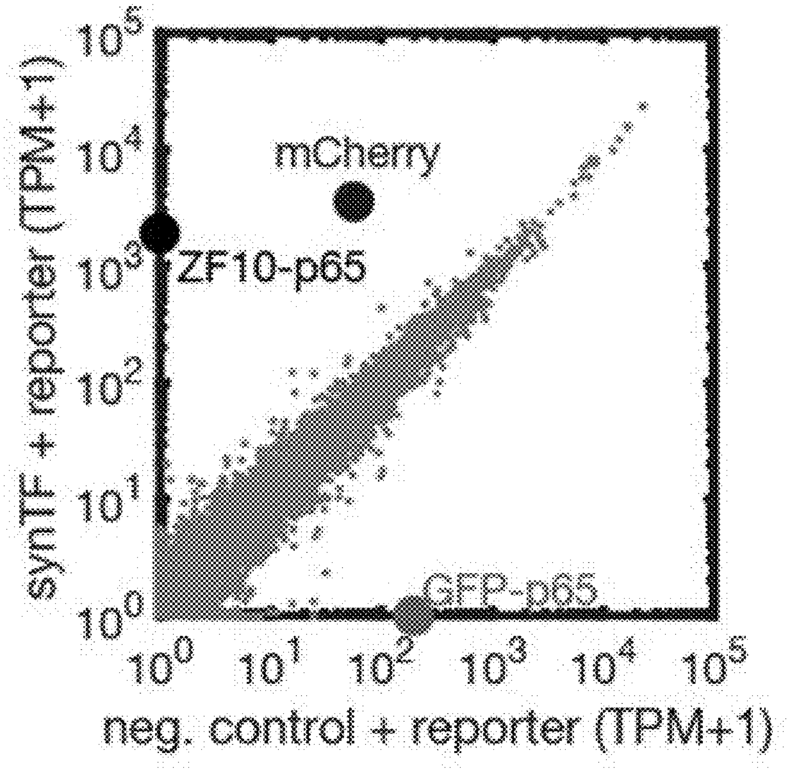
Figure 1H:
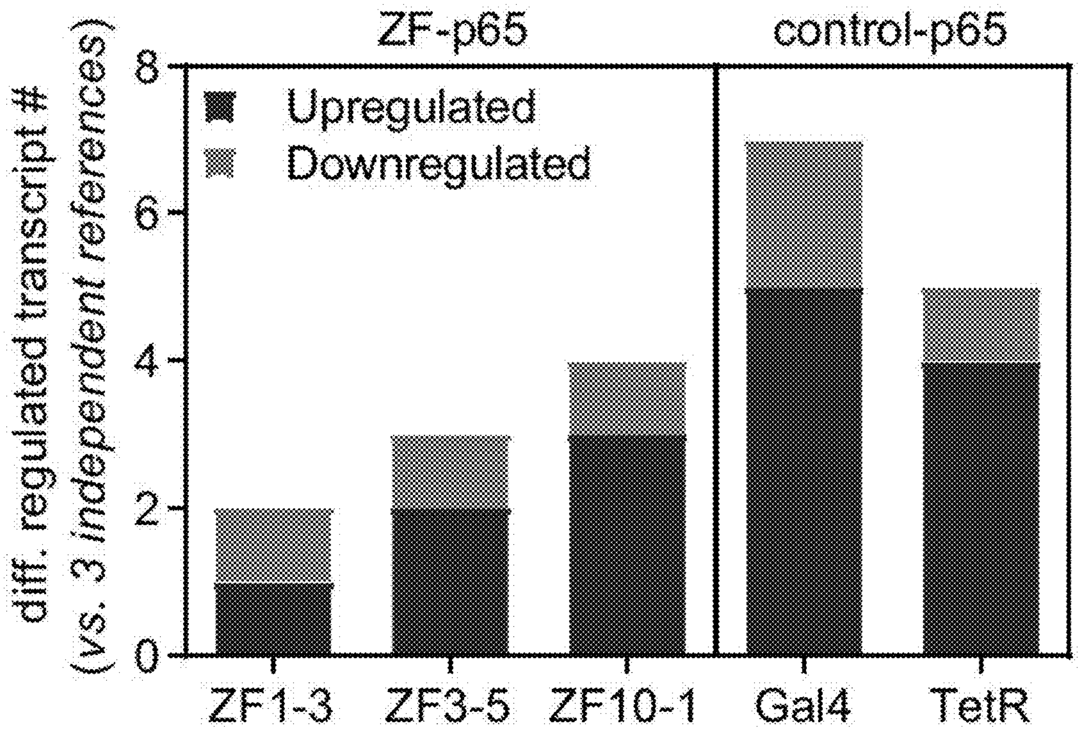

The following abbreviations used herein are defined as follows: synTF (synthetic transcription factor); ZF (zinc finger); HEK (human embryonic kidney 293 cells); ED (effector domain); AD (activator domain); RD (repressor domain); GOI (gene of interest); OUT (output); DBM (DNA binding motif); pUb (Ubiquitin C promoter); p65 (Transcription Factor P65); minCMV (minimal cytomegalovirus promoter); AAVS1 (adeno-associated virus integration site 1); chr19 (human chromosome 19); GFP (green fluorescent protein); TPM (transcripts per million; i.e., a normalized value of each individual RNA transcript across the total pool of RNA transcripts for the sequenced samples); ABI (ABA-insensitive); PYL (PYR1-like, protein pyrabactin resistance 1-like); ABA (abscisic acid); ERT2 (a mutated variant of the estrogen receptor ligand binding domain), 4OHT (4-hydroxytamoxifen); NS3 (nonstructural protein 3 of HCV); GZV or GRZ (grazoprevir); SMASh (small molecule assisted shut-off); a.u. (arbitrary units or relative emission intensity); IFNγ (interferon gamma); IL-2 (interleukin 2); IL-4 (interleukin 4); CD19 (Cluster of Differentiation 19); mCh (mCherry); pSFFV (silencing-prone spleen focus forming virus promoter); minTK (minimal promoter fragment from the HSV thymidine kinase (TK) promoter); lenti (lentivirus).

DETAILED DESCRIPTION

Described herein are synTFs for use in the methods and compositions as disclosed herein, where the synTFs comprise (i) a DNA binding domain (DBD) which binds to a target nucleic acid sequence (or target DNA binding motif (DBM)), (ii) an effector domain (ED) and a regulator protein (RP), where the regulator protein controls the coupling or linkage of the DNA binding domain (DBD) with the effector domain (ED) (such coupling can also be referred to as a "mediator domain"), or controls the cellular localization of the ED, such that when the ED and DBD are attached and/or located in the nucleus, the ED can function to recruit or repress translation machinery to the promoter to regulate gene expression of a gene of interest.

In some embodiments of any of the aspects, regulator proteins can be activated or inhibited by to a variety of inputs, non-limiting examples of which include: inducers (e.g., small molecules), light-inducible control (e.g., dimerization, assembly, localization), temperature, pH, phosphorylation, oxygen, lipid, magnetic, electric, spatial mechanisms (e.g., intracellular and/or extracellular; e.g., synthetic receptors and/or soluble factors), endogenous ligands (e.g., biomarkers), cell-cycle state, native signaling pathways, or disease and/or pathogenic states (e.g., aggregation, infection).

In some embodiments of the systems, compositions and methods as disclosed herein, the regulator protein of the SynTF is selected from a protease, a pair of inducible proximity domains (IPDs), a translocation domain (i.e., a cytosolic sequestering protein), or an induced degradation domain, each of which are described herein and in more detail below.

Described herein are four general frameworks of inducible or drug-controllable synthetic transcription factors: (1) a synTF comprising a repressible protease, referred to as a repressible protease synTF; (2) a synTF comprising induced proximity domains, referred to as a induced proximity domain SynTF; (3) a synTF system comprising a cytosolic sequestering domain, referred to as a cytosolic sequestering synTF; and (4) a synTF comprising an induced degradation domain referred to as an induced degradation domain synTF. Also described herein are polynucleotides and vector encoding said synTF polypeptides, cells expressing said synTF polypeptides, pharmaceutical compositions comprising said synTF polypeptides, and methods of using said synTF polypeptides.

Described herein is a class of engineered transcription factor proteins (synTFs) and corresponding responsive artificial engineered promoters capable of precisely controlling gene expression in a wide range of eukaryotic cells and organisms, including mammalian cells. These synTFs are specifically designed to have reduced or minimal binding potential in the host genome (i.e., "orthogonal" activity to the host genome). The synTF proteins described herein comprise a DNA binding domain (DBD) which are based on engineered zinc finger (ZF) arrays that are designed to target and bind specific 18-20 nucleotide sequences that are distant and different from the host genome sequences, when the synTF proteins are used in the selected hosts. This strategy limits non-specific interactions of the synTF proteins with the host's genome; such non-specific interactions are not ideal and therefore, are not desired.

The synTFs described herein are designed, in some aspects, according to the following parameters: (1) targetable DNA sequences (also known as ZF binding sites) are identified for the ZF arrays that are specifically designed to have reduced binding potential in a host genome; (2) ZF arrays are designed and assembled; (3) synTFs are designed by coupling engineered (i.e., covalently linked) ZF arrays to transcriptional and/or epigenetic effector domains; (4) corresponding responsive promoters are designed by placing instances of the targetable DNA sequences (i.e., ZF binding sites) upstream of constitutive promoters. The targetable DNA sequences are operably linked to the promoters such that the occupancy of synTFs on the targetable DNA sequences regulates the activity of the promoter in gene expression. The combination of a synTFs and a targetable DNA sequence-promoter forms a unique expression system that is artificial, scalable, and regulatable, for the expressions of desired genes placed within the expression systems, with no or minimal effects on the expression of endogenous genes, meaning no or minimal off-site gene regulation of endogenous genes.

The synTFs described herein have reduced or minimal functional binding potential in the host genome, which provides, in part, advantages of no or minimal off-site DNA targeting by the synTFs. In addition, the synthetic ZF-based proteins (synTFs) described herein are derived from mammalian protein scaffolds, conferring minimal degree of immunogenicity over other prokaryotically-derived domains. In contrast to other classes of programmable DNA-targeting domains, these zinc-finger-based regulatory proteins are considerably smaller (~4-5×) than TALE and dCas9 proteins, less repetitive than TALE repeat proteins, and are not as constrained by lentiviral packaging limits, enabling convenient packaging in lentiviral delivery constructs and affording space for other desirable control elements.

I. Synthetic Transcription Factor Domains

In multiple aspects described herein are synTF polypeptides or synTF polypeptide systems that comprise at least one of the following domains: transcriptional effector domain, a DNA-binding domain, at least one regulator protein selected from the group consisting of repressible protease, induced proximity domain, cytosolic sequestration domain, induced degradation domain, at least one linker peptide, at least one detectable marker, and/or self-cleaving peptide, or any combination thereof. In some embodiments of any of the aspects, a synTF polypeptide or a synTF polypeptide system collectively (i.e., the first polypeptide and/or the second polypeptide) comprises at least the following: a transcriptional effector domain, a DNA-binding domain, at least one regulator protein selected from the group consisting of repressible protease, induced proximity domain, cytosolic sequestration domain, and/or induced degradation domain. In some embodiments of any of the aspects, a synTF polypeptide or system further comprises at least one linker peptide, or at least one detectable marker, and/or at least one self-cleaving peptide, or any combination thereof. Specific synTFs described herein are not to be construed as limitations. For example, the following combinations are contemplated herein (see e.g., Table 8):

TABLE 8

Exemplary Combinations of Domains in a synTF Polypeptide or synTF Polypeptide System.

| PRO | IPD | CS | DD | LP | DM | SP | PRO | IPD | CS | DD | LP | DM | SP |
|---|---|---|---|---|---|---|---|---|---|---|---|---|---|
| | | | | | | | X | X | X | | | X | |
| X | | | | | | | | | | X | | X | |
| | X | | | | | | X | | | X | | X | |
| X | X | | | | | | | X | | X | | X | |
| | | X | | | | | X | X | | X | | X | |
| X | | X | | | | | | | X | X | | X | |
| | X | X | | | | | X | | X | X | | X | |
| X | X | X | | | | | | X | X | X | | X | |
| | | | X | | | | X | X | X | X | | X | |
| X | | | X | | | | | | | | X | X | |
| | X | | X | | | | X | | | | X | X | |
| X | X | | X | | | | | X | | | X | X | |
| | | X | X | | | | X | X | | | X | X | |
| X | | X | X | | | | | | X | | X | X | |
| | X | X | X | | | | X | | X | | X | X | |
| X | X | X | X | | | | | X | X | | X | X | |
| | | | | X | | | X | X | X | | X | X | |
| X | | | | X | | | | | | X | X | X | |
| | X | | | X | | | X | | | X | X | X | |
| X | X | | | X | | | | X | | X | X | X | |
| | | X | | X | | | X | X | | X | X | X | |
| X | | X | | X | | | | | X | X | X | X | |
| | X | X | | X | | | X | | X | X | X | X | |
| X | X | X | | X | | | | X | X | X | X | X | |
| | | | X | X | | | X | X | X | X | X | X | |
| X | | | X | X | | | | | | | | | X |
| | X | | X | X | | | X | | | | | | X |
| X | X | | X | X | | | | X | | | | | X |
| | | X | X | X | | | X | X | | | | | X |
| X | | X | X | X | | | | | X | | | | X |
| | X | X | X | X | | | X | | X | | | | X |

TABLE 8-continued

Exemplary Combinations of Domains in a synTF Polypeptide or synTF Polypeptide System.

| PRO | IPD | CS | DD | LP | DM | SP | PRO | IPD | CS | DD | LP | DM | SP |
|---|---|---|---|---|---|---|---|---|---|---|---|---|---|
| X | X | X | X | X | | | | X | X | | | | X |
| | | | | | X | | X | X | X | | | | X |
| X | | | | | X | | | | | X | | | X |
| | X | | | | X | | X | | | X | | | X |
| X | X | | | | X | | | X | | X | | | X |
| | | X | | | X | | X | X | | X | | | X |
| X | | X | | | X | | | | X | X | | | X |
| | X | X | | | X | | X | | X | X | | | X |
| | X | X | X | | | X | X | X | X | | | X | X |
| X | X | X | X | | | X | | | | X | | X | X |
| | | | | X | | X | X | | | X | | X | X |
| X | | | | X | | X | | X | | X | | X | X |
| | X | | | X | | X | X | X | | X | | X | X |
| X | X | | | X | | X | | | X | X | | X | X |
| | | X | | X | | X | X | | X | X | | X | X |
| X | | X | | X | | X | | X | X | X | | X | X |
| | X | X | | X | | X | X | X | X | X | | X | X |
| X | X | X | | X | | X | | | | | X | X | X |
| | | | X | X | | X | X | | | | X | X | X |
| X | | | X | X | | X | | X | | | X | X | X |
| | X | | X | X | | X | X | X | | | X | X | X |
| X | X | | X | X | | X | | | X | | X | X | X |
| | | X | X | X | | X | X | | X | | X | X | X |
| X | | X | X | X | | X | | X | X | | X | X | X |
| | X | X | X | X | | X | X | X | X | | X | X | X |
| X | X | X | X | X | | X | | | | X | X | X | X |
| | | | | | X | X | X | | | X | X | X | X |
| X | | | | | X | X | | X | | X | X | X | X |
| | X | | | | X | X | X | X | | X | X | X | X |
| X | X | | | | X | X | | | X | X | X | X | X |
| | | X | | | X | X | X | | X | X | X | X | X |
| X | | X | | | X | X | | X | X | X | X | X | X |
| | X | X | | | X | X | X | X | X | X | X | X | X |

Each exemplary synTF polypeptide shown in Table 8 also comprises a transcriptional effector domain and a DNA-binding domain.
The domains can be in any order.
"PRO" indicates repressible protease.
"IPD" indicates induced proximity domain.
"CS" indicates cytosolic sequestering domain.
"DD" indicates induced degron domain.
"LP" indicates linker peptide.
"DM" indicates detectable marker.
"SP" indicates self-cleaving peptide.

Transcriptional Effector Domain (ED)

Described herein are synTFs comprising a transcriptional effector domain (ED), which can also be referred to herein as an effector domain. In one embodiment of any aspect described herein, the transcriptional effector domain (ED) of the synTF is a transcription activating domain (TA) or a transcription repressor domain (also referred to herein as a transcriptional repressor (TR)). For example, the transcriptional effector domain is selected from the group consisting of a Herpes Simplex Virus Protein 16 (VP16) activation domain; an activation domain consisting of four tandem copies of VP16, a VP64 activation domain; a p65 activation domain of NFkB or functional fragment thereof; an Epstein-Barr virus R transactivator (Rta) activation domain or functional fragment thereof; a tripartite activator consisting of the VP64, the p65, and the Rta activation domains, wherein the tripartite activator is known as a VPR activation domain; a miniVPR; a histone acetyltransferase (HAT) core domain of the human E1A-associated protein p300, known as a p300 HAT core activation domain; a CBP HAT domain; a Krüppel associated box (KRAB) repression domain; KRAB-MeCP2; a DNA (cytosine-5)-methyltransferase 3B (DNMT3B) repressor domain; a HDAC4 domain; an HP1 alpha repression domain; and an EED (Embryonic Ectoderm Development) repressor domain.

In some embodiments of any of the aspects, a synTF polypeptide as described herein (or a synTF polypeptide system collectively) comprises 1, 2, 3, 4, 5, or transcriptional effector domain(s). In some embodiments of any of the aspects, the synTF polypeptide or system comprises one transcriptional effector domain. In embodiments comprising multiple transcriptional effector domains, the multiple transcriptional effector domains can be different individual transcriptional effector domains or multiple copies of the same transcriptional effector domain, or a combination of the foregoing.

In some embodiments of any of the aspects, the transcriptional ED is a transcriptional activator (TA) domain. As used herein, the term "transcriptional activator" domain refers to an effector that increases gene expression. In some embodiments of any of the aspects, the TA is selected from the group consisting of: p65; Rta; miniVPR; full VPR; VP16; VP64; p300; p300 HAT Core; and a CBP HAT domain. See e.g., U.S. Pat. Nos. 10,138,493; 10,590,182; Khalil et al., Cell Volume 150, Issue 3, 3 Aug. 2012, Pages 647-658; Vora et al., Rational design of a compact CRISPR-Cas9 activator for AAV-mediated delivery, bioRxiv 2018 doi.org/10.1101/298620; Chavez et al., Nat Methods. 2015 April, 12(4): 326-328; Park et al., Cell. 2019 Jan. 10, 176(1-2):227-238, e20; Hilton et al., Nature Biotechnology volume 33, pages 510-517(2015); Sajwan et al., Sci Rep. 2019; 9: 18104; the contents of each of which are incorporated herein by reference in their entireties.

In some embodiments of any of the aspects, the TA is p65, or a functional fragment thereof. Transcription factor p65 also known as nuclear factor NF-kappa-B p65 subunit is a protein that in humans is encoded by the RELA gene. In some embodiments of any of the aspects, p65 comprises SEQ ID NO: 69 or a protein having at least 85% sequence identity to SEQ ID NO: 69. In some embodiments of any of the aspects, p65 comprises SEQ ID NO: 117 or a protein having at least 85% sequence identity to SEQ ID NO: 117. In some embodiments of any of the aspects, p65 comprises SEQ ID NO: 118 or a portion of SEQ ID NO: 118, e.g., residues 150-261, 100-261, 200-261, 1-200, 1-50, 1-100, or 50-100 of SEQ ID NO: 118. In some embodiments of any of the aspects, p65 comprises one of SEQ ID NOs: 69, 117-121, 193-197 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 69, 117-121, 193-197 that maintains its function. In some embodiments of any of the aspects, p65 comprises SEQ ID NO: 120 (p65 100-261) or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 120 that maintains the same function.

SEQ ID NO: 69, p65 (amino acids 361-551 of NFkB) Activation Domain (191 aa)
DEFPTMVFPSGQISQASALAPAPPQVLPQAPAPAPAPAMVSALAQAPAPV

PVLAPGPPQAVAPPAPKPTQAGEGTLSEALLQLQFDDEDLGALLGNSTDP

AVFTDLASVDNSEFQQLLNQGIPVAPHTTEPMLMEYPEAITRLVTGAQRP

PDPAPAPLGAPGLPNGLLSGDEDFSSIADMDFSALLSQISS

SEQ ID NO: 117, p65 (full sequence, 551 aa), transcription factor p65 isoform 1 [*Homo sapiens*], NCBI Reference Sequence: NP_068810.3
MDELFPLIFPAEPAQASGPYVEIIEQPKQRGMRFRYKCEGRSAGSIPGER

STDTTKTHPTIKINGYTGPGTVRISLVTKDPPHRPHPHELVGKDCRDGFY

EAELCPDRCIHSFQNLGIQCVKKRDLEQAISQRIQTNNNPFQVPIEEQRG

DYDLNAVRLCFQVTVRDPSGRPLRLPPVLSHPIFDNRAPNTAELKICRVN

RNSGSCLGGDEIFLLCDKVQKEDIEVYFTGPGWEARGSFSQADVHRQVAI

VFRTPPYADPSLQAPVRVSMQLRRPSDRELSEPMEFQYLPDTDDRHRIEE

KRKRTYETFKSIMKKSPFSGPTDPRPPPRRIAVPSRSSASVPKPAPQPYP

FTSSLSTINYDEFPTMVFPSGQISQASALAPAPPQVLPQAPAPAPAPAMV

SALAQAPAPVPVLAPGPPQAVAPPAPKPTQAGEGTLSEALLQLQFDDEDL

GALLGNSTDPAVFTDLASVDNSEFQQLLNQGIPVAPHTTEPMLMEYPEAI

TRLVTGAQRPPDPAPAPLGAPGLPNGLLSGDEDFSSIADMDFSALLSQIS

S

SEQ ID NO: 118, p65 1-261 (261 aa)
SQYLPDTDDRHRIEEKRKRTYETFKSIMKKSPFSGPTDPRPPPRRIAVPS

RSSASVPKPAPQPYPFTSSLSTINYDEFPTMVFPSGQISQASALAPAPPQ

VLPQAPAPAPAPAMVSALAQAPAPVPVLAPGPPQAVAPPAPKPTQAGEGT

-continued

LSEALLQLQFDDEDLGALLGNSTDPAVFTDLASVDNSEFQQLLNQGIPVA

PHTTEPMLMEYPEAITRLVTGAQRPPDPAPAPLGAPGLPNGLLSGDEDFS

SIADMDFSALL

SEQ ID NO: 119, p65 150-261 (112 aa)
SLSEALLQLQFDDEDLGALLGNSTDPAVFTDLASVDNSEFQQLLNQGIPV

APHTTEPMLMEYPEAITRLVTGAQRPPDPAPAPLGAPGLPNGLLSGDEDF

SSIADMDFSALL

SEQ ID NO: 120, p65 100-261 (162 aa)
SVLPQAPAPAPAPAMVSALAQAPAPVPVLAPGPPQAVAPPAPKPTQAGEG

TLSEALLQLQFDDEDLGALLGNSTDPAVFTDLASVDNSEFQQLLNQGIPV

APHTTEPMLMEYPEAITRLVTGAQRPPDPAPAPLGAPGLPNGLLSGDEDF

SSIADMDFSALL

SEQ ID NO: 121, p65 200-261 (62 aa)
SPHTTEPMLMEYPEAITRLVTGAQRPPDPAPAPLGAPGLPNGLLSGDEDF

SSIADMDFSALL

SEQ ID NO: 193, p65 1-200 (200 aa)

SQYLPDTDDRHRIEEKRKRTYETFKSIMKKSPFSGPTDPRPPPRRIAVPS

RSSASVPKPAPQPYPFTSSLSTINYDEFPTMVFPSGQISQASALAPAPPQ

VLPQAPAPAPAPAMVSALAQAPAPVPVLAPGPPQAVAPPAPKPTQAGEGT

LSEALLQLQFDDEDLGALLGNSTDPAVFTDLASVDNSEFQQLLNQGIPVA

SEQ ID NO: 194, p65 1-150 (150 aa)
SQYLPDTDDRHRIEEKRKRTYETFKSIMKKSPFSGPTDPRPPPRRIAVPS

RSSASVPKPAPQPYPFTSSLSTINYDEFPTMVFPSGQISQASALAPAPPQ

VLPQAPAPAPAPAMVSALAQAPAPVPVLAPGPPQAVAPPAPKPTQAGEGT

SEQ ID NO: 195, p65 1-100 (100 aa)
SQYLPDTDDRHRIEEKRKRTYETFKSIMKKSPFSGPTDPRPPPRRIAVPS

RSSASVPKPAPQPYPFTSSLSTINYDEFPTMVFPSGQISQASALAPAPPQ

SEQ ID NO: 196, p65 50-150 (101 aa)
SRSSASVPKPAPQPYPFTSSLSTINYDEFPTMVFPSGQISQASALAPAPP

QVLPQAPAPAPAPAMVSALAQAPAPVPVLAPGPPQAVAPPAPKPTQAGEG

T

SEQ ID NO: 197, p65 143-261 (119 aa)
PTQAGEGTLSEALLQLQFDDEDLGALLGNSTDPAVFTDLASVDNSEFQQL

LNQGIPVAPHTTEPMLMEYPEAITRLVTGAQRPPDPAPAPLGAPGLPNGL

LSGDEDFSSIADMDFSALL

In some embodiments of any of the aspects, the TA is Rta, or a functional fragment thereof. Rta is an Epstein-Barr virus R transactivator (Rta) activation domain. In some embodiments of any of the aspects, Rta comprises SEQ ID NO: 198 or a protein having at least 85% sequence identity to SEQ ID NO: 198. In some embodiments of any of the aspects, Rta comprises a portion of SEQ ID NO: 198, e.g., residues 75-190, 125-190, 50-175, 75-175, 100-175, or 125-175 of SEQ ID NO: 198. In some embodiments of any of the aspects, Rta comprises one of SEQ ID NOs: 198-204 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 198-204 that maintains its function. In some embodiments of any of the aspects, Rta comprises SEQ ID NO: 200 (Rta 125-190) or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 200 that maintains the same function.

SEQ ID NO: 198, Rta (full sequence, 1-190; 190 aa)
RDSREGMFLPKPEAGSAISDVFEGREVCQPKRIRPFHPPGSPWANRPLPA
SLAPTPTGPVHEPVGSLTPAPVPQPLDPAPAVTPEASHLLEDPDEETSQA
VKALREMADTVIPQKEEAAICGQMDLSHPPPRGHLDELTTTLESMTEDLN
LDSPLTPELNEILDTFLNDECLLHAMHISTGLSIFDTSLF SEQ ID NO: 199, Rta (75-190, 116 aa)
PLDPAPAVTPEASHLLEDPDEETSQAVKALREMADTVIPQKEEAAICGQM
DLSHPPPRGHLDELTTTLESMTEDLNLDSPLTPELNEILDTFLNDECLLH
AMHISTGLSIFDTSLF SEQ ID NO: 200, Rta (125-190, 66 aa)
DLSHPPPRGHLDELTTTLESMTEDLNLDSPLTPELNEILDTFLNDECLLH
AMHISTGLSIFDTSLF SEQ ID NO: 201, Rta (50-175, 126 aa)
SSLAPTPTGPVHEPVGSLTPAPVPQPLDPAPAVTPEASHLLEDPDEETSQ
AVKALREMADTVIPQKEEAAICGQMDLSHPPPRGHLDELTTTLESMTEDL
NLDSPLTPELNEILDTFLNDECLLHA SEQ ID NO: 202, Rta (75-175, 101 aa)
PLDPAPAVTPEASHLLEDPDEETSQAVKALREMADTVIPQKEEAAICGQM
DLSHPPPRGHLDELTTTLESMTEDLNLDSPLTPELNEILDTFLNDECLLH
A SEQ ID NO: 203, Rta (100-175, 76 aa)
SVKALREMADTVIPQKEEAAICGQMDLSHPPPRGHLDELTTTLESMTEDL
NLDSPLTPELNEILDTFLNDECLLHA SEQ ID NO: 204, Rta (125-175, 51 aa)
DLSHPPPRGHLDELTTTLESMTEDLNLDSPLTPELNEILDTFLNDECLLH
A In some embodiments of any of the aspects, the TA is VPR, or a functional fragment thereof. VPR is a tripartite activator consisting of the VP64, the p65, and the Rta activation domains. In some embodiments of any of the aspects, VPR comprises VP64 (e.g., SEQ ID NO: 208), p65 (e.g., any one of SEQ ID NOs: 69, 117-121 or 193-197 or a polypeptide with at least 85% sequence identity to any one of SEQ ID NOs: 69, 117-121 or 193-197 that maintains the same function), and Rta (e.g., any one of SEQ ID NOs: 198-204 or a polypeptide with at least 85% sequence identity to any one of SEQ ID NOs: 198-204 that maintains the same function). In some embodiments of any of the aspects, VPR comprises one of SEQ ID NOs: 205, 206, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 205 or 206, that maintains its function.

SEQ ID NO: 205, miniVPR, comprising the p65 (100-261aa; SEQ ID NO: 120) truncation and the RTA (125-190aa; SEQ ID NO: 200) truncation; bold text indicates VP64 (SEQ ID NO: 208); italicized text indicates SV40 NLS (SEQ ID NO: 65); bold italicized text indicates p65 (100-261aa; SEQ ID NO: 120); double underlined text indicates RTA (125-190aa; SEQ ID NO: 200).

GRADALDDFDLDMLGSDALDDFDLDMLGSDALDDFDLDMLGSDALDDFDL
DMLINSRSSGS*PKKKRKV*GSGGGSGGSGS*VLPQAPAPAP*
*APAMVSALAQAPAPVPVLAPGPPQAVAPPAPKPTQAG*
*EGTLSEALLQLQFDDEDLGALLGNSTDPAVFTDLASVD*
*NSEFQQLLNQGIPVAPHTTEPMLMEYPEAITRLVTGA*
*QRPPDPAPAPLGAPGLPNGLLSGDEDFSSIADMDFSALL*
SGGGSGGSGSDLSHPPPRGHLDELTTTLESMTEDLNLDSPLTPELNEILD
TFLNDECLLHAMHISTGLSIFDTSLF

SEQ ID NO: 206, full VPR; bold text indicates VP64 (SEQ ID NO: 208); italicized text indicates SV40 NLS (SEQ ID NO: 65); bold italicized text indicates p65 (SEQ ID NO: 118); double underlined text indicates RTA (SEQ ID NO: 198).

GRADALDDFDLDMLGSDALDDFDLDMLGSDALDDFDLDMLGSDALDDFDL
DMLINSRSSGS*PKKKRKVG*SQYLPDTDDR*
*HRIEEKRKRTYETFKSIMKKSPFSGPTDPRPPP*
*RRIAVPSRSSASVPKPAPQPYPFTSSL*
*STINYDEFPTMVFPSGQISQASALAPAPPQVLPQAP*
*APAPAPAMVSALAQAPAPVPVLAPGPPQ*
*AVAPPAPKPTQAGEGTLSEALLQLQFDDEDLGALLG*
*NSTDPAVFTDLASVDNSEFQQLLNQGIPV*
*APHTTEPMLMEYPEAITRLVTGAQRPPDPAPAPL*
*GAPGLPNGLLSGDEDFSSIA DMDFSALL*GSGSGSRDSREGM
FLPKPEAGSAISDVFEGREVCQPKRIRPFHPPGSPWANRPLPASLAPTPT
GPVHEPVGSLTPAPVPQPLDPAPAVTPEASHLLEDPDEETSQAVKALREM
ADTVIPQKEEAAICGQMDLSHPPPRGHLDELTTTLESMTEDLNLDSPLTP
ELNEILDTFLNDECLLHAMHISTGLSIFDTSLF

In some embodiments of any of the aspects, the TA comprises the Herpes Simplex Virus Protein 16 (VP16) activation domain. In some embodiments of any of the aspects, the TA comprises the VP64 activation domain, which comprises four tandem copies of VP16. In some embodiments of any of the aspects, the TA comprises one of SEQ ID NOs: 207, 208, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 207 or 208 that maintains its function.

SEQ ID NO: 207, VP16 (11 aa)
DALDDFDLDML

SEQ ID NO: 208, VP64 (53 aa), with the VP16 domain indicated by bold text,
GRADALDDFDLDMLGSDALDDFDLDMLGSDALDDFDLDMLGSDALDDFD
LDML

In some embodiments of any of the aspects, the TA comprises p300 or a functional fragment thereof. The adenovirus E1A-associated cellular p300 transcriptional co-activator protein functions as histone acetyltransferase that regulates transcription via chromatin remodeling. In some embodiments of any of the aspects, p300 comprises SEQ ID NO: 209 or a protein having at least 85% sequence identity to SEQ ID NO: 209. In some embodiments of any of the aspects, p300 comprises a portion of SEQ ID NO: 209, e.g., residues 1048-1664 of SEQ ID NO: 209. In some embodiments of any of the aspects, the TA comprises the p300 HAT Core activation domain. In some embodiments of any of the aspects, p300 comprises SEQ ID NO: 210 or a protein having at least 85% sequence identity to SEQ ID NO: 210. In some embodiments of any of the aspects, the TA comprises one of SEQ ID NOs: 209, 210, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 209 or 210, that maintains its function.

SEQ ID NO: 209, human acetyltransferase p300 (2414 aa), bold text indicates the core activation domain MAENVVEPGPPSAKRPKLSSPALSASASDGTDFGSLFDLEHDLPDELINS
TELGLTNGGDINQLQTSLGMVQDAASKHKQLSELLRSGSSPNLNMGVGGP
GQVMASQAQQSSPGLGLINSMVKSPMTQAGLTSPNMGMGTSGPNQGPTQS
TGMMNSPVNQPAMGMNTGMNAGMNPGMLAAGNGQGIMPNQVMNGSIGAGR
GRQNMQYPNPGMGSAGNLLTEPLQQGSPQMGGQTGLRGPQPLKMGMMNNP
NPYGSPYTQNPGQQIGASGLGLQIQTKTVLSNNLSPFAMDKKAVPGGGMP
NMGQQPAPQVQQPGLVTPVAQGMGSGAHTADPEKRKLIQQQLVLLLHAHK
CQRREQANGEVRQCNLPHCRTMKNVLNHMTHCQSGKSCQVAHCASSRQII
SHWKNCTRHDCPVCLPLKNAGDKRNQQPILTGAPVGLGNPSSLGVGQQSA
PNLSTVSQIDPSSIERAYAALGLPYQVNQMPTQPQVQAKNQQNQQPGQSP
QGMRPMSNMSASPMGVNGGVGVQTPSLLSDSMLHSAINSQNPMMSENASV
PSLGPMPTAAQPSTTGIRKQWHEDITQDLRNHLVHKLVQAIFPTPDPAAL
KDRRMENLVAYARKVEGDMYESANNRAEYYHLLAEKIYKIQKELEEKRRT
RLQKQNMLPNAAGMVPVSMNPGPNMGQPQPGMTSNGPLPDPSMIRGSVPN
QMMPRITPQSGLNQFGQMSMAQPPIVPRQTPPLQHHGQLAQPGALNPPMG
YGPRMQQPSNQGQFLPQTQFPSQGMNVTNIPLAPSSGQAPVSQAQMSSSS
CPVNSPIMPPGSQGSHIHCPQLPQPALHQNSPSPVPSRTPTPHHTPPSIG
AQQPPATTIPAPVPTPPAMPPGPQSQALHPPPRQTPTPPTTQLPQQVQPS
LPAAPSADQPQQQPRSQQSTAASVPTPTAPLLPPQPATPLSQPAVSIEGQ
VSNPPSTSSTEVNSQAIAEKQPSQEVKMEAKMEVDQPEPADTQPEDISES
KVEDCKMESTETEERSTELKTEIKEEEDQPSTSATQSSPAPGQSKKKIFK
PEELRQALMPTLEALYRQDPESLPFRQPVDPQLLGIPDYFDIVKSPMDLS
TIKRKLDTGQYQEPWQYVDDIWLMFNNAWLYNRKTSRVYKYCSKLSEVFE
QEIDPVMQSLGYCCGRKLEFSPQTLCCYGKQLCTIPRDATYYSYQNRYHF
CEKCFNEIQGESVSLGDDPSQPQTTINKEQFSKRKNDTLDPELFVECTEC
GRKMHQICVLHHEIIWPAGFVCDGCLKKSARTRKENKFSAKRLPSTRLGT
FLENRVNDFLRRQNHPESGEVTVRVVHASDKTVEVKPGMKARFVDSGEMA

-continued

ESFPYRTKALFAFEEIDGVDLCFFGMHVQEYGSDCPPPNQRRVYISYLDS
VHFFRPKCLRTAVYHEILIGYLEYVKKLGYTTGHIWACPPSEGDDYIFHC
HPPDQKIPKPKRLQEWYKKMLDKAVSERIVHDYKDIFKQATEDRLTSAKE
LPYFEGDFWPNVLEESIKELEQEEEERKREENTSNESTDVTKGDSKNAKK
KNNKKTSKNKSSLSRGNKKKPGMPNVSNDLSQKLYATMEKHKEVFFVIRL
IAGPAANSLPPIVDPDPLIPCDLMDGRDAFLTLARDKHLEFSSLRRAQWS
TMCMLVELHTQSQDRFVYTCNECKHHVETRWHCTVCEDYDLCITCYNTKN
HDHKMEKLGLGLDDESNNQQAAATQSPGDSRRLSIQRCIQSLVHACQCRN
ANCSLPSCQKMKRVVQHTKGCKRKTNGGCPICKQLIALCCYHAKHCQENK
CPVPFCLNIKQKLRQQQLQHRLQQAQMLRRRMASMQRTGVVGQQQGLPSP
TPATPTTPTGQQPTTPQTPQPTSQPQPTPPNSMPPYLPRTQAAGPVSQGK
AAGQVTPPTPPQTAQPPLPGPPPAAVEMAMQIQRAAETQRQMAHVQIFQR
PIQHQMPPMTPMAPMGMNPPPMTRGPSGHLEPGMGPTGMQQQPPWSQGGL
PQPQQLQSGMPRPAMMSVAQHGQPLNMAPQPGLGQVGISPLKPGTVSQQA
LQNLLRTLRSPSSPLQQQQVLSILHANPQLLAAFIKQRAAKYANSNPQPI
PGQPGMPQGQPGLQPPTMPGQQGVHSNPAMQNMNPMQAGVQRAGLPQQQP
QQQLQPPMGGMSPQAQQMNMNHNTMPSQFRDILRRQQMMQQQQQQGAGPG
IGPGMANHNQFQQPQGVGYPPQQQQRMQHHMQQMQQGNMGQIGQLPQALG
AEAGASLQAYQQRLLQQQMGSPVQPNPMSPQQHMLPNQAQSPHLQGQQIP
NSLSNQVRSPQPVPSPRPQSQPPHSSPSPRMQPQPSPHHVSPQTSSPHPG
LVAAQANPMEQGHFASPDQNSMLSQLASNPGMANLHGASATDLGLSTDNS
DLNSNLSQSTLDIH

SEQ ID NO: 210, p300 HAT Core activation domain (617 aa)

IFKPEELRQALMPTLEALYRQDPESLPFRQPVDPQLLGIPDYFDIVKSPM
DLSTIKRKLDTGQYQEPWQYVDDIWLMFNNAWLYNRKTSRVYKYCSKLSE
VFEQEIDPVMQSLGYCCGRKLEFSPQTLCCYGKQLCTIPRDATYYSYQNR
YHFCEKCFNEIQGESVSLGDDPSQPQTTINKEQFSKRKNDTLDPELFVEC
TECGRKMHQICVLHHEIIWPAGFVCDGCLKKSARTRKENKFSAKRLPSTR
LGTFLENRVNDFLRRQNHPESGEVTVRVVHASDKTVEVKPGMKARFVDSG
EMAESFPYRTKALFAFEEIDGVDLCFFGMHVQEYGSDCPPPNQRRVYISY
LDSVHFFRPKCLRTAVYHEILIGYLEYVKKLGYTTGHIWACPPSEGDDYI
FHCHPPDQKIPKPKRLQEWYKKMLDKAVSERIVHDYKDIFKQATEDRLTS
AKELPYFEGDFWPNVLEESIKELEQEEEERKREENTSNESTDVTKGDSKN
AKKKNNKKTSKNKSSLSRGNKKKPGMPNVSNDLSQKLYATMEKHKEVFFV
IRLIAGPAANSLPPIVDPDPLIPCDLMDGRDAFLTLARDKHLEFSSLRRA
QWSTMCMLVELHTQSQD

In some embodiments of any of the aspects, the TA comprises CBP or a functional fragment thereof. CBP (CREB (Cyclic AMP-Responsive Element-Binding Protein) Binding Protein; CREBBP) is involved in the transcriptional coactivation of many different transcription factors and has intrinsic histone acetyltransferase activity. In some embodiments of any of the aspects, CBP is derived from *Homo sapiens, Drosophila melanogaster*, or any other organism expressing a homologous CBP protein. In some embodiments of any of the aspects, the TA comprises the CBP HAT Core activation domain. In some embodiments of any of the aspects, the TA comprises one of SEQ ID NOs: 211-213, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 211-213, that maintains its function.

SEQ ID NO: 211, *Homo sapiens* CBP, histone acetyltransferase (HAT)-domain; residues 1342-1649 of CREB-binding protein isoform a [*Homo sapiens*], NCBI Reference Sequence: NP_004371.2; residues 1304-1611 of CREB-binding protein isoform b [*Homo sapiens*], NCBI Reference Sequence: NP_001073315.1.

VNKFLRRQNHPEAGEVFVRVVASSDKTVEVKPGMKSRFVDSGEMSESFP

YRTKALFAFEEIDGVDVCFFGMHVQEYGSDCPPPNTRRVYISYLDSIHF

FRPRCLRTAVYHEILIGYLEYVKKLGYVTGHIWACPPSEGDDYIFHCHP

PDQKIPKPKRLQEWYKKMLDKAFAERIIHDYKDIFKQATEDRLTSAKEL

PYFEGDFWPNVLEESIKELEQEEEERKKEESTAASETTEGSQGDSKNAK

KKNNKKTNKNKSSISRANKKKPSMPNVSNDLSQKLYATMEKHKEVFFVI

HLHAGPVINTLPPI

SEQ ID NO: 212, residues 1954-2267 of nejire, isoform E [*Drosophila melanogaster*], NCBI Reference Sequence: NP_001259387.1, HAT_KAT11, Histone acetylation protein

VNNFLKKKEAGAGEVHIRVVSSSDKCVEVKPGMRRRFVEQGEMMNEFPY

RAKALFAFEEVDGIDVCFFGMHVQEYGSECPAPNTRRVYIAYLDSVHFF

RPRQYRTAVYHEILLGYMDYVKQLGYTMAHIWACPPSEGDDYIFHCHPT

DQKIPKPKRLQEWYKKMLDKGMIERIIQDYKDILKQAMEDKLGSAAELP

YFEGDFWPNVLEESIKELDQEEEEKRKQAEAAEAAAAANLFSIEENEVS

GDGKKKGQKKAKKSNKSKAAQRKNSKKSNEHQSGNDLSTKIYATMEKHK

EVFFVIRLHSAQSAASLAPI

SEQ ID NO: 213, aa 1696-2329 from *Drosophila* CBP (nejire), NCBI Reference Sequence: NP_001259387.1, including the bromodomain, PHD domain, and HAT domain

NGKYSDPWEYVDDVWLMFDNAWLYNRKTSRVYRYCTKLSEVFEAEIDPV

MQALGYCCGRKYTFNPQVLCCYGKQLCTIPRDAKYYSYQNRYTYCQKCF

NDIQGDTVTLGDDPLQSQTQIKKDQFKEMKNDHLELEPFVNCQECGRKQ

HQICVLWLDSIWPGGFVCDNCLKKKNSKRKENKFNAKRLPTTKLGVYIE

TRVNNFLKKKEAGAGEVHIRVVSSSDKCVEVKPGMRRRFVEQGEMMNEF

PYRAKALFAFEEVDGIDVCFFGMHVQEYGSECPAPNTRRVYIAYLDSVH

FFRPRQYRTAVYHEILLGYMDYVKQLGYTMAHIWACPPSEGDDYIFHCH

PTDQKIPKPKRLQEWYKKMLDKGMIERIIQDYKDILKQAMEDKLGSAAE

LPYFEGDFWPNVLEESIKELDQEEEEKRKQAEAAEAAAAANLFSIEENE

VSGDGKKKGQKKAKKSNKSKAAQRKNSKKSNEHQSGNDLSTKIYATMEK

HKEVFFVIRLHSAQSAASLAPIQDPDPLLTCDLMDGRDAFLTLARDKHF

EFSSLRRAQFSTLSMLYELHNQGQDKFVYTCNHCKTAVETRYHCTVCDD

FDLCIVCKEKVGHQHKMEKLGFDIDDGSALADHKQANPQEARKQSI.

In some embodiments of any of the aspects, the transcriptional ED is a transcriptional repressor (TR) domain. As used herein, the term "transcriptional repressor" domain refers to an effector that decreases gene expression. In some embodiments of any of the aspects, the TR is selected from the group consisting of: KRAB; KRAB-MeCP2; Hp1a; DNMT3B; EED; and HDAC4. See e.g., U.S. Pat. Nos. 10,138,493; 10,590,182; Khalil et al., Cell Volume 150, Issue 3, 3 Aug. 2012, Pages 647-658; Park et al., Cell. 2019 Jan. 10, 176(1-2):227-238, e20; Yeo et al., Nature Methods volume 15, pages 611-616(2018); Bintu et al., Science. 2016 Feb. 12; 351(6274): 720-724; the contents of each of which are incorporated herein by reference in their entireties.

In some embodiments of any of the aspects, the TR comprises KRAB, or a functional fragment thereof. The Krüppel associated box (KRAB) domain is a category of transcriptional repression domains present in approximately 400 human zinc finger protein-based transcription factors (KRAB zinc finger proteins), and it associates with other chromatin regulators that write or read H3K9me3. In some embodiments of any of the aspects, the TR comprises KRAB-MeCP2, a bipartite repressor domain. In some embodiments of any of the aspects, KRAB domain comprises one of SEQ ID NOs: 72, 97, 214-215, or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 72, 97, or 214-215 that maintains its function. In some embodiments of any of the aspects, the TR comprises the transcription repression domain (TRD) domain of MeCP2, or a functional fragment thereof. In some embodiments of any of the aspects, the transcription repression domain (TRD) domain of MeCP2 comprises SEQ ID NO: 216 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 216, that maintains its function.

SEQ ID NO: 72: KRAB repressor domain (96 aa)

DAKSLTAWSRTLVTFKDVFVDFTREEWKLLDTAQQILYRNVMLENYKNLV

SLGYQLTKPDVILRLEKGEEPWLVEREIHQETHPDSETAFEIKSSV

SEQ ID NO: 97: KRAB repressor domain (65 aa)

LAVSVTFEDVAVLFTRDEWKKLDLSQRSLYREVMLENYSNLASMAGFLFT

KPKVISLLQQGEDPW

SEQ ID NO: 214, KRAB-MeCP2 (382 aa), comprising KRAB domain (bold text), glycine-serine rich linker (unformatted text) and transcription repression domain (TRD) domain of MeCP2 (italicized text).

MDAKSLTAWSRTLVTFKDVFVDFTREEWKLLDTAQQIVYRNVMLENYKNL

VSLGYQLTKPDVILRLEKGEEPWLVSGGGSGGSGS*SPKKKRKVEASVQVK*

*RVLEKSPGKLLVKMPFQASPGGKGEGGGATTSAQVMVIKRPGRKRKAEAD*

*PQAIPKKRGRKPGSVVAAAAAEAKKKAVKESSIRSVQETVLPIKKRKTRE*

*TVSIEVKEVVKPLLVSTLGEKSGKGLKTCKSPGRKSKESSPKGRSSSASS*

*PPKKEHHHHHHHAESPKAPMPLLPPPPPPEPQSSEDPISPPEPQDLSSSI*

*CKEEKMPRAGSLESDGCPKEPAKTQPMVAAAATTTTTTTTTVAEKYKHRG*

*EGERKDIVSSSMPRPNREEPVDSRTPVTERVS*

-continued

SEQ ID NO: 215, KRAB repressor domain (74 aa)
DAKSLTAWSRTLVTFKDVFVDFTREEWKLLDTAQQIVYRNVMLENYKNLV

SLGYQLTKPDVILRLEKGEEPWLV

SEQ ID NO: 216, transcription repression domain (TRD) domain of MeCP2 (296 aa)
PKKKRKVEASVQVKRVLEKSPGKLLVKMPFQASPGGKGEGGGATTSAQVM

VIKRPGRKRKAEADPQAIPKKRGRKPGSVVAAAAAEAKKKAVKESSIRSV

QETVLPIKKRKTRETVSIEVKEVVKPLLVSTLGEKSGKGLKTCKSPGRKS

KESSPKGRSSSASSPPKKEHHHHHHHAESPKAPMPLLPPPPPPEPQSSED

PISPPEPQDLSSSICKEEKMPRAGSLESDGCPKEPAKTQPMVAAAATTTT

TTTTTVAEKYKHRGEGERKDIVSSSMPRPNREEPVDSRTPVTERVS

In some embodiments of any of the aspects, the TR comprises a Hp1a repressor domain, or a functional fragment thereof. Heterochromatin protein 1 (HP1a in *Drosophila*) is a conserved eukaryotic chromosomal protein that is prominently associated with pericentric heterochromatin and mediates the concomitant gene silencing. HP1a binds H3K9me2/3 through its chromo domain, and binds SU(VAR)3-9, one of the histone methyltransferases that methylates histone H3 on K9, through its chromo shadow domain. In some embodiments of any of the aspects, the Hp1a repressor domain comprises SEQ ID NO: 98 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 98, that maintains its function.

SEQ ID NO: 98: Hp1a repressor domain (190 aa)
GKKTKRTADSSSSEDEEEYVVEKVLDRRVVKGQVEYLLKWKGFSEEHNTW

EPEKNLDCPELISEFMKKYKKMKEGENNKPREKSESNKRKSNFSNSADDI

KSKKKREQSNDIARGFERGLEPEKIIGATDSCGDLMFLMKWKDTDEADLV

LAKEANVKCPQIVIAFYEERLTWHAYPEDAENKEKETAKS

In some embodiments of any of the aspects, the TR comprises an EED repressor domain, or a functional fragment thereof. EED (Embryonic Ectoderm Development) functions as part of the Polycomb repressive complex 2 (PRC2), which methylates histone H3 at lysine 27 (H3K27me3). Polycomb family members form multimeric protein complexes, which are involved in maintaining the transcriptional repressive state of genes over successive cell generations. In some embodiments of any of the aspects, the EED repressor domain comprises SEQ ID NO: 99 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 99, that maintains its function.

SEQ ID NO: 99: EED repressor domain (440 aa)
SEREVSTAPAGTDMPAAKKQKLSSDENSNPDLSGDENDDAVSIESGTNTE

RPDTPTNTPNAPGRKSWGKGKWKSKKCKYSFKCVNSLKEDHNQPLFGVQF

NWHSKEGDPLVFATVGSNRVTLYECHSQGEIRLLQSYVDADADENFYTCA

WTYDSNTSHPLLAVAGSRGIIRIINPITMQCIKHYVGHGNAINELKFHPR

-continued

DPNLLLSVSKDHALRLWNIQTDTLVAIFGGVEGHRDEVLSADYDLLGEKI

MSCGMDHSLKLWRINSKRMMNAIKESYDYNPNKTNRPFISQKIHFPDFST

RDIHRNYVDCVRWLGDLILSKSCENAIVCWKPGKMEDDIDKIKPSESNVT

ILGRFDYSQCDIWYMRFSMDFWQKMLALGNQVGKLYVWDLEVEDPHKAKC

TTLTFIHKCGAAIRQTSFSRDSSILIAVCDDASIWRWDRLR

In some embodiments of any of the aspects, the TR comprises a DNA (cytosine-5)-methyltransferase 3B (DNMT3B) repressor domain, or a functional fragment thereof. DNMT3B is involved in CpG methylation, which is an epigenetic modification that is important for embryonic development, imprinting, and X-chromosome inactivation. In some embodiments of any of the aspects, the DNMT3B repressor domain comprises SEQ ID NO: 217 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 217, that maintains its function.

SEQ ID NO: 217, DNMT3B repressor domain (792 aa), Uniprot identifier Q9UBC3-5, DNM3B_HUMAN Isoform 5 of DNA (cytosine-5)-methyltransferase
MKGDTRHLNGEEDAGGREDSILVNGACSDQSSDSPPILEAIRTPEIRGRR

SSSRLSKREVSSLLSYTQDLTGDGDGEDGDGSDTPVMPKLFRETRTRSES

PAVRTRNNNSVSSRERHRPSPRSTRGRQGRNHVDESPVEFPATRSLRRRA

TASAGTPWPSPPSSYLTIDLTDDTEDTHGTPQSSSTPYARLAQDSQQGGM

ESPQVEADSGDGDSSEYQDGKEFGIGDLVWGKIKGFSWWPAMVVSWKATS

KRQAMSGMRWVQWFGDGKFSEVSADKLVALGLFSQHFNLATFNKLVSYRK

AMYHALEKARVRAGKTFPSSPGDSLEDQLKPMLEWAHGGFKPTGIEGLKP

NNTQPENKTRRRTADDSATSDYCPAPKRLKTNCYNNGKDRGDEDQSREQM

ASDVANNKSSLEDGCLSCGRKNPVSFHPLFEGGLCQTCRDRFLELFYMYD

DDGYQSYCTVCCEGRELLLCSNTSCCRCFCVECLEVLVGTGTAAEAKLQE

PWSCYMCLPQRCHGVLRRRKDWNVRLQAFFTSDTGLEYEAPKLYPAIPAA

RRRPIRVLSLFDGIATGYLVLKELGIKVGKYVASEVCEESIAVGTVKHEG

NIKYVNDVRNITKKNIEEWGPFDLVIGGSPCNDLSNVNPARKGLYEGTGR

LFFEFYHLLNYSRPKEGDDRPFFWMFENVVAMKVGDKRDISRFLECNPVM

IDAIKVSAAHRARYFWGNLPGMNRPVIASKNDKLELQDCLEYNRIAKDLW

LSCALHRRVQHGPWCPPEAAGKVLERACHPTPLRPSEGLLCM

In some embodiments of any of the aspects, the TR comprises a histone deacetylase 4 (HDAC4) repressor domain, or a functional fragment thereof. HDAC4 removes acetyl groups from histones H3 and H4. In some embodiments of any of the aspects, the HDAC4 repressor domain comprises SEQ ID NO: 218 or a polypeptide comprising a sequence that is at least 60%, at least 65%, at least 70%, at least 75%, at least 80%, at least 85%, at least 90%, at least 95%, at least 96%, at least 97%, at least 98%, or at least 99% identical to SEQ ID NO: 218, that maintains its function.

SEQ ID NO: 218, a HDAC4 domain, GenBank: AAD29046.1 (1084 aa)

MSSQSHPDGLSGRDQPVELLNPARVNHMPSTVDVATALPLQVAPSAVPMD

LRLDHQFSLPVAEPALREQQLQQELLALKQKQQIQRQILIAEFQRQHEQL

SRQHEAQLHEHIKQQQEMLAMKHQQELLEHQRKLERHRQEQELEKQHREQ

KLQQLKNKEKGKESAVASTEVKMKLQEFVLNKKKALAHRNLNHCISSDPR

YWYGKTQHSSLDQSSPPQSGVSTSYNHPVLGMYDAKDDFPLRKTASEPNL

KLRSRLKQKVAERRSSPLLRRKDGPVVTALKKRPLDVTDSACSSAPGSGP

SSPNNSSGSVSAENGIAPAVPSIPAETSLAHRLVAREGSAAPLPLYTSPS

LPNITLGLPATGPSAGTAGQQDTERLTLPALQQRLSLFPGTHLTPYLSTS

PLERDGGAAHSPLLQHMVLLEQPPAQAPLVTGLGALPLHAQSLVGADRVS

PSIHKLRQHRPLGRTQSAPLPQNAQALQHLVIQQQHQQFLEKHKQQFQQQ

QLQMNKIIPKPSEPARQPESHPEETEEELREHQALLDEPYLDRLPGQKEA

HAQAGVQVKQEPIESDEEEAEPPREVEPGQRQPSEQELLFRQQALLLEQQ

RIHQLRNYQASMEAAGIPVSFGGHRPLSRAQSSPASATFPVSVQEPPTKP

RFTTGLVYDTLMLKHQCTCGSSSSHPEHAGRIQSIWSRLQETGLRGKCEC

IRGRKATLEELQTVHSEAHTLLYGTNPLNRQKLDSKKLLGSLASVFVRLP

CGGVGVDSDTIWNEVHSAGAARLAVGCVVELVFKVATGELKNGFAVVRPP

GHHAEESTPMGFCYFNSVAVAAKLLQQRLSVSKILIVDWDVHHFIGNGTQ

QAFYSDPSVLYMSLHRYDDGNFFPGSGAPDEVGTGPGVGFNVNMAFTGGL

DPPMGDAEYLAAFRTVVMPIASEFAPDVVLVSSGFDAVEGHPTPLGGYNL

SARCFGYLTKQLMGLAGGRIVLALEGGHDLTAICDASEACVSALLGNELD

PLPEKVLQQRPNANAVRSMEKVMEIHSKYWRCLQRTTSTAGRSLIEAQTC

ENEEAETVTAMASLSVGVKPAEKRPDEEPMEEEPPL

In another embodiment of any aspect described herein, in the synTF described or the ZF-containing fusion protein described herein, the transcriptional effector domain is an epigenetic effector domain. For example, at least one ZF protein domain is fused to one or more chromatin regulating enzymes that (1) catalyze chemical modifications of DNA or histone residues (e.g. DNA methyltransferases, histone methyltransferases, histone acetyltransferases) or (2) remove chemical modifications (e.g. DNA demethylases, DNA di-oxygenases, DNA hydroxylases, histone demethylases, histone deacetylases). For example, a DNA methyltransferase DNMT (DNMT1, DNMT3) catalyzes the transfer of methyl group to cytosine, which typically results in transcriptional repression through the recruitment of repressive regulatory proteins. Another example is CBP/p300 histone acetyltransferase, which is typically associated with transcriptional activation through the interactions with multiple transcription factors. Related epigenetic effector domains associated with the deposition of biochemical marks on DNA or histone residue(s) include HAT1, GCN5, PCAF, MLL, SET, DOT1, SUV39H, G9a, KAT2A/B and EZH1/2. Related epigenetic effector domains associated with the removal of biochemical marks from DNA or histone residue(s) include TET1/2, SIRT family, LSD1, and KDM family.

DNA-Binding Domain

Described herein are synTFs comprising at least one DNA-binding domain (DBD). In some embodiments of any of the aspects, a synTF polypeptide as described herein (or a synTF polypeptide system collectively) comprises 1, 2, 3, 4, 5, or more DBD(s). In some embodiments of any of the aspects, the synTF polypeptide or system comprises one DBD. In embodiments comprising multiple DBDs, the multiple DBDs can be different individual DBDs or multiple copies of the same DBDs, or a combination of the foregoing.

In some embodiments of any of the aspects, the at least one DBD is an engineered zinc finger (ZF) binding domain. A zinc finger (ZF) is a finger-shaped fold in a protein that permits it to interact with nucleic acid sequences such as DNA and RNA. Such a fold is well known in the art. The fold is created by the binding of specific amino acids in the protein to a zinc atom. Zinc-finger containing proteins (also known as ZF proteins) can regulate the expression of genes as well as nucleic acid recognition, reverse transcription and virus assembly.

A ZF is a relatively small polypeptide domain comprising approximately 30 amino acids, which folds to form an α-helix adjacent an antiparallel ρ-sheet (known as a ββα-fold). The fold is stabilized by the co-ordination of a zinc ion between four largely invariant (depending on zinc finger framework type) Cys and/or His residues, as described further below. Natural zinc finger domains have been well studied and described in the literature, see for example, Miller et al., (1985) EMBO J. 4: 1609-1614; Berg (1988) Proc. Natl. Acad. Sci. USA 85: 99-102; and Lee et al., (1989) Science 245: 635-637. A ZF domain recognizes and binds to a nucleic acid triplet, or an overlapping quadruplet (as explained below), in a double-stranded DNA target sequence. However, ZFs are also known to bind RNA and proteins (Clemens, K. R. et al. (1993) Science 260: 530-533; Bogenhagen, D. F. (1993) Mol. Cell. Biol. 13: 5149-5158; Searles, M. A. et al. (2000) J. Mol. Biol. 301: 47-60; Mackay, J. P. & Crossley, M. (1998) Trends Biochem. Sci. 23: 1-4).

In one embodiment, as used herein, the term "zinc finger" (ZF) or "zinc finger motif" (ZF motif) or "zinc finger domain" (ZF domain) refers to an individual "finger", which comprises a beta-beta-alpha (ββα)-protein fold stabilized by a zinc ion as described elsewhere herein. The Zn-coordinated ββα protein fold produces a finger-like protrusion, a "finger." Each ZF motif typically includes approximately 30 amino acids. The term "motif" as used herein refers to a structural motif. The ZF motif is a supersecondary structure having the ββα-fold that stabilized by a zinc ion.

In one embodiment, the term "ZF motif" according to its ordinary usage in the art, refers to a discrete continuous part of the amino acid sequence of a polypeptide that can be equated with a particular function. ZF motifs are largely structurally independent and may retain their structure and function in different environments. Because the ZF motifs are structurally and functionally independent, the motifs also qualify as domains, thus are often referred as ZF domains. Therefore, ZF domains are protein motifs that contain multiple finger-like protrusions that make tandem contacts with their target molecule. Typically, a ZF domain binds a triplet or (overlapping) quadruplet nucleotide sequence. Adjacent ZF domains arranged in tandem are joined together by linker sequences to form an array. A ZF peptide typically contains a ZF array and is composed of a plurality of "ZF domains", which in combination do not exist in nature. Therefore, they are considered to be artificial or synthetic ZF peptides or proteins.

$C_2H_2$ zinc fingers ($C_2H_2$-ZFs) are the most prevalent type of vertebrate DNA-binding domain, and typically appear in tandem arrays (ZFAs), with sequential $C_2H_2$-ZFs each contacting three (or more) sequential bases. $C_2H_2$-ZFs can be assembled in a modular fashion. Given a set of modules with defined three-base specificities, modular assembly also presents a way to construct artificial proteins with specific DNA-binding preferences.

ZF-containing proteins generally contain strings or chains of ZF motifs, forming an array of ZF (ZFA). Thus, a natural ZF protein may include 2 or more ZF, i.e., a ZFA consisting of 2 or more ZF motifs, which may be directly adjacent one another (i.e. separated by a short (canonical) linker sequence), or may be separated by longer, flexible or structured polypeptide sequences. Directly adjacent ZF domains are expected to bind to contiguous nucleic acid sequences, i.e. to adjacent trinucleotides/triplets. In some cases cross-binding may also occur between adjacent ZF and their respective target triplets, which helps to strengthen or enhance the recognition of the target sequence, and leads to the binding of overlapping quadruplet sequences (Isalan et al., (1997) Proc. Natl. Acad. Sci. USA, 94: 5617-5621). By comparison, distant ZF domains within the same protein may recognize (or bind to) non-contiguous nucleic acid sequences or even to different molecules (e.g. protein rather than nucleic acid).

Engineered ZF-containing proteins are chimeric proteins composed of a DNA-binding zinc finger protein domain (ZF protein domain) and another domain through which the protein exerts its effect (effector domain). The effector domain may be a transcriptional activator or repressor, a methylation domain or a nuclease. DNA-binding ZF protein domain would contain engineered zinc finger arrays (ZFAs). See e.g., Khalil et al., Cell Volume 150, Issue 3, 3 Aug. 2012, Pages 647-658; U.S. Pat. No. 10,138,493; US Patent Application US20200002710A1; the contents of each of which are incorporated herein by reference in their entireties.

Engineered ZF-containing proteins are non-natural and suitably contain 3 or more, for example, 4, 5, 6, 8, 9, 10, 11, 12, 13, 14, 15, 16, 17, 18 or more (e.g. up to approximately 30 or 32) ZF motifs arranged adjacent one another in tandem, forming arrays of ZF motifs or ZFA. Particularly ZF-containing synTF proteins (ZF-containing synTF fusion protein, or simply synTF) of the disclosure include at least 3 ZF, at least 4 ZF motifs, at least 5 ZF motifs, or at least 6 ZF motifs, at least 7 ZF motifs, at least 8 ZF motifs, at least 9 ZF motifs, at least 10 ZF motifs, at least 11 or at least 12 ZF motifs; and in some cases at least 18 ZF motifs. In other embodiments, the ZF synTF contains up to 6, 7, 8, 10, 11, 12, 16, 17, 18, 22, 23, 24, 28, 29, 30, 34, 35, 36, 40, 41, 42, 46, 47, 48, 54, 55, 56, 58, 59, or 60 ZF motifs. In some embodiments, the ZF array comprises 1 or more ZF motif. The ZF-containing synTF of the disclosure bind to contiguous orthogonal target nucleic acid binding sites. That is, the ZFs or ZFAs comprising in the ZF domain of the fusion protein binds orthogonal target nucleic acid sequences.

In one embodiment, as used herein, an "engineered synthetic transcription factor" or "engineered synTF" or "synTF" refers to an engineered ZF-containing chimeric protein having at least one of the following characteristics and may have more than one: bind target orthogonal specific DNA sequences and have, for example, reduced or minimal functional binding potential in a host eukaryotic genome; are derived from mammalian protein scaffolds, conferring minimal degree of immunogenicity over other prokaryotically-derived domains; and can be packaging in viral delivery systems, such as lentiviral delivery constructs.

In another embodiment, as used herein, the term "engineered synthetic transcription factor" or "engineered synTF," abbreviated as "synTF" or "ZF synTF," refers to an engineered ZF containing synthetic transcription factor that is a polypeptide, in other words, a ZF-containing synthetic transcription factor protein. These synTFs contain ZF arrays (ZFA) therein for binding to specific target nucleic acid sequences. The synTF is a chimeric, fusion protein that comprises a DNA-binding, ZF-containing protein domain and an effector domain through which the synTF exerts its effect on gene expression. These synTFs can modulate gene expression, wherein the modulation is by increasing or decreasing the expression of a gene that is operably linked to a promoter that is also operably linked to the specific target nucleic acid sequence to which the DNA-binding, ZF-containing protein domain of the synTF binds.

As used herein, the term "ZF array," abbreviated as "ZFA" refers to an array, or a string, or a chain of ZF motifs arranged in tandem. A ZFA can have six ZF motifs (a 6-finger ZFA), seven ZF motifs (a 7-finger ZFA), or eight ZF motifs (an 8-finger ZFA).

As used herein, the term "engineered responsive/response promoter," "engineered promoter," or "engineered responsive/response promoter element" refers is a nucleic acid construct containing a promoter sequence that has at least one orthogonal DNA target sequence operably linked upstream of the promoter sequence such that the orthogonal DNA target sequence confer a responsive property to the promoter when the orthogonal DNA target sequence is bound by its respective transcription factor, the responsive property being whether gene transcription initiation from that promoter is enhanced or repressed when the upstream nearby orthogonal DNA target sequences are bound by a ZF-containing synthetic transcription factor. There may be more than one orthogonal DNA target sequence operably linked upstream of the promoter sequence. When there is one orthogonal DNA target sequence, the promoter is referred to a "1×" promoter, where the "1×" refers to the number of orthogonal DNA target sequence present in the promoter construct. For example, a 4× responsive promoter would be identified as having four orthogonal DNA target sequences in the engineered response promoter construct, and the four orthogonal DNA target sequences are upstream of the promoter sequence.

The ZF protein domain is modular in design, with zinc finger arrays (ZFA) as the main components, and each ZFA is made of 6-8 ZF motifs. The ZF protein domain comprises at least one ZFA, and can contain as many as up to ten ZFA. The ZF protein domain can have one and up to ten ZFA.

The design of the synTF or any engineered fusion protein described herein is also modular, meaning the synTF is made up of modules of ZF domains (ZFA) and modules of effector domains/protein interaction domains/ligand binding domains/dimerization domains, the individual modules are covalently conjugated together as described herein, and the individual modules function independently of each other. The number of ZFA can range from one, two, three, four, five, six, seven, eight, nine, and up to ten. When there are two or more ZFA, the ZFAs are covalently conjugated to each other in tandem, e.g., by a L1 peptide linker, in an $NH_2$— to COOH— terminus arrangement to form an array of ZFA. The ZFAs, as a whole, forms the ZF protein domain, is covalently linked to the N-terminus or the C-terminus of the effector domain or the regulator protein. When there are two or more ZFAs present in the ZF protein domain of a synTF or a ZF containing fusion protein described herein, the ZFAs can be the same, or different.

Figure 2:
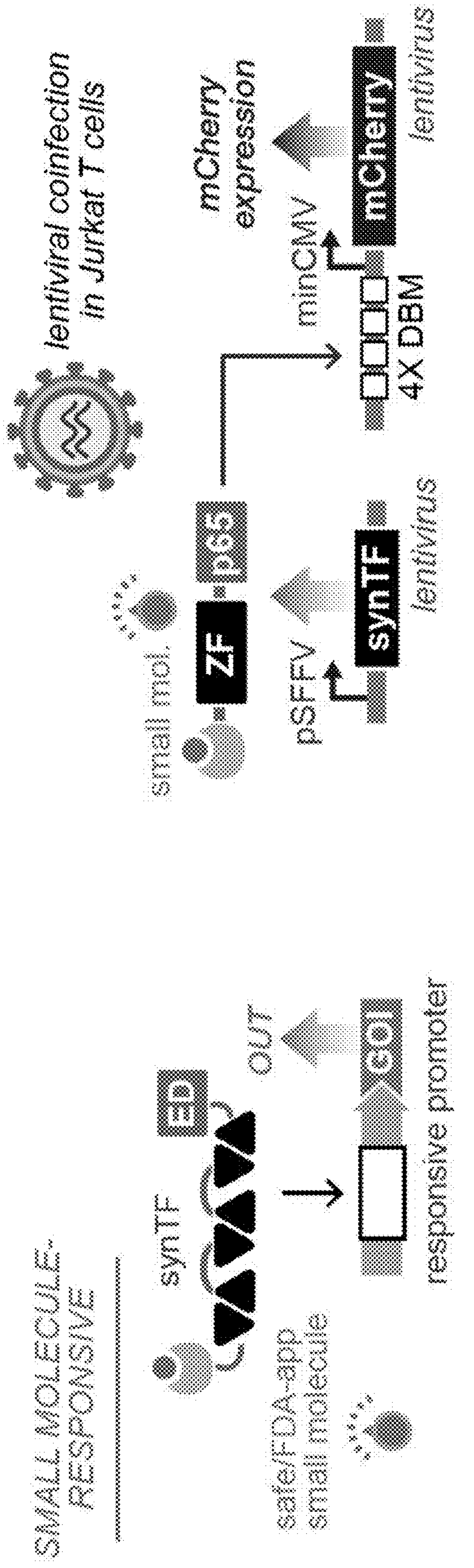
FIG. 2 is a schematic showing a small molecule-responsive synTF system.

Each modular ZFA in the ZF protein domain of a synTF disclosed herein or a ZF containing fusion protein described herein is comprised of six to eight ZF motifs. See FIG. 2B for an example of a single ZFA having seven ZF motifs, a seven-finger ZFA. The ZF motif is a small protein structural motif consisting of an α helix and an antiparallel p sheet (app) and is characterized by the coordination of one zinc ion by two histidine residues and two cysteine residues in the motif in order to stabilize the finger-like protrusion fold, the "finger". The ZF motif in the ZF protein domain of a synTF disclosed herein is a $Cys_2His_2$ zinc finger motif. In one embodiment, the ZF motif comprises, consisting essentially of, or consisting of a peptide of formula 1: $[X_{0-3}CX_{1-5}CX_{2-7}$-(helix)-$HX_{3-6}H]$ (SEQ ID NO: 219) wherein X is any amino acid, the subscript numbers indicate the possible number of amino acid residues, C is cysteine, H is histidine, and (helix) is a-six (or seven) contiguous amino acid residue peptide that forms a short alpha helix. The helix is variable. This short alpha helix forms one facet of the finger formed by the coordination of the zinc ion by two histidine residues and two cysteine residues in the ZF motif. For each ZFA, the six to eight ZF motifs therein are linked to each other, $NH_2$— to COOH— terminus by a peptide linker having about four to six amino acid residues to form an array of ZF motifs or ZF. The finger-like protrusion fold of each ZF motif interacts with and binds nucleic acid sequence. Approximately a peptide sequence for two ZF motif interacts with and binds a ~six-base pair (bp) nucleic acid sequence. The multiple ZF motifs in a ZFA form finger-like protrusions that would make contact with an orthogonal target DNA sequence. Hence, for example, a ZFA with six ZF motifs or finger-like protrusions (a six-finger ZFA) interacts and binds a ~18-20 bp nucleic acid sequence, and an eight-finger ZFA would bind a ~24-26 bp nucleic acid sequence. Accordingly, in one embodiment, the ZFA in the ZF protein domain of a synTF comprises, consists essentially of, or consists of a sequence: N'-[(formula 1)-$L_2]_{6-8}$—C', where the subscript 6-8 indicates the number of ZF motifs, the $L_2$ is a linker peptide having 4-6 amino acid residues, and the N'— and C'— indicates the N-terminus and C-terminus respectively of the peptide sequence. For example, for a ZFA consists essentially of six ZF motifs, the sequence is N'-[(formula 1)-$L_2$]-[(formula 1)-$L_2$]-[(formula 1)-$L_2$]-[(formula 1)-$L_2$]-[(formula 1)-$L_2$]-[(formula 1)-$L_2$]-C', and a ZFA consists essentially of eight ZF motifs, the sequence is N'-[(formula 1)-$L_2$]-[(formula 1)-$L_2$]-[(formula 1)-$L_2$]-[(formula 1)-$L_2$]-[(formula 1)-$L_2$]-[(formula 1)-$L_2$]-]-[(formula 1)-$L_2$]-[(formula 1)-$L_2$]-C'.

```
SEQ ID NO: 219:
XXXCXXXXXCXXXXXXXXXXXXXHXXXXXXH
```

In another embodiment of any aspect described herein, the ZF motif comprises a peptide of formula 2: $[X_3CX_2CX_5$-(helix)-$HX_3H]$ (SEQ ID NO: 220) wherein X is any amino acid, the subscript numbers indicate the possible number of amino acid residues, C is cysteine, H is histidine, and (helix) is a-six (or seven) contiguous amino acid residue peptide that forms a short alpha helix. Accordingly, in one embodiment, the ZFA in the ZF protein domain of a synTF comprises, consists essentially of, or consists of a sequence: N'-[(formula 2)-$L_2]_{6-8}$-C', where the subscript 6-8 indicates the number of ZF motifs, the $L_2$ is a linker peptide having 4-6 amino acid residues, and the N'— and C'— indicates the N-terminus and C-terminus respectively of the peptide sequence. For example, for a ZFA consists essentially of six ZF motifs, the sequence is N'-[(formula 2)-$L_2$]-[(formula 2)-$L_2$]-[(formula 2)-$L_2$]-[(formula 2)-$L_2$]-[(formula 2)-$L_2$]-[(formula 2)-$L_2$]-C' and a ZFA consists essentially of eight ZF motifs, the sequence is N'-[(formula 2)-$L_2$]-[(formula 2)-$L_2$]-[(formula 2)-$L_2$]-[(formula 2)-$L_2$]-[(formula 2)-$L_2$]-[(formula 2)-$L_2$]-]-[(formula 2)-$L_2$]-[(formula 2)-$L_2$]-C'.

```
SEQ ID NO: 220:
XXXCXXCXXXXXXXXXXXXHXXXH
```

In one embodiment of any aspect described herein, for a single ZFA is the ZF protein domain of a synTF disclosed herein, the ZFA in the ZF protein domain comprises, consists essentially of, or consists of a sequence: N'-PGERPFQCRICMRNFS-(Helix 1)-HTRTHTGEKPFQCRICMRNFS-(Helix 2)-HLRTHTGSQK PFQCRICMRNFS-(Helix 3)-HTRTHTGEK PFQCRICMRNFS-(Helix 4)-HLRTHTGSQKPFQCRICMRNFS-(Helix 5)-HTRTHTGEK PFQCRICMRNFS-(Helix 6)-HLRTHLR-C' (SEQ ID NO: 380), wherein the (Helix) is a-six (or seven) contiguous amino acid residue peptide that forms a short alpha helix and can also be represented as plain text "xxxxxxx".

SEQ ID NO: 377, Zinc Finger Domain scaffold; italicizeddoubleunderlinedtext indicates the restriction sites; plain text "xxxxxxx" indicates six ZF helices, e.g., from N terminus to C terminus: helix 1, helix 2, helix 3, helix 4, helix 5, and helix 6

```
SRPGERPFQCRICMRNFSxxxxxxxHTRTHTGEKPFQCRICMRNFSxxx
xxxxHLRTHTGSQKPFQCRICMRNFSxxxxxxxHTRTHTGEKPFQCRIC
MRNFSxxxxxxxHLRTHTGSQKPFQCRICMRNFSxxxxxxxHTRTHTGE
KPFQCRICMRNFSxxxxxxxHLRTHLRGS
```

SEQ ID NO: 101, Zinc Finger Domain scaffold, wherein [Helix 1], [Helix 2], [Helix 3], [Helix 4], [Helix 5], and [Helix 6] can also be represented as plain text "xxxxxxx"

```
PGERPFQCRICMRNFS[Helix1]
HTRTHTGEKPFQCRICMRNFS[Helix 2]
HLRTHTGSQKPFQCRICMRNFS[Helix 3]
HLRTHTGEKPFQCRICMRNFS[Helix 4]
HLKTHTGSQKPFQCRICMRNFS[Helix 5]
HLRTHTGEKPFQCRICMRNFS[Helix 6]HLRTHLR
```

SEQ ID NO: 76, Zinc Finger Domain scaffold; italicizeddoubleunderlinedtext indicates the restriction sites; plain text "xxxxxxx" indicates six ZF helices, e.g., from N terminus to C terminus: helix 1, helix 2, helix 3, helix 4, helix 5, and helix 6

```
SRPGERPFQCRICMRNFSxxxxxxxHTRTHTGEKPFQCRICMRNFSxxx
xxxxHLRTHTGSQKPFQCRICMRNFSxxxxxxxHLRTHTGEKPFQCRIC
MRNFSxxxxxxxHLKTHTGSQKPFQCRICMRNFSxxxxxxxHLRTHTGE
KPFQCRICMRNFSxxxxxxxHLRTHLRGS
```

In some embodiments of any of the aspects, the zinc finger scaffold comprises one of SEQ ID NOs: 76, 101, 377, 380 or an amino acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 76, 101, 377, or 380 that maintains the same function.

In one embodiment, all six of the helix 1, 2, 3, 4, 5 and 6 are distinct and different from each other. In another embodiment, all six of the helix 1, 2, 3, 4, 5 and 6 are identical to each other. Alternatively, at least two of the six helices are identical and the same with each other. In other embodiments, at least three of the six helices in a ZFA are identical and the same with each other, at least four of the six helices in a ZFA are identical and the same with each other, or at least five of the six helices in a ZFA are identical and the same with each other.

In some embodiments of any aspect described herein, the helices of the six to eight ZF motifs of an individual ZFA disclosed herein are selected from the six-amino acid (or seven-amino acid) residue peptide sequences disclosed in one of the following Groups 1-11 (e.g., SEQ ID NOs: 122-180, 192). In some embodiments, at least four of the ZF motifs in an individual ZFA disclosed herein are selected from the six-amino acid (or seven-amino acid) residue peptide sequences disclosed in one of the following Groups 1-11. In other embodiments, all of the ZF motifs, i.e. the six, seven or eight ZF motifs in an individual ZFA disclosed herein, are selected from the six (or seven) amino acid residue peptide sequences disclosed in one of the following Groups 1-11. In any individual ZFA, the helix selected for a single ZF comprising the ZFA can be repeated twice or more in the ZFA. This means that for any given single ZFA, at least four or all the helices in the ZFA are selected from the same group disclosed herein. For example, wherein a ZFA consists essentially of six ZF motifs, that means there are six alpha helices. All the 6-8 helices (Helix 1; Helix 2; Helix 3; Helix 4; Helix 5; Helix 6; Helix 7; Helix 8) of the ZFs in an individual ZFA is selected from one of the following group 1-11, for example, all six helices are selected from group 2. That is, all the helices for all the ZF comprising a single ZFA come from the same group. Alternatively, at least four of the six helices are selected from the same group, a group selected from group 1-11. For example, four of the six helices are selected from group 5, and the reminder two helices of the six-ZF motif ZFA are selected from the other groups 1-4, 6-11, or can be any other helices that would form a short alpha helix. The other remaining helices making up the ZFA can those that are known in the art.

TABLE 10

| Groups 1-4 helices | | | | | | | |
|---|---|---|---|---|---|---|---|
| Group 1 | SEQ ID NO: | Group 2 | SEQ ID NO: | Group 3 | SEQ ID NO: | Group 4 | SEQ ID NO: |
| DEANLRR | 122 | QRSSLVR | 131 | QRSSLVR | 131 | QQTNLTR | 126 |
| DPSVLKR | 123 | DMGNLGR | 132 | DKSVLAR | 140 | QGTSLAR | 146 |
| QSANLLR | 124 | RSHDLTR | 133 | QTNNLGR | 141 | VRHNLTR | 147 |
| DPSSLKR | 125 | HKSSLTR | 134 | THAVLTR | 142 | DKSVLAR | 140 |
| QQTNLTR | 126 | DSSNLRR | 135 | DRGNLTR | 138 | DSSNLRR | 135 |
| DATQLVR | 127 | DQGNLIR | 136 | TKSLLAR | 143 | DQGNLIR | 136 |
| ERRSLAR | 128 | QKQALTR | 137 | QKQALDR | 144 | EKQNLAR | 148 |
| EEANLRR | 129 | DRGNLTR | 138 | DTSVLNR | 145 | DPSNLRR | 149 |
| DHSSLKR | 130 | RSHDLTV | 139 | QRNNLGR | 192 | DHSNLSR | 150 |
| | | | | | | QSTSLQR | 151 |

TABLE 11

| Groups 5-7 helices | | | | | |
|---|---|---|---|---|---|
| Group 5 | SEQ ID NO: | Group 6 | SEQ ID NO: | Group 7 | SEQ ID NO: |
| NMSNLTR | 152 | QQTNLTR | 126 | QRSSLVR | 131 |
| DRSVLRR | 153 | QGGNLAL | 160 | QRGNLNM | 164 |
| LQENLTR | 154 | DHSSLKR | 130 | RPQELRR | 165 |
| DRSSLRR | 155 | RADMLRR | 161 | DHSSLKR | 130 |
| QSGTLHR | 156 | DSSNLRR | 135 | RQDNLGR | 166 |
| QLANLAR | 157 | DQGNLIR | 136 | DGGNLGR | 167 |
| DQTTLRR | 158 | EKQNLAR | 148 | QQGNLQL | 168 |
| DPSNLAR | 159 | DPSNLRR | 149 | RRQELTR | 169 |
| | | QKANLGV | 162 | DPSNLRR | 149 |
| | | RLDMLAR | 163 | | |

TABLE 12

| Groups 8-11 helices | | | | | | | |
|---|---|---|---|---|---|---|---|
| Group 8 | SEQ ID NO: | Group 9 | SEQ ID NO: | Group 10 | SEQ ID NO: | Group 11 | SEQ ID NO: |
| QASNLTR | 170 | DSSNLRR | 135 | RRHGLDR | 175 | QLSNLTR | 177 |
| DHSSLKR | 130 | DQGNLIR | 136 | DHSSLKR | 130 | DRSSLKR | 178 |
| RAHNLLL | 171 | RAHNLLL | 171 | VRHNLTR | 147 | QRSSLVR | 131 |
| QRSSLVR | 131 | QRSSLVR | 131 | DHSNLSR | 150 | RLDMLAR | 163 |
| QSTTLKR | 172 | QSTTLKR | 172 | QRSSLVR | 131 | VRHSLTR | 179 |
| DPSNLRR | 149 | DPSNLRR | 149 | ESGHLKR | 176 | ESGALRR | 180 |
| QGTTLKR | 173 | EKQNLAR | 148 | | | | |
| QRSNLAR | 174 | DSSNLRR | 135 | | | | |

Non-limiting examples of the combinations and arrangements of six helices in a single ZFA where the helices are selected from Group 1 and where the motifs are in an $NH_2$— to COOH— terminus arrangement, (Group 1 ZFA helix combo), are as follows:

ZF 1-1: N'-DEANLRR, DPSVLKR, QSANLLR, DPSSLKR, QQTNLTR, DATQLVR-C' (SEQ ID NOS 122, 123, 124, 125, 126, and 127, respectively, in order of appearance)

ZF 1-2: N'-DEANLRR, DPSVLKR, QSANLLR, DPSSLKR, QQTNLTR, ERRSLAR-C' (SEQ ID NOS 122, 123, 124, 125, 126, and 128, respectively, in order of appearance)

ZF 1-3: N'-EEANLRR, DHSSLKR, QSANLLR, DPSSLKR QQTNLTR, DATQLVR-C' (SEQ ID NOS 129, 130, 124, 125, 126, and 127, respectively, in order of appearance)

ZF 1-4: N'-EEANLRR, DHSSLKR, QSANLLR, DPSSLKR QQTNLTR, ERRSLAR-C'(SEQ ID NOS 129, 130, 124, 125, 126, and 128, respectively, in order of appearance)

ZF 1-5: N'-DEANLRR, DPSVLKR, QQTNLTR, ERRSLAR QQTNLTR, DATQLVR-C' (SEQ ID NOS 122, 123, 126, 128, 126, and 127, respectively, in order of appearance)

ZF 1-6: N'-DEANLRR, DPSVLKR, QQTNLTR, ERRSLAR QQTNLTR, ERRSLAR-C' (SEQ ID NOS 122, 123, 126, 128, 126, and 128, respectively, in order of appearance)

ZF 1-7: N'-EEANLRR, DHSSLKR, QQTNLTR, ERRSLAR QQTNLTR, DATQLVR-C' (SEQ ID NOS 129, 130, 126, 128, 126, and 127, respectively, in order of appearance)

ZF 1-8: N'-EEANLRR, DHSSLKR, QQTNLTR, ERRSLAR QQTNLTR, ERRSLAR-C' (SEQ ID NOS 129, 130, 126, 128, 126, and 128, respectively, in order of appearance)

Non-limiting examples of the combinations and arrangements of six helices in a single six-finger ZFA where the helices are selected from Group 2 and where the motifs are in an $NH_2$— to COOH— terminus arrangement, (Group 2 ZFA helix combo), are as follows:

ZF 2-1: N'-QRSSLVR, DMGNLGR, RSHDLTR, HKSSLTR, DSSNLRR, DQGNLIR-C' (SEQ ID NOS 131, 132, 133, 134, 135, and 136, respectively, in order of appearance)

ZF 2-2: N'-QKQALTR, DRGNLTR, RSHDLTR, HKSSLTR, DSSNLRR, DQGNLIR-C' (SEQ ID NOS 137, 138, 133, 134, 135, and 136, respectively, in order of appearance)

ZF 2-3: N'-QRSSLVR, DMGNLGR, RSHDLTV, HKSSLTR, DSSNLRR, DQGNLIR-C' (SEQ ID NOS 131, 132, 139, 134, 135, and 136, respectively, in order of appearance)

ZF 2-4: N'-QKQALTR, DRGNLTR, RSHDLTV, HKSSLTR, DSSNLRR, DQGNLIR-C' (SEQ ID NOS 137, 138, 139, 134, 135, and 136, respectively, in order of appearance)

ZF 2-5: N'-QRSSLVR, DMGNLGR, RSHDLTR, HKSSLTR, EKQNLAR, DPSNLRR-C' (SEQ ID NOS 131, 132, 133, 134, 148, and 149, respectively, in order of appearance)

ZF 2-6: N'-QKQALTR, DRGNLTR, RSHDLTR, HKSSLTR, EKQNLAR, DPSNLRR-C' (SEQ ID NOS 137, 138, 133, 134, 148, and 149, respectively, in order of appearance)

ZF 2-7: N'-QRSSLVR, DMGNLGR, RSHDLTV, HKSSLTR, EKQNLAR, DPSNLRR-C' (SEQ ID NOS 131, 132, 139, 134, 148, and 149, respectively, in order of appearance)

ZF 2-8: N'-QKQALTR, DRGNLTR, RSHDLTV, HKSSLTR, EKQNLAR, DPSNLRR-C' (SEQ ID NOS 137, 138, 139, 134, 148, and 149, respectively, in order of appearance)

Non-limiting examples of the combinations and arrangements of six helices in a single six-finger ZFA where the helices are selected from Group 3 and where the motifs are in an $NH_2$— to COOH— terminus arrangement, (Group 3 ZFA helix combo), are as follows:

ZF 3-1: N'-QRSSLVR, DKSVLAR, QRSSLVR, QTNNLGR, THAVLTR, DRGNLTR-C' (SEQ ID NOS 131, 140, 131, 141, 142, and 138, respectively, in order of appearance)

ZF 3-2: N'-QRSSLVR, DKSVLAR, QRSSLVR, QTNNLGR, TKSLLAR, DRGNLTR-C' (SEQ ID NOS 131, 140, 131, 141, 143, and 138, respectively, in order of appearance)

ZF 3-3: N'-QKQALDR, DTSVLNR, QRSSLVR, QTNNLGR, THAVLTR, DRGNLTR-C' (SEQ ID NOS 144, 145, 131, 141, 142, and 138, respectively, in order of appearance)

ZF 3-4: N'-QKQALDR, DTSVLNR, QRSSLVR, QTNNLGR, TKSLLAR, DRGNLTR-C' (SEQ ID NOS 144, 145, 131, 141, 143, and 138, respectively, in order of appearance)

ZF 3-5: N'-QRSSLVR, DKSVLAR, QRSSLVR, QTNNLGR, THAVLTR, DRGNLTR-C' (SEQ ID NOS 131, 140, 131, 141, 142, and 138, respectively, in order of appearance)

ZF 3-6: N'-QRSSLVR, DKSVLAR, QRSSLVR, QTNNLGR, TKSLLAR, DRGNLTR-C' (SEQ ID NOS 131, 140, 131, 141, 143, and 138, respectively, in order of appearance)

ZF 3-7: N'-QKQALDR, DTSVLNR, QRSSLVR, QTNNLGR, THAVLTR, DRGNLTR-C' (SEQ ID NOS 144, 145, 131, 141, 142, and 138, respectively, in order of appearance)

ZF 3-8: N'-QKQALDR, DTSVLNR, QRSSLVR, QTNNLGR, TKSLLAR, DRGNLTR-C' (SEQ ID NOS 144, 145, 131, 141, 143, and 138, respectively, in order of appearance)

In some embodiments of any of the aspects, QRNNLGR (SEQ ID NO: 192) is used in place of QTNNLGR (SEQ ID NO: 141). Non-limiting examples of the combinations and arrangements of six helices in a single six-finger ZFA where the helices are selected from Group 3 and where the motifs are in an $NH_2$— to COOH— terminus arrangement, (Group 3 ZFA helix combo), are as follows:

ZF 3-1: N'-QRSSLVR, DKSVLAR, QRSSLVR, QRNNLGR, THAVLTR, DRGNLTR-C' (SEQ ID NOS 131, 140, 131, 192, 142, and 138, respectively, in order of appearance)

ZF 3-2: N'-QRSSLVR, DKSVLAR, QRSSLVR, QRNNLGR, TKSLLAR, DRGNLTR-C' (SEQ ID NOS 131, 140, 131, 192, 143, and 138, respectively, in order of appearance)

ZF 3-3: N'-QKQALDR, DTSVLNR, QRSSLVR, QRNNLGR, THAVLTR, DRGNLTR-C' (SEQ ID NOS 144, 145, 131, 192, 142, and 138, respectively, in order of appearance)

ZF 3-4: N'-QKQALDR, DTSVLNR, QRSSLVR, QRNNLGR, TKSLLAR, DRGNLTR-C' (SEQ ID NOS 144, 145, 131, 192, 143, and 138, respectively, in order of appearance)

ZF 3-5: N'-QRSSLVR, DKSVLAR, QRSSLVR, QRNNLGR, THAVLTR, DRGNLTR-C' (SEQ ID NOS 131, 140, 131, 192, 142, and 138, respectively, in order of appearance)

ZF 3-6: N'-QRSSLVR, DKSVLAR, QRSSLVR, QRNNLGR, TKSLLAR, DRGNLTR-C' (SEQ ID NOS 131, 140, 131, 192, 143, and 138, respectively, in order of appearance)

ZF 3-7: N'-QKQALDR, DTSVLNR, QRSSLVR, QRNNLGR, THAVLTR, DRGNLTR-C' (SEQ ID NOS 144, 145, 131, 192, 142, and 138, respectively, in order of appearance)

ZF 3-8: N'-QKQALDR, DTSVLNR, QRSSLVR, QRNNLGR, TKSLLAR, DRGNLTR-C' (SEQ ID NOS 144, 145, 131, 192, 143, and 138, respectively, in order of appearance)

Non-limiting examples of the combinations and arrangements of six helices in a single six-finger ZFA where the helices are selected from Group 4 and where the motifs are in an $NH_2$— to COOH— terminus arrangement, (Group 4 ZFA helix combo), are as follows:

ZF 4-1: N'-QQTNLTR, QGTSLAR, VRHNLTR, DKSVLAR, DSSNLRR, DQGNLIR-C' (SEQ ID NOS 126, 146, 147, 140, 135, and 136, respectively, in order of appearance)

ZF 4-2: N'-QQTNLTR, QGTSLAR, VRHNLTR, DKSVLAR, EKQNLAR, DPSNLRR-C' (SEQ ID NOS 126, 146, 147, 140, 148, and 149, respectively, in order of appearance)

ZF 4-3: N'-QQTNLTR, QGTSLAR, VRHNLTR, DHSNLSR, DSSNLRR, DQGNLIR-C' (SEQ ID NOS 126, 146, 147, 150, 135, and 136, respectively, in order of appearance)

ZF 4-4: N'-QQTNLTR, QGTSLAR, VRHNLTR, DHSNLSR, EKQNLAR, DPSNLRR-C' (SEQ ID NOS 126, 146, 147, 150, 148, and 149, respectively, in order of appearance)

ZF 4-5: N'-QQTNLTR, QSTSLQR, VRHNLTR, DKSVLAR, DSSNLRR, DQGNLIR-C' (SEQ ID NOS 126, 151, 147, 140, 135, and 136, respectively, in order of appearance)

ZF 4-6: N'-QQTNLTR, QSTSLQR, VRHNLTR, DKSVLAR, EKQNLAR, DPSNLRR-C' (SEQ ID NOS 126, 151, 147, 140, 148, and 149, respectively, in order of appearance)

ZF 4-7: N'-QQTNLTR, QSTSLQR, VRHNLTR, DHSNLSR, DSSNLRR, DQGNLIR-C' (SEQ ID NOS 126, 151, 147, 150, 135, and 136, respectively, in order of appearance)

ZF 4-8: N'-QQTNLTR, QSTSLQR, VRHNLTR, DHSNLSR, EKQNLAR, DPSNLRR-C' (SEQ ID NOS 126, 151, 147, 150, 148, and 149, respectively, in order of appearance)

Non-limiting examples of the combinations and arrangements of six helices in a single six-finger ZFA where the helices are selected from Group 5 and where the motifs are in an $NH_2$— to COOH— terminus arrangement, (Group 5 ZFA helix combo), are as follows:

ZF 5-1: N'-NMSNLTR, DRSVLRR, LQENLTR, DRSSLRR, QSGTLHR, QSGTLHR-C' (SEQ ID NOS 152, 153, 154, 155, 156, and 156, respectively, in order of appearance)

ZF 5-2: N'-QLANLAR, DQTTLRR, LQENLTR, DRSSLRR, QSGTLHR, QSGTLHR-C' (SEQ ID NOS 157, 158, 154, 155, 156, and 156, respectively, in order of appearance)

ZF 5-3: N'-NMSNLTR, DRSVLRR, DPSNLAR, DRSSLRR, QSGTLHR, QSGTLHR-C' (SEQ ID NOS 152, 153, 159, 155, 156, and 156, respectively, in order of appearance)

ZF 5-4: N'-QLANLAR, DQTTLRR, DPSNLAR, DRSSLRR, QSGTLHR, QSGTLHR-C' (SEQ ID NOS 157, 158, 159, 155, 156, and 156, respectively, in order of appearance)

ZF 5-5: N'-NMSNLTR, DRSVLRR, LQENLTR, DRSSLRR, QSGTLHR, QSGTLHR-C' (SEQ ID NOS 152, 153, 154, 155, 156, and 156, respectively, in order of appearance)

ZF 5-6: N'-QLANLAR, DQTTLRR, LQENLTR, DRSSLRR, QSGTLHR, QSGTLHR-C' (SEQ ID NOS 157, 158, 154, 155, 156, and 156, respectively, in order of appearance)

ZF 5-7: N'-NMSNLTR, DRSVLRR, DPSNLAR, DRSSLRR, QSGTLHR, QSGTLHR-C' (SEQ ID NOS 152, 153, 159, 155, 156, and 156, respectively, in order of appearance)

ZF 5-8: N'-QLANLAR, DQTTLRR, DPSNLAR, DRSSLRR, QSGTLHR, QSGTLHR-C' (SEQ ID NOS 157, 158, 159, 155, 156, and 156, respectively, in order of appearance)

Non-limiting examples of the combinations and arrangements of six helices in a single six-finger ZFA where the helices are selected from Group 6 and where the motifs are in an $NH_2$— to COOH— terminus arrangement, (Group 6 ZFA helix combo), are as follows:

ZF 6-1: N'-QQTNLTR, QGGNLAL, DHSSLKR, RADMLRR, DSSNLRR, DQGNLIR-C' (SEQ ID NOS 126, 160, 130, 161, 135, and 136, respectively, in order of appearance)

ZF 6-2: N'-QQTNLTR, QGGNLAL, DHSSLKR, RADMLRR, EKQNLAR, DPSNLRR-C' (SEQ ID NOS 126, 160, 130, 161, 148, and 149, respectively, in order of appearance)

ZF 6-3: N'-QQTNLTR, QKANLGV, DHSSLKR, RADMLRR, DSSNLRR, DQGNLIR-C' (SEQ ID NOS 126, 162, 130, 161, 135, and 136, respectively, in order of appearance)

ZF 6-4: N'-QQTNLTR, QKANLGV, DHSSLKR, RADMLRR, EKQNLAR, DPSNLRR-C' (SEQ ID NOS 126, 162, 130, 161, 148, and 149, respectively, in order of appearance)

ZF 6-5: N'-QQTNLTR, QGGNLAL, DHSSLKR, RLDMLAR, DSSNLRR, DQGNLIR-C' (SEQ ID NOS 126, 160, 130, 163, 135, and 136, respectively, in order of appearance)

ZF 6-6: N'-QQTNLTR, QGGNLAL, DHSSLKR, RLDMLAR, EKQNLAR, DPSNLRR-C' (SEQ ID NOS 126, 160, 130, 163, 148, and 149, respectively, in order of appearance)

ZF 6-7: N'-QQTNLTR, QKANLGV, DHSSLKR, RLDMLAR, DSSNLRR, DQGNLIR-C' (SEQ ID NOS 126, 162, 130, 163, 135, and 136, respectively, in order of appearance)

ZF 6-8: N'-QQTNLTR, QKANLGV, DHSSLKR, RLDMLAR, EKQNLAR, DPSNLRR-C' (SEQ ID NOS 126, 162, 130, 163, 148, and 149, respectively, in order of appearance)

Non-limiting examples of the combinations and arrangements of six helices in a single six-finger ZFA where the helices are selected from Group 7 and where the motifs are in an $NH_2$— to COOH— terminus arrangement, (Group 7 ZFA helix combo), are as follows:

ZF 7-1: N'-QRSSLVR, QRGNLNM, RPQELRR, DHSSLKR, RQDNLGR, DGGNLGR-C' (SEQ ID NOS 131, 164, 165, 130, 166, and 167, respectively, in order of appearance)

ZF 7-2: N'-QRSSLVR, QQGNLQL, RPQELRR, DHSSLKR, RQDNLGR, DGGNLGR-C' (SEQ ID NOS 131, 168, 165, 130, 166, and 167, respectively, in order of appearance)

ZF 7-3: N'-QRSSLVR, QRGNLNM, RRQELTR, DHSSLKR, RQDNLGR, DGGNLGR-C' (SEQ ID NOS 131, 164, 169, 130, 166, and 167, respectively, in order of appearance)

ZF 7-4: N'-QRSSLVR, QQGNLQL, RRQELTR, DHSSLKR, RQDNLGR, DGGNLGR-C' (SEQ ID NOS 131, 168, 169, 130, 166, and 167, respectively, in order of appearance)

ZF 7-5: N'-QRSSLVR, QRGNLNM, RPQELRR, DHSSLKR, RQDNLGR, DPSNLRR-C' (SEQ ID NOS 131, 164, 165, 130, 166, and 149, respectively, in order of appearance)

ZF 7-6: N'-QRSSLVR, QQGNLQL, RPQELRR, DHSSLKR, RQDNLGR, DPSNLRR-C' (SEQ ID NOS 131, 168, 165, 130, 166, and 149, respectively, in order of appearance)

ZF 7-7: N'-QRSSLVR, QRGNLNM, RRQELTR, DHSSLKR, RQDNLGR, DPSNLRR-C' (SEQ ID NOS 131, 164, 169, 130, 166, and 149, respectively, in order of appearance)

ZF 7-8: N'-QRSSLVR, QQGNLQL, RRQELTR, DHSSLKR, RQDNLGR, DPSNLRR-C' (SEQ ID NOS 131, 168, 169, 130, 166, and 149, respectively, in order of appearance)

Non-limiting examples of the combinations and arrangements of six helices in a single six-finger ZFA where the helices are selected from Group 8 and where the motifs are in an $NH_2$— to COOH— terminus arrangement, (Group 8 ZFA helix combo), are as follows:

ZF 8-1: N'-QASNLTR, DHSSLKR, RAHNLLL, QRSSLVR, QSTTLKR, DPSNLRR-C' (SEQ ID NOS 170, 130, 171, 131, 172, and 149, respectively, in order of appearance)

ZF 8-2: N'-QASNLTR, DHSSLKR, RAHNLLL, QRSSLVR, QGTTLKR, DPSNLRR-C' (SEQ ID NOS 170, 130, 171, 131, 173, and 149, respectively, in order of appearance)

ZF 8-3: N'-QRSNLAR, DHSSLKR, RAHNLLL, QRSSLVR, QSTTLKR, DPSNLRR-C' (SEQ ID NOS 174, 130, 171, 131, 172, and 149, respectively, in order of appearance)

ZF 8-4: N'-QRSNLAR, DHSSLKR, RAHNLLL, QRSSLVR, QGTTLKR, DPSNLRR-C' (SEQ ID NOS 174, 130, 171, 131, 173, and 149, respectively, in order of appearance)

Non-limiting examples of the combinations and arrangements of six helices in a single six-finger ZFA where the helices are selected from Group 9 and where the motifs are in an $NH_2$— to COOH— terminus arrangement, (Group 9 ZFA helix combo), are as follows:

ZF 9-1: N'-DSSNLRR, DQGNLIR, RAHNLLL, QRSSLVR, QSTTLKR, DPSNLRR-C' (SEQ ID NOS 135, 136, 171, 131, 172, and 149, respectively, in order of appearance)

ZF 9-2: N'-EKQNLAR, DPSNLRR, RAHNLLL, QRSSLVR, QSTTLKR, DPSNLRR-C' (SEQ ID NOS 148, 149, 171, 131, 172, and 149, respectively, in order of appearance)

ZF 9-3: N'-DSSNLRR, DQGNLIR, RAHNLLL, QRSSLVR, QGTTLKR, DPSNLRR-C' (SEQ ID NOS 135, 136, 171, 131, 173, and 149, respectively, in order of appearance)

ZF 9-4: N'-EKQNLAR, DPSNLRR, RAHNLLL, QRSSLVR, QGTTLKR, DPSNLRR-C' (SEQ ID NOS 148, 149, 171, 131, 173, and 149, respectively, in order of appearance)

A non-limiting example of the combination and arrangement of six helices in a single six-finger ZFA where the helices are selected from Group 10 and where the motif are in an $NH_2$— to COOH— terminus arrangement, (Group 10 ZFA helix combo), is as follows:

ZF 10-1: N'-RRHGLDR, DHSSLKR, VRHNLTR, DHSNLSR, QRSSLVR, ESGHLKR-C' (SEQ ID NOS 175, 130, 147, 150, 131, and 176, respectively, in order of appearance)

A non-limiting example of the combination and arrangement of six helices in a single six-finger ZFA where the helices are selected from Group 11 and where the motif are in an $NH_2$— to COOH— terminus arrangement, (Group 11 ZFA helix combo), is as follows:

ZF 11-1: N'-QLSNLTR, DRSSLKR, QRSSLVR, RLDMLAR, VRHSLTR, ESGAIRR-C' (SEQ ID NOS 177, 178, 131, 163, 179, and 180, respectively, in order of appearance)

Accordingly, provided herein, in some aspects, are engineered synTF or ZF-containing fusion proteins described herein comprising a ZF protein domain, an effector domain, and a regulator protein, wherein the ZF protein domain comprises at least one ZFA having the ZFA helix combo selected from one of the ZFA helix combo Groups 1-11 disclosed herein. Where there are two or more ZFAs, (i.e., a ZF array) in the ZF protein domain, each ZFAs in the domain has a ZFA helix combo selected from one of the ZFA helix combo Groups 1-11 disclosed herein, and the selected ZFA helix combo groups can be different or duplicated for the each ZFAs in the ZF protein domain of the synTF. For example, when a synTF comprises a ZF protein domain consisting essentially of three ZFAs (ZFA-1-ZFA-2-ZFA-3 in a three-ZFA array) and an effector domain, ZFA-1 has a ZFA helix combo selected from the Group 1 ZFA helix combo, ZFA-2 has a ZFA helix combo selected from the Group 5 ZFA helix combo, and ZFA-3 has a ZFA helix combo selected from the Group 7 ZFA helix combo. In other embodiments, the selected ZFA helix combo groups can be duplicated or triplicated for the ZF array in the synTF. For example, in a three-ZFA array-containing ZF protein domain of a synTF, two of the ZFAs comprises ZFA helix combo selected from the same ZFA helix combo group, e.g., Group 2, and the third ZFA has a ZFA helix combo selected from a different ZFA helix combo group, e.g., Group 4. The two ZFAs having ZFA helix combos selected from the same Group 2 ZFA helix combo can have different or the same actual combination and arrangement of the helices ZFAs. For example, when the synTF comprises of a ZF protein domain consisting essentially of five ZFAs (ZFA-1-ZFA-2-ZFA-3-ZFA-4-ZFA-5 in a five-ZFA array) and an effector domain, ZFA-1 has a ZFA helix combo selected from the Group 1 ZFA helix combo, ZFA-2 has a ZFA helix combo selected from the Group 5 ZFA helix combo, ZFA-3 has a ZFA helix combo also selected from the Group 1 ZFA helix combo, ZFA-4 has a ZFA helix combo selected from the Group 4 ZFA helix combo, and ZFA-5 has a ZFA helix combo selected from the Group 2 ZFA helix combo. While ZFA-1 and ZFA-3 both have ZFA helix combo selected from the Group 1 ZFA helix combo, the actual combination and arrangement of the helices within ZFA-1 and ZFA-3 can be different or the same. For example, ZFA-1 and ZFA-3 have the ZFA helix combo ZF 1-1 and ZF 1-5 respectively, or both ZFA-1 and ZFA-3 have the ZFA helix combo ZF 1-1.

In other aspects, provided herein are engineered synTF or a ZF-containing fusion protein described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA having a ZFA helix combo selected from the group consisting of ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2- 8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4- 5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6- 2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7- 7, ZF 7-8, ZF 8-1, ZF 8-2, ZF 8-3, ZF 8-4, ZF 9-1, ZF 9-2, ZF 9-3, ZF 9-4, ZF 10-1, and ZF 11-1 disclosed herein.

In some embodiments of any of the aspects, the ZF protein domain comprises at least one ZFA having a ZFA helix combo selected from the group consisting of ZF1-3, ZF2-6, ZF3-5, ZF4-8, ZF5-7, ZF6-4, ZF7-3, ZF8-1, ZF9-2, ZF10-1, and ZF11-1, which are also referred to herein as ZF1, ZF2, ZF3, ZF4, ZF5, ZF6, ZF7, ZF8, ZF9, ZF10, and ZF 11, respectively.

In some embodiments of any aspect described herein, in the synTF described or any ZF-containing fusion protein described herein, the individual ZFA therein described are specifically designed to bind orthogonal target DNA sequences (also referred to herein as DNA binding motifs) such as the following:

```
Target 1:
                                 (SEQ ID NO: 181)
5' C GTC GAA GTC GAA GTC GAC C 3'

Target 2:
                                 (SEQ ID NO: 182)
5' G GAC GAC GTT ACG GAC GTA C 3'

Target 3:
                                 (SEQ ID NO: 183)
5' A GAC GTC GAA GTA GCC GTA G 3'

Target 4:
                                 (SEQ ID NO: 184)
5' G GAC GAC GCC GAT GTA GAA G 3'

Target 5:
                                 (SEQ ID NO: 185)
5' T GAA GCA GTC GAC GCC GAA G 3'

Target 6:
                                 (SEQ ID NO: 186)
5' G GAC GAC GCG GTC TAA GAA G 3'

Target 7:
                                 (SEQ ID NO: 187)
5' C GAC GAG GTC GCA TAA GTA G 3'

Target 8:
                                 (SEQ ID NO: 188)
5' A GAC GCA GTA TAG GTC GAA C 3'

Target 9:
                                 (SEQ ID NO: 189)
5' A GAC GCA GTA TAG GAC GAC G 3'

Target 10:
                                 (SEQ ID NO: 190)
5' C GGC GTA GCC GAT GTC GCG C 3'

Target 11:
                                 (SEQ ID NO: 191)
5' G GTC GTT GCG GTA GTC GAA G 3'
```

In some embodiments of any the aspects, the ZF binding domain specifically binds to a sequence comprising at least one of SEQ ID NOs: 181-191 or to a nucleic acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 181-191 that maintains the same function.

In some embodiments of any of the aspects, ZF 1-1, ZF 1-2, ZF 1-3, ZF 1-4, ZF 1-5, ZF 1-6, ZF 1-7, and ZF 1-8 bind to Target 1. In some embodiments of any of the aspects, ZF 2-1, ZF 2-2, ZF 2-3, ZF 2-4, ZF 2-5, ZF 2-6, ZF 2-7, and ZF 2-8 bind to Target 2. In some embodiments of any of the aspects, ZF 3-1, ZF 3-2, ZF 3-3, ZF 3-4, ZF 3-5, ZF 3-6, ZF 3-7, and ZF 3-8 bind to Target 3. In some embodiments of any of the aspects, ZF 4-1, ZF 4-2, ZF 4-3, ZF 4-4, ZF 4-5, ZF 4-6, ZF 4-7, ZF 4-8 bind to Target 4. In some embodiments of any of the aspects, ZF 5-1, ZF 5-2, ZF 5-3, ZF 5-4, ZF 5-5, ZF 5-6, ZF 5-7, and ZF 5-8 bind to Target 5. In some embodiments of any of the aspects, ZF 6-1, ZF 6-2, ZF 6-3, ZF 6-4, ZF 6-5, ZF 6-6, ZF 6-7, and ZF 6-8 bind to Target 6. In some embodiments of any of the aspects, ZF 7-1, ZF 7-2, ZF 7-3, ZF 7-4, ZF 7-5, ZF 7-6, ZF 7-7, and ZF 7-8 bind to Target 7. In some embodiments of any of the aspects, ZF 8-1, ZF 8-2, ZF 8-3, and ZF 8-4 bind to Target 8. In some embodiments of any of the aspects, ZF 9-1, ZF 9-2, ZF 9-3, and ZF 9-4 bind to Target 9. In some embodiments of any of the aspects, ZF10-1 binds to Target 10. In some embodiments of any of the aspects, ZF11-1 binds to Target 11.

In one embodiment of any aspect described herein, provided herein is a ZFA that comprises, consists of, or consist essentially of a sequence: N'-[(formula 1)-$L_2]_{6-8}$-C' or a sequence N'-[(formula 2)-$L_2]_{6-8}$-C' that targets a target DNA sequence selected from Target 1-11, wherein the formula 1 is [$X_{0-3}CX_{1-5}CX_{2-7}$-(helix)-$HX_{3-6}H$] (SEQ ID NO: 219) and the formula 2 is [$X_3CX_2CX_5$-(helix)-$HX_3H$] (SEQ ID NO: 220).

In other aspects, provided herein are engineered synTF or the ZF containing fusion protein described herein comprising a ZF protein domain and an effector domain, or comprising a ZF protein domain, an effector domain, and a ligand binding domain, or comprising a ZF protein domain and a ligand binding domain or a dimerization domain, wherein the ZF protein domain comprises at least one ZFA, wherein the an least ZFA comprises, consists of, or consist essentially of a sequence: N'-[(formula 1)-$L_2]_{6-8}$-C' or a sequence N'-[(formula 2)-$L_2]_{6-8}$-C', and wherein the ZFA(s) therein targets a target DNA sequence selected from Target 1-11, wherein the formula 1 is [$X_{0-3}CX_{1-5}CX_{2-7}$-(helix)-$HX_{3-6}H$] (SEQ ID NO: 219) and the formula 2 is [$X_3CX_2CX_5$-(helix)-$HX_3H$] (SEQ ID NO: 220).

In some embodiments of any of the aspects, the ZF binding domain comprises one of SEQ ID NOs: 1-3, or an amino acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 1-3 that maintains the same function.

```
Sequence of ZF1-3 (ZF1)
                                          SEQ ID NO: 1
SRPGERPFQCRICMRNFSEEANLRRHTRTHTGEKPFQCRICMRNFSDHSS

LKRHLRTHTGSQKPFQCRICMRNFSQSANLLRHTRTHTGEKPFQCRICMR

NFSDPSSLKRHLRTHTGSQKPFQCRICMRNFSQQTNLTRHTRTHTGEKPF

QCRICMRNFSDATQLVRHLRTHLRGS,

Sequence of ZF3-5 (ZF3)
                                          SEQ ID NO: 2
SRPGERPFQCRICMRNFSQRSSLVRHTRTHTGEKPFQCRICMRNFSDKSV

LARHLRTHTGSQKPFQCRICMRNFSQRSSLVRHTRTHTGEKPFQCRICMR

NFSQRNNLGRHLRTHTGSQKPFQCRICMRNFSTHAVLTRHTRTHTGEKPF

QCRICMRNFSDRGNLTRHLRTHLRGS,

Sequence of ZF10-1 (ZF10)
                                          SEQ ID NO: 3
SRPGERPFQCRICMRNFSRRHGLDRHTRTHTGEKPFQCRICMRNFSDHSS

LKRHLRTHTGSQKPFQCRICMRNFSVRHNLTRHLRTHTGEKPFQCRICMR

NFSDHSNLSRHLKTHTGSQKPFQCRICMRNFSQRSSLVRHLRTHTGEKPF

QCRICMRNFSESGHLKRHLRTHLRGS,
```

In some embodiments of any of the aspects, the DBD comprises a 3-unit ZF protein. In some embodiments of any of the aspects, the 3-unit ZF protein comprises one of SEQ ID NOs: 221-228 or an amino acid sequence that is at least 60%, at least 65%, at least 70%, at least 75%, at least 80%, at least 85%, at least 90%, at least 95%, at least 96%, at least 97%, at least 98%, or at least 99% identical to one of SEQ ID NOs: 221-228 that maintains the same function.

```
high affinity scaffold (bolded letter shows
mutated residue, and plain text "xxxxxxx"
indicates three ZF helices, e.g., from N terminus:
helix 1, helix 2, helix 3, respectively)
                                    SEQ ID NO: 221
GERPFQCRICMANFSxxxxxxxHTRTHTGEKPFQCRICMANFSxxxxxxx

HLRTHTGEKPFQCRICMANFSxxxxxxxHLKTHLR

low affinity scaffold (bolded letter shows
mutated residue, and bold italic text
indicates helices 1, 2, and 3 respectively)
                                    SEQ ID NO: 222
GEAPFQCRICMANFSxxxxxxxHTRTHTGEKPFQCRICMANFSxxxxxxx

HLRTHTGEKPFQCRICMANFSxxxxxxxHLKTHLR
```

In some embodiments of any of the aspects, the at least one DBD is selected from the group consisting of: 13-6, 14-3, 21-16, 36-4, 37-12, 42-10, 43-8, 54-8, 55-1, 62-1, 92-1, 93-10, 97-4, 129-3, 150-4, 151-1, 158-2, 172-5, and 173-3; see e.g., Khalil et al., Cell Volume 150, Issue 3, 3 Aug. 2012, Pages 647-658; U.S. Pat. No. 10,138,493; US Patent Application US20200002710A1; the contents of each of which are incorporated herein by reference in their entireties. In some embodiments of any of the aspects, the at least one DBD is selected from one or more of any of: 36-4 (SEQ ID NO: 223), 43-8 (SEQ ID NO: 224 or 225), 42-10 (SEQ ID NO: 226-227), 97-4 (SEQ ID NO: 228).

```
36-4 (bold italic text indicates helices 1, 2, and 3 respectively)
                                                              SEQ ID NO: 223
GERPFQCRICMANFS GRQALDRHTRTHTGEKPFQCRICMANFS DKANLTRHLRTHTGEKPFQCRI

CMANFS QRNNLGRHLKTHLR,

43-8 low affinity (bolded letter shows mutated resi-
due, and bold italic text
indicates helices 1, 2, and 3 respectively)
                                                              SEQ ID NO: 224
GEAPFQCRICMANFS RQDRLDRHTRTHTGEKPFQCRICMANFS QKEHLAG HLRTHTGEKPFQCRI

CMANFS RRDNLNRHLKTHLR

43-8 high affinity (bolded letter shows mutated resi-
due, and bold italic text
indicates helices 1, 2, and 3 respectively)
                                                              SEQ ID NO: 225
GERPFQCRICMANFS RQDRLDRHTRTHTGEKPFQCRICMANFS QKEHLAG HLRTHTGEKPFQCRI

CMANFS RRDNLNRHLKTHLR

42-10 low affinity (bolded letter shows mutated residue, and bold italic
text indicates helices 1, 2, and 3 respectively)
                                                              SEQ ID NO: 226
GEAPFQCRICMANFSTGQILDRHTRTHTGEKPFQCRICMANFS VAHSLKRHLRTHTGEKPFQCRTC

MANFS DPSNLRRHLKTHLR

42-10 high affinity (bolded letter shows mutated residue, and bold italic
text indicates helices 1, 2, and 3 respectively)
                                                              SEQ ID NO: 227
GERPFQCRICMANFSTGQILDRHTRTHTGEKPFQCRICMANFS VAHSLKRHLRTHTGEKPFQCRTC

MANFS DPSNLRRHLKTHLR

97-4 (bold italic text indicates helices 1, 2, and 3 respectively)
                                                              SEQ ID NO: 228
GERPFQCRICMRNFS RQSNLSRHTRTHTGEKPFQCRICMRNFS RNEHLVLHLRTHTGEKPFQCRIC

MRNFS QKTGLRV HLKTHLR,
```

In some embodiments of any of the aspects, the DBD binds to DNA binding motifs (DBM) comprising any of: SEQ ID NOs: 229-240.

SEQ ID NO: 229 is an exemplary DBM (DNA binding motif) nucleic acid sequence for 36-4: c GAA GAC GCT g.

SEQ ID NO: 230-SEQ ID NO: 232 are exemplary DBM affinity variant nucleic acid sequences for 43-8. Bold text indicates residues mutated from the WT sequence. SEQ ID NO: 230 is 43-8 DBM1-aGAGTGAGGAc. SEQ ID NO: 231 is 43-8 DBM2-aCAGTGAGGAc. SEQ ID NO: 232 is 43-8 DBM3-aTAGTGAGGAc.

SEQ ID NOS 233-239 are exemplary DBM affinity variant nucleic acid sequences for 42-10. Bold text indicates residues mutated from the WT sequence. SEQ ID NO: 233 is 42-10 DBM1-aGACGCTGCTc. SEQ ID NO: 234 is 42-10 DBM2-tGACGCTGCTt. SEQ ID NO: 235 is 42-10 DBM3-aGACGGTGCTc. SEQ ID NO: 236 is 42-10 DBM4-aCACGCTGCTc. SEQ ID NO: 237 is 42-10 DBM5-aGACGCTACTc. SEQ ID NO: 238 is 42-10 DBM6-aGACGCTGCTa. SEQ ID NO: 239 is 42-10 DBM7-aGACTCTGCTc.

SEQ ID NO: 240 is an exemplary DBM (DNA binding motif) nucleic acid sequence for 97-4: a TTA TGG GAG a.

Repressible Protease Domain

In some embodiments of any of the aspects, a synTF as described herein comprises a regulator protein, wherein the regulator protein is a repressible protease domain (referred to herein as PRO or RPD). As used herein, the term "repressible protease" refers to a protease that can be inactivated by the presence or absence of a specific agent (e.g., that specifically binds to the protease). In some embodiments, a repressible protease is active (e.g., cleaves a protease cleavage site) in the absence of the specific agent and is inactive (e.g., does not cleave a protease cleavage site) in the presence of the specific agent. In some embodiments, the specific agent is a protease inhibitor. In some embodiments, the protease inhibitor specifically inhibits a given repressible protease as described herein.

In some embodiments of any of the aspects, a synTF polypeptide as described herein (or a synTF polypeptide system collectively) comprises 1, 2, 3, 4, 5, or more repressible protease(s). In some embodiments of any of the aspects, the synTF polypeptide or system comprises one repressible protease. In embodiments comprising multiple repressible proteases, the multiple repressible proteases can be different individual repressible proteases or multiple copies of the same repressible protease, or a combination of the foregoing.

Non-limiting examples of repressible proteases include hepatitis C virus proteases (e.g., NS3 and NS2-3); HIV1 protease; coronavirus (main) protease; Tobacco etch virus (TEV) protease; signal peptidase; proprotein convertases of the subtilisin/kexin family (furin, PCI, PC2, PC4, PACE4, PC5, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N; insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; T F alpha secretase; FAS ligand secretase; TNF receptor-I and -II secretases; CD30 secretase; KL1 and KL2 secretases; IL6 receptor secretase; CD43, CD44 secretase; CD 16-1 and CD 16-11 secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H. For a discussion of proteases, see, e.g., V. Y. H. Hook, Proteolytic and cellular mechanisms in prohormone and proprotein processing, RG Landes Company, Austin, Tex., USA (1998); N. M. Hooper et al., Biochem. J. 321: 265-279 (1997); Z. Werb, Cell 9 1: 439-442 (1997); T. G. Wolfsberg et al., J. Cell Biol. 131: 275-278 (1995); K. Murakami and J. D. Etlinger, Biochem. Biophys. Res. Comm. 146: 1249-1259 (1987); T. Berg et al., Biochem. J. 307: 313-326 (1995); M. J. Smyth and J. A. Trapani, Immunology Today 16: 202-206 (1995); R. V. Talanian et al., J. Biol. Chem. 272: 9677-9682 (1997); and N. A. Thomberry et a, J. Biol. Chem. 272: 17907-1791 1 (1997); International Patent Application WO2019118518; Rajakuberan et al., Methods Mol Biol. 2012; 903:393-405; Gao et al. Science 21 Sep. 2018: Vol. 361, Issue 6408, pp. 1252-1258; Tague et al., Nat Methods. 2018 July; 15(7):519-522; Lin et al. PNAS Jun. 3, 2008 105 (22) 7744-7749; U.S. patent application Ser. No. 16/832,751 filed Mar. 27, 2020; the contents of each of which are incorporated herein by reference in their entireties.

In some embodiments of any of the aspects, the repressible protease is hepatitis C virus (HCV) nonstructural protein 3 (NS3). NS3, also known as p-70, is a viral nonstructural protein that is a 70 kDa cleavage product of the hepatitis C virus polyprotein. The 631-residue HCV NS3 protein is a dual-function protein, containing the trypsin/chymotrypsin-like serine protease in the N-terminal region and a helicase and nucleoside triphosphatase in the C-terminal region. The minimal sequences required for a functional serine protease activity comprise the N-terminal 180 amino acids of the NS3 protein, which can also be referred to as "NS3a". Deletion of up to 14 residues from the N terminus of the NS3 protein is tolerated while maintaining the serine protease activity. Accordingly, the repressible proteases described herein comprise at the least residues 14-180 of the wildtype NS3 protein.

HCV has at least seven genotypes, labeled 1 through 7, which can also be further designated with "a" and "b" subtypes. Accordingly, the repressible protease can be an HCV genotype 1 NS3, an HCV genotype 1a NS3, an HCV genotype 1b NS3, an HCV genotype 2 NS3, an HCV genotype 2a NS3, an HCV genotype 2b NS3, an HCV genotype 3 NS3, an HCV genotype 3a NS3, an HCV genotype 3b NS3, an HCV genotype 4 NS3, an HCV genotype 4a NS3, an HCV genotype 4b NS3, an HCV genotype 5 NS3, an HCV genotype 5a NS3, an HCV genotype 5b NS3, an HCV genotype 6 NS3, an HCV genotype 6a NS3, an HCV genotype 6b NS3, an HCV genotype 7 NS3, an HCV genotype 7a NS3, or an HCV genotype 7b NS3. In some embodiments of any of the aspects, the repressible protease can be any known HCV NS3 genotype, variant, or mutant, e.g., that maintains the same function. In some embodiments of any of the aspects, the NS3 sequence comprises residues 1-180 of the NS3 protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin, Chapter 6: HCV NS3-4A Serine Protease, Hepatitis C Viruses: Genomes and Molecular Biology, Editor: Tan S L, Norfolk (UK): Horizon Bioscience, 2006; the content of which is incorporated herein by reference in its entirety). In some embodiments of any of the aspects, the repressible protease is a chimera of 2, 3, 4, 5, or more different NS3 genotypes, variants, or mutants as described herein, such that the protease maintains its cleavage and/or binding functions.

In some embodiments of any of the aspects, the repressible protease of a synTF polypeptide as described herein comprises SEQ ID NOs: 82, 91, 241-255 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 82, 91, 241-255 that maintains the same function.

In some embodiments of any of the aspects, the repressible protease of a synTF polypeptide as described herein does not comprise at most the first (i.e., N-terminal) residues of SEQ ID NOs: 82, 91, 241-255. In some embodiments of any of the aspects, the repressible protease of a synTF polypeptide as described herein comprises residues 1-180, 2-180, 3-180, 4-180, 5-180, 6-180, 7-180, 8-180, 9-180, 10-180, 11-180, 12-180, 13-180, 14-180, 15-180, 16-180, 17-180, 18-180, 19-180, 20-180, 21-180, 22-180, 23-180, 24-180, 25-180, 26-180, 27-180, 28-180, 29-180, or 30-180 of SEQ ID NOs: 82, 91, 241-255.

NS3 (genotype 1A), 189 aa; bold text indicates His-57 of the catalytic triad; *italicized double underlined text* indicates Asp-81 of the catalytic triad; *bold italicized* indicates Ser-139 of the catalytic triad; double underlined text indicates Asp-168.

SEQ ID NO: 82

APITAYAQQTRGLLGCIITSLTGRDKNQVEGEVQIVSTATQTFLATCINGVCWAVYHGAGTRTIA

SPKGPVIQMYTNVDQ*D*LVGWPAPQGSRSLTPCTCGSSDLYLVTRHADVIPVRRRGDSRGSLLSPR

PISYLKGS*S*GGPLLCPAGHAVGLFRAAVCTRGVAKAVDFIPVENLETTMRSPVFTDNSS,

NS3 protease domain (genotype 1A)

SEQ ID NO: 91

APITAYAQQTRGLLGCIITSLTGRDKNQVEGEVQIVSTATQTFLATCINGVCWAVYHGAGTRTIA

SPKGPVIQMYTNVDQDLVGWPAPQGSRSLTPCTCGSSDLYLVTRHADVIPVRRRGDSRGSLLSPR

PISYLKGSSGGPLLCPAGHAVGLFRAAVCTRGVAKAVDFIPVENLETTMRSPVFTD,

NS3 (genotype 1A), 180 aa (see e.g., residues 1027-1206 of Hepatitis C virus genotype 1 polyprotein, NCBI Reference Sequence: NP_671491.1.

SEQ ID NO: 241

APITAYAQQTRGLLGCIITSLTGRDKNQVEGEVQIVSTATQTFLATCINGVCWTVYHGAGTRTIA

SPKGPVIQMYTNVDQDLVGWPAPQGSRSLTPCTCGSSDLYLVTRHADVIPVRRRGDSRGSLLSPR

PISYLKGSSGGPLLCPAGHAVGLFRAAVCTRGVAKAVDFIPVENLETTMR,

NS3 (genotype 1B), 180 aa (see e.g., residues 1-180 Chain A. Ns3 Protease, PDB: 4K8B_A)

SEQ ID NO: 242

APITAYSQQTRGLLGCIITSLTGRDKNQVEGEVQVVSTATQSFLATCVNGVCWTVYHGAGSKTLA

GPKGPITQMYTNVDQDLVGWQAPPGARSLTPCTCGSSDLYLVTRHADVIPVRRRGDSRGSLLSP

RPVSYLKGSSGGPLLCPSGHAVGIFRAAVCTRGVAKAVDFVPVESMETTMR,

NS3 (genotype 2), 180 aa (see e.g., residues 1031-1210 of Hepatitis C virus genotype 2 polyprotein, NCBI Reference Sequence: YP_001469630.1

SEQ ID NO: 243

APITAYAQQTRGLLGTIVVSMTGRDKTEQAGEIQVLSTVTQSFLGTSISGVLWTVYHGAGNKTLA

GSRGPVTQMYSSAEGDLVGWPSPPGTKSLEPCTCGAVDLYLVTRNADVIPARRRGDKRGALLSPR

PLSTLKGSSGGPVLCPRGHAVGVFRAAVCSRGVAKSIDFIPVETLDIVTR,

NS3 (genotype 3), 180 aa (see e.g., residues 1033-1212 of Hepatitis C virus genotype 3 polyprotein, NCBI Reference Sequence: YP_001469631.1)

SEQ ID NO: 244

APITAYAQQTRGLLGTIVTSLTGRDKNVVTGEVQVLSTATQTFLGTTVGGVIWTVYHGAGSRTL

AGAKHPALQMYTNVDQDLVGWPAPPGAKSLEPCACGSSDLYLVTRDADVIPARRRGDSTASLLS

PRPLACLKGSSGGPVMCPSGHVAGIFRAAVCTRGVAKSLQFIPVETLSTQAR,

NS3 (genotype 4), 180 aa (see e.g., residues 1027-1206 of Hepatitis C virus genotype 4 polyprotein, NCBI Reference Sequence: YP_001469632.1)

SEQ ID NO: 245

APITAYAQQTRGLFSTIVTSLTGRDTNENCGEVQVLSTATQSFLGTAVNGVMWTVYHGAGAKTI

SGPKGPVNQMYTNVDQDLVGWPAPPGVRSLAPCTCGSADLYLVTRHADVIPVRRRGDTRGALLS

PRPISILKGS SGGPLLCPMGHRAGIFRAAVCTRGVAKAVDFVPVESLETTMR,

NS3 (genotype 5), 180 aa (see e.g., residues 1028-1207 of Hepatitis C virus genotype 5 polyprotein, NCBI Reference Sequence: YP_001469633.1)

SEQ ID NO: 246

APITAYAQQTRGVLGAIVLSLTGRDKNEAEGEVQFLSTATQTFLGICINGVMWTLFHGAGSKTLA

GPKGPVVQMYTNVDKDLVGWPSPPGKGSLTRCTCGSADLYLVTRHADVIPARRRGDTRASLLSPR

PISYLKGSSGGPIMCPSGHVVGVFRAAVCTRGVAKALEFVPVENLETTMR,

-continued

NS3 (genotype 6), 180 aa (see e.g., residues 1032-1211 of Hepatitis C virus genotype 6 polyprotein, NCBI Reference Sequence: YP_001469634.1)

SEQ ID NO: 247

APITAYAQQTRGLVGTIVTSLTGRDKNEAEGEVQVVSTATQSFLATTINGVLWTVYHGAGSKNL

AGPKGPVCQMYTNVDQDLVGWPAPLGARSLAPCTCGSSDLYLVTRGADVIPARRRGDTRAALLS

PRPISTLKGSSGGPLMCPSGHVVGLFRAAVCTRGVAKALDFIPVENMDTTMR,

NS3 (genotype 7), 180 aa (see e.g., residues 1031-1210 of Hepatitis C virus genotype 7 polyprotein, NCBI Reference Sequence: YP_009272536.1)

SEQ ID NO: 248

APISAYAQQTRGLISTLVVSLTGRDKNETAGEVQVLSTSTQTFLGTNVGGVMWGPYHGAGTRTV

AGRGGPVLQMYTSVSDDLVGWPAPPGSKSLEPCSCGSADLYLVTRNADVLPLRRKGDGTASLLS

PRPVSSLKGSSGGPVLCPQSHCVGIFRAAVCTRGVAKAVQFVPIEKMQVAQR,

NS3 genotype 1a (HCV-H), 180 aa

SEQ ID NO: 249

APITAYAQQTRGLLGCIITSLTGRDKNQVEGEVQIVSTATQTFLATCINGVCWTVYHGAGTRTI

ASPKGPVIQMYTNVDQDLVGWPAPQGSRSLTPCTCGSSDLYLVTRHADVIPVRRRGDSRGSLLS

PRPISYLKGSSGGPLLCPAGHAVGLFRAAVCTRGVTKAVDFIPVENLETTMR,

NS3 genotype 1b (HCV-BK), 180 aa

SEQ ID NO: 250

APITAYSQQTRGLLGCIITSLTGRDKNQVEGEVQVVSTATQSFLATCVNGVCWTVYHGAGSKTL

AAPKGPITQMYTNVDQDLVGWPKPPGARSLTPCTCGSSDLYLVTRHADVIPVRRRGDSRGSLLS

PRPVSYLKGSSGGPLLCPFGHAVGIFRAAVCTRGVAKAVDFVPVESMETTMR,

NS3 genotype 2a (HCV-J6), 180 aa

SEQ ID NO: 251

APITAYAQQTRGLLGTIVVSMTGRDKTEQAGEIQVLSTVTQSFLGTTISGVLWTVYHGAGNKTL

AGSRGPVTQMYSSAEGDLVGWPSPPGTKSLEPCTCGAVDLYLVTRNADVIPARRRGDKRGALLS

PRPLSTLKGSSGGPVLCPRGHAVGVFRAAVCSRGVAKSIDFIPVETLDIVTR,

NS3 genotype 2b (HCV-J8), 180 aa

SEQ ID NO: 252

APITAYTQQTRGLLGAIVVSLTGRDKNEQAGQVQVLSSVTQTFLGTSISGVLWTVYHGAGNKTL

AGPKGPVTQMYTSAEGDLVGWPSPPGTKSLDPCTCGAVDLYLVTRNADVIPVRRKDDRRGALLS

PRPLSTLKGSSGGPVLCSRGHAVGLFRAAVsynTFGVAKSIDFIPVESLDVATR,

NS3 genotype 3a (HCV-Nz11), 180 aa

SEQ ID NO: 253

APITAYAQQTRGLLGTIVTSLTGRDKNVVTGEVQVLSTATQTFLGTTVGGVIWTVYHGAGSRTL

AGAKHPALQMYTNVDQDLVGWPAPPGAKSLEPCACGSSDLYLVTRDADVIPARRRGDSTASLLS

PRPLACLKGSSGGPVMCPSGHVAGIFRAAVCTRGVAKSLQFIPVETLSTQAR,

In some embodiments of any of the aspects, a repressible protease as described herein is resistant to 1, 2, 3, 4, 5, or more different protease inhibitors as described herein. Non-limiting examples of NS3 amino acid substitutions conferring resistance to HCV NS3 protease inhibitors include: V36L (e.g., genotype 1b), V36M (e.g., genotype 2a), T54S (e.g., genotype 1b), Y56F (e.g., genotype 1b), Q80L (e.g., genotype 1b), Q80R (e.g., genotype 1b), Q80K (e.g., genotype 1a, 1b, 6a), Y1321 (e.g., genotype 1b), A156S (e.g., genotype 2a), A156G, A156T, A156V, D168A (e.g., genotype 1b), 1170V (e.g., genotype 1b), S20N, R26K, Q28R, A39T, Q41R, I71V, Q80R, Q86R, P89L, P89S, S101N, All IS, P115S, S122R, R155Q, L144F, A150V, R155W, V158L, D168A, D168G, D168H, D168N, D168V, D168E, D168Y, E176K, T178S, M179I, M179V, and M179T. See e.g., Sun et al., Gene Expr. 2018, 18(1): 63-69; Kliemann et al., World J Gastroenterol. 2016 Oct. 28, 22(40): 8910-8917; U.S. Pat. Nos. 7,208,309; 7,494,660; the contents of each of which are incorporated herein by reference in their entireties.

In some embodiments of any of the aspects, a synTF polypeptide as described herein comprises an NS3 protease comprising at least one resistance mutation as described herein or any combination thereof. In some embodiments of any of the aspects, a synTF polypeptide as described herein comprises an NS3 protease that is resistant to one protease inhibitor but responsive to at least one other protease inhibitor. In some embodiments of any of the aspects, a synTF system comprises: (a) a first synTF polypeptide comprising a repressible protease (e.g., NS3) that is resistant to a first protease inhibitor and that is susceptible to a second protease inhibitor; and (b) a second synTF polypeptide comprising a repressible protease (e.g., NS3) that is susceptible to a first protease inhibitor and that is resistant to a second protease inhibitor. Accordingly, presence of the first protease inhibitor can modulate the activity of the second synTF polypeptide but not the first synTF polypeptide, while the presence of the second protease inhibitor can modulate the activity of the first synTF polypeptide but not the second synTF polypeptide.

In some embodiments of any of the aspects, a repressible protease as described herein is sensitive to 1, 2, 3, 4, 5, or more different protease inhibitors as described herein. In some embodiments of any of the aspects, the NS3 protease comprises at least one of the following mutations: V36M, T54A, S122G, F43L, Q80K, S122R, D168Y, or any combination thereof. In some embodiments of any of the aspects, the NS3 protease comprises at least one of the following mutations: V36M, T54A, S122G, or any combination thereof, such a protease is also referred to herein as $NS3^{AI}$, as these mutations increase its sensitivity to asunaprevir (see e.g., SEQ ID NO: 254). In some embodiments of any of the aspects, the NS3 protease comprises at least one of the following mutations: F43L, Q80K, S122R, D168Y, or any combination thereof, such a protease is also referred to herein as $NS3^{TI}$, as these mutations increase its sensitivity to telaprevir (see e.g., SEQ ID NO: 255). See e.g., WO2019023164; Jacobs et al., StaPLs: versatile genetically encoded modules for engineering drug-inducible proteins, Nat Methods. 2018 July; 15(7): 523-526; the contents of each of each are incorporated herein by reference in their entireties.

$NS3^{AI}$; the V36M, T54A, S122G mutations are shown in bold double underlined text, respectively

SEQ ID NO: 254

APITAYAQQTRGLLGCIITSLTGRDKNQVEGEVQIMSTATQTFLATC

INGVCWAVYHGAGTRTIASPKGPVIQMYTNVDQDLVGWPAPQGSRSL

TPCTCGSSDLYLVTRHADVIPVRRRGDGRGSLLSPRPISYLKGSSGG

PLLCPAGHAVGLFRAAVCTRGVAKAVDFIPVENLETTMRSPVFTD, $NS3^{TI}$; the F43L, Q80K, S122R, D168Y mutations are shown in bold double underlined text, respectively

SEQ ID NO: 255

APITAYAQQTRGLLGCIITSLTGRDKNQVEGEVQIVSTATQTLLATC

INGVCWAVYHGAGTRTIASPKGPVIQMYTNVDKDLVGWPAPQGSRSL

TPCTCGSSDLYLVTRHADVIPVRRRGDRRGSLLSPRPISYLKGSSGG

PLLCPAGHAVGLFRAAVCTRGVAKAVYFIPVENLETTMRSPVFTD,

In some embodiments of any of the aspects, the polypeptide further comprising a cofactor for the repressible protease. As used herein the term "cofactor for the repressible protease" refers to a molecule that increases the activity of the repressible protease. In some embodiments of any of the aspects, a synTF polypeptide as described herein comprises 1, 2, 3, 4, 5, or more cofactors for the repressible protease. In some embodiments of any of the aspects, the synTF polypeptide comprises one cofactor for each repressible protease. In embodiments comprising multiple cofactors for the repressible protease, the multiple cofactors for the repressible protease can be different individual cofactors or multiple copies of the same cofactor, or a combination of the foregoing.

In some embodiments of any of the aspects, the cofactor is an HSV NS4A domain, and the repressible protease is HSV NS3. The nonstructural protein 4a (NS4A) is the smallest of the nonstructural HCV proteins. The NS4A protein has multiple functions in the HCV life cycle, including (1) anchoring the NS3-4A complex to the outer leaflet of the endoplasmic reticulum and mitochondrial outer membrane, (2) serving as a cofactor for the NS3A serine protease, (3) augmenting NS3A helicase activity, and (4) regulating NS5A hyperphosphorylation and viral replication. The interactions between NS4A and NS4B control genome replication and between NS3 and NS4A play a role in virus assembly.

In some embodiments of any of the aspects, a synTF polypeptide as described herein comprises the portion of the NS4a polypeptide that serves as a cofactor for NS3. Deletion analysis has shown that the central region (approximately residues 21 to 34) of the 54-residue NS4A protein is essential and sufficient for the cofactor function of the NS3 serine protease. Accordingly, in some embodiments of any of the aspects, the repressible protease cofactor comprises a 14-residue region of the wildtype NS4A protein.

In some embodiments of any of the aspects, the cofactor for the repressible protease can be an HCV genotype 1 NS4A, an HCV genotype 1a NS4A, an HCV genotype 1b NS4A, an HCV genotype 2 NS4A, an HCV genotype 2a NS4A, an HCV genotype 2b NS4A, an HCV genotype 3 NS4A, an HCV genotype 3a NS4A, an HCV genotype 3b NS4A, an HCV genotype 4 NS4A, an HCV genotype 4a NS4A, an HCV genotype 4b NS4A, an HCV genotype 5 NS4A, an HCV genotype 5a NS4A, an HCV genotype 5b NS4A, an HCV genotype 6 NS4A, an HCV genotype 6a NS4A, an HCV genotype 6b NS4A, an HCV genotype 7 NS4A, an HCV genotype 7a NS4A, or an HCV genotype 7b NS4A. In some embodiments of any of the aspects, the cofactor for the repressible protease can be any known NS4A genotype, variant, or mutant, e.g., that maintains the same function. In some embodiments of any of the aspects, the NS4A sequence comprises residues 21-31 of the NS4A protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin 2006 supra; see e.g., Table 13).

In some embodiments of any of the aspects, the cofactor for a repressible protease of a synTF polypeptide as described herein comprises SEQ ID NOs: 48, 98, 137-156, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 48, 98, 137-156 that maintains the same functions as one of SEQ ID NOs: 48, 98, 137-156. In some embodiments of any of the aspects, the cofactor for a repressible protease of a synTF polypeptide as described herein comprises SEQ ID NOs: 81, 93, 96, 255-276, or an amino acid sequence that is at least 95% identical to the sequence of one of SEQ ID NOs: 81, 93, 96, 255-276 that maintains the same function.

In some embodiments of any of the aspects, the cofactor for the repressible protease of a synTF polypeptide as described herein comprises residues 1-14, 1-13, 1-12, 1-11, 1-10, 2-14, 2-13, 2-12, 2-11, 2-10, 3-14, 3-13, 3-12, 3-11, 3-10, 4-14, 4-13, 4-12, 4-11, or 4-10 of any of SEQ ID NOs: 81, 93, 96, 255-276.

NS4A (genotype 1A), 13 aa,

SEQ ID NO: 81

GCVVIVGRIVLSG,

NS4A domain (genotype 1a)

SEQ ID NO: 93

STWVLVGGVLAALAAYCLSTGCVVIVGRIVLSGKPAIIPDREVLY,

NS4 (with L6 linker in bold text)

SEQ ID NO: 96

STWVLVGGVLAALAAYCLSTGCVVIVGRIVLSGKPAGSSGSSIIPDREV

LY,

NS4A domain,

SEQ ID NO: 106

IDTKYIMTCMSADLEVVTSTWVLVGGVLAALAAYCLSTGCVVIVGRIVL

SGKPAIIPDREVLY,

NS4A (genotype 1B), 12 aa,

SEQ ID NO: 256

GSVVIVGRIILS;,
see e.g., Chain C, Nonstructural Protein, PDB: 4K8B_C.

NS4A (genotype 1), 14 aa
(see e.g., residues 1678-1691 of Hepatitis C virus genotype 1 polyprotein, NCBI Reference Sequence: NP_671491.1):

SEQ ID NO: 257

GCVVIVGRIVLSGK,

NS4A (genotype 2), 14 aa
(see e.g., residues 1682-1695 of Hepatitis C virus genotype 2 polyprotein, NCBI Reference Sequence: YP_001469630.1):

SEQ ID NO: 258

GCVCIIGRLHINQR,

-continued

NS4A (genotype 3), 14 aa
(see e.g., residues 1684-1697 of Hepatitis C virus genotype 3 polyprotein, NCBI Reference Sequence: YP_001469631.1):

SEQ ID NO: 259

GCVVIVGHIELEGK,

NS4A (genotype 4), 14 aa
(see e.g., residues 1678-1691 of Hepatitis C virus genotype 4 polyprotein, NCBI Reference Sequence: YP_001469632.1):

SEQ ID NO: 260

GSVVIVGRVVLSGQ,

NS4A (genotype 5), 14 aa
(see e.g., residues 1679-1692 of Hepatitis C virus genotype 5 polyprotein, NCBI Reference Sequence: YP_001469633.1):

SEQ ID NO: 261

GSVAIVGRIILSGR,

NS4A (genotype 6), 14 aa
(see e.g., residues 1683-1696 of Hepatitis C virus genotype 6 polyprotein, NCBI Reference Sequence: YP_001469634.1):

SEQ ID NO: 262

GCVVIVGRIVTSGK,

NS4A (genotype 7), 14 aa
(see e.g., residues 1682-1695 of Hepatitis C virus genotype 7 polyprotein, NCBI Reference Sequence: YP_001469636.1):

SEQ ID NO: 263

GSVVVVGRVVLGSN,

In some embodiments of any of the aspects, the NS4A sequence is selected from Table 13. In one embodiment, the NS4A comprises residues 21-31 of SEQ ID NO: 264-276 or a sequence that is at least 70% identical.

TABLE 13

Exemplary NS4A sequences (see e.g., Chao Lin 2006 supra). Residues 21-31 are bolded.

| SEQ ID NO | Genotype (strain) | Sequence |
|---|---|---|
| 264 | 1a (HCV-H) | STWVL VGGVL AALAA YCLST **GCVVI VGRIV LS**GKP AIIPD REVLY QEFDE MEEC |
| 265 | 1a (HCV-1) | STWVL VGGVL AALAA YCLST **GCVVI VGRVV LS**GKP AIIPD REVLY REFDE MEEC |
| 266 | 1a (HCV-J1) | STWVL VGGVL AALAA YCLST **GCVVI VGRIV LS**GRP AIIPD REVLY REFDE MEEC |
| 267 | 1b (HCV-BK) | STWVL VGGVL AALAA YCLTT **GSVVI VGRII LS**GRP AIVPD RELLY QEFDE MEEC |
| 268 | 1b (HCV-JK1) | STWVL VGGVL AALAA YCLTT **GSVVI VGRII LS**GRP AIIPD RELLY QEFDE MEEC |
| 269 | 1b (HCV-J4) | STWVL VGGVL AALAA YCLTT **GSVVI VGRII LS**GKP AVVPD RELLY QEFDE MEEC |
| 270 | 1b (HCV-J) | STWVL VGGVL AALAA YCLTT **GSVVI VGRII LS**GRP AVIPD RELLY REFDE MEEC |
| 271 | 2a (HCV-J6) | STWVL AGGVL AAVAA YCLAT **GCVCI IGRLH VN**QRA VVAPD KEVLY EAFDE MEEC |
| 272 | 2a (D14112) | STWVL AGGVL AAVAA YCLAT **GCVSI IGRLH IN**GRA VVAPD KEVLY EAFDE MEEC |
| 273 | 2b (HCV-J8) | SSWVL AGGVL AAVAA YCLAT **GCISI IGRLH LN**DRV VVAPD KEILY EAFDE MEEC |
| 274 | 2b (D14114) | STWVL AGGVL AAVAA YCLAT **GCVSI IGRLH LN**DQV VVTPD KEILY EAFDE MEEC |
| 275 | 3a (HCV-Nz11) | STWVL LGGVL AALAA YCLSV **GCVVI VGHIE LE**GKP ALVPD KEVLY QQYDE MEEC |
| 276 | 3a (HCV-K3a) | STWVL LGGVL AAVAA YCLSV **GCVVI VGHIE LG**GKP ALVPD KEVLY QQYDE MEEC |

In some embodiments of any of the aspects, a synTF polypeptide as described herein can comprise any combination of NS3 and NS4A genotypes, variants, or mutants as described herein. In one embodiment, the NS3 and NS4A are selected from selected from the same genotype as each other. In some embodiments of any of the aspects, the NS3 is genotype 1a and the NS4A is genotype 1b. In some embodiments of any of the aspects, the NS3 is genotype 1b and the NS4A is genotype 1a.

In some embodiments of any of the aspects, a synTF polypeptide as described herein comprises an HSV NS4A domain adjacent to the NS3 repressible protease. In some embodiments of any of the aspects, the NS4A domain is N-terminal of the NS3 repressible protease. In some embodiments of any of the aspects, the NS4A domain is C-terminal of the NS3 repressible protease. In some embodiments of any of the aspects, the synTF polypeptide comprises a peptide linker between the NS4A domain and the NS3 repressible protease. Non-limiting examples of linker (e.g., between the NS4A domain and the NS3 repressible protease) include: SGTS (SEQ ID NO: 277) and GSGS (SEQ ID NO: 278).

In some embodiments of any of the aspects, any two domains as described herein in a synTF polypeptide can be joined into a single polypeptide by positioning a peptide linker, e.g., a flexible linker between them. As used herein "peptide linker" refers to an oligo- or polypeptide region from about 2 to 100 amino acids in length, which links together any of the sequences of the polypeptides as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable.

Described herein are synTF polypeptides comprising protease cleavage sites. As used herein, the term "protease cleavage site" refers to a specific sequence or sequence motif recognized by and cleaved by the repressible protease. A cleavage site for a protease includes the specific amino acid sequence or motif recognized by the protease during proteolytic cleavage and typically includes the surrounding one to six amino acids on either side of the scissile bond, which bind to the active site of the protease and are used for recognition as a substrate. In some embodiments of any of the aspects, the protease cleavage site can be any site specifically bound by and cleaved by the repressible protease. In some embodiments of any of the aspects, a synTF polypeptide as described herein (or the synTF polypeptide system collectively) comprises 1, 2, 3, 4, 5, or more protease cleavage sites. In some embodiments of any of the aspects, the synTF polypeptide comprises two protease cleavage sites. In embodiments comprising multiple protease cleavage sites, the multiple protease cleavage sites can be different individual protease cleavage sites or multiple copies of the same protease cleavage sites, or a combination of the foregoing.

As a non-limiting example, during HCV replication, the NS3-4A serine protease is responsible for the proteolytic cleavage at four junctions of the HCV polyprotein precursor: NS3/NS4A (self-cleavage), NS4A/NS4B, NS4B/NS5A, and NS5A/NS5B. Accordingly, the protease cleavage site of a synTF polypeptide as described herein can be a NS3/NS4A cleavage site, a NS4A/NS4B cleavage site, a NS4B/NS5A cleavage site, or a NS5A/NS5B cleavage site. The protease cleavage site can be a protease cleavage sites from HCV genotype 1, genotype 1a, genotype 1b, genotype 2, genotype 2a, genotype 2b, genotype 3, genotype 3a, genotype 3b, genotype 4, genotype 4a, genotype 4b, genotype 5, genotype 5a, genotype 5b, genotype 6, genotype 6a, genotype 6b, genotype 7, genotype 7a NS4A, or genotype 7b. In some embodiments of any of the aspects, the protease cleavage site can be any known NS3/NS4A protease cleavage site or variant or mutant thereof, e.g., that maintains the same function. In some embodiments of any of the aspects, the NS4A sequence comprises residues 21-31 of the NS4A protein from HCV-H, HCV-1, HCV-J1, HCV-BK, HCV-JK1, HCV-J4, HCV-J, HCV-J6, C14112, HCV-J8, D14114, HCV-Nz11, or HCV-K3a (see e.g., Chao Lin 2006 supra).

In some embodiments of any of the aspects, the protease cleavage site of a synTF polypeptide as described herein comprises SEQ ID NOs: 78, 83, 87, 279-301, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 78, 83, 87, 279-301 that maintains the same function.

In some embodiments of any of the aspects, the protease cleavage site of a synTF polypeptide as described herein comprises residues 1-20, 1-19, 1-18, 1-17, 1-16, 1-15, 2-20, 2-19, 2-18, 2-17, 2-16, 2-15, 3-20, 3-19, 3-18, 3-17, 3-16, 3-15, 4-20, 4-19, 4-18, 4-17, 4-16, 4-15, 5-20, 5-19, 5-18, 5-17, 5-16, or 5-15, of any of SEQ ID NOs: 78, 83, 87, 279-301.

NS5A/5B cut site (CC), 10 aa,
SEQ ID NO: 78
EDVVCCHSIY,

NS4A/4B cut site (CS), 14 aa,
SEQ ID NO: 83
LYQEFDEMEECSQH,

N3 cleavage site (NS4A/4B cut site),
SEQ ID NO: 87
DEMEECSQHL,

SEQ ID NO: 279
QEFEDVVPCSMGS,

NS5A/5B cut site,
SEQ ID NO: 280
EDVVCCHSI,

NS4A/4B cut site,
SEQ ID NO: 281
DEMEECSQH,

TABLE 14

Exemplary NS3/NS4A protease cleavage sites (see e.g., Chao Lin 2006 supra).

| Cleavage Site Type | SEQ ID NO | Genotype (Strain) | Sequence (cleavage site shown with space) |
|---|---|---|---|
| NS3/NS4A | 282 | 1a (HCV-H) | CMSADLEVVT STWVLVGGVL |
| | 283 | 1b (HCV-BK) | CMSADLEVVT STWVLVGGVL |
| | 284 | 2a (HCV-J6) | CMQADLEVMT STWVLAGGVL |
| | 285 | 2b (HCV-J8) | CMQADLEIMT SSWVLAGGVL |
| | 286 | 3a (HCV-Nz11) | CMSADLEVTT STWVLLGGVL |
| NS4A/NS4B | 287 | 1a (HCV-H) | YQEFDEMEEC SQHLPYIEQG |
| | 288 | 1b (HCV-BK) | YQEFDEMEEC ASHLPYIEQG |
| | 289 | 2a (HCV-J6) | YEAFDEMEEC ASRAALIEEG |
| | 290 | 2b (HCV-J8) | YEAFDEMEEC ASKAALIEEG |
| | 291 | 3a (HCV-Nz11) | YQQYDEMEEC SQAAPYIEQA |

TABLE 14-continued

Exemplary NS3/NS4A protease cleavage sites (see e.g., Chao Lin 2006 supra).

| Cleavage Site Type | SEQ ID NO | Genotype (Strain) | Sequence (cleavage site shown with space) |
|---|---|---|---|
| NS4B/NS5A | 292 | 1a (HCV-H) | WISSECTTPC SGSWLRDVWD |
| | 293 | 1b (HCV-BK) | WINEDCSTPC SGSWLRDVWD |
| | 294 | 2a (HCV-J6) | WITEDCPIPC SGSWLRDVWD |
| | 295 | 2b (HCV-J8) | WITEDCPVPC SGSWLQDIWD |
| | 296 | 3a (HCV-Nz11) | WINEDYPSPC SDDWLRTIWD |
| NS5A/NS5B | 297 | 1a (HCV-H) | GADTEDVVCC SMSYSWTGAL |
| | 298 | 1b (HCV-BK) | EEASEDVVCC SMSYTWTGAL |
| | 299 | 2a (HCV-J6) | SEEDDSVVCC SMSYSWTGAL |
| | 300 | 2b (HCV-J8) | SDQEDSVICC SMSYSWTGAL |
| | 301 | 3a (HCV-Nz11) | DSEEQSVVCC SMSYSWTGAL |

In some embodiments of any of the aspects, a synTF polypeptide as described herein comprises two protease cleavage sites, with one N-terminal of the NS3-NS4A complex, and the other C-terminal of the NS3-NS4A complex (see e.g., Table 15). In some embodiments of any of the aspects, the two protease cleavage sites can be the same cleavage sites or different cleavage sites.

TABLE 15

Exemplary Protease Cleavage Site Combinations.

| | | | | | | | | |
|---|---|---|---|---|---|---|---|---|
| N | 3/4A | | | | 4A/4B | | | |
| C | 3/4A | 4A/4B | 4B/5A | 5A/5B | 3/4A | 4A/4B | 4B/5A | 5A/5B |
| N | 4B/5A | | | | 5A/5B | | | |
| C | 3/4A | 4A/4B | 4B/5A | 5A/5B | 3/4A | 4A/4B | 4B/5A | 5A/5B |

"N" indicates N-terminal of the NS3-NS4A complex.
"C" indicates C-terminal of the NS3-NS4A complex.
"3/4A" indicates the NS3/NS4A cleavage site.
"4A/4B" indicates the NS4A/NS4B cleavage site.
"4B/5A" indicates the NS4B/NS5A cleavage site.
"5A/5B" indicates the NS5A/NS5B cleavage site.

In some embodiments of any of the aspects, a synTF polypeptide as described herein comprise any known genotypes, variants, or mutants of NS3/NS4A, NS4A/NS4B, NS4B/NS5A, and NS5A/NS5B cleavage sites. In one embodiment, the two protease cleavage sites are selected from selected from the same genotype as each other.

In some embodiments of any of the aspects, the protease cleavage site is located or engineered such that, when the synTF cleaves itself using the repressible protease in the absence of a protease inhibitor, the resulting amino acid at the N-terminus of the newly cleaved polypeptide(s) causes the polypeptide(s) to degrade at a faster rate and have a shorter half-life compared to other cleaved polypeptides. According to the N-end rule, newly cleaved polypeptides comprising the amino acid His, Tyr, Gln, Asp, Asn, Phe, Leu, Trp, Lys, or Arg at the N-terminus exhibit a high degradation rate and a short half-life (e.g., 10 minutes or less in yeast; 1-5.5 hours in mammalian reticulocytes). Comparatively, newly cleaved polypeptides comprising the amino acid Val, Met, Gly, Pro, Ala, Ser, Thr, Cys, Ile, or Glu at the N-terminus exhibit a lower degradation rate and a longer half-life (e.g., 30 minutes or more in yeast; 1-100 hours in mammalian reticulocytes). See e.g., Gonda et al., Universality and Structure of the N-end Rule, The Journal of Biological Chemistry, Vol. 264 (28), pp. 16700-16712, 1989, the content of which is incorporated herein by reference in its entirety. Accordingly, in some embodiments of any of the aspects, the resulting amino acid at the N-terminus of a newly cleaved synTF polypeptide as described herein is His, Tyr, Gln, Asp, Asn, Phe, Leu, Trp, Lys, or Arg. In some embodiments of any of the aspects, the resulting amino acid at the N-terminus of the newly cleaved synTF polypeptide as described herein is not Val, Met, Gly, Pro, Ala, Ser, Thr, Cys, Ile, or Glu.

In some embodiments of any of the aspects, the N-terminus of a newly cleaved synTF polypeptide as described herein comprises SEQ ID NO: 79 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 79 that maintains a His or another highly degraded amino acid at the N-terminus. SEQ ID NO: 79, N-end rule, 8 aa, HSIYGKKK.

In some embodiments of any of the aspects, a synTF polypeptide as described herein comprises a repressible protease that is catalytically active. For HCV NS3, the catalytic triad comprises His-57, Asp-81, and Ser-139. In regard to a repressible protease, "catalytically active" refers to the ability to cleave at a protease cleavage site. In some embodiments of any of the aspects, the catalytically active repressible protease can be any repressible protease as described further herein that maintains the catalytic triad, i.e., comprises no non-synonymous substitutions at His-57, Asp-81, and/or Ser-139.

In some embodiments of any of the aspects, the synTF comprises NS3 protease domain, NS4A and/or at least one protease cleavage site. In some embodiments of any of the aspects, the synTF comprises SEQ ID NOs: 85 or 102 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 85 or 102.

SEQ ID NO: 85, NS3 domain, comprising: a portion of the N-end rule (SEQ ID NO: 79, bold text), AU1 tag (SEQ ID NO: 80, *italicized double underlined text*), NS4A (SEQ ID NO: 81, *bold italicized text*), and NS3 protease (SEQ ID NO: 82, *italicized text*):

GKKKGDI *DTYRYI*GSSGT*GCVVIVGRIVLSG* SGTS*APITAYAQQTRGLLGCHTSLTGRDKNQVEGEVQ*

*IVSTATQTFLATCINGVCWAVYHGAGTRTIASPKGPVIQMYTNVDQDLVGWPAPQGSRSLTPCTCGSSD*

*LYLVTRHADVIPVRRRGDSRGSLLSPRPISYLKGSSGGPLLCPAGHAVGLFRAAVCTRGVAKAVDFIPV*

*ENLETTMRSPVFTDNSS*PPAVTLTHPITKIDREV

-continued

SEQ ID NO: 102, NS3 domain, comprising: NS3 cleavage sites (SEQ ID NOs: 78 and 83, double underlined text), N-end rule (SEQ ID NO: 79, bold text), AU1 tag (SEQ ID NO: 80, *italicized text*), NS4A (SEQ ID NO: 81, *bold italicized text*), and NS3 protease (SEQ ID NO: 82, *italicized double underline text**italicized double underlined text*):

EDVVCC HSIYHSIYGKKKGDIDTYRYI *DTYRYI*GSSGT*GCVVIVGRIVLSG* SGTS*APITAYAQQTRGLLGCHTSLTGR*

*DKNQVEGEVQIVSTATQTFLATCINGVCWAVYHGAGTRTIASPKGPVIQMYTNVDQDLVGWPAPQGSR*

*SLTPCTCGSSDLYLVTRHADVIPVRRRGDSRGSLLSPRPISYLKGSSGGPLLCPAGHAVGLFRAAVCT*

*RGVAKAVDFIPVENLETTMRSPVFTDNSS*PPAVTLTHPITKIDREVLYQEFDEMEECSQH

In some embodiments of any of the aspects, the synTF comprises a stabilizable polypeptide linkage (StaPL) domain. In some embodiments of any of the aspects, the StaPL domain comprises NS4A, the NS3 protease domain, and a portion of the NS3 helicase domain. In some embodiments of any of the aspects, the partial NS3 helicase domain comprises SEQ ID NOs: 92, 105, 302, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 92, 105, 302.

SEQ ID NO: 92, NS3 Partial Helicase Domain,
NSSPPAVTLTHPITKIDTKYIMTCMSADLEVVT

SEQ ID NO: 105, NS3 Partial Helicase Domain,
NSSPPAVTLTHPITK

SEQ ID NO: 302, NS3 partial helicase domain,
NSSPPAVTLTH

In some embodiments of any of the aspects, the StaPL domain further comprises a protease cleavage site at the N terminus, e.g., selected from EDVVCCHSI (SEQ ID NO: 280) or DEMEECSQH (SEQ ID NO: 281), directly linked or indirectly linked through a peptide linker. In some embodiments of any of the aspects, the StaPL domain comprises SEQ ID NOs: 304-306, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 304-306.

SEQ ID NO: 304, StaPL domain, comprising: NS4A (SEQ ID NO: 81, *bold italicized text*), and NS3 protease (SEQ ID NO: 82, *italicized text*); linkers (SEQ ID NOs: 277 and 303, double underlined text); NS3 helicase (SEQ ID NO: 302, *bold italicized double underlined text*

T *GCVVIVGRIVLSG*SGTS*APITAYAQQTRGLLGCIITSLTGRDKNQVEGEVQIVSTATQTFLATCINGVC*

*WAVYHGAGTRTIASPKGPVIQMYTNVDQDLVGWPAPQGSRSLTPCTCGSSDLYLVTRHADVIPVRRRG*

*DSRGSLLSPRPISYLKGSSGGPLLCPAGHAVGLFRAAVCTRGVAKAVDFIPVENLETTMRSPVFTD* *NSSP*

*PAVTLTH*GGSGGS

In some embodiments of any of the aspects, StaPL domain comprises a repressible protease that comprises at least one mutation that increases its sensitivity to at least one protease inhibitor. In some embodiments of any of the aspects, the NS3 protease (e.g., of the StaPL domain) comprises at least one of the following mutations: V36M, T54A, S122G, F43L, Q80K, S122R, D168Y, or any combination thereof. In some embodiments of any of the aspects, the NS3 protease (e.g., of the StaPL domain) comprises at least one of the following mutations: V36M, T54A, S122G, or any combination thereof, such a StaPL is also referred to herein as $StaPL^{AI}$, as these mutations increase its sensitivity to asunaprevir (see e.g., SEQ ID NO: 254, 305). In some embodiments of any of the aspects, the NS3 protease (e.g., of the StaPL domain) comprises at least one of the following mutations: F43L, Q80K, S122R, D168Y, or any combination thereof, such a protease is also referred to herein as $StaPL^{TI}$, as these mutations increase its sensitivity to telaprevir (see e.g., SEQ ID NO: 255, 306).

SEQ ID NO: 305, StaPL[AI] domain, comprising: NS4A (SEQ ID NO: 81, *bold italicized text*), and NS3 protease (SEQ ID NO: 82, *italicized text*); linkers (SEQ ID NOs: 277 and 303, double underlined text); NS3 helicase (SEQ ID NO: 302, *bold italicized double underlined text*; the V36M, T54A, S122G mutations are shown in bold double underlined textbold double underlined text, respectively.

T *GCVVIVGRIVLSG*SGTS*APITAYAQQTRGLLGCIITSLTGRDKNQVEGEVQI* M *STATQTFLATCINGVC*
*W* A *YHGAGTRTIASPKGPVIQMYTNVDQDLVGWPAPQGSRSLTPCTCGSSDLYLVTRHADVIPVRRRG*

*D*G G *RGSLLSPRPISYLKGSSGGPLLCPAGHAVGLFRAAVCTRGVAKAVFIPVENLETTMRSPVFTD* *NSS*

***PPAVTLTH*GGSGGS**

SEQ ID NO: 306, StaPL[TI] domain, comprising: NS4A (SEQ ID NO: 81, *bold italicized text*), and NS3 protease (SEQ ID NO: 82, *italicized text*); linkers (SEQ ID NOs: 277 and 303, double underlined text); NS3 helicase (SEQ ID NO: 302, *bold italicized double underlined text*); the F43L, Q80K, S122R, D168Y mutations are shown in bold double underlined textbold double underlined text, respectively.

T *GCVVIVGRIVLSG*SGTS *APITAYAQQTRGLLGCIITSLTGRDKNQVEGEVQIVSTATQT* L *LATCINGVC*

*WAVYHGAGTRTIASPKGPVIQMYTNVD*K *DLVGWPAPQGSRSLTPCTCGSSDLYLVTRHADVIPVRRRG*

*D* R *RGSLLSPRPISYLKGSSGGPLLCPAGHAVGLFRAAVCTRGVAKAV* Y *FIPVENLETTMRSPVFTD* *NSS*

***PPAVTLTH*GGSGGS**

In some embodiments of any of the aspects, the synTF comprises a TimeSTAMP domain (a time-specific tag for the age measurement of proteins). In some embodiments of any of the aspects, the TimeSTAMP comprises a repressible protease, at least one protease cleavage site, and a detectable marker. The detectable marker is removed from the synTF immediately after translation by the activity of the repressible protease until the time a protease inhibitor is added, after which newly synthesized synTF polypeptides retain their markers. TimeSTAMP allows for time-specific tagging of the age measurement of proteins, and allows sensitive and nonperturbative visualization and quantification of newly synthesized proteins of interest with exceptionally tight temporal control.

In some embodiments of any of the aspects, the repressible protease exhibits increased solubility compared to the wild-type protease. As a non-limiting example, the NS3 protease can comprise at least one of the following mutations or any combination thereof: Leu13 is substituted to Glu; Leu14 is substituted to Glu; Ile17 is substituted to Gln; Ile18 is substituted to Glu; and/or Leu21 is substituted to Gln. In some embodiments of any of the aspects, a synTF polypeptide as described herein comprises a repressible protease comprising SEQ ID NOs: 307-315, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 307-315 that maintains the same functions (e.g., serine protease; increased solubility) as SEQ ID NOs: 307-315; see e.g., U.S. Pat. No. 6,333,186 and US Patent Publication US20020106642, the contents of each are incorporated herein by reference in their entireties.

SEQ ID NO: 307, soluble NS3, 182 aa
MAPITAYAQQTRGLLGCIITSLTGRDKNQVEGEVQIVSTAAQTFLATCINGVCWTVYHGAGTRTI

ASPKGPVIQMYTNVDKDLVGWPAPQGSRSLTPCTCGSSDLYLVTRHADVIPVRRRGDSRGSLLSP

RPISYLKGSSGGPLLCPAGHAVGIFRAAVCTRGVAKAVDFIPVESLETTMRS

SEQ ID NO: 308, soluble NS3/NS4A, 195 aa
MKKKGSVVIVGRIVLNGAYAQQTRGLLGCIITSLTGRDKNQVEGEVQIVSTAAQTFLATCINGVC

WTVYHGAGTRTIASPKGPVIQMYTNVDKDLVGWPAPQGSRSLTPCTCGSSDLYLVTRHADVIPV

RRRGDSRGSLLSPRPISYLKGSSGGPLLCPAGHAVGIFRAAVCTRGVAKAVDFIPVESLETTMRSP

SEQ ID NO: 309, soluble NS3/NS4A, 195 aa
MKKKGSVVIVGRIVLNGAYAQQTRGEEGCQETSQTGRDKNQVEGEVQIVSTAAQTFLATCINGV

CWTVYHGAGTRTIASPKGPVIQMYTNVDKDLVGWPAPQGSRSLTPCTCGSSDLYLVTRHADVIP

VRRRGDSRGSLLSPRPISYLKGSSGGPLLCPAGHAVGIFRAAVCTRGVAKAVDFIPVESLETTMRSP

SEQ ID NO: 310, soluble NS3/NS4A, 197 aa
MKKKGSVVIVGRINLSGDTAYAQQTRGEEGCQETSQTGRDKNQVEGEVQIVSTAAQTFLATCIN

GVCWTVYHGAGTRTIASPKGPVIQMYTNVDKDLVGWPAPQGSRSLTPCTCGSSDLYLVTRHAD

VIPVRRRGDSRGSLLSPRPISYLKGSSGGPLLCPAGHAVGIFRAAVCTRGVAKAVDFIPVESLETT

MRSP

-continued

SEQ ID NO: 311, soluble NS3/NS4A, 197 aa
MKKKGSVVIVGRINLSGDTAYAQQTRGEEGCQETSQTGRDKNQVEGEVQIVSTATQTFLATCIN

GVCWTVYHGAGTRTIASPKGPVTQMYTNVDKDLVGWQAPQGSRSLTPCTCGSSDLYLVTRHA

DVIPVRRRGDSRGSLLSPRPISYLKGSSGGPLLCPAGHAVGIFRAAVCTRGVAKAVDFIPVESLET

TMRSP

SEQ ID NO: 312, soluble NS3/NS4A, 197 aa
MKKKGSVVIVGRINLSGDTAYAQQTRGEEGCQETSQTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP

SEQ ID NO: 313, soluble NS3/NS4A, 197 aa
MKKKGSVVIVGRINLSGDTAYAQQTRGEQGCQKTSHTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP

SEQ ID NO: 314, soluble NS3/NS4A, 197 aa
MKKKGSVVIVGRINLSGDTAYAQQTRGEQGTQKTSHTGRDKNQVEGEVQIVSTATQTFLATSIN

GVLWTVYHGAGTRTIASPKGPVTQMYTNVDKDLVGWQAPQGSRSLTPCTCGSSDLYLVTRHAD

VIPVRRRGDSRGSLLSPRPISYLKGSSGGPLLCPAGHAVGIFRAAVSTRGVAKAVDFIPVESLETT

MRSP

SEQ ID NO: 315, NS3aH1, soluble NS3/NS4A (S139A), 196 aa
KKKGSVVIVGRINLSGDTAYAQQTRGEEGCQETSQTGRDKNQVEGEVQIVSTATQTFLATSINGV

LWTVYHGAGTRTIASPKGPVTQMYTNVDKDLVGWQAPQGSRSLTPCTCGSSDLYLVTRHADVI

PVRRRGDSRGSLLSPRPISYLKGSAGGPLLCPAGHAVGIFRAAV STRGVAKAVDFIPVESLETTMR

SP

In some embodiments of any of the aspects, the repressible protease comprises mutations to increase binding affinity for a specific ligand. As a non-limiting example, NS3aH1 (e.g., SEQ ID NO: 315) comprises four mutations needed for interaction with the ANR peptide (e.g., SEQ ID NO: 316, GELDELVYLLDGPGYDPIHSD): A7S, E13L, I35V and T42S. Accordingly, in some embodiments of any of the aspects, a repressible protease as described herein comprises at least one of the following mutations: A7S, E13L, I35V and T42S, or any combination thereof.

In some embodiments of any of the aspects, a synTF polypeptide as described herein is in combination with a protease inhibitor. As used herein, "in combination with" refers to two or more substances being present in the same formulation in any molecular or physical arrangement, e.g., in an admixture, in a solution, in a mixture, in a suspension, in a colloid, in an emulsion. The formulation can be a homogeneous or heterogeneous mixture. In some embodiments of any of the aspects, the active compound(s) can be comprised by a superstructure, e.g., nanoparticles, liposomes, vectors, cells, scaffolds, or the like, said superstructure is which in solution, mixture, admixture, suspension, etc., with the synTF polypeptide or synTF polypeptide system. In some embodiments of any of the aspects, the synTF polypeptide is bound to a protease inhibitor bound to the repressible protease. In some embodiments of any of the aspects, the synTF polypeptide is bound specifically to a protease inhibitor bound to the repressible protease.

In some embodiments of any of the aspects, the synTF polypeptide is in combination with 1, 2, 3, 4, 5, or more protease inhibitors. In some embodiments of any of the aspects, the synTF polypeptide is in combination with one protease inhibitor. In embodiments comprising multiple protease inhibitors, the multiple protease inhibitors can be different individual protease inhibitors or multiple copies of the same protease inhibitor, or a combination of the foregoing.

In some embodiments of any of the aspects, the protease inhibitor is grazoprevir (abbreviated as GZV or GZP; see e.g., PubChem CID: 44603531). In some embodiments of any of the aspects, the protease inhibitor is danoprevir (DNV; see e.g., PubChem CID: 11285588). In some embodiments of any of the aspects, the protease inhibitor is an approved NS3 protease inhibitor, such as but not limited to grazoprevir, danoprevir, simeprevir, asunaprevir, ciluprevir, boceprevir, sovaprevir, paritaprevir, ombitasvir, paritaprevir, ritonavir, dasabuvir, and telaprevir. Additional non-limiting examples of NS3 protease inhibitors are listed in Table 16 (see e.g., McCauley and Rudd, Hepatitis C virus NS3/4a protease inhibitors, Current Opinion in Pharmacology 2016, 30:84-92; the content of which is incorporated herein by reference in its entirety).

TABLE 16
| Exemplary NS3/NS4A protease inhibitors | |
|---|---|
| Description or Name(s) | Structure |
| The N-terminal hexapeptide product of substrate cleavage (e.g., DDIVPC-OH) | 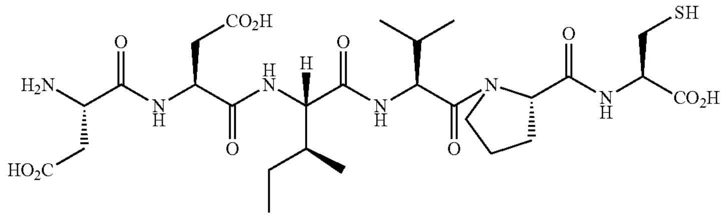<br>1 |
| One of the products of cleavage of the NS4a-NS4b peptide (e.g., Ac-DEMEEC-OH) | 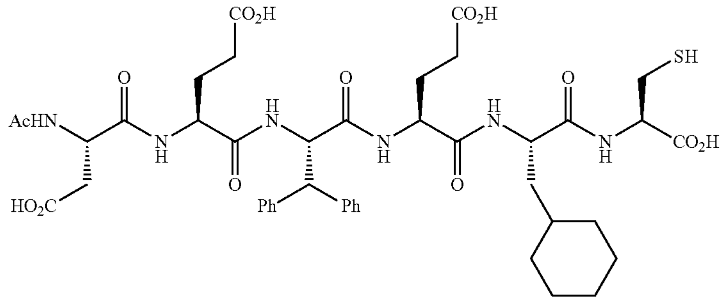<br>2 |
| VICTRELIS ™ boceprevir SCH503034 | 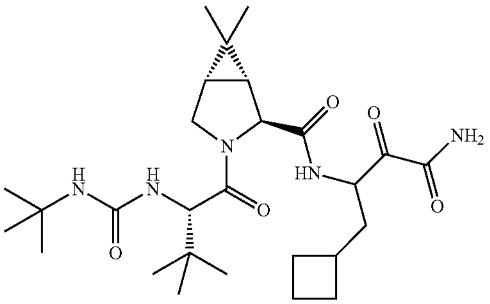 [SMILES: CC(C)(C)NC(=O)N[C@H](C(=O)N1C[C@H]2[C@@H]([C@H]1C(=O)NC(CC1CCC1)C(=O)C(N)=O)C2(C)C)C(C)(C)C] |
| INCIVEK ™, INCIVIO ™, telaprevir, VX-950 | 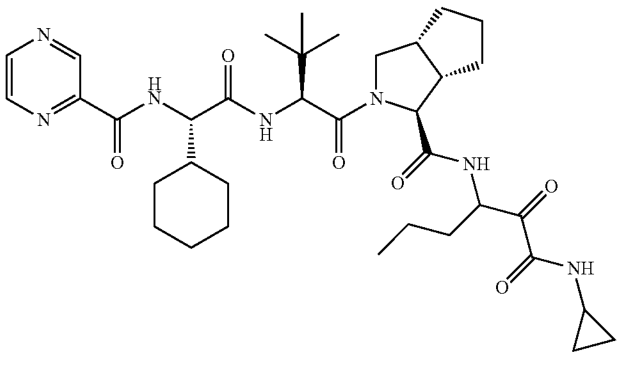 [SMILES: CCCC(NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1] |

TABLE 16-continued
| Exemplary NS3/NS4A protease inhibitors | |
|---|---|
| Description or Name(s) | Structure |
| Ciluprevir; BILN-2061 | 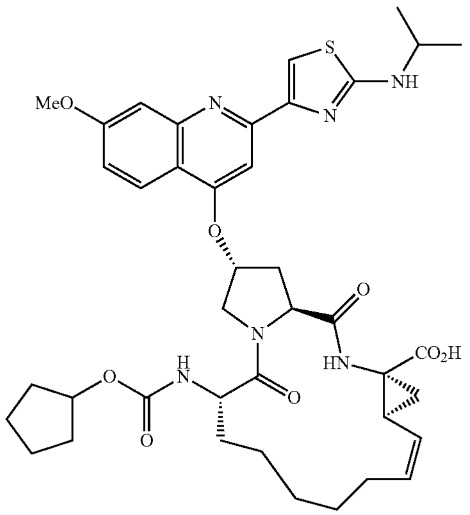 [SMILES: COc1ccc2c(O[C@@H]3C[C@H]4C(=O)N[C@]5(C(=O)O)C[C@H]5/C=C\CCCCC[C@H](NC(=O)OC5CCCC5)C(=O)N4C3)cc(-c3csc(NC(C)C)n3)nc2c1] |
| BMS-605339 | 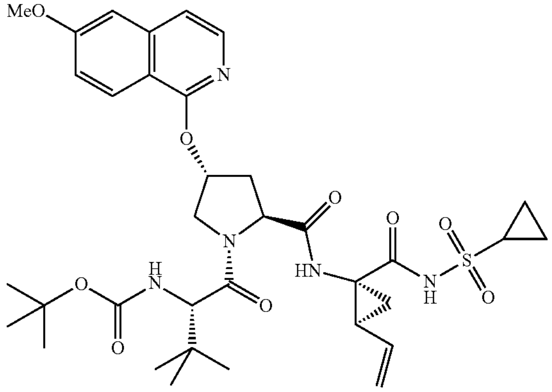 |
| MK-4519 | 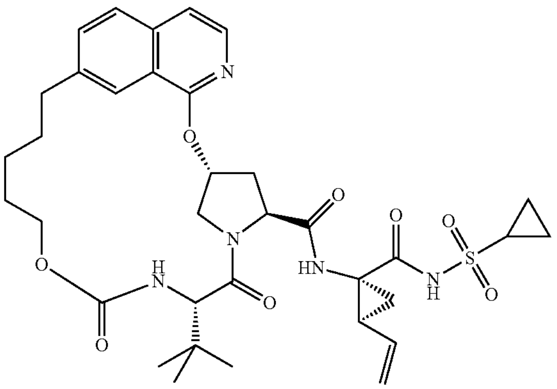 [SMILES: C=C[C@@H]1C[C@]1(NC(=O)[C@@H]1C[C@@H]2CN1C(=O)[C@H](C(C)(C)C)NC(=O)OCCCCCc1ccc3ccnc(c3c1)O2)C(=O)NS(=O)(=O)C1CC1] |

TABLE 16-continued
| Exemplary NS3/NS4A protease inhibitors | |
|---|---|
| Description or Name(s) | Structure |
| faldaprevir, BI-201335 | 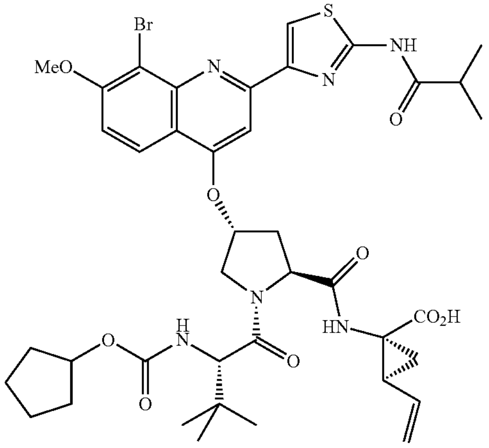 |
| Danoprevir, ITMN-191, R7227 | 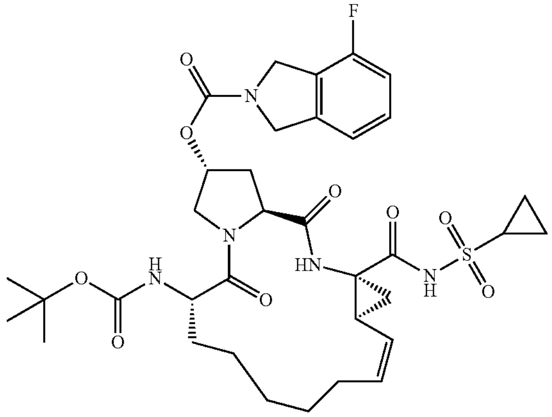 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](OC(=O)N3Cc4cccc(F)c4C3)CN2C1=O] |
| SUNVEPRA ™, asunaprevir, BMS-650032 | 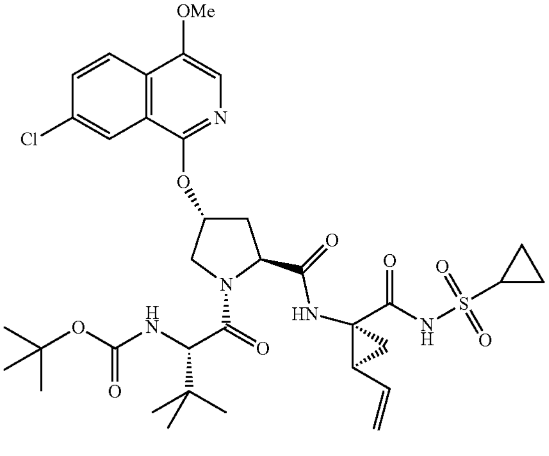 |

TABLE 16-continued
| Exemplary NS3/NS4A protease inhibitors | |
|---|---|
| Description or Name(s) | Structure |
| VANIHEP ™, vaniprevir, MK-7009 | 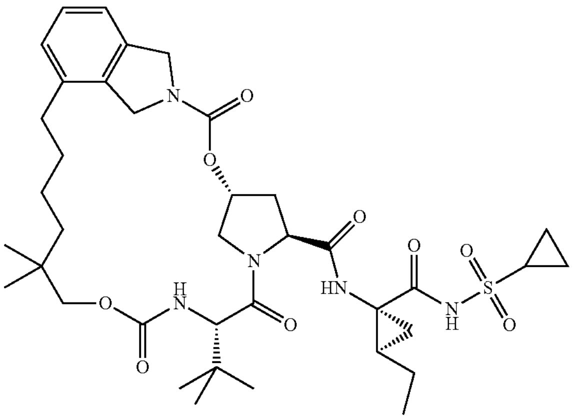 [SMILES: CC[C@@H]1C[C@]1(NC(=O)[C@@H]1C[C@@H]2CN1C(=O)[C@H](C(C)(C)C)NC(=O)OCC(C)(C)CCCCc1cccc3c1CN(C3)C(=O)O2)C(=O)NS(=O)(=O)C1CC1] |
| OLYSIO ™, simeprevir, TMC-435350 | 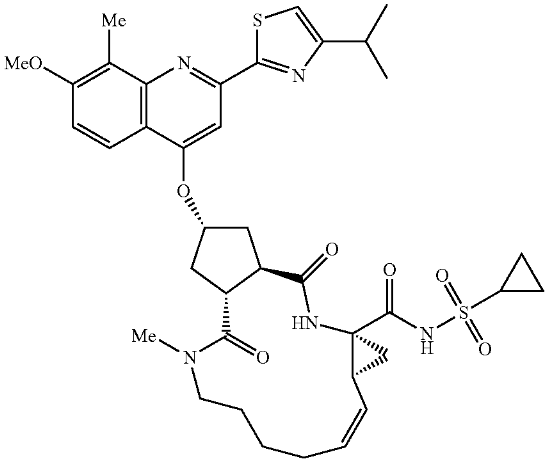 [SMILES: COc1ccc2c(O[C@@H]3C[C@H]4C(=O)N[C@]5(C(=O)NS(=O)(=O)C6CC6)C[C@H]5/C=C\CCCCN(C)C(=O)[C@@H]4C3)cc(-c3nc(C(C)C)cs3)nc2c1C] |
| Sovaprevir, ACH-1625 | 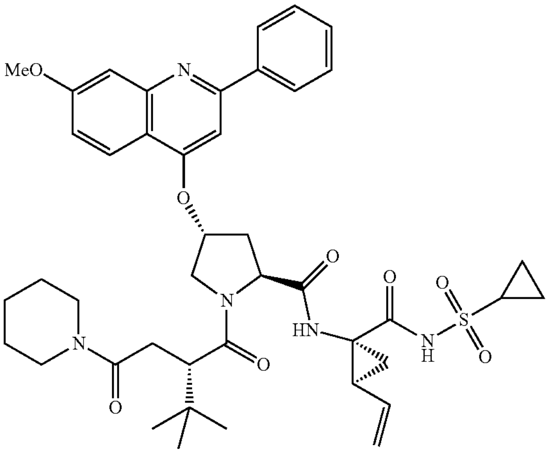 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] |

TABLE 16-continued
| Exemplary NS3/NS4A protease inhibitors | |
|---|---|
| Description or Name(s) | Structure |
| Deldeprevir/neceprevir, ACH-2684 | 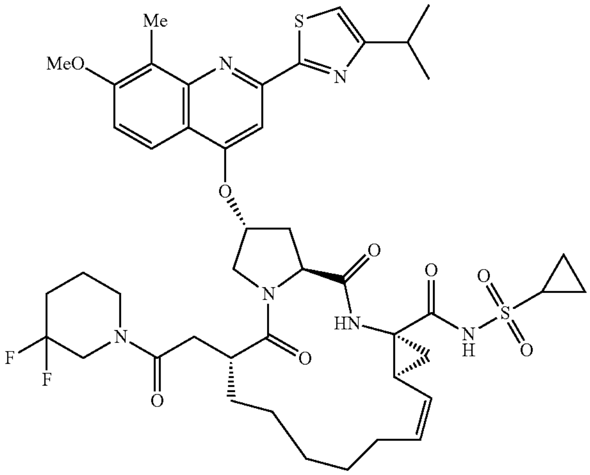 [SMILES: COc1ccc2c(O[C@@H]3C[C@H]4C(=O)N[C@]5(C(=O)NS(=O)(=O)C6CC6)C[C@H]5/C=C\CCCCC[C@H](CC(=O)N5CCCC(F)(F)C5)C(=O)N4C3)cc(-c3nc(C(C)C)cs3)nc2c1C] |
| IDX320 | 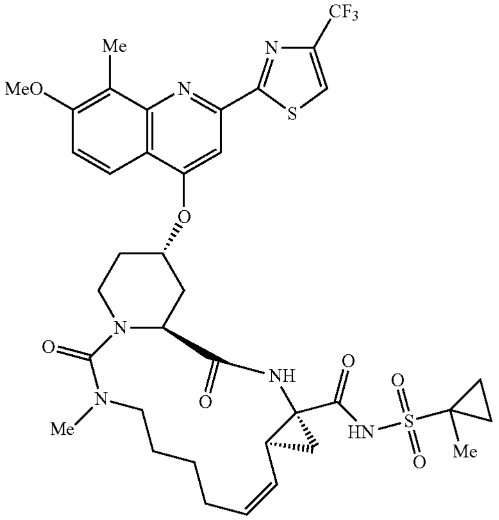 [SMILES: COc1ccc2c(O[C@H]3CCN4C(=O)N(C)CCCC/C=C\[C@@H]5C[C@@]5(C(=O)NS(=O)(=O)C5(C)CC5)NC(=O)[C@@H]4C3)cc(-c3nc(C(F)(F)F)cs3)nc2c1C] |
| GS-9256 | 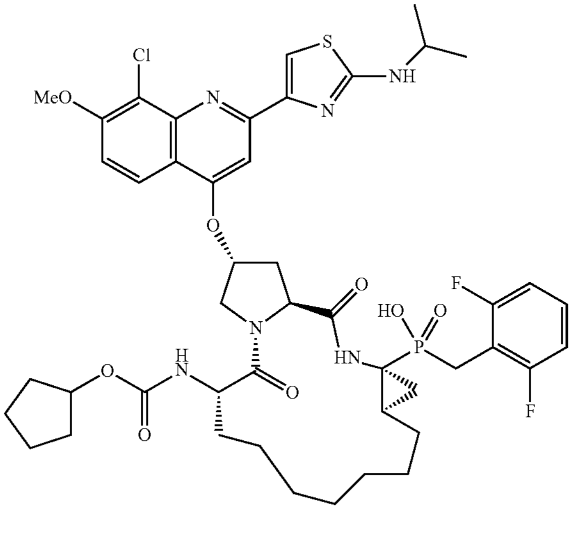 |

TABLE 16-continued
| Exemplary NS3/NS4A protease inhibitors | |
|---|---|
| Description or Name(s) | Structure |
| PHX1766 | 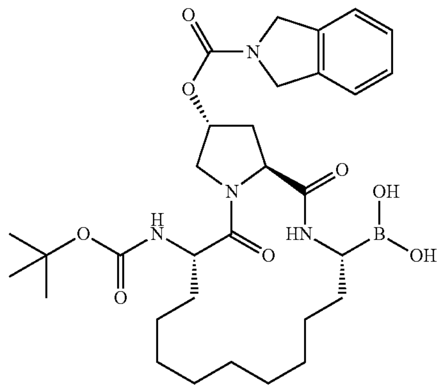 [SMILES: CC(C)(C)OC(=O)N[C@H]1CCCCCCCCC[C@@H](B(O)O)NC(=O)[C@@H]2C[C@@H](OC(=O)N3Cc4ccccc4C3)CN2C1=O] |
| MK-2748 | 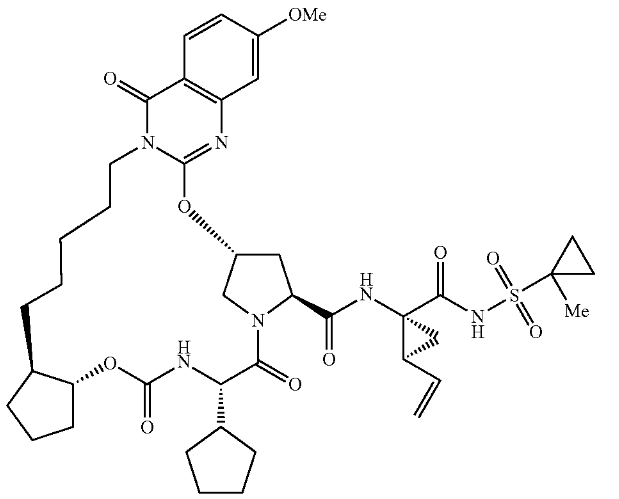 [SMILES: C=C[C@@H]1C[C@]1(NC(=O)[C@@H]1C[C@@H]2CN1C(=O)[C@H](C1CCCC1)NC(=O)O[C@@H]1CCC[C@H]1CCCCCn1c(nc3cc(OC)ccc3c1=O)O2)C(=O)NS(=O)(=O)C1(C)CC1] |
| Vedrorevir, GS-9451, GS-9451 | 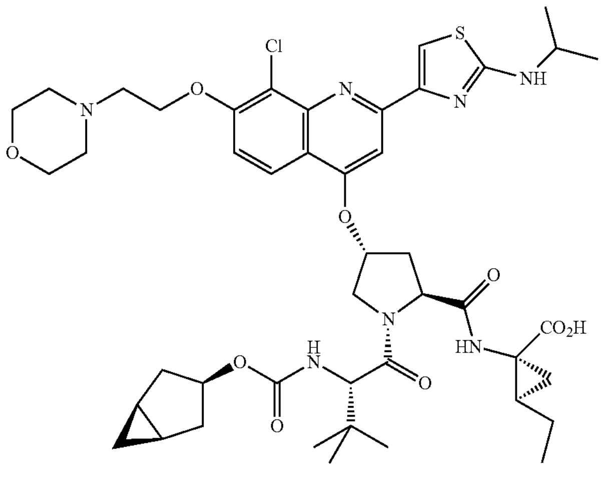 |

TABLE 16-continued
| Exemplary NS3/NS4A protease inhibitors | |
|---|---|
| Description or Name(s) | Structure |
| MK-6325 | 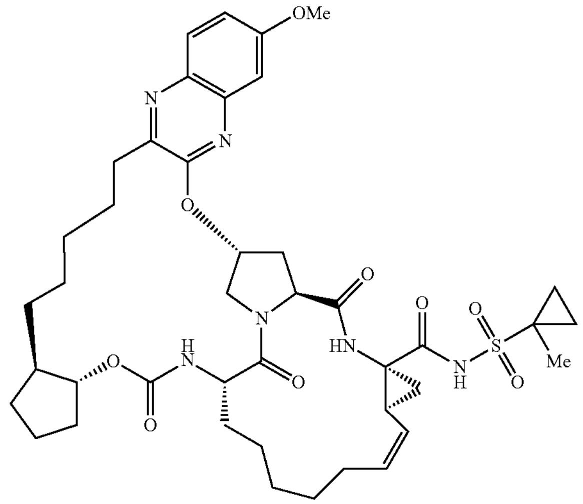 [SMILES: COc1ccc2nc3c(nc2c1)O[C@@H]1C[C@H]2C(=O)N[C@]4(C(=O)NS(=O)(=O)C5(C)CC5)C[C@H]4/C=C\CCCCC[C@H](NC(=O)O[C@@H]4CCC[C@H]4CCCCC3)C(=O)N2C1] |
| MK-8831 | 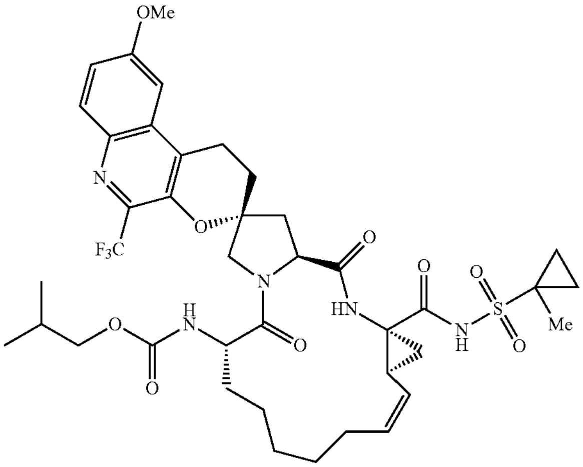 [SMILES: COc1ccc2nc(C(F)(F)F)c3c(c2c1)CC[C@]1(C[C@H]2C(=O)N[C@]4(C(=O)NS(=O)(=O)C5(C)CC5)C[C@H]4/C=C\CCCCC[C@H](NC(=O)OCC(C)C)C(=O)N2C1)O3] |
| VIKERA PAK ™, paritaprevir, ABT-450 | 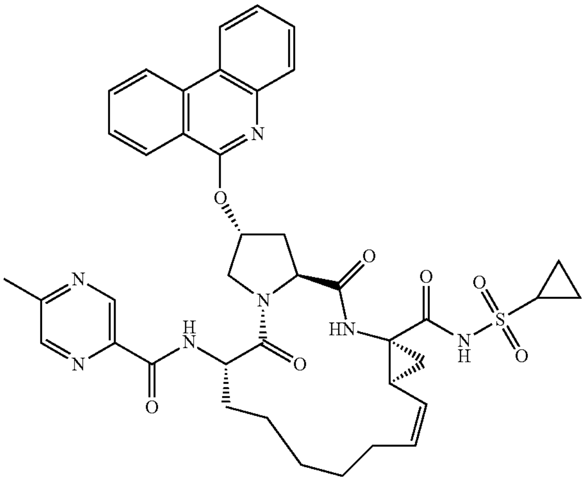 |

TABLE 16-continued

| Exemplary NS3/NS4A protease inhibitors | |
|---|---|
| Description or Name(s) | Structure |
| ZEPATIER ™, grazoprevir, MK-5172 | 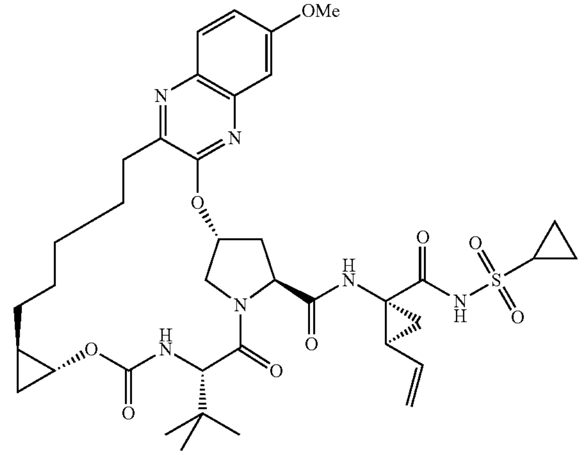 [SMILES: C=C[C@@H]1C[C@]1(NC(=O)[C@@H]1C[C@@H]2CN1C(=O)[C@H](C(C)(C)C)NC(=O)O[C@@H]1C[C@H]1CCCCCc1nc3ccc(OC)cc3nc1O2)C(=O)NS(=O)(=O)C1CC1] |
| Glecaprevir, ABT-493 | 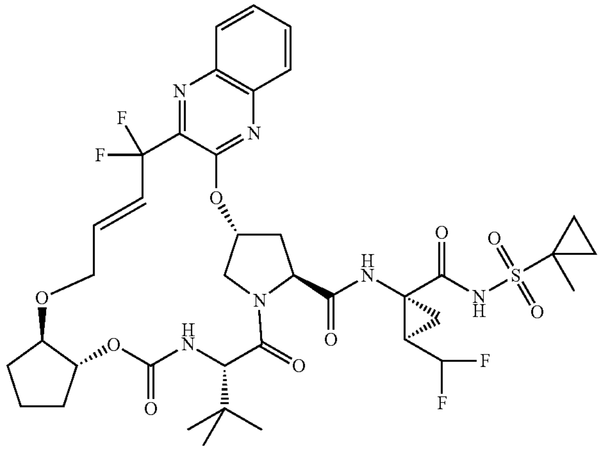 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O] |
| Voxilaprevir, GS-9857 | 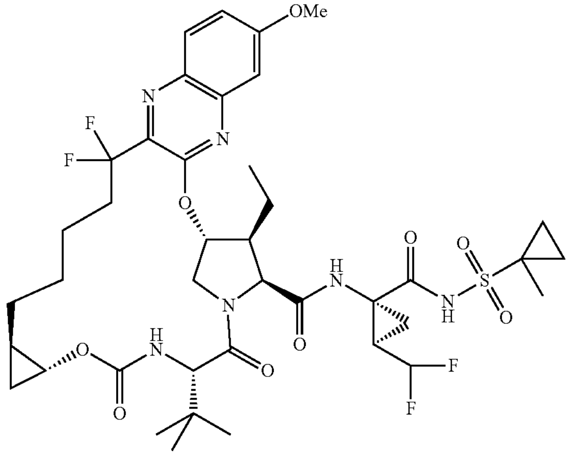 [SMILES: CC[C@@H]1[C@@H]2CN(C(=O)[C@H](C(C)(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F] |

Degron Domain

In several aspects, described herein are synTF polypeptides comprising a degron domain. As used herein, the term "degron domain" refers to a sequence that promotes degradation of an attached protein, e.g., through the proteasome or autophagy-lysosome pathways; in some embodiments of any of the aspects, the terms "degron", "degradation domain" and "degradation domain" can be used interchangeably with "degron domain". In some embodiments, a degron domain is a polypeptide that destabilize a protein such that half-life of the protein is reduced at least two-fold, when fused to the protein. In some embodiments of any of the aspects, a synTF polypeptide as described herein (or a synTF polypeptide system collectively) comprises 1, 2, 3, 4, 5, or more degron domains. In some embodiments of any of the aspects, the synTF polypeptide or system comprises one degron domain. In embodiments comprising multiple degron domains, the multiple degron domains can be different individual degron domains or multiple copies of the same degron domain, or a combination of the foregoing.

Many different degron sequences/signals (e.g., of the ubiquitin-proteasome system) have been described, any of which can be used as provided herein. A degron domain may be operably linked to a cell receptor, but need not be contiguous or immediately adjacent with it as long as the degron domain still functions to direct degradation of the cell receptor. In some embodiments, the degron domain induces rapid degradation of the cell receptor. For a discussion of degron domains and their function in protein degradation, see, e.g., Kanemaki et al. (2013) Pflugers Arch. 465(3):419-425, Erales et al. (2014) Biochim Biophys Acta 1843(1):216-221, Schrader et al. (2009) Nat. Chem. Biol. 5(11): 815-822, Ravid et al. (2008) Nat. Rev. Mol. Cell. Biol. 9(9):679-690, Tasaki et al. (2007) Trends Biochem Sci. 32(1 1):520-528, Meinnel et al. (2006) Biol. Chem. 387(7): 839-851, Kim et al. (2013) Autophagy 9(7): 1100-1103, Varshavsky (2012) Methods Mol. Biol. 832: 1-11, and Fayadat et al. (2003) Mol Biol Cell. 14(3): 1268-1278; Chassin et al., Nature Communications volume 10, Article number: 2013 (2019); Natsume and Kanemaki Annu Rev Genet. 2017 Nov. 27, 51:83-102; the contents of each of which is incorporated herein by reference in its entirety.

In some embodiments of any of the aspects, the degron domain comprises a ubiquitin tag, including but not limited to: UbR, UbP, UbW, UbH, UbI, UbK, UbQ, UbV, UbL, UbD, UbN, UbG, UbY, UbT, UbS, UbF, UbA, UbC, UbE, UbM, 3xUbVR, 3xUbVV, 2xUbVR, 2xUbVV, UbAR, UbVV, UbVR, UbAV, 2xUbAR, 2xUbAV. In some embodiments of any of the aspects, the degron domain comprises a self-excising degron, which refers to a complex comprising a repressible protease, a protease cleavage site, and a degron domain. In some embodiments of any of the aspects, the degron domain is a conditional degron domain, wherein the degradation is induced by ligands (e.g., a degron stabilizer) or another input such as temperature shift or a specific wave length of light. Non-limiting examples of conditional degron domains include the eDHFR degron (e.g., TMP inducer); FKBP12 (e.g., rapamycin analog inducer); temperature-sensitive dihydrofolate reductase (R-DHFRts, or ts-DHFR); an HCV NS3/NS4A degron; a modified version of R-DHFRts termed the low-temperature degron (lt-degron); auxin-inducible degradation (AID); HaloTag-Hydrophobic Tag, HaloPROTAC, and dTAG system (e.g., HyT13 or HyT36 inducer); photosensitive degron (PSD); blue-light-inducible degron (B-LID); tobacco etch virus (TEV) protease-induced protein inactivation (TIPI)-degron system; deGradFP (degrade green fluorescent protein; e.g., induced by NSlmb-vhhGFP expression); or split ubiquitin for the rescue of function (SURF; e.g., induced by rapamycin).

In some embodiments of any of the aspects, the degron domain is the *E. coli* dihydrofolate reductase (eDHFR) degron. The eDHFR degron permits extensive depletion of exogenously expressed proteins in mammalian cells and *C. elegans*. The eDHFR degron is stabilized by tight binding to the antibiotic and degron stabilizer trimethoprim (TMP), shown below, which is innocuous in eukaryotic cells.

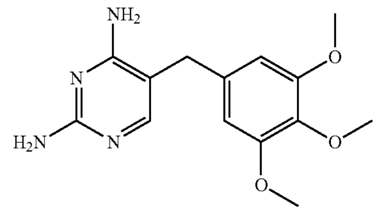 [SMILES: COc1cc(Cc2cnc(N)nc2N)cc(OC)c1OC]

Proteins tagged with eDHFR are constitutively degraded unless the cells are exposed to TMP. The level of tagged protein can be directly controlled by modulating the TMP concentration in the growth medium. Unlike shRNA methods this degron-based strategy is advantageous since depletion kinetics are not limited by the natural protein half-life, which allows for more rapid knockdown of stable proteins. TMP stabilizes the DD-target protein fusion in a dose-dependent manner up to 100-fold, which gives the system a substantial dynamic range. The ligand TMP works by itself and does not require dimerization with a second protein. This system is so effective that it can control the levels of transmembrane proteins, such as the synTF polypeptides described herein; see e.g., Schrader et al., Chem Biol. 2010 Sep. 24, 17(9): 917-918; Ryan M. Sheridan and David L. Bentley, Biotechniques. 2016, 60(2): 69-74; Iwamoto et al., Chem Biol. 2010 Sep. 24; 17(9):981-8.

In some embodiments of any of the aspects, the degron domain comprises an amino acid sequence derived from an FK506- and rapamycin-binding protein (FKBP12) (UniProtKB-P62942 (FKB1A_HUMAN), incorporated herein by reference), or a variant thereof. In some embodiments of any of the aspects, the FKBP12 derived amino acid sequence comprises a mutation of the phenylalanine (F) at amino acid position 36 (as counted without the methionine) to valine (V) (F36V) (also referred to as FKBP12* or FKBP*). In some embodiments of any of the aspects, the degron stabilizer is a rapamycin analog, such as Shield-1, shown below. See e.g., Banaszynski et al., Cell. 2006 Sep. 8; 126(5): 995-1004; US Patent Application US20180179522; U.S. Pat. No. 10,137,180; the content of each of which is incorporated herein by reference in its entirety.

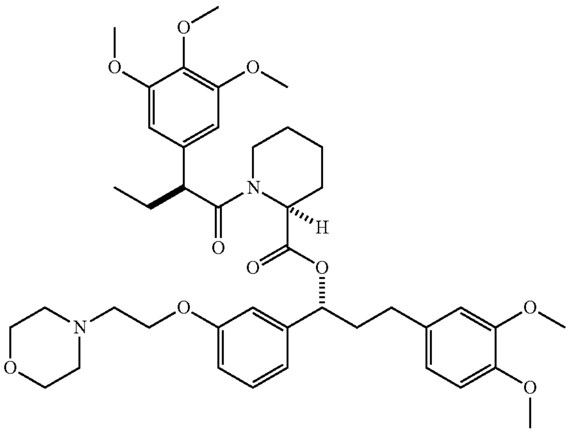 [SMILES: CC[C@H](C(=O)N1CCCC[C@H]1C(=O)O[C@H](CCc1ccc(OC)c(OC)c1)c1cccc(OCCN2CCOCC2)c1)c1cc(OC)c(OC)c(OC)c1]

In some embodiments of any of the aspects, the degron domain of a synTF polypeptide as described herein comprises SEQ ID NOs: 317 or 318, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NOs: 317 or 318 that maintains the same function (e.g., degradation, binding to TMP or Shield-1).

```
SEQ ID NO: 317, DHFR (V19A), 158 aa,
ISLIAALAVDYVIGMENAMPWNLPADLAWFKRNTLNKPVIMGRHTWESIGRPLPGRKNIILSSQP

STDDRVTWVKSVDEAIAACGDVPEIMVIGGGRVIEQFLPKAQKLYLTHIDAEVEGDTHFPDYEPD

DWESVFSEFHDADAQNSHSYCFEILERR

SEQ ID NO: 318, FK506- and rapamycin-binding protein (FKBP), 107 aa
GVQVETISPGDGRTFPKRGQTCVVHYTGMLEDGKKFDSSRDRNKPFKFMLGKQEVIRGWEEGV

AQMSVGQRAKLTISPDYAYGATGHPGIIPPHATLVFDVELLKLE
```

In some embodiments of any of the aspects, the destabilizing degron domain comprises at least one mutation that causes almost complete removal or degradation of the synTF polypeptide. Non-limiting examples of DHFR (e.g., SEQ ID NO: 317) mutations include: V19A, Y100I, G121V, H12Y, H12L, R98H, F103S, M42T, H114R, I61F, T68S, H12Y/Y100I, H12L/Y100I, R98H/F103S, M42T/H114R, and I61F/T68S, or any combinations thereof, see e.g., U.S. Pat. No. 8,173,792, the content of which is incorporated herein by reference in its entirety.

In some embodiments of any of the aspects, the degron domain comprises a ligand-induced degradation (LID) domain. Proteins comprising a LID domain are destabilized and degraded in the presence of a degron destabilizer. In some embodiments of any of the aspects, the LID domain of a degron domain can bind to a degron destabilizer, promoting the degradation of the attached protein. The system is reversible and when the degron destabilizer is withdrawn, the protein is not destabilized and/or not degraded. In some embodiments of any of the aspects, a synTF polypeptide is bound to a degron destabilizer bound to the degron domain. In some embodiments of any of the aspects, the synTF polypeptide is bound specifically to a degron destabilizer bound to the degron domain.

In some embodiments of any of the aspects, the synTF polypeptide is in combination with 1, 2, 3, 4, 5, or more degron destabilizers. In some embodiments of any of the aspects, the synTF polypeptide is in combination with one degron destabilizer. In embodiments comprising multiple degron destabilizers, the multiple degron destabilizers can be different individual degron destabilizers or multiple copies of the same degron stabilizer, or a combination of the foregoing.

In some embodiments of any of the aspects, the LID degron domain comprises the FK506- and rapamycin-binding protein (FKBP), further comprising a degron fused to the C terminus of FKBP, e.g., with an intervening linker such as the 10-amino acid linker (Gly4SerGly4Ser) or another linker as described herein. In some embodiments of any of the aspects, the degron fused to the C terminus of FKBP (e.g., SEQ ID NO: 318) comprises the 19 amino acid sequence: TRGVEEVAEGVVLLRRRGN (SEQ ID NO: 319), or a sequence that is at least 95% identical that maintains the same function. In the absence of the small molecule Shield-1, the 19-aa degron is bound to the FKBP fusion protein, and the protein is stable. When present, Shield-1 binds tightly to FKBP, displacing the 19-aa degron and inducing rapid and processive degradation of the LID domain and any fused partner protein. In some embodiments of any of the aspects, the degron destabilizer is Shield-1, shown above, or an analog thereof, see e.g., Bonger et al., Nat Chem Biol. 2011 Jul. 3; 7(8):531-7.

In some embodiments of any of the aspects, the degron domain comprises an auxin-inducible degradation (AID). Proteins fused to AID (also known as indole-3-acetic acid inducible 17 or AUX/IAA transcriptional regulator family protein) are rapidly degraded. Degradation requires the ectopic expression of the plant F-Box protein TIR1, which recruits proteins tagged with AID in an auxin-dependent manner to the SKP1-CUL1-F-Box (SCF) ubiquitin E3 ligases resulting in their ubiquitylation and proteasomal degradation. In some embodiments of any of the aspects, the degron domain comprises residues 65-133, 65-130, 70-130, or 70-120 of SEQ ID NO: 320. In some embodiments of any of the aspects, the degron domain of a synTF polypeptide as described herein comprises SEQ ID NOs: 320 or 321, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NOs: 320 or 321 that maintains the same function. See e.g., Daniel et al., Nat Commun. 2018 Aug. 17; 9(1):3297; the content of which is incorporated herein by reference in its entirety.

```
SEQ ID NO: 320, AUX/IAA transcriptional regulator
family protein [Arabidopsis thaliana],
NCBI Reference Sequence: NP_171921.1, 229 aa
MMGSVELNLRETELCLGLPGGDTVAPVTGNKRGFSETVDLKLNLNNEPA

NKEGSTTHDVVTFDSKEKSACPKDPAKPPAKAQVVGWPPVRSYRKNVMV

SCQKSSGGPEAAAFVKVSMDGAPYLRKIDLRMYKSYDELSNALSNMFSS

FTMGKHGGEEGMIDFMNERKLMDLVNSWDYVPSYEDKDGDWMLVGDVPW

PMFVDTCKRLRLMKGSDAIGLAPRAMEKCKSRA

SEQ ID NO: 321, mAID (minimal AID), 68 aa
KEKSACPKDPAKPPAKAQVVGWPPVRSYRKNVMVSCQKSSGGPEAAAFV

KVSMDGAPYLRKIDLRMYK
```

In some embodiments of any of the aspects, the degron domain comprises a modified portion of the NS3 helicase and NS4A. The arrangement of NS3pro and NS4A sequences in the construct creates a functional degron. During HCV replication, the free NS4A N-terminus forms a hydrophobic α-helix that is inserted into the endoplasmic reticulum membrane. This N-terminus is created by cleavage of the HCV nonstructural polypeptide at the NS3/4A junction due to its positioning in the protease active site by the NS3 helicase domain. The engineered construct lacks the helicase domain, so NS3/4A cleavage does not occur. The hydrophobic sequences of NS4A, unable to insert into the membrane without a free N-terminus, then exhibit degron-like activity. See e.g., U.S. Pat. No. 10,550,379; Chung et al., Nat Chem Biol. 2015 September; 11(9): 713-720; the contents of which are incorporated herein by reference in their entireties.

In some embodiments of any of the aspects, the degron domain comprises SEQ ID NO: 322, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 322 that maintains the same function.

```
SEQ ID NO: 322, HCV NS3/NS4A degron domain (42 aa)
PITKIDTKYIMTCMSADLEVVTSTWVLVGGVLAALAAYCLST
```

Induced Degradation Domain

In several aspects, described herein are synTF polypeptides comprising an induced degradation domain, also referred to herein as a self-excising degron or a small molecule-assisted shutoff (SMASh) domain. In some embodiments of any of the aspects, the SMASh domain comprises a repressible protease, at least one protease cleavage site, and a degron domain. In the absence of the protease inhibitor, the repressible protease cleaves the degron from the synTF, and the synTF is not degraded. In the presence of the protease inhibitor, the repressible protease does not cleave the degron from the synTF, and the degron domain leads to the degradation of the synTF.

In some embodiments of any of the aspects, a synTF polypeptide as described herein (or a synTF polypeptide system collectively) comprises 1, 2, 3, 4, 5, or more induced degradation domain(s). In some embodiments of any of the aspects, the synTF polypeptide or system comprises one induced degradation domain. In embodiments comprising multiple induced degradation domains, the multiple induced degradation domains can be different individual induced degradation domains or multiple copies of the same induced degradation domain, or a combination of the foregoing.

In some embodiments of any of the aspects, degron domain (e.g., of the SMASh domain) is selected from the group consisting of: a ubiquitin tag; eDHFR degron (e.g., TMP inducer); FKBP12 (e.g., rapamycin analog inducer); temperature-sensitive dihydrofolate reductase (R-DHFRts, or ts-DHFR); an HCV NS3/NS4A degron; a modified version of R-DHFRts termed the low-temperature degron (lt-degron); auxin-inducible degradation (AID); HaloTag-Hydrophobic Tag, HaloPROTAC, and dTAG system (e.g., HyT13 or HyT36 inducer); photosensitive degron (PSD); blue-light-inducible degron (B-LID); tobacco etch virus (TEV) protease-induced protein inactivation (TIPI)-degron system; deGradFP (degrade green fluorescent protein; e.g., induced by NSlmb-vhhGFP expression); or split ubiquitin for the rescue of function (SURF; e.g., induced by rapamycin).

In some embodiments of any of the aspects, the degron domain (e.g., of the SMASh domain) comprises a modified portion of the NS3 helicase and NS4A. In some embodiments of any of the aspects, the degron domain (e.g., of the SMASh domain) comprises SEQ ID NO: 322, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 322 that maintains the same function.

In some embodiments of any of the aspects, the SMASh tag comprises a repressible protease, a partial protease helical domain, and a cofactor domain. In some embodiments of any of the aspects, the SMASh tag comprises a repressible protease, a partial protease helical domain, a cofactor domain, and at least one protease cleavage site. In some embodiments of any of the aspects, the SMASh tag comprises an NS3 repressible protease, an NS3 partial protease helical domain, an NS3 cofactor domain (i.e., NS4A), and at least one protease cleavage site of the NS3 repressible protease.

In some embodiments of any of the aspects, the SMASh tag is a C-terminal SMASh tag, e.g., the tag is engineered to be attached to the C-terminus of the synTF. In some embodiments of any of the aspects, the C-terminal SMASh tag comprises a protease cleavage site at the N-terminus of the tag. In some embodiments of any of the aspects, the C-terminal SMASh tag comprises in a N-terminal to C-terminal order: a NS3 cleavage site, at least one linker, a NS3 domain, a NS3 partial helicase, a NS4A domain. In some embodiments of any of the aspects, the C-terminal SMASh tag is fused to the C-terminus of the transcriptional effector domain of the synTF. In some embodiments of any of the aspects, the C-terminal SMASh tag is fused to the C-terminus of the DNA-binding domain of the synTF.

In some embodiments of any of the aspects, the C-terminal SMASh tag comprises SEQ ID NOs: 86, 324, 327, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 86, 324, 327 that maintains the same function.

SEQ ID NO: 86, C-terminal SMASh domain (304 aa); bold text indicates NS3 Cleavage Site (SEQ ID NO: 87); italicizeddoubleunderlinedtext indicates a Linker (SEQ ID NO: 88 or 90); *bold italicized text* indicates the FLAG tag (SEQ ID NO: 89); italicized text indicates the NS3 Protease Domain (SEQ ID NO: 91); unformatted text indicates NS3 Partial Helicase (SEQ ID NO: 92); *bold italicized double underlined text* indicates NS4A Domain (SEQ ID NO: 93):

DEMEECSQHL*PGAGSSGDIMPGASSGDIM**DYKDDDDK**GSSGTGSGSGTS*APITAYAQQTRGLLGCHTSLTGRDKN

*QVEGEVQIVSTATQTFLATCINGVCWAVYHGAGTRTIASPKGPVIQMYTNVDQDLVGWPAPQGSRSLT*

*PCTCGSSDLYLVTRHADVIPVRRRGDSRGSLLSPRPISYLKGSSGGPLLCPAGHAVGLFRAAVCTRGVAK*

*AVDFIPVENLETTMRSPVFTD*NSSPPAVTLTHPITKIDTKYIMTCMSADLEVVT *STWVLVGGVLAA*

*LAAYCLSTGCVVIVGRIVLSGKPAIIPDREVLY*

In some embodiments of any of the aspects, the SMASh tag is a N-terminal SMASh tag, e.g., the tag is engineered to be attached to the N-terminus of the synTF. In some embodiments of any of the aspects, the N-terminal SMASh tag comprises a protease cleavage site at the C-terminus of the tag. In some embodiments of any of the aspects, the N-terminal SMASh tag comprises in a N-terminal to C-terminal order at least one Linker, a NS3 domain, a NS3 partial helicase, a NS4 domain, and a NS3 cleavage site. In some embodiments of any of the aspects, the N-terminal SMASh tag is fused to the N-terminus of the transcriptional effector domain of the synTF. In some embodiments of any of the aspects, the N-terminal SMASh tag is fused to the N-terminus of the DNA-binding domain of the synTF.

In some embodiments of any of the aspects, the N-terminal SMASh tag comprises SEQ ID NOs: 94, 95, 325, 326, 328, 329, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 94, 95, 325, 326, 328, or 329, that maintains the same function.

SEQ ID NO: 94, N-terminal SMASh domain (297 aa), italicizeddoubleunderlinedtext indicates a Linker (SEQ ID NO: 88 or 90); *bold italicized text* indicates the FLAG tag (SEQ ID NO: 89); italicized text indicates the NS3 Protease Domain (SEQ ID NO: 91); unformatted text indicates NS3 Partial Helicase (SEQ ID NO: 92); *bold italicized double underlined text* indicates NS4A Domain (SEQ ID NO: 93); bold text indicates NS3 Cleavage Site (SEQ ID NO: 279):

*DYKDDDDK* GSSGTGSGSGTSA*GSSGTGSGSGTS* *APITAYAQQTRGLLGCIITSLTGRDKNQVEGEVQIVSTATQT-FLATCING*

*VCWAVYHGAGTRTIASPKGPVIQMYTNVDQDLVGWPAPQGSRSLTPCTCGSSDLYLVTRHADVIPVRR*

*RGDSRGSLLSPRPISYLKGSSGGPLLCPAGHAVGLFRAAVCTRGVAKAVDFIPVENLETTMRSPVFTD*N

SSPPAVTLTHPITKIDTKYIMTCMSADLEVVT *STWVLVGGVLAALAAYCISTGCVVIVGRIVLSGK*

*PAIIPDREVLY* QEFEDVVPCSMGS

SEQ ID NO: 95, N-terminal SMASh domain (303 aa, with GSSGSS (SEQ ID NO: 323) L6 domain in NS4A), italicizeddoubleunderlinedtext indicates a Linker; *bold italicized text* indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site.

*DYKDDDDK**GSSGTGSGSGTS* *APITAYAQQTRGLLGCIITSLTGRDKNQVEGEVQIVSTATQTFLATCING*

*VCWAVYHGAGTRTIASPKGPVIQMYTNVDQDLVGWPAPQGSRSLTPCTCGSSDLYLVTRHADVIPVRR*

*RGDSRGSLLSPRPISYLKGSSGGPLLCPAGHAVGLFRAAVCTRGVAKAVDFIPVENLETTMRSPVFTD*N

SSPPAVTLTHPITKIDTKYIMTCMSADLEVVT *STWVLVGGVLAALAAYCLSTGCVVIVGRIVLSGK*

*PAGSSGSSIIPDREVLY* QEFEDVVPCSMGS

In some embodiments of any of the aspects, SMASh domain comprises a repressible protease that comprises at least one mutation that increases its sensitivity to at least one protease inhibitor. In some embodiments of any of the aspects, the NS3 protease (e.g., of the SMASh domain) comprises at least one of the following mutations: V36M, T54A, S122G, F43L, Q80K, S122R, D168Y, or any combination thereof. In some embodiments of any of the aspects, the NS3 protease (e.g., of the SMASh domain) comprises at least one of the following mutations: V36M, T54A, S122G, or any combination thereof, such a SMASh is also referred to herein as $SMASh^{AI}$, as these mutations increase its sensitivity to asunaprevir (see e.g., SEQ ID NOs: 254, 324, 325, 326). In some embodiments of any of the aspects, the NS3 protease (e.g., of the SMASh domain) comprises at least one of the following mutations: F43L, Q80K, S122R, D168Y, or any combination thereof, such a protease is also referred to herein as $SMASh^{TI}$, as these mutations increase its sensitivity to telaprevir (see e.g., SEQ ID NOs: 255, 327, 328, 329).

SEQ ID NO: 324, C-terminal SMASh$^{AI}$ domain with (304 aa); bold text indicates NS3 Cleavage Site; italicizeddoubleunderlinedtext indicates a Linker; bold italicized text indicates the FLAG bold italicized text tag; italicized text indicates the NS3 Protease Domain; unformatted text indicates NS3 Partial Helicase; bold italicized double underlined text indicates NS4A Domain; the V36M, T54A, S122G mutations are shown in bold double underlined text, respectively.

DEMEECSQHLPGAGSSGDIM PGAGSSGDIMDYKDDDDKGSSGTGSGSGTSAPITAYAQQTRGLLGCIITSLTGRDKN

QVEGEVQI M STATQTFLATCINGVCW A VYHGAGTRTIASPKGPVIQMYTNVDQDLVGWPAPQGSRSLT

PCTCGSSDLYLVTRHADVIPVRRRGDSR G SLLSPRPISYLKGSSGGPLLCPAGHAVGLFRAAVCTRGVA

KAVDFIPVENLETTMRSPVFTDNSSPPAVTLTHPITKIDTKYIMTCMSADLEVVT STWVLVGGVLA

ALAAYCLSTGCVVIVGRIVLSGKPAIIPDREVLY

SEQ ID NO: 325, N-terminal SMASh$^{AI}$ domain (297 aa), italicizeddoubleunderlinedtext indicates a Linker; bold italicized text indicates the FLAG tag; italicized text indicates the NS3 Protease Domain; unformatted text indicates NS3 Partial Helicase; bold italicized double underlined text indicates NS4A Domain; bold text indicates NS3 Cleavage Site; the V36M, T54A, S122G mutations are shown in bold double underlined text, respectively.

PGAGSSGDIMDYKDDDDK GSSGTGSGSGTSAPITAYAQQTRGLLGCIITSLTGRDKNQVEGEVQI M STATQTFLATCIN

GVCW A VYHGAGTRTIASPKGPVIQMYTNVDQDLVGWPAPQGSRSLTPCTCGSSDLYLVTRHADVIPVR

RRGDSR G SLLSPRPISYLKGSSGGPLLCPAGHAVGLFRAAVCTRGVAKAVDFIPVENLETTMRSPVFTD

NSSPPAVTLTHPITKIDTKYIMTCMSADLEVVTSTWVLVGGVLAALAAYCLSTGCVVIVGRIVLSG

KPAIIPDREVLYQEFEDVVPCSMGS

SEQ ID NO: 326, N-terminal SMASh$^{AI}$ domain 303 aa, with L6 domain in NS4A), italicizeddoubleunderlinedtext indicates a Linker; bold italicized text indicates the FLAG tag; italicized text indicates the NS3 Protease Domain; unformatted text indicates NS3 Partial Helicase; bold italicized double underlined text indicates NS4A Domain; bold text indicates NS3 Cleavage Site; the V36M, T54A, S122G mutations are shown in bold double underlined text, respectively.

DEMEECSQHLPGAGSSGDIMDYKDDDDKGSSGTGSGSGTS

APITAYAQQTRGLLGCIITSLTGRDKNQVEGEVQIVSTATQTLLATCIN

GVCWAVYHGAGTRTIASPKGPVIQMYTNVDKDLVGWPAPQGSRSLTPCT

CGSSDLYLVTRHADVIPVRRRGDRRGSLLSPRPISYLKGSSGGPLLCP

PGAGSSGDIMDYKDDDDKGSSGTGSGSGTSA GSSGTGSGSGTSAPITAYAQQTRGLLGCIITSLTGRDKNQVEGEVQI
M STATQTFLATCIN

GVCW A VYHGAGTRTIASPKGPVIQMYTNVDQDLVGWPAPQGSRSLTPCTCGSSDLYLVTRHADVIPVR

RRGDSR G SLLSPRPISYLKGSSGGPLLCPAGHAVGLFRAAVCTRGVAKAVDFIPVENLETTMRSPVFTD

NSSPPAVTLTHPITKIDTKYIMTCMSADLEVVTSTWVLVGGVIAALAAYCLSTGCVVIVGRIVLSG

KPAGSSGSSIIPDREVLYQEFEDVVPCSMGS

SEQ ID NO: 327, C-terminal SMASh$^{TI}$ domain with (304 aa); bold text indicates NS3 Cleavage Site; italicizeddoubleunderlinedtext indicates a Linker; bold italicized text indicates the FLAG tag; italicized text indicates the NS3 Protease Domain; unformatted text indicates NS3 Partial Helicase; bold italicized double underlined text indicates NS4A Domain; the F43L, Q80K, S122R, D168Y mutations are shown in bold double underlined text, respectively.

-continued

AGHAVGLFRAAVCTRGVAKAVYFIPVENLETTMRSPVFTDNSSPPAVT

LTHPITKIDTKYIMTCMSADLEVVTSTWVLVGGVLAALAAYCLSTG

CVVIVGRIVLSGKPAIIPDREVLY

SEQ ID NO: 328, N-terminal SMASh$^{TI}$ domain (297 aa), italicizeddoubleunderlinedtext indicates a Linker; bold italicized text indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site; the F43L, Q80K, S122R, D168Y mutations are shown in bold double underlined text, respectively.

```
DYKDDDDKGSSGTGSGSGTSAPITAYAQQTRGLLGCIITSLTGRDKNQV
EGEVQIVSTATQT LLATCINGVCWAVYHGAGTRTIASPKGPVIQMYTNV
D KDLVGWPAPQGSRSLTPCTCGSSDLYLVTRHADVIPVRRRGD RRGSL
LSPRPISYLKGSSGGPLLCPAGHAVGLFRAAVCTRGVAKAVYFIPVENL
ETTMRSPVFTDNSSPPAVTLTHPITKIDTKYIMTCMSADLEVVT
STWVLVGGVLAALAAYCLSTGCVVIVGRIVLSGK
PAIIPDREVLYPDREVLYQEFEDVVPCSMGS
```

SEQ ID NO: 329, N-terminal SMASh$^{TI}$ domain (303 aa, with L6 domain in NS4A), italicizeddoubleunderlinedtext indicates a Linker; *bold italicized text* indicates the FLAG tag; italicized text indicates the NS3 Protease Domain; unformatted text indicates NS3 Partial Helicase; *bold italicized double underlined text* indicates NS4A Domain; bold text indicates NS3 Cleavage Site; the F43L, *bold italicized* Q80K, S122R, D168Y mutations are shown in bold double underlined text, respectively.

```
DYKDDDDKGSSGTGSGSGTSAPITAYAQQTRGLLGCIITSLTGRDKNQV
EGEVQIVSTATQT LLATCINGVCWAVYHGAGTRTIASPKGPVIQMYTN
VD K DLVGWPAPQGSRSLTPCTCGSSDLYLVTRHADVIPVRRRGD RRGS
LLSPRPISYLKGSSGGPLLCPAGHAVGLFRAAVCTRGVAKAVYFIPVEN
LETTMRSPVFTDNSSPPAVTLTHPITKIDTKYIMTCMSADLEVVT
STWVLVGGVLAALAAYCLSTGCVVIVGRIVLSGK
PAGSSGSSIIPDREVLYQEFEDVVPCSMGS
```

In some embodiments of any of the aspects, the SMASh domain of the synTF polypeptide is in combination with 1, 2, 3, 4, 5, or more protease inhibitors. In some embodiments of any of the aspects, the SMASh domain of the synTF polypeptide is in combination with one protease inhibitor. In embodiments comprising multiple protease inhibitors, the multiple protease inhibitors can be different individual protease inhibitors or multiple copies of the same protease inhibitor, or a combination of the foregoing.

In some embodiments of any of the aspects, the protease inhibitor is grazoprevir (abbreviated as GZV or GZP; see e.g., PubChem CID: 44603531). In some embodiments of any of the aspects, the protease inhibitor is danoprevir (DNV; see e.g., PubChem CID: 11285588). In some embodiments of any of the aspects, the protease inhibitor is an approved NS3 protease inhibitor, such as but not limited to grazoprevir, danoprevir, simeprevir, asunaprevir, ciluprevir, boceprevir, sovaprevir, paritaprevir, ombitasvir, paritaprevir, ritonavir, dasabuvir, and telaprevir. Additional non-limiting examples of NS3 protease inhibitors are listed in Table 16 (see e.g., McCauley and Rudd, Hepatitis C virus NS3/4a protease inhibitors, Current Opinion in Pharmacology 2016, 30:84-92; the content of which is incorporated herein by reference in its entirety).

Induced Proximity Domains

In several aspects, described herein are synTF polypeptides comprising at least two induced proximity domains, also referred to herein as heterodimerization domains. As used herein the term "induced proximity domains" refers to at least two domains that are induced to dimerize or come into close proximity in the presence of a stimulus (e.g., chemical inducer, light, etc.). In some embodiments of any of the aspects, the induced proximity domain pair comprises a first induced proximity domain (IPD$^A$) and at least a second induced proximity domain (IPD$^B$), wherein in the presence of an inducer agent or inducer signal, the IPD$^A$ and IPD$^B$ come together. In some embodiments of any of the aspects, the synTF effector domain is linked to IPD$^A$ (or IPD$^B$) in a first polypeptide, and the synTF DBD is linked to IPD$^B$(or IPD$^A$) in a second polypeptide. Thus, in the presence of an inducer agent or inducer signal, the IPD$^A$ and IPD$^B$ come together linked to resulting in the linkage of the ED to the DBD of the synthetic TF. In the absence of an inducer agent or inducer signal, the ED is uncoupled or unlinked to the DBD of the synthetic TF.

In some embodiments of any of the aspects, a synTF polypeptide as described herein (or a synTF polypeptide system collectively) comprises 1, 2, 3, 4, 5, or more induced proximity domain(s). In some embodiments of any of the aspects, the synTF polypeptide or system comprises one induced proximity domain. In embodiments comprising multiple induced proximity domains, the multiple induced proximity domains can be different individual induced proximity domains or multiple copies of the same induced proximity domain, or a combination of the foregoing.

In some embodiments of any of the aspects, the induced proximity domain pair (IPD pair) comprises a IPD$^A$ and IPD$^B$ selected from any one or more of: (1) a IPD$^A$ comprising a GID1 domain or a fragment thereof, and a IPD$^B$ comprising a GAI domain, wherein the GID1 domain and GAI domain bind to the inducer agent Gibberellin Ester (GIB); (2) a IPD$^A$ comprising a FKBP domain or a fragment thereof, and a IPD$^B$ comprising a FRB domain, wherein the FKBP domain and FRB domain bind to the inducer agent Rapalog (RAP); (3) a IPD$^A$ comprising a PYL domain or a fragment thereof, and a IPD$^B$ comprising a ABI domain, wherein the PYL domain and ABI domain bind to the inducer agent Abscisic acid (ABA); (4) a IPD$^A$ comprising a Light-inducible dimerization domain (LIDD), wherein a LIDD dimerizes with a complementary LIDD (IPD$^B$) upon exposure to a light inducer signal of an appropriate wavelength.

In some embodiments of any of the aspects, the synTF polypeptide is in combination with 1, 2, 3, 4, 5, or more inducer agents, i.e., that induce dimerization or proximity of the IPDs. In some embodiments of any of the aspects, the synTF polypeptides are in combination with one inducer agent. In embodiments comprising multiple inducer agents, the multiple inducer agents can be different individual inducer agents or multiple copies of the same inducer agent, or a combination of the foregoing.

In some embodiments of any of the aspects, the IPD pair comprises a ABI (ABA insensitive) domain and a PYL (pyrabactin resistance-like) domain, derived from components of the Abscisic acid (ABA) signaling pathway from *Arabidopsis thaliana*. In some embodiments of any of the aspects, the IPD pair comprises the interacting complementary surfaces (CSs) of PYL1 (PYLcs, amino acids 33 to 209) and ABI1 (ABIcs, amino acids 126 to 423). In some embodiments of any of the aspects, the ABI domain (e.g., SEQ ID NO: 66) comprises mutations A18D and E108G. In some embodiments of any of the aspects, the ABI domain further comprises a detectable marker (e.g., a FLAG tag). In some embodiments of any of the aspects, the PYL domain further comprises a detectable marker (e.g., an HA tag).

In some embodiments of any of the aspects, the ABI domain comprises SEQ ID NOs: 66 or 107 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 66 or 107, that maintains the same function.

In some embodiments of any of the aspects, the PYL domain comprises SEQ ID NOs: 71 or 108 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 71 or 108, that maintains the same function.

```
SEQ ID NO: 66, ABI cs C01 (298 aa)
VPLYGFTSICGRRPEMEAAVSTIPRFLQSSSGSMLDGRFDPQSAAHFFGV

YDGHGGSQVANYCRERMHLALAEEIAKEKPMLCDGDTWLEKWKKALFNSF

LRVDSEIESVAPETVGSTSVVAVVFPSHIFVANCGDSRAVLCRGKTALPL

SVDHKPDREDEAARIEAAGGKVIQWNGARVFGVLAMSRSIGDRYLKPSII

PDPEVTAVKRVKEDDCLILASDGVWDVMTDEEACEMARKRILLWHKKNAV

AGDASLLADERRKEGKDPAAMSAAEYLSKLAIQRGSKDNISVVVVDLK

SEQ ID NO: 71, PYL1cs Domain (177 aa)
TQDEFTQLSQSIAEFHTYQLGNGRCSSLLAQRIHAPPETVWSVVRRFDRP

QIYKHFIKSCNVSEDFEMRVGCTRDVNVISGLPANTSRERLDLLDDDRRV

TGFSITGGEHRLRNYKSVTTVHRFEKEEEEERIWTVVLESYVVDVPEGNS

EEDTRLFADTVIRLNLQKLASITEAMN

SEQ ID NO: 107, Alternative ABI binding motif
PLYGFTSICGRRPEMEDAVSTIPRFLQSSSGSMLDGRFDPQSAAHFFGVY

DGHGGSQVANYCRERMHLALAEEIAKEKPMLCDGDTWLEKWKKALFNSFL

RVDSEIGSVAPETVGSTSVVAVVFPSHIFVANCGDSRAVLCRGKTALPLS

VDHKPDREDEAARIEAAGGKVIQWNGARVFGVLAMSRSIGDRYLKPSIIP

DPEVTAVKRVKEDDCLILASDGVWDVMTDEEACEMARKRILLWHKKNAVA

GDASLLADERRKEGKDPAAMSAAEYLSKLAIQRGSKDNISVVVVDLKDYK

DDDDK

SEQ ID NO: 108, Alternative PYL binding motif
APTQDEFTQLSQSIAEFHTYQLGNGRCSSLLAQRIHAPPETVWSVVRRFD

RPQIYKHFIKSCNVSEDFEMRVGCTRDVNVISGLPANTSRERLDLLDDDR

RVTGFSITGGEHRLRNYKSVTTVHRFEKEEEEERIWTVVLESYVVDVPEG

NSEEDTRLFADTVIRLNLQKLASITEAMNYPYDVPDYA
```

In some embodiments of any of the aspects, the proximity inducer agent (e.g., for ABI and PYL domains) is abscisic acid (ABA):

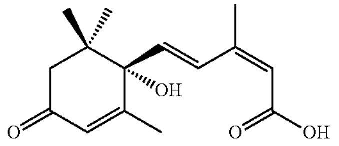

In some embodiments, the IPD pair are FKBP (FK506- and rapamycin-binding protein) and FKBP12-rapamycin-binding protein (FRB) proteins, which come together and dimerize in the presence of a rapalog. In some embodiments of any of the aspects, the FKBP domain comprises SEQ ID NOs: 109 or 318 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 109 or 318, that maintains the same function. In some embodiments of any of the aspects, the FRB domain comprises SEQ ID NO: 110 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 110, that maintains the same function.

```
SEQ ID NO: 109, FKBP aa binding motif:
SRGVQVETISPGDGRTFPKRGQTCVVHYTGMLEDGKKFDSSRDRNKPFK

FMLGKQEVIRGWEEGVAQMSVGQRAKLTISPDYAYGATGHPGIIPPHAT

LVFDVELLKLE

SEQ ID NO: 110, FRB binding motif,
ILWHEMWHEGLEEASRLYFGERNVKGMFEVLEPLHAMMERGPQTLKETS

FNQAYGRDLMEAQEWCRKYMKSGNVKDLLQAWDLYYHVFRRIS
```

In some embodiments of any of the aspects, the proximity inducer agent (e.g., for FKBP and FRB domains) is rapamycin shown below. In some embodiments of any of the aspects, the proximity inducer agent (e.g., for FKBP and FRB domains) is a rapalog, i.e., a rapamycin analog. In some embodiments of any of the aspects, the rapalog is Sheild-1, as described further herein.

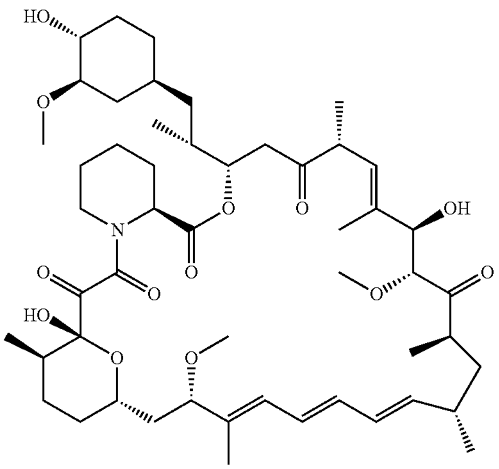 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

In other embodiments, the IPD pair are GAI (Gibberellin insensitive) and GID1 (Gibberellin insensitive dwarf1) proteins, derived from, *Arabidopsis thaliana*, which come together in the presence of Gibberellin Ester (GE). In some embodiments of any of the aspects, the GAI domain comprises SEQ ID NO: 111 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 111, that maintains the same function. In some embodiments of any of the aspects, the GAI domain comprises the amino-terminal DELLA domain of GAI. In some embodiments of any of the aspects, the GID domain comprises SEQ ID NO: 112 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 112, that maintains the same function.

SEQ ID NO: 111, GAI binding motif,
MKRDHHHHHHQDKKTMMMNEEDDGNGMDELLAVLGYKVRSSEMADVAQKL

EQLEVMMSNVQEDDLSQLATETVHYNPAELYTWLDSMLTDLN

SEQ ID NO: 112, GID1 binding motif
MAASDEVNLIESRTVVPLNTWVLISNFKVAYNILRRPDGTFNRHLAEYLD

RKVTANANPVDGVFSFDVLIDRRINLLSRVYRPAYADQEQPPSILDLEKP

VDGDIVPVILFFHGGSFAHSSANSAIYDTLCRRLVGLCKCVVVSVNYRRA

PENPYPCAYDDGWIALNWVNSRSWLKSKKDSKVHIFLAGDSSGGNIAHNV

ALRAGESGIDVLGNILLNPMFGGNERTESEKSLDGKYFVTVRDRDWYWKA

FLPEGEDREHPACNPFSPRGKSLEGVSFPKSLVVVAGLDLIRDWQLAYAE

GLKKAGQEVKLMHLEKATVGFYLLPNNNHFHNVMDEISAFVNAEC

In some embodiments of any of the aspects, the proximity inducer agent (e.g., for GAI and GID1 domains) is a bioactive gibberellin (shown below), a Gibberellin Ester (GE), or another gibberellin analog.

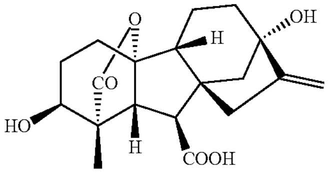

In some embodiments, the IPD pair comprises a caffeine-induced dimerization system, such as a VHH camelid antibody (referred to as aCaffVHH) that has high affinity (Kd=500 nM) and homodimerizes in the presence of caffeine. In some embodiments, the IPD pair is selected from a combinatorial binders-enabled selection of chemically induced dimerization systems (COMBINES-CID), using a specific chemical ligand. As a non-limiting example, the ligand can be CBD (cannabidiol). In some embodiments, the IPD pair comprises human antibody-based chemically induced dimerizes (AbCIDs), which are derived from known small-molecule-protein complexes by selecting for synthetic antibodies that recognize the chemical epitope created by the small molecule bound to the protein (e. g ABT-737). In some embodiments, the IPD pair comprises Calcineurin and FKBP, which come together in the presence of FK506. In some embodiments, the IPD pair comprises Calcineurin and prolyl isomerase CyP, which come together in the presence of Cyclosporine A. In some embodiments, the IPD pair comprises CyP and FKBP, which come together in the presence of FKCsA, a fusion of FK506 and Cyclosprin A. In some embodiments, the IPD pair comprises two copies of FKBP, which come together in the presence of FK2012, a fusion of two FK506 molecules. See e.g., Franco et al., Journal of Chromatography B, Volume 878, Issue 2, 15 Jan. 2010, Pages 177-186; Liang et al. Sci Signal 2011 Mar. 15; 4(164):rs2; Laura A. Banaszynski et al. JACS 2005 Apr. 6; 127(13):4715-21; Miyamoto et al. Nat Chem Biol Nature Chemical Biology volume 8, pages 465-470(2012); Bojar et al. Nature Communications volume 9, Article number: 2318 (2018); Kang et al. JACS 2019 Jul. 17; 141(28): 10948-10952; Hill et al. Nat ChemBio 2018 February; 14(2):112-117; Stanton et al. Science 2018 Mar. 9; 359(6380): eaao5902; Weinberg et al. Nat Biotech 2017 May; 35(5): 453-462; Matthew J Kennedy, Nature Methods volume 7, pages 973-975(2010); US Patent Applications US20180163195 and US20170183654; U.S. Pat. No. 8,735,096; the contents of each of which are incorporated herein by reference in their entireties.

In some embodiments, the IPD pair comprises a light-inducible dimerization domain (LIDD) pair, non-limiting examples of which include nMag/nMag, CRY2/CIBN, and photochromic proteins. In some embodiments, the IPD pair comprises a light-inducible dimerization domain (LIDD) pair, such as nMag and pMag proteins, which come together and dimerize in a blue light signal, e.g., after a blue light pulse signal, or pulse of a light of an appropriate wavelength. In some embodiments of any of the aspects, the nMag domain comprises SEQ ID NO: 113 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 113, that maintains the same function. In some embodiments of any of the aspects, the pMag domain comprises SEQ ID NO: 114 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 114, that maintains the same function.

SEQ ID NO: 113, nMag binding motif
HTLYAPGGYDIMGYLDQIGNRPNPQVELGPVDTSCALILCDLKQKDTPIV

YASEAFLYMTGYSNAEVLGRNCRFLQSPDGMVKPKSTRKYVDSNTINTMR

KAIDRNAEVQVEVVNFKKNGQRFVNFLTMIPVRDETGEYRYSMGFQCETE

SEQ ID NO: 114, pMag binding motif
HTLYAPGGYDIMGYLRQIRNRPNPQVELGPVDTSCALILCDLKQKDTPIV

YASEAFLYMTGYSNAEVLGRNCRFLQSPDGMVKPKSTRKYVDSNTINTMR

KAIDRNAEVQVEVVNFKKNGQRFVNFLTMIPVRDETGEYRYSMGFQCETE

In some embodiments, the IPD pair comprises a light-inducible dimerization domain (LIDD) pair, such as cryptochrome 2 (CRY2) and CIBN (a truncated version of CIB1 (CRY2 interacting basic-helix-loop-helix 1)) and proteins, derived from *Arabidopsis thaliana*, which come together and dimerize in a blue light signal, e.g., after a blue light pulse signal, or pulse of a light of an appropriate wavelength. In some embodiments of any of the aspects, the CIBN domain comprises SEQ ID NO: 115 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 115, that maintains the same function. In some embodiments of any of the aspects, the CRY2 domain comprises SEQ ID NO: 116 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 116, that maintains the same function.

```
SEQ ID NO: 115, CIBN LIDD
MNGAIGGDLLLNFPDMSVLERQRAHLKYLNPTFDSPLAGFFADSSMITG

GEMDSYLSTAGLNLPMMYGETTVEGDSRLSISPETTLGTGNFKKRKFDT

ETKDCNEKKKKMTMNRDDLVEEGEEEKSKITEQNNGSTKSIKKMKHKAK

KEENNFSNDSSKVTKELEKTDYIH

SEQ ID NO: 116, CRY2 LIDD
MKMDKKTIVWFRRDLRIEDNPALAAAAHEGSVFPVFIWCPEEEGQFYPGR

ASRWWMKQSLAHLSQSLKALGSDLTLIKTHNTISAILDCIRVTGATKVVF

NHLYDPVSLVRDHTVKEKLVERGISVQSYNGDLLYEPWEIYCEKGKPFTS

FNSYWKKCLDMSIESVMLPPPWRLMPITAAAEAIWACSIEELGLENEAEK

PSNALLTRAWSPGWSNADKLLNEFIEKQLIDYAKNSKKVVGNSTSLLSPY

LHFGEISVRHVFQCARMKQIIWARDKNSEGEESADLFLRGIGLREYSRYI

CFNFPFTHEQSLLSHLRFFPWDADVDKFKAWRQGRTGYPLVDAGMRELWA

TGWMHNRIRVIVSSFAVKFLLLPWKWGMKYFWDTLLDADLECDILGWQYI

SGSIPDGHELDRLDNPALQGAKYDPEGEYIRQWLPELARLPTEWIHHPWD

APLTVLKASGVELGTNYAKPIVDIDTARELLAKAISRTREAQIMIGAAPD

EIVADSFEALGANTIKEPGLCPSVSSNDQQVPSAVRYNGSKRVKPEEEEE

RDMKKSRGFDERELFSTAESSSSSSVFFVSQSCSLASEGKNLEGIQDSSD

QITTSLGKNGCK
```

In some embodiments, the IPD pair comprises a light-inducible dimerization domain (LIDD) pair, such as photochromic protein domains including, but not limited to Dronpa, Padron, rsTagRFP, and mApple, or a variant or polypeptide fragment thereof having fluorescence characteristics (e.g., Dronpa-145N, Padron-145N, or mApple-162H-164A). Such photochromic protein domains dimerize in the presence of a specific wavelength (e.g., blue light). In some embodiments of any of the aspects, the photochromic protein domain comprises one of SEQ ID NOs: 330-333 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 330-333, that maintains the same function.

```
SEQ ID NO: 330, Dropna-145K (224 aa)
MSVIKPDMKIKLRMEGAVNGHPFAIEGVGLGKPFEGKQSMDLKVKEGGPL

PFAYDILTTVFCYGNRVFAKYPENIVDYFKQSFPEGYSWERSMNYEDGGI
```

-continued

```
CNATNDITLDGDCYIYEIRFDGVNFPANGPVMQKRTVKWEPSTEKLYVRD

GVLKGDVNMALSLEGGGHYRCDFKTTYKAKKVVQLPDYHFVDHHIEIKSH

DKDYSNVNLHEHAEAHSELPRQAK

SEQ ID NO: 331, Dropna-145N (224 aa)
MSVIKPDMKIKLRMEGAVNGHPFAIEGVGLGKPFEGKQSMDLKVKEGGPL

PFAYDILTTVFCYGNRVFAKYPENIVDYFKQSFPEGYSWERSMNYEDGGI

CNATNDITLDGDCYIYEIRFDGVNFPANGPVMQKRTVKWEPSTENLYVRD

GVLKGDVNMALSLEGGGHYRCDFKTTYKAKKVVQLPDYHFVDHHIEIKSH

DKDYSNVNLHEHAEAHSELPRQAK

SEQ ID NO: 332, Padron-145N (224 aa)
MSVIKPDMKIKLRMEGAVNGHPFAIEGVGLGKPFEGKQSMDLKVKEGGPL

PFAYDILTMAFCYGNRVFAKYPENIVDYFKQSFPEGYSWERSMHYEDGGS

CNATNDITLDGDCYIYEIRFDGVNFPANGPVMQKRTVKWERSTENLYVRD

GVLKSDGNYALSLEGGGHYRCDFKTTYKAKKVVQLPDYHSVDHHIEIKSH

DKDYSNVNLHEHAEAHSELPRQAN

SEQ ID NO: 333, mApple-162H-164A (236 aa)
MVSKGEENNMAIIKEFMRFKVHMEGSVNGHEFEIEGEGEGRPYEAFQTAK

LKVTKGGPLPFAWDILSPQFMYGSKVYIKHPADIPDYFKLSFPEGFRWER

VMNFEDGGIIHVNQDSSLQDGVFIYKVKLRGTNFPSDGPVMQKKTMGWEA

SEERMYPEDGAHKAEIKKRLKLKDGGHYAAEVKTTYKAKKPVQLPGAYIV

DIKLDIVSHNEDYTIVEQYERAEGRHSTGGMDELYK
```

Cytosolic Sequestering Domain

In several aspects, described herein are synTF polypeptides comprising a cytosolic sequestering domain or protein, also referred to herein as a translocation domain. As used herein, the term "cytosolic sequestering domain" refers to a domain that influences the subcellular location of the synTF to which it is linked, e.g., through the binding of a ligand.

In some embodiments of any of the aspects, a synTF polypeptide as described herein (or a synTF polypeptide system collectively) comprises 1, 2, 3, 4, 5, or more cytosolic sequestering domain(s). In some embodiments of any of the aspects, the synTF polypeptide or system comprises one cytosolic sequestering domain. In embodiments comprising multiple cytosolic sequestering domains, the multiple cytosolic sequestering domains can be different individual cytosolic sequestering domains or multiple copies of the same cytosolic sequestering domain, or a combination of the foregoing.

In some embodiments of any of the aspects, the cytosolic sequestering protein comprises a ligand binding domain (LBD), wherein in the presence of the ligand, the sequestering of the protein to the cytosol is inhibited. In some embodiments of any of the aspects, cytosolic sequestering protein further comprises a nuclear localization signal (NLS), wherein in the absence of the ligand the NLS is inhibited thereby preventing translocation of the sequestering protein to the nucleus, and wherein in the presence of the ligand the nuclear localization signal is exposed enabling translocation of the sequestering protein to the nucleus. Accordingly, when the ligand is absent, the synTF is sequestered to the cytosol. When the ligand is absent, the synTF is translocated to the nucleus.

In some embodiments of any of the aspects, the sequestering protein comprises at least a portion of the estrogen receptor (ER). The ER naturally associates with cytoplasmic factors in the cell in the absence of cognate ligands, effectively sequestering itself in the cytoplasm. Binding of cognate ligands, such as estrogen or other steroid hormone derivatives, cause a conformational change to the receptor that allow dissociation from the cytoplasmic complexes and expose a nuclear localization signal, permitting translocation into the nucleus.

In some embodiments of any of the aspects, the sequestering protein comprises SEQ ID NO: 334 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 334 that maintains the same function. In some embodiments of any of the aspects, the sequestering protein comprises a portion of the ER (e.g., SEQ ID NO: 334), e.g., the C-terminal ligand-binding and nuclear localization domains of ER. In some embodiments of any of the aspects, the sequestering protein comprises residues 282-595 of SEQ ID NO: 334 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to residues 282-595 of SEQ ID NO: 334.

SEQ ID NO: 334, estrogen receptor isoform 1 [*Homo sapiens*]; NCBI Reference Sequence: NP_000116.2 (595 aa)

MTMTLHTKASGMALLHQIQGNELEPLNRPQLKIPLERPLGEVYLDSSKPA

VYNYPEGAAYEFNAAAAANAQVYGQTGLPYGPGSEAAAFGSNGLGGFPPL

NSVSPSPLMLLHPPPQLSPFLQPHGQQVPYYLENEPSGYTVREAGPPAFY

RPNSDNRRQGGRERLASTNDKGSMAMESAKETRYCAVCNDYASGYHYGVW

SCEGCKAFFKRSIQGHNDYMCPATNQCTIDKNRRKSCQACRLRKCYEVGM

MKGGIRKDRRGGRMLKHKRQRDDGEGRGEVGSAGDMRAANLWPSPLMIKR

-continued

SKKNSLALSLTADQMVSALLDAEPPILYSEYDPTRPFSEASMMGLLTNLA

DRELVHMMWAKRVPGFVDLTLHDQVHLLECAWLEILMIGLVWRSMEHPGK

LLFAPNLLLDRNQGKCVEGMVEIFDMLLATSSRFRMMNLQGEEFVCLKSI

ILLNSGVYTFLSSTLKSLEEKDHIHRVLDKITDTLIHLMAKAGLTLQQQH

QRLAQLLLILSHIRHMSNKGMEHLYSMKCKNVVPLYDLLLEMLDAHRLHA

PTSRGGASVEETDQSHLATAGSTSSHSLQKYYITGEAEGFPATV

In some embodiments of any of the aspects, the estrogen receptor comprises at least one mutation that decreases its ability to bind to its natural ligands (e.g., estradiol) but maintains the ability to bind to synthetic ligands such as tamoxifen and analogs thereof. In some embodiments of any of the aspects, the estrogen receptor comprises at least one of the following mutations: G400V, G521R, L539A, L540A, M543A, L544A, V595A or any combination thereof. In some embodiments of any of the aspects, a triple G400V/MS43A/L544A ER mutant is referred to herein as ERT2. In some embodiments of any of the aspects, the sequestering protein further comprises a V595A mutation from ER (e.g., SEQ ID NO: 334). In some embodiments of any of the aspects, the sequestering protein comprises an estrogen ligand binding domain (ERT2) or a variant thereof. In some embodiments of any of the aspects, the sequestering protein comprises ERT, ERT2, ERT3, or a variant thereof. In some embodiments of any of the aspects, the sequestering protein comprises one of SEQ ID NOs: 74, 335-337 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 74, 335-337, that maintains the same function. See e.g., U.S. Pat. No. 7,112,715; Feil et al., Biochemical and Biophysical Research Communications, Volume 237, Issue 3, 28 Aug. 1997, Pages 752-757; Felker et al., PLoS One. 2016 Apr. 14; 11(4):e0152989; the contents of each of which are incorporated herein by reference in their enteritis.

SEQ ID NO: 74, ERT2 (314 aa), G400V, M543A, L544A, and V595A mutations from ER (e.g., SEQ ID NO: 334) shown in bold, double underlined text

SAGDMRAANLWPSPLMIKRSKKNSLALSLTADQMVSALLDAEPPILYSEYDPTRPFSEASMMGL

LTNLADRELVHMMWAKRVPGFVDLTLHDQVHLLECAWLEILMIGLVWRSMEHPVKLLFAPNL

LLDRNQGKCVEGMVEIFDMLLATSSRFRMMNLQGEEFVCLKSIILLNSGVYTFLSSTLKSLEEKD

HIHRVLDKITDTLIHLMAKAGLTLQQQHQRLAQLLLILSHIRHMSNKGMEHLYSMKCKNVVPLY

DLLLEAADAHRLHAPTSRGGASVEETDQSHLATAGSTSSHSLQKYYITGEAEGFPATA

SEQ ID NO: 335, ERT (314 aa), G521R mutation from ER (e.g., SEQ ID NO: 334) shown in bold, double underlined text

SAGDMRAANLWPSPLMIKRSKKNSLALSLTADQMVSALLDAEPPILYSEYDPTRPFSEASMMGL

LTNLADRELVHMMWAKRVPGFVDLTLHDQVHLLECAWLEILMIGLVWRSMEHPGKLLFAPNL

LLDRNQGKCVEGMVEIFDMLLATSSRFRMMNLQGEEFVCLKSIILLNSGVYTFLSSTLKSLEEKD

HIHRVLDKITDTLIHLMAKAGLTLQQQHQRLAQLLLILSHIRHMSNKRMEHLYSMKCKNVVPLY

DLLLEMLDAHRLHAPTSRGGASVEETDQSHLATAGSTSSHSLQKYYITGEAEGFPATV

SEQ ID NO: 336, ERT3 (314 aa), M543A, L544A, and V595A mutations from ER (e.g., SEQ ID NO: 334) shown in bold, double underlined text

SAGDMRAANLWPSPLMIKRSKKNSLALSLTADQMVSALLDAEPPILYSEYDPTRPFSEASMMGL

LTNLADRELVHMMWAKRVPGFVDLTLHDQVHLLECAWLEILMIGLVWRSMEHPGKLLFAPNL

-continued

LLDRNQGKCVEGMVEIFDMLLATSSRFRMMNLQGEEFVCLKSIILLNSGVYTFLSSTLKSLEEKD

HIHRVLDKITDTLIHLMAKAGLTLQQQHQRLAQLLLILSHIRHMSNKGMEHLYSMKCKNVVPLY

DLLLE AA DAHRLHAPTSRGGASVEETDQSHLATAGSTSSHSLQKYYITGEAEGFPAT A

SEQ ID NO: 337, ERT (314 aa), G400V, L539A, L540A mutations from ER (e.g., SEQ ID NO: 334) shown in bold, double underlined text
SAGDMRAANLWPSPLMIKRSKKNSLALSLTADQMVSALLDAEPPILYSEYDPTRPFSEASMMGL

LTNLADRELVHMMWAKRVPGFVDLTLHDQVHLLECAWLEILMIGLVWRSMEHP V KLLFAPNL

LLDRNQGKCVEGMVEIFDMLLATSSRFRMMNLQGEEFVCLKSIILLNSGVYTFLSSTLKSLEEKD

HIHRVLDKITDTLIHLMAKAGLTLQQQHQRLAQLLLILSHIRHMSNKGMEHLYSMKCKNVVPLY

D AA LEMLDAHRLHAPTSRGGASVEETDQSHLATAGSTSSHSLQKYYITGEAEGFPATV

In some embodiments of any of the aspects, the sequestering protein of the synTF polypeptide is in combination with 1, 2, 3, 4, 5, or more ligands. In some embodiments of any of the aspects, the sequestering protein of the synTF polypeptide is in combination with one ligand. In embodiments comprising multiple ligands, the multiple ligands can be different individual ligands or multiple copies of the same ligands, or a combination of the foregoing.

In some embodiments of any of the aspects, the ligand is estradiol (PubChem CID: 5757), or an analog thereof. In some embodiments of any of the aspects, the ligand is a synthetic ligand of the estrogen receptor, such as tamoxifen or a derivative thereof the ligand is selected from: tamoxifen, 4-hydroxytamoxifen (4OHT), endoxifen, and Fulvestrant, wherein binding of the ligand to the ERT (e.g., ERT2) exposes the NLS and results in nuclear translocation of the ERT. In some embodiments of any of the aspects, the ligand is 4-hydroxytamoxifen (4-OHT), shown below (PubChem CID: 449459), which can also be referred to as afimoxifene. In some embodiments of any of the aspects, the ligand is 4-Hydroxy-N-desmethyltamoxifen, shown below (PubChem CID: 10090750), which can also be referred to as endoxifen. In some embodiments of any of the aspects, the ligand is Fulvestrant shown below (PubChem CID 104741), which can also be referred to as ICI 182,780.

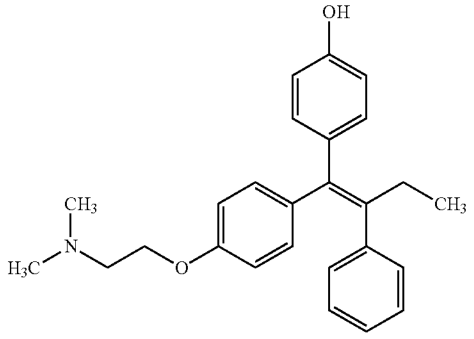

trans-4-OHT

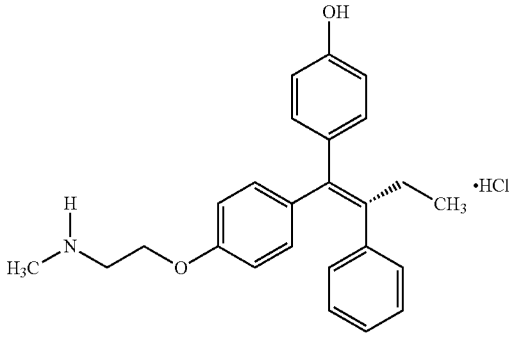

Endoxifen

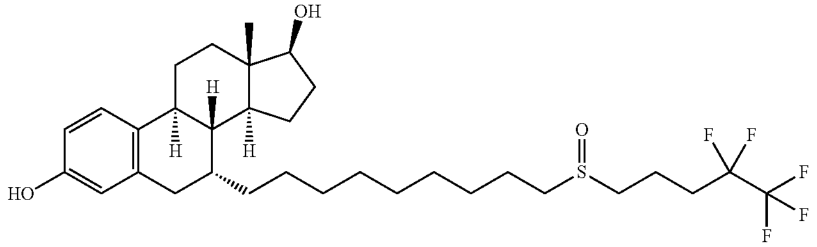

Fulvestrant

In some embodiments of any of the aspects, the sequestering protein of the synTF is a transmembrane receptor sequestering protein, and the DNA-binding domain (DBD) and transcriptional effector (TE) domain of the synTF are linked to the cytosolic side of the transmembrane domain of the receptor. In the absence of a specific ligand for the transmembrane protein, the DBD and TA of the synTF are sequestered to the cellular membrane. In the presence of a specific ligand for the transmembrane protein, the transmembrane protein cleaves itself such that the DBD and TA of the synTF are released into the cytosol to be transported to the nucleus. Non-limiting examples of transmembrane receptor sequestering protein include a synthetic notch receptor or first and second exogenous extracellular sensors, described further herein.

In some embodiments of any the aspects, the cytosolic sequestering protein comprises a Notch receptor or a variant of endogenous Notch receptor, such as a synthetic Notch (synNotch) receptor. In some embodiments of any the aspects, the synTF comprising a synNotch comprises: (a) an extracellular domain comprising a first member of a specific binding pair that is heterologous to the Notch receptor; (b) a Notch receptor regulatory region; and (c) an intracellular domain comprising the DNA binding domain and transcriptional effector domain of the synTF. In the presence of a second member of the specific binding pair, binding of the first member of the specific binding pair to the second member of the specific binding pair induces cleavage of the binding-induced proteolytic cleavage site to activate the intracellular domain, thereby permitting the synTF to translocate to the nucleus. In the absence of a second member of the specific binding pair, the synTF remains sequestered at the cellular membrane. In some embodiments of any of the aspects, the sequestering protein comprises one of SEQ ID NOs: 338-339 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 74, 335-337, that maintains the same function. See e.g., U.S. Pat. No. 10,590,182; Morsut et al., Cell. 2016 Feb. 11; 164(4):780-91; the contents of which are incorporated herein by reference in their entireties. In some embodiments of any of the aspects, the Notch receptor regulatory region comprises Lin-12 Notch repeats A-C, heterodimerization domains HD-N and HD-C, a binding-induced proteolytic cleavage site, and a transmembrane domain. In some embodiments of any the aspects, the Notch variant is a Notch receptor where the Notch extracellular subunit (NEC) (which includes the negative regulatory region (NRR)) is partially or completely removed. In some embodiments of any of the aspects, the Notch receptor regulatory region is a truncated or modified variant of synNotch, e.g., lacking one or more of the following domains: Lin-12 Notch repeats A-C, heterodimerization domains HD-N and HD-C, a binding-induced proteolytic cleavage site, the Notch extracellular domain (NEC), the negative regulatory region (NRR), or a transmembrane domain.

SEQ ID NO: 338, synNotch (306 aa)
PPQIEEACELPECQVDAGNKVCNLQCNNHACGWDGGDCSLNFNDPWKNCT

QSLQCWKYFSDGHCDSQCNSAGCLFDGFDCQLTEGQCNPLYDQYCKDHFS

DGHCDQGCNSAECEWDGLDCAEHVPERLAAGTLVLVVLLPPDQLRNNSFH

FLRELSHVLHTNVVFKRDAQGQQMIFPYYGHEEELRKHPIKRSTVGWATS

SLLPGTSGGRQRRELDPMDIRGSIVYLEIDNRQCVQSSSQCFQSATDVAA

FLGALASLGSLNIPYKIEAVKSEPVEPPLPSQLHLMYVAAAAFVLLFFVG

CGVLLS

SEQ ID NO: 339, synNotch (358 aa)
PCVGSNPCYNQGTCEPTSENPFYRCLCPAKFNGLLCHILDYSFTGGAGRD

IPPPQIEEACELPECQVDAGNKVCNLQCNNHACGWDGGDCSLNFNDPWKN

CTQSLQCWKYFSDGHCDSQCNSAGCLFDGFDCQLTEGQCNPLYDQYCKDH

FSDGHCDQGCNSAECEWDGLDCAEHVPERLAAGTLVLVVLLPPDQLRNNS

FHFLRELSHVLHTNVVFKRDAQGQQMIFPYYGHEEELRKHPIKRSTVGWA

TSSLLPGTSGGRQRRELDPMDIRGSIVYLEIDNRQCVQSSSQCFQSATDV

AAFLGALASLGSLNIPYKIEAVKSEPVEPPLPSQLHLMYVAAAAFVLLFF

VGCGVLLS

Suitable first members of a specific binding pairs (e.g., of the synNotch) include, but are not limited to, antibody-based recognition scaffolds; antibodies (i.e., an antibody-based recognition scaffold, including antigen-binding antibody fragments); non-antibody-based recognition scaffolds; antigens (e.g., endogenous antigens; exogenous antigens; etc.); a ligand for a receptor; a receptor; a target of a non-antibody-based recognition scaffold; an Fc receptor (e.g., FcγRIIIa; FcγRIIIb; etc.); an extracellular matrix component; and the like.

Specific binding pairs (e.g., of the synNotch) include, e.g., antigen-antibody specific binding pairs, where the first member is an antibody (or antibody-based recognition scaffold) that binds specifically to the second member, which is an antigen, or where the first member is an antigen and the second member is an antibody (or antibody-based recognition scaffold) that binds specifically to the antigen; ligand-receptor specific binding pairs, where the first member is a ligand and the second member is a receptor to which the ligand binds, or where the first member is a receptor, and the second member is a ligand that binds to the receptor; non-antibody-based recognition scaffold-target specific binding pairs, where the first member is a non-antibody-based recognition scaffold and the second member is a target that binds to the non-antibody-based recognition scaffold, or where the first member is a target and the second member is a non-antibody-based recognition scaffold that binds to the target; adhesion molecule-extracellular matrix binding pairs; Fc receptor-Fc binding pairs, where the first member comprises an immunoglobulin Fc that binds to the second member, which is an Fc receptor, or where the first member is an Fc receptor that binds to the second member which comprises an immunoglobulin Fc; and receptor-co-receptor binding pairs, where the first member is a receptor that binds specifically to the second member which is a co-receptor, or where the first member is a co-receptor that binds specifically to the second member which is a receptor.

In some embodiments of any the aspects, the transmembrane receptor sequestering protein comprises first and second exogenous extracellular sensors, wherein said first exogenous extracellular sensor comprises: (a) a ligand binding domain, (b) a transmembrane domain, (c) a protease cleavage site, and (d) the DBD and TA of the synTF; and wherein said second exogenous extracellular sensor comprises: (e) a ligand binding domain, (f) a transmembrane domain, and (g) a protease domain. Such a system can also be referred to as a modular extracellular sensor architecture (MESA) system. In the presence of a ligand for the first and second exogenous extracellular sensors, the two receptors are brought into proximity, permitting the protease to cleave the protease cleavage site and release the DBD and TA of the synTF into the cytosol to be translocated to the nucleus. In the absence of a ligand for the first and second exogenous extracellular sensors, the DBD and TA of the synTF remains sequestered at the cell membrane. In some embodiments of any of the aspects, the protease comprises any protease as described herein (e.g., NS3), and the protease cleavage site comprises an NS3 protease cleavage site as described herein. See e.g., US Patent Application 2014/0234851; Daringer et al., ACS Synth. Biol. 2014, 3, 12, 892-902.

Any type of suitable ligand binding domain (LB) can be employed with transmembrane receptor sequestering protein. Ligand binding domains can, for example, be derived from either an existing receptor ligand-binding domain or from an engineered ligand binding domain. Existing ligand-binding domains could come, for example, from cytokine receptors, chemokine receptors, innate immune receptors (TLRs, etc.), olfactory receptors, steroid and hormone receptors, growth factor receptors, mutant receptors that occur in cancer, neurotransmitter receptors. Engineered ligand-binding domains can be, for example, single-chain antibodies (see scFv constructs discussion below), engineered fibronectin based binding proteins, and engineered consensus-derived binding proteins (e.g., based upon leucine-rich repeats or ankyrin-rich repeats, such as DARPins). The ligand can be any cognate ligand of such ligand-binding domains.

Linker Peptide

In several aspects, described herein are synTF polypeptides comprising at least one linker peptide. As used herein "linker peptide" (used interchangeably with "peptide linker") refers to an oligo- or polypeptide region from about 2 to 100 amino acids in length, which links together any of the sequences of the polypeptides as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable.

In some embodiments of any of the aspects, a synTF polypeptide as described herein (or a synTF polypeptide system collectively) comprises 1, 2, 3, 4, 5, or more linker peptide(s). In some embodiments of any of the aspects, the synTF polypeptide or system comprises one linker peptide. In embodiments comprising multiple linker peptides, the multiple linker peptides can be different individual linker peptides or multiple copies of the same linker peptide, or a combination of the foregoing. In some embodiments of any of the aspects, the linker peptide can be positioned anywhere, between any two domains as described herein: e.g., between the DBD and the regulator protein, between the regulator protein and the effector domain, between the DBD and effector domain, or any combination thereof. In some embodiments of any of the aspects, the linker peptide can be positioned within the DBD, effector domain, or regulator protein, e.g., to link constituents of the domain.

In some embodiments of any one aspects described herein, the linkers connect several ZFs to each other in tandem to form a ZF array. In some embodiments of any one aspects described herein, the linker connects a first ZFA with a second ZFA. In some embodiments of any one aspects described herein, the linkers connect several ZFAs to each other to in tandem to form a ZF-containing ZF protein domain. Non-limiting examples of peptide linker molecules useful in the polypeptides described herein include glycine-rich peptide linkers (see, e.g., U.S. Pat. No. 5,908,626), wherein more than half of the amino acid residues are glycine. Preferably, such glycine-rich peptide linkers consist of about 20 or fewer amino acids. A linker molecule may also include non-peptide or partial peptide molecules. For instance, the peptides can be linked to peptides or other molecules using well known cross-linking molecules such as glutaraldehyde or EDC (Pierce, Rockford, Illinois). In some embodiments of the engineered synTFs described herein, the ZF arrays (ZFAs) in the ZF protein domain of the synTF are joined together in the respective fusion protein with a linker peptide.

Non-limiting examples of linker peptide include, but are not limited to: PGER (SEQ ID NO: 340), TGSQK (SEQ ID NO: 341), TGEKP (SEQ ID NO: 342), THLR (SEQ ID NO: 343), TGGGEKP (SEQ ID NO: 344), FHYDRNNIAVGADESVVKEAHREVINSSTEGLLLNIDKDIR- KILSGYIVEIEDTE (SEQ ID NO: 345); VEIEDTE (SEQ ID NO: 346), KDIRKILSGYIVEIEDTE (SEQ ID NO: 347); STEGLLLNIDKDIRKILSGYIVEIEDTE (SEQ ID NO: 348), EVKQENRLLNESES (SEQ ID NO: 349); VGADESVVKEAHREVINSSTEGLLLNIDKDIRKI-LSGYIVEIEDTE (SEQ ID NO: 350); GGSGG (SEQ ID NO: 67); GGGSG (SEQ ID NO: 70); CVRGS (SEQ ID NO: 73), GGGGSG (SEQ ID NO: 75), GGSGSGSAC (SEQ ID NO: 100), LEGGGGSGG (SEQ ID NO: 103), GGGGSGGT (SEQ ID NO: 104), SGGGSGGSGSS (SEQ ID NO: 345); PGAGSSGDIM (SEQ ID NO: 88) GSSGTGSGSGTS (SEQ ID NO: 90); SGTS (SEQ ID NO: 277); GSGS (SEQ ID NO: 278), GGSGGS (SEQ ID NO: 303), and GSSGSS (SEQ ID NO: 323).

For examples, TGSQK (SEQ ID NO: 341) or TGEKP (SEQ ID NO: 342) or TGGGEKP (SEQ ID NO: 344) is used as linker between ZFAs; VEIEDTE (SEQ ID NO: 346), GGSGGS (SEQ ID NO: 303), GGSGG (SEQ ID NO: 67), GGGSG (SEQ ID NO: 70), CVRGS (SEQ ID NO: 73), GGGGSG (SEQ ID NO: 75), GGSGSGSAC (SEQ ID NO: 100), LEGGGGSGG (SEQ ID NO: 103), GGGGSGGT (SEQ ID NO: 104), SGGGSGGSGSS (SEQ ID NO: 345) are used to link ZF domains and effector domains together; PGAGSSGDIM (SEQ ID NO: 88) GSSGTGSGSGTS (SEQ ID NO: 90); SGTS (SEQ ID NO: 277); GSGS (SEQ ID NO: 278), GSSGSS (SEQ ID NO: 323) are used to link regions of a SMASh domain, a StaPL domain, or an NS3/NS4a domain, described further herein.

Flexible linkers are generally composed of small, non-polar or polar residues such as Gly, Ser and Thr. In one embodiment of any fusion protein described herein that includes a linker, the linker peptide comprises at least one amino acid that is Gly or Ser. In one embodiment of a fusion protein described herein that includes a linker, the linker is a flexible polypeptide between 1 and 25 residues in length. Common examples of flexible peptide linkers include (GGS)n, where n=1 to 8 (SEQ ID NO: 351, GGSGGSGGS-GGSGGSGGSGGSGGS), or $(Gly_4Ser)n$ repeat where n=1-8 (SEQ ID NO: 352, GGGGSGGGGSGGG-GSGGGGSGGGGSGGGGSGGGGSGGGGS), preferably, n=3, 4, 5, or 6, that is (Gly-Gly-Gly-Gly-Ser)n (SEQ ID NO: 353), GGGGS, where n indicates the number of repeats of the motif. For example, the flexible linker is $(GGS)_2$ (SEQ ID NO: 354, GGSGGS). Alternatively, flexible peptide linkers include Gly-Ser repeats $(Gly\text{-}Ser)_p$ where p indicates the number of Gly-Ser repeats of the motif, p=1-8 (SEQ ID NO: 355 GSGSGSGSGSGSGSGS), preferably, n=3, 4, 5, or 6. Another example of a flexible linker is TGSQK (SEQ ID NO: 341).

In one embodiment of the engineered synTFs described herein, wherein the ZF protein domains and effector domains are joined together with a linker peptide, the linker peptide is about 1-20 amino acids long. In one embodiment, the linker peptide does not comprise Lys, or does not comprise, or does not comprise both Lys and Arg.

In some embodiments of the engineered synTFs described herein, the ZF protein domains and effector domains are joined together chemical cross-linking agents. Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage.

General methods for cross-linking molecules have been reviewed (see, e.g., Means and Feeney, Bioconjugate Chem., 1: 2-12 (1990)).

Homobifunctional cross-linker molecules have two reactive sites which are chemically the same. Non-limiting examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., disuccinimidyl suberate, dithiobis (succinimidyl propionate), and soluble bis-sulfonic acid and salt thereof (see, e.g., Pierce Chemicals, Rockford, Illinois; Sigma-Aldrich Corp., St. Louis, Missouri).

A bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the disclosure include, without limitation, m-maleimidobenzoyl-N-hydroxysuccinimide ester (see, Green et al., Cell, 28: 477-487 (1982); Palker et al., Proc. Natl. Acad. Sci (USA), 84: 2479-2483 (1987)); m-maleimido-benzoylsulfosuccinimide ester; maleimidobutyric acid N-hydroxysuccinimide ester; and N-succinimidyl 3-(2-pyridyl-dithio)propionate (see, e.g., Carlos et al., Biochem. J., 173: 723-737 (1978); Sigma-Aldrich Corp., St. Louis, Missouri).

In some embodiments of any aspect described herein, in the synTF described or the ZF-containing fusion protein described herein, all the helices within a ZFA are linked by peptide linkers ($L_2$) having four to six amino acid residues.

In some embodiments of any aspect described herein, in the synTF described or the ZF-containing fusion protein described herein, all the helices within an individual ZFA are linked by rigid peptide linkers such as TGEKP (SEQ ID NO: 342) or TGSKP (SEQ ID NO: 356) or TGQKP (SEQ ID NO: 357) or TGGKP (SEQ ID NO: 358). The rigid linker aids in conferring synergistic binding of the ZF motifs to its target DNA sequence.

In one embodiment of any aspect described herein, in the synTF described or the ZF containing fusion protein described herein, the ($L_1$) or ($L_2$) is a flexible linker. Non-limiting examples include: TGSQKP (SEQ ID NO: 359) and TGGGEKP (SEQ ID NO: 344). In one embodiment, the linker flexible peptide is 1-20 amino acids long. The flexible linker aid in weakening cooperativity between adjacent ZF motifs.

In one embodiment of any aspect described herein, in the synTF described or the ZF containing fusion protein described herein, the (L1) or (L2) is a rigid linker. Non-limiting examples include: TGEKP (SEQ ID NO: 342), TGSKP (SEQ ID NO: 356), TGQKP (SEQ ID NO: 357) and TGGKP (SEQ ID NO: 358).

In some embodiments of any aspect described herein, in the synTF described or the ZF containing fusion protein described herein, where there are two or more ZFAs, the individual ZFAs are linked by flexible peptide linkers, such as TGSQKP (SEQ ID NO: 359). In another embodiment, the ZFAs are linked by chemical crosslinkers. Chemical crosslinkers are known in the art.

In some embodiments of any aspect described herein, in the synTF described or the ZF containing fusion protein described herein, all the helices within an individual ZFA are linked by a combination of rigid peptide linkers and flexible peptide linkers. In some embodiments of any of the aspects, the rigid peptide linkers and flexible peptide linkers are used alternatingly to connect the fingers.

Self-Cleaving Peptide

In several aspects, described herein are synTF polypeptides comprising a self-cleaving peptide. As used herein, the term "self-cleaving peptide" refers to a short amino acid sequence (e.g., approximately 18-22 aa-long peptides) that can catalyze its own cleavage. In some embodiments of any of the aspects, a multi-component synTF system as described herein (e.g., induced proximity synTF system) comprises at least two polypeptides that are physically linked to one another through a self-cleaving peptide domain. The self-cleaving peptide allows the nucleic acids of the first polypeptide and second polypeptide (and/or third polypeptide, etc.) to be present in the same vector, but after translation the self-cleaving peptide cleaves the translated polypeptide into the multiple separate polypeptides.

In some embodiments of any of the aspects, a synTF polypeptide as described herein (or a synTF polypeptide system collectively) comprises 1, 2, 3, 4, 5, or more self-cleaving peptides, e.g., in between each synTF polypeptide. In some embodiments of any of the aspects, the synTF polypeptide or system comprises one self-cleaving peptide, e.g., in between a first polypeptide and a second polypeptide of a synTF polypeptide system. In embodiments comprising multiple self-cleaving peptides, the multiple self-cleaving peptides can be different individual self-cleaving peptides or multiple copies of the same self-cleaving peptide, or a combination of the foregoing.

In some embodiments, self-cleaving peptides are used, for example, in heterodimerization domain synTFs. As a non-limiting example, FIGS. 19 and 20 show a 2A self-cleaving peptide in between a first polypeptide region comprising [ABI]-[ZF] and a second polypeptide region comprising [ED]-[PYL]. Following translation of the polypeptide, the 2A sequence, which is a self-cleaving peptide, cleaves the polypeptide into two polypeptides: [ABI]-[ZF] and [ED]-[PYL], which in the presence of ABA can form a [ED]-[PYL]-ABA-[ABI]-[ZF] complex, thus coupling the DBD (ZF) and ED (e.g., p65 or KRAB).

In some embodiments of any of the aspects, the self-cleaving peptide belongs to the 2A peptide family, which can also be referred to as a 2A Ribosomal Skip Sequence. Non-limiting examples of 2A peptides include P2A, E2A, F2A and T2A (see e.g., Table 18). F2A is derived from foot-and-mouth disease virus 18; E2A is derived from equine rhinitis A virus; P2A is derived from porcine teschovirus-1 2A; T2A is derived from *Thosea asigna* virus 2A. In some embodiments of any of the aspects, the N-terminal of the 2A peptide comprises the sequence "GSG" (Gly-Ser-Gly). In some embodiments of any of the aspects, the N-terminal of the 2A peptide does not comprise the sequence "GSG" (Gly-Ser-Gly).

TABLE 18

Exemplary Self-Cleaving Peptides

| SEQ ID NO: | Name | Sequence |
|---|---|---|
| 360 | T2A | (GSG) EGRGSLLTCGDVEENPGP |
| 68 | P2A | (GSG) ATNFSLLKQAGDVEENPGP |
| 361 | E2A | (GSG) QCTNYALLKLAGDVESNPGP |
| 362 | F2A | (GSG) VKQTLNFDLLKLAGDVESNPGP |

The 2A-peptide-mediated cleavage commences after protein translation. The cleavage is triggered by breaking of peptide bond between the Proline (P) and Glycine (G) in the C-terminal of the 2A peptide. The molecular mechanism of 2A-peptide-mediated cleavage involves ribosomal "skipping" of glycyl-prolyl peptide bond formation rather than true proteolytic cleavage. Different 2A peptides have different efficiencies of self-cleaving, with P2A being the most efficient and F2A the least efficient. Therefore, up to 50% of F2A-linked proteins can remain in the cell as a fusion protein.

In some embodiments of any of the aspects, the self-cleaving peptide of a synTF polypeptide system as described herein comprises SEQ ID NOs: 68, 360-362, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 68, 360-362, that maintains the same function (e.g., self-cleavage).

In some embodiments of any of the aspects, providing the multiple polypeptides of the synTF systems as described herein in a 1:1 (or 1:1:1, etc.) stoichiometric ratio is advantageous (e.g., this stoichiometric ratio results in optimal functionality). In embodiments where a 1:1 (or 1:1:1, etc.) ratio of the first and second (and third etc.) polypeptides of a synTF system is advantageous, then the first and second polypeptides can be provided in a single vector, flanking a self-cleaving peptide(s) as described herein. In embodiments where a 1:1 (or 1:1:1, etc.) ratio of the first and second (and third etc.) polypeptides of a synTF system is not advantageous (e.g., this stoichiometric ratio results in suboptimal functionality, and other ratios result in optimal functionality) then the first and second polypeptides can be provided in multiple separate vectors, e.g., at the desired stoichiometric ratios.

Detectable Marker

In several aspects, described herein are synTF polypeptides comprising at least one detectable marker. As used herein, the term "detectable marker" refers to a moiety that, when attached to the synTF polypeptide, confers detectability upon that polypeptide or another molecule to which the polypeptide binds. In some embodiments of any of the aspects, the synTF polypeptide (or the synTF polypeptide system collectively) comprises 1, 2, 3, 4, 5, or more detectable markers. In some embodiments of any of the aspects, the synTF polypeptide or system comprises one detectable marker. In embodiments comprising multiple detectable markers, the multiple detectable markers can be different individual detectable markers or multiple copies of the same detectable markers, or a combination of the foregoing.

In some embodiments of any of the aspects, fluorescent moieties can be used as detectable markers, but detectable markers also include, for example, isotopes, fluorescent proteins and peptides, enzymes, components of a specific binding pair, chromophores, affinity tags as defined herein, antibodies, colloidal metals (i.e. gold) and quantum dots. Detectable markers can be either directly or indirectly detectable. Directly detectable markers do not require additional reagents or substrates in order to generate detectable signal. Examples include isotopes and fluorophores. Indirectly detectable markers require the presence or action of one or more co-factors or substrates. Examples include enzymes such as β-galactosidase which is detectable by generation of colored reaction products upon cleavage of substrates such as the chromogen X-gal (5-bromo-4-chloro-3-indoyl-β-D-galactopyranoside), horseradish peroxidase which is detectable by generation of a colored reaction product in the presence of the substrate diaminobenzidine and alkaline phosphatase which is detectable by generation of colored reaction product in the presence of nitroblue tetrazolium and 5-bromo-4-chloro-3-indolyl phosphate, and affinity tags. Non-limiting examples of affinity tags include Strep-tags, chitin binding proteins (CBP), maltose binding proteins (MBP), glutathione-S-transferase (GST), FLAG-tags, HA-tags, Myc-tags, poly(His)-tags as well as derivatives thereof. In some embodiments of any of the aspects, the detectable marker is selected from GFP, V5, HA1, Myc, VSV-G, HSV, FLAG, HIS, mCherry, AU1, and biotin.

SEQ ID NO: 65, NLS,
PKKKRKV

SEQ ID NO: 77, 3X FLAG Tag + Nuclear Localization Sequence (in bold text)
DYKDHDGDYKDHDIDYKDDDDKMAPKKKRKVGIHGVPGG SEQ ID NO: 80, AU1 tag,
DTYRYI SEQ ID NO: 84, HA tag,
YPYDVPDYA SEQ ID NO: 89, FLAG Tag,
DYKDDDDK SEQ ID NO: 372, mCherry:
VSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWE

RVMNFEDGGVVTVTQDSSLQDGEFIYKVKLRGTNFPSDGPVMQKKTMGW

QASSERMYPEDGALKGEIKQRLKLKDGGHYDAEVKTTYKAKKPVQLPGA

YNVNIKLDITSHNEDYTIVEQYERAEGRHSTGGMDELYK

SEQ ID NO: 376, huEGFRt (a truncated human EGFR polypeptide)
RKVCNGIGIGEFKDSLSINATNIKHFKNCTSISGDLHILPVAFRGDSFT

HTPPLDPQELDILKTVKEITGFLLIQAWPENRTDLHAFENLEIIRGRTK

QHGQFSLAVVSLNITSLGLRSLKEISDGDVIISGNKNLCYANTINWKKL

FGTSGQKTKIISNRGENSCKATGQVCHALCSPEGCWGPEPRDCVSCRNV

SRGRECVDKCNLLEGEPREFVENSECIQCHPECLPQAMNITCTGRGPDN

CIQCAHYIDGPHCVKTCPAGVMGENNTLVWKYADAGHVCHLCHPNCTYG

CTGPGLEGCPTNGPKIPSIATGMVGALLLLLVVALGIGLFM

In some embodiments of any of the aspects, the detectable marker of a synTF polypeptide as described herein comprises SEQ ID NOs: 65, 77, 80, 80, 89, 372, 376, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 65, 77, 80, 80, 89, 372, or 376, that maintains the same (e.g., detection of the synTF polypeptide or cleaved fragments of the synTF polypeptide).

In some embodiments of any of the aspects, the detectable marker can be located anywhere within a synTF polypeptide as described herein. In one embodiment, the detectable marker is located between any domain of a synTF polypeptide as described herein, but is not found within a functional domain or does not disrupt the function of a domain. In some embodiments of any of the aspects, the detectable marker is located adjacent to and C terminal of the extracellular binding domain. Such a marker can be used to detect the expression of the synTF polypeptide, including cytosolic expression or nuclear translocation.

In some embodiments of any of the aspects, the detectable marker is located between the repressible protease and a protease cleavage site; such a marker can be used to detect the cleavage and/or expression of the synTF polypeptide. In some embodiments of any of the aspects, the detectable marker that is located between the repressible protease and a protease cleavage site comprises the AU1 tag, the HA1 tag, or any other marker as described herein.

In some embodiments of any of the aspects, the detectable marker is located adjacent and N-terminal to the repressible protease. In some embodiments of any of the aspects, the detectable marker is located adjacent and N-terminal to the repressible protease and C-terminal to a first protease cleavage site. In some embodiments of any of the aspects, the detectable marker is located adjacent to and C terminal to the repressible protease. In some embodiments of any of the aspects, the detectable marker is located adjacent to and C terminal to the repressible protease and N-terminal to a second protease cleavage site.

In some embodiments of any of the aspects, the detectable marker is located at the C-terminal end of the polypeptide. Such a marker can be used to detect the intracellular expression of the synTF polypeptide. In some embodiments of any of the aspects, the detectable marker located at the C-terminal end of the polypeptide comprises mCherry or another marker as described herein.

In some embodiments of any of the aspects, synTF polypeptides as described herein, especially those that are administered to a subject or those that are part of a pharmaceutical composition, do not comprise detectable markers that are immunogenic. In some embodiments of any of the aspects, synTF polypeptides as described herein do not comprise GFP, mCherry, HA1, or any other immunogenic markers.

II. Inducible Synthetic Transcription Factors

In multiple aspects described herein are synthetic transcription factors comprising: (a) at least one DNA binding domain (DBD), (b) a transcriptional effector domain (ED), and (c) at least one regulator protein (RP). In some embodiments of any of the aspects, the ED is directly coupled or linked to the DBD. In some embodiments of any of the aspects, the ED is indirectly coupled or linked to the DBD. In some embodiments of any of the aspects, the coupling of the ED to the DBD is regulated by the at least one RP. In some embodiments of any of the aspects, the cellular localization of the ED is regulated by the at least one regulator protein. In some embodiments of any of the aspects, at least one regulator protein is selected from the group consisting of repressible protease, induced degradation domain, induced proximity domain, and cytosolic sequestering domain.

In some embodiments of any of the aspects, the domains of the synTF can be in order, e.g., from N-terminus to C-terminus: DBD-ED-RP; DBD-RP-ED; ED-DBD-RP; ED-RP-DBD; RP-DBD-ED; or RP-ED-DBD. In embodiments comprising two regulator proteins (i.e., RP1 and RP2), the domains of the synTF can be in order, e.g., from N-terminus to C-terminus: DBD-ED-RP1-RP2; ED-DBD-RP1-RP2; RP1-DBD-ED-RP2; DBD-RP1-ED-RP2; ED-RP1-DBD-RP2; RP1-ED-DBD-RP2; RP1-ED-RP2-DBD; ED-RP1-RP2-DBD; RP2-RP1-ED-DBD; RP1-RP2-ED-DBD; ED-RP2-RP1-DBD; RP2-ED-RP1-DBD; RP2-DBD-RP1-ED; DBD-RP2-RP1-ED; RP1-RP2-DBD-ED; RP2-RP1-DBD-ED; DBD-RP1-RP2-ED; RP1-DBD-RP2-ED; ED-DBD-RP2-RP1; DBD-ED-RP2-RP1; RP2-ED-DBD-RP1; ED-RP2-DBD-RP1; DBD-RP2-ED-RP1; and RP2-DBD-ED-RP1.

In some embodiments and by way of an example only, an exemplary RP1 is selected from an induced proximity domain (IPD), or cytosolic sequestering domain (CS), and the RP2 is selected from the induced degradation domain (comprising a SMASh domain), as disclosed herein. In another embodiment, an exemplary RP1 is an induced degradation domain (comprising a SMASh domain) and the PR2 is selected from an induced proximity domain (IPD) or a cytosolic sequestering domain (IPD).

In multiple aspects, described herein are exemplary synTF polypeptides. In some embodiments of any of the aspects, a synTF polypeptide comprises one of SEQ ID NOs: 4-15, 40-51, or 378-379, or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 4-15, 40-51, or 378-379.

A. Repressible Protease SynTF

In some embodiments of any of the aspects, the regulator protein is a repressible protease. Accordingly, in one aspect described herein is a synTF comprising: (a) a DBD; (b) an ED; and (c) a repressible protease domain (referred to herein as a PRO or RPD). In some embodiments of any of the aspects, the domains of the synTF can be in order, e.g., from N-terminus to C-terminus: DBD-ED-PRO; DBD-PRO-ED; ED-DBD-PRO; ED-PRO-DBD; PRO-DBD-ED; or PRO-ED-DBD.

In some embodiments of any of the aspects, the repressible protease synTF further comprises at least one protease cleavage site (PC), as described further herein. In a preferred embodiment, the at least one protease cleavage site is located in between the DBD and ED, such that when the protease cleaves at the protease cleavage site, the DBD and ED are uncoupled. Accordingly, in some embodiments, the repressible protease synTF comprises from N-terminus to C-terminus: PRO-ED-PC-DBD; ED-PRO-PC-DBD; ED-PC-PRO-DBD; DBD-PC-PRO-ED; DBD-PRO-PC-ED; PRO-DBD-PC-ED; ED-PC-DBD-PRO; and DBD-PC-ED-PRO.

In some embodiments of any of the aspects, the repressible protease synTF comprises two protease cleavage sites (PC). In some embodiments of any of the aspects, the two protease cleavage sites are located directly N terminal and C terminal of the repressible protease domain, e.g., from N-terminus to C-terminus: PC1-PRO-PC2. In some embodiments of any of the aspects, the repressible protease synTF comprises from N-terminus to C-terminus: DBD-PC1-PRO-PC2-ED, or ED-PC1-PRO-PC2-DBD.

In some embodiments of any of the aspects, the repressible protease synTF further comprises a cofactor for the repressible protease (CO), as described further herein. In some embodiments of any of the aspects, the cofactor for the repressible protease is directly linked to the repressible protease, e.g., from N-terminus to C-terminus: CO-PRO or PRO-CO. In some embodiments of any of the aspects, the repressible protease synTF comprises from N-terminus to C-terminus: DBD-ED-PRO-CO; DBD-PRO-CO-ED; ED-DBD-PRO-CO; ED-PRO-CO-DBD; PRO-CO-DBD-ED; PRO-CO-ED-DBD; DBD-ED-CO-PRO; DBD-CO-PRO-ED; ED-DBD-CO-PRO; ED-CO-PRO-DBD; CO-PRO-DBD-ED; CO-PRO-ED-DBD; DBD-PC1-PRO-CO-PC2-

ED; ED-PC1-PRO-CO-PC2-DBD; DBD-PC1-CO-PRO-PC2-ED; or ED-PC1-CO-PRO-PC2-DBD.

In some embodiments of any of the aspects, the DBD of the repressible protease synTF comprises ZF10-1. In some embodiments of any of the aspects, the DBD of the repressible protease synTF comprises SEQ ID NO: 3 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 3, that maintains the same function.

In some embodiments of any of the aspects, the effector domain (ED) comprises a transcriptional activator. In one aspect, described herein is a repressible protease synTF comprising from N-terminus to C-terminus: (a) DBD, (b) a repressible protease; and (c) a transcriptional activator domain. In some embodiments of any of the aspects, the repressible protease synTF comprises SEQ ID NOs: 8 or 44 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 8 or 44, that maintains the same function.

In some embodiments of any of the aspects, the repressible protease synTF is encoded by a vector or polynucleotide comprising SEQ ID NOs: 20 or 32 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 20 or 32, that maintains the same function of the encoded polypeptide, or a codon-optimized version of SEQ ID NOs: 20 or 32.

In some embodiments of any of the aspects, the effector domain (ED) comprises a transcriptional repressor. In one aspect, described herein is a repressible protease synTF comprising from N-terminus to C-terminus: (a) a transcriptional repressor domain, (b) a repressible protease; and (c) DBD. In some embodiments of any of the aspects, the repressible protease synTF comprises SEQ ID NOs: 9 or 45 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 9 or 45, that maintains the same function.

In some embodiments of any of the aspects, the repressible protease synTF is encoded by a vector or polynucleotide comprising SEQ ID NOs: 21 or 33 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 21 or 33, that maintains the same function of the encoded polypeptide, or a codon-optimized version of SEQ ID NOs: 21 or 33.

B. Induced Degradation Domain SynTF

In some embodiments of any of the aspects, the regulator protein is an induced degradation domain. Accordingly, in one aspect described herein is a synTF comprising: (a) a DBD; (b) an ED; and (c) induced degradation domain (SMASh). As described herein, the SMASh domain can be a C-terminal SMASh domain or an N-terminal SMASh domain. In some embodiments of any of the aspects, the domains of the synTF can be in order, e.g., from N-terminus to C-terminus: DBD-ED-SMASh; ED-DBD-SMASh; SMASh-DBD-ED; or SMASh-ED-DBD.

In some embodiments of any of the aspects, the DBD of the SMASh synTF comprises ZF10-1. In some embodiments of any of the aspects, the DBD of the SMASh synTF comprises SEQ ID NO: 3 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 3, that maintains the same function.

In some embodiments of any of the aspects, the effector domain (ED) comprises a transcriptional activator. In one aspect, described herein is a SMASh synTF comprising from N-terminus to C-terminus: (a) DBD, (b) a transcriptional activator domain, and (c) an induced degradation (e.g., SMASh) domain. In some embodiments of any of the aspects, the SMASh synTF comprises SEQ ID NOs: 12 or 48 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 12 or 48, that maintains the same function.

In some embodiments of any of the aspects, the SMASh synTF is encoded by a vector or polynucleotide comprising SEQ ID NOs: 24 or 36 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 24 or 36, that maintains the same function of the encoded polypeptide, or a codon-optimized version of SEQ ID NOs: 24 or 36.

In some embodiments of the aspects, the induced degradation domain synTF further comprises a second regulator protein, e.g., a cytosolic sequestering domain (CS). Accordingly, in one aspect described herein is a synTF comprising: (a) a DBD; (b) an ED; (c) induced degradation domain (SMASh); and (d) a cytosolic sequestering domain (CS). In some embodiments of any of the aspects, the synTF comprises from N-terminus to C-terminus: DBD-ED-SMASh-CS; ED-DBD-SMASh-CS; SMASh-DBD-ED-CS; DBD-SMASh-ED-CS; ED-SMASh-DBD-CS; SMASh-ED-DBD-CS; SMASh-ED-CS-DBD; ED-SMASh-CS-DBD; CS-SMASh-ED-DBD; SMASh-CS-ED-DBD; ED-CS-SMASh-DBD; CS-ED-SMASh-DBD; CS-DBD-SMASh-ED; DBD-CS-SMASh-ED; SMASh-CS-DBD-ED; CS-SMASh-DBD-ED; DBD-SMASh-CS-ED; SMASh-DBD-CS-ED; ED-DBD-CS-SMASh; DBD-ED-CS-SMASh; CS-ED-DBD-SMASh; ED-CS-DBD-SMASh; DBD-CS-ED-SMASh; and CS-DBD-ED-SMASh. In preferred embodiments, the SMASh domain is at the C-terminus or N-terminus: e.g., SMASh-DBD-ED-CS; SMASh-ED-DBD-CS; SMASh-ED-CS-DBD; SMASh-CS-ED-DBD; SMASh-CS-DBD-ED; SMASh-DBD-CS-ED; ED-DBD-CS-SMASh; DBD-ED-CS-SMASh; CS-ED-DBD-SMASh; ED-CS-DBD-SMASh; DBD-CS-ED-SMASh; and CS-DBD-ED-SMASh.

In some embodiments of any of the aspects, the DBD of the SMASh/cytosolic sequestering synTF comprises ZF3-5. In some embodiments of any of the aspects, the DBD of the SMASh/cytosolic sequestering synTF comprises SEQ ID NO: 2 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 2, that maintains the same function.

In some embodiments of any of the aspects, the effector domain (ED) comprises a transcriptional activator. In one aspect, described herein is a SMASh/cytosolic sequestering synTF comprising from N-terminus to C-terminus: (a) DBD, (b) a transcriptional activator domain, (c) a cytosolic sequestering domain, and (d) an induced degradation (e.g., SMASh) domain. In another aspect, described herein is a SMASh/cytosolic sequestering synTF comprising from N-terminus to C-terminus: (a) an induced degradation (e.g., SMASh) domain, (b) DBD, (c) a transcriptional activator domain, and (d) a cytosolic sequestering domain. In some embodiments of any of the aspects, the SMASh/cytosolic sequestering synTF comprises SEQ ID NOs: 10, 11, 46, 47, or 379 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 10, 11, 46, 47, or 379 that maintains the same function.

In some embodiments of any of the aspects, the SMASh/cytosolic sequestering synTF is encoded by a vector or polynucleotide comprising SEQ ID NOs: 22, 23, 34, or 35 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 22, 23, 34, or 35, that maintains the same function of the encoded polypeptide, or a codon-optimized version of SEQ ID NOs: 22, 23, 34, or 35.

In some embodiments of any of the aspects, the effector domain (ED) comprises a transcriptional repressor. In one aspect, described herein is a SMASh/cytosolic sequestering synTF comprising from N-terminus to C-terminus: (a) a transcriptional repressor domain, (b) DBD, (c) a cytosolic sequestering domain and (d) an induced degradation (e.g., SMASh) domain. In another aspect, described herein is a SMASh/cytosolic sequestering synTF comprising from N-terminus to C-terminus: (a) an induced degradation (e.g., SMASh) domain, (b) a transcriptional repressor domain, (c) DBD, and (d) a cytosolic sequestering domain. In some embodiments of any of the aspects, the SMASh/cytosolic sequestering synTF comprises one of SEQ ID NOs: 13-15 or 49-51 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 13-15 or 49-51, that maintains the same function.

In some embodiments of any of the aspects, the SMASh/cytosolic sequestering synTF is encoded by a vector or polynucleotide comprising one of SEQ ID NOs: 25-27 or 37-39 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 22, 23, 34, or 35, that maintains the same function of the encoded polypeptide, or a codon-optimized version of SEQ ID NOs: 25-27 or 37-39.

In some embodiments of the aspects, the induced degradation domain synTF further comprises a second regulator protein, e.g., a repressible domain (PRO). Accordingly, in one aspect described herein is a synTF comprising: (a) a DBD; (b) an ED; (c) induced degradation domain (SMASh); and (d) a repressible protease domain (PRO). In some embodiments of any of the aspects, the synTF comprises from N-terminus to C-terminus: DBD-ED-SMASh-PRO; ED-DBD-SMASh-PRO; SMASh-DBD-ED-PRO; DBD-SMASh-ED-PRO; ED-SMASh-DBD-PRO; SMASh-ED-DBD-PRO; SMASh-ED-PRO-DBD; ED-SMASh-PRO-DBD; PRO-SMASh-ED-DBD; SMASh-PRO-ED-DBD; ED-PRO-SMASh-DBD; PRO-ED-SMASh-DBD; PRO-DBD-SMASh-ED; DBD-PRO-SMASh-ED; SMASh-PRO-DBD-ED; PRO-SMASh-DBD-ED; DBD-SMASh-PRO-ED; SMASh-DBD-PRO-ED; ED-DBD-PRO-SMASh; DBD-ED-PRO-SMASh; PRO-ED-DBD-SMASh; ED-PRO-DBD-SMASh; DBD-PRO-ED-SMASh; and PRO-DBD-ED-SMASh. In some embodiments, the SMASh domain is at the C-terminus or N-terminus and the PRO domain is in between the DBD and ED domains: e.g., SMASh-ED-PRO-DBD; SMASh-DBD-PRO-ED; ED-PRO-DBD-SMASh; and DBD-PRO-ED-SMASh.

In some embodiments, the sequence of each domain is selected from exemplary domain sequences as described herein. In some embodiments, the ED of the PRO/SMASh synTF system is a transcriptional activator. In some embodiments, the ED of the PRO/SMASh synTF system is a transcriptional repressor. When a protease inhibitor for the PRO domain is present, the ED and DBD are coupled and the synTF is ON, and when protease inhibitor for the PRO domain is absent, the ED and DBD are uncoupled and the synTF is OFF. When an inducer of the induced degradation pair is present (e.g., a protease inhibitor), the PRO/SMASh synTF system is degraded. When an inducer of the induced degradation pair is absent (e.g., a protease inhibitor), the SMASh tag is degraded and the PRO/SMASh synTF system is not degraded. In some embodiments of any of the aspects, the repressible protease domain and the induced degradation domain each comprise a different protease or each comprise an NS3 protease with sensitivities to different NS3 protease inhibitors, such that a separate protease inhibitor can be used to separately regulate the PRO domain and the SMASh domain.

In some embodiments of the aspects, the induced degradation domain synTF further comprises a second regulator protein, e.g., an induced proximity pair (IPD). Accordingly, in one aspect described herein is a synTF system comprising: (a) a DBD; (b) an ED; (c) induced degradation domain (SMASh); and (d) an induced proximity pair (IPD). The induced degradation domain can be linked to either polypeptide of the IPD synTF system. In one aspect described herein is a synTF system comprising: (a) first polypeptide comprising: (i) a DBD, (ii) a first member of an induced proximity pair (IP1), and (iii) an induced degradation domain (SMASh); and (b) a second polypeptide comprising: (i) an ED and (ii) a second member of an induced proximity pair (IP2). In another aspect described herein is a synTF system comprising: (a) first polypeptide comprising: (i) a DBD and (ii) a first member of an induced proximity pair (IP1); and (b) a second polypeptide comprising: (i) an ED, (ii) a second member of an induced proximity pair (IP2), and (iii) an induced degradation domain (SMASh). In another aspect described herein is a synTF system comprising: (a) first polypeptide comprising: (i) a DBD, (ii) a first member of an induced proximity pair (IP1), and (iii) an induced degradation domain (SMASh); and (b) a second polypeptide comprising: (i) an ED, (ii) a second member of an induced proximity pair (IP2), and (iii) an induced degradation domain (SMASh). The SMASh is linked such that it does not impede binding of IPD1 and IPD2 in the presence of an inducer agent, e.g., through the use of a flexible linker peptide. Non-limiting examples of 1st and 2nd a IPD/SMASh synTF systems are shown in Table 19.

TABLE 19

Exemplary Pairs of 1st and 2nd IPD/SMASh synTF systems, with each polypeptide shown from N-terminus to C-terminus.

| 1st | 2nd | 1st | 2nd | 1st | 2nd |
|---|---|---|---|---|---|
| DBD-IP1 | ED-IP2 | SMASh-DBD-IP1 | ED-IP2 | DBD-IP1-SMASh | ED-IP2 |
| | IP2-ED | | IP2-ED | | IP2-ED |
| | SMASh-ED-IP2 | | SMASh-ED-IP2 | | SMASh-ED-IP2 |
| | SMASh-IP2-ED | | SMASh-IP2-ED | | SMASh-IP2-ED |
| | ED-IP2-SMASh | | ED-IP2-SMASh | | ED-IP2-SMASh |
| | IP2-ED-SMASh | | IP2-ED-SMASh | | IP2-ED-SMASh |
| IP1-DBD | ED-IP2 | SMASh-IP1-DBD | ED-IP2 | IP1-DBD-SMASh | ED-IP2 |
| | IP2-ED | | IP2-ED | | IP2-ED |
| | SMASh-ED-IP2 | | SMASh-ED-IP2 | | SMASh-ED-IP2 |
| | SMASh-IP2-ED | | SMASh-IP2-ED | | SMASh-IP2-ED |
| | ED-IP2-SMASh | | ED-IP2-SMASh | | ED-IP2-SMASh |
| | IP2-ED-SMASh | | IP2-ED-SMASh | | IP2-ED-SMASh |

In some embodiments, the sequence of each domain is selected from exemplary domain sequences as described herein. In some embodiments, the ED of the IPD/SMASh synTF system is a transcriptional activator. In some embodiments, the ED of the IPD/SMASh synTF system is a transcriptional repressor. When an inducer of the induced proximity pair is present, the IP1 and IP2 bind to the inducer resulting in formation of a protein complex comprising both polypeptides of the IPD/SMASh system, and when the inducer is absent, the polypeptides of the IPD/SMASh system do not form a complex. When an inducer of the induced degradation pair is present (e.g., a protease inhibitor), the IPD/SMASh synTF system is degraded. When an inducer of the induced degradation pair is absent (e.g., a protease inhibitor), the SMASh tag is degraded and the IPD/SMASh synTF system is not degraded.

C. Induced Proximity Domain SynTF

In some embodiments of any of the aspects, the regulator protein is a pair of induced proximity domains. Each of two members of the induced proximity pair is directly linked to the DBD or ED. Accordingly, in one aspect described herein is a synTF system comprising: (a) first polypeptide comprising: (i) a DBD and (ii) a first member of an induced proximity pair (IP1); and (b) a second polypeptide comprising: (i) an ED and (ii) a second member of an induced proximity pair (IP2). In some embodiments of any of the aspects, the domains of the synTF can be in order, e.g., from N-terminus to C-terminus: DBD-IP1 and ED-IP2; DBD-IP1 and IP2-ED; IP1-DBD and ED-IP2; or IP1-DBD and IP2-ED. That is, the DBD is attached to one member of the induced proximity pair (i.e., IP1), and the ED is attached to the other member or cognate member of the induced proximity pair (i.e., IP2), such that that when an inducer of the induced proximity pair is present, the IP1 and IP2 bind to the inducer resulting in formation of a protein complex comprising DBD-IP1:IP2-ED, and when the inducer is absent, the DBD-IP1 and ED-IP2 do not form a complex.

In some embodiments of any of the aspects, the two polypeptides of the induced proximity synTF are linked by a self-cleaving peptide (SCP), such that the synTF system is expressed by one vector and the two polypeptides are cleaved from each following translation. Accordingly, the induced proximity synTF system can comprise from N-terminus to C-terminus: DBD-IP1-SCP-ED-IP2; DBD-IP1-SCP-IP2-ED; IP1-DBD-SCP-ED-IP2; or IP1-DBD-SCP-IP2-ED In some embodiments of any of the aspects, the DBD of the induced proximity synTF comprises ZF1-3. In some embodiments of any of the aspects, the DBD of the induced proximity synTF comprises SEQ ID NO: 1 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 1, that maintains the same function.

In some embodiments of any of the aspects, the effector domain (ED) comprises a transcriptional activator. In one aspect, described herein is an induced proximity synTF, wherein: (a) the first polypeptide comprises from N-terminus to C-terminus: (i) a first member of an induced proximity pair and (ii) DBD; and (b) the second polypeptide comprises from N-terminus to C-terminus: (i) a transcriptional activator domain and (ii) a second member of an induced proximity pair. In some embodiments of any of the aspects, the first and second induced proximity synTFs are linked by a self-cleaving peptide. In some embodiments of any of the aspects, the induced proximity synTF comprises SEQ ID NOs: 4 or 40 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 4 or 40, that maintains the same function.

In some embodiments of any of the aspects, the induced proximity synTF is encoded by a vector or polynucleotide comprising SEQ ID NOs: 16 or 28 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 16 or 28, that maintains the same function of the encoded polypeptide, or a codon-optimized version of SEQ ID NOs: 16 or 28.

In some embodiments of any of the aspects, the effector domain (ED) comprises a transcriptional repressor. In one aspect, described herein is an induced proximity synTF, wherein: (a) the first polypeptide comprises from N-terminus to C-terminus: (i) a first member of an induced proximity pair and (ii) DBD; and (b) the second polypeptide comprises from N-terminus to C-terminus: (i) a transcriptional repressor domain and (ii) a second member of an induced proximity pair. In some embodiments of any of the aspects, the first and second induced proximity synTFs are linked by a self-cleaving peptide. In some embodiments of any of the aspects, the induced proximity synTF comprises SEQ ID NOs: 5 or 41 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 5 or 41, that maintains the same function.

In some embodiments of any of the aspects, the induced proximity synTF is encoded by a vector or polynucleotide comprising SEQ ID NOs: 17 or 29 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 17 or 29, that maintains the same function of the encoded polypeptide, or a codon-optimized version of SEQ ID NOs: 17 or 29.

D. Cytosolic Sequestering Domain SynTF

In some embodiments of any of the aspects, the regulator protein is a cytosolic sequestering protein. Accordingly, in one aspect described herein is a synTF comprising: (a) a DBD; (b) an ED; and (c) a cytosolic sequestering protein (CS). In some embodiments of any of the aspects, the domains of the synTF can be in order, e.g., from N-terminus to C-terminus: DBD-ED-CS; DBD-CS-ED; ED-DBD-CS; ED-CS-DBD; CS-DBD-ED; or CS-ED-DBD.

In some embodiments of any of the aspects, the DBD of the cytosolic sequestering synTF comprises ZF3-5. In some embodiments of any of the aspects, the DBD of the cytosolic sequestering synTF comprises SEQ ID NO: 2 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the SEQ ID NO: 2, that maintains the same function.

In some embodiments of any of the aspects, the effector domain (ED) comprises a transcriptional activator. In one aspect, described herein is a cytosolic sequestering synTF comprising from N-terminus to C-terminus: (a) DBD, (b) a transcriptional activator domain, and (c) a cytosolic sequestering domain. In some embodiments of any of the aspects, the cytosolic sequestering synTF comprises SEQ ID NOs: 6 or 42 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 6 or 42, that maintains the same function.

In some embodiments of any of the aspects, the cytosolic sequestering synTF is encoded by a vector or polynucleotide comprising SEQ ID NOs: 18 or 30 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 18 or 30, that maintains the same function of the encoded polypeptide, or a codon-optimized version of SEQ ID NOs: 18 or 30.

In some embodiments of any of the aspects, the effector domain (ED) comprises a transcriptional repressor. In one aspect, described herein is a cytosolic sequestering synTF comprising from N-terminus to C-terminus: (a) a transcriptional repressor domain, (b) a DBD, and (c) a cytosolic sequestering domain. In some embodiments of any of the aspects, the cytosolic sequestering synTF comprises SEQ ID NOs: 7, 43, or 378 or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 7, 43, or 378, that maintains the same function.

In some embodiments of any of the aspects, the cytosolic sequestering synTF is encoded by a vector or polynucleotide comprising SEQ ID NOs: 19 or 31 or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 19 or 31, that maintains the same function of the encoded polypeptide, or a codon-optimized version of SEQ ID NOs: 19 or 31.

III. Polynucleotides and Vectors

In multiple aspects, described herein are polynucleotides that encode for synTFs. In some embodiments of any of the aspects, a synTF polynucleotide comprises one of SEQ ID NOs: 28-39 (see e.g., Table 2), or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 28-39, that as a polypeptide maintains the same function (e.g., inducible transcription factor).

In some embodiments, the synTF polynucleotide is a codon-optimized version of SEQ ID NOs: 28-39. In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

In some embodiments, one or more of the genes described herein (e.g., synTF, gene of interest) is expressed in a recombinant expression vector or plasmid. As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences, comprising DNA-binding domains as described herein, and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the polypeptides described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

In some embodiments of any of the aspects, the promoter is a eukaryotic or human constitutive promoter, including but not limited to: a human elongation factor-1 alpha (EF-1alpha, EF1a) promoter; a silencing-prone spleen focus forming virus (SFFV); cytomegalovirus (CMV) promoter; a ubiquitin C (UbiC, pUb, UbC) promoter; phosphoglycerate kinase 1 (PGK, pGK) promoter; cytomegalovirus (CMV) enhancer fused to the chicken beta-actin promoter (CAG/CAGG); Simian virus 40 (SV40) enhancer and early promoter; beta actin (ACTB) promoter; and the like. In some embodiments of any of the aspects, the promoter is a minimal promoter or a core promoter. The minimal or core promoter, by definition, is the sequence located between the −35 to +35 region with respect to transcription start site; the minimal promoter is typically shorter than full promoters, and does not comprise additional elements such as enhancers or silencers. Non-limiting examples of minimal promoters include minCMV; CMV53 (minCMV with the addition of an upstream GC box); minSV40 (minimal simian virus 40 promoter); miniTK (the −33 to +32 region of the Herpes simplex thymidine kinase promoter); MLP (the −38 to +6 region of the adenovirus major late promoter); pJB42CAT5 (a minimal promoter derived from the human junB gene); ybTATA (a synthetic minimal promoter), and the TATA box alone. See e.g., Ede et al., ACS Synth Biol. 2016 May 20, 5(5): 395-404; Qin et al., PLoS One. 2010, 5(5): e10611; Norman et al., PLoS One. 2010 Aug. 26, 5(8):e12413; the contents of each of which are incorporated herein by reference in their entireties.

In some embodiments of any of the aspects, the vector (e.g., SEQ ID NOs: 16-27, 58-60, 64) comprises a SFFV promoter (e.g., SEQ ID NO: 363). In some embodiments of any of the aspects, the vector (e.g., SEQ ID NOs: 55-57) comprises a full CMV promoter (e.g., SEQ ID NO: 364). In some embodiments of any of the aspects, the vector (e.g., SEQ ID NOs: 52-54, 62) comprises a minCMV promoter (e.g., SEQ ID NO: 365). In some embodiments of any of the aspects, the vector (e.g., SEQ ID NOs: 61, 63, 64) comprises a minTK promoter (e.g., SEQ ID NO: 366). In some embodiments of any of the aspects, the vector comprises a Kozak sequence (e.g., GCCGCCACC), which is a nucleic acid motif that functions as the protein translation initiation site in eukaryotic mRNA transcripts.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

In some embodiments of any of the aspects, a synTF vector comprises one of SEQ ID NOs: 16-27 or SEQ ID NOs: 52-64 (see e.g., Tables 1 or 2) or a sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 236-261, that maintains the same functions as one of SEQ ID NOs: 16-27 or SEQ ID NOs: 52-64 (e.g., lentivirus vector, synTF polypeptide expression).

In some embodiments, the vector is a pHR vector. In some embodiments, the vector is a lentiviral vector. The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

In some embodiments of any of the aspects, the lentiviral vector comprises a central polypurine tract (cPPT; e.g., SEQ ID NO: 367). A central polypurine tract/central termination sequence creates a "DNA flap" that increases nuclear importation of the viral genome during target-cell infection. The cPPT/CTS element improves vector integration and transduction efficiency. In some embodiments of any of the aspects, the lentiviral vector comprises a woodchuck hepatitis virus posttranscriptional regulatory element (WPRE; e.g., SEQ ID NO: 368), which prevents poly(A) site readthrough, promotes RNA processing and maturation, and increases nuclear export of RNA. In genomic transcripts, it enhances vector packaging and increases titer. In transduced target cells, the WPRE boosts transgene expression by facilitating mRNA transcript maturation. In some embodiments of any of the aspects, the lentiviral vector comprises long terminal repeats (LTRs; e.g., SEQ ID NO: 369 and 370). LTRs are identical sequences of DNA that repeat hundreds or thousands of times found at either end of retrotransposons or proviral DNA formed by reverse transcription of retroviral RNA; they are used by viruses to insert their genetic material into the host genomes. In some embodiments of any of the aspects, the lentiviral vector comprises Rev response elements (RRE; e.g., SEQ ID NO: 371), which is required for producing high titer vectors.

Without limitations, the genes described herein can be included in one vector or separate vectors. For example, a polynucleotide encoding a synTF and a polynucleotide encoding a gene of interest can be included in the same vector. In some embodiments of any of the aspects, a polynucleotide encoding a synTF and a polynucleotide encoding a gene of interest can be included in different vectors. In some embodiments of any of the aspects, a single vector can comprise at least one polynucleotide encoding a synTF. In some embodiments of any of the aspects, a single vector can comprise at least one polynucleotide encoding a gene of interest. In some embodiments of any of the aspects, a single vector can comprise at least one polynucleotide encoding a synTF and at least one polynucleotide encoding a gene of interest.

In one aspect, described herein are synTF lentiviral expression vectors (e.g., SEQ ID NO: 16-27). In some embodiments, the synTF lentiviral expression vector comprises a polynucleotide encoding a synTF that is operably linked to a promoter (e.g., SFFV). In another aspect, described herein are lentiviral reporter vectors (e.g., SEQ ID NOs: 52-60). In some embodiments, the lentiviral reporter vector comprises: (i) at least one (e.g., 1, 2, 3, 4, or more) DNA-binding motif (DBM) for the DBD of a synTF; (ii) a promoter sequence located 3' of the at least one DBM; and (iii) a detectable marker (i.e., a reporter; e.g., mCherry) that is operably linked to the promoter sequence. In some embodiments, the lentiviral reporter vector is an activation reporter (e.g., SEQ ID NO: 52-54) for a synTF comprising a transcriptional activation domain, such that when the inducible synTF is ON, the DBD of the synTF binds to the DBM of the reporter and, the transcriptional activation domain activates transcription of the detectable marker; when the DBD of the inducible synTF is OFF and not bound to the DBM of the reporter, the detectable marker is not produced as it is operably linked to only a core or minimal promoter (e.g., minCMV). In some embodiments, the lentiviral reporter vector is a repression reporter (e.g., SEQ ID NO: 55-60) for an inducible synTF comprising a transcriptional repressor domain, such that when the synTF is ON, the DBD of the synTF binds to the DBM of the reporter, and the transcriptional repressor domain represses transcription of the detectable marker; when the synTF is OFF, the DBD of the synTF is not bound to the DBM of the reporter, and the detectable marker is produced as it is operably linked to a full, constitutive promoter (e.g., full CMV or SFFV).

In one aspect, described herein are gene of interest (GOI) lentiviral expression vectors (e.g., 61-64). In some embodiments, the GOI vector comprises a gene of interest that is operably linked to at least one (e.g., 1, 2, 3, 4, or more) DNA-binding motif (DBM) for the DBD of a synTF and a minimal promoter. In some embodiments, the GOI vector comprises a reporter vector as described herein, wherein the detectable marker is replaced with or fused to a gene of interest; as such the synTF can induce the expression of the gene of interest, or can repress the expression of a gene of interest, in the presence or absence of the regulator protein inducer.

In some embodiments, the polypeptide encoded by the gene of interest is selected from the group consisting of: a chemokine, a chemokine receptor, a chimeric antigen receptor, a cytokine, a cytokine receptor, a differentiation factor, a growth factor, a growth factor receptor, a hormone, a metabolic enzyme, a pathogen derived protein, a proliferation inducer, a receptor, a RNA guided nuclease, a site-specific nuclease, a small molecule 2nd messenger synthesis enzyme, a T cell receptor, a toxin derived protein, a transcription activator, a transcription repressor, a transcriptional activator, a transcriptional repressor, a translation regulator, a translational activator, a translational repressor, an activating immunoreceptor, an antibody, an apoptosis inhibitor, an apoptosis inducer, an engineered T cell receptor, an immunoactivator, an immunoinhibitor, an inhibiting immunoreceptor, and an RNA guided DNA binding protein. In some embodiments, the polypeptide encoded by the gene of interest would benefit a subject in need of treatment, e.g., a subject with cancer, autoimmunity, or need of regenerative medicine.

In some embodiments, the polypeptide encoded by the gene of interest is a CD19 CAR (e.g., SEQ ID NOs: 61, 373), e.g., linked to a detectable marker such as mCherry (e.g., SEQ ID NO: 372). In some embodiments, the polypeptide encoded by the gene of interest is IL2 (e.g., SEQ ID NOs: 62, 374), which can be linked to a detectable marker, e.g., (huEGFRt), using a self-cleaving peptide. In some embodiments, the polypeptide encoded by the gene of interest is IL10 (e.g., SEQ ID NOs: 63-64, 375).

In one aspect described herein is a lentiviral vector that comprises both a synTF operably linked to a constitutive promoter and a gene of interest operably linked to at least one (e.g., 1, 2, 3, 4, or more) DNA-binding motif (DBM) for the DBD of a synTF and a minimal promoter (e.g., SEQ ID NO: 64). Accordingly, described herein is a nucleic acid construct comprising in the 5' to 3' direction: (a) a nucleic acid sequence encoding a gene of interest (GOI) in the inverse orientation; (b) a first promoter sequence in the inverse orientation and operatively linked to the nucleic acid encoding the GOI; (c) a nucleic acid sequence comprising at least one target DNA binding motif (DBM) comprising a target nucleic acid for binding of the at least one DBD of a synTF, wherein binding of the DBD of the synTF places the effector domain (ED) in the proximity of the promoter sequence operatively linked to the GOI; (d) a second promoter sequence; and (e) a nucleic acid sequence encoding the synthetic transcription factor (synTF), operatively linked to the second promoter sequence, wherein the encoded synTF comprises at least one DBD that binds to the at least DBM of the nucleic acid sequence of (c).

In some embodiments of any of the aspects, the promoter sequence operatively linked to the GOI is selected from any of: miniCMV promoter, miniTK promoter, ybTATA promoter, minSV40 promoter, CMV53 promoter, pJB42CAT5 promoter, MLP promoter, and TATA promoter. In some embodiments of any of the aspects, wherein the promoter sequence operatively linked to the nucleic acid encoding the synTF is a pSFFV promoter, CMV promoter, pUb/UbC promoter, EF1a promoter, PGK/pGK promoter, CAG/CAGG promoter, SV40 promoter, and beta actin/ACTB promoter.

In some embodiments, the polynucleotide encoding the synTF is operatively linked to an inducible promoter, which is active in the presence of the promoter activator or the absence of the promoter repressor, and inactive in the absence of the promoter inducer or the presence of the promoter repressor. Non-limiting examples of inducible promoters include: a doxycycline-inducible promoter, the lac promoter, the lacUV5 promoter, the tac promoter, the trc promoter, the T5 promoter, the T7 promoter, the T7-lac promoter, the araBAD promoter, the rha promoter, the tet promoter, an isopropyl β-D-1-thiogalactopyranoside (IPTG)-dependent promoter, an AlcA promoter, a LexA promoter, a temperature inducible promoter (e.g., Hsp70 or Hsp90-derived promoters), or a light inducible promoter (e.g., pDawn/YFI/FixK2 promoter/CI/pR promoter system).

In some embodiments, the vector comprises a selectable marker, e.g., for selectively amplifying the vector in bacteria. Non-limiting examples of selectable marker genes for use in bacteria include antibiotic resistance genes conferring resistance to ampicillin, tetracycline and kanamycin. The tetracycline (tet) and ampicillin (amp) resistance marker genes can be obtained from any of a number of commercially available vectors including pBR322 (available from New England BioLabs, Beverly, Mass., cat. no. 303-3s). The tet coding sequence is contained within nucleotides 86-476; the amp gene is contained within nucleotides 3295-4155. The nucleotide sequence of the kanamycin (kan) gene is available from vector pACYC 177, from New England BioLabs, Cat no. 401-L, GenBank accession No. X06402.

In some embodiments, one or more of the recombinantly expressed genes can be integrated into the genome of the cell.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

IV. synTF Systems

Another aspect of the technology relates to synTF system for controlling gene expression of a gene of interest (GOI), where a system comprises a synTF described herein and a nucleic acid construct comprising the elements that the synTF binds to regulate gene expression. In one aspect described herein is a system for controlling gene expression, comprising: (a) at least one synthetic transcription factor (synTF) as described herein; and (b) at least one nucleic acid construct as described herein, e.g., a nucleic acid construct comprising: (i) at least one target DNA binding motif (DBM) comprising a target nucleic acid for binding of the at least one DBD of the synTF; (ii) a promoter sequence located 3' of the at least one DBM, and (iii) a gene of interest operatively linked to the promoter sequence.

Exemplary systems are shown in FIGS. 1B, 2, 5C, 10B, 11A, 12A, 13A, 14A, and 15A-15B showing the synTF and the nucleic acid sequence construct comprising the gene of interest (e.g., mCherry, CD19 CAR, IL4, IL10). In synTF embodiments where the synTF is a protease synTF or induced proximity domain synTF, (i.e., where the coupling of the ED to the DBD is regulated by the at least one protease RP or at least one induced proximity pair), in the presence of the RP inducer, the coupling of the ED to the DBD of the synTF is maintained, such that when the DBD binds to the DNA binding motif (DBM) it enables the ED to be in proximity to the promoter sequence and promotes initiation or inhibition of gene expression of the gene of interest ("ED-on"). Alternatively, in the absence of the RP inducer, the coupling of the ED to the DBD of the synTF is severed, preventing the ED from being in proximity to the promoter sequence when the DBD binds to the DNA binding motif (DBM), preventing the ED from regulating the expression of the gene of interest ("ED-off"). Depending on whether the effector domain is a transcriptional activator (TA) or a transcriptional repressor (TR), the ED-on and ED-off will have differing effects—that is, if the ED is a TA, when the synTF is in the "ED-on" configuration, gene expression can occur, whereas if the ED is a transcriptional repressor (TR), the ED-on configuration will result in repression of gene expression (e.g., no expression). Conversely, if the ED is a TA, when the synTF is in the "ED-off" configuration, gene expression is OFF, whereas if the ED is a transcriptional repressor (TR), the "ED-off" configuration will depress the repression of gene expression, so gene expression is ON. A summary of the effect of each regulator promoter inducer on the ultimate gene expression depending on the different synTF and the effector domain is summarized in Table 20 herein.

Similarly, and by way of example only, in a synTF embodiment where the synTF is a cytosolic sequestering domain synTF, (i.e., where the cellular localization of the ED-DBD fusion protein is regulated by the at least one cytosolic sequestering regulator protein), in the presence of the RP inducer, the ED-DBD is not sequestered in the cytosol, enabling the DBD to bind to the DNA binding motif (DBM) and placing the transcriptional effector domain (ED) to be in proximity to the promoter sequence to control the expression of the gene of interest ("ED-on"). Accordingly, in the presence of the inducer, if the ED is a TA the ED-on configuration will enable gene expression to occur (referred to as "TA-on"), whereas if the ED is a TR, the ED-on configuration will result in repression of gene expression (e.g., referred to as "TR-on" and no gene expression). Alternatively, in the absence of the RP inducer, the ED coupled to the DBD of the synTF is sequestered in the cytosol, preventing the DBD of the synTF from binding to the DBM, and preventing the effector domain (ED) from being in proximity to the promoter sequence, preventing expression of the gene of interest ("ED-off"). Accordingly, in the absence of the inducer, in embodiments where the ED is a transcriptional activator (TA), it results in turning off the gene expression ("TA-off" (no expression)), whereas in embodiments where the ED is a transcriptional repressor protein (TR), it turns on gene expression ("TR-off", therefore repression is off, therefore enabling gene expression to occur).

In some embodiments of any of the aspect described herein, the synTF is an induced degradation domain synTF or further comprises a N-terminal or C-terminal Small molecule-Assisted Shutoff (SMASh) domain. As described herein, the SMASh domain comprises a self-cleaving SMASh protease, a partial protease helical domain and a cofactor domain. In some embodiments of any of the aspects, in the presence of an inhibitor to the SMASh protease (referred to as a "SMASh inhibitor"), the SMASh protease activity is inhibited resulting in the synTF being degraded, which prevents the DBD binding to the DBM and controlling the expression or repression of the gene of interest ("synTF-degradation"; ED-off). In some embodiments of any of the aspects, in the absence of an inhibitor to the SMASh protease, the SMASh protease is active and self cleaves/uncouples from the synTF, resulting the SMASh domain being targeted for degradation and allowing the DBD of the synTF to bind to the DBM and the ED of synTF to control the expression of the gene of interest ("SMASh-degradation, TA-on (yes-expression), TR-on (no-expression)).

TABLE 20A

Table summarizing the effect of the presence or absence of regulator protein inducers on the ultimate expression of the gene of interest.

| SynTF | Presence or absence of RP inducer → effect on the SynTF → effect on binding to the DBM | Effector domain → ED on/off | Gene expression ON or OFF |
|---|---|---|---|
| Protease | Present → DBD-ED is coupled → "ED-On" | TA → "TA-on" | ON |
| domain | | RP → "RP-on" | OFF |
| synTF | Absent → DBD-ED is uncoupled → ED-Off | TA → "TA-off" | OFF |
| | | RP → "RP-off" | ON |
| Induced | Present → DBD-ED is coupled → ED-On | TA → "TA-on" | ON |
| proximity | | RP → "RP-on" | OFF |
| domain | Absent → DBD-ED is uncoupled → ED-Off | TA → "TA-off" | OFF |
| synTF | | RP → "RP-off" | ON |
| Translocation | Present → SynTF translocates to nucleus | TA → "TA-on" | ON |
| domain | (sequestering is inhibited) → ED-On | RP → "RP-on" | OFF |
| synTF | Absent → SynTF is sequestered in cytosol | TA → "TA-off" | OFF |
| | → ED-Off | RP → "RP-off" | ON |
| Induced | Present → SynTF-degradation → ED-Off | TA → "TA-off" | OFF |
| degradation | | RP → "RP-off" | ON |
| domain | Absent → SMASh degradation, ED available | TA → "TA-on" | ON |
| synTF | → ED-On | RP → "RP-on" | OFF |

Accordingly, the expression of the GOI is dependent on 3 levels of control, including but not limited to; (i) the type of regulator protein in the synTF, (ii) the presence or absence of a regulator protein inducer (RP inducer), and (iii) the type of effector domain. In some embodiments, if the synTF comprises an induced degradation domain or SMASh domain, it can also provide an additional level of control on the expression of the GOI. The ultimate expression of the GOI of synTF comprising a SMASh domain are shown in Table 20B.

TABLE 20B

| SynTF | SMASh inhibitor | Effect of SMASh inhibitor | Regulator Protein inducer | Effect of RP inducer | Effector domain | Gene expression |
|---|---|---|---|---|---|---|
| Protease | Present | SynTF | n/a | n/a | TA (TA-off) | OFF |
| domain | | degradation | n/a | n/a | TR (TA-off) | ON |
| synTF: PD- | | (ED-OFF) | | | | |
| SynTF: SMASh | Absent | SMASh | Protease | "ED on" | TA (TA-on) | ON |
| | | degradation | inhibitor | (DBD-ED coupled) | TR (TR-on) | OFF |
| | | | Present | | | |

TABLE 20B-continued

| SynTF | SMASh inhibitor | Effect of SMASh inhibitor | Regulator Protein inducer | Effect of RP inducer | Effector domain | Gene expression |
|---|---|---|---|---|---|---|
| | | | Protease inhibitor Absent | "ED off" (DBD and ED uncoupled) | TA (TA-off)<br>TR (TR-off) | OFF<br>ON |
| Induced proximity domain | Present | SynTF degradation (ED-OFF) | n/a<br>n/a | n/a<br>n/a | TA (TA-off)<br>TR (TA-off) | OFF<br>ON |
| synTF: IPD-SynTF: SMASh | Absent | SMASh degradation | IPD inducer Present | "ED on" (DBD-ED coupled) | TA (TA-on)<br>TR (TR-on) | ON<br>OFF |
| | | | IPD inducer Absent | "ED off" (DBD and ED uncoupled) | TA (TA-off)<br>TR (TR-off) | OFF<br>ON |
| Cytosolic sequestering: CS-synTF: SMASh | Present | SynTF degradation (ED-OFF) | n/a<br>n/a | n/a<br>n/a | TA (TA-off)<br>TR (TA-off) | OFF<br>ON |
| | Absent | SMASh degradation | Cytosolic sequestering ligand Present | "ED on" (CS-synTF translocates to nucleus (sequestering is inhibited)) | TA (TA-on)<br>TR (TR-on) | ON<br>OFF |
| | | | Cytosolic sequestering ligand Absent | "ED off" (CS-SynTF sequestered in cytosol) | TA (TA-off)<br>TR (TR-off) | OFF<br>ON |

As indicated in Table 20B, if the SMASh inhibitor is present, then even in the absence or presence of the regulator protein inducer (e.g., protease inhibitor, IPD inducer agent or ligand for CS-SynTF), the synTF is degraded and the expression of the GOI depends on whether the ED is a TA or TR. However, in the absence of the SMASh inhibitor, the expression of the GOI is dependent on the presence or absence of the regulator protein inducer, as shown in Table 20B.

Accordingly, in one aspect, described herein is a system for controlling gene expression, comprising: (a) at least one synthetic transcription factor (synTF) comprising at least one DNA binding domain (DBD), a transcriptional effector domain (ED), and at least one regulator protein (RP), wherein the ED is directly or indirectly coupled or linked to the DBD, and wherein the coupling is regulated by the at least one RP, or wherein the cellular localization of the ED linked to the DBD is regulated by the at least one RP, wherein the at least one RP is regulated by an RP inducer, wherein the DBD can bind to a target DNA binding motif (DBM) located upstream of a promoter operatively linked to a gene; (b) a nucleic acid construct comprising: (i) at least one target DNA binding motif (DBM) comprising a target nucleic acid for binding of the at least one DBD of the synTF, and (ii) a promoter sequence located 3' of the at least one DBM, and (iii) a gene of interest operatively linked to the promoter sequence; wherein for synTFs where the coupling of the ED to the DBD is regulated by the at least one RP; in the presence of the RP inducer, the coupling of the ED to the DBD of the synTF is maintained, enabling the ED to be in proximity to the promoter sequence when the DBD binds to the DNA binding motif (DBM), where the ED controls the expression of the gene of interest ("ED-on"), or in the absence of the RP inducer, the coupling of the ED to the DBD of the synTF is severed, preventing the ED from being in proximity to the promoter sequence when the DBD binds to the DNA binding motif (DBM), preventing gene expression of the gene of interest ("ED-off"); and wherein for synTFs where the cellular localization of the ED linked to the DBD is regulated by the at least one regulator protein; in the presence of the RP inducer, the ED coupled to the DBD of the synTF is not sequestered in the cytosol, enabling the DBD to bind to the DNA binding motif (DBM) and enabling the transcriptional effector domain (ED) to be in proximity to the promoter sequence to control the expression of the gene of interest ("ED-on"), or in the absence of the RP inducer, the ED coupled to the DBD of the synTF is sequestered in the cytosol, preventing the DBD of the synTF from binding to the DBM, and preventing the effector domain (ED) from being in proximity to the promoter sequence, preventing expression of the gene of interest ("ED-off").

Nucleic Acid Constructs Encoding the GOI for Regulation by the synTF

Figure 5A:
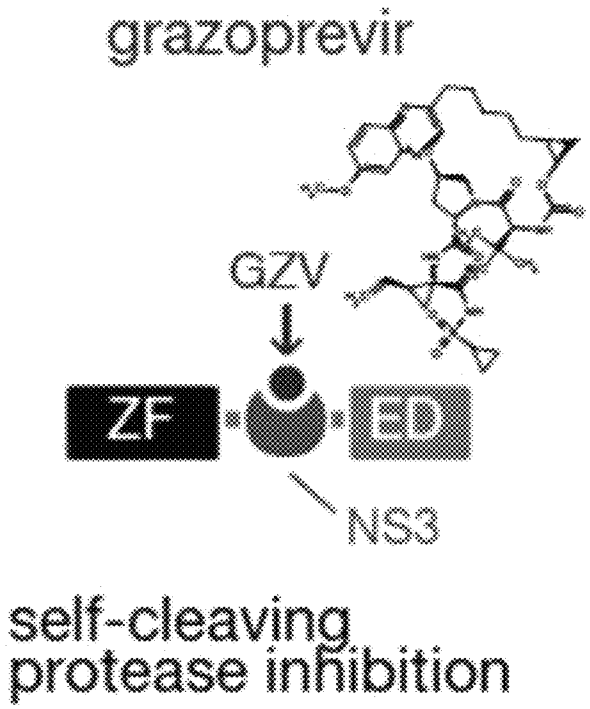
FIG. 5A-5C is a series of schematics showing an exemplary synTF regulated by self-cleaving protease inhibition.
Figure 5B:
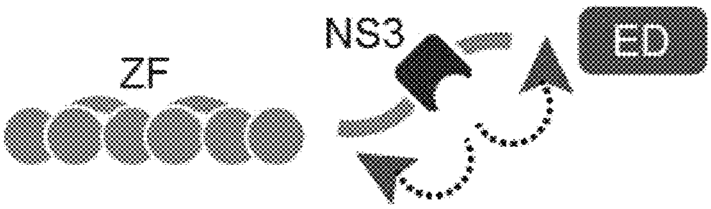
Figure 5C:
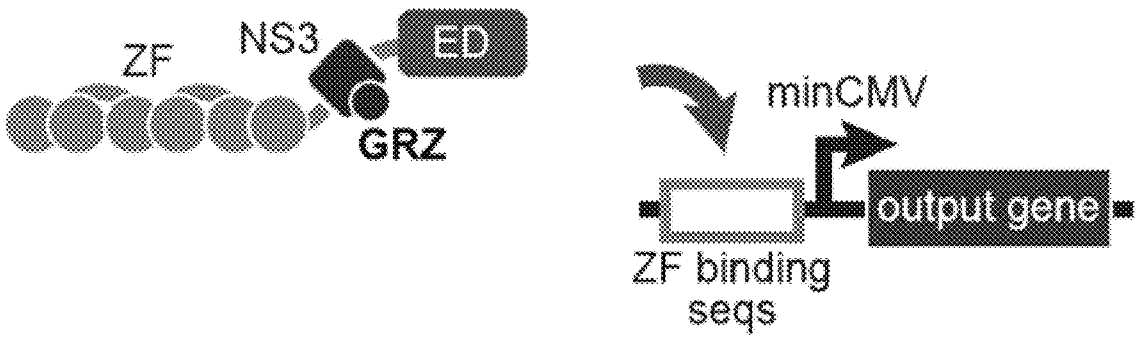
Figure 12A:
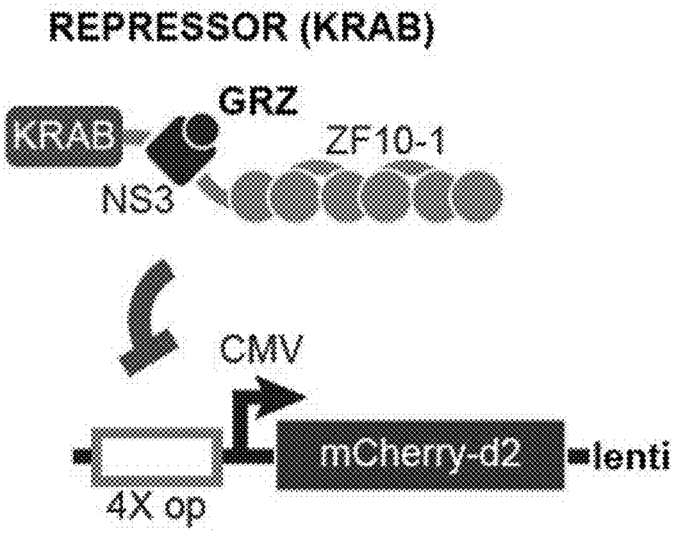
FIG. 12A-12C is a series of schematics and graphs showing inducible synthetic transcriptional repression of a fluorescent protein in human cell lines.

As described herein, in some aspects, the system comprises a synTF as described herein and a nucleic acid construct comprising the GOI. In some embodiments, the nucleic acid construct comprises in the 5' to 3' direction, (i) a DBA binding motif (DBM) that enables binding of the DBD of the synTF, (ii) a promoter sequence, and (iii) a nucleic acid encoding the GOI, where the nucleic acid encoding the GOI is operatively linked to the promoter sequence. An exemplary system is shown in FIGS. 5C and 12A.

In some embodiments, the system further comprises a nucleic acid sequence encoding the synTF, operatively linked to a promoter, for example, where the promoter is a constitutive promoter, see, e.g. FIGS. 10B, 13A, 14A and 15A for exemplary systems. In such an embodiment, when the inducer to the promoter is present, the synTF can be expressed, and the activity of the synTF on controlling gene expression of the GOI is dependent on the presence or absence of the regulator protein inducer and/or SMASh inducer if a SMASh domain is attached.

In some embodiments, the nucleic acid construct comprises (i) a first nucleic acid encoding the synTF under a promoter and (ii) a second nucleic acid construct comprising (i) a DBA binding motif (DBM) that enables binding of the DBD of the expressed synTF, (ii) a promoter sequence, and (iii) a nucleic acid encoding the GOI, where the nucleic acid encoding the GOI is operatively linked to the promoter sequence. Accordingly, the nucleic acid encoding the inducible synTF and the GOI are present on the same nucleic acid construct, see, for example, FIG. 15B for such an exemplary system.

Figure 15A:
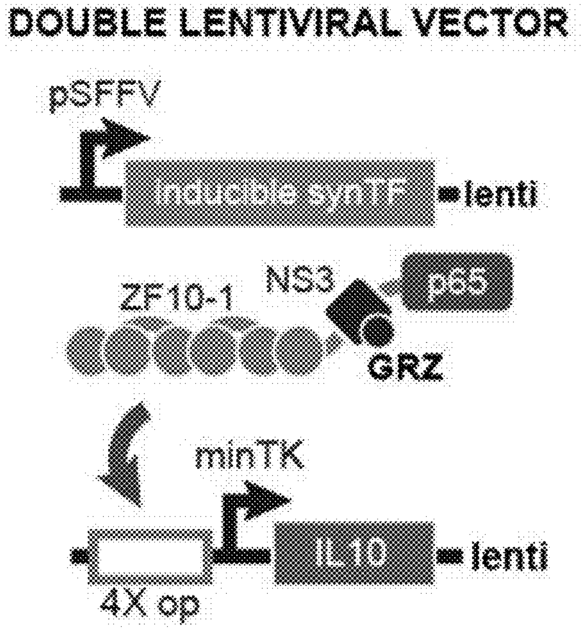
FIG. 15A-15C is a series of schematics showing nucleic acid constructs for a system for controlling gene expression and graphs showing that administration of a small molecule (grazoprevir) led to temporal activation of a cytokine (IL10) from a ZF-responsive promoter in Jurkat T cell lines.
Figure 15B:
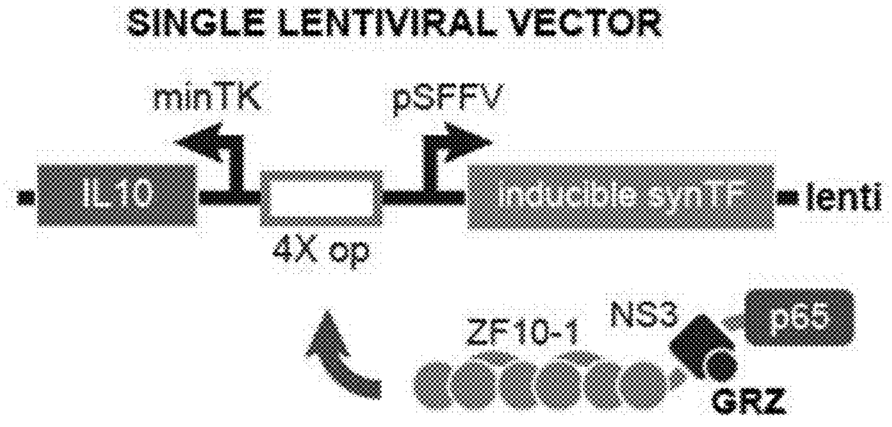

In some embodiments, the nucleic acid construct comprises (i) a first promoter operatively linked to a nucleic acid encoding the synTF, and (ii) a nucleic acid encoding a GOI, operatively linked to a second promoter, where 5' to the second promoter is the DBM for the synTF protein which is expressed under control of the first promoter. In some embodiments, as shown in FIG. 15B, the construct comprises the following in a 5' to 3' orientation: (i) a nucleic acid encoding a GOI in the antisense orientation, (ii) a first promoter in the antisense orientation which is operatively linked to the GOI, (iii) a DBD in the antisense orientation, (iv) a second promoter in the sense orientation, and (v) a nucleic acid encoding a synTF in the sense orientation which is operatively linked to the second promoter. Such a system allows the expression of the synTF, where the expressed synTF can be used to regulate the expression of the GOI in the presence or absence of inducers for the synTF.

In some embodiments of any of the aspects, the promoter which is operatively linked to the GOI or to the synTF is selected from any of miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1a promoter, PGK/pGK promoter, CAG/CAGG promoter, SV40 promoter, and beta actin/ACTB promoter.

Figure 14A:
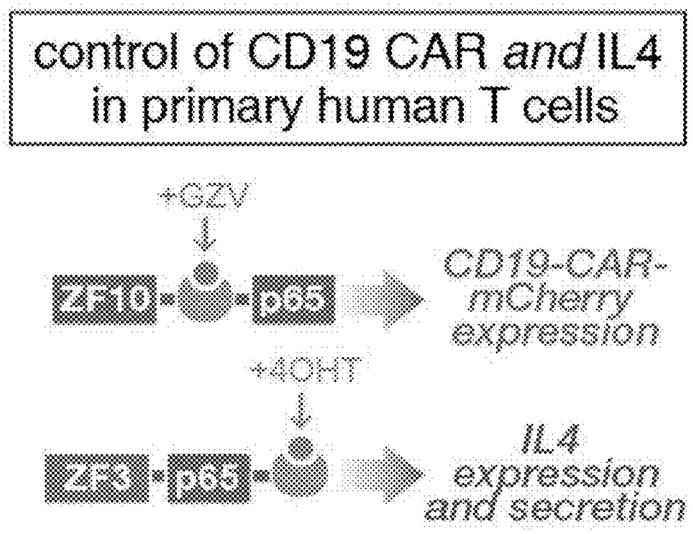
FIG. 14A-14B is a series of schematics and graphs showing the control of CD19 CAR and IL-4 expression in primary human T cells.
Figure 14B:
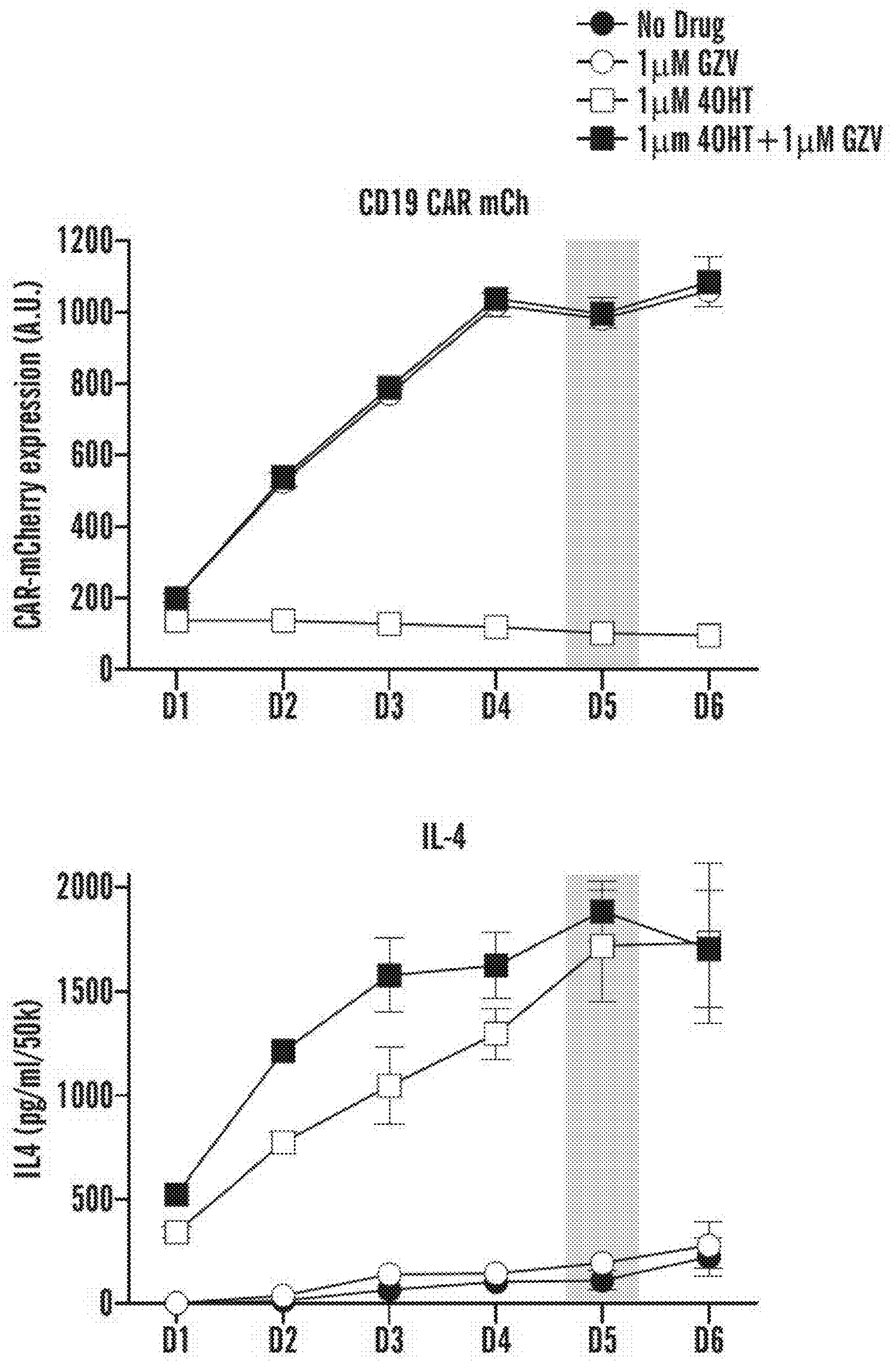
Figure 14C:
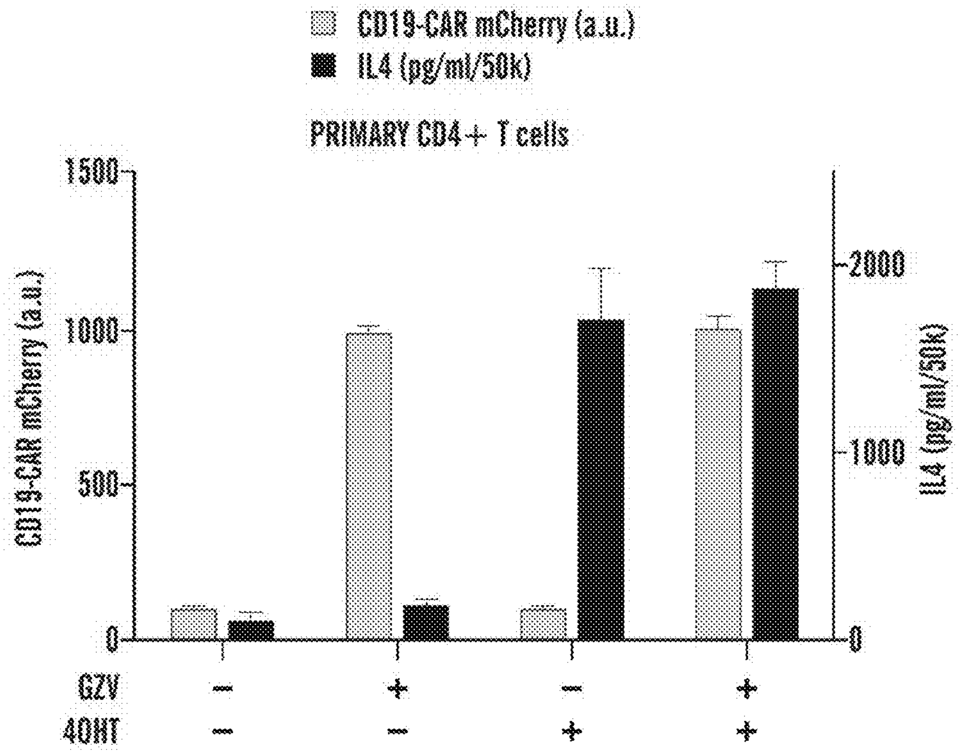
FIG. 14C is a bar graph showing CD19-CAR expression (light grey, left axis) and IL-4 expression (dark grey, right axis) in the presence or absence of GZV or 4OHT, as indicated, at day 5.

In some embodiments of any of the aspects, the at least one synTF expressed by the system is selected from any of those described herein. In some embodiments of any of the aspects, a synTF system can comprise any combination of at least two synTF polypeptides as described herein, controlling the same or different GOIs. As a non-limiting example, FIG. 14A-14C shows a system comprising two synTFs each with a separate regulator protein and GOI: a repressible protease synTF that controls CD19 CAR expression and a cytosolic sequestering domain synTF that controls IL4 expression. Table 9 below shows non-limiting examples of such synTF system combinations. In some embodiments of any of the aspects, the examples shown in Table 9 can be in combination with a regulator protein inducer (e.g., a small molecule drug such as grazoprevir, ABA, 4OHT).

TABLE 9 synTF systems.

| PRO | ID | IPD | CS | PRO | ID | IPD | CS |
|---|---|---|---|---|---|---|---|
| X | | | | X | | | X |
| | X | | | | X | X | |
| | | X | | | X | | X |
| | | | X | | | X | X |
| X | X | | | X | X | X | |
| X | | X | | X | X | | X |
| X | | X | X | X | X | X | X |
| | X | X | X | | | | |

"PRO" indicates the repressible protease synTF polypeptides and systems as described herein.
"ID" indicates the induced degradation synTF polypeptides and systems as described herein.
"IPD" indicates the induced proximity synTF polypeptides and systems as described herein.
"CS" indicates the cytosolic sequestering domain synTF polypeptides and systems as described herein.

V. Cells

In one aspect, described herein is a cell or population thereof comprising the at least one synTF polypeptide, synTF system, synTF polynucleotide, or synTF vector as described herein (see e.g., Tables 1-2). In some embodiments of any of the aspects, the cell or population thereof can comprise any combination of synTF polypeptides or systems (see e.g., Table 9).

In one aspect, the invention provides a cell (e.g., T cell) engineered to express a synTF, wherein the activity of the synTF cell can be controlled by a small molecule. In one aspect a cell is transformed with the synTF, and the synTF is expressed on the cell surface. In some embodiments, the cell (e.g., T cell) is transduced with a viral vector encoding a synTF. In some embodiments, the viral vector is a retroviral vector. In some embodiments, the viral vector is a lentiviral vector. In some such embodiments, the cell may stably express the synTF. In another embodiment, the cell (e.g., T cell) is transfected with a nucleic acid, e.g., mRNA, cDNA, DNA, encoding a synTF. In some such embodiments, the cell may transiently express the synTF.

In one aspect described herein is a cell comprising: a nucleic acid sequence comprising at least one target DNA binding motif (DBM) comprising a target nucleic acid for binding of the at least one DBD of a synTF, a promoter sequence located 3' of the at least one DBM, and a nucleic acid encoding a gene of interest (GOI) operatively linked to the promoter sequence.

In one aspect described herein is a cell comprising: (a) a first nucleic acid sequence comprising at least one target DNA binding motif (DBM) comprising a target nucleic acid for binding of the at least one DBD of a synTF, a promoter sequence located 3' of the at least one DBM, and a nucleic acid encoding a gene of interest (GOI) operatively linked to the promoter sequence, and (b) a second nucleic acid sequence comprising a nucleic acid encoding a synthetic transcription factor (synTF) as described herein, operatively linked to an inducible or constitutive promoter.

In some embodiments of any of the aspects, the cell comprises a nucleic acid construct comprising in the 5' to 3' direction: (a) a nucleic acid sequence encoding a gene of interest (GOI) in the inverse orientation; (b) a first promoter sequence in the inverse orientation and operatively linked to the nucleic acid encoding the GOI; (c) a nucleic acid sequence comprising at least one target DNA binding motif (DBM) comprising a target nucleic acid for binding of the at least one DBD of a synTF, wherein binding of the DBD of the synTF places the effector domain (ED) in the proximity of the promoter sequence operatively linked to the GOI; (d) a second promoter sequence; and (e) a nucleic acid sequence encoding the synthetic transcription factor (synTF), operatively linked to the second promoter sequence, wherein the encoded synTF comprises at least one DBD that binds to the at least DBM of the nucleic acid sequence of (c).

In some embodiments of any of the aspects, the promoter sequence operatively linked to the GOI is selected from any of: miniCMV promoter, miniTK promoter, ybTATA promoter, minSV40 promoter, CMV53 promoter, pJB42CAT5 promoter, MLP promoter, and TATA promoter. In some embodiments of any of the aspects, wherein the promoter sequence operatively linked to the nucleic acid encoding the synTF is a pSFFV promoter, CMV promoter, pUb/UbC promoter, EF1a promoter, PGK/pGK promoter, CAG/CAGG promoter, SV40 promoter, and beta actin/ACTB promoter.

In some embodiments of any of the aspects, the cell comprises an immune cell. In some embodiments of any of the aspects, the immune cell comprises a CD4+ T cell, a CD8+ T cell, a regulatory T cell (Treg), or a natural killer (NK) cell. In one embodiment, the cell comprises a T cell. In one embodiment, the cell comprises a CD4+ T cell. In one embodiment, the cell comprises a CD8+ T cell. In other embodiments, the cell comprises a B cell.

In some embodiments of any of the aspects, the cells are isolated from a subject. The term "isolated" as used herein signifies that the cells are placed into conditions other than their natural environment. The term "isolated" does not preclude the later use of these cells thereafter in combinations or mixtures with other cells. In some embodiments of any of the aspects, an immune cell (e.g., T cell) is: (a) isolated from the subject; (b) genetically modified to express a synTF system as described herein; and (c) administered to the subject. In some embodiments of any of the aspects, the cells are isolated from a first subject and administered to a second subject. In some embodiments of any of the aspects, the immune cells are first differentiated from a somatic cell sample from the subject and then genetically modified to express a synTF system as described herein.

In some embodiments of any of the aspects, the cell comprises an inactivating modification of at least one HLA Class I gene in the cell. In some embodiments, an endogenous HLA (e.g., class I and/or class II major histocompatibility complexes) can be edited or removed, e.g., to reduce immunogenicity. In some embodiments, the genetic modification can comprise introduction and expression of non-canonical HLA-G and HLA-E to prevent NK cell-mediated lysis (see e.g., Riolobos L et al. 2013), which can provide a source of universal T cells for immunotherapy, e.g., cancer immune therapy.

In some embodiments, methods of genetically modifying a cell to express a synTF system can comprise but are not limited to: transfection or electroporation of a cell with a vector encoding a synTF; transduction with a viral vector (e.g., retrovirus, lentivirus) encoding a synTF system; gene editing using zinc finger nucleases (ZFNs), transcription activator-like effector nucleases (TALENs), meganuclease-TALENs, or CRISPR-Cas; or any other methods known in the art of genetically modifying a cell to express a synTF system.

VI. Pharmaceutical Compositions and Administration

In some embodiments, the methods described herein relate to treating a subject having or diagnosed as having a disease or disorder (e.g., cancer or autoimmunity) with a synTF system as described herein. Subjects having such a disease or disorder can be identified by a physician using current methods of diagnosis for cancer or autoimmunity. Symptoms and/or complications which characterize these conditions and aid in diagnosis are known in the art. A family history of cancer or autoimmunity, or exposure to risk factors for cancer or autoimmunity can also aid in determining if a subject is likely to have such a disease or disorder, or in making a diagnosis of cancer or autoimmunity.

The compositions described herein can be administered to a subject having or diagnosed as having cancer or autoimmunity. In some embodiments, the methods described herein comprise administering an effective amount of compositions described herein, e.g. a synTF system as described herein to a subject in order to alleviate a symptom of cancer or autoimmunity. As used herein, "alleviating a symptom" is ameliorating any condition or symptom associated with the cancer or autoimmunity. As compared with an equivalent untreated control, such reduction is by at least 5%, 10%, 20%, 40%, 50%, 60%, 80%, 90%, 95%, 99% or more as measured by any standard technique.

A variety of means for administering the compositions described herein to subjects are known to those of skill in the art. An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, intratumorally, and can be delivered by peristaltic means, if desired, or by other means known by those skilled in the art. In some embodiments of any of the aspects, the compounds used herein are administered orally, intravenously or intramuscularly. Administration can be local or systemic. Local administration, e.g., directly to the site of an organ or tissue transplant is specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

In embodiments where the subject is administered a synTF cell and a regulator protein inducer to modulate the activity of the synTF polypeptide(s) (e.g., grazoprevir, ABA, 4OHT), the cells and drug(s) can be administered together or separately. In embodiments where the subject is separately administered a synTF cell and a drug to modulate the activity of the synTF polypeptide(s), each of the compositions can be administered, separately, according to any of the dosages and administration routes/routines described herein.

The term "effective amount" as used herein refers to the amount of a synTF system as described herein and/or a regulator protein inducer (e.g., grazoprevir, ABA, 4OHT) needed to alleviate at least one or more symptom of the disease or disorder, and relates to a sufficient amount of pharmacological composition to provide the desired effect. The term "therapeutically effective amount" therefore refers to an amount of a synTF system as described herein and/or a regulator protein inducer (e.g., grazoprevir, ABA, 4OHT) that is sufficient to provide a particular anti-tumor or anti-autoimmune effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized.

The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a synTF system as described herein and/or a regulator protein inducer (e.g., grazoprevir, ABA, 4OHT)), which achieves a half-maximal inhibition of symptoms) as determined in cell culture, or in an appropriate animal model. Levels in plasma can be measured, for example, by high performance liquid chromatography for the regulator protein inducer or flow cytometry for synTF cells. The effects of any particular dosage can be monitored by a suitable bioassay. The dosage can be determined by a physician and adjusted, as necessary, to suit observed effects of the treatment.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the route of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay, e.g., assay for tumor growth and/or size among others. The dosage can be determined by a physician and adjusted, as necessary, to suit observed effects of the treatment.

It can generally be stated that a pharmaceutical composition comprising the synTF-system-expressing cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. SynTF-system-expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response. In some embodiments, the dosage can be from about $1\times10^5$ cells to about $1\times10^8$ cells per kg of body weight. In some embodiments, the dosage can be from about $1\times10^6$ cells to about $1\times10^7$ cells per kg of body weight. In some embodiments, the dosage can be about $1\times10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

In certain embodiments, an effective dose of a regulatory protein inducer (e.g., grazoprevir, ABA, 4OHT; also referred to herein as an inducer agent) that regulates the activity of a synTF as described herein can be administered to a patient once. In certain embodiments, an effective dose of a regulatory protein inducer can be administered to a patient repeatedly. In some embodiments of any of the aspects, the effective dose of ABA is about 1 mM. In some embodiments of any of the aspects, the effective dose of 4OHT is about 4 μM. In some embodiments of any of the aspects, the effective dose of grazoprevir is about 4 μM.

In some embodiments of any of the aspects, the effective dose of a regulatory protein inducer (e.g., grazoprevir) is at least 0.05 mM, at least 0.1 mM, at least 0.15 mM, at least 0.2 mM, at least 0.25 mM, at least 0.3 mM, at least 0.35 mM, at least 0.4 mM, at least 0.45 mM, at least 0.5 mM, at least 0.55 mM, at least 0.6 mM, at least 0.65 mM, at least 0.7 mM, at least 0.75 mM, at least 0.8 mM, at least 0.85 mM, at least 0.9 mM, at least 0.95 mM, at least 1 mM, at least 1.05 mM, at least 1.1 mM, at least 1.15 mM, at least 1.2 mM, at least 1.25 mM, at least 1.3 mM, at least 1.35 mM, at least 1.4 mM, at least 1.45 mM, at least 1.5 mM, at least 1.55 mM, at least 1.6 mM, at least 1.65 mM, at least 1.7 mM, at least 1.75 mM, at least 1.8 mM, at least 1.85 mM, at least 1.9 mM, at least 1.95 mM, at least 2 mM, at least 2.05 mM, at least 2.1 mM, at least 2.15 mM, at least 2.2 mM, at least 2.25 mM, at least 2.3 mM, at least 2.35 mM, at least 2.4 mM, at least 2.45 mM, at least 2.5 mM, at least 2.55 mM, at least 2.6 mM, at least 2.65 mM, at least 2.7 mM, at least 2.75 mM, at least 2.8 mM, at least 2.85 mM, at least 2.9 mM, at least 2.95 mM, at least 3 mM, at least 3.05 mM, at least 3.1 mM, at least 3.15 mM, at least 3.2 mM, at least 3.25 mM, at least 3.3 mM, at least 3.35 mM, at least 3.4 mM, at least 3.45 mM, at least 3.5 mM, at least 3.55 mM, at least 3.6 mM, at least 3.65 mM, at least 3.7 mM, at least 3.75 mM, at least 3.8 mM, at least 3.85 mM, at least 3.9 mM, at least 3.95 mM, at least 4 mM, at least 4.05 mM, at least 4.1 mM, at least 4.15 mM, at least 4.2 mM, at least 4.25 mM, at least 4.3 mM, at least 4.35 mM, at least 4.4 mM, at least 4.45 mM, at least 4.5 mM, at least 4.55 mM, at least 4.6 mM, at least 4.65 mM, at least 4.7 mM, at least 4.75 mM, at least 4.8 mM, at least 4.85 mM, at least 4.9 mM, at least 4.95 mM, or at least 5 mM.

In some embodiments of any of the aspects, the effective dose of a regulatory protein inducer (e.g., ABA, 4OHT) is at least 0.05 μM, at least 0.1 μM, at least 0.15 μM, at least 0.2 μM, at least 0.25 μM, at least 0.3 μM, at least 0.35 μM, at least 0.4 μM, at least 0.45 μM, at least 0.5 μM, at least 0.55 μM, at least 0.6 μM, at least 0.65 μM, at least 0.7 μM, at least 0.75 μM, at least 0.8 μM, at least 0.85 μM, at least 0.9 μM, at least 0.95 μM, at least 1 μM, at least 1.05 μM, at least 1.1 μM, at least 1.15 μM, at least 1.2 μM, at least 1.25 μM, at least 1.3 μM, at least 1.35 μM, at least 1.4 μM, at least 1.45 μM, at least 1.5 μM, at least 1.55 μM, at least 1.6 μM, at least 1.65 μM, at least 1.7 μM, at least 1.75 μM, at least 1.8 μM, at least 1.85 μM, at least 1.9 μM, at least 1.95 μM, at least 2 μM, at least 2.05 μM, at least 2.1 μM, at least 2.15 μM, at least 2.2 μM, at least 2.25 μM, at least 2.3 μM, at least 2.35 μM, at least 2.4 μM, at least 2.45 μM, at least 2.5 μM, at least 2.55 μM, at least 2.6 μM, at least 2.65 μM, at least 2.7 μM, at least 2.75 μM, at least 2.8 μM, at least 2.85 μM, at least 2.9 μM, at least 2.95 μM, at least 3 μM, at least 3.05 μM, at least 3.1 μM, at least 3.15 μM, at least 3.2 μM, at least 3.25 μM, at least 3.3 μM, at least 3.35 μM, at least 3.4 μM, at least 3.45 μM, at least 3.5 μM, at least 3.55 μM, at least 3.6 μM, at least 3.65 μM, at least 3.7 μM, at least 3.75 μM, at least 3.8 μM, at least 3.85 μM, at least 3.9 μM, at least 3.95 μM, at least 4 μM, at least 4.05 μM, at least 4.1 μM, at least 4.15

μM, at least 4.2 μM, at least 4.25 μM, at least 4.3 μM, at least 4.35 μM, at least 4.4 μM, at least 4.45 μM, at least 4.5 μM, at least 4.55 μM, at least 4.6 μM, at least 4.65 μM, at least 4.7 μM, at least 4.75 μM, at least 4.8 μM, at least 4.85 μM, at least 4.9 μM, at least 4.95 μM, or at least 5 μM.

For systemic administration, subjects can be administered a therapeutic amount of a regulatory protein inducer, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 $mg/m^2$ to about 700 $mg/m^2$. In some embodiments, the dose can be about 250 $mg/m^2$. In some embodiments, the dose can be about 375 $mg/m^2$. In some embodiments, the dose can be about 400 $mg/m^2$. In some embodiments, the dose can be about 500 $mg/m^2$.

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m2 to about 400 mg/m2 administered intravenously about every week. In some embodiments, the dose can be from about 200 mg/m2 to about 400 mg/m2 administered intravenously about every 2 weeks. In some embodiments, the dose can be from about 200 mg/m2 to about 400 mg/m2 administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a synTF cell and/or regulatory protein inducer as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the synTF system and/or the regulatory protein inducer. The desired dose or amount can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a synTF system as described herein can be administered over a period of time, such as over a 5 minute, 10 minute, 15 minute, 20 minute, or 25 minute period.

The dosage ranges for the administration of a synTF system, according to the methods described herein depend upon, for example, the form of the synTF system, its potency, and the extent to which symptoms, markers, or indicators of a condition described herein are desired to be reduced, for example the percentage reduction desired for the disease or disorder (e.g., cancer or autoimmunity). The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a synTF system in, e.g. the treatment of a condition described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. tumor size.

In vitro and animal model assays are provided herein which allow the assessment of a given dose of a synTF system. The efficacy of a given dosage combination can also be assessed in an animal model, e.g. a specific cancer animal model.

In one aspect, described herein is a pharmaceutical composition comprising the at least one synTF polypeptide, synTF system, synTF polynucleotide, synTF vector, or synTF-comprising cell as described herein, which are collectively referred to as a "synTF composition" (see e.g., Tables 1-2). In some embodiments of any of the aspects, the pharmaceutical composition can comprise any combination of synTF polypeptides or systems (see e.g., Table 9). In some embodiments of any of the aspects, the pharmaceutical composition can further comprise a regulator protein inducer (e.g., grazoprevir, ABA, 4OHT).

In some embodiments, the technology described herein relates to a pharmaceutical composition comprising a synTF composition and/or regulator protein inducer as described herein, and optionally a pharmaceutically acceptable carrier. In some embodiments, the active ingredients of the pharmaceutical composition comprise the synTF system and/or the regulator protein inducer as described herein. In some embodiments, the active ingredients of the pharmaceutical composition consist essentially of the synTF system and/or the regulator protein inducer as described herein. In some embodiments, the active ingredients of the pharmaceutical composition consist of the synTF system and/or the regulator protein inducer as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; (24) $C_2$-$C_{12}$ alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. the synTF polypeptide, the synTF system, and/or the regulator protein inducer as described herein.

In some embodiments, the pharmaceutical composition comprising a synTF composition and/or a regulator protein inducer as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of synTF compositions and/or a regulator protein inducer as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Pharmaceutical compositions comprising synTF compositions and/or a regulator protein inducer can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the synTF composition and/or regulator protein inducer described herein is administered as a monotherapy, e.g., another treatment for the disease or disorder (e.g., cancer) is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclophosphamide; alkyl sulfonates such as busulfan, improsulfan and piposulfan; aziridines such as benzodopa, carboquone, meturedopa, and uredepa; ethylenimines and methylmelamines including altretamine, triethylenemelamine, trietylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomycins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

VII. Treatment Methods

The synTF compositions described herein can be administered to a subject in need thereof, in particular the treatment of cancer or autoimmunity. Autoimmunity is the system of immune responses of an organism against its own healthy cells and tissues. Any disease that results from such an aberrant immune response is termed an "autoimmune disease". In some embodiments of any of the aspects, the subject has a genetic disorder in need of regenerative medicine and/or immunotherapy.

In some embodiments, the synTF system expresses a gene of interest (e.g., a therapeutic protein, analyte), which is controlled by at least one inducible synTF, that is itself regulated by at least one regulator protein and its corresponding regulator protein inducer. As such, the expression of the gene of interest can be specifically regulated by the presence, absence, or increased or decreased level of the regulator protein inducer (e.g., an FDA-approved small molecule such as grazoprevir, ABA, or 4OHT) for the treatment of a disease such as cancer, autoimmunity, or a genetic disorder.

Figure 15C:
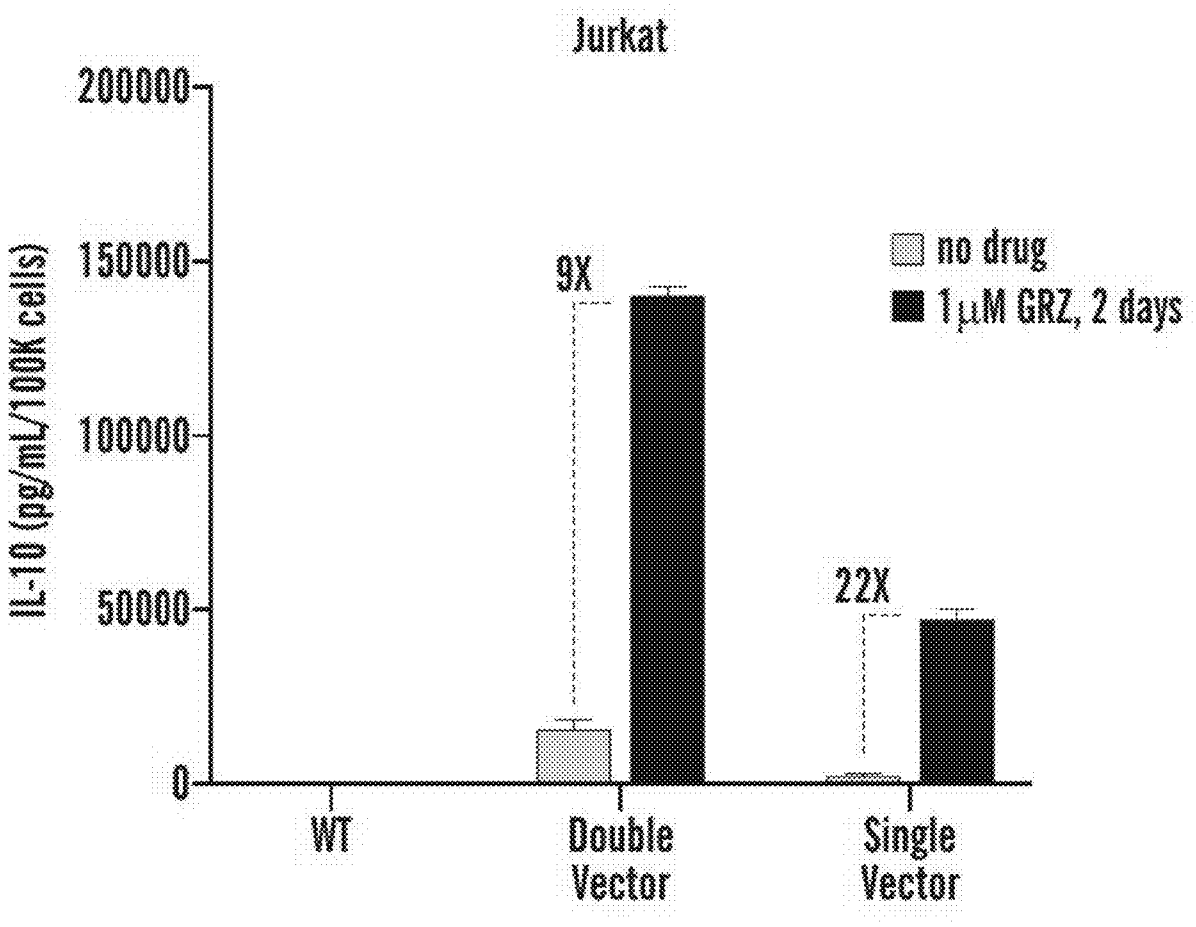

By way of example only, FIG. 13A-13D shows an exemplary system to treat cancer where CD19-CAR is regulated by a repressible protease synTF. As another non-limiting example, FIG. 14A-14C shows an exemplary system to treat cancer where CD19-CAR and IL4 are regulated by a repressible protease synTF and a cytosolic sequestering synTF, respectively. As another non-limiting example, FIG. 15A-15C shows an exemplary system to treat autoimmune disease where IL10 is regulated by a repressible protease synTF, which can be expressed from a single vector system or a double vector system.

In some embodiments, the method of treatment can comprise first diagnosing a subject or patient who can benefit from treatment by a composition described herein. In some embodiments, such diagnosis comprises detecting or measuring an abnormal level of a marker (e.g., the tumor antigens as described herein) in a sample from the subject or patient. In some embodiments, the method further comprises administering to the patient a synTF composition as described herein.

In some embodiments, the subject has previously been determined to have an abnormal level of an analyte described herein relative to a reference. In some embodiments, the reference level can be the level in a sample of similar cell type, sample type, sample processing, and/or obtained from a subject of similar age, sex and other demographic parameters as the sample/subject. In some embodiments, the test sample and control reference sample are of the same type, that is, obtained from the same biological source, and comprising the same composition, e.g. the same number and type of cells.

The term "sample" or "test sample" as used herein denotes a sample taken or isolated from a biological organism, e.g., a blood or plasma sample from a subject. In some embodiments of any of the aspects, the technology described herein encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject.

In some embodiments of any of the aspects, the step of determining if the subject has an abnormal level of an analyte described herein can comprise i) obtaining or having obtained a sample from the subject and ii) performing or having performed an assay on the sample obtained from the subject to determine/measure the level of the analyte in the subject. In some embodiments of any of the aspects, the step of determining if the subject has an abnormal level of an analyte described herein can comprise performing or having performed an assay on a sample obtained from the subject to determine/measure the level of analyte in the subject. In some embodiments of any of the aspects, the step of determining if the subject has an abnormal level of an analyte described herein can comprise ordering or requesting an assay on a sample obtained from the subject to determine/measure the level of the analyte in the subject. In some embodiments of any of the aspects, the step of determining if the subject has an abnormal level of an analyte described herein can comprise receiving the results of an assay on a sample obtained from the subject to determine/measure the level of the analyte in the subject. In some embodiments of any of the aspects, the step of determining if the subject has an abnormal level of an analyte described herein can comprise receiving a report, results, or other means of identifying the subject as a subject with a decreased level of the analyte.

In one aspect of any of the embodiments, described herein is a method of treating cancer (or another disease or disorder as described herein) in a subject in need thereof, the method comprising: a) determining if the subject has an abnormal level of an analyte described herein; and b) instructing or directing that the subject be administered a synTF composition as described herein if the level of the analyte is increased or otherwise abnormal relative to a reference. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In one aspect, described herein is a method of regulating the activity of a synTF, comprising the steps of: (a) providing a population of cells comprising a synTF as described herein; and (b) contacting the population of cells with an effective amount of a regulator protein inducer.

In one aspect, described herein is a method of regulating the expression of a gene of interest, comprising the steps of: (a) providing a population of cells comprising a synTF system as described herein; and (b) contacting the population of cells with an effective amount of a regulator protein inducer.

In one aspect, described herein is a method of treating a subject in need of a cell-based therapy. In some embodiments of any of the aspects, a subject in need of a cell-based therapy comprises any subject that would benefit from regulated expression of a gene of interest. In some embodiments of any of the aspects, a subject in need of a cell-based therapy comprises a subject with cancer, autoimmunity, or another disease or disorder as described herein. In some embodiments of any of the aspects, the subject has a genetic disorder in need of regenerative medicine and/or immunotherapy. Accordingly, the method comprises the steps of: (a) administering to the subject a population of cells comprising a synTF system as described herein; and (b) administering to the subject an effective amount of a regulator protein inducer.

In embodiments wherein the synTF comprises a transcriptional activator and a repressible protease, induced proximity domain, and/or cytosolic sequestering domain, in the presence of the regulator protein inducer, the synTF is ON and the transcription of the gene of interest is ON; and in the absence of the regulator protein inducer, the synTF is OFF and the transcription of the gene of interest is OFF.

In embodiments wherein the synTF comprises a transcriptional repressor and a repressible protease, induced proximity domain, and/or cytosolic sequestering domain, in the presence of the regulator protein inducer, the synTF is ON and the transcription of the gene of interest is OFF; and in the absence of the regulator protein inducer, the synTF is OFF and the transcription of the gene of interest is ON.

In embodiments wherein the synTF comprises a transcriptional activator and an induced degradation domain (e.g., SMASh), in the presence of the regulator protein inducer, the synTF is OFF and the transcription of the gene of interest is OFF; and in the absence of the regulator protein inducer, the synTF is ON and the transcription of the gene of interest is ON.

In some embodiments of any of the aspects, the population of cells comprises immune cells. In some embodiments of any of the aspects, the population of immune cells comprises CD4+ T cells, CD8+ T cells, Tregs, or NK cells.

In some embodiments of any of the aspects, the regulator protein inducer is administered at the same time the population of cells is administered. In some embodiments of any of the aspects, the regulator protein inducer is administered after the population of cells is administered. As a non-limiting example, the regulator protein inducer is administered at least 1 minute, at least 2 minutes, at least 3 minutes, at least 4 minutes, at least 5 minutes, at least 10 minutes, at least 20 minutes, at least 30 minutes, at least 1 hour, at least 2 hours, at least 3 hours, at least 6 hours, at least 12 hours, at least 24 hours, at least 2 days, at least 3 days, at least 4 days, at least 5 days, at least 6 days, at least 7 days, at least 1.5 weeks, at least 2 weeks, at least 3 weeks, at least 4 weeks, at least 5 weeks, at least 6 weeks, at least 7 weeks, at least 8 weeks, at least 9 weeks, at least 10 weeks, at least 1 month, at least 2 months, at least 3 months, at least 4 months, at least 5 months, at least 6 months, at least 7 months, at least 8 months, at least 9 months, at least 10 months, at least 11 months, or at least 1 year after the population of cells is administered. In some embodiments of any of the aspects, the regulator protein inducer is administered continuously, e.g., using an IV.

Cancer

In various embodiments, a cell comprising a synTF system can be used to treat a cancer. In some embodiments, an immune cell (e.g., T cell) comprising a synTF system expressing an anti-cancer gene of interest to treat a cancer.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastases. Cancers which migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

Autoimmune Diseases

In various embodiments, an cell comprising a synTF system can be used to treat an autoimmune disease. In some embodiments, an immune cell (e.g., T cell) comprising a synTF system expressing a gene of interest directed against an autoimmune disease-specific antigen can be used to treat an autoimmune disease. "Autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include neoplastic cells.

Autoantigens, as used herein, are endogenous proteins or fragments thereof that elicit this pathogenic immune response. Autoantigen can be any substance or a portion thereof normally found within a mammal that, in an autoimmune disease, becomes the primary (or a primary) target of attack by the immune system. The term also includes antigenic substances that induce conditions having the characteristics of an autoimmune disease when administered to mammals. Additionally, the term includes peptic subclasses consisting essentially of immunodominant epitopes or immunodominant epitope regions of autoantigens. Immunodominant epitopes or regions in induced autoimmune conditions are fragments of an autoantigen that can be used instead of the entire autoantigen to induce the disease. In humans afflicted with an autoimmune disease, immunodominant epitopes or regions are fragments of antigens specific to the tissue or organ under autoimmune attack and recognized by a substantial percentage (e.g. a majority though not necessarily an absolute majority) of autoimmune attack T-cells.

Autoantigens that are known to be associated with autoimmune disease include myelin proteins with demyelinating diseases, e.g. multiple sclerosis and experimental autoimmune myelitis; collagens and rheumatoid arthritis; insulin, proinsulin, glutamic acid decarboxylase 65 (GAD65); islet cell antigen (ICA512; ICA 12) with insulin dependent diabetes.

A common feature in a number of autoimmune related diseases and inflammatory conditions is the involvement of pro-inflammatory CD4+ T cells. These T cells are responsible for the release of inflammatory, Th1 type cytokines. Cytokines characterized as Th1 type include interleukin 2 (IL-2), γ-interferon, TNFα and IL-12. Such pro-inflammatory cytokines act to stimulate the immune response, in many cases resulting in the destruction of autologous tissue. Cytokines associated with suppression of T cell response are the Th2 type, and include IL-10, IL-4 and TGF-β. It has been found that Th1 and Th2 type T cells may use the identical antigen receptor in response to an immunogen; in the former producing a stimulatory response and in the latter a suppressive response.

Provided herein is a method of treating an autoimmune disease, which comprises administering an effective amount of a synTF composition to a patient in need thereof. In one embodiment of any one of the methods described, the autoimmune disorder is selected from the group consisting of thyroiditis, type 1 diabetes mellitus, Hashimoto's thyroiditis, Graves' disease, celiac disease, multiple sclerosis, Guillain-Barre syndrome, Addison's disease, and Raynaud's phenomenon, Goodpasture's disease, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus *foliaceus*, pemphigus mucus-membrane pemphigoid, and pemphigus erythematosus), autoimmune polyendocrinopathies, Reiter's disease or syndrome, an immune complex disorder such as immune complex nephritis, antibody-mediated nephritis, polyneuropathies, chronic neuropathy such as IgM polyneuropathies or IgM-mediated neuropathy, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, lupoid hepatitis, giant-cell hepatitis, autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies including channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, Sampter's syndrome, Caplan's syndrome, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, cyclitis such as chronic cyclitis, heterochronic cyclitis, iridocyclitis (acute or chronic), or Fuch's cyclitis, Henoch-Schonlein purpura, SCID, sepsis, endotoxemia, post-vaccination syndromes, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, idiopathic nephritic syndrome, minimal change nephropathy, benign familial and ischemia-reperfusion injury, transplant organ reperfusion, retinal autoimmunity, aphthae, aphthous stomatitis, arteriosclerotic disorders, aspermiogenesis, autoimmune hemolysis, Boeck's disease, enteritis allergica, erythema nodosum leprosum, idiopathic facial paralysis, chronic fatigue syndrome, febris rheumatica, Hamman-Rich's disease, sensoneural hearing loss, ileitis regionalis, leucopenia, transverse myelitis, primary idiopathic myxedema, ophthalmia symphatica, polyradiculitis acuta, pyoderma gangrenosum, acquired splenic atrophy, vitiligo, toxic-shock syndrome, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, rheumatic diseases, mixed connective tissue disease, nephrotic syndrome, insulitis, polyendocrine failure, autoimmune polyglandular syndrome type I, adult-onset idiopathic hypoparathyroidism (AOIH), myocarditis, nephrotic syndrome, primary sclerosing cholangitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, granulomas containing eosinophils, seronegative spondyloarthritides, polyendocrine autoimmune disease, sclerosing cholangitis, sclera, episclera, Bruton's syndrome, transient hypogammaglobulinemia of infancy, Wiskott-Aldrich syndrome, ataxia telangiectasia syndrome, angiectasis, autoimmune disorders associated with collagen disease, rheumatism, allergic hypersensitivity disorders, glomerulonephritides, reperfusion injury, ischemic reperfusion disorder, lymphomatous tracheobronchitis, inflammatory dermatoses, dermatoses with acute inflammatory components, and autoimmune uveoretinitis (AUR).

Genetic Disorders

In various embodiments, a cell comprising a synTF system can be used to treat a genetic disorder. In some embodiments, a cell comprising a synTF system expressing a gene of interest that replaces a defective gene can be used to treat a genetic disorder. In some embodiments, the cell is a stem cell.

Non-limiting examples of genetic disorders that can be treated using a synTF system or cell as described herein include: hemoglobinopathies; b-Thalassemia major; a-Thalassemia major; Sickle cell anemia; Immunodeficiency Diseases; Severe combined immunodeficiency syndrome; Bare lymphocyte syndrome; Chronic granulomatous disease; Wiskott-Aldrich syndrome; Infantile agranulocytosis (Kostman's syndrome); Lazy leukocyte syndrome (neutrophil actin deficiency); Neutrophil membrane GP-180 deficiency; Agammaglobulinemia; X-linked lymphoproliferative syndrome; X-linked hyper-IgM syndrome; inborn errors of metabolism; Mucopolysaccharidoses; Hurler's disease (MPS-1) (a-iduronidase deficiency); Hurler-Scheie syndrome; Hunter disease (MPS-II) (iduronate sulfatase deficiency); Sanfillippo B (MPS-IIIB) (a-glycosaminidase deficiency); Morquio (MPS-IV) (hexosamine-6-sulfatase deficiency); Maroteaux-Lamy syndrome (MPS-VI) (arylsulfatase B deficiency); Sly syndrome (MPS-VII) (b-glucuronidase deficiency); Mucolipidoses; Fabry disease (a-galactosidase A deficiency); Gaucher disease (glucocerebrosidase deficiency); Krabbe disease (galactosylceramidase deficiency); Metachromatic leukodystrophy (arylsulfatase A deficiency; Niemann-Pick disease (sphingomyelinase deficiency; Adrenal leukodystrophy; I-cell mucolipidosis II; hematopoietic diseases; Osteopetrosis; Diamond-Blackfan syndrome; and Fanconi anemia.

VIII. Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the term "engineered responsive reporter" or "engineered transcription unit" is a nucleic acid construct containing an engineered promoter that is operably linked to a reporter gene, and the expression of the reporter gene is controlled by upstream regulatory elements such orthogonal DNA target sequence(s) in the engineered promoter. A reporter gene is typically one where the gene product, the transcribed protein, is easily detected and monitored, e.g., the green fluorescent protein.

As used herein, the term "promoter" as used in the art, is a region of DNA that initiates transcription of a particular gene and is at which RNA polymerase binds and initiates transcription. Promoters are located near the transcription start sites of genes, on the same strand and upstream on the DNA As used herein, the term "orthogonal" when used in DNA sequences and genome biology "orthogonal" means DNA sequences that are so dissimilar from that which is naturally occurring in nature in the eukaryotic system.

As used herein, the term "responsive" in the context of an engineered promoter or engineered transcription unit or engineered responsive reporter, the term refers to whether gene transcription initiation from the promoter is enhanced or repressed when upstream nearby orthogonal DNA target sequences are bound by their respective ZF-containing synthetic transcription factors.

As used herein, the term "operably linked" when used in context of the orthogonal DNA target sequences described herein or the promoter sequence (RNA polymerase binding site) in a nucleic acid construct, an engineered responsive reporter, and in an engineered transcription unit means that the orthogonal DNA target sequences and the promoters are in-frame and in proper spatial and distance away from a nucleic acid coding for a protein or peptide or an RNA to permit the effects of the respective binding by transcription factors or RNA polymerase on transcription.

The terms "nucleic acid", "polynucleotide", and "oligonucleotide" are used interchangeably and refer to a deoxyribonucleotide (DNA) or ribonucleotide (RNA) polymer, in linear or circular conformation, and in either single- or double-stranded form. For the purposes of the present disclosure such DNA or RNA polymers may include natural nucleotides, non-natural or synthetic nucleotides, and mixtures thereof. Non-natural nucleotides may include analogues of natural nucleotides, as well as nucleotides that are modified in the base, sugar and/or phosphate moieties (e.g. phosphorothioate backbones). Non-limiting examples of modified nucleic acids are PNAs and morpholino nucleic acids. Generally an analogue of a particular nucleotide has the same base-pairing specificity, i.e. an analogue of G will base-pair with C. For the purposes of the disclosure, these terms are not to be considered limiting with respect to the length of a polymer.

A "gene", as used herein, is the segment of nucleic acid (typically DNA) that is involved in producing a polypeptide or ribonucleic acid gene product. It includes regions preceding and following the coding region (leader and trailer) as well as intervening sequences (introns) between individual coding segments (exons). Conveniently, this term also includes the necessary control sequences for gene expression (e.g. enhancers, silencers, promoters, terminators etc.), which may be adjacent to or distant to the relevant coding sequence, as well as the coding and/or transcribed regions encoding the gene product.

As used herein the term "modulation", in relation to the expression of a gene refers to a change in the gene's activity. Modulation includes both activation (i.e. increase in activity or expression level) and repression or inhibition of gene activity. In preferred embodiments of the disclosure, the therapeutic molecules (e.g. peptides) of the disclosure are repressors of gene expression or activity.

A nucleic acid "target", "target site" or "target sequence" or "DNA target sequence", as used herein, is a nucleic acid sequence to which a ZFA in a synTF of the disclosure will bind, provided that conditions of the binding reaction are not prohibitive. A target site may be a nucleic acid molecule or a portion of a larger polynucleotide. In accordance with the disclosure, a target sequence for a ZFA in a synTF of the disclosure may comprise a single contiguous nucleic acid sequence. These terms may also be substituted or supplemented with the terms "binding site", "binding sequence", "recognition site" or recognition sequence", which are used interchangeably.

As used herein, "binding" refers to a non-covalent interaction between macromolecules (e.g. between a ZF-array containing protein and a nucleic acid target site). In some cases binding will be sequence-specific, such as between one or more specific nucleotides (or base pairs) and one or more specific amino acids. It will be appreciated, however, that not all components of a binding interaction need be sequence-specific (e.g. non-covalent interactions with phosphate residues in a DNA backbone). Binding interactions between a nucleic acid sequence and a ZF peptide of the disclosure may be characterized by binding affinity and/or dissociation constant (Kd). A suitable dissociation constant for a ZF peptide of the disclosure binding to its target site may be in the order of 1 μM or lower, 1 nM or lower, or 1 pM or lower. "Affinity" refers to the strength of binding, such that increased binding affinity correlates with a lower Kd value. ZF synTF of the disclosure may have DNA-binding activity, RNA-binding activity, and/or even protein-binding activity. In some embodiments, the ZF synTF of the disclosure are designed or selected to have sequence specific dsDNA-binding activity. For example, the target site for a particular ZF array or protein is a sequence to which the ZF concerned is capable of nucleotide-specific binding. It will be appreciated, however, that depending on the amino acid sequence of a ZF array or protein it may bind to or recognize more than one target sequence, although typically one sequence will be bound in preference to any other recognized sequences, depending on the relative specificity of the individual non-covalent interactions. Generally, specific binding is preferably achieved with a dissociation constant (Kd) of 1 nM or lower, 100 pM or lower; or 10 pM or lower. In some embodiments, a ZF synTF of the disclosure binds to a specific target sequence with a dissociation constant of 1 nM or lower, or 1 pM or lower, or 0.1 pM or lower, or even 10 fM or lower.

By "non-target" it is meant that the nucleic acid sequence concerned is not appreciably bound by the relevant ZF peptide. In some embodiments it may be considered that, where a ZF peptide described herein has a known sequence-specific target sequence, all other nucleic acid sequences may be considered to be non-target. From a practical perspective it can be convenient to define an interaction between a non-target sequence and a particular ZF peptide as being sub-physiological (i.e. not capable of creating a physiological response under physiological target sequence/ZF peptide concentrations). For example, if any binding can be measured between the ZF peptide and the non-target sequence, the dissociation constant (Kd) is typically weaker than 1 μM, such as 10 μM or weaker, 100 μM or weaker, or at least 1 mM.

As used herein, the term "interaction" when used in the context of a receptor and its ligand refers to the binding between the receptor and its ligand as a result of the non-covalent bonds between the ligand-binding site (or fragment) of the receptor and the receptor-binding site (or fragment) of the ligand. In the context of two entities, e.g., molecules or proteins, having some binding affinity for each other, the term "interaction" refers to the binding of the two entities as a result of the non-covalent bonds between the two entities. A term "interaction", "complexing" and "bonding" are used interchangeably when used in the context of a receptor and its ligand and in the context of two binding entities.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for the disease or disorder (e.g., cancer) or the one or more complications related to the disease or disorder (e.g., cancer). Alternatively, a subject can also be one who has not been previously diagnosed as having the disease or disorder (e.g., cancer) or one or more complications related to the disease or disorder (e.g., cancer). For example, a subject can be one who exhibits one or more risk factors for the disease or disorder (e.g., cancer) or one or more complications related to the disease or disorder (e.g., cancer) or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. function and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wild-type reference polypeptide's activity according to the assays described below herein. A functional fragment can comprise conservative substitutions of the sequences disclosed herein. In some embodiments of any of the aspects, a polypeptide can comprise the first N-terminal amino acid methionine. In embodiments where a polypeptide does not comprise a first N-terminal methionine, it is understood that a variant of the polypeptide does comprise a first N-terminal methionine.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA, cDNA, or vector DNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the synTF polypeptides described herein is exogenous. In some embodiments of any of the aspects, the synTF polypeptides described herein is ectopic. In some embodiments of any of the aspects, the synTF polypeptides described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

As described herein, an "antigen" is a molecule that is bound by a binding site on an antibody agent (e.g., extracellular binding domain). Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

In some embodiments, a nucleic acid encoding a polypeptide as described herein (e.g. a synTF polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with the disease or disorder (e.g., cancer, autoimmunity, genetic disorder). Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, transfection, transduction, perfusion, injection, or other delivery method known to one skilled in the art. In some embodiments, contacting comprises physical human activity, e.g., an injection; an act of dispensing, mixing, and/or decanting; and/or manipulation of a delivery device or machine.

As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology:

a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A synthetic transcription factor (synTF) comprising;
   a. at least one DNA binding domain (DBD),
   b. a transcriptional effector domain (ED),
   c. at least one regulator protein (RP), and
      wherein the ED is directly or indirectly coupled or linked to the DBD, and
      wherein the coupling is regulated by the at least one RP, or
      wherein the cellular localization of the ED is regulated by the at least one regulator protein.
2. The synTF of paragraph 1, wherein the transcriptional ED is a transcriptional activator (TA) domain.
3. The synTF of paragraph 2, wherein the TA is selected from the group consisting of: p65; Rta; miniVPR; full VPR; VP16; VP64; p300; p300 HAT Core; and a CBP HAT domain.
4. The synTF of paragraph 2, wherein the TA is p65, or a variant thereof.
5. The synTF of paragraph 4, wherein the p65 comprises one of SEQ ID NOs: 69, 117-121, 193-197 or a protein having at least 85% sequence identity one of SEQ ID NOs: 69, 117-121, 193-197.
6. The synTF of paragraph 1, wherein the transcriptional ED is a transcriptional repressor (TR) domain.
7. The synTF of paragraph 6, wherein the TR is selected from the group consisting of: KRAB; KRAB-MeCP2; Hp1a; DNMT3B; EED; and HDAC4.
8. The synTF of paragraph 6, wherein the TR is KRAB, or a variant thereof.
9. The synTF of paragraph 8, wherein the KRAB comprises one of SEQ ID NOs: 72, 97, or 214-215, or a protein having at least 85% sequence identity to one of SEQ ID NO: 72, 97, or 214-215.

10. The synTF of paragraph 1, wherein the at least one DBD is an engineered zinc finger (ZF) binding domain.
11. The synTF of any of paragraph 10, wherein the ZF-binding domain comprises 2 or more ZF motifs.
12. The synTF of any of paragraph 11, wherein the ZF-binding domain comprises any one of: 3, 4, 5, 6, 7, 8, 9, 10, 11, 12, 13, 14, 15, 16, 17, 18, or more ZF motifs arranged adjacent to each other in tandem to form a ZF array (ZFA).
13. The synTF of any of paragraphs 1-12, wherein the ZF binding domain is selected from any of: ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2- 4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3- 8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5- 4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6- 8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8- 4, ZF 9-1, ZF 9-2, ZF 9-3, ZF 9-4, ZF 10-1 and ZF 11-1.
14. The synTF of any of paragraphs 1-13, wherein the ZF binding domain is selected from any of SEQ ID NOs: 1-3, 76, 101, 377, or 380.
15. The synTF of paragraph 14, wherein the ZF binding domain specifically binds to a sequence comprising at least one of SEQ ID NOs: 181-191.
16. The synTF of any one of paragraphs 1-15, wherein the at least one DBD is selected from one or more of any of: SEQ ID NO: 221 or 222, 36-4 (SEQ ID NO: 223), 43-8 (SEQ ID NO: 224 or 225), 42-10 (SEQ ID NO: 226 or 227), 97-4 (SEQ ID NO: 228), or wherein the DBD binds to DNA binding motifs (DBM) comprising any of: SEQ ID NOs: 229-240.
17. The synTF of paragraph 1, wherein the regulator protein is located between the DBD and the transcriptional effector domain.
18. The synTF of paragraph any of paragraphs 1-17, wherein the regulator protein is a repressible protease.
19. The synTF of any of paragraphs 1-18, wherein the regulator protein is a NS3 protease protein.
20. The synTF of any of paragraphs 1-19, wherein the regulator protein comprises the amino acid of SEQ ID NOs: 82, 85, 91, 102, 241-255, 304-315, or a homologue of at least 85% sequence identity to SEQ ID NOs: 82, 85, 91, 102, 241-255, 304-315.
21. The synTF of any of paragraphs 1-19, wherein in the presence of a protease inhibitor, or an inhibitor of NS3 the NS3 protease protein is inhibited, thereby maintaining the coupling of the DBD to the effector domain.
22. The synTF of any of paragraphs 1-19, wherein in the absence of a protease inhibitor or an inhibitor to NS3, the NS3 protease protein is active and result in its excision from the DBD, thereby uncoupling the linkage between the DBD and the effector domain.
23. The synTF of paragraph 21 or 22, wherein an inhibitor of NS3 is selected from any of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir
24. The synTF of paragraph 1, wherein the at least one RP is a pair of induced proximity domains (IPD pair), wherein the IPD pair comprises:
    a first induced proximity domain ($IPD^A$) and at least a second complementary IPD ($IPD^B$),
    wherein in the presence of an inducer agent or inducer signal, the $IPD^A$ and $IPD^B$ come together resulting in the linkage of the ED to the DBD of the synthetic TF, and
    wherein in the absence of an inducer agent or inducer signal, the ED is uncoupled or unlinked to the DBD of the synthetic TF.
25. The synTF of paragraph 24, wherein the induced proximity domain pair (IPD pair) comprises a $IPD^A$ and $IPD^B$ selected from any one or more of:
    a. a $IPD^A$ comprising a GID1 domain or a fragment thereof, and a $IPD^B$ comprising a GAI domain, wherein the GID1 domain and GAI domain bind to the inducer agent Gibberellin Ester (GIB);
    b. a $IPD^A$ comprising a FKBP domain or a fragment thereof, and a $IPD^B$ comprising a FRB domain, wherein the FKBP domain and FRB domain bind to the inducer agent Rapalog (RAP);
    c. a $IPD^A$ comprising a PYL domain or a fragment thereof, and a $IPD^B$ comprising a ABI domain, wherein the PYL domain and ABI domain bind to the inducer agent Abscisic acid (ABA);
    d. a $IPD^A$ comprising a Light-inducible dimerization domain (LIDD), wherein a LIDD dimerizes with a complementary LIDD ($IPD^B$) upon exposure to a light inducer signal of an appropriate wavelength.
26. The synTF of paragraph 24, wherein the induced proximity domain pair (IPD pair) comprises a $IPD^A$ and $IPD^B$ comprising a PYL domain or a fragment thereof and a ABI domain, wherein the PYL domain and ABI domain bind to the inducer agent Abscisic acid (ABA).
27. The synTF of paragraph 24, wherein the LIDD is nMag or CIBN or a photochromic protein domain, wherein nMag can dimerize with the complementary LIDD pMag upon exposure to a blue light inducer signal, and wherein CIBN can dimerize with the complementary CRY2 upon exposure to a blue inducer light signal, and wherein the photochromic proteins can dimerize upon exposure to a blue inducer light signal.
28. The synTF of paragraph 24, wherein the light inducer signal is a pulse light signal.
29. The synTF of any of paragraphs 1-17, wherein the at least one RP is a cytosolic sequestering protein.
30. The synTF of paragraph 29, wherein the sequestering protein comprises a ligand binding domain (LBD), wherein in the presence of the ligand, the sequestering of the protein to the cytosol is inhibited.
31. The synTF of paragraph 29, wherein the cytosolic sequestering protein comprises a ligand binding domain and a nuclear localization signal (NLS), wherein in the absence of the ligand the NLS is inhibited thereby preventing translocation of the sequestering protein to the nucleus, and wherein in the presence of the ligand the nuclear localization signal is exposed enabling translocation of the sequestering protein to the nucleus.
32. The synTF of any of paragraphs 29-31, wherein the sequestering protein comprises at least a portion of the estrogen receptor (ER).
33. The synTF of any of paragraphs 29-32, wherein the sequestering protein comprises an estrogen ligand binding domain (ERT) or a variant thereof, selected from the group consisting of: ERT2, ERT, and ERT3.
34. The synTF of paragraph 33, wherein the ERT binds to one or more ligands selected from: tamoxifen, 4-hydroxytamoxifen (4OHT), endoxifen, Fulvestrant, wherein binding of the ligand to ERT exposes the NLS and results in nuclear translocation of the ERT.

35. The synTF of paragraph 29, wherein the cytosolic sequestering protein comprises a transmembrane receptor sequestering protein.

36. The synTF of any of paragraphs 1-35, wherein the synTF comprises a N-terminal DBD, the sequestering protein, and a C-terminal effector domain.

37. The synTF of paragraph 36, wherein the effector domain is a transcriptional activator (TA).

38. The synTF of any of paragraphs 1-35, wherein the synTF comprises a N-terminal effector domain, a DBD and a C-terminal cytosolic sequestering protein.

39. The synTF of paragraph 38, wherein the effector domain is a transcriptional repressor (TR).

40. The synTF of any of paragraphs 1-23, wherein the NS3 protein is part of a Small molecule-Assisted Shutoff (SMASh) domain, wherein the SMASh domain comprises the NS3 protein, a partial protease helical domain and a NS4A domain.

41. The synTF of any of paragraphs 1-9 and 24-40, wherein synTF further comprises a Small molecule-Assisted Shutoff (SMASh) tag, wherein the SMASh tag is a N-terminal or C-terminal SMASh domain comprising a repressible protease, a partial protease helical domain and a cofactor domain.

42. The synTF of paragraph 41, wherein the SMASh tag is a C-terminal SMASh domain comprising in a N-terminal to C-terminal order: a NS3 cleavage site, at least one linker, a NS3 domain, a NS3 partial helicase, a NS4A domain, wherein the SMASh tag is fused to the C-terminus of the effector domain of the synTF.

43. The synTF of paragraph 41, wherein the SMASh tag is a N-terminal SMASh domain comprising in a N-terminal to C-terminal order: at least one Linker, a NS3 domain, a NS3 partial helicase, a NS4 domain, and a NS3 cleavage site, wherein the SMASh tag is fused to the N-terminus of the synTF.

44. The synTF of paragraphs 40-43, wherein in the absence of an inhibitor for the NS3 protease, the NS3 protease is active and self cleaves/uncouples from the synTF, thereby resulting in the SMASh tag targeted for degradation ("SMASh-degradation", synTF-on/TA-on/RP-on), and wherein in the presence of an inhibitor for NS3 protease, NS3 protease activity is inhibited thereby resulting in the SMASh tagged synTF targeted for degradation ("synTF-degradation", synTF-OFF/TA-off/RP-off").

45. The synTF of paragraph 44, wherein the inhibitor for NS3 protease is selected from any of: grazoprevir (GRZ/GZV), danoprevir, simeprevir, asunaprevir, ciluprevir, boceprevir, sovaprevir, paritaprevir, ombitasvir, paritaprevir, ritonavir, dasabuvir, and telaprevir.

46. The synTF of any one of paragraphs 24-45, wherein the synTF comprises a SMASh tag and a cytosolic sequestering protein.

47. The synTF of paragraph 46, wherein the synTF is active in the presence of the ligand for the cytosolic sequestering protein and the absence of the inhibitor for the NS3 protease; and wherein the synTF is inactive in the absence of the ligand for the cytosolic sequestering protein and the presence of the inhibitor for the NS3 protease.

48. The synTF of any of paragraphs 1-47, further comprising a linker peptide, wherein the linker peptide can be positioned anywhere from: between the DBD and the regulator protein; between the regulator protein and the effector domain; between the DBD and effector domain; within the DBD, effector domain, or regulator protein; or any combination thereof.

(SEQ ID NO: 340)
PGER, (SEQ ID NO: 341)
TGSQK, (SEQ ID NO: 342)
TGEKP, (SEQ ID NO: 343)
THLR, (SEQ ID NO: 344)
TGGGEKP, (SEQ ID NO: 345)
FHYDRNNIAVGADESVVKEAHREVINSSTEGLLLNIDKDIRKILSGYIVE
IEDTE;

(SEQ ID NO: 346)
VEIEDTE, (SEQ ID NO: 347)
KDIRKILSGYIVEIEDTE;

(SEQ ID NO: 348)
STEGLLLNIDKDIRKILSGYIVEIEDTE, (SEQ ID NO: 349)
EVKQENRLLNESES;

(SEQ ID NO: 350)
VGADESVVKEAHREVINSSTEGLLLNIDKDIRKILSGYIVEIEDTE;

(SEQ ID NO: 67)
GGSGG;

(SEQ ID NO: 70)
GGGSG;

(SEQ ID NO: 73)
CVRGS, (SEQ ID NO: 75)
GGGGSG, (SEQ ID NO: 100)
GGSGSGSAC, (SEQ ID NO: 103)
LEGGGGSGG, (SEQ ID NO: 104)
GGGGSGGT, (SEQ ID NO: 345)
SGGGSGGSGSS;

(SEQ ID NO: 88)
PGAGSSGDIM (SEQ ID NO: 90)
GSSGTGSGSGTS;

(SEQ ID NO: 277)
SGTS;

(SEQ ID NO: 278)
GSGS, (SEQ ID NO: 303)
GGSGGS,
and (SEQ ID NO: 323)
GSSGSS.

49. A system for controlling gene expression, comprising:

a. at least one synthetic transcription factor (synTF) comprising at least one DNA binding domain (DBD), a transcriptional effector domain (ED), and at least one regulator protein (RP), wherein the ED is directly or indirectly coupled or linked to the DBD, and wherein the coupling is regulated by the at least one RP, or wherein the cellular localization of the ED linked to the DBD is regulated by the at least one RP, wherein the at least one RP is regulated by an RP inducer, wherein the DBD can bind to a target DNA binding motif (DBM) located upstream of a promoter operatively linked to a gene, b. a nucleic acid construct comprising:

i. at least one target DNA binding motif (DBM) comprising a target nucleic acid for binding of the at least one DBD of the synTF, and ii. a promoter sequence located 3' of the at least one DBM, and iii. a gene of interest operatively linked to the promoter sequence, wherein for synTFs where the coupling of the ED to the DBD is regulated by the at least one RP;

in the presence of the RP inducer, the coupling of the ED to the DBD of the synTF is maintained, enabling the ED to be in proximity to the promoter sequence when the DBD binds to the DNA binding motif (DBM), where the ED controls the expression of the gene of interest ("ED-on"), or in the absence of the RP inducer, the coupling of the ED to the DBD of the synTF is severed, preventing the ED from being in proximity to the promoter sequence when the DBD binds to the DNA binding motif (DBM), preventing gene expression of the gene of interest ("ED-off"), and wherein for synTFs where the cellular localization of the ED linked to the DBD is regulated by the at least one regulator protein;

in the presence of the RP inducer, the ED coupled to the DBD of the synTF is not sequestered in the cytosol, enabling the DBD to bind to the DNA binding motif (DBM) and enabling the transcriptional effector domain (ED) to be in proximity to the promoter sequence to control the expression of the gene of interest ("ED-on"), or in the absence of the RP inducer, the ED coupled to the DBD of the synTF is sequestered in the cytosol, preventing the DBD of the synTF from binding to the DBM, and preventing the effector domain (ED) from being in proximity to the promoter sequence, preventing expression of the gene of interest ("ED-off").

50. The system of paragraph 49, wherein the transcriptional effector domain (ED) is a transcriptional activator (TA), wherein a. for synTFs where the coupling of the ED to the DBD is regulated by the at least one RP;

i. in the presence of the RP inducer, the coupling of the ED to the DBD of the synTF is maintained, enabling the TA domain to be in proximity to the promoter sequence when the DBD binds to the DNA binding motif (DBM), where the TA turns on the expression of the gene of interest ("TA-on"), or ii. in the absence of the RP inducer, the coupling of the ED to the DBD of the synTF is severed, preventing the TA domain from being in proximity to the promoter sequence when the DBD binds to the DNA binding motif (DBM), preventing expression of the gene of interest ("TA-off"), and b. for synTFs where the cellular localization of the ED linked to the DBD is regulated by the at least one RP;

i. in the presence of the RP inducer, the ED coupled to the DBD of the synTF is not sequestered in the cytosol, enabling the DBD to bind to the DNA binding motif (DBM) and enabling the TA domain to be in proximity to the promoter sequence to turn on expression of the gene of interest ("TA-on"), or ii. in the absence of the RP inducer, the ED coupled to the DBD of the synTF is sequestered in the cytosol, preventing the DBD from binding to the DBM, and preventing the TA domain from being in proximity to the promoter sequence, preventing expression of the gene of interest ("TA-off").

51. The system of paragraph 49, wherein the ED is a transcriptional repressor (TR), wherein a. for synTFs where the coupling of the ED to the DBD is regulated by the at least one regulator protein;

i. in the presence of the RP inducer, the coupling of the ED to the DBD of the synTF is maintained, enabling the transcriptional repressor (TR) to be in proximity to the promoter sequence when the DBD binds to the DNA binding motif (DBM), where the TR prevents expression of the gene of interest ("TR-on" (no-expression), or ii. in the absence of the RP inducer, the coupling of the ED to the DBD of the synTF is severed, preventing the transcriptional repressor (TR) from being in proximity to the promoter sequence when the DBD binds to the DNA binding motif (DBM), allowing expression of the gene of interest ("TR-off" (yes-expression), and b. for synTFs where the cellular localization of the ED linked to the DBD is regulated by the at least one regulator protein;

i. in the presence of the RP inducer, the ED coupled to the DBD of the synTF is not sequestered in the cytosol, enabling the DBD to bind to the DNA binding motif (DBM) and enabling the transcriptional repressor (TR) to be in proximity to the promoter sequence to turn off expression of the gene of interest ("TR-on" (no-expression), or ii. in the absence of the RP inducer, the ED coupled to the DBD of the synTF is sequestered in the cytosol, preventing the DBD from binding to the DBM, and preventing the transcriptional repressor (TR) from being in proximity to the promoter sequence, allowing expression of the gene of interest ("TR-off" yes-expression).

52. The system of any of paragraphs 49-51, wherein the synTF are selected from any of those in paragraphs 1-48.

53. The system of any of paragraph 49-52, wherein the at least one synTF further comprises a N-terminal or C-terminal Small molecule-Assisted Shutoff (SMASh) domain, wherein SMASh domain comprises a self-cleaving SMASh protease, a partial protease helical domain and a cofactor domain, wherein in the presence of an inhibitor to the SMASh protease, the SMASh protease activity is inhibited, resulting in the synTF being degraded and preventing the DBD of the synTF binding to the DBM and controlling the expression or repression of the gene of interest ("synTF-degradation"; TA-off (no expression), TR-off (yes-expression)), wherein in the absence of an inhibitor to the SMASh protease, the SMASh protease is active and self cleaves/uncouples from the synTF, resulting the SMASh domain being targeted for degradation and allowing the DBD of the synTF to bind to the DBM and the ED of synTF to control the expression of the gene of interest ("SMASh-degradation, TA-on (yes-expression), TR-on (no-expression)).

54. The system of any of paragraphs 49-53, wherein the promoter is selected from any of: miniCMV promoter, miniTK promoter, ybTATA promoter, minSV40 promoter, CMV53 promoter, pJB42CAT5 promoter, MLP promoter, TATA promoter, pSFFV promoter, CMV promoter, pUb/UbC promoter, EF1a promoter, PGK/pGK promoter, CAG/CAGG promoter, SV40 promoter, and beta actin/ACTB promoter.

55. A cell comprising
  a. a first nucleic acid sequence comprising at least one target DNA binding motif (DBM) comprising a target nucleic acid for binding of the at least one DBD of a synTF, a promoter sequence located 3' of the at least one DBM, and a nucleic acid encoding a gene of interest (GOI) operatively linked to the promoter sequence, and
  b. a second nucleic acid sequence comprising a nucleic acid encoding a synthetic transcription factor (synTF) according to paragraphs 1-48, operatively linked to an inducible or constitutive promoter.

56. The cell of paragraph 55, wherein the cell comprises a nucleic acid construct comprising in the 5' to 3' direction:
  a. a nucleic acid sequence encoding a gene of interest (GOI) in the inverse orientation,
  b. a first promoter sequence in the inverse orientation and operatively linked to the nucleic acid encoding the GOI,
  c. a nucleic acid sequence comprising at least one target DNA binding motif (DBM) comprising a target nucleic acid for binding of the at least one DBD of a synTF, wherein binding of the DBD of the synTF places the effector domain (ED) in the proximity of the promoter sequence operatively linked to the GOI,
  d. a second promoter sequence, and
  e. a nucleic acid sequence encoding the synthetic transcription factor (synTF), operatively linked to the second promoter sequence, wherein the encoded synTF comprises at least one DBD that binds to the at least DBM of the nucleic acid sequence of (c).

57. The cell of paragraph 55 or 56, wherein the promoter sequence operatively linked to the GOI is selected from any of: miniCMV promoter, miniTK promoter, ybTATA promoter, minSV40 promoter, CMV53 promoter, pJB42CAT5 promoter, MLP promoter, and TATA promoter.

58. The cell of paragraph 55 or 56, wherein the promoter sequence operatively linked to the nucleic acid encoding the synTF is a pSFFV promoter, CMV promoter, pUb/UbC promoter, EF1a promoter, PGK/pGK promoter, CAG/CAGG promoter, SV40 promoter, and beta actin/ACTB promoter.

59. A polynucleotide encoding the synTF of any one of paragraphs 1-48, or the synTF system of any one of paragraphs 49-54.

60. A vector comprising the polynucleotide of paragraph 59.

61. A composition comprising the synTF of any one of paragraphs 1-48, the synTF system of any one of paragraphs 49-54, the synTF cell of any one of paragraphs 55-58, a polynucleotide of paragraph 59, or the vector of paragraph 60.

62. A pharmaceutical composition comprising the synTF of any one of paragraphs 1-48, the synTF system of any one of paragraphs 49-54, the synTF cell of any one of paragraphs 55-58, a polynucleotide of paragraph 59, or the vector of paragraph 60, and a pharmaceutically acceptable carrier.

63. A method of regulating the activity of a synTF, comprising the steps of:
  a. providing a population of cells of any one of paragraphs 55-58; and
  b. contacting the population of cells with an effective amount of a regulator protein inducer.

64. A method of regulating the expression of a gene of interest, comprising the steps of:
  a. providing a population of cells of any one of paragraphs 55-58; and
  b. contacting the population of cells with an effective amount of a regulator protein inducer.

65. A method of treating a subject in need of a cell-based therapy, comprising the steps of:
  a. administering to the subject a population of cells of any one of paragraphs 55-58; and
  b. administering to the subject an effective amount of a regulator protein inducer.

66. The method of any one of paragraphs 63-65, wherein the population of cells comprises immune cells.

67. The method of paragraph 65, wherein the population of immune cells comprises CD4+ T cells, CD8+ T cells, Tregs, or NK cells.

68. The method of any one of paragraphs 65-67, wherein the regulator protein inducer is administered at the same time the population of cells is administered.

69. The method of any one of paragraphs 65-67, wherein the regulator protein inducer is administered after the population of cells is administered.

EXAMPLES

Example 1: Inducible Synthetic Transcription Factors (NS3 SynTFs)

Overview

Described herein are synthetic transcription factors (synTFs) and responsive promoters for precise, human genome-orthogonal regulation. Synthetic transcription factor proteins are minimal, modular fusions of DNA binding and effector domains that together can locally regulate the expression of genes at responsive promoters. They fundamentally couple engineered zinc finger (ZF) DNA binding arrays to transcriptional or epigenetic effector domains.

The engineered ZF arrays described herein are derived from native mammalian ZF scaffolds but re-designed to target specific 18-20 nucleotide sequences that are distant from human genome sequences; this feature confers reduced off-target binding potential in the human genome.

The transcriptional and epigenetic effector domains include naturally-occurring human effector domains such as the p65 transcriptional activator and KRAB repressor. When coupled with engineered ZF arrays, they can locally regulate transcription at targeted loci in engineered cells (i.e. activating or repressing downstream genes).

Corresponding responsive promoters are designed by placing instances of ZF binding sites upstream of constitutive promoters to enable precise and local gene expression control in mammalian cells.

Described herein is a library of synthetic transcription factors that strongly regulate gene expression at their corresponding responsive promoters and minimally impact the expression of off-target genes in the human genome (see e.g., FIG. 1A-1H).

In the absence of a small molecule, the synthetic transcription factor is rendered inactive. In the presence of a cognate small molecule, the transcription factor can regulate expression of an output gene from a responsive promoter (see e.g., FIG. 2A-2B).

Induced Proximity Domains

ABI/PYL induced proximity domains that are responsive to a small molecule (abscisic acid=ABA) can be used to regulate a synTF as described herein (see e.g., Liang et al. Sci Signal, 2011). The ABA-insensitive 1 (ABI1) and PYR1-like (PYL) domains originating form *Arabidopsis thaliana* have complementary surfaces that can conditionally interact when coordinated by the small molecule abscisic acid (ABA). ABA is a plant hormone that is naturally present at low levels within the human diet, and is subsequently presumed to be a safe small molecule for human administration.

The expression of two fusion proteins—one with the ZF DNA binding domain fused to the ABI1 (or PYL) domain and one with the effector domain fused to the PYL (or ABI1) domain—permit separation of the synTF sub-domains, thereby rendering the local gene regulation functionality inactive.

Figure 3:
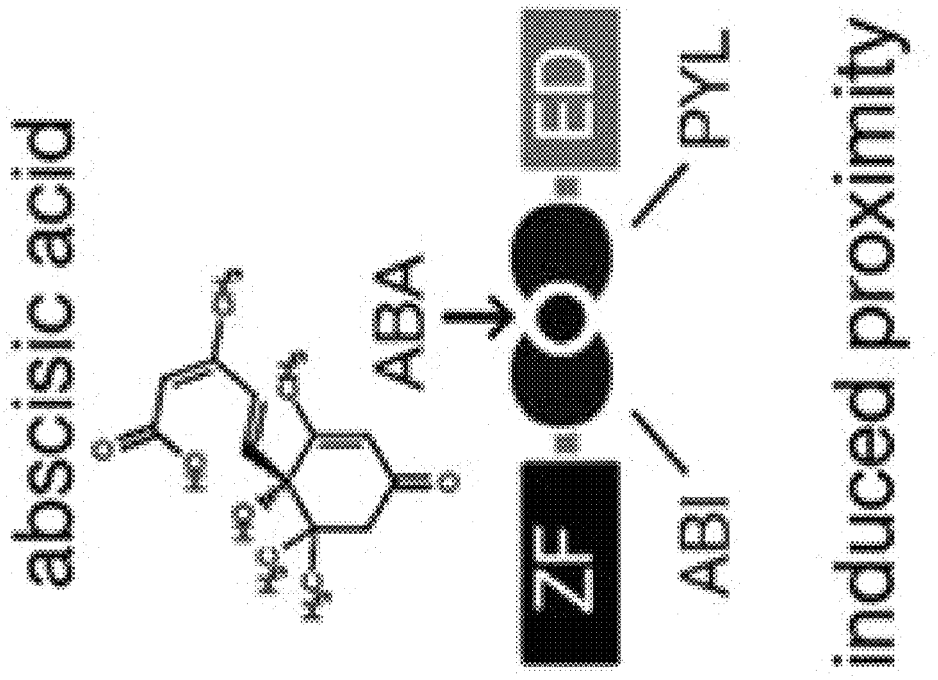
FIG. 3 is a schematic showing an exemplary synTF regulated by induced proximity.

Subsequently, the administration of ABA can allow conditional dimerization between the ABI1 and PYL subunits, allowing the ZF and effector domains to remain locally coupled and retaining synTF functionality (see e.g., FIG. 3).

Translocation Domain

ERT2 nuclear translocation domain, which is responsive to a small molecule (4-hydroxytamoxifen=4OHT), can be used to regulate a synTF as described herein (see e.g., Indra et al. Nucleic Acids Res (1999)). The human estrogen receptor (ER) contains a ligand responsive domain that, when fused to other protein domains, can yield ligand-dependent control over activity. The domain naturally associates with cytoplasmic factors in the cell in the absence of cognate ligands, effectively sequestering itself in the cytoplasm. Binding of cognate ligands, such as estrogen or other steroid hormone derivatives, cause a conformational change to the receptor that allow dissociation from the cytoplasmic complexes and expose a nuclear localization signal, permitting translocation into the nucleus. A mutated variant of this estrogen receptor ligand binding domain (ERT2) has enhanced sensitivity to certain "orthogonal" ligands (e.g. tamoxifen, 4-hydroxytamoxifen) and decreased sensitivity to endogenous ligands (e.g. estradiol).

4-hydroxytamoxifen (4OHT) is a selective modulator of the estrogen receptor that has been FDA-approved as a treatment for certain breast cancers.

The expression of a fusion protein containing the ZF DNA binding domain, effector domain, and ERT2 domain permits cytoplasmic localization of the synTF, thereby rendering the local gene regulation functionally inactive, as the gene expression cassette resides in the nucleus/genome.

Figure 4:
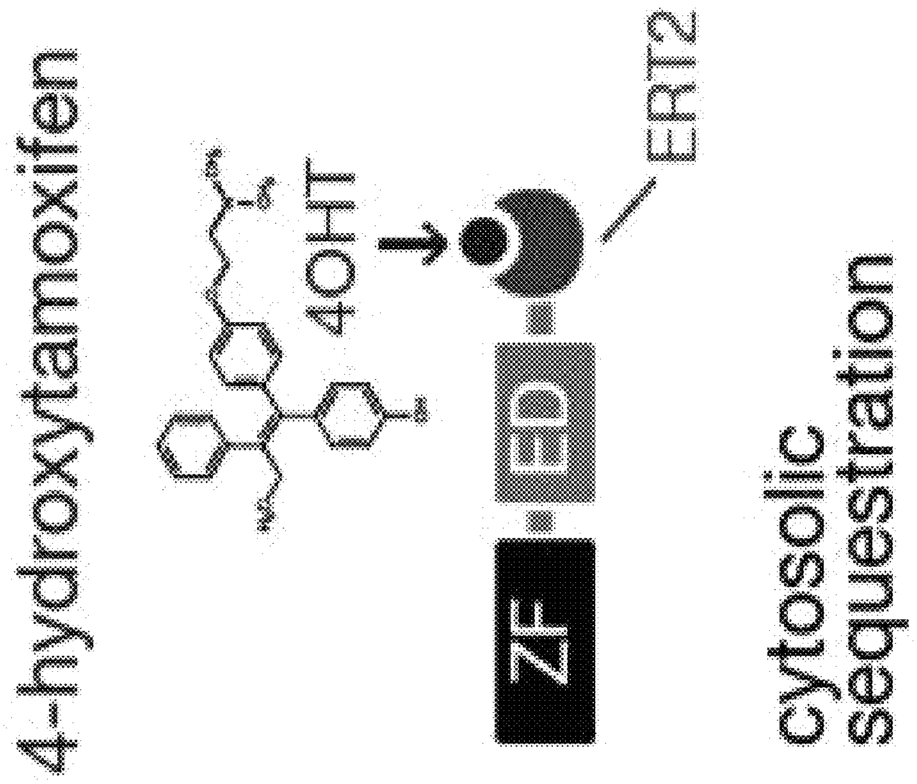
FIG. 4 is a schematic showing an exemplary synTF regulated by cytosolic sequestration.

Subsequently, the administration of 4OHT can allow conditional nuclear translocation of the synTF, allowing synTF functionality in the cellular nucleus (see e.g., FIG. 4).

Self-Cleaving Protease Domain

Non-structural protein 3 (NS3) domain can be used for small molecule regulated control over synTF activity (see e.g., Lin et al. PNAS (2008)). The non-structural protein 3 (NS3) is a serine protease originating from the hepatitis C virus and is naturally capable of self-excision from expressed proteins. As such, the development of an expressed fusion protein with the NS3 protein domain placed between the ZF and effector domains permits auto-cleavage and separation of the synTF sub-domains, thereby rendering the local gene regulation functionality inactive.

Many FDA-approved small molecules have been developed to target the NS3 protease and inhibit its cleavage activity as HepC therapeutic intervention strategies.

Subsequently, the administration of one of these small molecules—e.g. grazoprevir—can prevent self-excision of NS3 from the fusion protein, allowing the ZF and effector domains to remain locally coupled and retaining synTF functionality.

In the absence of a small molecule, the NS3 protease self-excises from the expressed fusion protein, rendering the synthetic transcription factor inactive through the separation of the DNA binding and effector domains. In the presence of a small molecule, the NS3 protease activity is inhibited and the fusion protein complex is stabilized, permitting the transcription factor to regulate expression of an output gene from a responsive promoter (see e.g., FIG. 5A-5C).

Induced Degradation Domain

SMASh (Small Molecule-Assisted Shutoff) domain, which contains NS3 domain, can be used for small molecule regulated control over synTF activity. The small molecule-assisted shutoff (SMASh) tag is an engineered protein domain containing: the NS3 protease, a partial NS3 helicase domain, and a NS4A domain. All of the individual elements are derived from the hepatitis C virus.

The combined arrangement of the NS3 protease with the partial NS3 helicase and NS4A domain led to a "degron" sequence, facilitating rapid degradation of the domain (see e.g., Chung et al. Nat Chem Biol 2015).

The fusion of the SMASh domain to either the N- or C-terminus of a protein of interest results in its auto-cleavage and its separation from the protein, rendering the protein of interest expressed while the SMASh domain targeted for degradation.

Subsequently, the administration of an NS3 inhibitor small molecule, e.g., grazoprevir, can prevent self-excision of the SMASh from the protein of interest, rendering the entire fusion protein targeted for degradation and thus the protein of interest is not expressed.

Figure 6A:
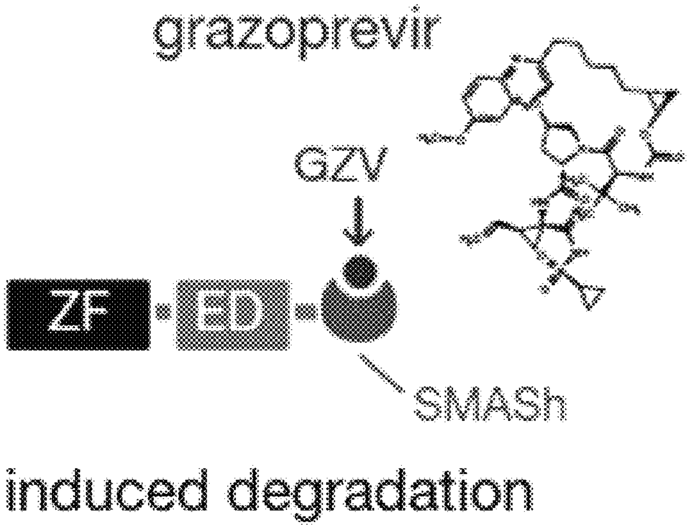
FIG. 6A-6B is a series of schematics showing an exemplary synTF regulated by induced degradation.
Figure 6B:
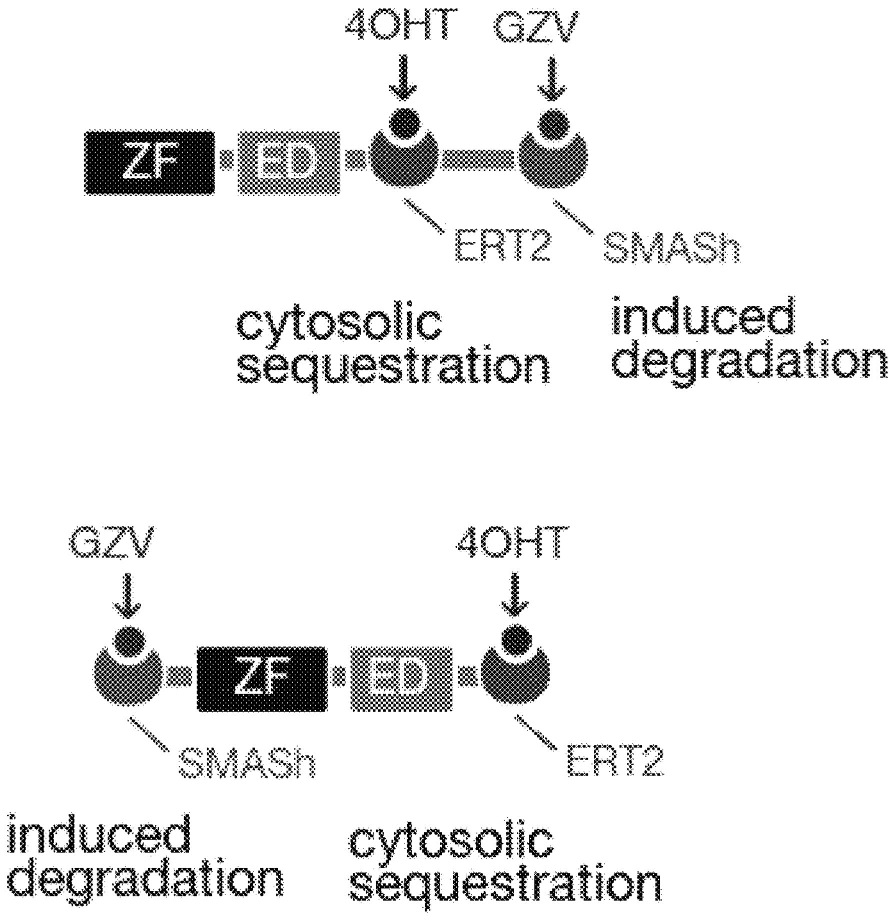

The NS3-containing SMASh protein has been used herein to post-translationally regulate activity of a synthetic transcription factor (see e.g., FIG. 6A-6B).

Experimental Assays and Supporting Data

Figure 7A:
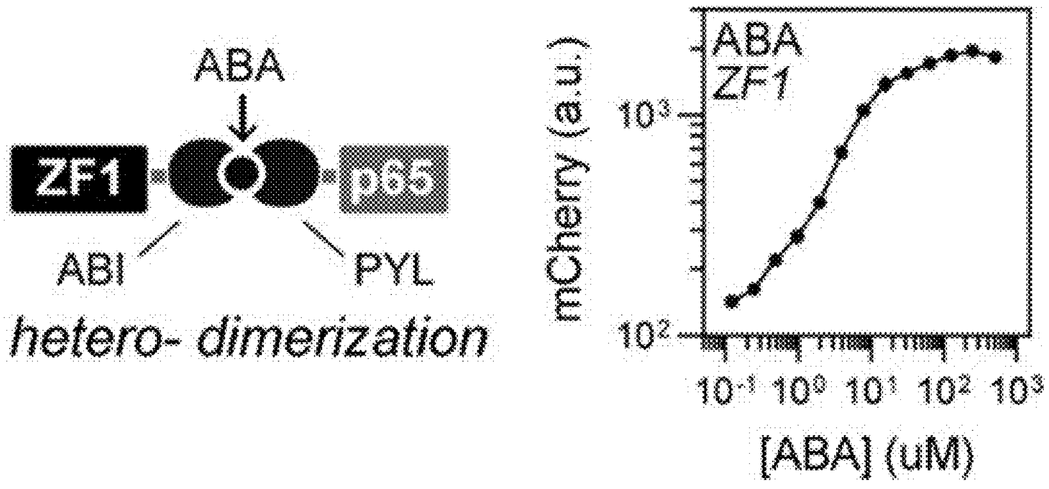
FIG. 7A-7C is a series of schematics showing an exemplary heterodimerization synTF and graphs showing that administration of a small molecule (ABA) led to temporal activation of a fluorescent protein output from a ZF-responsive promoter in Jurkat cell lines.
Figure 7B:
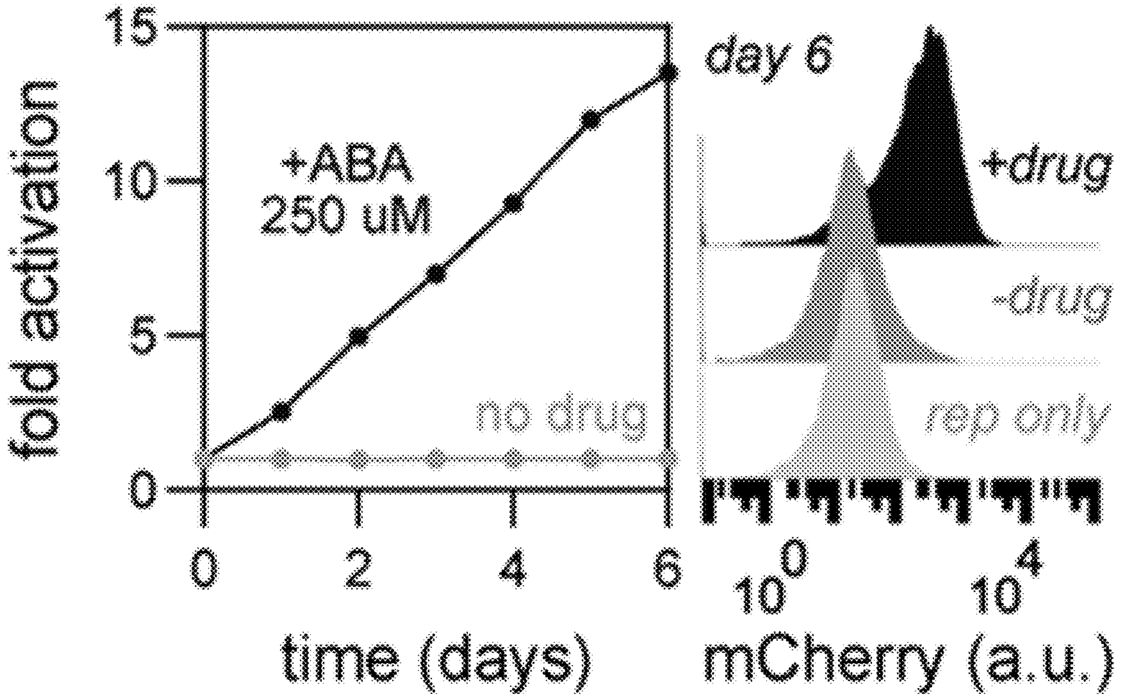

Dose- and time-inducible synthetic transcriptional activation of a fluorescent protein in human cell lines using ABI/PYL domains: Administration of a small molecule (ABA) led to temporal activation of a fluorescent protein output from a ZF-responsive promoter in Jurkat cell lines. Output fluorescence was measured as a function of several different ABA treatment concentrations as indicated (dose response; see e.g., FIG. 7A). Administration of a small molecule (ABA) led to temporal activation of a fluorescent protein output from a ZF-responsive promoter in Jurkat cell lines. This level of expression was compared to an untreated cell line which did not activate output expression (see e.g., FIG. 7B). Removal of a small molecule (ABA) after four days led to temporal de-activation of a fluorescent protein output from a ZF-responsive promoter in Jurkat cell lines.

Figure 7C:
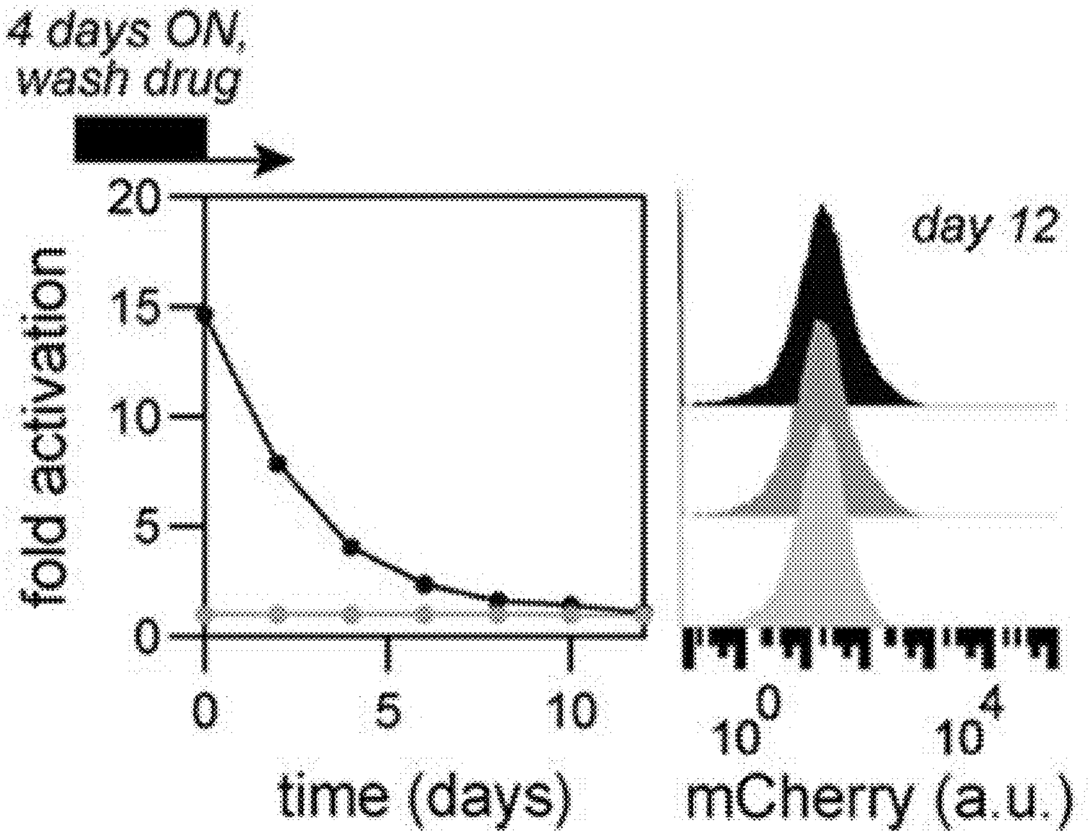

This level of expression was compared to an untreated cell line which did not activate output expression (see e.g., FIG. 7C).

Figure 8A:
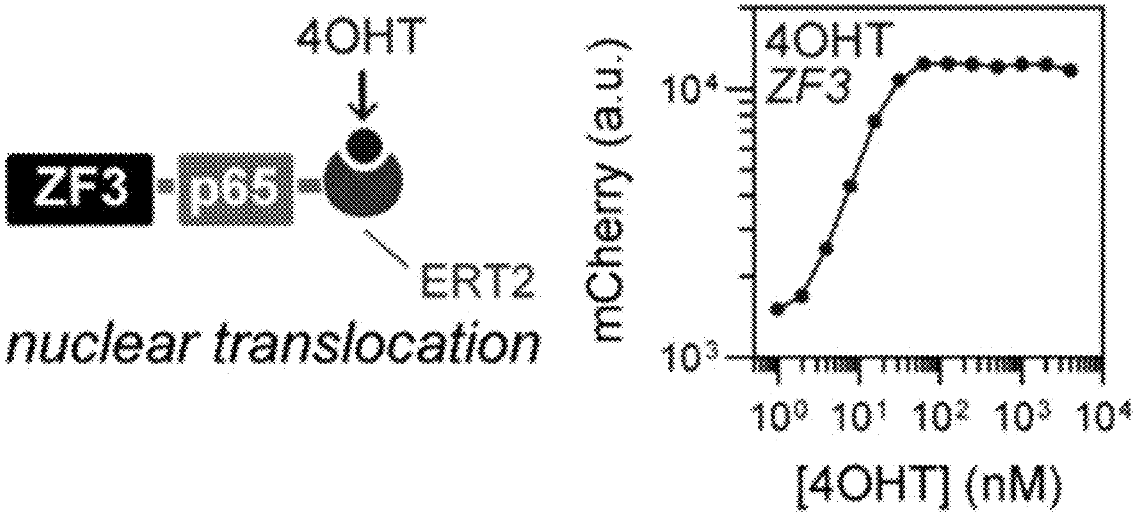
FIG. 8A-8C is a series of schematics showing an exemplary cytosolic sequestering synTF and graphs showing that administration of a small molecule (4OHT) led to temporal activation of a fluorescent protein output from a ZF-responsive promoter in Jurkat cell lines.
Figure 8B:
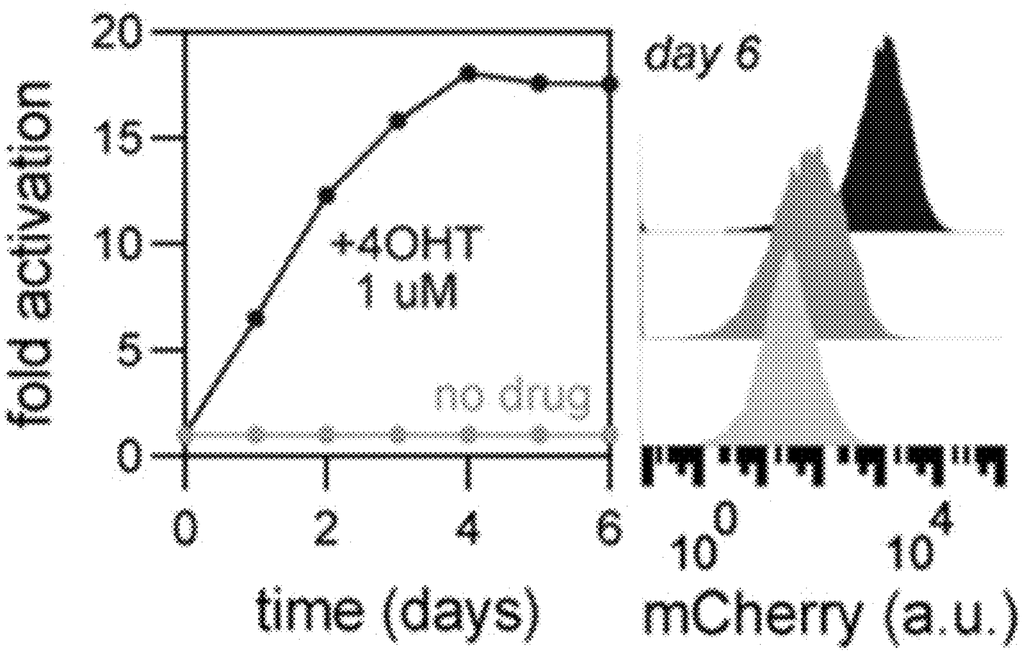
Figure 8C:
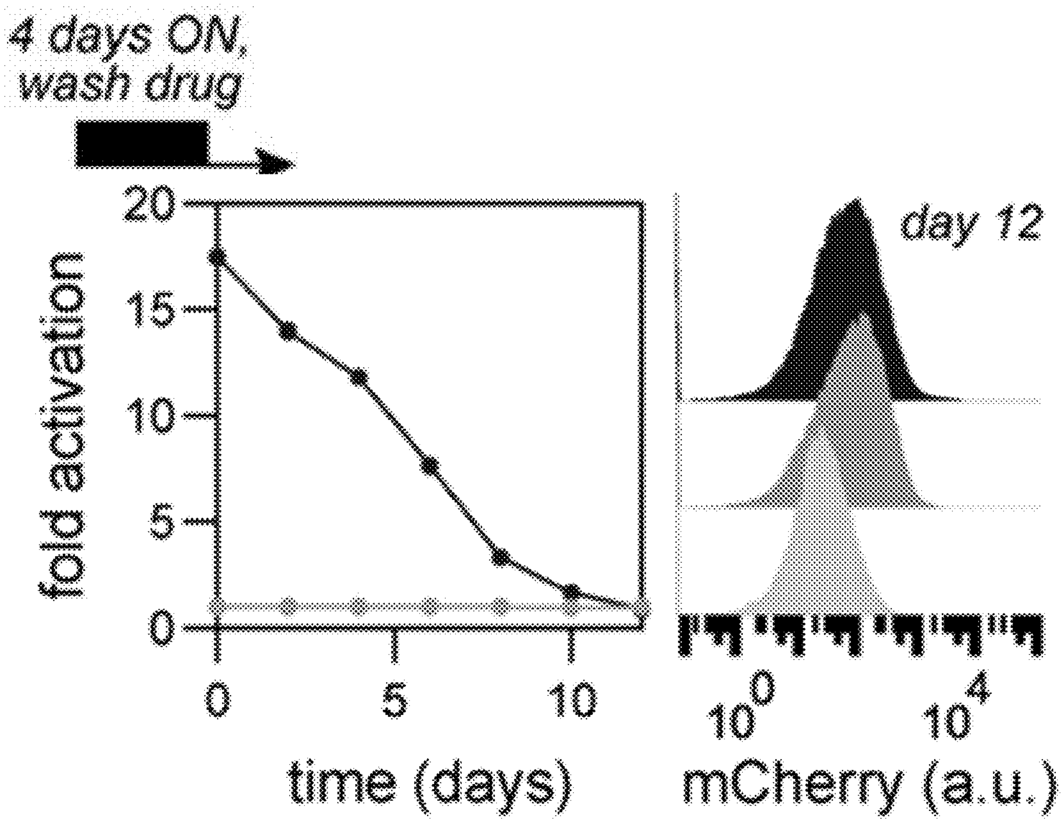

Dose- and time-inducible synthetic transcriptional activation of a fluorescent protein in human cell lines using ERT2 domain: Administration of a small molecule (4OHT) led to temporal activation of a fluorescent protein output from a ZF-responsive promoter in Jurkat cell lines. Output fluorescence was measured as a function of several different 4OHT treatment concentrations as indicated (dose response; see e.g., FIG. 8A). Administration of a small molecule (4OHT) led to temporal activation of a fluorescent protein output from a ZF-responsive promoter in Jurkat cell lines. This level of expression was compared to an untreated cell line which did not activate output expression (see e.g., FIG. 8B). Removal of a small molecule (4OHT) after four days led to temporal de-activation of a fluorescent protein output from a ZF-responsive promoter in Jurkat cell lines. This level of expression was compared to an untreated cell line which did not activate output expression (see e.g., FIG. 8C).

Dose- and time-inducible synthetic transcriptional activation of a fluorescent protein in human cell line using NS3: Administration of a small molecule (grazoprevir) led to temporal activation of a fluorescent protein output from a ZF-responsive promoter in Jurkat cell lines. Output fluorescence was measured as a function of several different grazoprevir treatment concentrations as indicated (dose response) (see e.g., FIG. 9A). Administration of a small molecule (grazoprevir) led to temporal activation of a fluorescent protein output from a ZF-responsive promoter in Jurkat cell lines (see e.g., FIG. 9B). This level of expression was compared to an untreated cell line which did not activate output expression. Removal of a small molecule (grazoprevir) after four days led to temporal de-activation of a fluorescent protein output from a ZF-responsive promoter in Jurkat cell lines. This level of expression was compared to an untreated cell line which did not activate output expression (see e.g., FIG. 9C).

Administration of a small molecule (e.g., ABA, 4OHT, or grazoprevir) led to temporal activation of a fluorescent protein output from a ZF-responsive promoter in both HEK293 and Jurkat cell lines (see e.g., FIG. 10A-10D). This enhanced level of expression was compared to an untreated cell line which did not activate output expression. Output fluorescence as a function of several different small molecule (e.g., ABA, 4OHT, or grazoprevir) treatment concentrations is also indicated here.

Figure 11A:
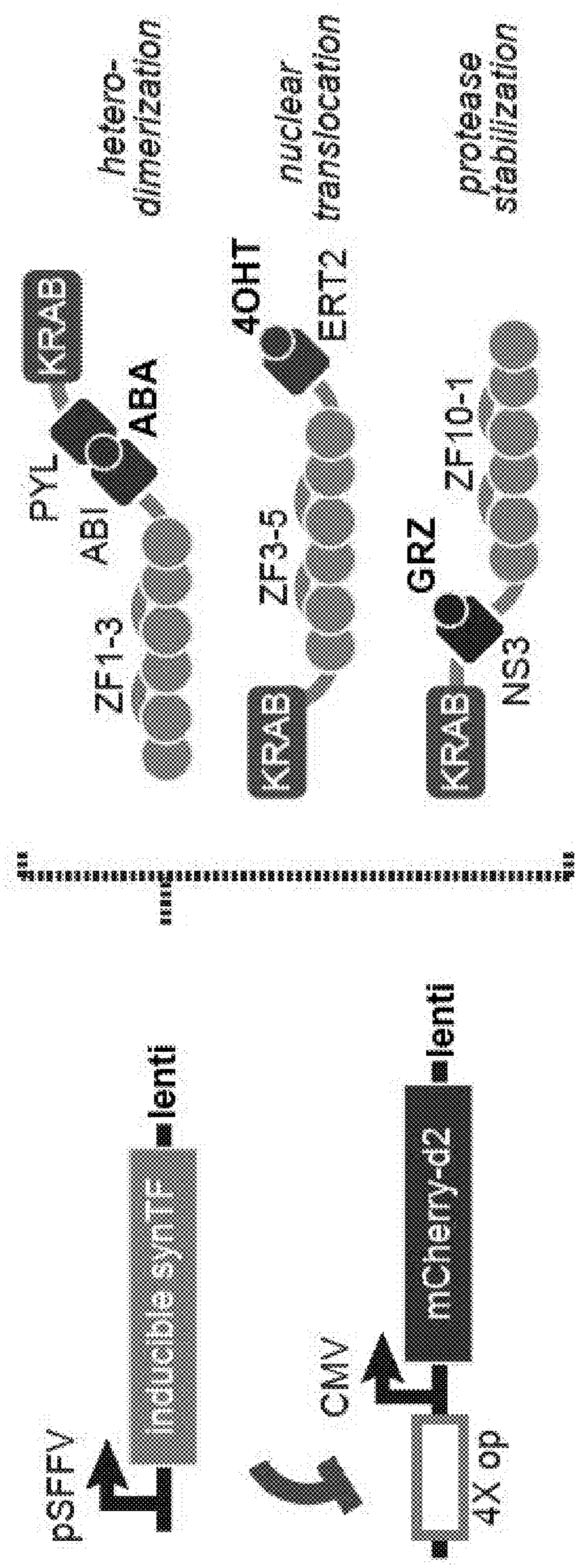
FIG. 11A-11B is a series of schematics and graphs showing inducible synthetic transcriptional repression of a fluorescent protein in human cell lines.
Figure 11B:
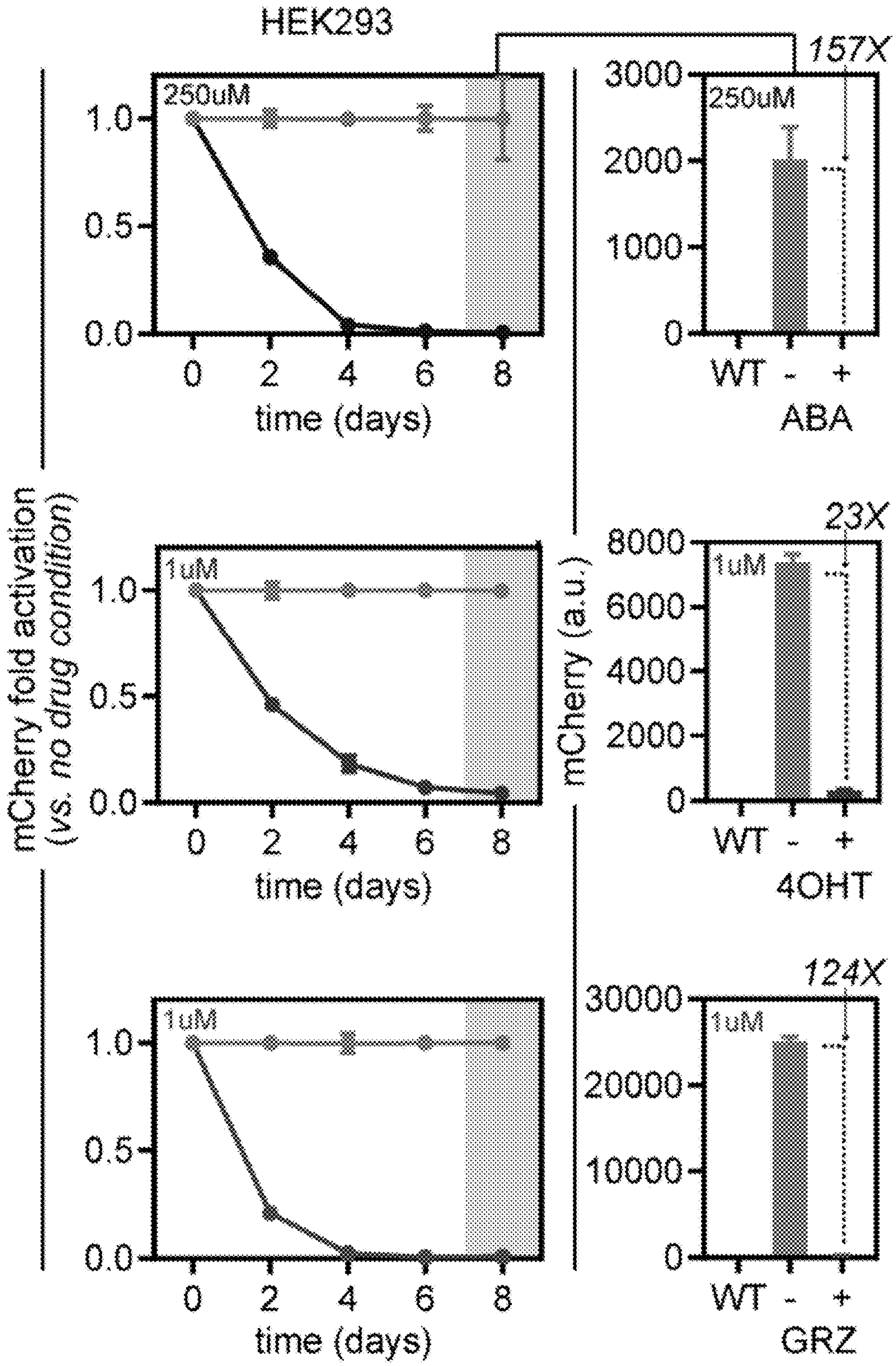

Inducible synthetic transcriptional repression of a fluorescent protein in human cell lines: Administration of a small molecule (ABA) led to temporal silencing of a fluorescent protein output from a ZF-responsive promoter in HEK293 cell lines. This decreased level of expression was compared to an untreated cell line which did not silence output expression (see e.g., FIG. 11B, top graph). Administration of a small molecule (4OHT) led to temporal silencing of a fluorescent protein output from a ZF-responsive promoter in HEK293 cell lines. This decreased level of expression was compared to an untreated cell line which does not silence output expression (see e.g., FIG. 11B, middle graph). Administration of a small molecule (GRZ) led to temporal silencing of a fluorescent protein output from a ZF-responsive promoter in HEK293 cell lines. This decreased level of expression was compared to an untreated cell line which does not silence output expression (see e.g., FIG. 11B, bottom graph).

Figure 12B:
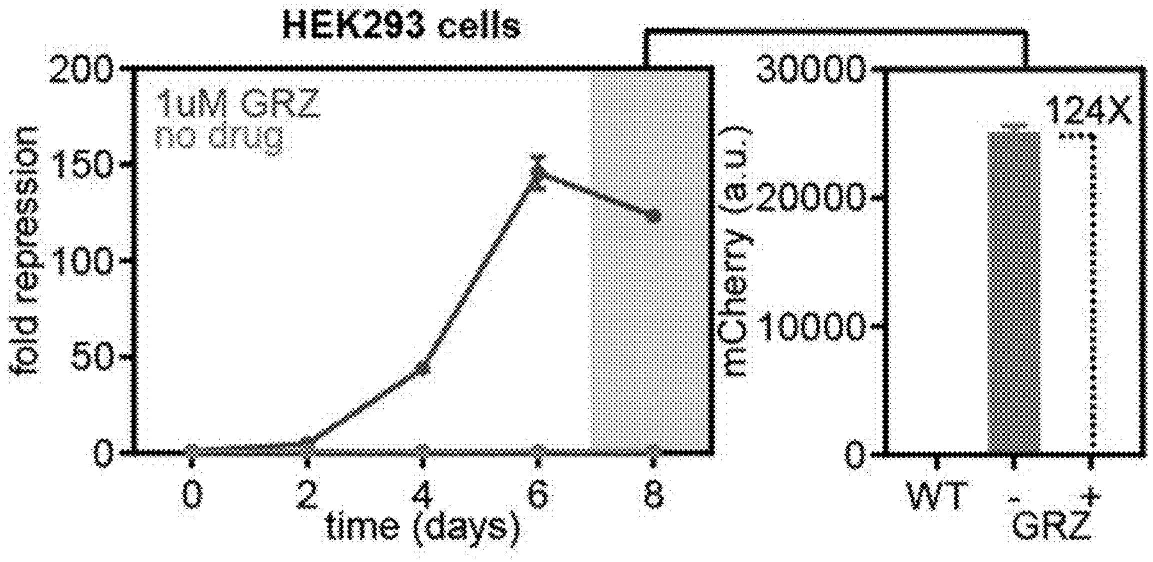
Figure 12C:
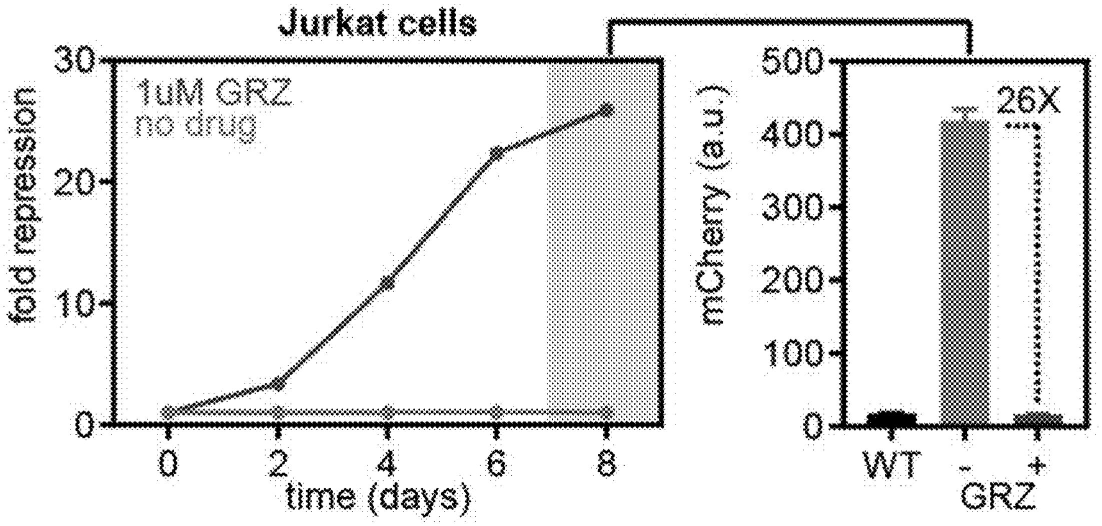
Figure 13A:
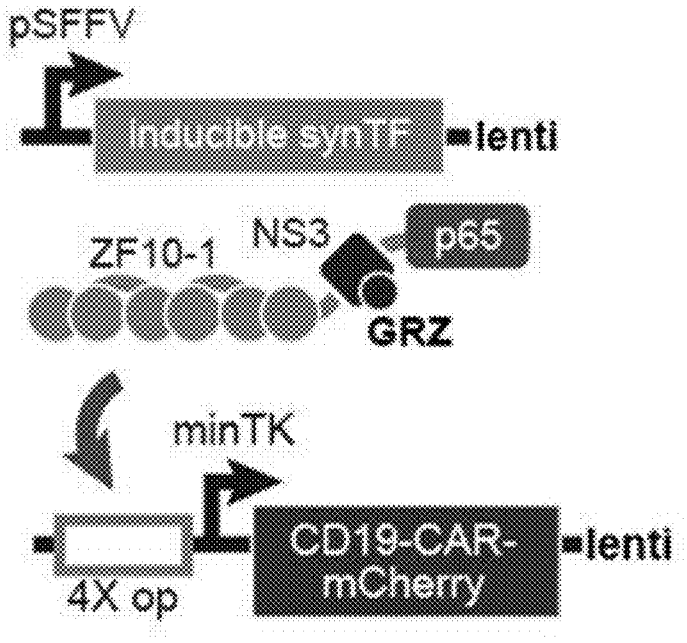
FIG. 13A-13D is a series of schematics and graphs showing that administration of a small molecule (grazoprevir) led to temporal activation of a fluorescently-tagged chimeric antigen receptor (CD19-CAR) protein from a ZF-responsive promoter in CD4+ primary human T cells.
Figure 13B:
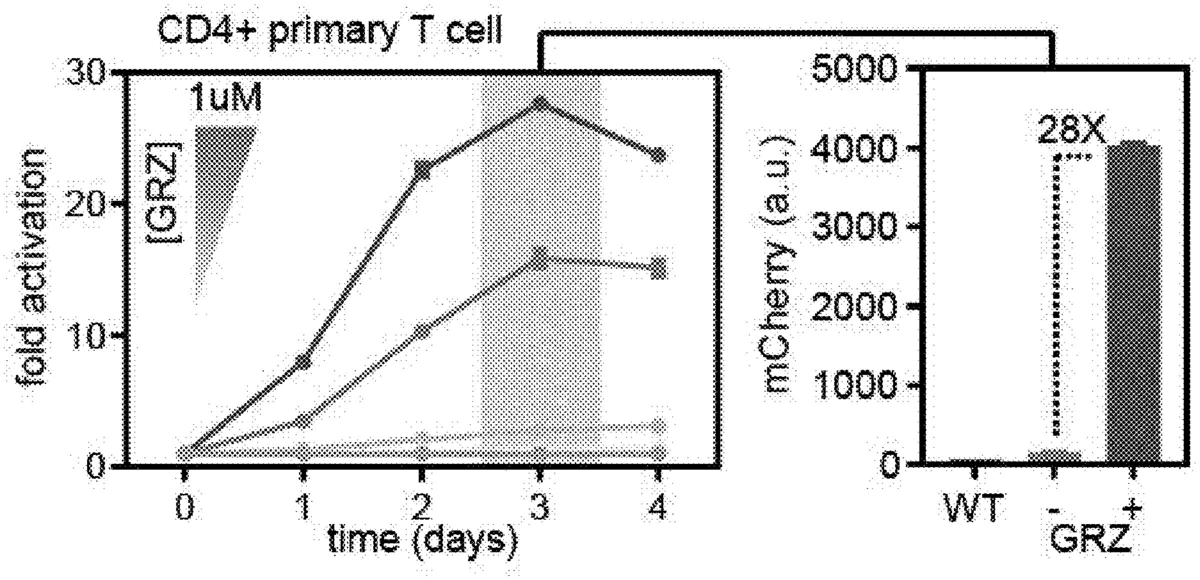
Figure 13C:
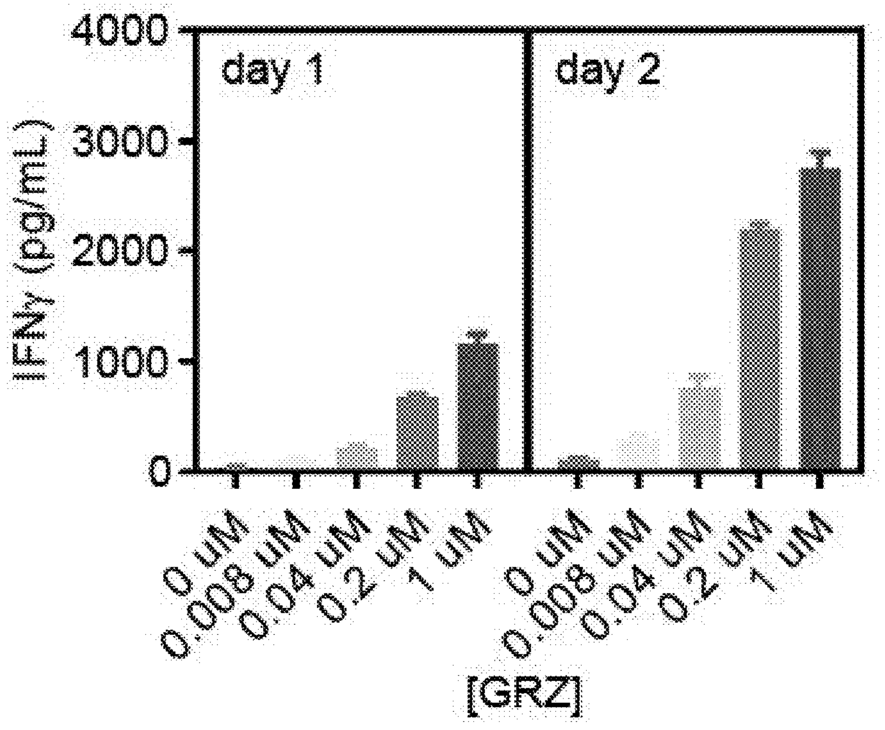
Figure 13D:
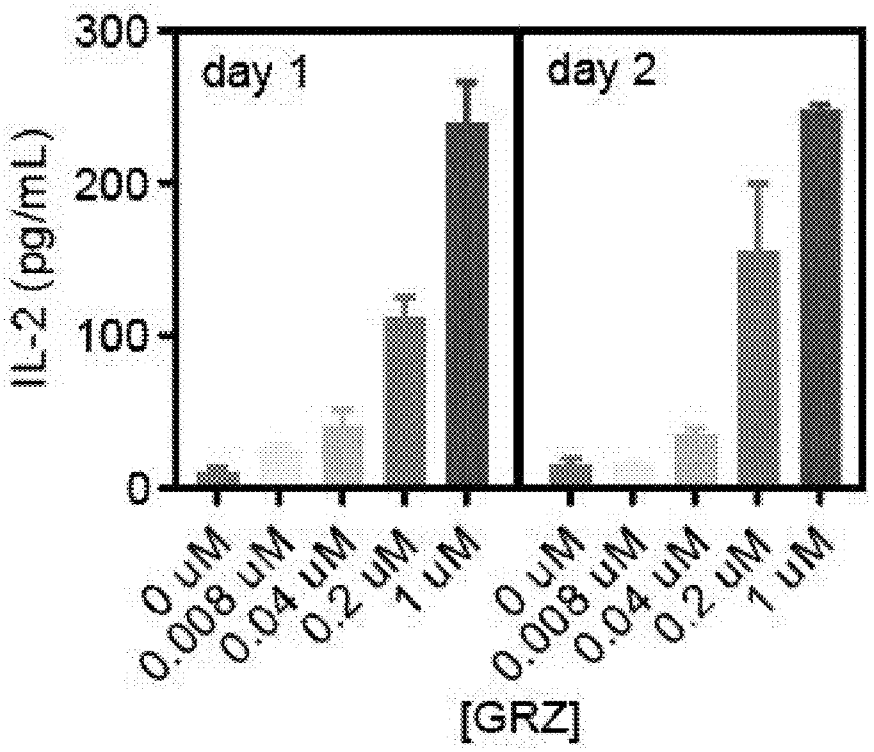

Inducible synthetic transcriptional repression of a fluorescent protein in human cell lines: Administration of a small molecule (grazoprevir) led to temporal silencing of a fluorescent protein output from a ZF-responsive promoter in HEK293 and Jurkat cell lines. This decreased level of expression was compared to an untreated cell line which did not silence output expression (see e.g., FIG. 12A-12C).

Inducible synthetic transcriptional activation of a Chimeric Antigen Receptor in primary human cells: Administration of a small molecule (grazoprevir) led to temporal activation of a fluorescently-tagged chimeric antigen receptor (CD19-CAR) protein from a ZF-responsive promoter in CD4+ primary human T cells. This enhanced level of expression was compared to an untreated cell line which did not activate output expression. Output fluorescence as a function of several different grazoprevir treatment concentrations is also indicated here. Subsequent co-culture of these primary cells with CD19 antigen-presenting target cells resulted in T-cell activation, measured by enhanced production of cytokines. This enhanced level of cytokine production was compared to an untreated cell line which did not activate cytokine expression. Cytokine production as a function of several different grazoprevir treatment concentrations is also indicated here (see e.g., FIG. 13A-13D).

Inducible synthetic transcriptional activation of a Chimeric Antigen Receptor (in dual-drug regulated context) in primary human cells: Administration of a small molecule (4OHT) led to expression and secretion of IL4 cytokine from a ZF-responsive promoter in CD4+ primary human T cells. This system was used in conjunction with another small molecule (grazoprevir) regulated activation of a fluorescently-tagged chimeric antigen receptor (CD19-CAR) protein from an orthogonal ZF-responsive promoter. The ERT2-synTF was only responsive to 4OHT and was unaffected by the presence of grazoprevir. Likewise, the NS3-synTF was only responsive to grazoprevir and was unaffected by the presence of 4OHT. (see e.g., FIG. 14A-14B).

Inducible synthetic transcriptional activation of a Cytokine in Jurkat human cell lines: Administration of a small molecule (grazoprevir) led to temporal activation of a cytokine (IL10) from a ZF-responsive promoter in Jurkat T cell lines. This enhanced level of expression was compared to an untreated cell line which did not activate output expression. This inducible activation can be achieved through the delivery of separate lentiviral cassettes for NS3-synTF expression and IL10 production ("double lentiviral vector"), or through the delivery of a single lentiviral cassette expressing the NS3-synTF as well as regulating IL10 production (see e.g., FIG. 15A-15C).

Figure 16A:
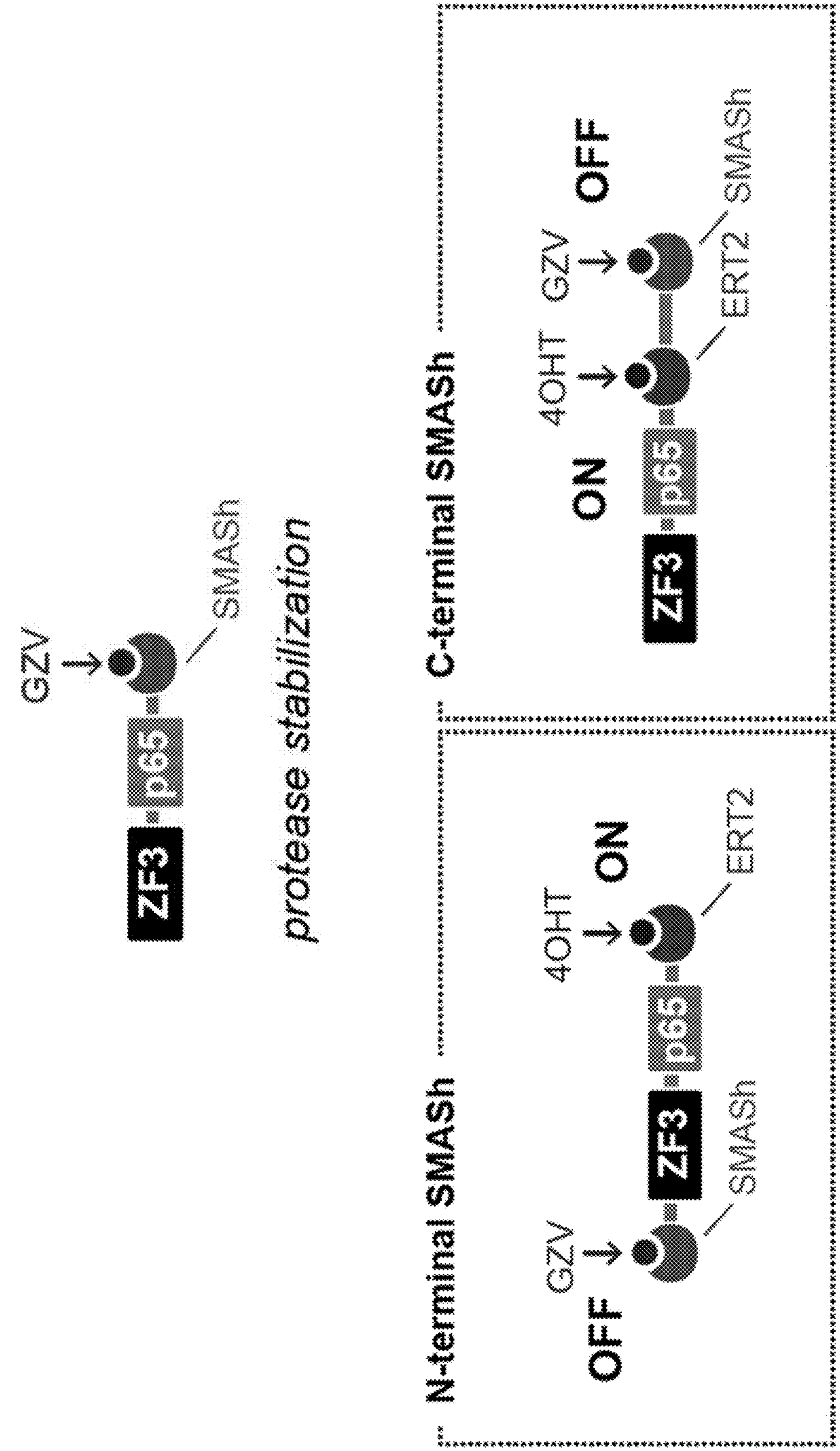
FIG. 16A-16B is a series of schematics and graphs showing inducible synthetic transcriptional activation and tunable deactivation of a fluorescent protein in human cell lines using a cytosolic sequestering and induced degradation synTF comprising ERT2 and SMASh domains, respectively.
Figure 16B:
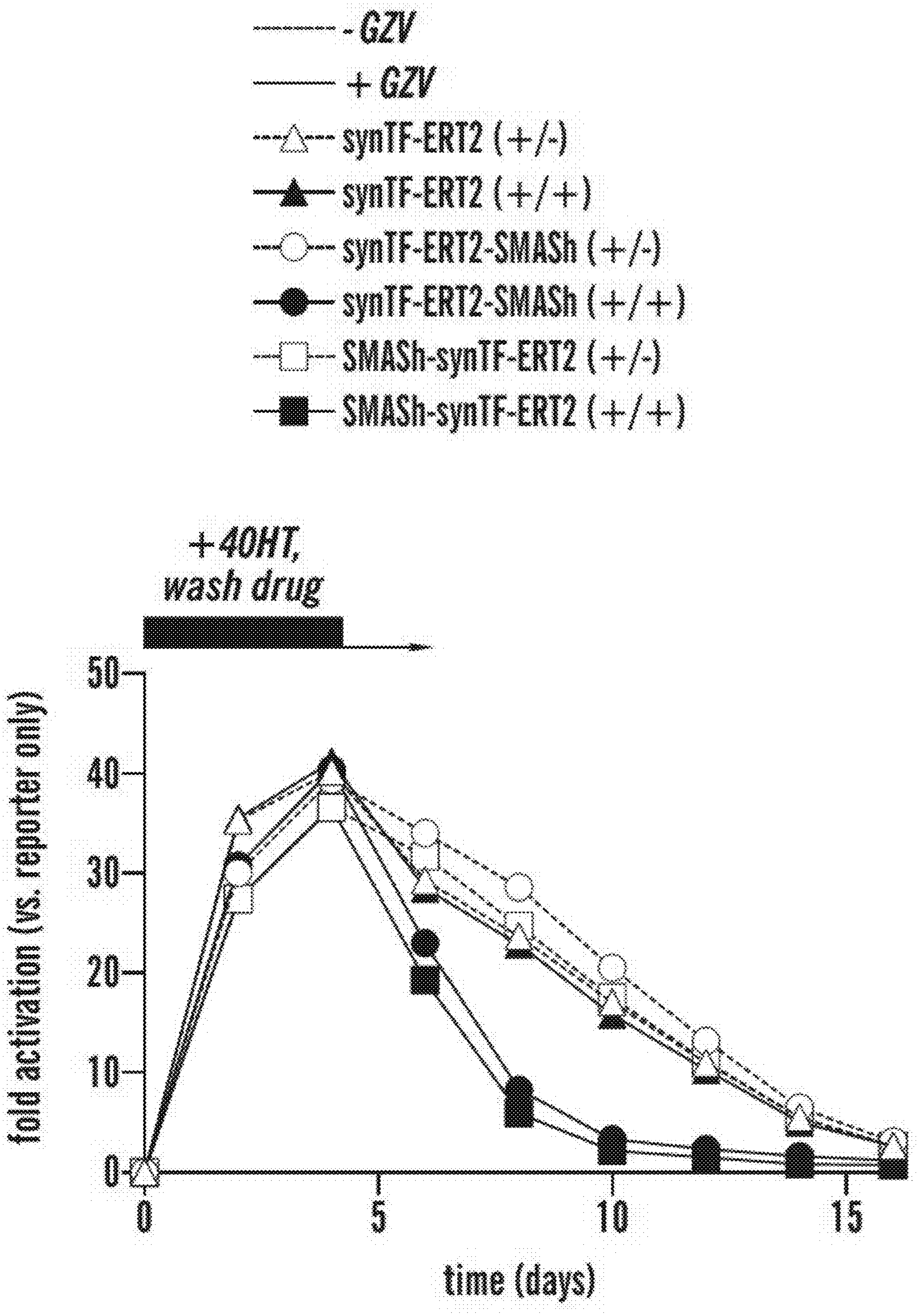

Inducible synthetic transcriptional activation and tunable deactivation of a fluorescent protein in human cell lines using ERT2 and SMASh domains: Three Jurkat T cell lines were tested: (1) ZF-p65-ERT2 (no SMASh, see e.g., FIG. 4); (2) ZF-p65-ERT2-SMASh (C-terminal SMASh); and (3) SMASh-ZF-p65-ERT2 (N-terminal SMASh) (see e.g., FIG. 16A). Administration of an ERT2-responsive small molecule (4OHT) for 4 days led to temporal activation of a fluorescent protein from a ZF-responsive promoter in all cell lines. Subsequent removal of a small molecule (4OHT) from days 6-16 led to temporal deactivation of the fluorescent protein in all cell lines. Absence of a SMASh-responsive small molecule (grazoprevir) for 12 days led to equivalent, slow deactivation of the reporter to baseline levels. Administration of a SMASh-responsive small molecule (grazoprevir) for 12 days leads to fast deactivation of the reporter to the baseline levels. This rapid deactivation of the reporter was compared to the condition lacking the SMASh domain, which led to equivalent slow deactivation as in the "absence of grazoprevir" condition (see e.g., FIG. 16B).

Figure 17:
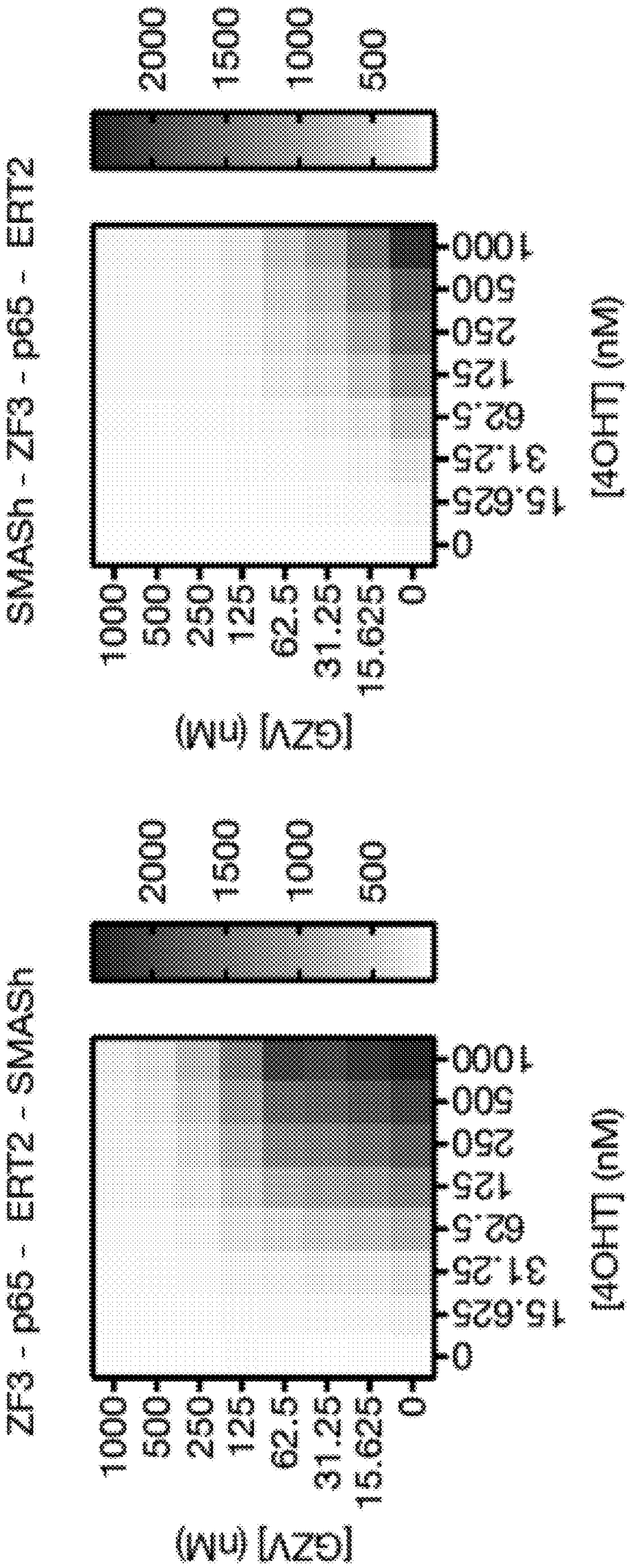
FIG. 17 is a series of heat maps showing tunable synthetic transcriptional activation of a fluorescent protein in human cell lines using ERT2 and SMASh domains with C-terminal SMASh synTF (left heat map) and N-terminal SMASh synTF (right heat map).

Tunable synthetic transcriptional activation of a fluorescent protein in human cell lines using ERT2 and SMASh domains: Two Jurkat T cell lines were tested: (1) ZF-p65-ERT2-SMASh (C-terminal SMASh) and (2) SMASh-ZF-p65-ERT2 (N-terminal SMASh). Co-administration of varying amounts of an ERT2-responsive small molecule (4OHT) and SMASh-responsive small molecule (GZV) for 4 days led to varying levels of temporal activation of a fluorescent protein from a ZF-responsive promoter. Absence or minimal 4OHT in all conditions led to little-to-no activation. Presence or near-maximal led in all conditions led to little-to-no activation. Presence of 4OHT AND absence of GZV leads to maximal activation. C-terminal and N-terminal SMASh variants exhibited differential sensitivities to GZV concentration (see e.g., FIG. 17).

Figure 18:
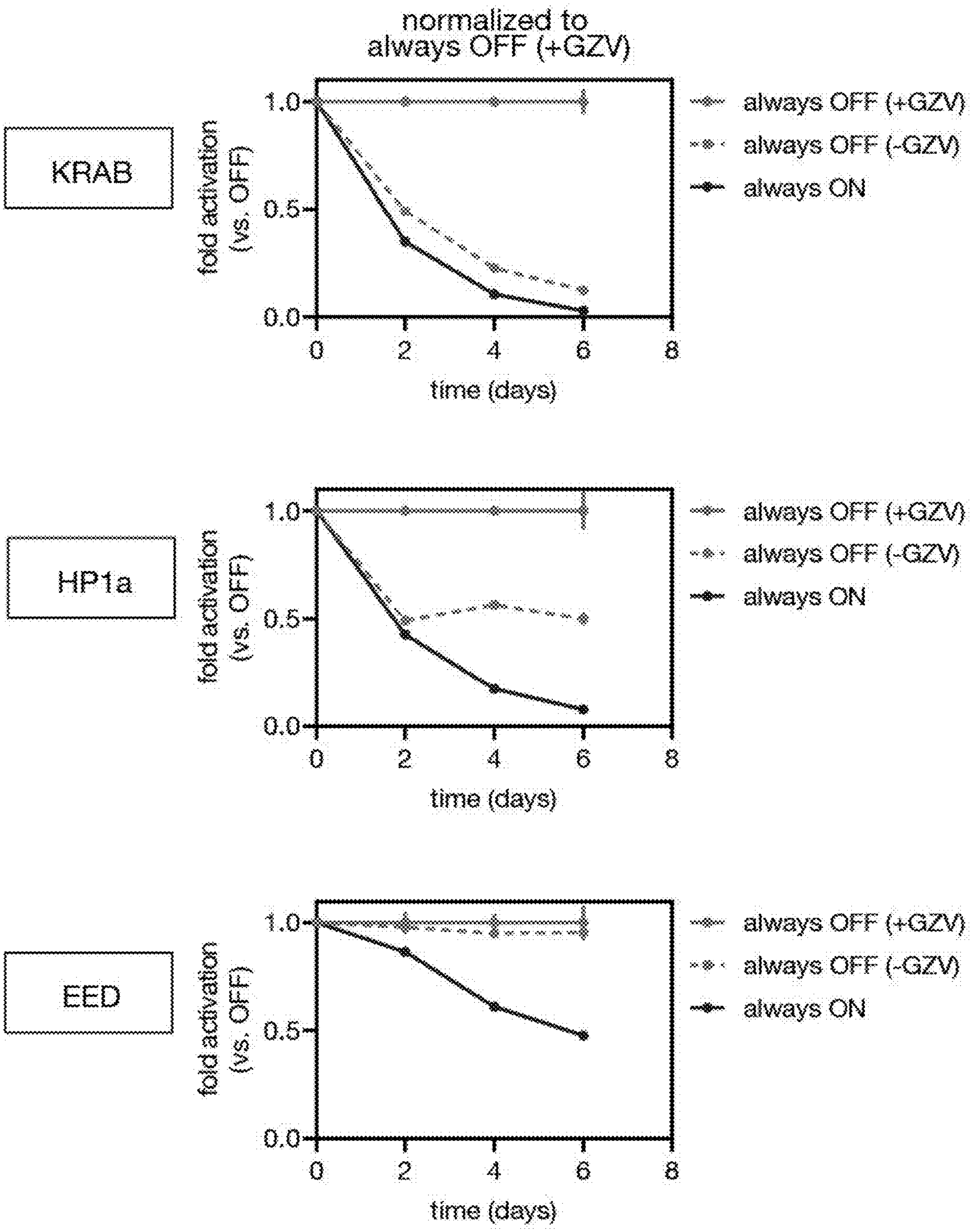
FIG. 18 is a series of line graphs showing inducible synthetic transcriptional repression of a fluorescent protein in human cell lines using KRAB-ZF-ERT2-SMASh (top graph), HP1a-ZF-ERT2-SMASh (middle graph), and EED-ZF-ERT2-SMASh (bottom graph). "Always OFF (+GZV)" indicates the presence of grazoprevir and the absence of 4OHT. "Always OFF (−GZV)" indicates the absence of both grazoprevir and 4OHT. "Always ON" indicates the absence of grazoprevir and the presence of 4OHT.

Inducible synthetic transcriptional repression of a fluorescent protein in human cell lines using ERT2 & SMASh domains: Three Jurkat T cell lines were tested: (1) KRAB-ZF-ERT2-SMASh; (2) HP1a-ZF-ERT2-SMASh; and (3) EED-ZF-ERT2-SMASh. Administration of an ERT2-responsive small molecule (4OHT) for 6 days led to temporal repression of a fluorescent protein from a ZF-responsive promoter in all cell lines. Absence of a SMASh-responsive small molecule (GZV) in the negative control led to significant "leaky" repression in the absence of 4OHT (see e.g., FIG. 18).

Example 2: Mammalian-Optimized, Cooperatively Self-Assembling Synthetic Transcription Factors (synTFs) and Drug-Inducible Controllers of Mammalian Gene Expression Cells activate precise gene expression programs in response to multifactorial chemical and biological stimuli. The purposeful manipulation of this process is a principal goal of synthetic biology, and its application to human cells can lead to breakthroughs in the understanding of human biology and in the development of next-generation diagnostics and therapeutics that respond in sophisticated ways to disease. Indeed, diverse applications, from basic studies of oncoproteins to cell reprogramming to cell therapy development, demand precise and tunable control of gene expression outputs in response to input signals. Unfortunately, tools to artificially control gene expression in mammalian cells have significant limitations, greatly constraining the ability to study fundamental biological processes and engineer designer cell-based therapies. The most widely-used tools are older generation technology, derived from bacterial transcriptional systems; these impose restrictions on the number of genes that can be simultaneously controlled, are not tunable, and cannot flexibly integrate new input signals. As a consequence, researchers are unable to create sophisticated gene expression controllers that can flexibly sense and integrate biochemical signals (e.g. ligands, chemical inducers, morphogenetic cues), and correspondingly produce tunable activation profiles. Among the many biomedical applications that would be transformed by these precision gene expression controllers in mammalian cells is the development of cell-based therapeutics for cancer, autoimmunity, and regenerative medicine, which can suffer from issues related to over-activation and tissue specificity.

Described herein are compositions, methods, and systems for controlling gene expression control in mammalian cells. Described herein is an expansion of the "signal processing" capacity of designer human cells to enhance their specificity, control, and activity for desired biomedical applications. Without wishing to be bound by theory, the central hypothesis is that this expanded signal processing can be achieved using cooperative, combinatorial transcriptional regulation schemes, in lieu of current gene expression systems that are based on "simple", one-to-one regulation. Such a hypothesis is based on the observation that in metazoa, signals are processed and integrated using large, multivalent transcription factor (TF) complexes that cooperatively assemble to activate gene expression.

Described herein is an information-processing module for mammalian gene expression control. Functionality is demonstrated in human primary immune cells because of the fundamental role that they play in human physiology and their use in cellular immunotherapy. Described herein are inducible controllers regulated by orthogonal, FDA-approved drugs. The controllers are expressed by standard viral vectors, and they are demonstrated to drive regulated expression of reporters or gene products (synTFs and cytokines) of therapeutic importance for autoimmunity and cancer. Accordingly, described herein are mammalian-optimized, cooperatively self-assembling synthetic transcription factors (synTFs) and drug-inducible controllers of mammalian gene expression.

Such drug-inducible controllers permit precision gene expression control across mammalian systems. In addition to expanding the sense-and-response capabilities of engineered human cells for improving cellular therapies, such controllers are broadly useful for basic biomedical research. This includes permitting drug-inducible, temporal control over multiple gene products simultaneously (e.g. oncoproteins or reprogramming factors).

Gene Expression Control Systems: Promise and Limitations.

The purposeful manipulation of information flow in living systems is the ultimate goal of synthetic biology, and its application to human cells can lead to breakthroughs in the understanding of human biology and in the development of next-generation diagnostics and therapeutics. In particular, gene expression technologies have played a vital role in regulating such information flow in cells for a wide range of applications. For example, the developmental process to form organoids is genomically encoded in stem cells in the form of gene regulatory networks (GRNs). Manipulation of GRNs through gene expression control circuits has proven to be fruitful in programming and guiding morphogenesis in vitro. In animal model development, tissue-specific and small molecule inducible promoters are often used to achieve organ-specific and temporal control of gene expression. Furthermore, the c-fos promoter has been used to functionally label activated neurons in mice and control the expression of an optogenetic channel rhodopsin protein to artificially recall fear memory with light stimulation. Finally, ectopic overexpression of chimeric antigen receptors (CARs), fusions of an antigen-specific scFv and T cell signaling domains, in human T cells can redirect their specificity toward cancer, with high efficacy against acute lymphoblastic leukemia (ALL) in recent clinical trials.

While current gene expression technologies have led to fundamental and therapeutic breakthroughs, their shortcomings are also abundant. For instance, the inefficiency of cell reprogramming from induced pluripotent stem cells is often attributed to key proteins and transcription factors not being expressed at the right concentrations and times. Also, the c-fos promoter is known to have variable activity in different neurons, rendering it unusable in many applications. Furthermore, many off-target effects have been documented for tissue-specific promoters, thus confounding data interpretation. Lastly, while promising, cellular immunotherapy has also shown (fatal) adverse side effects often due to a combination of issues related to cell specificity, over-activation, and unexpected interactions with the native immune system and tissue microenvironments.

Cumulatively, the aforementioned issues are the result of fundamental limitations in current gene expression control systems, which has restricted researchers' abilities to engineer sophisticated "signal processing" into mammalian cells. First, the number of transcriptional control systems in use is small, exacerbated by the existence of one well-developed and widely-used chemically inducible gene expression system (TetR-based tTa). This means that researchers can only reliably conditionally induce one gene product at a time in mammalian cells. Second, the systems are virtually all derivatives of canonical microbial transcriptional systems (e.g. TetR). While highly active, these systems have fixed response profiles, and strategies for predictively reshaping their activation profiles to precisely tune how a therapeutic protein is produced are non-trivial. Thus, whether designing cell-autonomous or exogenously inducible controllers, current tools cannot flexibly integrate novel input signals and produce customized transcriptional programs (outputs) for desired applications.

Described herein is a powerful information-processing module for mammalian gene expression control. The synTF framework is compatible for human cell engineering applications: it is composed of small, entirely human-derived protein domains that are highly tunable and is easily delivered using established viral vectors. Functionality is demonstrated in human primary immune cells because of their importance to human physiology and their use in cellular immunotherapy. To showcase its flexibility and generalizability, this core system is used as the basis of constructing different types of useful gene expression controllers in engineered immune cells, such as inducible controllers that are exogenously controlled by administration of orthogonal, FDA-approved drugs. These controllers are linked to the production of therapeutic genes (synTFs and cytokines), thereby informing applications of the controllers to enhance signal processing features (increased specificity, control and activity) of next-generation cellular therapeutics for cancer, autoimmunity and regenerative medicine.

Key innovations include a new class of synthetic TF systems specifically optimized for mammalian cell regulation, with the following characteristics: human-derived components, compact genetic payloads for facile delivery using established viral vectors, modular domains with tunable molecular properties, and specific regulation that is orthogonal to the native transcriptome. Also described herein is a set of new and orthogonal drug-inducible gene expression systems for mammalian cells, demonstrated to allow tunable control of synTF and cytokine production in human primary immune cells.

Current tools for controlling gene expression in mammalian cells are severely limited. Creating new precision gene expression controllers in human cells requires development of transcriptional systems (1) with an expanded set of orthogonal DNA-binding moieties, (2) that are responsive to safe deliverable chemicals beyond tetracycline antibiotics, and (3) that permit highly tunable activation/response profiles. Described herein is the characterization a new class of "mammalian-optimized" synthetic TF (synTF) systems that fulfill these requirements. These synTFs are used in drug-inducible controllers to tune activation profiles of therapeutic gene products in human primary immune cells.

Generation and Characterization of Mammalian synTFs Based on Orthogonal Zinc Finger Arrays Mammalian synTFs were developed for precise, effective, and orthogonal transcriptional control in human cells. The synTFs are based on artificial C2H2 zinc finger (ZF) arrays. ZFs are the most common DNA recognition motifs amongst natural human (and all eukaryotic) TFs. ZFs offer four key advantages as a basis for engineering artificial transcription control systems in human cells: (1) They are human-derived (unlike TALEs or CRISPR/Cas9) and thus less likely to elicit undesired immune responses. Indeed, older-generation ZF systems were shown to be clinically viable strategies for achieving long-term regulation of a therapeutic gene product in primates. (2) Unlike their bulkier counterparts (e.g. CRISPR/Cas9), ZF proteins are small (~30-AA domain binds 3 bp of DNA), permitting compact genetic payload designs that are easily packaged and delivered using common viral vectors. (3) As described below, ZF-based synTFs have a modular design with highly tunable molecular properties. (4) ZF arrays with customized DNA-binding specificities can be engineered to generate diverse synTF-DBM specificities. ZF-based synthetic transcriptional regulators that target genome-orthogonal DBMs have yet to be developed for mammalian engineering applications.

Generation and Evaluation of a Library of Mammalian, Orthogonal synTFs

Described herein is a workflow for creating 6-unit ZF arrays that target defined 20-bp DBMs, a length that in principle provides unique addressability in the human genome. The workflow leverages modular assembly and functional selection of 6-unit arrays from of 2-unit building blocks. Using this approach, a library of eleven 6-unit arrays was created with binding specificities chosen to maximize orthogonality to the human genome (see e.g., US Patent Publication US20180057838, the content of which is incorporated herein by reference in its entirety). We fused these arrays to human transcriptional effector domains (p65 activation domain, KRAB/HP1a silencing domains) to create humanized minimal synTFs (see e.g., FIG. 1A). To test their activity, corresponding HEK293FT reporter lines were generated harboring synTF-responsive reporter constructs, composed of 4 tandem 20-bp DBMs upstream of a minimal promoter driving transcription of a fluorescent protein (see e.g., FIG. 1B). Transduction of reporter cells with each synTF expression construct revealed strong activation of their corresponding reporters (see e.g., FIG. 1C), but did not activate non-cognate reporters (see e.g., FIG. 1D). Next, RNA-seq measurements were used to map the impact of the synTFs on genome-wide transcription. synTF regulation profiles were highly specific, showing minimal effects on native transcript profiles (see e.g., FIG. 1E-1G). Importantly synTF transcriptome profiles compared favorably with classic Gal4 and TetR-based systems, with some synTFs demonstrating superior specificity based on differential regulation analysis (see e.g., FIG. 1H). A rigorous framework was used to perform this analysis, including assessing profiles against 3 independent biological references. Together, these data demonstrate that the 6-unit ZF arrays can be used to engineer synTFs that are specific and effective regulators of mammalian gene expression. These experiments also establish a pipeline for creating and evaluating synTFs. Further supporting the rigor of the tool development is that one of these ZF synTFs was used to permit robust and specific epigenetic regulation in mammalian cells (see e.g., Park et al. Cell 176, 227-238 e220, (2019)).

Generation of synTF Affinity Variants as "Parts" for Design of Gene Expression Controllers Two orthogonal synTFs from the library (ZF1 and ZF10) that show exceptionally high in vivo activity and transcriptomic specificity were selected for further development. synTF/DBM affinity ($K_t$) variants for these synTFs were generated. Affinity variants serve multiple purposes. First, modulating synTF binding affinity is a useful strategy for tuning transcriptional output levels. To populate the mammalian "parts" toolkit, affinity series of ~10 variants were generated for each synTF (see e.g., Tables 10-12, SEQ ID NOs: 122-180, 192).

A combination of three strategies were used to generate ZF-DBM affinity variants spanning low nM-mid μM: (1) Alanine mutation of conserved arginine residues in the ZF (outside of the DNA recognition helix) that mediate DNA phosphate backbone interactions. (2) Truncation of full-length 6-unit ZF arrays to 4-unit subarrays. (3) Nucleotides mutations both within and directly flanking the core DBM. The activity of these variants can be evaluated using the above-described in vivo reporter assay. Subsequently, affinities can be directly measured using in vitro binding assays. Briefly, ZF-MBP fusion proteins are purified for each variant. Fluorescence anisotropy (FA) binding measurements are conducted, performing a competitive titration of DBM species against a pre-bound FITC-labeled oligo probe harboring a single WT DBM. Binding curves can be obtained for the full set of DBM variants, and $K_t$ values are extracted by fitting the data to a quadratic binding equation. The outcome of this work is a set of mammalian synTF "parts" (with measured DBM-binding affinities) that can be used to design gene expression controllers.

Development of Drug-Inducible synTF Controllers and Testing of their Ability to Temporally Control synTF and Cytokine Outputs in Human Primary Immune Cells Described herein are inducible gene expression controllers responsive to orthogonal FDA-approved drugs, offering the ability to multiplex gene expression and permit temporal expression control over desired proteins in mammalian cells. Controllers were engineered by fusing synTFs with ligand responsive domains and their performance were evaluated in human T cells (e.g., primary T cell lines and Jurkat T cell line), which were chosen based on their established importance to human physiology and translational research. Precise control of gene expression in human T cells remains challenging, especially in primary T cells. Thus, establishing these systems in these cells provides a basis for applying them in other challenging cell types. The inducible systems were used to control anti-Her2 synTF and IL-12 expression. Anti-Her2 synTF T cells have shown promise in treating sarcoma in clinical trials, but can have devastating on-target-off-tumor side effects. Similarly, IL-12 has potent anti-tumor activity, but is complicated by dose-limiting toxicity. Therefore, regulated expression of anti-Her2 and IL-12 can improve their safety profile.

Figure 9A:
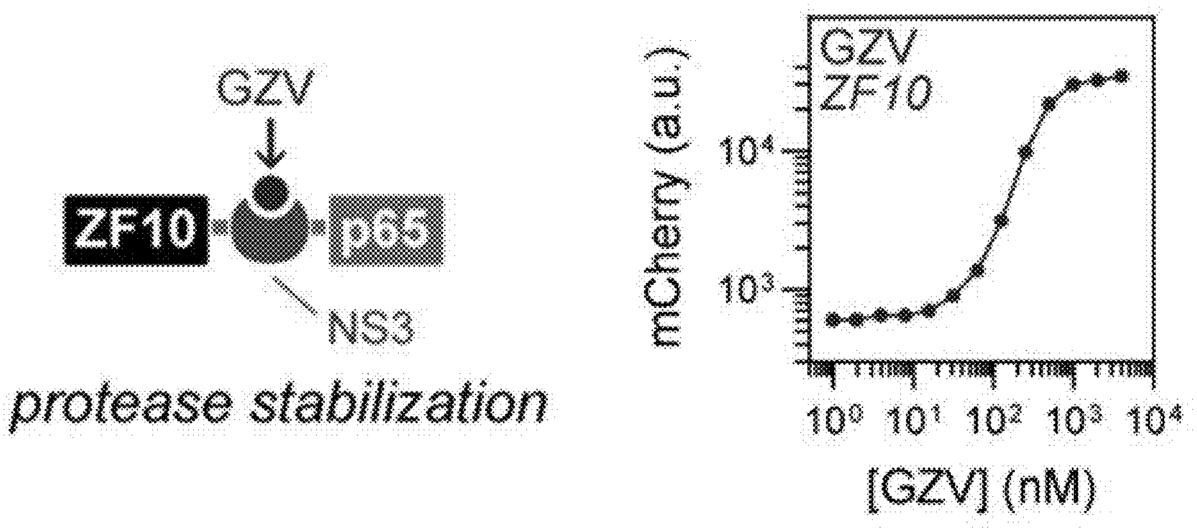
FIG. 9A-9C is a series of schematics of an exemplary repressible protease synTF, with NS3 as the protease, and graphs showing that administration of a small molecule (grazoprevir) led to temporal activation of a fluorescent protein output from a ZF-responsive promoter in Jurkat cell lines.
Figure 9B:
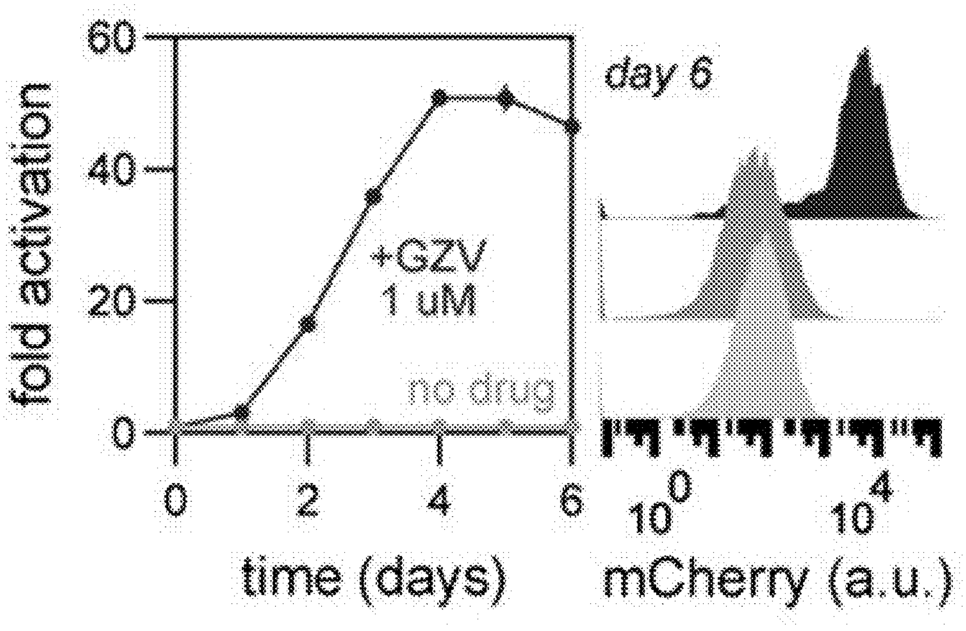
Figure 9C:
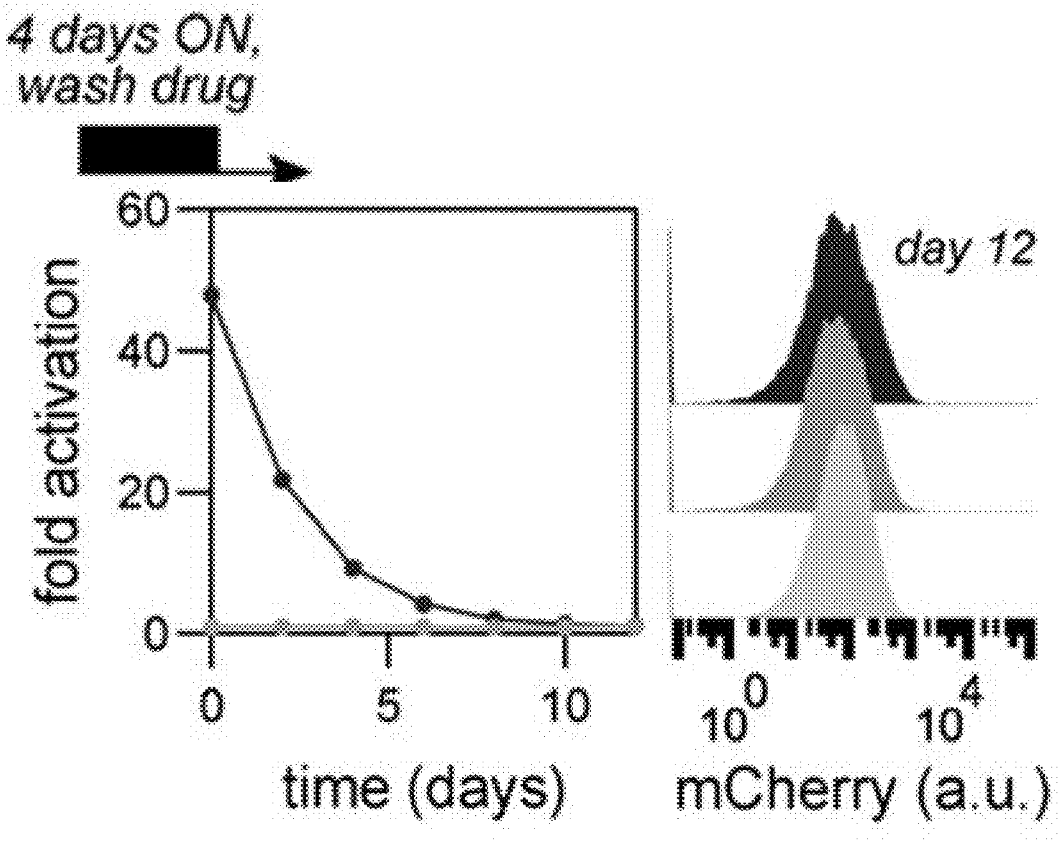
Figure 10A:
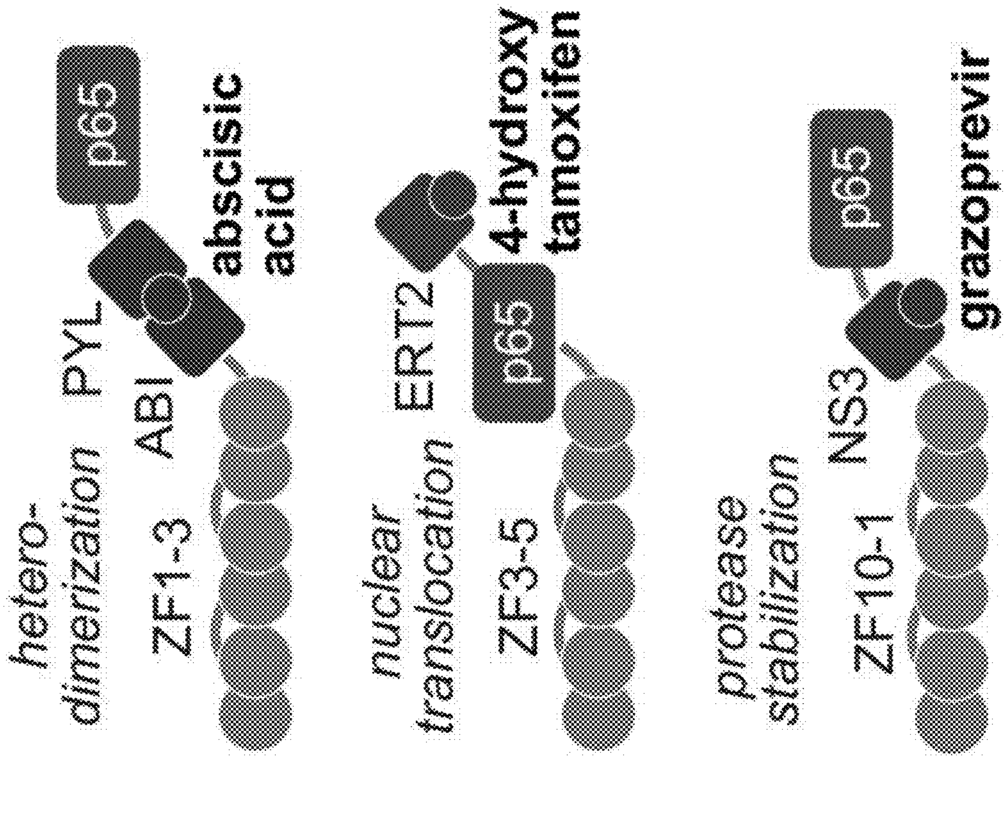
FIG. 10A-10D is a series of schematics showing exemplary synTFs and graphs showing that administration of a small molecule (e.g., ABA, 4OHT, or grazoprevir) led to temporal activation of a fluorescent protein output from a ZF-responsive promoter in both HEK293 and Jurkat cell lines.
Figure 10B:
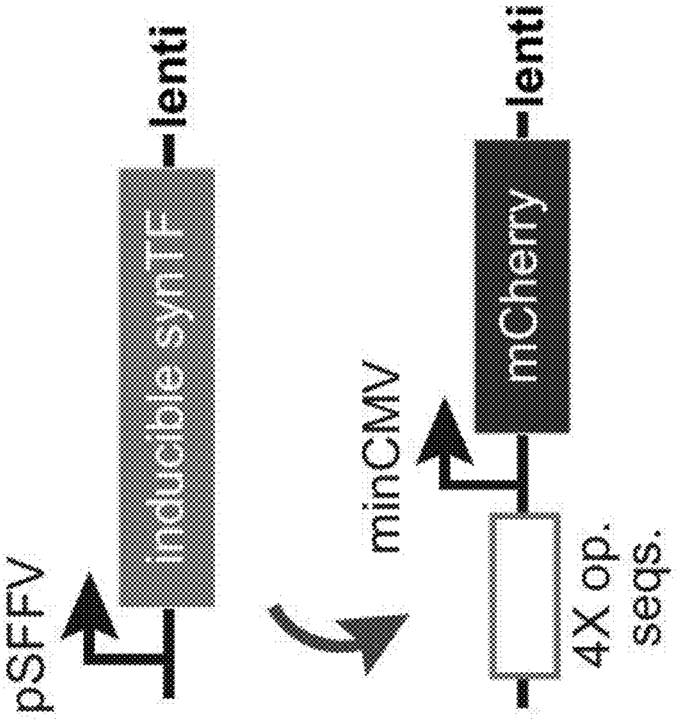
Figure 10C:
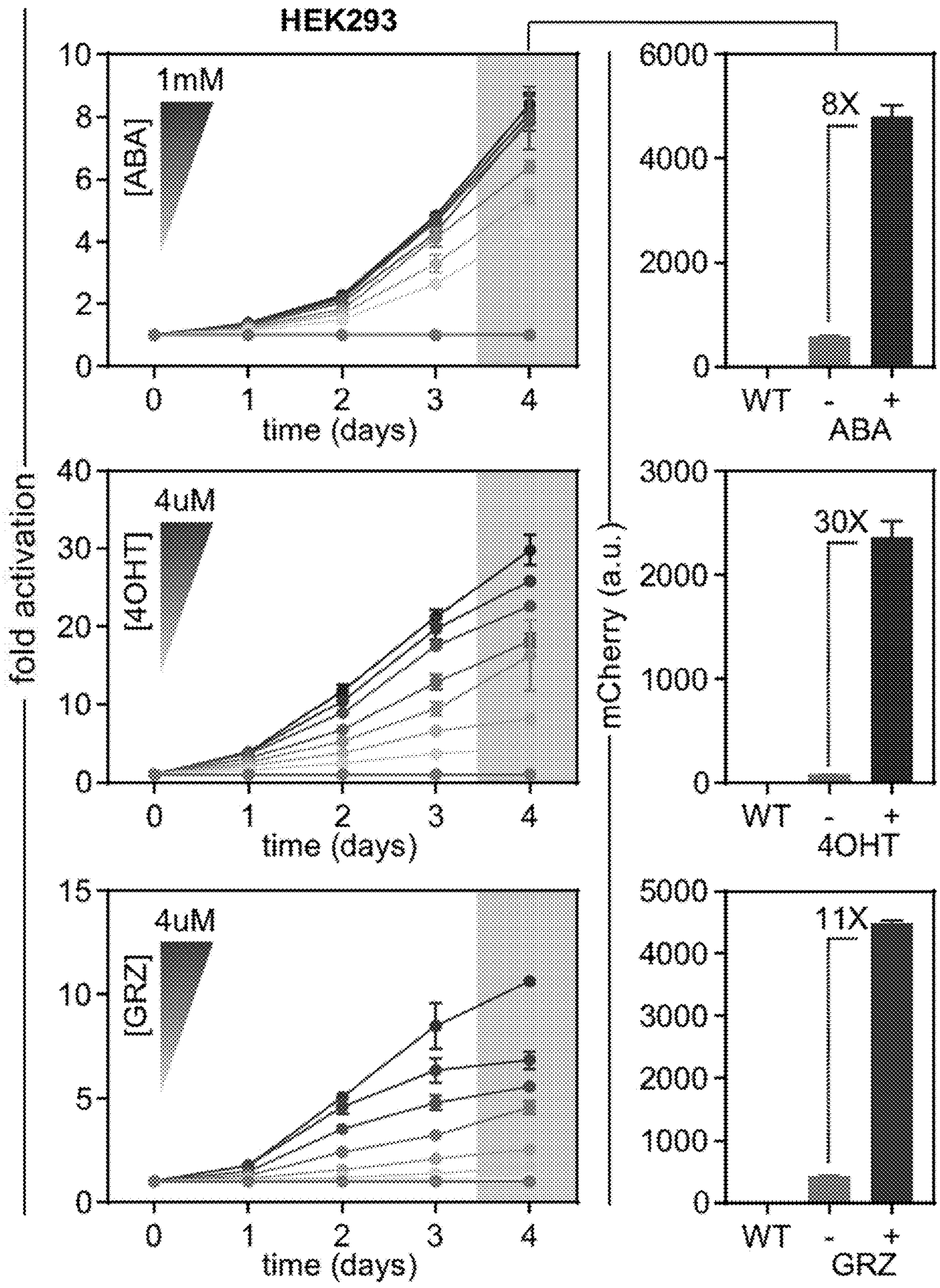
Figure 10D:
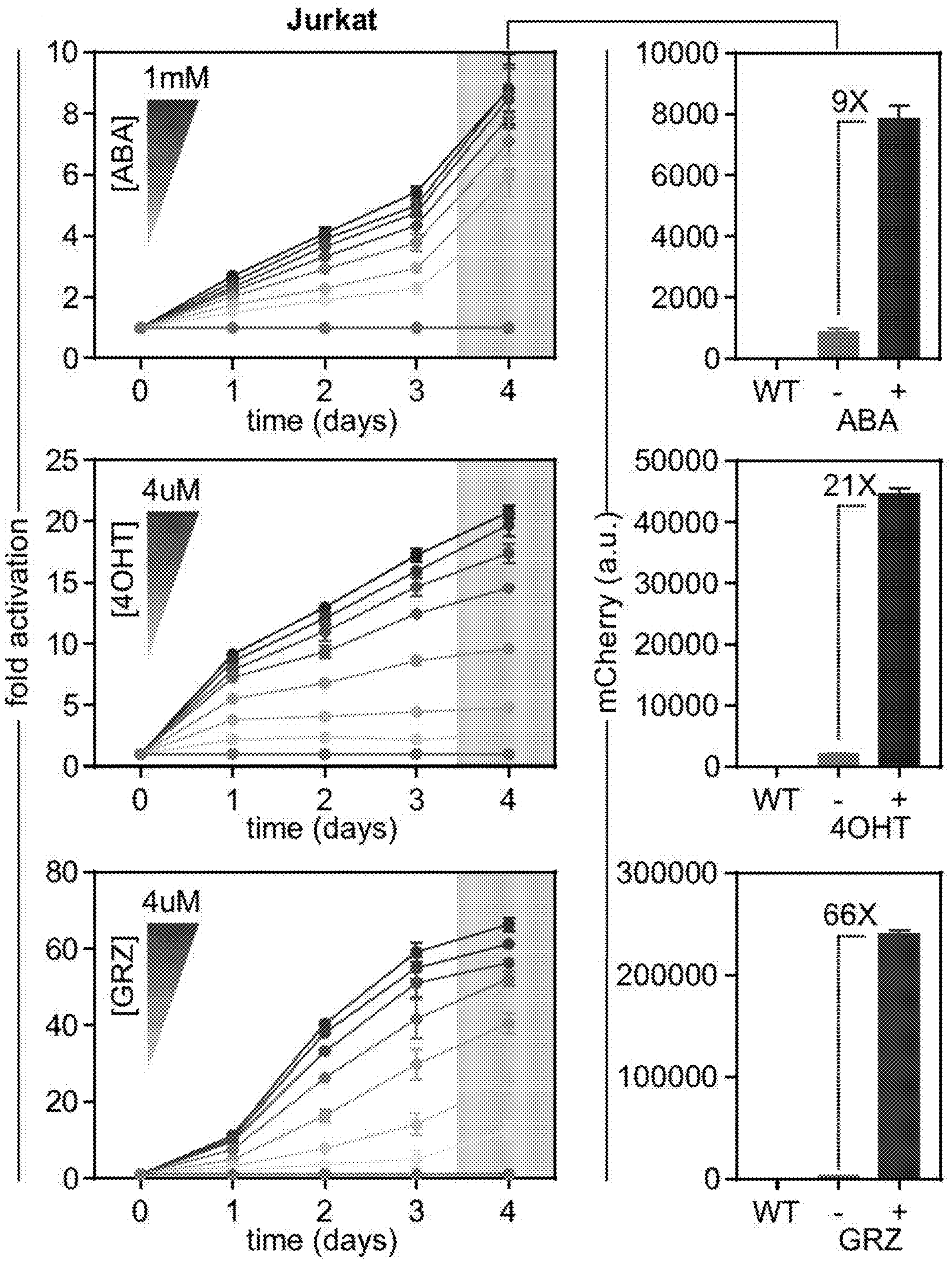

Drug-Inducible synTFs Enable Regulated Expression Control of Therapeutic Gene Products in Primary Human Immune Cells To obtain control over synTF activity, a non-structural protein (NS3) domain was fused to a synTF (see e.g., FIG. 9A-9B). NS3 is a self-cleaving protease that originates from the hepatitis C virus (HCV), and has been used as a degradation tag for controlling protein expression. In the absence of drug, NS3 cleaves the p65 activation domain away from the ZF domain, preventing gene transcription. When the cell-permeable FDA-approved inhibitor Grazoprevir (GZV) is present, NS3 protease activity is blocked, leaving the synTF intact. The NS3 system was chosen, in part, because of the exceptional safety profile of GZF, which is commonly taken at a high dose (e.g., 100 mg/day) for up to 12 weeks. Compact, GZV-inducible synTF controllers can be packaged into a single lentivirus. This permits regulated expression control of therapeutically-relevant transgenes in human immune cells (e.g. IL-10 controller; see e.g., FIG. 15A-15C), or dose- and time-dependent expression control of a CD19 CAR that functions in CD4+ primary human T cells (see e.g., FIG. 13A-13D). These studies demonstrate of the utility of drug-inducible synTF controllers for modulating mammalian gene expression.

Development and Evaluation of Orthogonal Drug-Inducible Gene Expression Controllers System Design: Developing synTF controllers that are responsive to orthogonal FDA-approved drugs offers the ability to multiplex gene expression control. Described herein are engineered controllers that are regulated by: (1) 4-Hydroxytamoxifen (4OHT), a metabolite of the FDA-approved breast cancer drug tamoxifen that selectively modulates the activity of molecules fused to estrogen receptor variants (such as $ER^{T2}$), and (2) GZV (as described above). 4OHT- and GZV-inducible systems were generated by fusing the ligand binding domains to two orthogonal synTFs. Human p65 was used as the activation domain, and expression of the synTF was controlled by a constitutive promoter (e.g., EF1-a). The inducible synTF was placed in the same pHR lentiviral vector as the corresponding synTF-responsive promoter driving a gene of interest.

System Evaluation: Described herein are assays for GFP, synTF, and cytokine expression, as well as assays for synTF activity in Jurkat or human primary T cells. The relative performance of the different genetic circuits in Jurkat T cell line can be evaluated by testing in human primary CD8 T cells. Jurkat cells were used because of their value to the understanding of T cell biology, and their ability to scale the assay pipeline at cost. Strongly expressing synTFs in Jurkat are similarly strong in primary T cells.

Inducible synTFs were first characterized using GFP (or another detectable marker such as mCherry) as the reporter. The whole system was introduced into Jurkat T cells via lentiviral transduction with multiplicity of infection of 25 to ensure high efficiency, quantifying viral copy number (VCN) with qPCR. To characterize the inducible synTF controllers, cells at $5\times10^4$ cells each in 96-well plates were inoculated with lentivirus, and eight different drug concentrations were added spanning three orders of magnitude (e.g., GZV 0-10 μM, 4OHT 0-1 μM), and GFP expression levels can be quantified with flow cytometry (see e.g., FIG. 10A-10D). Gene expression levels can be normalized to VCN. From these dose-responses, the dynamic range and threshold of activation can be defined. Since the single vector design can lack a selection marker, transduction efficiency was assumed to be equal to the percentage of GFP positive cells after induction by 4OHT or GZV.

To demonstrate translational potential, an inducible system demonstrating a larges dynamic range can be selected to control synTFs or cytokine expression in human primary CD8 T cells. Controller circuits can be engineered by replacing GFP with a therapeutic protein (e.g., anti-Her2 synTF or IL-12), introduced into human primary CD8 T cells via lentiviral transduction, and evaluated using methods as described herein. Briefly, using ROSETTASEP and SEPMATE kits (STEMCELL Technology), primary human T cells can be purified from leukopaks of anonymous male and female donors obtained from a blood bank. synTF expression levels in the presence or absence of inducer are measured by immunostaining for myc-tagged synTF, and IL-12 expression is measured by ELISA. To activate the synTF, $5\times10^4$ engineered T cells are mixed in 96-well plates with Her2 expressing K562 cells at 1:1 ratio. T cell activation is measured via cytokine production (e.g., IL-2 and IFN-g), cell killing, and proliferation. Cell killing is measured by the number of live K562 cells (e.g., fluorescently labeled) through flow cytometry. T cells constitutively expressing synTF or cytokine, and cells lacking synTF or cytokine are tested as controls. Each sample is performed in triplicate. Statistical significance between samples can be determined by student's T-test (two-tailed). Values of <0.05 are considered significant. To ensure reproducibility, each experiment is independently repeated >3 times.

Example 3: Synthetic Transcription Regulation for Immune Cell Therapy

Overview: Next generation cell therapies seek to create designer immune cells that can sense and respond to disease in sophisticated ways. Achieving this goal fundamentally requires engineered regulatory elements and circuitry that can be used to program human cell functions by processing complex environmental inputs and mediating precisely regulated expression of therapeutic agents. Towards this goal, synthetic transcriptional programs can interface with sense and response modules to enable new layers of regulation in cells (see e.g., FIG. 1A-1B).

To advance immune cell therapies beyond reliance on simple constitutive expression of therapeutic agents, there is a need for programmable genetic components that offer tunable and versatile regulatory profiles. Moreover, these components must themselves have properties that are compatible with the human therapeutic context, including high specificity, low immunogenicity, and deliverability.

Engineered zinc finger (ZF) domains are promising moieties for transcriptional regulation in human cells as they are able to address aforementioned considerations. These naturally compact DNA-binding elements are ubiquitous in eukaryotic transcription factors. They have a modular design with programmable sequence recognition and customizable molecular properties. There has been extensive foundational work to understand the structure and programmability of these motifs to achieve useful gene regulatory functions.

Described herein is a synthetic transcriptional regulatory platform suitable for applications in therapeutic gene regulation. A library of engineered ZF domains with recognition sequences that are unique and orthogonal to the human genome is engineered and utilized, and these minimal regulators are connected to drug-responsive domains to achieve controlled gene expression. This framework broadly permits sophisticated gene expression programs for immune cell therapy.

Such a platform for synthetic transcriptional regulation of therapeutic genes can be used in T cells. These core transcription factors of the synTFs are highly advantageous for therapy due to their compact size and native derivation from mammalian systems. These factors were connected to small molecule-responsive domains in order to control their activity (e.g., in T cells) by administration of safe and/or FDA-approved drugs.

Construction of Synthetic Zinc Finger-TF Library: A library of synthetic transcription factors was constructed utilizing engineered 6-unit zinc finger (ZF) domains with 18 bp binding motifs that are unique and putatively orthogonal to the human genome. The activity of minimal transcriptional regulators against cognate and non-cognate reporters was evaluated in HEK293 cell lines (see e.g., FIG. 1C-1D).

Evaluation of Transcriptome Response: Changes in cellular transcriptome response upon expression of our synthetic transcriptional regulators were measured in HEK293 cell lines. These global transcriptome profiles were compared to those of widely-used "orthogonal" DNA binding domains (e.g., Gal4, TetR) (see e.g., FIG. 1F-1H).

Development of Inducible Transcriptional Regulators: The transcriptional regulators were coupled to inducible domains to temporally modulate gene expression. Candidate inducible elements were selected that are responsive to small molecules that are FDA-approved drugs or known to be safe in humans. The dose- and time-dependent activity of the inducible transcriptional regulators was evaluated in both HEK293 and Jurkat cell lines (see e.g., FIG. 2-4, 5A-5C, 6A-6B, 7A-7C, 8A-8C, 9A-9C, 10A-10D).

Control of Immune Cell Function: One of our small molecule inducible regulatory systems (e.g., an NS3-regulated synTF) was utilized to temporally modulate the expression of a CD19 Chimeric Antigen Receptor in primary CD4+ T cells and to permit tunable production of cytokines upon cellular activation (see e.g., FIG. 13A-13D).

Example 4: A Platform for Synthetic Transcriptional Regulation in Human Cells Therapeutic cells can be engineered to sense and respond to disease in sophisticated ways. Cells are naturally capable of integrating and processing diverse environmental signals. Cells are naturally perceptive and adaptable devices that process information across space and time using their underlying genetic and epigenetic programs. Artificial genetic programs can endow human cells with new and increasingly complex therapeutic functions.

The field of synthetic biology has really contributed to all of these areas: (1) from developing strategies to identify diverse signals (e.g. artificial receptors, responsive proteins), (2) new platforms and cellular logic modules to interpret information (e.g. transcriptional networks, signaling cascades), and (3) translating these into desirable and effective responses and therapeutic outputs (e.g. corrective transgenes, stimulatory molecules). By engineering human cells with genetic programs, the cells are presented with new opportunities to integrate and process signals associated with disease, and to ultimately therapeutically respond in sophisticated ways.

Transcription factors (TFs) naturally regulate cellular behaviors. New genetic elements can advance the signal processing capabilities of therapeutic cells. With regard to information processing, transcription factors are often utilized as key mediating regulatory elements within circuits and genetic programs, due to their intrinsic ability to locally and conditionally the regulate expression of genes. TFs fundamentally govern genomic processes and interesting cellular behaviors (e.g., potent gene activation and silencing, differentiation, enhancers, etc.) These complex behaviors often emerge due to unique TF features in eukaryotic contexts (e.g., specificity for enhancer sequences, ability to modify DNA structure and chromatin, ability to interact cooperativity, ability to regulate different genes temporally and in sequence, etc.).

Historically, heterologous TFs have been co-opted from prokaryotic systems (e.g., Gal4, TetR, LacI and others) to "orthogonally" control programs in human cells. While this itself has permitted many significant foundational advancements in the mammalian synthetic biology field, there are a relatively limited amount of regulatory properties and useful behaviors that these "primitive" parts can be used to uncover.

There remains a persistent need for new regulatory elements that can allow cells to process more channels of information in more reliable ways. Synthetic transcriptional regulation can permit controllable expression. Described herein are artificial eukaryotic TFs with customizable properties, including an exploration of how engineered cooperative interactions between such TFs can give rise to complex signal processing behaviors.

Engineered genetic components can be used for precise and versatile transcriptional regulation in human cells.

Regarding the development of next-generation regulatory elements for therapeutic applications in human cells, the following are favorable properties of such TFs.

Such synthetic transcription factors meet the following requirements: (1) components derived from mammalian systems that are safe and non-immunogenic, (2) those that can very specifically recognize and regulate at their operator sequences with minimal off-target effects, (3) those that allow for programmable and tunable interactions with other molecular components, and (4) those that can be successfully delivered in human cells within established delivery vectors.

Engineered ZF domains are promising moieties for transcriptional regulation that address all of these considerations—they are naturally occurring, minimal DBDs in human TFs, and they can be adapted for synthetic regulation.

Engineered zinc finger domains can be used to build synthetic transcriptional regulators that can enhance the processing capabilities of human cells.

A set of artificial 6-unit ZF domains were developed that specifically recognize 18 bp DNA operators; they are distant from and orthologous to native human genomic sequences. Simple transcription regulation programs were developed by coupling these engineered binding domains to human-derived effector domains and developing responsive promoters. These programs can be interfaced in therapeutic circuits—generating inducible synTFs that are responsive to small molecules and using these controllable synTFs to modulate expression of therapeutic outputs.

Synthetic transcriptional operator sequences were identified that are orthogonal to the human genome. There exist specific challenges in programming ZF domains compared to other technologies (e.g., TALE, CRISPR) for which there is a convenient 1:1 recognition code. One ZF unit specifies 3 bp of DNA and they can be connected modularly to specify larger sequence arrays. However, there can be context-dependent activity when these ZF units are arranged within larger arrays.

To address the two-fold challenge of finding genome-orthogonal recognition sequences AND functional and active DNA binding domains, a set of 2-unit ZF subarrays was used (see e.g., J. Keith Joung (ZF Archive); U.S. Pat. No. 10,138,493 (2018)). 6 bp recognition sequences were identified that were underrepresented in the genome. Without wishing to be bound by theory, it was hypothesized that their concatenation would lead to highly distant 18 bp sequences (a length that can confer uniqueness). Arrangements of corresponding 6-unit ZFs were then screened to find those that could recognize these sequences, resulting in an initial library of 11 sequences ("operators") and corresponding 6-unit ZFs.

Figure 31:
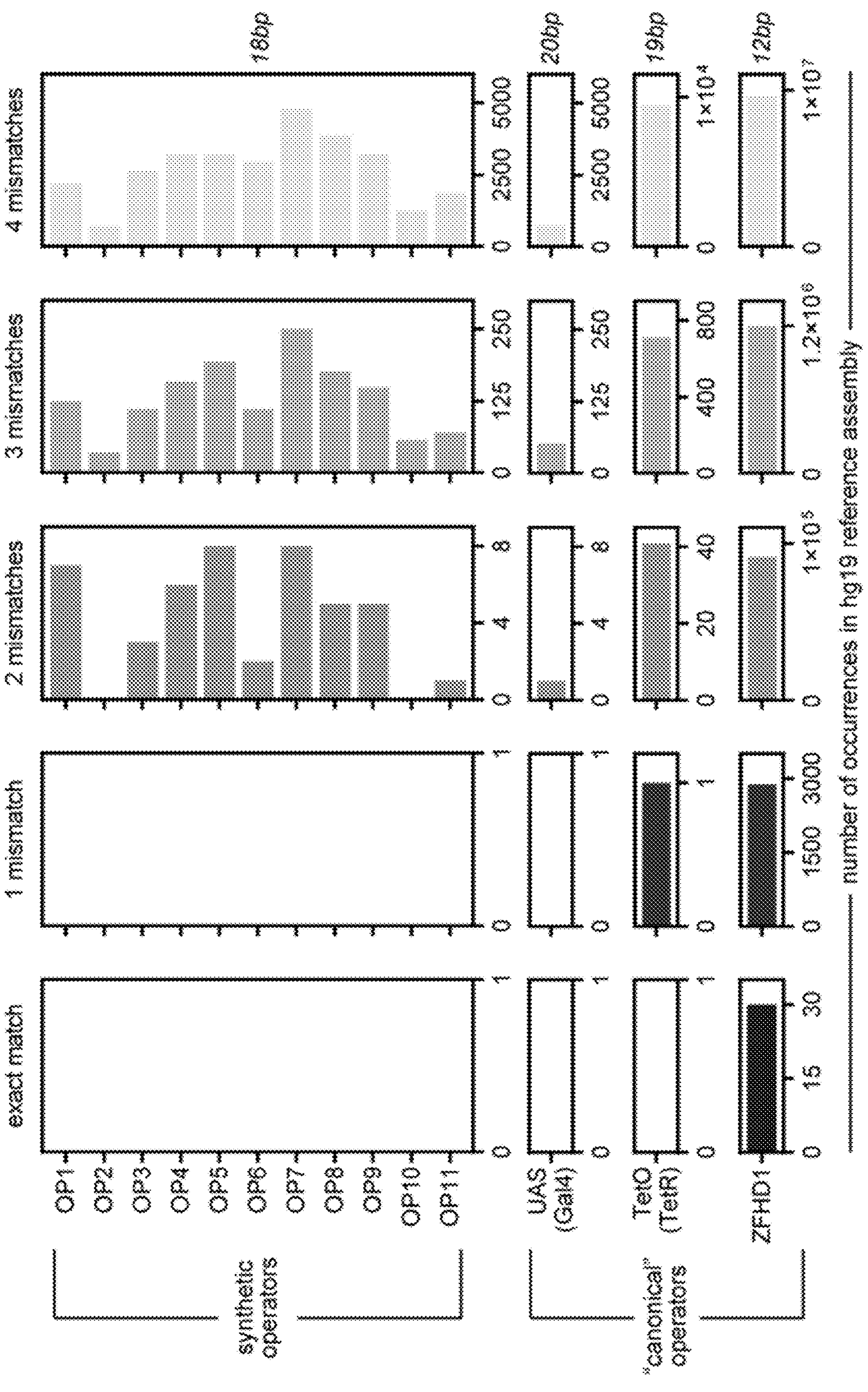
FIG. 31 is a series of graphs showing the identification of synthetic transcriptional operator sequences orthogonal to the human genome. A bioinformatic string matching algorithm called "Biostrings" was used to evaluate the occurrence of the operator sequences in the human genome. The x-axis here represents the number of occurrences of particular string(s) in the hg19 ref assembly; note that the scale changes for different sets and panels. On the top panel are the 11 "synthetic operators" and the instances of either exact or all possible mismatched sequences: this algorithm showed that there were no exact or 1-2 mismatch sequences for these, suggesting that the sequence composition can be considered genomically-distant. Several canonical TF operator sequences were also compared to the human genome. The synthetic operators described herein perform better relative to these "heterologous" recognition sequences of similar or shorter lengths.

A bioinformatic string matching algorithm called "Biostrings" was used to evaluate the occurrence of the operator sequences in the human genome. The synthetic operators were compared to several canonical TF operator sequences (e.g., UAS/Gal4, TetO/TetR, ZFHD1). The synthetic operators generated through the described workflow performed better relative to these "heterologous" recognition sequences of similar or shorter lengths (see e.g., FIG. 31).

Described herein is a library of synthetic operator sequences and cognate transcription factors. Responsive cell lines were developed by placing synthetic operator sequences upstream of minimal promoters driving a fluorescent output, and integrating them into HEK cells. The responsive (i.e., reporter) cell lines were then transiently transfected with minimal synthetic transcription factors composed of the engineered binding domains coupled to human-derived effector domains (such as p65). These proteins were capable of binding to the array and subsequently boosting expression of the fluorescent output. Each reporter was only turned on in the presence of its corresponding synTF, and not in the negative control case using a "mock TF" with a GFP replacing the ZF domain. Testing of the mutual orthogonality of this set demonstrated that the TFs were specific to their corresponding operators and not for non-cognate sequences (see e.g., FIG. 1A-1D).

Transcriptome measurements were used to elucidate synTF specificity and genome-wide activity. The specificity and genome-wide orthogonality of our synTFs were empirically evaluated in the human genome. A singly-integrated HEK cell line constitutively expressed a synTF alongside its cognate fluorescent reporter. Total RNA was collected and a transcriptome analysis was performed to examine into the on-target regulation of the fluorescent transcript compared to off-target misregulation. These differential expression levels were compared relative to a reference line containing a GFP-p65 "mock" TF. There was significant differential activation of the mCherry in the synTF cell line, but extremely high correlation of native cellular transcripts between both cell lines, indicating that the synTFs regulate expression specifically at their target sites (see e.g., FIG. 1E-1H).

As described herein, small molecule inducible regulation is useful for control of synTF activity. Drug-controllable versions of the synthetic transcription regulators were engineered by generating TFs responsive to the presence and concentration of relevant small molecules. These are useful for tunable and temporal control over the activity of the TFs. Reporters and synTFs were ported into lentiviral cassettes that were capable of delivering these payloads to various cell types. Three safe and/or FDA approved small molecules were used control the activity of the synTFs through different mechanisms; these mechanisms included: (1) the abscisic acid mediated hetero-dimerization of ABI/PYL domains; (2) the 4-hydroxytamoxifen mediated nuclear translocation of the ERT2 domain; and (3) the grazoprevir mediated stabilization of the viral NS3 self-excising protease. Three of the orthogonal synTF activators were connected to each inducible system (see e.g., FIG. 2-4, 5A-5C, 6A-6B, 7A-7C, 8A-8C, 9A-9C, 10A-10D).

Tunable gene activation was achieved using small molecule inducible synTFs. Inducibility profiles were determined for each of the three inducible synTF activators, in both HEK293 and Jurkat cell lines. The reporter expression was evaluated across time and varying drug concentrations. Day 4 represented the highest levels of expression that were assayed, indicating strong inducible expression in drug-treated lines relative to untreated cell lines (see e.g., FIG. 10A-10D).

Tunable gene silencing can also be achieved using small molecule inducible synTFs. Inducible synTFs were engineered that were capable of repressing gene expression. The responsive promoter was modified to constitutively express a fluorescent output. The p65 activation domain was replaced with a KRAB repression domain (human-derived silencer), and the same ZF-drug pairs were utilized as the synTF activators. Inducibility profiles were determined for each of the three inducible synTF repressors in HEK cell lines, and there was strong silencing of reporter expression over time in drug-treated lines relative to untreated cell lines (see e.g., FIG. 11A-11B, 12A-12C).

Inducible synTFs can regulate cytokine expression from a single lentiviral vector, demonstrating of the compact nature of the synTFs. A single lentiviral vector was engineered that was capable of expressing a grazoprevir-inducible synTF that would in turn regulate expression of IL-10. The size of this entire insert including expression elements was 3.5 kB, which is minimal and approaches the total payload packaging limits of certain vectors. Virus was produced to infected Jurkat cells, and there was saw strong induced expression of IL-10 in transduced cells after 2 days of grazoprevir administration, indicating that this is an efficient strategy of modulating therapeutic outputs in human cells (see e.g., FIG. 15A-15C).

Inducible synTFs can regulate synTF expression in primary cells. The grazoprevir-inducible synTF was used to control expression of a CD19-CAR in primary CD4+ cells. Using different administered concentrations of drug, dose-dependent expression of synTF was measured over time. On day 3 there was strong fold induction with the highest concentration. The grazoprevir-induced cells were then co-cultured with CD19+ antigen-presenting cells to activate the primary cells, and dose-dependent production of IFNgamma and IL-2 cytokines was subsequently measured across time. Such results highlight that the ability to reliably control expression of outputs from therapeutic, thus controlling their functionalities in increasingly complex settings (see e.g., FIG. 13A-13D).

In conclusion, building new transcriptional regulatory elements with favorable properties allows human cells to process information and regulate therapeutic functions in tunable and reliable ways. A library of orthogonal ZF binding domains and synthetic operator sequences was specifically developed, and these were used to engineer minimal transcriptional regulatory programs. As shown herein, these synTFs were used control therapeutic programs in circuits, thus demonstrating the utility of these synTFs in sophisticated gene expression programs.

Example 5: Exemplary Sequences

Induced Proximity Domains

[ABI]—[ZF]—[2A]—[p65]—[PYL] synthetic transcriptional activator: In this particular embodiment, the ZF is fused to the C-terminal of the ABI domain, while the p65 is fused N-terminal to the PYL domain. The two composite domains are expressed from the same promoter; they are separated by a 2A ribosomal skip sequence (see e.g., SEQ ID NO: 4, FIG. 19).

[ABI]—[ZF]—[2A]—[KRAB]—[PYL] synthetic transcriptional repressor: In this particular embodiment, the ZF is fused to the C-terminal of the ABI domain, while the KRAB is fused N-terminal to the PYL domain. The two composite domains are expressed from the same promoter; they are separated by a 2A ribosomal skip sequence (see e.g., SEQ ID NO: 5, FIG. 20).

Cytosolic Sequestering Domain

[ZF]—[p65]—[ERT2] synthetic transcriptional activator: In this particular embodiment, the p65 effector domain is fused C-terminal to the ZF domain. The ERT2 domain is fused C-terminal to the p65 domain (see e.g., SEQ ID NO: 6, FIG. 21).

[KRAB]—[ZF]—[ERT2] synthetic transcriptional repressor: In this particular embodiment, the KRAB effector domain is fused N-terminal to the ZF domain. The ERT2 domain is fused C-terminal to the ZF domain (see e.g., SEQ ID NO: 7, FIG. 22).

Self-Cleaving Protease Domain

[ZF]—[NS3]—[p65] synthetic transcriptional activator: In this particular embodiment, the zinc finger DNA binding domain is N-terminal to the NS3 domain, while the effector domain is C-terminal to the NS3 domain (see e.g., SEQ ID NO: 8, FIG. 23).

[KRAB]—[NS3]—[ZF] synthetic transcriptional repressor: In this particular embodiment, the effector domain is N-terminal to the NS3 domain, while the zinc finger DNA binding domain is C-terminal to the NS3 domain (see e.g., SEQ ID NO: 9, FIG. 24).

Induced Degradation Domain

[ZF]—[p65]—[ERT2]—[SMASh] synthetic transcriptional activator ("C-terminal SMASh"): In this particular embodiment, an ERT2 (mutated estrogen receptor domain responsive to 4OHT) is C-terminal to the zinc finger DNA binding domain and effector domain. The SMASh domain (containing NS3) is C-terminal to the rest of the domains (see e.g., SEQ ID NO: 10, FIG. 25).

[SMASh]—[ZF]—[p65]—[ERT2] synthetic transcriptional activator ("N-terminal SMASh"): In this particular embodiment, an ERT2 (mutated estrogen receptor domain responsive to 4OHT) is C-terminal to the zinc finger DNA binding domain and effector domain. The SMASh domain (containing NS3) is N-terminal to the rest of the domains (see e.g., SEQ ID NO: 11, FIG. 26).

[ZF]—[p65]—[SMASh]: In this particular embodiment, an SMASh domain (containing NS3) is C-terminal to the zinc finger DNA binding domain and effector domain (see e.g., SEQ ID NO: 12, FIG. 27).

[KRAB]—[ZF]—[ERT2]—[SMASh]: In this particular embodiment, an ERT2 (mutated estrogen receptor domain responsive to 4OHT) is C-terminal to the KRAB repressor domain and the zinc finger DNA binding domain. The SMASh domain (containing NS3) is C-terminal to the rest of the domains (see e.g., SEQ ID NO: 13, FIG. 28).

[HP1a]—[ZF]—[ERT2]—[SMASh]: In this particular embodiment, an ERT2 (mutated estrogen receptor domain responsive to 4OHT) is C-terminal to the HP1a repressor domain and the zinc finger DNA binding domain. The SMASh domain (containing NS3) is C-terminal to the rest of the domains (see e.g., SEQ ID NO: 14, FIG. 29).

[EED]—[ZF]—[ERT2]—[SMASh]: In this particular embodiment, an ERT2 (mutated estrogen receptor domain responsive to 4OHT) is C-terminal to the EED repressor domain and the zinc finger DNA binding domain. The SMASh domain (containing NS3) is C-terminal to the rest of the domains (see e.g., SEQ ID NO: 15, FIG. 30).

Sequence Tables

TABLE 1

| Exemplary Vectors | | | |
|---|---|---|---|
| Vector | SEQ ID NO | Description | Use with |
| Activation Reporter | | | |
| pO-066 | 52 | pHR-4X ZF1 BS-minCMV-mCherry | pMZ-314 |
| pO-081 | 53 | pHR-4X ZF3 BS-minCMV-mCherry | pO-082 |
| pO-070 | 54 | pHR-4X ZF10 BS-minCMV-mCherry | pO-080 |
| Repression Reporter | | | |
| pMN-243 | 55 | pHR-4X ZF1 BS-full CMV-mCherry-d2 | pMZ-343 |
| pMN-244 | 56 | pHR-4X ZF3 BS-full CMV-mCherry-d2 | pMZ-328 |
| pMN-245 | 57 | pHR-4X ZF10 BS-full CMV-mCherry-d2 | pMZ-329 |
| pMN-258 | 58 | pHR-4X ZF1 BS-SFFV-mCherry | pMZ-343 |
| pMN-259 | 59 | pHR-4X ZF3 BS-SFFV-mCherry | pMZ-328 |
| pMN-260 | 60 | pHR-4X ZF10 BS-SFFV-mCherry | pMZ-329 |
| Expression Vector | | | |
| pO-105 | 61 | pHR-4X ZF10 BS-minTK-CD19 CAR-mCherry | pO-080 |
| pMN-268 | 62 | pHR-4X ZF3 BS-minCMV-IL4-[2A]-huEGFRt | pO-082 |
| pO-093 | 63 | pHR-4X ZF10 BS-minTK-IL10 | pO-080 |
| pO-092 | 64 | pHR-IL10-minTK-4X ZF10 BS-pHR-pSFFV-ZF10-p65-NS3 | N/A |
| Activator Domain synTF | | | |
| pMZ-314 | 16 | pHR-pSFFV-ZF1-ABI-[2A]-PYL-p65 | pO-066 |
| pO-082 | 18 | pHR-pSFFV-ZF3-p65-ERT2 | pO-081 |
| pO-080 | 20 | pHR-pSFFV-ZF10-p65-NS3 | pO-070 |
| pMZ-431 | 22 | pHR-pSFFV-ZF3-p65-ERT2-SMASh | pO-081 |
| pMZ-432 | 23 | pHR-pSFFV-SMASh-ZF3-p65-ERT2 | pO-081 |
| pMZ-454 | 24 | pHR-pSFFV-ZF10-p65-SMASh | pO-070 |
| Repressor Domain synTF | | | |
| pMZ-343 | 17 | pHR-pSFFV-ABI-ZF1-[2A]-KRAB-PYL | pMN-243/ pMN-258 |
| pMZ-328 | 19 | pHR-pSFFV-KRAB-ZF3-ERT2 | pMN-244/ pMN-259 |
| pMZ-329 | 21 | pHR-pSFFV-KRAB-NS3-ZF10 | pMN-245/ pMN-260 |
| pMZ-440 | 25 | pHR-pSFFV-KRAB-ZF3-ERT2-SMASh | pMN-244/ pMN-259 |
| pMZ-441 | 26 | pHR-pSFFV-HPla-ZF3-ERT2-SMASh | pMN-244/ pMN-259 |
| pMZ-442 | 27 | pHR-pSFFV-EED-ZF3-ERT2-SMASh | pMN-244/ pMN-259 |

TABLE 2

| Exemplary SynTFs (the last three columns show exemplary SEQ ID NOs) | | | |
|---|---|---|---|
| Description | Vector | Polynucleotide | Polypeptide |
| Induced Proximity Domain | | | |
| ZF1-ABI-[2A]-PYL-p65 | 16 | 28 | 4, 40 |
| ABI-ZF1-[2A]-KRAB-PYL | 17 | 29 | 5, 41 |
| Cytosolic Sequestering Domain | | | |
| ZF3-p65-ERT2 | 18 | 30 | 6, 42 |
| KRAB-ZF3-ERT2 | 19 | 31 | 7, 43, 378 |
| Repressible Protease Domain | | | |
| ZF10-p65-NS3 | 20 | 32 | 8, 44 |
| KRAB-NS3-ZF10 | 21 | 33 | 9, 45 |
| Induced Degradation Domain | | | |
| ZF3-p65-ERT2-SMASh | 22 | 34 | 10, 46 |
| SMASh-ZF3-p65-ERT2 | 23 | 35 | 11, 47, 379 |

TABLE 2-continued

| Exemplary SynTFs (the last three columns show exemplary SEQ ID NOs) | | | |
|---|---|---|---|
| Description | Vector | Polynucleotide | Polypeptide |
| ZF10-p65-SMASh | 24 | 36 | 12, 48 |
| KRAB-ZF3-ERT2-SMASh | 25 | 37 | 13, 49 |
| HP1a-ZF3- ERT2-SMASh | 26 | 38 | 14, 50 |
| EED-ZF3- ERT2-SMASh | 27 | 39 | 15, 51 |

Table 3 shows the locations of specific domains in exemplary Heterodimerization Domain SynTFs polypeptide sequences.

TABLE 3

| Exemplary Induced Proximity Domain SynTFs | | |
|---|---|---|
| Element (SEQ ID NO) | ZF1-ABI-[2A]-PYL-p65 (SEQ ID NO: 4, 40) | ABI-ZF1-[2A]-KRAB-PYL (SEQ ID NO: 5, 41) |
| NLS (65) | 4-10 | 4-10 |
| ABI1cs CO1 (66) | 15-312 | 15-312 |
| Linker (67) | 313-317 | 313-317 |
| ZF (1 or 76) | 318-493 | 318-493 |
| NLS (65) | 494-500 | 522-528 |
| P2A (68) | 504-525 | 497-518 |
| p65 (69) | 529-719 | |
| KRAB (72) | | 529-624 |
| Linker (70) | 720-724 | 625-629 |
| PYL1cs (71) | 727-903 | 632-808 |

Table 4 shows the locations of specific domains in exemplary Translocation Domain SynTFs polypeptide sequences.

TABLE 4

| Exemplary Cytosolic Sequestering Domain SynTFs | | |
|---|---|---|
| Element (SEQ ID NO) | ZF3-p65-ERT2 (SEQ ID NO: 6, 42) | KRAB-ZF3-ERT2 (SEQ ID NO: 7 or 43; SEQ ID NO: 378) |
| KRAB (72) | | 2-97; 2-97 |
| Linker (75) | | 100-105; 100-105 |
| ZF (2 or 76) | 2-177 | 110-285; 109-284 |
| p65 (69) | 181-374 | |
| Linker (73) | 374-378 | 288-292; 287-291 |
| Ert2 (74) | 379-692 | 292-606; 292-605 |

Table 5 shows the locations of specific domains in exemplary Self-Cleaving Protease Domain SynTFs polypeptide sequences.

TABLE 5

| Exemplary Repressible Protease SynTFs | | |
|---|---|---|
| Element (SEQ ID NO) | ZF10-p65-N53 (SEQ ID NO: 8, 44) | KRAB-N53-ZF10 (SEQ ID NO: 9, 45) |
| KRAB (72) | | 2-97 |
| ZF (3 or 76) | 2-177 | |
| 3XFlag-NLS (77) | 181-219 | 101-139 |
| Linker (75) | 222-227 | 142-147 |
| NS5A/5B cut site (CC) (78) | 230-239 | 150-159 |
| NS3 Domain (85) | 240-480 | 160-400 |
| N-end rule (79) | 236-243 | 156-163 |
| AU1 (80) | 247-252 | 167-172 |
| NS4A (81) | 258-270 | 178-190 |
| NS3 (82) | 275-463 | 195-383 |

TABLE 5-continued

| Exemplary Repressible Protease SynTFs | | |
|---|---|---|
| Element (SEQ ID NO) | ZF10-p65-N53 (SEQ ID NO: 8, 44) | KRAB-N53-ZF10 (SEQ ID NO: 9, 45) |
| NS4A/4B cut site (CS) (83) | 481-494 | 401-414 |
| HA tag (84) | 495-503 | 415-423 |
| Linker (75) | 504-509 | 424-429 |
| p65 (69) | 512-702 | 432-607 |

Tables 6 and 7 shows the locations of specific domains in exemplary Induced Degradation Domain SynTFs polypeptide sequences.

TABLE 6

| Exemplary Induced Degradation Domain SynTFs (Activator Domain) | | | |
|---|---|---|---|
| Element (SEQ ID NO) | ZF3-p65 SMASh-ERT2- (SEQ ID NO: 10, 46) | SMASh-ZF3-p65-ERT2 (SEQ ID NO: 379; (SEQ ID NOs: 11, 47) | ZF10-p65-SMASh (SEQ ID NO: 12 or 48) |
| 3XFlag-NLS (77) | | | 2-40 |
| Linker (75) | | | 43-48 |
| N-terminal SMASh (94 or 95) | | 2-298; 2-304 | |
| FLAG (89) | | 2-9; 2-9 | |
| Linker (90) | | 10-21; 10-21 | |
| NS3 protease (91) | | 22-207; 22-207 | |
| NS3 helicase (92) | | 208-240; 208-240 | |
| NS4A (93 or 96) | | 241-285; 241-291 | |
| NS3 5A/5B cleavage site (279) | | 286-298; 292-304 | |
| ZF (2, 3, or 76) | 2-177 | 301-474; 307-482 | 53-228 |
| p65 (69) | 181-371 | 480-670; 486-676 | 232-422 |
| Linker (73) | 374-378 | 673-677; 679-683 | |
| Ert2 (74) | 379-692 | 678-991; 684-997 | |
| C-terminal SMASh (86) | 695-998 | | 425-728 |

TABLE 6-continued

| Exemplary Induced Degradation Domain SynTFs (Activator Domain) | | | |
|---|---|---|---|
| Element (SEQ ID NO) | ZF3-p65 SMASh-ERT2- (SEQ ID NO: 10, 46) | SMASh-ZF3-p65-ERT2 (SEQ ID NO: 379; (SEQ ID NOs: 11, 47) | ZF10-p65-SMASh (SEQ ID NO: 12 or 48) |
| NS3 cleavage site (87) | 695-704 | | 425-434 |
| linker (88) | 705-714 | | 435-444 |
| FLAG (89) | 715-722 | | 445-452 |
| linker (90) | 723-734 | | 453-464 |
| NS3 protease (91) | 735-920 | | 465-650 |
| NS3 helicase (92) | 921-953 | | 651-683 |
| NS4A (93) | 954-998 | | 684-728 |

TABLE 7

| Exemplary Induced Degradation Domain SynTFs (Repressor Domain) | | | |
|---|---|---|---|
| Element (SEQ ID NO) | KRAB-ZF3-ERT2-SMASh (SEQ ID NO: 13, 49) | HPla-ZF3-ERT2-SMASh (SEQ ID NO: 14, 50) | EED-ZF3-ERT2-SMASh (SEQ ID NO: 15, 51) |
| KRAB (97) | 2-66 | | |
| HP1a (98) | | 2-191 | |
| EED (99) | | | 2-441 |
| Linker (100) | 67-75 | 192-200 | 442-450 |
| ZF (2 or 76) | 76-251 | 201-376 | 451-626 |
| Linker (73) | 254-258 | 379-383 | 629-633 |
| Ert2 (74) | 259-572 | 384-697 | 634-947 |
| C-terminal SMASh (86) | 575-878 | 700-1003 | 950-1253 |
| NS3 cleavage site (87) | 575-584 | 700-709 | 950-959 |
| linker (88) | 585-594 | 710-719 | 960-969 |
| FLAG (89) | 595-602 | 720-727 | 970-977 |
| linker (90) | 603-614 | 728-739 | 978-989 |
| NS3 protease (91) | 615-800 | 740-925 | 990-1175 |
| NS3 helicase (92) | 801-833 | 926-958 | 1176-1208 |
| NS4A (93) | 834-878 | 959-1003 | 1209-1253 |

What is claimed herein is:

1. A synthetic transcription factor (synTF) comprising;

a. at least one DNA binding domain (DBD), wherein the DBD comprises an engineered zinc-finger binding domain which binds to a DNA-binding motif (DBM), b. a transcriptional effector domain (ED), c. at least one cytosolic sequestering protein, wherein the cytosolic sequestering protein is an estrogen ligand binding domain (ERT) or a variant thereof, or comprises at least a portion of the estrogen receptor (ER), and wherein the ED is directly or indirectly coupled or linked to the DBD, and wherein the cellular localization of the ED is regulated by the cytosolic sequestering protein.

2. The synTF of claim 1, wherein the transcriptional ED is a transcriptional activator (TA) domain or a transcriptional repressor (TR) domain.

3. The synTF of claim 2, wherein the TA is selected from the group consisting of: p65; Rta; miniVPR; full VPR; VP16; VP64; p300; p300 HAT Core; and a CBP HAT domain, or wherein the TR is selected from the group consisting of: KRAB; KRAB-MeCP2; Hp1a; DNA methyltransferase DNMT; EED; and HDAC4.

4. The synTF of claim 3, wherein the p65 comprises one of SEQ ID NOs: 69, 117-121, 193-197 or a protein having at least 85% sequence identity one of SEQ ID NOs: 69, 117-121, 193-197.

5. The synTF of claim 3, wherein the KRAB comprises one of SEQ ID NOs: 72, 97, or 214-215, or a protein having at least 85% sequence identity to one of SEQ ID NO: 72, 97, or 214-215.

6. The synTF of claim 1, wherein the ZF-binding domain comprises any one of: 2, 3, 4, 5, 6, 7, 8, 9, 10, 11, 12, 13, 14, 15, 16, 17, 18, or more ZF motifs arranged adjacent to each other in tandem to form a ZF array (ZFA).

7. The synTF of claim 1, wherein the ZF binding domain is selected from any of:

a. ZF 1-1, ZF 1-2, ZF 1-3, ZF 1-4, ZF 1-5, ZF 1-6, ZF 1-7, ZF 1-8, ZF 2-1, ZF 2-2, ZF 2-3, ZF 2-4, ZF 2-5, ZF 2-6, ZF 2-7, ZF 2-8, ZF 3-1, ZF 3-2, ZF 3-3, ZF 3-4, ZF 3-5, ZF 3-6, ZF 3-7, ZF 3-8, ZF 4-1, ZF 4-2, ZF 4-3, ZF 4-4, ZF 4-5, ZF 4-6, ZF 4-7, ZF 4-8, ZF 5-1, ZF 5-2, ZF 5-3, ZF 5-4, ZF 5-5, ZF 5-6, ZF 5-7, ZF 5-8, ZF 6-1, ZF 6-2, ZF 6-3, ZF 6-4, ZF 6-5, ZF 6-6, ZF 6-7, ZF 6-8, ZF 7-1, ZF 7-2, ZF 7-3, ZF 7-4, ZF 7-5, ZF 7-6, ZF 7-7, ZF 7-8, ZF 8-1, ZF 8-2, ZF 8-3, ZF 8-4, ZF 9-1, ZF 9-2, ZF 9-3, ZF 9-4, ZF 10-1 and ZF 11-1 or a ZF binding domain is selected from any of SEQ ID Nos: 1-3, 76, 101, 377, or 380; or b. a ZF binding domain that specifically binds to a sequence comprising at least one of SEQ ID NOs: 181-191.

8. The synTF of claim 1, wherein the at least one DBD is selected from one or more of any of: SEQ ID NO: 221 or 222, 36-4 (SEQ ID NO: 223), 43-8 (SEQ ID NO: 224 or 225), 42-10 (SEQ ID NO: 226 or 227), 97-4 (SEQ ID NO: 228), or wherein the DBD binds to DNA binding motifs (DBM) comprising any of: SEQ ID NOs: 229-240.

9. The synTF of claim 1, wherein the cytosolic sequestering protein comprises a ligand binding domain (LBD), wherein in the presence of the ligand, the sequestering of the protein to the cytosol is inhibited.

10. The synTF of claim 1, wherein the cytosolic sequestering protein comprises a ligand binding domain and a nuclear localization signal (NLS), wherein in the absence of the ligand the NLS is inhibited thereby preventing translocation of the sequestering protein to the nucleus, and wherein in the presence of the ligand the nuclear localization signal is exposed enabling translocation of the sequestering protein to the nucleus.

11. The synTF of claim 1, wherein the cytosolic sequestering protein is selected from the group consisting of: ERT2, ERT, and ERT3.

12. The synTF of claim 1, wherein the ERT binds to one or more ligands selected from: tamoxifen, 4-hydroxytamoxifen (4OHT), endoxifen, Fulvestrant, wherein binding of the ligand to ERT exposes a NLS and results in nuclear translocation of the ERT.

13. The synTF of claim 1, wherein the cytosolic sequestering protein comprises the amino acid of SEQ ID NOs: 74, 335-337, or a homologue of at least 85% sequence identity to SEQ ID NOs: 74, 335-337.

14. The synTF of claim 1, wherein the cytosolic sequestering protein comprises a transmembrane receptor sequestering protein.

15. The synTF of claim 1, wherein the synTF comprises:

a N-terminal DBD, the cytosolic sequestering protein, and a C-terminal effector domain; or a N-terminal effector domain, a DBD and a C-terminal cytosolic sequestering protein.

16. The synTF of claim 1, wherein synTF further comprises a Small molecule-Assisted Shutoff (SMASh) tag, wherein the SMASh tag is a N-terminal or C-terminal SMASh domain comprising a repressible protease, a partial protease helical domain and a cofactor domain.

17. The synTF of claim 16, wherein the SMASh tag is selected from:

a. a C-terminal SMASh domain comprising in a N-terminal to C-terminal order: a NS3 cleavage site, at least one linker, a NS3 domain, a NS3 partial helicase, a NS4A domain, wherein the SMASh tag is fused to the C-terminus of the effector domain of the synTF, or b. a N-terminal SMASh domain comprising in a N-terminal to C-terminal order: at least one Linker, a NS3 domain, a NS3 partial helicase, a NS4 domain, and a NS3 cleavage site, wherein the SMASh tag is fused to the N-terminus of the synTF.

18. The synTF of claim 16, wherein in the absence of an inhibitor for the NS3 protease, the NS3 protease is active and self cleaves/uncouples from the synTF, thereby resulting in the SMASh tag targeted for degradation ("SMASh-degradation", synTF-on/TA-on/RP-on), wherein the synTF is active in the presence of the ligand for the cytosolic sequestering protein and the absence of the inhibitor for the NS3 protease; and wherein in the presence of an inhibitor for NS3 protease, NS3 protease activity is inhibited thereby resulting in the SMASh tagged synTF targeted for degradation ("synTF-degradation", synTF-OFF/TA-off/RP-off"), wherein the synTF is inactive in the absence of the ligand for the cytosolic sequestering protein and the presence of the inhibitor for the NS3 protease.

19. A system for controlling gene expression, comprising:

a. at least one synthetic transcription factor (synTF) comprising at least one DNA binding domain (DBD), a transcriptional effector domain (ED), and at least one cytosolic sequestering protein, wherein the ED is directly or indirectly coupled or linked to the DBD, wherein the cellular localization of the ED is regulated by the cytosolic sequestering protein, and wherein the cytosolic sequestering protein is an estrogen ligand binding domain (ERT) or a variant thereof, or comprises at least a portion of the estrogen receptor (ER), wherein the DBD can bind to a target DNA binding motif (DBM) located upstream of a promoter operatively linked to a gene, b. a nucleic acid construct comprising:

i. at least one target DNA binding motif (DBM) comprising a target nucleic acid for binding of the at least one DBD of the synTF, and ii. a promoter sequence located 3' of the at least one DBM, and iii. a gene of interest operatively linked to the promoter sequence, wherein for synTFs where the cellular localization of the ED linked to the DBD is regulated by the at least one cytosolic sequestering protein;

in the presence of a ligand for the at least one cytosolic sequestering protein, the ED coupled to the DBD of the synTF is not sequestered in the cytosol, enabling the DBD to bind to the DNA binding motif (DBM) and enabling the transcriptional effector domain (ED) to be in proximity to the promoter sequence to control the expression of the gene of interest ("ED-on"), or in the absence of the ligand for the at least one cytosolic sequestering protein, the ED coupled to the DBD of the synTF is sequestered in the cytosol, preventing the DBD of the synTF from binding to the DBM, and preventing the effector domain (ED) from being in proximity to the promoter sequence, preventing expression of the gene of interest ("ED-off").

20. The system of claim 19, wherein the transcriptional effector domain (ED) is a transcriptional activator (TA), wherein for synTFs where the cellular localization of the ED linked to the DBD is regulated by the at least one cytosolic sequestering protein;

i. in the presence of a ligand for the at least one cytosolic sequestering protein, the ED coupled to the DBD of the synTF is not sequestered in the cytosol, enabling the DBD to bind to the DNA binding motif (DBM) and enabling the TA domain to be in proximity to the promoter sequence to turn on expression of the gene of interest ("TA-on"), or ii. in the absence of the ligand for the at least one cytosolic sequestering protein, the ED coupled to the DBD of the synTF is sequestered in the cytosol, preventing the DBD from binding to the DBM, and preventing the TA domain from being in proximity to the promoter sequence, preventing expression of the gene of interest ("TA-off").

21. The system of claim 19, wherein the ED is a transcriptional repressor (TR), wherein for synTFs where the cellular localization of the ED linked to the DBD is regulated by the at least one cytosolic sequestering protein;

i. in the presence of a ligand for the at least one cytosolic sequestering protein, the ED coupled to the DBD of the synTF is not sequestered in the cytosol, enabling the DBD to bind to the DNA binding motif (DBM) and enabling the transcriptional repressor (TR) to be in proximity to the promoter sequence to turn off expression of the gene of interest ("TR-on" (no-expression)), or ii. in the absence of the ligand for the at least one cytosolic sequestering protein, the ED coupled to the DBD of the synTF is sequestered in the cytosol, preventing the DBD from binding to the DBM, and preventing the transcriptional repressor (TR) from being in proximity to the promoter sequence, allowing expression of the gene of interest ("TR-off" (yes-expression)).

22. The system of claim 19, wherein the at least one synTF further comprises a N-terminal or C-terminal Small molecule-Assisted Shutoff (SMASh) domain, wherein SMASh domain comprises a self-cleaving SMASh protease, a partial protease helical domain and a cofactor domain, wherein in the presence of an inhibitor to the SMASh protease, the SMASh protease activity is inhibited, resulting in the synTF being degraded and preventing the DBD of the synTF binding to the DBM and controlling the expression or repression of the gene of interest, wherein the synTF is inactive in the absence of a ligand for the cytosolic sequestering protein and the presence of the inhibitor for the SMASh protease ("synTF-degradation"; TA-off (no expression), TR-off (yes-expression)), wherein in the absence of an inhibitor to the SMASh protease, the SMASh protease is active and self cleaves/uncouples from the synTF, resulting the SMASh domain being targeted for degradation and, in the presence of the ligand for the cytosolic sequestering protein, allowing the DBD of the synTF to bind to the DBM and the ED of synTF to control the expression of the gene of interest, wherein the synTF is active in the presence of the ligand for the cytosolic sequestering protein and the absence of the inhibitor for the NS3 protease ("SMASh-degradation, TA-on (yes-expression), TR-on (no-expression)).

23. A cell comprising a. a first nucleic acid sequence comprising at least one target DNA binding motif (DBM) comprising a target nucleic acid for binding of the at least one DBD of a synTF, a promoter sequence located 3' of the at least one DBM, and a nucleic acid encoding a gene of interest (GOI) operatively linked to the promoter sequence, and b. a second nucleic acid sequence comprising a nucleic acid encoding a synthetic transcription factor (synTF) according to claim 1, operatively linked to an inducible or constitutive promoter.

* * * * *

SEQUENCE LISTING

```
Sequence total quantity: 380
SEQ ID NO: 1            moltype = AA  length = 176
FEATURE                 Location/Qualifiers
REGION                  1..176
                        note = synthetic polypeptide
source                  1..176
                        mol_type = protein
                        organism = synthetic construct
SEQUENCE: 1
SRPGERPFQC RICMRNFSEE ANLRRHTRTH TGEKPFQCRI CMRNFSDHSS LKRHLRTHTG  60
SQKPFQCRIC MRNFSQSANL LRHTRTHTGE KPFQCRICMR NFSDPSSLKR HLRTHTGSQK  120
PFQCRICMRN FSQQTNLTRH TRTHTGEKPF QCRICMRNFS DATQLVRHLR THLRGS      176

SEQ ID NO: 2            moltype = AA  length = 176
FEATURE                 Location/Qualifiers
REGION                  1..176
                        note = synthetic polypeptide
source                  1..176
                        mol_type = protein
                        organism = synthetic construct
SEQUENCE: 2
SRPGERPFQC RICMRNFSQR SSLVRHTRTH TGEKPFQCRI CMRNFSDKSV LARHLRTHTG  60
SQKPFQCRIC MRNFSQRSSL VRHTRTHTGE KPFQCRICMR NFSQRNNLGR HLRTHTGSQK  120
PFQCRICMRN FSTHAVLTRH TRTHTGEKPF QCRICMRNFS DRGNLTRHLR THLRGS      176

SEQ ID NO: 3            moltype = AA  length = 176
FEATURE                 Location/Qualifiers
REGION                  1..176
                        note = synthetic polypeptide
```

```
source                  1..176
                        mol_type = protein
                        organism = synthetic construct
SEQUENCE: 3
SRPGERPFQC RICMRNFSRR HGLDRHTRTH TGEKPFQCRI CMRNFSDHSS LKRHLRTHTG  60
SQKPFQCRIC MRNFSVRHNL TRHLRTHTGE KPFQCRICMR NFSDHSNLSR HLKTHTGSQK  120
PFQCRICMRN FSQRSSLVRH LRTHTGEKPF QCRICMRNFS ESGHLKRHLR THLRGS      176

SEQ ID NO: 4            moltype = AA  length = 903
FEATURE                 Location/Qualifiers
REGION                  1..903
                        note = synthetic polypeptide
REGION                  336..342
                        note = misc_feature - Xaa can be any naturally occurring
                         amino acid
REGION                  364..370
                        note = misc_feature - Xaa can be any naturally occurring
                         amino acid
REGION                  393..399
                        note = misc_feature - Xaa can be any naturally occurring
                         amino acid
REGION                  421..427
                        note = misc_feature - Xaa can be any naturally occurring
                         amino acid
REGION                  450..456
                        note = misc_feature - Xaa can be any naturally occurring
                         amino acid
REGION                  478..484
                        note = misc_feature - Xaa can be any naturally occurring
                         amino acid
source                  1..903
                        mol_type = protein
                        organism = synthetic construct
SEQUENCE: 4
MFEPKKKRKV FETSVPLYGF TSICGRRPEM EAAVSTIPRF LQSSSGSMLD GRFDPQSAAH  60
FFGVYDGHGG SQVANYCRER MHLALAEEIA KEKPMLCDGD TWLEKWKKAL FNSFLRVDSE  120
IESVAPETVG STSVVAVVFP SHIFVANCGD SRAVLCRGKT ALPLSVDHKP DREDEAARIE  180
AAGGKVIQWN GARVFGVLAM SRSIGDRYLK PSIIPDPEVT AVKRVKEDDC LILASDGVWD  240
VMTDEEACEM ARKRILLWHK KNAVAGDASL LADERRKEGK DPAAMSAAEY LSKLAIQRGS  300
KDNISVVVVD LKGGSGGSRP GERPFQCRIC MRNFSXXXXX XXHTRTHTGE KPFQCRICMR  360
NFSXXXXXXX HLRTHTGSQK PFQCRICMRN FSXXXXXXXH LRTHTGEKPF QCRICMRNFS  420
XXXXXXXHLK THTGSQKPFQ CRICMRNFSX XXXXXXHLRT HTGEKPFQCR ICMRNFSXXX  480
XXXXHLRTHL RGSPKKKRKV TCRGSGATNF SLLKQAGDVE ENPGPGHHDE FPTMVFPSGQ  540
ISQASALAPA PPQVLPQAPA PAPAPAMVSA LAQAPAPVPV LAPGPPQAVA PPAPKPTQAG  600
EGTLSEALLQ LQFDDEDLGA LLGNSTDPAV FTDLASVDNS EFQQLLNQGI PVAPHTTEPM  660
LMEYPEAITR LVTGAQRPPD PAPAPLGAPG LPNGLLSGDE DFSSIADMDF SALLSQISSG  720
GGSGQLTQDE FTQLSQSIAE FHTYQLGNGR CSSLLAQRIH APPETVWSVV RRFDRPQIYK  780
HFIKSCNVSE DFEMRVGCTR DVNVISGLPA NTSRERLDLL DDDRRVTGFS ITGGEHRLRN  840
YKSVTTVHRF EKEEEEERIW TVVLESYVVD VPEGNSEEDT RLFADTVIRL NLQKLASITE  900
AMN                                                               903

SEQ ID NO: 5            moltype = AA  length = 808
FEATURE                 Location/Qualifiers
REGION                  1..808
                        note = synthetic polypeptide
REGION                  336..342
                        note = misc_feature - Xaa can be any naturally occurring
                         amino acid
REGION                  364..370
                        note = misc_feature - Xaa can be any naturally occurring
                         amino acid
REGION                  393..399
                        note = misc_feature - Xaa can be any naturally occurring
                         amino acid
REGION                  421..427
                        note = misc_feature - Xaa can be any naturally occurring
                         amino acid
REGION                  450..456
                        note = misc_feature - Xaa can be any naturally occurring
                         amino acid
REGION                  478..484
                        note = misc_feature - Xaa can be any naturally occurring
                         amino acid
source                  1..808
                        mol_type = protein
                        organism = synthetic construct
SEQUENCE: 5
MFEPKKKRKV FETSVPLYGF TSICGRRPEM EAAVSTIPRF LQSSSGSMLD GRFDPQSAAH  60
FFGVYDGHGG SQVANYCRER MHLALAEEIA KEKPMLCDGD TWLEKWKKAL FNSFLRVDSE  120
```

```
IESVAPETVG STSVVAVVFP SHIFVANCGD SRAVLCRGKT ALPLSVDHKP DREDEAARIE  180
AAGGKVIQWN GARVFGVLAM SRSIGDRYLK PSIIPDPEVT AVKRVKEDDC LILASDGVWD  240
VMTDEEACEM ARKRILLWHK KNAVAGDASL LADERRKEGK DPAAMSAAEY LSKLAIQRGS  300
KDNISVVVVD LKGGSGGSRP GERPFQCRIC MRNFSXXXXX XXHTRTHTGE KPFQCRICMR  360
NFSXXXXXXX HLRTHTGSQK PFQCRICMRN FSXXXXXXXH LRTHTGEKPF QCRICMRNFS  420
XXXXXXXHLK THTGSQKPFQ CRICMRNFSX XXXXXXHLRT HTGEKPFQCR ICMRNFSXXX  480
XXXXHLRTHL RGSTCRGSGA TNFSLLKQAG DVEENPGPGH HPKKKRKVDA KSLTAWSRTL  540
VTFKDVFVDF TREEWKLLDT AQQILYRNVM LENYKNLVSL GYQLTKPDVI LRLEKGEEPW  600
LVEREIHQET HPDSETAFEI KSSVGGGSGQ LTQDEFTQLS QSIAEFHTYQ LGNGRCSSLL  660
AQRIHAPPET VWSVVRRFDR PQIYKHFIKS CNVSEDFEMR VGCTRDVNVI SGLPANTSRE  720
RLDLLDDDRR VTGFSITGGE HRLRNYKSVT TVHRFEKEEE EERIWTVVLE SYVVDVPEGN  780
SEEDTRLFAD TVIRLNLQKL ASITEAMN                                     808

SEQ ID NO: 6            moltype = AA  length = 692
FEATURE                 Location/Qualifiers
REGION                  1..692
                        note = synthetic polypeptide
REGION                  20..26
                        note = misc_feature - Xaa can be any naturally occurring
                         amino acid
REGION                  48..54
                        note = misc_feature - Xaa can be any naturally occurring
                         amino acid
REGION                  77..83
                        note = misc_feature - Xaa can be any naturally occurring
                         amino acid
REGION                  105..111
                        note = misc_feature - Xaa can be any naturally occurring
                         amino acid
REGION                  134..140
                        note = misc_feature - Xaa can be any naturally occurring
                         amino acid
REGION                  162..168
                        note = misc_feature - Xaa can be any naturally occurring
                         amino acid
source                  1..692
                        mol_type = protein
                        organism = synthetic construct
SEQUENCE: 6
MSRPGERPFQ CRICMRNFSX XXXXXXHTRT HTGEKPFQCR ICMRNFSXXX XXXXHLRTHT  60
GSQKPFQCRI CMRNFSXXXX XXXHLRTHTG EKPFQCRICM RNFSXXXXXX XHLKTHTGSQ  120
KPFQCRICMR NFSXXXXXXX HLRTHTGEKP FQCRICMRNF SXXXXXXXHL RTHLRGSTCR  180
DEFPTMVFPS GQISQASALA PAPPQVLPQA PAPAPAPAMV SALAQAPAPV PVLAPGPPQA  240
VAPPAPKPTQ AGEGTLSEAL LQLQFDDEDL GALLGNSTDP AVFTDLASVD NSEFQQLLNQ  300
GIPVAPHTTE PMLMEYPEAI TRLVTGAQRP PDPAPAPLGA PGLPNGLLSG DEDFSSIADM  360
DFSALLSQIS SQLCVRGSSA GDMRAANLWP SPLMIKRSKK NSLALSLTAD QMVSALLDAE  420
PPILYSEYDP TRPFSEASMM GLLTNLADRE LVHMINWAKR VPGFVDLTLH DQVHLLECAW  480
LEILMIGLVW RSMEHPVKLL FAPNLLLDRN QGKCVEGMVE IFDMLLATSS RFRMMNLQGE  540
EFVCLKSIIL LNSGVYTFLS STLKSLEEKD HIHRVLDKIT DTLIHLMAKA GLTLQQQHQR  600
LAQLLLILSH IRHMSNKGME HLYSMKCKNV VPLYDLLLEA ADAHRLHAPT SRGGASVEET  660
DQSHLATAGS TSSHSLQKYY ITGEAEGFPA TA                                692

SEQ ID NO: 7            moltype = AA  length = 605
FEATURE                 Location/Qualifiers
REGION                  1..605
                        note = synthetic polypeptide
REGION                  127..133
                        note = misc_feature - Xaa can be any naturally occurring
                         amino acid
REGION                  155..161
                        note = misc_feature - Xaa can be any naturally occurring
                         amino acid
REGION                  184..190
                        note = misc_feature - Xaa can be any naturally occurring
                         amino acid
REGION                  212..218
                        note = misc_feature - Xaa can be any naturally occurring
                         amino acid
REGION                  241..247
                        note = misc_feature - Xaa can be any naturally occurring
                         amino acid
REGION                  269..275
                        note = misc_feature - Xaa can be any naturally occurring
                         amino acid
source                  1..605
                        mol_type = protein
                        organism = synthetic construct
SEQUENCE: 7
MDAKSLTAWS RTLVTFKDVF VDFTREEWKL LDTAQQILYR NVMLENYKNL VSLGYQLTKP  60
```

-continued

```
DVILRLEKGE EPWLVEREIH QETHPDSETA FEIKSSVLEG GGGSGTCRSR PGERPFQCRI  120
CMRNFSXXXX XXXHTRTHTG EKPFQCRICM RNFSXXXXXX XHLRTHTGSQ KPFQCRICMR  180
NFSXXXXXXX HLRTHTGEKP FQCRICMRNF SXXXXXXXHL KTHTGSQKPF QCRICMRNFS  240
XXXXXXXHLR THTGEKPFQC RICMRNFSXX XXXXXHLRTH LRGSQLCVRG SSAGDMRAAN  300
LWPSPLMIKR SKKNSLALSL TADQMVSALL DAEPPILYSE YDPTRPFSEA SMMGLLTNLA  360
DRELVHMINW AKRVPGFVDL TLHDQVHLLE CAWLEILMIG LVWRSMEHPV KLLFAPNLLL  420
DRNQGKCVEG MVEIFDMLLA TSSRFRMMNL QGEEFVCLKS IILLNSGVYT FLSSTLKSLE  480
EKDHIHRVLD KITDTLIHLM AKAGLTLQQQ HQRLAQLLLI LSHIRHMSNK GMEHLYSMKC  540
KNVVPLYDLL LEAADAHRLH APTSRGGASV EETDQSHLAT AGSTSSHSLQ KYYITGEAEG  600
FPATA                                                              605

SEQ ID NO: 8            moltype = AA  length = 704
FEATURE                 Location/Qualifiers
REGION                  1..704
                        note = synthetic polypeptide
REGION                  20..26
                        note = misc_feature - Xaa can be any naturally occurring
                         amino acid
REGION                  48..54
                        note = misc_feature - Xaa can be any naturally occurring
                         amino acid
REGION                  77..83
                        note = misc_feature - Xaa can be any naturally occurring
                         amino acid
REGION                  105..111
                        note = misc_feature - Xaa can be any naturally occurring
                         amino acid
REGION                  134..140
                        note = misc_feature - Xaa can be any naturally occurring
                         amino acid
REGION                  162..168
                        note = misc_feature - Xaa can be any naturally occurring
                         amino acid
source                  1..704
                        mol_type = protein
                        organism = synthetic construct
SEQUENCE: 8
MSRPGERPFQ CRICMRNFSX XXXXXXHTRT HTGEKPFQCR ICMRNFSXXX XXXXHLRTHT  60
GSQKPFQCRI CMRNFSXXXX XXXHLRTHTG EKPFQCRICM RNFSXXXXXX XHLKTHTGSQ  120
KPFQCRICMR NFSXXXXXXX HLRTHTGEKP FQCRICMRNF SXXXXXXXHL RTHLRGSTCR  180
DYKDHDGDYK DHDIDYKDDD DKMAPKKKRK VGIHGVPGGL EGGGGSGGTE DVVCCHSIYG  240
KKKGDIDTYR YIGSSGTGCV VIVGRIVLSG SGTSAPITAY AQQTRGLLGC IITSLTGRDK  300
NQVEGEVQIV STATQTFLAT CINGVCWAVY HGAGTRTIAS PKGPVIQMYT NVDQDLVGWP  360
APQGSRSLTP CTCGSSDLYL VTRHADVIPV RRRGDSRGSL LSPRPISYLK GSSGGPLLCP  420
AGHAVGLFRA AVCTRGVAKA VDFIPVENLE TTMRSPVFTD NSSPPAVTLT HPITKIDREV  480
LYQEFDEMEE CSQHYPYDVP DYAGGGGSGG TDEFPTMVFP SGQISQASAL APAPPQVLPQ  540
APAPAPAPAM VSALAQAPAP VPVLAPGPPQ AVAPPAPKPT QAGEGTLSEA LLQLQFDDED  600
LGALLGNSTD PAVFTDLASV DNSEFQQLLN QGIPVAPHTT EPMLMEYPEA ITRLVTGAQR  660
PPDPAPAPLG APGLPNGLLS GDEDFSSIAD MDFSALLSQI SSQL                   704

SEQ ID NO: 9            moltype = AA  length = 609
FEATURE                 Location/Qualifiers
REGION                  1..609
                        note = synthetic polypeptide
REGION                  450..456
                        note = misc_feature - Xaa can be any naturally occurring
                         amino acid
REGION                  478..484
                        note = misc_feature - Xaa can be any naturally occurring
                         amino acid
REGION                  507..513
                        note = misc_feature - Xaa can be any naturally occurring
                         amino acid
REGION                  535..541
                        note = misc_feature - Xaa can be any naturally occurring
                         amino acid
REGION                  564..570
                        note = misc_feature - Xaa can be any naturally occurring
                         amino acid
REGION                  592..598
                        note = misc_feature - Xaa can be any naturally occurring
                         amino acid
source                  1..609
                        mol_type = protein
                        organism = synthetic construct
SEQUENCE: 9
MDAKSLTAWS RTLVTFKDVF VDFTREEWKL LDTAQQILYR NVMLENYKNL VSLGYQLTKP  60
DVILRLEKGE EPWLVEREIH QETHPDSETA FEIKSSVTCR DYKDHDGDYK DHDIDYKDDD  120
DKMAPKKKRK VGIHGVPGGL EGGGGSGGTE DVVCCHSIYG KKKGDIDTYR YIGSSGTGCV  180
```

-continued

```
VIVGRIVLSG SGTSAPITAY AQQTRGLLGC IITSLTGRDK NQVEGEVQIV STATQTFLAT  240
CINGVCWAVY HGAGTRTIAS PKGPVIQMYT NVDQDLVGWP APQGSRSLTP CTCGSSDLYL  300
VTRHADVIPV RRRGDSRGSL LSPRPISYLK GSSGGPLLCP AGHAVGLFRA AVCTRGVAKA  360
VDFIPVENLE TTMRSPVFTD NSSPPAVTLT HPITKIDREV LYQEFDEMEE CSQHYPYDVP  420
DYAGGGGSGG TSRPGERPFQ CRICMRNFSX XXXXXXHTRT HTGEKPFQCR ICMRNFSXXX  480
XXXXHLRTHT GSQKPFQCRI CMRNFSXXXX XXXHLRTHTG EKPFQCRICM RNFSXXXXXX  540
XHLKTHTGSQ KPFQCRICMR NFSXXXXXXX HLRTHTGEKP FQCRICMRNF SXXXXXXXHL  600
RTHLRGSQL                                                          609

SEQ ID NO: 10          moltype = AA  length = 998
FEATURE                Location/Qualifiers
REGION                 1..998
                       note = synthetic polypeptide
REGION                 20..26
                       note = misc_feature - Xaa can be any naturally occurring
                        amino acid
REGION                 48..54
                       note = misc_feature - Xaa can be any naturally occurring
                        amino acid
REGION                 77..83
                       note = misc_feature - Xaa can be any naturally occurring
                        amino acid
REGION                 105..111
                       note = misc_feature - Xaa can be any naturally occurring
                        amino acid
REGION                 134..140
                       note = misc_feature - Xaa can be any naturally occurring
                        amino acid
REGION                 162..168
                       note = misc_feature - Xaa can be any naturally occurring
                        amino acid
source                 1..998
                       mol_type = protein
                       organism = synthetic construct
SEQUENCE: 10
MSRPGERPFQ CRICMRNFSX XXXXXXHTRT HTGEKPFQCR ICMRNFSXXX XXXXHLRTHT  60
GSQKPFQCRI CMRNFSXXXX XXXHLRTHTG EKPFQCRICM RNFSXXXXXX XHLKTHTGSQ  120
KPFQCRICMR NFSXXXXXXX HLRTHTGEKP FQCRICMRNF SXXXXXXXHL RTHLRGSTCR  180
DEFPTMVFPS GQISQASALA PAPPQVLPQA PAPAPAPAMV SALAQAPAPV PVLAPGPPQA  240
VAPPAPKPTQ AGEGTLSEAL LQLQFDDEDL GALLGNSTDP AVFTDLASVD NSEFQQLLNQ  300
GIPVAPHTTE PMLMEYPEAI TRLVTGAQRP PDPAPAPLGA PGLPNGLLSG DEDFSSIADM  360
DFSALLSQIS SQLCVRGSSA GDMRAANLWP SPLMIKRSKK NSLALSLTAD QMVSALLDAE  420
PPILYSEYDP TRPFSEASMM GLLTNLADRE LVHMINWAKR VPGFVDLTLH DQVHLLECAW  480
LEILMIGLVW RSMEHPVKLL FAPNLLLDRN QGKCVEGMVE IFDMLLATSS RFRMMNLQGE  540
EFVCLKSIIL LNSGVYTFLS STLKSLEEKD HIHRVLDKIT DTLIHLMAKA GLTLQQQHQR  600
LAQLLLILSH IRHMSNKGME HLYSMKCKNV VPLYDLLLEA ADAHRLHAPT SRGGASVEET  660
DQSHLATAGS TSSHSLQKYY ITGEAEGFPA TAPGDEMEEC SQHLPGAGSS GDIMDYKDDD  720
DKGSSGTGSG SGTSAPITAY AQQTRGLLGC IITSLTGRDK NQVEGEVQIV STATQTFLAT  780
CINGVCWAVY HGAGTRTIAS PKGPVIQMYT NVDQDLVGWP APQGSRSLTP CTCGSSDLYL  840
VTRHADVIPV RRRGDSRGSL LSPRPISYLK GSSGGPLLCP AGHAVGLFRA AVCTRGVAKA  900
VDFIPVENLE TTMRSPVFTD NSSPPAVTLT HPITKIDTKY IMTCMSADLE VVTSTWVLVG  960
GVLAALAAYC LSTGCVVIVG RIVLSGKPAI IPDREVLY                          998

SEQ ID NO: 11          moltype = AA  length = 997
FEATURE                Location/Qualifiers
REGION                 1..997
                       note = synthetic polypeptide
REGION                 325..331
                       note = misc_feature - Xaa can be any naturally occurring
                        amino acid
REGION                 353..359
                       note = misc_feature - Xaa can be any naturally occurring
                        amino acid
REGION                 382..388
                       note = misc_feature - Xaa can be any naturally occurring
                        amino acid
REGION                 410..416
                       note = misc_feature - Xaa can be any naturally occurring
                        amino acid
REGION                 439..445
                       note = misc_feature - Xaa can be any naturally occurring
                        amino acid
REGION                 467..473
                       note = misc_feature - Xaa can be any naturally occurring
                        amino acid
source                 1..997
                       mol_type = protein
                       organism = synthetic construct
SEQUENCE: 11
```

-continued

```
MDYKDDDDKG SSGTGSGSGT SAPITAYAQQ TRGLLGCIIT SLTGRDKNQV EGEVQIVSTA  60
TQTFLATCIN GVCWAVYHGA GTRTIASPKG PVIQMYTNVD QDLVGWPAPQ GSRSLTPCTC  120
GSSDLYLVTR HADVIPVRRR GDSRGSLLSP RPISYLKGSS GGPLLCPAGH AVGLFRAAVC  180
TRGVAKAVDF IPVENLETTM RSPVFTDNSS PPAVTLTHPI TKIDTKYIMT CMSADLEVVT  240
STWVLVGGVL AALAAYCLST GCVVIVGRIV LSGKPAGSSG SSIIPDREVL YQEFEDVVPC  300
SMGSPGSRPG ERPFQCRICM RNFSXXXXXX XHTRTHTGEK PFQCRICMRN FSXXXXXXXH  360
LRTHTGSQKP FQCRICMRNF SXXXXXXXHL RTHTGEKPFQ CRICMRNFSX XXXXXXHLKT  420
HTGSQKPFQC RICMRNFSXX XXXXXHLRTH TGEKPFQCRI CMRNFSXXXX XXXHLRTHLR  480
GSTCRDEFPT MVFPSGQISQ ASALAPAPPQ VLPQAPAPAP APAMVSALAQ APAPVPVLAP  540
GPPQAVAPPA PKPTQAGEGT LSEALLQLQF DDEDLGALLG NSTDPAVFTD LASVDNSEFQ  600
QLLNQGIPVA PHTTEPMLME YPEAITRLVT GAQRPPDPAP APLGAPGLPN GLLSGDEDFS  660
SIADMDFSAL LSQISSQLCV RGSSAGDMRA ANLWPSPLMI KRSKKNSLAL SLTADQMVSA  720
LLDAEPPILY SEYDPTRPFS EASMMGLLTN LADRELVHMI NWAKRVPGFV DLTLHDQVHL  780
LECAWLEILM IGLVWRSMEH PVKLLFAPNL LLDRNQGKCV EGMVEIFDML LATSSRFRMM  840
NLQGEEFVCL KSIILLNSGV YTFLSSTLKS LEEKDHIHRV LDKITDTLIH LMAKAGLTLQ  900
QQHQRLAQLL LILSHIRHMS NKGMEHLYSM KCKNVVPLYD LLLEAADAHR LHAPTSRGGA  960
SVEETDQSHL ATAGSTSSHS LQKYYITGEA EGFPATA                          997

SEQ ID NO: 12           moltype = AA  length = 728
FEATURE                 Location/Qualifiers
REGION                  1..728
                        note = synthetic polypeptide
REGION                  71..77
                        note = misc_feature - Xaa can be any naturally occurring
                         amino acid
REGION                  99..105
                        note = misc_feature - Xaa can be any naturally occurring
                         amino acid
REGION                  128..134
                        note = misc_feature - Xaa can be any naturally occurring
                         amino acid
REGION                  156..162
                        note = misc_feature - Xaa can be any naturally occurring
                         amino acid
REGION                  185..191
                        note = misc_feature - Xaa can be any naturally occurring
                         amino acid
REGION                  213..219
                        note = misc_feature - Xaa can be any naturally occurring
                         amino acid
source                  1..728
                        mol_type = protein
                        organism = synthetic construct
SEQUENCE: 12
MDYKDHDGDY KDHDIDYKDD DDKMAPKKKR KVGIHGVPGG LEGGGGSGGT ASSRPGERPF  60
QCRICMRNFS XXXXXXXHTR THTGEKPFQC RICMRNFSXX XXXXXHLRTH TGSQKPFQCR  120
ICMRNFSXXX XXXXHLRTHT GEKPFQCRIC MRNFSXXXXX XXHLKTHTGS QKPFQCRICM  180
RNFSXXXXXX XHLRTHTGEK PFQCRICMRN FSXXXXXXXH LRTHLRGSTC RDEFPTMVFP  240
SGQISQASAL APAPPQVLPQ APAPAPAPAM VSALAQAPAP VPVLAPGPPQ AVAPPAPKPT  300
QAGEGTLSEA LLQLQFDDED LGALLGNSTD PAVFTDLASV DNSEFQQLLN QGIPVAPHTT  360
EPMLMEYPEA ITRLVTGAQR PPDPAPAPLG APGLPNGLLS GDEDFSSIAD MDFSALLSQI  420
SSPGDEMEEC SQHLPGAGSS GDIMDYKDDD DKGSSGTGSG SGTSAPITAY AQQTRGLLGC  480
IITSLTGRDK NQVEGEVQIV STATQTFLAT CINGVCWAVY HGAGTRTIAS PKGPVIQMYT  540
NVDQDLVGWP APQGSRSLTP CTCGSSDLYL VTRHADVIPV RRRGDSRGSL LSPRPISYLK  600
GSSGGPLLCP AGHAVGLFRA AVCTRGVAKA VDFIPVENLE TTMRSPVFTD NSSPPAVTLT  660
HPITKIDTKY IMTCMSADLE VVTSTWVLVG GVLAALAAYC LSTGCVVIVG RIVLSGKPAI  720
IPDREVLY                                                          728

SEQ ID NO: 13           moltype = AA  length = 878
FEATURE                 Location/Qualifiers
REGION                  1..878
                        note = synthetic polypeptide
REGION                  94..100
                        note = misc_feature - Xaa can be any naturally occurring
                         amino acid
REGION                  122..128
                        note = misc_feature - Xaa can be any naturally occurring
                         amino acid
REGION                  151..157
                        note = misc_feature - Xaa can be any naturally occurring
                         amino acid
REGION                  179..185
                        note = misc_feature - Xaa can be any naturally occurring
                         amino acid
REGION                  208..214
                        note = misc_feature - Xaa can be any naturally occurring
                         amino acid
REGION                  236..242
                        note = misc_feature - Xaa can be any naturally occurring
```

```
                         amino acid
source                  1..878
                        mol_type = protein
                        organism = synthetic construct
SEQUENCE: 13
MLAVSVTFED VAVLFTRDEW KKLDLSQRSL YREVMLENYS NLASMAGFLF TKPKVISLLQ  60
QGEDPWGGSG SGSACSRPGE RPFQCRICMR NFSXXXXXXX HTRTHTGEKP FQCRICMRNF  120
SXXXXXXXHL RTHTGSQKPF QCRICMRNFS XXXXXXXHLR THTGEKPFQC RICMRNFSXX  180
XXXXXHLKTH TGSQKPFQCR ICMRNFSXXX XXXXHLRTHT GEKPFQCRIC MRNFSXXXXX  240
XXHLRTHLRG SQLCVRGSSA GDMRAANLWP SPLMIKRSKK NSLALSLTAD QMVSALLDAE  300
PPILYSEYDP TRPFSEASMM GLLTNLADRE LVHMINWAKR VPGFVDLTLH DQVHLLECAW  360
LEILMIGLVW RSMEHPVKLL FAPNLLLDRN QGKCVEGMVE IFDMLLATSS RFRMMNLQGE  420
EFVCLKSIIL LNSGVYTFLS STLKSLEEKD HIHRVLDKIT DTLIHLMAKA GLTLQQQHQR  480
LAQLLLILSH IRHMSNKGME HLYSMKCKNV VPLYDLLLEA ADAHRLHAPT SRGGASVEET  540
DQSHLATAGS TSSHSLQKYY ITGEAEGFPA TAPGDEMEEC SQHLPGAGSS GDIMDYKDDD  600
DKGSSGTGSG SGTSAPITAY AQQTRGLLGC IITSLTGRDK NQVEGEVQIV STATQTFLAT  660
CINGVCWAVY HGAGTRTIAS PKGPVIQMYT NVDQDLVGWP APQGSRSLTP CTCGSSDLYL  720
VTRHADVIPV RRRGDSRGSL LSPRPISYLK GSSGGPLLCP AGHAVGLFRA AVCTRGVAKA  780
VDFIPVENLE TTMRSPVFTD NSSPPAVTLT HPITKIDTKY IMTCMSADLE VVTSTWVLVG  840
GVLAALAAYC LSTGCVVIVG RIVLSGKPAI IPDREVLY                          878

SEQ ID NO: 14           moltype = AA  length = 1003
FEATURE                 Location/Qualifiers
REGION                  1..1003
                        note = synthetic polypeptide
REGION                  219..225
                        note = misc_feature - Xaa can be any naturally occurring
                         amino acid
REGION                  247..253
                        note = misc_feature - Xaa can be any naturally occurring
                         amino acid
REGION                  276..282
                        note = misc_feature - Xaa can be any naturally occurring
                         amino acid
REGION                  304..310
                        note = misc_feature - Xaa can be any naturally occurring
                         amino acid
REGION                  333..339
                        note = misc_feature - Xaa can be any naturally occurring
                         amino acid
REGION                  361..367
                        note = misc_feature - Xaa can be any naturally occurring
                         amino acid
source                  1..1003
                        mol_type = protein
                        organism = synthetic construct
SEQUENCE: 14
MGKKTKRTAD SSSSEDEEEY VVEKVLDRRV VKGQVEYLLK WKGFSEEHNT WEPEKNLDCP  60
ELISEFMKKY KKMKEGENNK PREKSESNKR KSNFSNSADD IKSKKKREQS NDIARGFERG  120
LEPEKIIGAT DSCGDLMFLM KWKDTDEADL VLAKEANVKC PQIVIAFYEE RLTWHAYPED  180
AENKEKETAK SGGSGSGSAC SRPGERPFQC RICMRNFSXX XXXXXHTRTH TGEKPFQCRI  240
CMRNFSXXXX XXXHLRTHTG SQKPFQCRIC MRNFSXXXXX XXHLRTHTGE KPFQCRICMR  300
NFSXXXXXXX HLKTHTGSQK PFQCRICMRN FSXXXXXXXH LRTHTGEKPF QCRICMRNFS  360
XXXXXXXHLR THLRGSQLCV RGSSAGDMRA ANLWPSPLMI KRSKKNSLAL SLTADQMVSA  420
LLDAEPPILY SEYDPTRPFS EASMMGLLTN LADRELVHMI NWAKRVPGFV DLTLHDQVHL  480
LECAWLEILM IGLVWRSMEH PVKLLFAPNL LLDRNQGKCV EGMVEIFDML LATSSRFRMM  540
NLQGEEFVCL KSIILLNSGV YTFLSSTLKS LEEKDHIHRV LDKITDTLIH LMAKAGLTLQ  600
QQHQRLAQLL LILSHIRHMS NKGMEHLYSM KCKNVVPLYD LLLEAADAHR LHAPTSRGGA  660
SVEETDQSHL ATAGSTSSHS LQKYYITGEA EGFPATAPGD EMEECSQHLP GAGSSGDIMD  720
YKDDDDKGSS GTGSGSGTSA PITAYAQQTR GLLGCIITSL TGRDKNQVEG EVQIVSTATQ  780
TFLATCINGV CWAVYHGAGT RTIASPKGPV IQMYTNVDQD LVGWPAPQGS RSLTPCTCGS  840
SDLYLVTRHA DVIPVRRRGD SRGSLLSPRP ISYLKGSSGG PLLCPAGHAV GLFRAAVCTR  900
GVAKAVDFIP VENLETTMRS PVFTDNSSPP AVTLTHPITK IDTKYIMTCM SADLEVVTST  960
WVLVGGVLAA LAAYCLSTGC VVIVGRIVLS GKPAIIPDRE VLY                    1003

SEQ ID NO: 15           moltype = AA  length = 1253
FEATURE                 Location/Qualifiers
REGION                  1..1253
                        note = synthetic polypeptide
REGION                  469..475
                        note = misc_feature - Xaa can be any naturally occurring
                         amino acid
REGION                  497..503
                        note = misc_feature - Xaa can be any naturally occurring
                         amino acid
REGION                  526..532
                        note = misc_feature - Xaa can be any naturally occurring
                         amino acid
REGION                  554..560
```

-continued

```
                        note = misc_feature - Xaa can be any naturally occurring
                         amino acid
REGION                  583..589
                        note = misc_feature - Xaa can be any naturally occurring
                         amino acid
REGION                  611..617
                        note = misc_feature - Xaa can be any naturally occurring
                         amino acid
source                  1..1253
                        mol_type = protein
                        organism = synthetic construct
SEQUENCE: 15
MSEREVSTAP AGTDMPAAKK QKLSSDENSN PDLSGDENDD AVSIESGTNT ERPDTPTNTP  60
NAPGRKSWGK GKWKSKKCKY SFKCVNSLKE DHNQPLFGVQ FNWHSKEGDP LVFATVGSNR  120
VTLYECHSQG EIRLLQSYVD ADADENFYTC AWTYDSNTSH PLLAVAGSRG IIRIINPITM  180
QCIKHYVGHG NAINELKFHP RDPNLLLSVS KDHALRLWNI QTDTLVAIFG GVEGHRDEVL  240
SADYDLLGEK IMSCGMDHSL KLWRINSKRM MNAIKESYDY NPNKTNRPFI SQKIHFPDFS  300
TRDIHRNYVD CVRWLGDLIL SKSCENAIVC WKPGKMEDDI DKIKPSESNV TILGRFDYSQ  360
CDIWYMRFSM DFWQKMLALG NQVGKLYVWD LEVEDPHKAK CTTLTHHKCG AAIRQTSFSR  420
DSSILIAVCD DASIWRWDRL RGGSGSGSAC SRPGERPFQC RICMRNFSXX XXXXXHTRTH  480
TGEKPFQCRI CMRNFSXXXX XXXHLRTHTG SQKPFQCRIC MRNFSXXXXX XXHLRTHTGE  540
KPFQCRICMR NFSXXXXXXX HLKTHTGSQK PFQCRICMRN FSXXXXXXXH LRTHTGEKPF  600
QCRICMRNFS XXXXXXXHLR THLRGSQLCV RGSSAGDMRA ANLWPSPLMI KRSKKNSLAL  660
SLTADQMVSA LLDAEPPILY SEYDPTRPFS EASMMGLLTN LADRELVHMI NWAKRVPGFV  720
DLTLHDQVHL LECAWLEILM IGLVWRSMEH PVKLLFAPNL LLDRNQGKCV EGMVEIFDML  780
LATSSRFRMM NLQGEEFVCL KSIILLNSGV YTFLSSTLKS LEEKDHIHRV LDKITDTLIH  840
LMAKAGLTLQ QQHQRLAQLL LILSHIRHMS NKGMEHLYSM KCKNVVPLYD LLLEAADAHR  900
LHAPTSRGGA SVEETDQSHL ATAGSTSSHS LQKYYITGEA EGFPATAPGD EMEECSQHLP  960
GAGSSGDIMD YKDDDDKGSS GTGSGSGTSA PITAYAQQTR GLLGCIITSL TGRDKNQVEG  1020
EVQIVSTATQ TFLATCINGV CWAVYHGAGT RTIASPKGPV IQMYTNVDQD LVGWPAPQGS  1080
RSLTPCTCGS SDLYLVTRHA DVIPVRRRGD SRGSLLSPRP ISYLKGSSGG PLLCPAGHAV  1140
GLFRAAVCTR GVAKAVDFIP VENLETTMRS PVFTDNSSPP AVTLTHPITK IDTKYIMTCM  1200
SADLEVVTST WVLVGGVLAA LAAYCLSTGC VVIVGRIVLS GKPAIIPDRE VLY        1253

SEQ ID NO: 16           moltype = DNA  length = 11661
FEATURE                 Location/Qualifiers
misc_feature            1..11661
                        note = synthetic vector
source                  1..11661
                        mol_type = other DNA
                        organism = synthetic construct
SEQUENCE: 16
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
```

-continued

```
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtcttttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggcccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
```

-continued

```
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc ccgataaaa taaaagattt  7800
tatttagtct ccagaaaaag gggggaatga aagaccccac ctgtaggtta tggcaagcta  7860
gctgcagtaa cgccattatt gcaaggcatg gaaaaatacc aaaccaagaa tagagaagtt  7920
cagatcaagg gcgggtacat gaaaatagct aacgtagggc caaacaggat atctgcggtg  7980
agcagtttcg gccccggccc ggggccaaga acagatggtc accgcagttt cggccccggc  8040
ccgaggccaa gagcagatgg tccccagata tggcccaacc ctcagcagtt tcttaagacc  8100
catcagatgt ttccaggctc ccccaaggac ctgaaatgac cctgcgcctt atttgaatta  8160
accaatcagc ctgcttctcg cttctgttcg cgcgcttctg cttcccgagc tctataaaag  8220
agctcacaac ccctcactcg gcgcgccagt cctccgacag actgagtcgc ccgggacgcg  8280
tttaattaag ccgccaccat gttcgaaccc aagaagaaga gaaaggtgtt cgaaactagt  8340
gtgcccctgt atggcttcac ttccatttgt ggccgacggc ctgaaatgga agccgcggtg  8400
tcaaccatac cacggtttct gcagagctca tcaggctcca tgctggacgg acgctttgat  8460
ccacagtctg ccgcacattt ctttggagtc tacgacggcc acgggggcag ccaggtcgcc  8520
aactactgca gggaaaggat gcatttggca cttgccgaag agatcgccaa agagaagccc  8580
atgttgtgtg atggggatac ctggctggag aagtggaaga aagcgctttt taactctttt  8640
ctgagagtgg attctgagat agaatctgtc gcacccgaga ccgtgggcag cacatccgtc  8700
gtagccgtag tgtttccctc ccacatattc gtcgccaact gcggcgacag tcgagccgtc  8760
ctctgccgag gtaagaccgc cctgcctctg agtgttgacc ataagcccga ccgggaggat  8820
gaggccgccc gaatcgaggc cgccggtgga aaagtcatcc aatggaacgg cgcaagagtg  8880
ttcggcgtgc tggcgatgtc caggagcatt ggagaccggt acctgaagcc cagcataatc  8940
ccagatcccg aagtgaccgc agtcaagagg gtgaaagagg acgattgtct gatcctggct  9000
agcgatggcg tatgggacgt gatgactgat gaggaggcgt gtgaaatggc ccgcaagcga  9060
atcctgctgt ggcataaaaa aaacgcagtc gcgggggacg cttctcttct ggcagacgaa  9120
aggcgcaaag aaggtaaaga cccggctgct atgagcgccg ccgaatatct cagtaagctg  9180
gcaattcagc gagggtccaa agacaacatt tccgtggtcg tggtagacct caaaggcggt  9240
tccggcggtt ctagaccagg cgaacgaccg tttcaatgcc ggatatgtat gaggaacttc  9300
tccgaggagg caaacttgag gcgccacacc cgaacacata caggagaaaa gccattccaa  9360
tgtcgaattt gtatgcgcaa tttttcagat cactcaagcc tcaagcgaca cctccgcaca  9420
catactggtt cacagaagcc ctttcagtgc aggatttgta tgcgcaactt tagccaatca  9480
gcgaaccttt tgcggcacac tagaacgcat acaggtgaga agcctttcca gtgtcgcatc  9540
tgtatgcgga acttcagcga ccccagttca ttgaagaggc atttgcgaac tcacaccggt  9600
tctcaaaaac cttttcagtg ccgaatttgt atgcgcaact tcagccaaca aacaaatttg  9660
acgagacaca cgcgcacgca caccggggaa aaaccgtttc aatgtcgaat ctgcatgcgc  9720
aattttagcg atgcgacaca acttgttagg catctgcgca cacacttgcg ggatccccg  9780
aagaaaaaac ggaaagtgac ctgcagggga agcggagcta ctaacttcag cctgctgaag  9840
caggctggag acgtggagga gaaccctgga cctggtcacc atgatgagtt tcccaccatg  9900
gtgtttcctt ctgggcagat cagccaggcc tcggccttgg ccccggcccc tccccaagtc  9960
ctgccccagg ctccagcccc tgcccctgct ccagccatgg tatcagctct ggcccaggcc  10020
ccagcccctg tcccagtcct agccccaggc cctcctcagg ctgtggcccc acctgccccc  10080
aagcccaccc aggctgggga aggaacgctg tcagaggccc tgctgcagct gcagtttgat  10140
gatgaagacc tgggggcctt gcttggcaac agcacagacc cagctgtgtt cacagacctg  10200
gcatccgtcg acaactccga gtttcagcag ctgctgaacc agggcatacc tgtggccccc  10260
cacacaactg agcccatgct gatggagtac cctgaggcta taactcgcct agtgacaggg  10320
gcccagaggc cccccgaccc agctcctgct ccactggggg ccccggggct ccccaatggc  10380
ctcctttcag gagatgaaga cttctcctcc attgcggaca tggacttctc agccctgctg  10440
agtcagatca gctccggtgg tggcagcggt caattgactc aagacgaatt cacccaactc  10500
tcccaatcaa tcgccgagtt ccacacgtac caactcggta acggccgttg ctcatctctc  10560
ctagctcagc gaatccacgc gccgccggaa acagtatggt ccgtggtgag acgtttcgat  10620
aggccacaga tttacaaaca cttcatcaaa agctgtaacg tgagtgaaga tttcgagatg  10680
cgagtgggat gcacgcgcga cgtgaacgtg ataagtggat taccggcgaa tacgtctcga  10740
gagagattag atctgttgga cgatgatcgg agagtgactg ggtttagtat aaccggtggt  10800
gaacataggc tgaggaatta taaatcggtt acgacggttc atagatttga gaaagaagaa  10860
gaagaagaaa ggatctggac cgttgttttg gaatcttatg ttgttgatgt accggaaggt  10920
aattcggagg aagatacgag attgtttgct gatacggtta ttagattgaa tcttcagaaa  10980
cttgcttcga tcactgaagc tatgaactaa agcggccgcg actctagagt cgacctgcag  11040
gcatgcaagc ttgatatcaa gcttatcgat aatcaacctc tggattacaa aatttgtgaa  11100
agattgactg gtattcttaa ctatgttgct ccttttacgc tatgtggata cgctgcttta  11160
atgcctttgt atcatgctat tgcttcccgt atggctttca ttttctcctc cttgtataaa  11220
tcctggttgc tgtctcttta tgaggagttg tggcccgttg tcaggcaacg tggcgtggtg  11280
tgcactgtgt ttgctgacgc aacccccact ggttggggca ttgccaccac ctgtcagctc  11340
ctttccggga ctttcgcttt ccccctccct attgccacgg cggaactcat cgccgcctgc  11400
cttgcccgct gctggacagg ggctcggctg ttgggcactg acaattccgt ggtgttgtcg  11460
gggaaatcat cgtcctttcc ttggctgctc gcctgtgttg ccacctggat tctgcgcggg  11520
acgtccttct gctacgtccc ttcggccctc aatccagcgg accttccttc ccgcggcctg  11580
ctgccggctc tgcggcctct tccgcgtctt cgccttcgcc ctcagacgag tcggatctcc  11640
ctttgggccg cctccccgca t                                           11661
```

```
SEQ ID NO: 17           moltype = DNA  length = 11376
FEATURE                 Location/Qualifiers
misc_feature            1..11376
                        note = synthetic vector
source                  1..11376
                        mol_type = other DNA
                        organism = synthetic construct
SEQUENCE: 17
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
```

-continued

```
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggtta tggcaagcta  7860
gctgcagtaa cgccattatt gcaaggcatg gaaaaatacc aaaccaagaa tagagaagtt  7920
cagatcaagg gcgggtacat gaaaatagct aacgtagggc caaacaggat atctgcggtg  7980
agcagtttcg gccccggccc ggggccaaga acagatggtc accgcagttt cggccccggc  8040
ccgaggccaa gagcagatgg tccccagata tggcccaacc ctcagcagtt tcttaagacc  8100
catcagatgt ttccaggctc ccccaaggac ctgaaatgac cctgcgcctt atttgaatta  8160
accaatcagc ctgcttctcg cttctgttcg cgcgcttctg cttcccgagc tctataaaag  8220
agctcacaac ccctcactcg gcgcgccagt cctccgacag actgagtcgc ccgggacgcg  8280
tttaattaag ccgccaccat gttcgaaccc aagaagaaga gaaaggtgtt cgaaactagt  8340
gtgcccctgt atggcttcac ttccatttgt ggccgacggc ctgaaatgga agccgcggtg  8400
tcaaccatac cacggtttct gcagagctca tcaggctcca tgctggacgg acgctttgat  8460
ccacagtctg ccgcacattt ctttggagtc tacgacggcc acgggggcag ccaggtcgcc  8520
aactactgca gggaaaggat gcatttggca cttgccgaag agatcgccaa agagaagccc  8580
atgttgtgtg atggggatac ctggctggag aagtggaaga aagcgctttt taactctttt  8640
ctgagagtgg attctgagat agaatctgtc gcacccgaga ccgtgggcag cacatccgtc  8700
gtagccgtag tgtttccctc ccacatattc gtcgccaact gcggcgacag tcgagccgtc  8760
ctctgccgag gtaagaccgc cctgcctctg agtgttgacc ataagcccga ccgggaggat  8820
gaggccgccc gaatcgaggc cgccggtgga aaagtcatcc aatggaacgg cgcaagagtg  8880
ttcggcgtgc tggcgatgtc caggagcatt ggagaccggt acctgaagcc cagcataatc  8940
```

-continued

```
ccagatcccg aagtgaccgc agtcaagagg gtgaaagagg acgattgtct gatcctggct  9000
agcgatggcg tatgggacgt gatgactgat gaggaggcgt gtgaaatggc ccgcaagcga  9060
atcctgctgt ggcataaaaa aaacgcagtc gcgggggacg cttctcttct ggcagacgaa  9120
aggcgcaaag aaggtaaaga cccggctgct atgagcgccg ccgaatatct cagtaagctg  9180
gcaattcagc gagggtccaa agacaacatt tccgtggtcg tggtagacct caaaggcggt  9240
tccggcggtt ctagaccagg cgaacgaccg tttcaatgcc ggatatgtat gaggaacttc  9300
tccgaggagg caaacttgag gcgccacacc cgaacacata caggagaaaa gccattccaa  9360
tgtcgaattt gtatgcgcaa tttttcagat cactcaagcc tcaagcgaca cctccgcaca  9420
catactggtt cacagaagcc ctttcagtgc aggatttgta tgcgcaactt tagccaatca  9480
gcgaaccttt tgcggcacac tagaacgcat acaggtgaga agcctttcca gtgtcgcatc  9540
tgtatgcgga acttcagcga ccccagttca ttgaagaggc atttgcgaac tcacaccggt  9600
tctcaaaaac cttttcagtg ccgaatttgt atgcgcaact tcagccaaca aacaaatttg  9660
acgagacaca cgcgcacgca caccggggaa aaaccgtttc aatgtcgaat ctgcatgcgc  9720
aattttagcg atgcgacaca acttgttagg catctgcgca cacacttgcg gggatccacc  9780
tgcaggggaa gcggagctac taacttcagc ctgctgaagc aggctggaga cgtggaggag  9840
aaccctggac ctggtcacca tccgaagaaa aaacggaaag tggatgctaa gtcactgact  9900
gcctggtccc ggacactggt gaccttcaag gatgtgtttg tggacttcac cagggaggag  9960
tggaagctgc tggacactgc tcagcagatc ctgtacagaa atgtgatgct ggagaactat  10020
aagaacctgg tttccttggg ttatcagctt actaagccag atgtgatcct ccggttggag  10080
aagggagaag agccctggct ggtggagaga gaaattcacc aagagaccca tcctgattca  10140
gagactgcat ttgaaatcaa atcatcagtt ggtggtggca gcggtcaatt gactcaagac  10200
gaattcaccc aactctccca atcaatcgcc gagttccaca cgtaccaact cggtaacggc  10260
cgttgctcat ctctcctagc tcagcgaatc cacgcgccgc cggaaacagt atggtccgtg  10320
gtgagacgtt tcgataggcc acagatttac aaacacttca tcaaaagctg taacgtgagt  10380
gaagatttcg agatgcgagt gggatgcacg cgcgacgtga acgtgataag tggattaccg  10440
gcgaatacgt ctcgagagag attagatctg ttggacgatg atcggagagt gactgggttt  10500
agtataaccg gtggtgaaca taggctgagg aattataaat cggttacgac ggttcataga  10560
tttgagaaag aagaagaaga agaaaggatc tggaccgttg ttttggaatc ttatgttgtt  10620
gatgtaccgg aaggtaattc ggaggaagat acgagattgt ttgctgatac ggttattaga  10680
ttgaatcttc agaaacttgc ttcgatcact gaagctatga actaaagcgg ccgcgactct  10740
agagtcgacc tgcaggcatg caagcttgat atcaagctta tcgataatca acctctggat  10800
tacaaaattt gtgaaagatt gactggtatt cttaactatg ttgctccttt tacgctatgt  10860
ggatacgctg ctttaatgcc tttgtatcat gctattgctt cccgtatggc tttcattttc  10920
tcctccttgt ataaatcctg gttgctgtct ctttatgagg agttgtggcc cgttgtcagg  10980
caacgtggcg tggtgtgcac tgtgtttgct gacgcaaccc ccactggttg gggcattgcc  11040
accacctgtc agctcctttc cgggactttc gctttccccc tccctattgc cacggcggaa  11100
ctcatcgccg cctgccttgc ccgctgctgg acaggggctc ggctgttggg cactgacaat  11160
tccgtggtgt tgtcggggaa atcatcgtcc tttccttggc tgctcgcctg tgttgccacc  11220
tggattctgc gcgggacgtc cttctgctac gtcccttcgg ccctcaatcc agcggacctt  11280
ccttcccgcg gcctgctgcc ggctctgcgg cctcttccgc gtcttcgcct tcgccctcag  11340
acgagtcgga tctccctttg ggccgcctcc ccgcat                            11376

SEQ ID NO: 18          moltype = DNA  length = 11044
FEATURE                Location/Qualifiers
misc_feature           1..11044
                       note = synthetic vector
source                 1..11044
                       mol_type = other DNA
                       organism = synthetic construct
SEQUENCE: 18
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatgggga  1740
```

-continued

```
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
```

-continued

```
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc  8280
tggagctctc gagaattctc acgcgtgccg ccaccatgtc tagaccaggc gaacgaccgt  8340
ttcaatgccg gatatgtatg aggaacttct cccagaggtc cagcttggta cggcacaccc  8400
gaacacatac aggagaaaag ccattccaat gtcgaatttg tatgcgcaat ttttcagaca  8460
agtctgtgtt ggctcgacac ctccgcacac atactggttc acagaagccc tttcagtgca  8520
ggatttgtat gcgcaacttt agccaacgct catccctggt aaggcacact agaacgcata  8580
caggtgagaa gcctttccag tgtcgcatct gtatgcggaa cttcagccag cggaataact  8640
tgggcaggca tttgcgaact cacaccggtt ctcaaaaacc ttttcagtgc cgaatttgta  8700
tgcgcaactt cagcacccac gccgtattga cacgacacac gcgcacgcac accggggaaa  8760
aaccgtttca atgtcgaatc tgcatgcgca attttagcga tagagggaac ctcactcgac  8820
atctgcgcac acacttgcgg ggatccacct gcagggatga gtttcccacc atggtgtttc  8880
cttctgggca gatcagccag gcctcggcct tggccccggc ccctccccaa gtcctgcccc  8940
aggctccagc ccctgcccct gctccagcca tggtatcagc tctggcccag gccccagccc  9000
ctgtcccagt cctagcccca ggccctcctc aggctgtggc cccacctgcc cccaagccca  9060
cccaggctgg ggaaggaacg ctgtcagagg ccctgctgca gctgcagttt gatgatgaag  9120
acctgggggc cttgcttggc aacagcacag acccagctgt gttcacagac ctggcatccg  9180
tcgacaactc cgagtttcag cagctgctga accagggcat acctgtggcc ccccacacaa  9240
ctgagcccat gctgatggag taccctgagg ctataactcg cctagtgaca ggggcccaga  9300
ggcccccga cccagctcct gctccactgg gggccccggg gctccccaat ggcctccttt  9360
caggagatga agacttctcc tccattgcgg acatggactt ctcagccctg ctgagtcaga  9420
tcagctccca attgtgcgta cgcggatcct ctgctggaga catgagagct gccaaccttt  9480
ggccaagccc gctcatgatc aaacgctcta agaagaacag cctggccttg tccctgacgg  9540
ccgaccagat ggtcagtgcc ttgttggatg ctgagccccc catactctat tccgagtatg  9600
atcctaccag accccttcagt gaagcttcga tgatgggctt actgaccaac ctggcagaca  9660
gggagctggt tcacatgatc aactgggcga agagggtgcc aggctttgtg gatttgaccc  9720
tccatgatca ggtccacctt ctagaatgtg cctggctaga gatcctgatg attggtctcg  9780
tctggcgctc catggagcac ccagtgaagc tactgtttgc tcctaacttg ctcttggaca  9840
ggaaccaggg aaaatgtgta gagggcatgg tggagatctt cgacatgctg ctggctacat  9900
catctcggtt ccgcatgatg aatctgcagg gagaggagtt tgtgtgcctc aaatctatta  9960
ttttgcttaa ttctggagtg tacacatttc tgtccagcac cctgaagtct ctggaagaga  10020
aggaccatat ccaccgagtc ctggacaaga tcacagacac tttgatccac ctgatggcca  10080
aggcaggcct gaccctgcag cagcagcacc agcggctggc ccagctcctc ctcatcctct  10140
cccacatcag gcacatgagt aacaaaggca tggagcatct gtacagcatg aagtgcaaga  10200
acgtggtgcc cctctatgac ctgctgctgg aggcggcgga cgcccaccgc ctacatgcgc  10260
ccactagccg tggaggggca tccgtggagg agacggacca aagccacttg gccactgcgg  10320
gctctacttc atcgcattcc ttgcaaaagt attacatcac gggggaggca gagggtttcc  10380
ctgccacagc ttaagcggcc gcgactctag agtcgacctg caggcatgca agcttgatat  10440
caagcttatc gataatcaac ctctggatta caaaatttgt gaaagattga ctggtattct  10500
taactatgtt gctcctttta cgctatgtgg atacgctgct ttaatgcctt tgtatcatgc  10560
tattgcttcc cgtatggctt tcattttctc ctccttgtat aaatcctggt tgctgtctct  10620
ttatgaggag ttgtggcccg ttgtcaggca acgtggcgtg gtgtgcactg tgtttgctga  10680
cgcaaccccc actggttggg gcattgccac cacctgtcag ctcctttccg ggactttcgc  10740
tttccccctc cctattgcca cggcggaact catcgccgcc tgccttgccc gctgctggac  10800
aggggctcgg ctgttgggca ctgacaattc cgtggtgttg tcggggaaat catcgtcctt  10860
tccttggctg ctcgcctgtg ttgccacctg gattctgcgc gggacgtcct tctgctacgt  10920
cccttcggcc ctcaatccag cggaccttcc ttcccgcggc ctgctgccgg ctctgcggcc  10980
tcttccgcgt cttcgccttc gccctcagac gagtcggatc tccctttggg ccgcctcccc  11040
gcat                                                               11044
```

SEQ ID NO: 19 moltype = DNA length = 10783

-continued

```
FEATURE                 Location/Qualifiers
misc_feature            1..10783
                        note = synthetic vector
source                  1..10783
                        mol_type = other DNA
                        organism = synthetic construct
SEQUENCE: 19
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
```

-continued

```
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc  8280
tggagctctc gagaattctc acgcgtgccg ccaccatgga tgctaagtca ctgactgcct  8340
ggtcccggac actggtgacc ttcaaggatg tgtttgtgga cttcaccagg gaggagtgga  8400
agctgctgga cactgctcag cagatcctgt acagaaatgt gatgctggag aactataaga  8460
acctggtttc cttgggttat cagcttacta agccagatgt gatcctccgg ttggagaagg  8520
gagaagagcc ctggctggtg gagagagaaa ttcaccaaga gacccatcct gattcagaga  8580
ctgcatttga aatcaaatca tcagttctcg agggaggcgg tggaagcggc acctgcaggt  8640
ctagaccagg cgaacgaccg tttcaatgcc ggatatgtat gaggaacttc tcccagaggt  8700
ccagcttggt acggcacacc cgaacacata caggagaaaa gccattccaa tgtcgaattt  8760
gtatgcgcaa tttttcagac aagtctgtgt tggctcgaca cctccgcaca catactggtt  8820
cacagaagcc ctttcagtgc aggatttgta tgcgcaactt tagccaacgc tcatccctgg  8880
taaggcacac tagaacgcat acaggtgaga agcctttcca gtgtcgcatc tgtatgcgga  8940
acttcagcca gcggaataac ttgggcaggc atttgcgaac tcacaccggt tctcaaaaac  9000
cttttcagtg ccgaatttgt atgcgcaact tcagcaccca cgccgtattg acacgacaca  9060
```

```
cgcgcacgca caccggggaa aaaccgtttc aatgtcgaat ctgcatgcgc aattttagcg  9120
atagagggaa cctcactcga catctgcgca cacacttgcg gggatcccaa ttgtgcgtac  9180
gcggatcctc tgctggagac atgagagctg ccaacctttg gccaagcccg ctcatgatca  9240
aacgctctaa gaagaacagc ctggccttgt ccctgacggc cgaccagatg gtcagtgcct  9300
tgttggatgc tgagcccccc atactctatt ccgagtatga tcctaccaga cccttcagtg  9360
aagcttcgat gatgggctta ctgaccaacc tggcagacag ggagctggtt cacatgatca  9420
actgggcgaa gagggtgcca ggctttgtgg atttgaccct ccatgatcag gtccaccttc  9480
tagaatgtgc ctggctagag atcctgatga ttggtctcgt ctggcgctcc atggagcacc  9540
cagtgaagct actgtttgct cctaacttgc tcttggacag gaaccaggga aaatgtgtag  9600
agggcatggt ggagatcttc gacatgctgc tggctacatc atctcggttc cgcatgatga  9660
atctgcaggg agaggagttt gtgtgcctca aatctattat tttgcttaat tctggagtgt  9720
acacatttct gtccagcacc ctgaagtctc tggaagagaa ggaccatatc caccgagtcc  9780
tggacaagat cacagacact ttgatccacc tgatggccaa ggcaggcctg accctgcagc  9840
agcagcacca gcggctggcc cagctcctcc tcatcctctc ccacatcagg cacatgagta  9900
acaaaggcat ggagcatctg tacagcatga agtgcaagaa cgtggtgccc ctctatgacc  9960
tgctgctgga ggcggcggac gcccaccgcc tacatgcgcc cactagccgt ggaggggcat  10020
ccgtggagga gacggaccaa agccacttgg ccactgcggg ctctacttca tcgcattcct  10080
tgcaaaagta ttacatcacg gggggaggcag agggtttccc tgccacagct taagcggccg  10140
cgactctaga gtcgacctgc aggcatgcaa gcttgatatc aagcttatcg ataatcaacc  10200
tctggattac aaaatttgtg aaagattgac tggtattctt aactatgttg ctccttttac  10260
gctatgtgga tacgctgctt taatgccttt gtatcatgct attgcttccc gtatggcttt  10320
cattttctcc tccttgtata aatcctggtt gctgtctctt tatgaggagt tgtggcccgt  10380
tgtcaggcaa cgtggcgtgg tgtgcactgt gtttgctgac gcaaccccca ctggttgggg  10440
cattgccacc acctgtcagc tcctttccgg gactttcgct ttccccctcc ctattgccac  10500
ggcggaactc atcgccgcct gccttgcccg ctgctggaca ggggctcggc tgttgggcac  10560
tgacaattcc gtggtgttgt cggggaaatc atcgtccttt ccttggctgc tcgcctgtgt  10620
tgccacctgg attctgcgcg ggacgtcctt ctgctacgtc ccttcggccc tcaatccagc  10680
ggaccttcct tcccgcggcc tgctgccggc tctgcggcct cttccgcgtc ttcgccttcg  10740
ccctcagacg agtcggatct ccctttgggc cgcctccccg cat                    10783

SEQ ID NO: 20          moltype = DNA  length = 11080
FEATURE                Location/Qualifiers
misc_feature           1..11080
                       note = synthetic vector
source                 1..11080
                       mol_type = other DNA
                       organism = synthetic construct
SEQUENCE: 20
tctcgcgcaa cctattttcc cctcgaacac tttttaagcc gtagataaac aggctgggac  60
acttcacatg agcgaaaaat acatcgtcac ctgggacatg ttgcagatcc atgcacgtaa  120
actcgcaagc cgactgatgc cttctgaaca atggaaaggc attattgccg taagccgtgg  180
cggtctgtac cgggtgcgtt actggcgcgt gaactgggta ttcgtcatgt cgataccgtt  240
tgtatttcca gctacgatca cgacaaccag cgcgagctta aagtgctgaa acgcgcagaa  300
ggcgatggcg aaggcttcat cgttattgat gacctggtgg ataccggtgg tactgcggtt  360
gcgattcgtg aaatgtatcc aaaagcgcac tttgtcacca tcttcgcaaa accggctggt  420
cgtccgctgg ttgatgacta tgttgttgat atcccgcaag atacctggat tgaacagccg  480
tgggatatgg gcgtcgtatt cgtcccgcca atctccggtc gctaatcttt tcaacgcctg  540
gcactgccgg gcgttgttct ttttaacttc aggcgggtta caatagtttc cagtaagtat  600
tctggaggct gcatccatga cacaggcaaa cctgagcgaa accctgttca aaccccgctt  660
taaacatcct gaaacctcga cgctagtccg ccgctttaat cacggcgcac aaccgcctgt  720
gcagtcggcc cttgatggta aaaccatccc tcactggtat cgcatgatta accgtctgat  780
gtggatctgg cgcggcattg acccacgcga aatcctcgac gtccaggcac gtattgtgat  840
gagcgatgcc gaacgtaccg acgatgattt atacgatacg gtgattggct accgtggcgg  900
caactggatt tatgagtggg ccccggatct ttgtgaagga accttacttc tgtggtgtga  960
cataattgga caaactacct acagagattt aaagctctaa ggtaaatata aaatttttaa  1020
gtgtataatg tgttaaacta ctgattctaa ttgtttgtgt attttagatt ccaacctatg  1080
gaactgatga atgggagcag tggtggaatg cctttaatga ggaaaacctg ttttgctcag  1140
aagaaatgcc atctagtgat gatgaggcta ctgctgactc tcaacattct actcctccaa  1200
aaaagaagag aaaggtagaa gaccccaagg actttccttc agaattgcta agttttttga  1260
gtcatgctgt gtttagtaat agaactcttg cttgctttgc tatttacacc acaaaggaaa  1320
aagctgcact gctatacaag aaaattatgg aaaaatattc tgtaaccttt ataagtaggc  1380
ataacagtta taatcataac atactgtttt ttcttactcc acacaggcat agagtgtctg  1440
ctattaataa ctatgctcaa aaattgtgta cctttagctt tttaatttgt aaaggggtta  1500
ataaggaata tttgatgtat agtgccttga ctagagatca taatcagcca taccacattt  1560
gtagaggttt tacttgcttt aaaaaaacctc ccacacctcc ccctgaacct gaaacataaa  1620
atgaatgcaa ttgttgttgt taacttgttt attgcagctt ataatggtta caaataaagc  1680
aatagcatca caaatttcac aaataaagca ttttttttcac tgcattctag ttgtggtttg  1740
tccaaactca tcaatgtatc ttatcatgtc tggatcaact ggataactca agctaaccaa  1800
aatcatccca aacttcccac cccatacccct attaccactg ccaattacct agtggtttca  1860
tttactctaa acctgtgatt cctctgaatt attttcattt taaagaaatt gtatttgtta  1920
aatatgtact acaaacttag tagttggaag ggctaattca ctcccaaaga agacaagata  1980
tccttgatct gtggatctac cacacacaag gctacttccc tgattagcag aactacacac  2040
cagggccagg ggtcagatat ccactgacct ttggatggtg ctacaagcta gtaccagttg  2100
agccagataa ggtagaagag gccaataaag gagagaacac cagcttgtta caccctgtga  2160
gcctgcatgg gatggatgac ccggagagag aagtgttaga gtggaggttt gacagccgcc  2220
tagcatttca tcacgtggcc cgagagctgc atccggagta cttcaagaac tgctgatatc  2280
gagcttgcta caagggactt tccgctgggg actttccagg gaggcgtggc ctgggcggga  2340
ctggggagtg gcgagccctc agatcctgca tataagcagc tgctttttgc ctgtactggg  2400
tctctctggt tagaccagat ctgagcctgg gagctctctg gctaactagg gaacccactg  2460
```

-continued

```
cttaagcctc aataaagctt gccttgagtg cttcaagtag tgtgtgcccg tctgttgtgt  2520
gactctggta actagagatc cctcagaccc ttttagtcag tgtggaaaat ctctagcagt  2580
ggcgcccgaa cagggacttg aaagcgaaag ggaaaccaga ggagctctct cgacgcagga  2640
ctcggcttgc tgaagcgcgc acggcaagag gcgagggggcg gcgactggtg agtacgccaa  2700
aaattttgac tagcggaggc tagaaggaga gagatgggtg cgagagcgtc agtattaagc  2760
gggggagaat tagatcgcga tgggaaaaaa ttcggttaag gccaggggga aagaaaaaat  2820
ataaattaaa acatatagta tgggcaagca gggagctaga acgattcgca gttaatcctg  2880
gcctgttaga aacatcagaa ggctgtagac aaatactggg acagctacaa ccatcccttc  2940
agacaggatc agaagaactt agatcattat ataatacagt agcaaccctc tattgtgtgc  3000
atcaaaggat agagataaaa gacaccaagg aagctttaga caagatagag gaagagcaaa  3060
acaaaagtaa gaccaccgca cagcaagcgg ccggccgctg atcttcagac ctggaggagg  3120
agatatgagg gacaattgga gaagtgaatt atataaatat aaagtagtaa aaattgaacc  3180
attaggagta gcacccacca aggcaaagag aagagtggtg cagagagaaa aaagagcagt  3240
gggaatagga gctttgttcc ttgggttctt gggagcagca ggaagcacta tgggcgcagc  3300
gtcaatgacg ctgacggtac aggccagaca attattgtct ggtatagtgc agcagcagaa  3360
caatttgctg agggctattg aggcgcaaca gcatctgttg caactcacag tctggggcat  3420
caagcagctc caggcaagaa tcctggctgt gaaagatacc taaaggatca acagctcctg  3480
gggatttggg gttgctctgg aaaactcatt tgcaccactg ctgtgccttg gaatgctagt  3540
tggagtaata aatctctgga acagatttgg aatcacacga cctggatgga gtgggacaga  3600
gaaattaaca attacacaag cttaatacac tccttaattg aagaatcgca aaaccagcaa  3660
gaaaagaatg aacaagaatt attggaatta gataaatggg caagtttgtg gaattggttt  3720
aacataacaa attggctgtg gtatataaaa ttattcataa tgatagtagg aggcttggta  3780
ggtttaagaa tagtttttgc tgtactttct atagtgaata gagttaggca gggatattca  3840
ccattatcgt ttcagaccca cctcccaacc ccgaggggac ccgacaggcc cgaaggaata  3900
gaagaagaag gtggagagag agacagagac agatccattc gattagtgaa cggatctcga  3960
cggtatcgcc aaatggcagt attcatccac aattttaaaa gaaaaggggg gattgggggg  4020
tacagtgcag gggaaagaat agtagacata atagcaacag acatacaaac taaagaatta  4080
caaaaacaaa ttacaaaaat tcaaaatttt cgggtttatt acagggacag cagagatcca  4140
gtttggatcg ataagcttga tatcgaattc ctgcagcccc gataaaataa aagattttat  4200
ttagtctcca gaaaaagggg ggaatgaaag accccacctg taggtttggc aagctagctg  4260
cagtaacgcc attttgcaag gcatggaaaa ataccaaacc aagaatagag aagttcagat  4320
caagggcggg tacatgaaaa tagctaacgt tgggccaaac aggatatctg cggtgagcag  4380
tttcggcccc ggcccggggc caagaacaga tggtcaccgc agtttcggcc ccggcccgag  4440
gccaagaaca gatggtcccc agatatggcc caaccctcag cagtttctta agacccatca  4500
gatgtttcca ggctccccca aggacctgaa atgaccctgc gccttatttg aattaaccaa  4560
tcagcctgct tctcgcttct gttcgcgcgc ttctgcttcc cgagctctat aaaagagctc  4620
acaacccctc actcggcgcg ccagtcctcc gacagactga gtcgcccggg ggggatctgg  4680
agctctcgag aattctcacg cgtgccgcca ccatgtctag acccggagag cgcccattcc  4740
agtgtcggat ttgcatgcgg aacttttcga gaagacacgg cctggacaga catacccgta  4800
ctcatacagg tgaaaaaccc tttcagtgtc ggatctgtat gcgaaatttc tccgaccaca  4860
gcagcctgaa gagacatcta cgtacccaca ccggcagcca gaagccattt cagtgtcgga  4920
tctgtatgcg gaacttctcc gtgagacaca acctgaccag acatctacgt acgcacaccg  4980
gagagaagcc attccaatgc cgaatatgca tgcgcaactt cagtgaccac agcaacctga  5040
gcagacacct aaaaacccac accggttccc agaagccatt tcagtgtcgg atctgtatgc  5100
ggaacttctc ccagcgcagc agcctggtga gacatctacg tacgcacacc ggagagaagc  5160
cattccaatg ccgaatatgc atgcgcaact tcagtgagag cggccacctg aagagacacc  5220
tgcgtacgca cctgagggga tccacctgca gggactacaa agaccatgac ggtgattata  5280
aagatcatga catcgattac aaggatgacg atgacaagat ggcccccaag aaaaagagga  5340
aggtgggcat tcacggggtg ccgggtggac tcgagggagg cggtggaagc ggcggtaccg  5400
aggacgtggt gtgctgccac tcaatctacg gcaagaagaa gggtgatatc gacacctacc  5460
gatacatagg ctcttccggg acaggctgcg tggtcatagt gggcaggatc gtcttgtccg  5520
gatccggcac tagtgcgccc atcacggcgt acgcccagca gacgagaggc ctcctagggt  5580
gtataatcac cagcctgact ggccgggaca aaaaccaagt ggagggtgag gtccagatcg  5640
tgtcaactgc tacccaaacc ttcctggcaa cgtgcatcaa tggggtatgc tgggcagtct  5700
accacggggc cggaacgagg accatcgcat cacccaaggg tcctgtcatc cagatgtata  5760
ccaatgtgga ccaagacctt gtgggctggc ccgctcctca aggttcccgc tcattgacac  5820
cctgtacctg cggctcctcg gacctttacc tggtcacgag gcacgccgat gtcattcccg  5880
tgcgccggcg aggtgatagc aggggtagcc tgctttcgcc ccggcccatt tcctacttga  5940
aaggctcctc gggggtccg ctgttgtgcc ccgcgggaca cgccgtgggc ctattcaggg  6000
ccgcggtgtg cacccgtgga gtggctaaag cggtggactt tatccctgtg gagaacctag  6060
agacaaccat gagatccccg gtgttcacgg acaactcctc tccaccagca gtcaccctga  6120
cgcacccaat caccaaaatc gatagggagg ttctctacca ggagttcgat gagatggaag  6180
agtgctctca gcactatccc tacgatgtgc ccgattacgc tggaggcggt ggaagcggcg  6240
gtaccgatga gtttcccacc atggtgtttc cttctgggca gatcagccag gcctcggcct  6300
tggccccggc ccctccccaa gtcctgcccc aggctccagc ccctgcccct gctccagcca  6360
tggtatcagc tctggcccag gccccagccc ctgtcccagt cctagcccca ggccctcctc  6420
aggctgtggc cccacctgcc cccaagccca cccaggctgg ggaaggaacg ctgtcagagg  6480
ccctgctgca gctgcagttt gatgatgaag acctgggggc cttgcttggc aacagcacag  6540
acccagctgt gttcacagac ctggcatccg tcgacaactc cgagtttcag cagctgctga  6600
accagggcat acctgtggcc ccccacacaa ctgagcccat gctgatggag taccctgagg  6660
ctataactcg cctagtgaca ggggcccaga ggccccccga cccagctcct gctccactgg  6720
gggccccggg gctccccaat ggcctccttt caggagatga agacttctcc tccattgcgg  6780
acatggactt ctcagccctg ctgagtcaga tcagctccca attgtaagcg gccgcgactc  6840
tagagtcgac ctgcaggcat gcaagcttga tatcaagctt atcgataatc aacctctgga  6900
ttacaaaatt tgtgaaagat tgactggtat tcttaactat gttgctcctt ttacgctatg  6960
tggatacgct gctttaatgc ctttgtatca tgctattgct tcccgtatgg ctttcatttt  7020
ctcctccttg tataaatcct ggttgctgtc tctttatgag gagttgtggc ccgttgtcag  7080
gcaacgtggc gtggtgtgca ctgtgtttgc tgacgcaacc cccactggtt ggggcattgc  7140
caccacctgt cagctccttt ccgggacttt cgctttcccc ctccctattg ccacggcgga  7200
```

```
actcatcgcc gcctgccttg cccgctgctg gacaggggct cggctgttgg gcactgacaa  7260
ttccgtggtg ttgtcgggga aatcatcgtc ctttccttgg ctgctcgcct gtgttgccac  7320
ctggattctg cgcgggacgt ccttctgcta cgtcccttcg gccctcaatc cagcggacct  7380
tccttcccgc ggcctgctgc cggctctgcg gcctcttccg cgtcttcgcc ttcgccctca  7440
gacgagtcgg atctcccttt gggccgcctc cccgcatcga taccgtcgac ctcgagggaa  7500
ttaattcgag ctcggtacct ttaagaccaa tgacttacaa ggcagctgta gatcttagcc  7560
actttttaaa agaaaagggg ggactggaag ggctaattca ctcccaacga agacaagatc  7620
tgcttttttgc ttgtactggg tctctctggt tagaccagat ctgagcctgg gagctctctg  7680
gctaactagg gaacccactg cttaagcctc aataaagctt gccttgagtg cttcaagtag  7740
tgtgtgcccg tctgttgtgt gactctggta actagagatc cctcagaccc ttttagtcag  7800
tgtggaaaat ctctagcagc atctagaatt aattccgtgt attctatagt gtcacctaaa  7860
tcgtatgtgt atgatacata aggttatgta ttaattgtag ccgcgttcta acgacaatat  7920
gtacaagcct aattgtgtag catctggctt actgaagcag accctatcat ctctctcgta  7980
aactgccgtc agagtcggtt tggttggacg aaccttctga gtttctggta acgccgtccc  8040
gcacccggaa atggtcagcg aaccaatcag cagggtcatc gctagccaga tcctctacgc  8100
cggacgcatc gtggccggca tcaccggcgc cacaggtgcg gttgctggcg cctatatcgc  8160
cgacatcacc gatggggaag atcgggctcg ccacttcggg ctcatgagcg cttgtttcgg  8220
cgtgggtatg gtggcaggcc ccgtggccgg gggactgttg ggcgccatct ccttgcatgc  8280
accattcctt gcggcggcgg tgctcaacgg cctcaaccta ctactgggct gcttcctaat  8340
gcaggagtcg cataagggag agcgtcgaat ggtgcactct cagtacaatc tgctctgatg  8400
ccgcatagtt aagccagccc cgacacccgc caacacccgc tgacgcgccc tgacgggctt  8460
gtctgctccc ggcatccgct tacagacaag ctgtgaccgt ctccgggagc tgcatgtgtc  8520
agaggttttc accgtcatca ccgaaacgcg cgagacgaaa gggcctcgtg atacgcctat  8580
ttttataggt taatgtcatg ataataatgg tttcttagac gtcaggtggc acttttcggg  8640
gaaatgtgcg cggaacccct atttgtttat ttttctaaat acattcaaat atgtatccgc  8700
tcatgagaca ataaccctga taaatgcttc aataatattg aaaaaggaag agtatgagta  8760
ttcaacattt ccgtgtcgcc cttattccct tttttgcggc attttgcctt cctgtttttg  8820
ctcacccaga aacgctggtg aaagtaaaag atgctgaaga tcagttgggt gcacgagtgg  8880
gttacatcga actggatctc aacagcggta agatccttga gagttttcgc cccgaagaac  8940
gttttccaat gatgagcact tttaaagttc tgctatgtgg cgcggtatta tcccgtattg  9000
acgccgggca agagcaactc ggtcgccgca tacactattc tcagaatgac ttggttgagt  9060
actcaccagt cacagaaaag catcttacgg atggcatgac agtaagagaa ttatgcagtg  9120
ctgccataac catgagtgat aacactgcgg ccaacttact tctgacaacg atcggaggac  9180
cgaaggagct aaccgctttt ttgcacaaca tgggggatca tgtaactcgc cttgatcgtt  9240
gggaaccgga gctgaatgaa gccataccaa acgacgagcg tgacaccacg atgcctgtag  9300
caatggcaac aacgttgcgc aaactattaa ctggcgaact acttactcta gcttcccggc  9360
aacaattaat agactggatg gaggcggata aagttgcagg accacttctg cgctcggccc  9420
ttccggctgg ctggtttatt gctgataaat ctggagccgg tgagcgtggg tctcgcggta  9480
tcattgcagc actggggcca gatggtaagc cctcccgtat cgtagttatc tacacgacgg  9540
ggagtcaggc aactatggat gaacgaaata gacagatcgc tgagataggt gcctcactga  9600
ttaagcattg gtaactgtca gaccaagttt actcatatat actttagatt gatttaaaac  9660
ttcattttta atttaaaagg atctaggtga agatcctttt tgataatctc atgaccaaaa  9720
tcccttaacg tgagttttcg ttccactgag cgtcagaccc cgtagaaaag atcaaaggat  9780
cttcttgaga tccttttttt ctgcgcgtaa tctgctgctt gcaaacaaaa aaaccaccgc  9840
taccagcggt ggtttgtttg ccggatcaag agctaccaac tctttttccg aaggtaactg  9900
gcttcagcag agcgcagata ccaaatactg tcttctagt gtagccgtag ttaggccacc  9960
acttcaagaa ctctgtagca ccgcctacat acctcgctct gctaatcctg ttaccagtgg  10020
ctgctgccag tggcgataag tcgtgtctta ccgggttgga ctcaagacga tagttaccgg  10080
ataaggcgca gcggtcgggc tgaacggggg gttcgtgcac acagcccagc ttggagcgaa  10140
cgacctacac cgaactgaga tacctacagc gtgagctatg agaaagcgcc acgcttcccg  10200
aagggagaaa ggcggacagg tatccggtaa gcggcagggt cggaacagga gagcgcacga  10260
gggagcttcc agggggaaac gcctggtatc tttatagtcc tgtcgggttt cgccacctct  10320
gacttgagcg tcgatttttg tgatgctcgt caggggggcg gagcctatgg aaaaacgcca  10380
gcaacgcggc ctttttacgg ttcctggcct tttgctggcc ttttgctcac atgttctttc  10440
ctgcgttatc ccctgattct gtggataacc gtattaccgc ctttgagtga gctgataccg  10500
ctcgccgcag ccgaacgacc gagcgcagcg agtcagtgag cgaggaagcg gaagagcgcc  10560
caatacgcaa accgcctctc cccgcgcgtt ggccgattca ttaatgcagc tgtggaatgt  10620
gtgtcagtta gggtgtggaa agtccccagg ctccccagca ggcagaagta tgcaaagcat  10680
gcatctcaat tagtcagcaa ccaggtgtgg aaagtcccca ggctccccag caggcagaag  10740
tatgcaaagc atgcatctca attagtcagc aaccatagtc ccgcccctaa ctccgcccat  10800
cccgccccta actccgccca gttccgccca ttctccgccc catggctgac taattttttt  10860
tatttatgca gaggccgagg ccgcctcggc ctctgagcta ttccagaagt agtgaggagg  10920
cttttttgga ggcctaggct tttgcaaaaa gcttggacac aagacaggct tgcgagatat  10980
gtttgagaat accactttat cccgcgtcag ggagaggcag tgcgtaaaaa gacgcggact  11040
catgtgaaat actggttttt agtgcgccag atctctataa                        11080

SEQ ID NO: 21          moltype = DNA  length = 10795
FEATURE                Location/Qualifiers
misc_feature           1..10795
                       note = synthetic vector
source                 1..10795
                       mol_type = other DNA
                       organism = synthetic construct
SEQUENCE: 21
tctcgcgcaa cctattttcc cctcgaacac tttttaagcc gtagataaac aggctgggac  60
acttcacatg agcgaaaaat acatcgtcac ctgggacatg ttgcagatcc atgcacgtaa  120
actcgcaagc cgactgatgc cttctgaaca atggaaaggc attattgccg taagccgtgg  180
cggtctgtac cgggtgcgtt actggcgcgt gaactgggta ttcgtcatgt cgataccgtt  240
tgtatttcca gctacgatca cgacaaccag cgcgagctta aagtgctgaa acgcgcagaa  300
```

-continued

```
ggcgatggcg aaggcttcat cgttattgat gacctggtgg ataccggtgg tactgcggtt  360
gcgattcgtg aaatgtatcc aaaagcgcac tttgtcacca tcttcgcaaa accggctggt  420
cgtccgctgg ttgatgacta tgttgttgat atcccgcaag atacctggat tgaacagccg  480
tgggatatgg gcgtcgtatt cgtcccgcca atctccggtc gctaatcttt tcaacgcctg  540
gcactgccgg gcgttgttct ttttaacttc aggcgggtta caatagtttc cagtaagtat  600
tctggaggct gcatccatga cacaggcaaa cctgagcgaa accctgttca aaccccgctt  660
taaacatcct gaaacctcga cgctagtccg ccgctttaat cacggcgcac aaccgcctgt  720
gcagtcggcc cttgatggta aaaccatccc tcactggtat cgcatgatta accgtctgat  780
gtggatctgg cgcggcattg acccacgcga aatcctcgac gtccaggcac gtattgtgat  840
gagcgatgcc gaacgtaccg acgatgattt atacgatacg gtgattggct accgtggcgg  900
caactggatt tatgagtggg ccccggatct ttgtgaagga accttacttc tgtggtgtga  960
cataattgga caaactacct acagagattt aaagctctaa ggtaaatata aaatttttaa  1020
gtgtataatg tgttaaacta ctgattctaa ttgtttgtgt attttagatt ccaacctatg  1080
gaactgatga atgggagcag tggtggaatg cctttaatga ggaaaacctg ttttgctcag  1140
aagaaatgcc atctagtgat gatgaggcta ctgctgactc tcaacattct actcctccaa  1200
aaaagaagag aaaggtagaa gaccccaagg actttccttc agaattgcta agttttttga  1260
gtcatgctgt gtttagtaat agaactcttg cttgctttgc tatttacacc acaaaggaaa  1320
aagctgcact gctatacaag aaaattatgg aaaaatattc tgtaaccttt ataagtaggc  1380
ataacagtta taatcataac atactgtttt ttcttactcc acacaggcat agagtgtctg  1440
ctattaataa ctatgctcaa aaattgtgta cctttagctt tttaatttgt aaaggggtta  1500
ataaggaata tttgatgtat agtgccttga ctagagatca taatcagcca taccacattt  1560
gtagaggttt tacttgcttt aaaaaacctc ccacacctcc ccctgaacct gaaacataaa  1620
atgaatgcaa ttgttgttgt taacttgttt attgcagctt ataatggtta caaataaagc  1680
aatagcatca caaatttcac aaataaagca tttttttcac tgcattctag ttgtggtttg  1740
tccaaactca tcaatgtatc ttatcatgtc tggatcaact ggataactca agctaaccaa  1800
aatcatccca aacttcccac cccatacccct attaccactg ccaattacct agtggtttca  1860
tttactctaa acctgtgatt cctctgaatt attttcattt taaagaaatt gtatttgtta  1920
aatatgtact acaaacttag tagttggaag ggctaattca ctcccaaaga agacaagata  1980
tccttgatct gtggatctac cacacacaag gctacttccc tgattagcag aactacacac  2040
cagggccagg ggtcagatat ccactgacct ttggatggtg ctacaagcta gtaccagttg  2100
agccagataa ggtagaagag gccaataaag gagagaacac cagcttgtta caccctgtga  2160
gcctgcatgg gatggatgac ccggagagag aagtgttaga gtggaggttt gacagccgcc  2220
tagcatttca tcacgtggcc cgagagctgc atccggagta cttcaagaac tgctgatatc  2280
gagcttgcta caagggactt tccgctgggg actttccagg gaggcgtggc ctgggcggga  2340
ctggggagtg gcgagccctc agatcctgca tataagcagc tgctttttgc ctgtactggg  2400
tctctctggt tagaccagat ctgagcctgg gagctctctg gctaactagg gaacccactg  2460
cttaagcctc aataaagctt gccttgagtg cttcaagtag tgtgtgcccg tctgttgtgt  2520
gactctggta actagagatc cctcagaccc ttttagtcag tgtggaaaat ctctagcagt  2580
ggcgcccgaa cagggacttg aaagcgaaag ggaaaccaga ggagctctct cgacgcagga  2640
ctcggcttgc tgaagcgcgc acggcaagag gcgaggggcg gcgactggtg agtacgccaa  2700
aaattttgac tagcggaggc tagaaggaga gagatgggtg cgagagcgtc agtattaagc  2760
gggggagaat tagatcgcga tgggaaaaaa ttcggttaag gccaggggga aagaaaaaat  2820
ataaattaaa acatatagta tgggcaagca gggagctaga acgattcgca gttaatcctg  2880
gcctgttaga aacatcagaa ggctgtagac aaatactggg acagctacaa ccatcccttc  2940
agacaggatc agaagaactt agatcattat ataatacagt agcaaccctc tattgtgtgc  3000
atcaaaggat agagataaaa gacaccaagg aagctttaga caagatagag gaagagcaaa  3060
acaaaagtaa gaccaccgca cagcaagcgg ccggccgctg atcttcagac ctggaggagg  3120
agatatgagg gacaattgga gaagtgaatt atataaatat aaagtagtaa aaattgaacc  3180
attaggagta gcacccacca aggcaaagag aagagtggtg cagagagaaa aaagagcagt  3240
gggaatagga gctttgttcc ttgggttctt gggagcagca ggaagcacta tgggcgcagc  3300
gtcaatgacg ctgacggtac aggccagaca attattgtct ggtatagtgc agcagcagaa  3360
caatttgctg agggctattg aggcgcaaca gcatctgttg caactcacag tctggggcat  3420
caagcagctc caggcaagaa tcctggctgt gaaagatacc taaaggatca acagctcctg  3480
gggatttggg gttgctctgg aaaactcatt tgcaccactg ctgtgccttg gaatgctagt  3540
tggagtaata aatctctgga acagatttgg aatcacacga cctggatgga gtgggacaga  3600
gaaattaaca attacacaag cttaatacac tccttaattg aagaatcgca aaaccagcaa  3660
gaaaagaatg aacaagaatt attggaatta gataaatggg caagtttgtg gaattggttt  3720
aacataacaa attggctgtg gtatataaaa ttattcataa tgatagtagg aggcttggta  3780
ggtttaagaa tagtttttgc tgtactttct atagtgaata gagttaggca gggatattca  3840
ccattatcgt ttcagaccca cctcccaacc ccgaggggac ccgacaggcc cgaaggaata  3900
gaagaagaag gtggagagag agacagagac agatccattc gattagtgaa cggatctcga  3960
cggtatcgcc aaatggcagt attcatccac aattttaaaa gaaaaggggg gattgggggg  4020
tacagtgcag gggaaagaat agtagacata atagcaacag acatacaaac taaagaatta  4080
caaaaacaaa ttacaaaaat tcaaaatttt cgggtttatt acagggacag cagagatcca  4140
gtttggatcg ataagcttga tatcgaattc ctgcagcccc gataaaataa aagattttat  4200
ttagtctcca gaaaaagggg ggaatgaaag accccacctg taggtttggc aagctagctg  4260
cagtaacgcc attttgcaag gcatggaaaa ataccaaacc aagaatagag aagttcagat  4320
caagggcggg tacatgaaaa tagctaacgt tgggccaaac aggatatctg cggtgagcag  4380
tttcggcccc ggcccggggc caagaacaga tggtcaccgc agtttcggcc ccggcccgag  4440
gccaagaaca gatggtcccc agatatggcc caaccctcag cagtttctta agacccatca  4500
gatgtttcca ggctcccccca aggacctgaa atgaccctgc gccttatttg aattaaccaa  4560
tcagcctgct tctcgcttct gttcgcgcgc ttctgcttcc cgagctctat aaaagagctc  4620
acaacccctc actcggcgcg ccagtcctcc gacagactga gtcgcccggg ggggatctgg  4680
agctctcgag aattctcacg cgtgccgcca ccatggatgc taagtcactg actgcctggt  4740
cccggacact ggtgaccttc aaggatgtgt ttgtggactt caccagggag gagtggaagc  4800
tgctggacac tgctcagcag atcctgtaca gaaatgtgat gctggagaac tataagaacc  4860
tggtttcctt gggttatcag cttactaagc cagatgtgat cctccggttg gagaagggag  4920
aagagccctg gctggtggag agagaaattc accaagagac ccatcctgat tcagagactg  4980
catttgaaat caaatcatca gttacctgca gggactacaa agaccatgac ggtgattata  5040
```

-continued

```
aagatcatga catcgattac aaggatgacg atgacaagat ggcccccaag aaaaagagga  5100
aggtgggcat tcacggggtg ccgggtggac tcgagggagg cggtggaagc ggcggtaccg  5160
aggacgtggt gtgctgccac tcaatctacg gcaagaagaa gggtgatatc gacacctacc  5220
gatacatagg ctcttccggg acaggctgcg tggtcatagt gggcaggatc gtcttgtccg  5280
gatccggcac tagtgcgccc atcacggcgt acgcccagca gacgagaggc ctcctagggt  5340
gtataatcac cagcctgact ggccgggaca aaaaccaagt ggagggtgag gtccagatcg  5400
tgtcaactgc tacccaaacc ttcctggcaa cgtgcatcaa tggggtatgc tgggcagtct  5460
accacggggc cggaacgagg accatcgcat cacccaaggg tcctgtcatc cagatgtata  5520
ccaatgtgga ccaagacctt gtgggctggc ccgctcctca aggttcccgc tcattgacac  5580
cctgtacctg cggctcctcg gacctttacc tggtcacgag gcacgccgat gtcattcccg  5640
tgcgccggcg aggtgatagc aggggtagcc tgctttcgcc ccggcccatt tcctacttga  5700
aaggctcctc gggggtccg ctgttgtgcc ccgcgggaca cgccgtgggc ctattcaggg  5760
ccgcggtgtg cacccgtgga gtggctaaag cggtggactt tatccctgtg gagaacctag  5820
agacaaccat gagatccccg gtgttcacgg acaactcctc tccaccagca gtcaccctga  5880
cgcacccaat caccaaaatc gatagggagg ttctctacca ggagttcgat gagatggaag  5940
agtgctctca gcactatccc tacgatgtgc ccgattacgc tggaggcggt ggaagcggcg  6000
gtacctctag acccggagag cgcccattcc agtgtcggat ttgcatgcgg aacttttcga  6060
gaagacacgg cctggacaga catacccgta ctcatacagg tgaaaaaccc tttcagtgtc  6120
ggatctgtat gcgaaatttc tccgaccaca gcagcctgaa gagacatcta cgtacccaca  6180
ccggcagcca gaagccattt cagtgtcgga tctgtatgcg gaacttctcc gtgagacaca  6240
acctgaccag acatctacgt acgcacaccg gagagaagcc attccaatgc cgaatatgca  6300
tgcgcaactt cagtgaccac agcaacctga gcagacacct aaaaacccac accggttccc  6360
agaagccatt tcagtgtcgg atctgtatgc ggaacttctc ccagcgcagc agcctggtga  6420
gacatctacg tacgcacacc ggagagaagc cattccaatg ccgaatatgc atgcgcaact  6480
tcagtgagag cggccacctg aagagacacc tgcgtacgca cctgagggga tcccaattgt  6540
aagcggccgc gactctagag tcgacctgca ggcatgcaag cttgatatca agcttatcga  6600
taatcaacct ctggattaca aaatttgtga aagattgact ggtattctta actatgttgc  6660
tccttttacg ctatgtggat acgctgcttt aatgcctttg tatcatgcta ttgcttcccg  6720
tatggctttc attttctcct ccttgtataa atcctggttg ctgtctcttt atgaggagtt  6780
gtggcccgtt gtcaggcaac gtggcgtggt gtgcactgtg tttgctgacg caacccccac  6840
tggttggggc attgccacca cctgtcagct cctttccggg actttcgctt tccccctccc  6900
tattgccacg gcggaactca tcgccgcctg ccttgcccgc tgctggacag gggctcggct  6960
gttgggcact gacaattccg tggtgttgtc ggggaaatca tcgtcctttc cttggctgct  7020
cgcctgtgtt gccacctgga ttctgcgcgg gacgtccttc tgctacgtcc cttcggccct  7080
caatccagcg gaccttcctt cccgcggcct gctgccggct ctgcggcctc ttccgcgtct  7140
tcgccttcgc cctcagacga gtcggatctc cctttgggcc gcctccccgc atcgataccg  7200
tcgacctcga gggaattaat tcgagctcgg tacctttaag accaatgact tacaaggcag  7260
ctgtagatct tagccacttt ttaaaagaaa aggggggact ggaagggcta attcactccc  7320
aacgaagaca agatctgctt tttgcttgta ctgggtctct ctggttagac cagatctgag  7380
cctgggagct ctctggctaa ctagggaacc cactgcttaa gcctcaataa agcttgcctt  7440
gagtgcttca agtagtgtgt gcccgtctgt tgtgtgactc tggtaactag agatccctca  7500
gaccctttta gtcagtgtgg aaaatctcta gcagcatcta gaattaattc cgtgtattct  7560
atagtgtcac ctaaatcgta tgtgtatgat acataaggtt atgtattaat tgtagccgcg  7620
ttctaacgac aatatgtaca agcctaattg tgtagcatct ggcttactga agcagaccct  7680
atcatctctc tcgtaaactg ccgtcagagt cggtttggtt ggacgaacct tctgagtttc  7740
tggtaacgcc gtcccgcacc cggaaatggt cagcgaacca atcagcaggg tcatcgctag  7800
ccagatcctc tacgccggac gcatcgtggc cggcatcacc ggcgccacag gtgcggttgc  7860
tggcgcctat atcgccgaca tcaccgatgg ggaagatcgg gctcgccact tcgggctcat  7920
gagcgcttgt ttcggcgtgg gtatggtggc aggccccgtg gccgggggac tgttgggcgc  7980
catctccttg catgcaccat tccttgcggc ggcggtgctc aacggcctca acctactact  8040
gggctgcttc ctaatgcagg agtcgcataa gggagagcgt cgaatggtgc actctcagta  8100
caatctgctc tgatgccgca tagttaagcc agccccgaca cccgccaaca cccgctgacg  8160
cgccctgacg ggcttgtctg ctcccggcat ccgcttacag acaagctgtg accgtctccg  8220
ggagctgcat gtgtcagagg ttttcaccgt catcaccgaa acgcgcgaga cgaaagggcc  8280
tcgtgatacg cctattttta taggttaatg tcatgataat aatggtttct tagacgtcag  8340
gtggcacttt tcggggaaat gtgcgcggaa cccctatttg tttatttttc taaatacatt  8400
caaatatgta tccgctcatg agacaataac cctgataaat gcttcaataa tattgaaaaa  8460
ggaagagtat gagtattcaa catttccgtg tcgcccttat tccctttttt gcggcatttt  8520
gccttcctgt ttttgctcac ccagaaacgc tggtgaaagt aaaagatgct gaagatcagt  8580
tgggtgcacg agtgggttac atcgaactgg atctcaacag cggtaagatc cttgagagtt  8640
ttcgccccga agaacgtttt ccaatgatga gcacttttaa agttctgcta tgtggcgcgg  8700
tattatcccg tattgacgcc gggcaagagc aactcggtcg ccgcatacac tattctcaga  8760
atgacttggt tgagtactca ccagtcacag aaaagcatct tacggatggc atgacagtaa  8820
gagaattatg cagtgctgcc ataaccatga gtgataacac tgcggccaac ttacttctga  8880
caacgatcgg aggaccgaag gagctaaccg cttttttgca caacatgggg gatcatgtaa  8940
ctcgccttga tcgttgggaa ccggagctga atgaagccat accaaacgac gagcgtgaca  9000
ccacgatgcc tgtagcaatg gcaacaacgt tgcgcaaact attaactggc gaactactta  9060
ctctagcttc ccggcaacaa ttaatagact ggatggaggc ggataaagtt gcaggaccac  9120
ttctgcgctc ggcccttccg gctggctggt ttattgctga taaatctgga gccggtgagc  9180
gtgggtctcg cggtatcatt gcagcactgg ggccagatgg taagccctcc cgtatcgtag  9240
ttatctacac gacggggagt caggcaacta tggatgaacg aaatagacag atcgctgaga  9300
taggtgcctc actgattaag cattggtaac tgtcagacca agtttactca tatatacttt  9360
agattgattt aaaacttcat ttttaattta aaaggatcta ggtgaagatc ctttttgata  9420
atctcatgac caaaatccct taacgtgagt tttcgttcca ctgagcgtca gaccccgtag  9480
aaaagatcaa aggatcttct tgagatcctt tttttctgcg cgtaatctgc tgcttgcaaa  9540
caaaaaaacc accgctacca gcggtggttt gtttgccgga tcaagagcta ccaactcttt  9600
ttccgaaggt aactggcttc agcagagcgc agataccaaa tactgtcttt ctagtgtagc  9660
cgtagttagg ccaccacttc aagaactctg tagcaccgcc tacatacctc gctctgctaa  9720
tcctgttacc agtggctgct gccagtggcg ataagtcgtg tcttaccggg ttggactcaa  9780
```

```
gacgatagtt accggataag gcgcagcggt cgggctgaac ggggggttcg tgcacacagc  9840
ccagcttgga gcgaacgacc tacaccgaac tgagatacct acagcgtgag ctatgagaaa  9900
gcgccacgct tcccgaaggg agaaaggcgg acaggtatcc ggtaagcggc agggtcggaa  9960
caggagagcg cacgagggag cttccagggg gaaacgcctg gtatctttat agtcctgtcg  10020
ggtttcgcca cctctgactt gagcgtcgat ttttgtgatg ctcgtcaggg gggcggagcc  10080
tatggaaaaa cgccagcaac gcggcctttt tacggttcct ggccttttgc tggccttttg  10140
ctcacatgtt ctttcctgcg ttatcccctg attctgtgga taaccgtatt accgcctttg  10200
agtgagctga taccgctcgc cgcagccgaa cgaccgagcg cagcgagtca gtgagcgagg  10260
aagcggaaga gcgcccaata cgcaaaccgc ctctccccgc gcgttggccg attcattaat  10320
gcagctgtgg aatgtgtgtc agttagggtg tggaaagtcc ccaggctccc cagcaggcag  10380
aagtatgcaa agcatgcatc tcaattagtc agcaaccagg tgtggaaagt ccccaggctc  10440
cccagcaggc agaagtatgc aaagcatgca tctcaattag tcagcaacca tagtcccgcc  10500
cctaactccg cccatcccgc ccctaactcc gcccagttcc gcccattctc cgccccatgg  10560
ctgactaatt ttttttattt atgcagaggc cgaggccgcc tcggcctctg agctattcca  10620
gaagtagtga ggaggctttt ttggaggcct aggcttttgc aaaaagcttg gacacaagac  10680
aggcttgcga gatatgtttg agaataccac tttatcccgc gtcagggaga ggcagtgcgt  10740
aaaaagacgc ggactcatgt gaaatactgg tttttagtgc gccagatctc tataa       10795

SEQ ID NO: 22           moltype = DNA  length = 11962
FEATURE                 Location/Qualifiers
misc_feature            1..11962
                        note = synthetic vector
source                  1..11962
                        mol_type = other DNA
                        organism = synthetic construct
SEQUENCE: 22
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtcttcct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
```

-continued

```
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
```

```
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc  8280
tggagctctc gagaattctc acgcgtgccg ccaccatgtc tagaccaggc gaacgaccgt  8340
ttcaatgccg gatatgtatg aggaacttct cccagaggtc cagcttggta cggcacaccc  8400
gaacacatac aggagaaaag ccattccaat gtcgaatttg tatgcgcaat ttttcagaca  8460
agtctgtgtt ggctcgacac ctccgcacac atactggttc acagaagccc tttcagtgca  8520
ggatttgtat gcgcaacttt agccaacgct catccctggt aaggcacact agaacgcata  8580
caggtgagaa gcctttccag tgtcgcatct gtatgcggaa cttcagccag cggaataact  8640
tgggcaggca tttgcgaact cacaccggtt ctcaaaaacc ttttcagtgc cgaatttgta  8700
tgcgcaactt cagcacccac gccgtattga cacgacacac gcgcacgcac accggggaaa  8760
aaccgtttca atgtcgaatc tgcatgcgca attttagcga tagagggaac ctcactcgac  8820
atctgcgcac acacttgcgg ggatccacct gcagggatga gtttcccacc atggtgtttc  8880
cttctgggca gatcagccag gcctcggcct tggccccggc ccctccccaa gtcctgcccc  8940
aggctccagc ccctgcccct gctccagcca tggtatcagc tctggcccag gccccagccc  9000
ctgtcccagt cctagcccca ggccctcctc aggctgtggc cccacctgcc cccaagccca  9060
cccaggctgg ggaaggaacg ctgtcagagg ccctgctgca gctgcagttt gatgatgaag  9120
acctgggggc cttgcttggc aacagcacag acccagctgt gttcacagac ctggcatccg  9180
tcgacaactc cgagtttcag cagctgctga accagggcat acctgtggcc ccccacacaa  9240
ctgagcccat gctgatggag taccctgagg ctataactcg cctagtgaca ggggcccaga  9300
ggccccccga cccagctcct gctccactgg gggccccggg gctccccaat ggcctccttt  9360
caggagatga agacttctcc tccattgcgg acatggactt ctcagccctg ctgagtcaga  9420
tcagctccca attgtgcgta cgcggatcct ctgctggaga catgagagct gccaaccttt  9480
ggccaagccc gctcatgatc aaacgctcta agaagaacag cctggccttg tccctgacgg  9540
ccgaccagat ggtcagtgcc ttgttggatg ctgagccccc catactctat tccgagtatg  9600
atcctaccag accccttcagt gaagcttcga tgatgggctt actgaccaac ctggcagaca  9660
gggagctggt tcacatgatc aactgggcga agagggtgcc aggctttgtg gatttgaccc  9720
tccatgatca ggtccacctt ctagaatgtg cctggctaga gatcctgatg attggtctcg  9780
tctggcgctc catggagcac ccagtgaagc tactgtttgc tcctaacttg ctcttggaca  9840
ggaaccaggg aaaatgtgta gagggcatgg tggagatctt cgacatgctg ctggctacat  9900
catctcggtt ccgcatgatg aatctgcagg gagaggagtt tgtgtgcctc aaatctatta  9960
ttttgcttaa ttctggagtg tacacatttc tgtccagcac cctgaagtct ctggaagaga  10020
aggaccatat ccaccgagtc ctggacaaga tcacagacac tttgatccac ctgatggcca  10080
aggcaggcct gaccctgcag cagcagcacc agcggctggc ccagctcctc ctcatcctct  10140
cccacatcag gcacatgagt aacaaaggca tggagcatct gtacagcatg aagtgcaaga  10200
acgtggtgcc cctctatgac ctgctgctgg aggcggcgga cgcccaccgc ctacatgcgc  10260
ccactagccg tggaggggca tccgtggagg agacggacca aagccacttg gccactgcgg  10320
gctctacttc atcgcattcc ttgcaaaagt attacatcac gggggaggca gagggtttcc  10380
ctgccacagc tcccggggat gagatggaag agtgctctca gcacttaccc ggcgccggca  10440
gtagtggcga tatcatggat tacaaggatg acgacgataa gggctcttcc gggacaggct  10500
ccggatccgg cactagtgcg cccatcacgg cgtacgccca gcagacgaga ggcctcctag  10560
ggtgtataat caccagcctg actggccggg acaaaaacca agtggagggt gaggtccaga  10620
tcgtgtcaac tgctacccaa accttcctgg caacgtgcat caatggggta tgctgggcag  10680
tctaccacgg ggccggaacg aggaccatcg catcacccaa gggtcctgtc atccagatgt  10740
ataccaatgt ggaccaagac cttgtgggct ggcccgctcc tcaaggttcc cgctcattga  10800
caccctgtac ctgcggctcc tcggaccttt acctggtcac gaggcacgcc gatgtcattc  10860
ccgtgcgccg gcgaggtgat agcaggggta gcctgctttc gccccggccc atttcctact  10920
tgaaaggctc ctctgggggt ccgctgttgt gccccgcggg acacgccgtg ggcctattca  10980
gggccgcggt gtgcacccgt ggagtggcta aagcggtgga ctttatccct gtggagaacc  11040
tagagacaac catgagatcc ccggtgttca cggacaactc ctctccacca gcagtcaccc  11100
tgacgcaccc aatcaccaaa atcgatacca aatacatcat gacatgcatg tcggccgacc  11160
tggaggtcgt cacgagcacc tgggtgctcg ttggcggcgt cctggctgct ctggccgcgt  11220
attgcctgtc aacaggctgc gtggtcatag tgggcaggat cgtcttgtcc gggaagccgg  11280
caattatacc tgacagggag gttctctact aagcggccgc gactctagag tcgacctgca  11340
ggcatgcaag cttgatatca agcttatcga taatcaacct ctggattaca aaatttgtga  11400
aagattgact ggtattctta actatgttgc tccttttacg ctatgtggat acgctgcttt  11460
aatgcctttg tatcatgcta ttgcttcccg tatggctttc attttctcct ccttgtataa  11520
atcctggttg ctgtctcttt atgaggagtt gtggcccgtt gtcaggcaac gtggcgtggt  11580
gtgcactgtg tttgctgacg caacccccac tggttggggc attgccacca cctgtcagct  11640
cctttccggg actttcgctt tccccctccc tattgccacg gcggaactca tcgccgcctg  11700
ccttgcccgc tgctggacag gggctcggct gttgggcact gacaattccg tggtgttgtc  11760
ggggaaatca tcgtcctttc cttggctgct cgcctgtgtt gccacctgga ttctgcgcgg  11820
gacgtccttc tgctacgtcc cttcggccct caatccagcg gaccttcctt cccgcggcct  11880
gctgccggct ctgcggcctc ttccgcgtct tcgccttcgc cctcagacga gtcggatctc  11940
cctttgggcc gcctccccgc at                                          11962

SEQ ID NO: 23          moltype = DNA  length = 11959
FEATURE                Location/Qualifiers
misc_feature           1..11959
                       note = synthetic vector
source                 1..11959
                       mol_type = other DNA
                       organism = synthetic construct
SEQUENCE: 23
cgataccgtc gacctcgagg gaattaattc gagctcggta cctttaagac caatgactta  60
caaggcagct gtagatctta gccacttttt aaaagaaaag gggggactgg aagggctaat  120
```

-continued

```
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
```

```
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc  8280
tggagctctc gagaattctc acgcgtgccg ccaccatgga ttacaaggat gacgacgata  8340
agggctcttc cgggacaggc tccggatccg gcactagtgc gcccatcacg gcgtacgccc  8400
agcagacgag aggcctccta gggtgtataa tcaccagcct gactggccgg gacaaaaacc  8460
aagtggaggg tgaggtccag atcgtgtcaa ctgctaccca aaccttcctg gcaacgtgca  8520
tcaatggggt atgctgggca gtctaccacg gggccggaac gaggaccatc gcatcaccca  8580
agggtcctgt catccagatg tataccaatg tggaccaaga ccttgtgggc tggcccgctc  8640
ctcaaggttc ccgctcattg acaccctgta cctgcggctc ctcggacctt tacctggtca  8700
cgaggcacgc cgatgtcatt cccgtgcgcc ggcgaggtga tagcaggggt agcctgcttt  8760
cgccccggcc catttcctac ttgaaaggct cctcgggggg tccgctgttg tgccccgcgg  8820
gacacgccgt gggcctattc agggccgcgg tgtgcacccg tggagtggct aaagcggtgg  8880
actttatccc tgtggagaac ctagagacaa ccatgagatc cccggtgttc acggacaact  8940
cctctccacc agcagtcacc ctgacgcacc caatcaccaa aatcgatacc aaatacatca  9000
tgacatgcat gtcggccgac ctggaggtcg tcacgagcac ctgggtgctc gttggcggcg  9060
tcctggctgc tctggccgcg tattgcctgt caacaggctg cgtggtcata gtgggcagga  9120
tcgtcttgtc cgggaagccg gcaggcagta gcggaagcag tattatacct gacagggagg  9180
ttctctacca ggagttcgaa gatgtcgtgc catgctcaat gggctcgccc gggtctagac  9240
caggcgaacg accgtttcaa tgccggatat gtatgaggaa cttctcccag aggtccagct  9300
tggtacggca cacccgaaca catacaggag aaaagccatt ccaatgtcga atttgtatgc  9360
gcaatttttc agacaagtct gtgttggctc gacacctccg cacacatact ggttcacaga  9420
agccctttca gtgcaggatt tgtatgcgca actttagcca acgctcatcc ctggtaaggc  9480
acactagaac gcatacaggt gagaagcctt tccagtgtcg catctgtatg cggaacttca  9540
gccagcggaa taacttgggc aggcatttgc gaactcacac cggttctcaa aaacctttc  9600
```

-continued

```
agtgccgaat ttgtatgcgc aacttcagca cccacgccgt attgacacga cacacgcgca  9660
cgcacaccgg ggaaaaaccg tttcaatgtc gaatctgcat gcgcaatttt agcgatagag  9720
ggaacctcac tcgacatctg cgcacacact tgcggggatc cacctgcagg gatgagtttc  9780
ccaccatggt gtttccttct gggcagatca gccaggcctc ggccttggcc ccggcccctc  9840
cccaagtcct gccccaggct ccagcccctg cccctgctcc agccatggta tcagctctgg  9900
cccaggcccc agcccctgtc ccagtcctag ccccaggccc tcctcaggct gtggccccac  9960
ctgcccccaa gcccacccag gctggggaag gaacgctgtc agaggccctg ctgcagctgc  10020
agtttgatga tgaagacctg gggggccttgc ttggcaacag cacagaccca gctgtgttca  10080
cagacctggc atccgtcgac aactccgagt ttcagcagct gctgaaccag ggcatacctg  10140
tggcccccca cacaactgag cccatgctga tggagtaccc tgaggctata actcgcctag  10200
tgacaggggc ccagaggccc cccgacccag ctcctgctcc actgggggcc ccggggctcc  10260
ccaatggcct cctttcagga gatgaagact tctcctccat tgcggacatg gacttctcag  10320
ccctgctgag tcagatcagc tcccaattgt gcgtacgcgg atcctctgct ggagacatga  10380
gagctgccaa cctttggcca agcccgctca tgatcaaacg ctctaagaag aacagcctgg  10440
ccttgtccct gacggccgac cagatggtca gtgccttgtt ggatgctgag cccccccatac  10500
tctattccga gtatgatcct accagaccct tcagtgaagc ttcgatgatg ggcttactga  10560
ccaacctggc agacagggag ctggttcaca tgatcaactg ggcgaagagg gtgccaggct  10620
ttgtggattt gaccctccat gatcaggtcc accttctaga atgtgcctgg ctagagatcc  10680
tgatgattgg tctcgtctgg cgctccatgg agcacccagt gaagctactg tttgctccta  10740
acttgctctt ggacaggaac cagggaaaat gtgtagaggg catggtggag atcttcgaca  10800
tgctgctggc tacatcatct cggttccgca tgatgaatct gcagggagag gagtttgtgt  10860
gcctcaaatc tattattttg cttaattctg gagtgtacac atttctgtcc agcaccctga  10920
agtctctgga agagaaggac catatccacc gagtcctgga caagatcaca gacactttga  10980
tccacctgat ggccaaggca ggcctgaccc tgcagcagca gcaccagcgg ctggcccagc  11040
tcctcctcat cctctcccac atcaggcaca tgagtaacaa aggcatggag catctgtaca  11100
gcatgaagtg caagaacgtg gtgcccctct atgacctgct gctggaggcg gcggacgccc  11160
accgcctaca tgcgcccact agccgtggag gggcatccgt ggaggagacg gaccaaagcc  11220
acttggccac tgcgggctct acttcatcgc attccttgca aaagtattac atcacggggg  11280
aggcagaggg tttccctgcc acagcttaag cggccgcgac tctagagtcg acctgcaggc  11340
atgcaagctt gatatcaagc ttatcgataa tcaacctctg gattacaaaa tttgtgaaag  11400
attgactggt attcttaact atgttgctcc ttttacgcta tgtggatacg ctgctttaat  11460
gcctttgtat catgctattg cttcccgtat ggctttcatt ttctcctcct tgtataaatc  11520
ctggttgctg tctctttatg aggagttgtg gcccgttgtc aggcaacgtg gcgtggtgtg  11580
cactgtgttt gctgacgcaa cccccactgg ttggggcatt gccaccacct gtcagctcct  11640
ttccgggact ttcgctttcc ccctccctat tgccacggcg gaactcatcg ccgcctgcct  11700
tgcccgctgc tggacagggg ctcggctgtt gggcactgac aattccgtgg tgttgtcggg  11760
gaaatcatcg tcctttcctt ggctgctcgc ctgtgttgcc acctggattc tgcgcgggac  11820
gtccttctgc tacgtccctt cggccctcaa tccagcggac cttccttccc gcggcctgct  11880
gccggctctg cggcctcttc cgcgtcttcg ccttcgccct cagacgagtc ggatctccct  11940
ttgggccgcc tccccgcat                                                 11959
```

```
SEQ ID NO: 24           moltype = DNA  length = 11128
FEATURE                 Location/Qualifiers
misc_feature            1..11128
                        note = synthetic vector
source                  1..11128
                        mol_type = other DNA
                        organism = synthetic construct
SEQUENCE: 24
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatgggggga  1740
tcatgtaact cgccttgatc gttgggaacc ggagctgaat gaagccatac caaacgacga  1800
```

-continued

```
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtcttcct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
```

-continued

```
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtggaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggtta tggcaagcta  7860
gctgcagtaa cgccattatt gcaaggcatg gaaaaatacc aaaccaagaa tagagaagtt  7920
cagatcaagg gcgggtacat gaaaatagct aacgtagggc caaacaggat atctgcggtg  7980
agcagtttcg gccccggccc ggggccaaga acagatggtc accgcagttt cggccccggc  8040
ccgaggccaa gagcagatgg tccccagata tggcccaacc ctcagcagtt tcttaagacc  8100
catcagatgt ttccaggctc cccccaaggac ctgaaatgac cctgcgcctt atttgaatta  8160
accaatcagc ctgcttctcg cttctgttcg cgcgcttctg cttcccgagc tctataaaag  8220
agctcacaac ccctcactcg gcgcgccagt cctccgacag actgagtcgc ccgggacgcg  8280
tgccgccacc atggactaca aagaccatga cggtgattat aaagatcatg acatcgatta  8340
caaggatgac gatgacaaga tggcccccaa gaaaaagagg aaggtgggca ttcacggggt  8400
gccgggtgga ctcgagggag gcggtggaag cggcggtacc gctagctcta gacccggaga  8460
gcgcccattc cagtgtcgga tttgcatgcg gaacttttcg agaagacacg gcctggacag  8520
acatacccgt actcatacag gtgaaaaacc ctttcagtgt cggatctgta tgcgaaattt  8580
ctccgaccac agcagcctga agagacatct acgtacccac accggcagcc agaagccatt  8640
tcagtgtcgg atctgtatgc ggaacttctc cgtgagacac aacctgacca gacatctacg  8700
tacgcacacc ggagagaagc cattccaatg ccgaatatgc atgcgcaact tcagtgacca  8760
cagcaacctg agcagacacc taaaaaccca caccggttcc cagaagccat ttcagtgtcg  8820
gatctgtatg cggaacttct cccagcgcag cagcctggtg agacatctac gtacgcacac  8880
cggagagaag ccattccaat gccgaatatg catgcgcaac ttcagtgaga gcggccacct  8940
gaagagacac ctgcgtacgc acctgagggg atccacctgc agggatgagt ttcccaccat  9000
ggtgtttcct tctgggcaga tcagccaggc ctcggccttg gccccggccc ctccccaagt  9060
cctgccccag gctccagccc ctgcccctgc tccagccatg gtatcagctc tggcccaggc  9120
cccagcccct gtcccagtcc tagccccagg ccctcctcag gctgtggccc cacctgcccc  9180
caagcccacc caggctgggg aaggaacgct gtcagaggcc ctgctgcagc tgcagtttga  9240
tgatgaagac ctgggggcct tgcttggcaa cagcacagac ccagctgtgt tcacagacct  9300
ggcatccgtc gacaactccg agtttcagca gctgctgaac cagggcatac ctgtggcccc  9360
ccacacaact gagcccatgc tgatggagta ccctgaggct ataactcgcc tagtgacagg  9420
ggcccagagg ccccccgacc cagctcctgc tccactgggg gccccggggc tccccaatgg  9480
cctcctttca ggagatgaag acttctcctc cattgcggac atggacttct cagccctgct  9540
gagtcagatc agctcccccg gggatgagat ggaagagtgc tctcagcact tacccggcgc  9600
cggcagtagt ggcgatatca tggattacaa ggatgacgac gataagggct cttccgggac  9660
aggctccgga tccggcacta gtgcgcccat cacggcgtac gcccagcaga cgagaggcct  9720
cctagggtgt ataatcacca gcctgactgg ccgggacaaa aaccaagtgg agggtgaggt  9780
ccagatcgtg tcaactgcta cccaaacctt cctggcaacg tgcatcaatg gggtatgctg  9840
ggcagtctac cacggggccg gaacgaggac catcgcatca cccaagggtc ctgtcatcca  9900
gatgtatacc aatgtggacc aagaccttgt gggctggccc gctcctcaag gttcccgctc  9960
attgacaccc tgtacctgcg gctcctcgga cctttacctg gtcacgaggc acgccgatgt  10020
cattcccgtg cgccggcgag gtgatagcag gggtagcctg ctttcgcccc ggcccatttc  10080
ctacttgaaa ggctcctctg gggtccgct gttgtgcccc gcgggacacg ccgtgggcct  10140
attcagggcc gcggtgtgca cccgtggagt ggctaaagcg gtggacttta tccctgtgga  10200
gaacctagag acaaccatga gatccccggt gttcacggac aactcctctc caccagcagt  10260
caccctgacg cacccaatca ccaaaatcga taccaaatac atcatgacat gcatgtcggc  10320
cgacctggag gtcgtcacga gcacctgggt gctcgttggc ggcgtcctgg ctgctctggc  10380
cgcgtattgc ctgtcaacag gctgcgtggt catagtgggc aggatcgtct tgtccgggaa  10440
gccggcaatt atacctgaca gggaggttct ctactaaagc ggccgcgact ctagagtcga  10500
cctgcaggca tgcaagcttg atatcaagct tatcgataat caacctctgg attacaaaat  10560
ttgtgaaaga ttgactggta ttcttaacta tgttgctcct tttacgctat gtggatacgc  10620
tgctttaatg cctttgtatc atgctattgc ttcccgtatg gctttcattt tctcctcctt  10680
gtataaatcc tggttgctgt ctctttatga ggagttgtgg cccgttgtca ggcaacgtgg  10740
cgtggtgtgc actgtgtttg ctgacgcaac ccccactggt tggggcattg ccaccacctg  10800
tcagctcctt tccgggactt tcgctttccc cctccctatt gccacggcgg aactcatcgc  10860
cgcctgcctt gcccgctgct ggacaggggc tcggctgttg ggcactgaca attccgtggt  10920
gttgtcgggg aaatcatcgt cctttccttg gctgctcgcc tgtgttgcca cctggattct  10980
gcgcgggacg tccttctgct acgtcccttc ggccctcaat ccagcggacc ttccttcccg  11040
cggcctgctg ccggctctgc ggcctcttcc gcgtcttcgc cttcgccctc agacgagtcg  11100
gatctccctt tgggccgcct ccccgcat                                    11128
```

SEQ ID NO: 25 moltype = DNA length = 11602

-continued

```
FEATURE                 Location/Qualifiers
misc_feature            1..11602
                        note = synthetic vector
source                  1..11602
                        mol_type = other DNA
                        organism = synthetic construct
SEQUENCE: 25
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
```

-continued

```
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc  8280
tggagctctc gagaattctc acgcgtgccg ccaccatgct agcagtgtca gtgacatttg  8340
aagatgtggc tgtgctcttt actcgggacg agtggaagaa gctggatctg tctcagagaa  8400
gcctgtaccg tgaggtgatg ctggagaatt acagcaacct ggcctccatg gcaggattcc  8460
tgtttaccaa accaaaggtg atctccctgt tgcagcaagg agaggatccc tggggggggta  8520
gcggcagcgg tagcgcatgc tctagaccag gcgaacgacc gtttcaatgc cggatatgta  8580
tgaggaactt ctcccagagg tccagcttgg tacggcacac ccgaacacat acaggagaaa  8640
agccattcca atgtcgaatt tgtatgcgca atttttcaga caagtctgtg ttggctcgac  8700
acctccgcac acatactggt tcacagaagc cctttcagtg caggatttgt atgcgcaact  8760
ttagccaacg ctcatccctg gtaaggcaca ctagaacgca tacaggtgag aagcctttcc  8820
agtgtcgcat ctgtatgcgg aacttcagcc agcggaataa cttgggcagg catttgcgaa  8880
ctcacaccgg ttctcaaaaa ccttttcagt gccgaatttg tatgcgcaac ttcagcaccc  8940
acgccgtatt gacacgacac acgcgcacgc acaccgggga aaaaccgttt caatgtcgaa  9000
tctgcatgcg caattttagc gatagaggga acctcactcg acatctgcgc acacacttgc  9060
```

-continued

```
ggggatccca attgtgcgta cgcggatcct ctgctggaga catgagagct gccaaccttt  9120
ggccaagccc gctcatgatc aaacgctcta agaagaacag cctggccttg tccctgacgg  9180
ccgaccagat ggtcagtgcc ttgttggatg ctgagccccc catactctat tccgagtatg  9240
atcctaccag acccttcagt gaagcttcga tgatgggctt actgaccaac ctggcagaca  9300
gggagctggt tcacatgatc aactgggcga agagggtgcc aggctttgtg gatttgaccc  9360
tccatgatca ggtccacctt ctagaatgtg cctggctaga gatcctgatg attggtctcg  9420
tctggcgctc catggagcac ccagtgaagc tactgtttgc tcctaacttg ctcttggaca  9480
ggaaccaggg aaaatgtgta gagggcatgg tggagatctt cgacatgctg ctggctacat  9540
catctcggtt ccgcatgatg aatctgcagg gagaggagtt tgtgtgcctc aaatctatta  9600
ttttgcttaa ttctggagtg tacacatttc tgtccagcac cctgaagtct ctggaagaga  9660
aggaccatat ccaccgagtc ctggacaaga tcacagacac tttgatccac ctgatggcca  9720
aggcaggcct gaccctgcag cagcagcacc agcggctggc ccagctcctc ctcatcctct  9780
cccacatcag gcacatgagt aacaaaggca tggagcatct gtacagcatg aagtgcaaga  9840
acgtggtgcc cctctatgac ctgctgctgg aggcggcgga cgcccaccgc ctacatgcgc  9900
ccactagccg tggaggggca tccgtggagg agacggacca aagccacttg gccactgcgg  9960
gctctacttc atcgcattcc ttgcaaaagt attacatcac gggggaggca gagggtttcc  10020
ctgccacagc tcccggggat gagatggaag agtgctctca gcacttaccc ggcgccggca  10080
gtagtggcga tatcatggat tacaaggatg acgacgataa gggctcttcc gggacaggct  10140
ccggatccgg cactagtgcg cccatcacgg cgtacgccca gcagacgaga ggcctcctag  10200
ggtgtataat caccagcctg actggccggg acaaaaacca agtggagggt gaggtccaga  10260
tcgtgtcaac tgctacccaa accttcctgg caacgtgcat caatggggta tgctgggcag  10320
tctaccacgg ggccggaacg aggaccatcg catcacccaa gggtcctgtc atccagatgt  10380
ataccaatgt ggaccaagac cttgtgggct ggcccgctcc tcaaggttcc cgctcattga  10440
caccctgtac ctgcggctcc tcggaccttt acctggtcac gaggcacgcc gatgtcattc  10500
ccgtgcgccg gcgaggtgat agcaggggta gcctgctttc gccccggccc atttcctact  10560
tgaaaggctc ctctgggggt ccgctgttgt gccccgcggg acacgccgtg ggcctattca  10620
gggccgcggt gtgcacccgt ggagtggcta aagcggtgga ctttatccct gtggagaacc  10680
tagagacaac catgagatcc ccggtgttca cggacaactc ctctccacca gcagtcaccc  10740
tgacgcaccc aatcaccaaa atcgatacca aatacatcat gacatgcatg tcggccgacc  10800
tggaggtcgt cacgagcacc tgggtgctcg ttggcggcgt cctggctgct ctggccgcgt  10860
attgcctgtc aacaggctgc gtggtcatag tgggcaggat cgtcttgtcc gggaagccgg  10920
caattatacc tgacagggag gttctctact aagcggccgc gactctagag tcgacctgca  10980
ggcatgcaag cttgatatca agcttatcga taatcaacct ctggattaca aaatttgtga  11040
aagattgact ggtattctta actatgttgc tccttttacg ctatgtggat acgctgcttt  11100
aatgcctttg tatcatgcta ttgcttcccg tatggctttc attttctcct ccttgtataa  11160
atcctggttg ctgtctcttt atgaggagtt gtggcccgtt gtcaggcaac gtggcgtggt  11220
gtgcactgtg tttgctgacg caacccccac tggttggggc attgccacca cctgtcagct  11280
cctttccggg actttcgctt tccccctccc tattgccacg gcggaactca tcgccgcctg  11340
ccttgcccgc tgctggacag gggctcggct gttgggcact gacaattccg tggtgttgtc  11400
ggggaaatca tcgtcctttc cttggctgct cgcctgtgtt gccacctgga ttctgcgcgg  11460
gacgtccttc tgctacgtcc cttcggccct caatccagcg gaccttcctt cccgcggcct  11520
gctgccggct ctgcggcctc ttccgcgtct tcgccttcgc cctcagacga gtcggatctc  11580
cctttgggcc gcctccccgc at                                            11602
```

```
SEQ ID NO: 26          moltype = DNA  length = 11977
FEATURE                Location/Qualifiers
misc_feature           1..11977
                       note = synthetic vector
source                 1..11977
                       mol_type = other DNA
                       organism = synthetic construct
SEQUENCE: 26
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
```

-continued gacagtaaga gaattatgca gtgctgccat aaccatgagt gataacactg cggccaactt 1680
acttctgaca acgatcggag gaccgaagga gctaaccgct tttttgcaca acatggggga 1740
tcatgtaact cgccttgatc gttgggaacc ggagctgaat gaagccatac caaacgacga 1800
gcgtgacacc acgatgcctg tagcaatggc aacaacgttg cgcaaactat taactggcga 1860
actacttact ctagcttccc ggcaacaatt aatagactgg atggaggcgg ataaagttgc 1920
aggaccactt ctgcgctcgg cccttccggc tggctggttt attgctgata aatctggagc 1980
cggtgagcgt gggtctcgcg gtatcattgc agcactgggg ccagatggta agccctcccg 2040
tatcgtagtt atctacacga cggggagtca ggcaactatg gatgaacgaa atagacagat 2100
cgctgagata ggtgcctcac tgattaagca ttggtaactg tcagaccaag tttactcata 2160
tatactttag attgatttaa aacttcattt ttaatttaaa aggatctagg tgaagatcct 2220
ttttgataat ctcatgacca aaatccctta acgtgagttt tcgttccact gagcgtcaga 2280
ccccgtagaa aagatcaaag gatcttcttg agatcctttt tttctgcgcg taatctgctg 2340
cttgcaaaca aaaaaaccac cgctaccagc ggtggtttgt ttgccggatc aagagctacc 2400
aactcttttt ccgaaggtaa ctggcttcag cagagcgcag ataccaaata ctgtctttct 2460
agtgtagccg tagttaggcc accacttcaa gaactctgta gcaccgccta catacctcgc 2520
tctgctaatc ctgttaccag tggctgctgc cagtggcgat aagtcgtgtc ttaccgggtt 2580
ggactcaaga cgatagttac cggataaggc gcagcggtcg ggctgaacgg ggggttcgtg 2640
cacacagccc agcttggagc gaacgaccta caccgaactg agatacctac agcgtgagct 2700
atgagaaagc gccacgcttc ccgaagggag aaaggcggac aggtatccgg taagcggcag 2760
ggtcggaaca ggagagcgca cgagggagct tccaggggga aacgcctggt atctttatag 2820
tcctgtcggg tttcgccacc tctgacttga gcgtcgattt ttgtgatgct cgtcaggggg 2880
gcggagccta tggaaaaacg ccagcaacgc ggccttttta cggttcctgg ccttttgctg 2940
gccttttgct cacatgttct ttcctgcgtt atcccctgat tctgtggata accgtattac 3000
cgcctttgag tgagctgata ccgctcgccg cagccgaacg accgagcgca gcgagtcagt 3060
gagcgaggaa gcggaagagc gcccaatacg caaaccgcct ctccccgcgc gttggccgat 3120
tcattaatgc agctgtggaa tgtgtgtcag ttagggtgtg gaaagtcccc aggctcccca 3180
gcaggcagaa gtatgcaaag catgcatctc aattagtcag caaccaggtg tggaaagtcc 3240
ccaggctccc cagcaggcag aagtatgcaa agcatgcatc tcaattagtc agcaaccata 3300
gtcccgcccc taactccgcc catcccgccc ctaactccgc ccagttccgc ccattctccg 3360
ccccatggct gactaatttt ttttatttat gcagaggccg aggccgcctc ggcctctgag 3420
ctattccaga agtagtgagg aggctttttt ggaggcctag gcttttgcaa aaagcttgga 3480
cacaagacag gcttgcgaga tatgtttgag aataccactt tatcccgcgt cagggagagg 3540
cagtgcgtaa aaagacgcgg actcatgtga aatactggtt tttagtgcgc cagatctcta 3600
taatctcgcg caacctattt tcccctcgaa cactttttaa gccgtagata aacaggctgg 3660
gacacttcac atgagcgaaa aatacatcgt cacctgggac atgttgcaga tccatgcacg 3720
taaactcgca agccgactga tgccttctga acaatggaaa ggcattattg ccgtaagccg 3780
tggcggtctg taccgggtgc gttactggcg cgtgaactgg gtattcgtca tgtcgatacc 3840
gtttgtattt ccagctacga tcacgacaac cagcgcgagc ttaaagtgct gaaacgcgca 3900
gaaggcgatg gcgaaggctt catcgttatt gatgacctgg tggataccgg tggtactgcg 3960
gttgcgattc gtgaaatgta tccaaaagcg cactttgtca ccatcttcgc aaaaccggct 4020
ggtcgtccgc tggttgatga ctatgttgtt gatatcccgc aagatacctg gattgaacag 4080
ccgtgggata tgggcgtcgt attcgtcccg ccaatctccg gtcgctaatc ttttcaacgc 4140
ctggcactgc cgggcgttgt tctttttaac ttcaggcggg ttacaatagt ttccagtaag 4200
tattctggag gctgcatcca tgacacaggc aaacctgagc gaaaccctgt tcaaaccccg 4260
ctttaaacat cctgaaacct cgacgctagt ccgccgcttt aatcacggcg cacaaccgcc 4320
tgtgcagtcg gcccttgatg gtaaaaccat ccctcactgg tatcgcatga ttaaccgtct 4380
gatgtggatc tggcgcggca ttgacccacg cgaaatcctc gacgtccagg cacgtattgt 4440
gatgagcgat gccgaacgta ccgacgatga tttatacgat acggtgattg gctaccgtgg 4500
cggcaactgg atttatgagt gggccccgga tctttgtgaa ggaaccttac ttctgtggtg 4560
tgacataatt ggacaaacta cctacagaga tttaaagctc taaggtaaat ataaaatttt 4620
taagtgtata atgtgttaaa ctactgattc taattgtttg tgtattttag attccaacct 4680
atggaactga tgaatgggag cagtggtgga atgcctttaa tgaggaaaac ctgttttgct 4740
cagaagaaat gccatctagt gatgatgagg ctactgctga ctctcaacat tctactcctc 4800
caaaaaagaa gagaaaggta gaagacccca aggactttcc ttcagaattg ctaagttttt 4860
tgagtcatgc tgtgtttagt aatagaactc ttgcttgctt tgctatttac accacaaagg 4920
aaaaagctgc actgctatac aagaaaatta tggaaaaata ttctgtaacc tttataagta 4980
ggcataacag ttataatcat aacatactgt tttttcttac tccacacagg catagagtgt 5040
ctgctattaa taactatgct caaaaattgt gtacctttag ctttttaatt tgtaaagggg 5100
ttaataagga atatttgatg tatagtgcct tgactagaga tcataatcag ccataccaca 5160
tttgtagagg ttttacttgc tttaaaaaac ctcccacacc tccccctgaa cctgaaacat 5220
aaaatgaatg caattgttgt tgttaacttg tttattgcag cttataatgg ttacaaataa 5280
agcaatagca tcacaaattt cacaaataaa gcattttttt cactgcattc tagttgtggt 5340
ttgtccaaac tcatcaatgt atcttatcat gtctggatca actggataac tcaagctaac 5400
caaaatcatc ccaaacttcc caccccatac cctattacca ctgccaatta cctagtggtt 5460
tcatttactc taaacctgtg attcctctga attattttca ttttaaagaa attgtatttg 5520
ttaaatatgt actacaaact tagtagttgg aagggctaat tcactcccaa agaagacaag 5580
atatccttga tctgtggatc taccacacac aaggctactt ccctgattag cagaactaca 5640
caccagggcc aggggtcaga tatccactga cctttggatg gtgctacaag ctagtaccag 5700
ttgagccaga taaggtagaa gaggccaata aaggagagaa caccagcttg ttacaccctg 5760
tgagcctgca tgggatggat gacccggaga gagaagtgtt agagtggagg tttgacagcc 5820
gcctagcatt tcatcacgtg gcccgagagc tgcatccgga gtacttcaag aactgctgat 5880
atcgagcttg ctacaaggga ctttccgctg gggactttcc agggaggcgt ggcctgggcg 5940
ggactgggga gtggcgagcc ctcagatcct gcatataagc agctgctttt tgcctgtact 6000
gggtctctct ggttagacca gatctgagcc tgggagctct ctggctaact agggaaccca 6060
ctgcttaagc ctcaataaag cttgccttga gtgcttcaag tagtgtgtgc ccgtctgttg 6120
tgtgactctg gtaactagag atccctcaga cccttttagt cagtgtggaa aatctctagc 6180
agtggcgccc gaacagggac ttgaaagcga aagggaaacc agaggagctc tctcgacgca 6240
ggactcggct tgctgaagcg cgcacggcaa gaggcgaggg gcggcgactg gtgagtacgc 6300
caaaaatttt gactagcgga ggctagaagg agagagatgg gtgcgagagc gtcagtatta 6360

```
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc cccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc  8280
tggagctctc gagaattctc acgcgtgccg ccaccatggg aaagaaaacc aagcggacag  8340
ctgacagttc ttcttcagag gatgaggagg agtatgtcgt ggagaaggtg ctagacaggc  8400
gcgtggttaa gggacaagtg gaatatctac tgaagtggaa aggcttttct gaggagcaca  8460
atacttggga acctgagaaa aacttggatt gccctgagct aatttctgaa tttatgaaaa  8520
agtataagaa gatgaaggag ggtgaaaata ataaacccag ggagaagtca gaaagtaaca  8580
agaggaaatc caatttctca aacagtgccg atgacatcaa atctaaaaaa aagagagagc  8640
agagcaatga tatcgctcgg ggctttgaga gaggactgga accagaaaag atcattgggg  8700
caacagattc ctgtggtgat ttaatgttcc taatgaaatg gaaagacaca gatgaagctg  8760
acctggttct tgcaaaagaa gctaatgtga aatgtccaca aattgtgata gcattttatg  8820
aagagagact gacatggcat gcatatcctg aggatgcgga aaacaaagag aaagaaacag  8880
caaagagcgg gggtagcggc agcggtagcg catgctctag accaggcgaa cgaccgtttc  8940
aatgccggat atgtatgagg aacttctccc agaggtccag cttggtacgg cacacccgaa  9000
cacatacagg agaaaagcca ttccaatgtc gaatttgtat gcgcaatttt tcagacaagt  9060
ctgtgttggc tcgacacctc cgcacacata ctggttcaca gaagcccttt cagtgcagga  9120
tttgtatgcg caactttagc caacgctcat ccctggtaag gcacactaga acgcatacag  9180
gtgagaagcc tttccagtgt cgcatctgta tgcggaactt cagccagcgg aataacttgg  9240
gcaggcattt gcgaactcac accggttctc aaaaaccttt tcagtgccga atttgtatgc  9300
gcaacttcag cacccacgcc gtattgacac gacacacgcg cacgcacacc ggggaaaaac  9360
cgtttcaatg tcgaatctgc atgcgcaatt ttagcgatag agggaacctc actcgacatc  9420
tgcgcacaca cttgcgggga tcccaattgt gcgtacgcgg atcctctgct ggagacatga  9480
gagctgccaa cctttggcca agcccgctca tgatcaaacg ctctaagaag aacagcctgg  9540
ccttgtccct gacggccgac cagatggtca gtgccttgtt ggatgctgag ccccccatac  9600
tctattccga gtatgatcct accagaccct tcagtgaagc ttcgatgatg ggcttactga  9660
ccaacctggc agacagggag ctggttcaca tgatcaactg ggcgaagagg gtgccaggct  9720
ttgtggattt gaccctccat gatcaggtcc accttctaga atgtgcctgg ctagagatcc  9780
tgatgattgg tctcgtctgg cgctccatgg agcacccagt gaagctactg tttgctccta  9840
acttgctctt ggacaggaac cagggaaaat gtgtagaggg catggtggag atcttcgaca  9900
tgctgctggc tacatcatct cggttccgca tgatgaatct gcagggagag gagtttgtgt  9960
gcctcaaatc tattattttg cttaattctg gagtgtacac atttctgtcc agcaccctga  10020
agtctctgga agagaaggac catatccacc gagtcctgga caagatcaca gacactttga  10080
tccacctgat ggccaaggca ggcctgaccc tgcagcagca gcaccagcgg ctggcccagc  10140
tcctcctcat cctctcccac atcaggcaca tgagtaacaa aggcatggag catctgtaca  10200
gcatgaagtg caagaacgtg gtgcccctct atgacctgct gctggaggcg gcggacgccc  10260
accgcctaca tgcgcccact agccgtggag gggcatccgt ggaggagacg gaccaaagcc  10320
acttggccac tgcgggctct acttcatcgc attccttgca aaagtattac atcacggggg  10380
aggcagaggg tttccctgcc acagctcccg gggatgagat ggaagagtgc tctcagcact  10440
tacccggcgc cggcagtagt ggcgatatca tggattacaa ggatgacgac gataagggct  10500
cttccgggac aggctccgga tccggcacta gtgcgcccat cacggcgtac gcccagcaga  10560
cgagaggcct cctagggtgt ataatcacca gcctgactgg ccgggacaaa aaccaagtgg  10620
agggtgaggt ccagatcgtg tcaactgcta cccaaacctt cctggcaacg tgcatcaatg  10680
ggtatgctg ggcagtctac cacggggccg gaacgaggac catcgcatca cccaagggtc  10740
ctgtcatcca gatgtatacc aatgtggacc aagaccttgt gggctggccc gctcctcaag  10800
gttcccgctc attgacaccc tgtacctgcg gctcctcgga cctttacctg gtcacgaggc  10860
acgccgatgt cattcccgtg cgccggcgag gtgatagcag gggtagcctg ctttcgcccc  10920
ggcccatttc ctacttgaaa ggctcctctg gggtccgct gttgtgcccc gcgggacacg  10980
ccgtgggcct attcagggcc gcggtgtgca cccgtggagt ggctaaagcg gtggacttta  11040
tccctgtgga gaacctagag acaaccatga gatccccggt gttcacggac aactcctctc  11100
```

```
caccagcagt caccctgacg cacccaatca ccaaaatcga taccaaatac atcatgacat  11160
gcatgtcggc cgacctggag gtcgtcacga gcacctgggt gctcgttggc ggcgtcctgg  11220
ctgctctggc cgcgtattgc ctgtcaacag gctgcgtggt catagtgggc aggatcgtct  11280
tgtccgggaa gccggcaatt atacctgaca gggaggttct ctactaagcg gccgcgactc  11340
tagagtcgac ctgcaggcat gcaagcttga tatcaagctt atcgataatc aacctctgga  11400
ttacaaaatt tgtgaaagat tgactggtat tcttaactat gttgctcctt ttacgctatg  11460
tggatacgct gctttaatgc ctttgtatca tgctattgct tcccgtatgg ctttcatttt  11520
ctcctccttg tataaatcct ggttgctgtc tctttatgag gagttgtggc ccgttgtcag  11580
gcaacgtggc gtggtgtgca ctgtgtttgc tgacgcaacc cccactggtt ggggcattgc  11640
caccacctgt cagctccttt ccgggacttt cgctttcccc ctccctattg ccacggcgga  11700
actcatcgcc gcctgccttg cccgctgctg gacaggggct cggctgttgg gcactgacaa  11760
ttccgtggtg ttgtcgggga aatcatcgtc ctttccttgg ctgctcgcct gtgttgccac  11820
ctggattctg cgcgggacgt ccttctgcta cgtcccttcg gccctcaatc cagcggacct  11880
tccttcccgc ggcctgctgc cggctctgcg gcctcttccg cgtcttcgcc ttcgccctca  11940
gacgagtcgg atctcccttt gggccgcctc cccgcat                           11977

SEQ ID NO: 27          moltype = DNA  length = 12727
FEATURE                Location/Qualifiers
misc_feature           1..12727
                       note = synthetic vector
source                 1..12727
                       mol_type = other DNA
                       organism = synthetic construct
SEQUENCE: 27
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc cctttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
```

-continued

```
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcctgcagc ccgataaaa taaaagattt  7800
tatttagtct ccagaaaaag gggggaatga aagaccccac ctgtaggttt ggcaagctag  7860
ctgcagtaac gccattttgc aaggcatgga aaaataccaa accaagaata gagaagttca  7920
gatcaagggc gggtacatga aaatagctaa cgttgggcca aacaggatat ctgcggtgag  7980
cagtttcggc cccggcccgg ggccaagaac agatggtcac cgcagtttcg gccccggccc  8040
```

-continued

```
gaggccaaga acagatggtc cccagatatg gcccaaccct cagcagtttc ttaagaccca  8100
tcagatgttt ccaggctccc ccaaggacct gaaatgaccc tgcgccttat ttgaattaac  8160
caatcagcct gcttctcgct tctgttcgcg cgcttctgct tcccgagctc tataaaagag  8220
ctcacaaccc ctcactcggc gcgccagtcc tccgacagac tgagtcgccc ggggggggatc 8280
tggagctctc gagaattctc acgcgtgccg ccaccatgtc cgagagggaa gtgtcgactg  8340
cgccggcggg aacagacatg cccgcggcca agaagcagaa gttgagcagc gacgagaaca  8400
gcaacccgga cctctcggga gacgaaaatg acgatgctgt cagtattgag agtggcacaa  8460
acacagaacg cccggacacg cccacaaata cgccaaatgc accaggaagg aaaagctggg  8520
gaaagggaaa atggaagtca aagaaatgca aatattcttt caaatgtgtg aacagcctca  8580
aggaagatca taaccagcca ttgtttggag ttcagtttaa ctggcacagt aaagaaggag  8640
accctctggt gtttgcaact gtgggaagca acagagtaac cttatacgaa tgccattcac  8700
agggggagat acggttattg cagtcctatg tagatgctga tgcagatgaa aacttttaca  8760
cttgtgcatg gacctatgat agcaacacca gccaccctct attagcagtt gctggatcta  8820
gaggcattat aagaataatt aatcctataa caatgcagtg tataaagcac tatgttggcc  8880
atggaaatgc tatcaatgag ctgaaattcc acccacgaga cccaaacctt ctcctgtcag  8940
taagtaaaga tcatgcttta cggttatgga atatccaaac agacactctt gtggcaatat  9000
tcggaggtgt ggaagggcac agagatgaag ttctgagtgc tgattatgat cttttgggtg  9060
aaaaaataat gtcctgtggt atggatcact ctcttaaact gtggagaatc aactcaaaga  9120
ggatgatgaa tgcaattaag gagtcttatg attataaccc aaacaaaact aacaggccat  9180
ttatttccca gaaaatccac tttcctgact tttctaccag agacatacat aggaattatg  9240
ttgattgtgt gcgatggtta ggcgatttga tactttccaa gtcttgtgaa aatgccattg  9300
tatgctggaa acctggcaaa atggaggatg atatagataa aattaaacct agtgagtcta  9360
atgtgactat tcttgggcga tttgattaca gccagtgtga catttggtac atgaggtttt  9420
ctatggattt ctggcaaaag atgcttgcat tgggcaatca ggttggcaaa ctgtatgttt  9480
gggatttaga agtagaagat cctcataaag ccaaatgcac aacactgacc catcataaat  9540
gtggcgcggc tattcgacaa accagtttca gtagggatag cagcatcctc atagctgtct  9600
gcgatgatgc cagcatttgg cgctgggatc gacttcgagg gggtagcggc agcggtagcg  9660
catgctctag accaggcgaa cgaccgtttc aatgccggat atgtatgagg aacttctccc  9720
agaggtccag cttggtacgg cacacccgaa cacatacagg agaaaagcca ttccaatgtc  9780
gaatttgtat gcgcaatttt tcagacaagt ctgtgttggc tcgacacctc cgcacacata  9840
ctggttcaca gaagcccttt cagtgcagga tttgtatgcg caactttagc caacgctcat  9900
ccctggtaag gcacactaga acgcatacag gtgagaagcc tttccagtgt cgcatctgta  9960
tgcggaactt cagccagcgg aataacttgg gcaggcattt gcgaactcac accggttctc  10020
aaaaaccttt tcagtgccga atttgtatgc gcaacttcag cacccacgcc gtattgacac  10080
gacacacgcg cacgcacacc ggggaaaaac cgtttcaatg tcgaatctgc atgcgcaatt  10140
ttagcgatag agggaacctc actcgacatc tgcgcacaca cttgcgggga tcccaattgt  10200
gcgtacgcgg atcctctgct ggagacatga gagctgccaa cctttggcca agcccgctca  10260
tgatcaaacg ctctaagaag aacagcctgg ccttgtccct gacggccgac cagatggtca  10320
gtgccttgtt ggatgctgag ccccccatac tctattccga gtatgatcct accagaccct  10380
tcagtgaagc ttcgatgatg ggcttactga ccaacctggc agacagggag ctggttcaca  10440
tgatcaactg ggcgaagagg gtgccaggct ttgtggattt gaccctccat gatcaggtcc  10500
accttctaga atgtgcctgg ctagagatcc tgatgattgg tctcgtctgg cgctccatgg  10560
agcacccagt gaagctactg tttgctccta acttgctctt ggacaggaac cagggaaaat  10620
gtgtagaggg catggtggag atcttcgaca tgctgctggc tacatcatct cggttccgca  10680
tgatgaatct gcagggagag gagtttgtgt gcctcaaatc tattattttg cttaattctg  10740
gagtgtacac atttctgtcc agcaccctga agtctctgga agagaaggac catatccacc  10800
gagtcctgga caagatcaca gacactttga tccacctgat ggccaaggca ggcctgaccc  10860
tgcagcagca gcaccagcgg ctggcccagc tcctcctcat cctctcccac atcaggcaca  10920
tgagtaacaa aggcatggag catctgtaca gcatgaagtg caagaacgtg gtgcccctct  10980
atgacctgct gctggaggcg gcggacgccc accgcctaca tgcgcccact agccgtggag  11040
gggcatccgt ggaggagacg gaccaaagcc acttggccac tgcgggctct acttcatcgc  11100
attccttgca aaagtattac atcacggggg aggcagaggg tttccctgcc acagctcccg  11160
gggatgagat ggaagagtgc tctcagcact tacccggcgc cggcagtagt ggcgatatca  11220
tggattacaa ggatgacgac gataagggct cttccgggac aggctccgga tccggcacta  11280
gtgcgcccat cacggcgtac gcccagcaga cgagaggcct cctagggtgt ataatcacca  11340
gcctgactgg ccgggacaaa aaccaagtgg agggtgaggt ccagatcgtg tcaactgcta  11400
cccaaacctt cctggcaacg tgcatcaatg ggtatgctg ggcagtctac cacggggccg  11460
gaacgaggac catcgcatca cccaagggtc ctgtcatcca gatgtatacc aatgtggacc  11520
aagaccttgt gggctggccc gctcctcaag gttcccgctc attgacaccc tgtacctgcg  11580
gctcctcgga cctttacctg gtcacgaggc acgccgatgt cattcccgtg cgccggcgag  11640
gtgatagcag gggtagcctg ctttcgcccc ggcccatttc ctacttgaaa ggctcctctg  11700
ggggtccgct gttgtgcccc gcgggacacg ccgtgggcct attcagggcc gcggtgtgca  11760
cccgtggagt ggctaaagcg gtggacttta tccctgtgga gaacctagag acaaccatga  11820
gatccccggt gttcacggac aactcctctc caccagcagt caccctgacg cacccaatca  11880
ccaaaatcga taccaaatac atcatgacat gcatgtcggc cgacctggag gtcgtcacga  11940
gcacctgggt gctcgttggc ggcgtcctgg ctgctctggc cgcgtattgc ctgtcaacag  12000
gctgcgtggt catagtgggc aggatcgtct tgtccgggaa gccggcaatt atacctgaca  12060
gggaggttct ctactaagcg gccgcgactc tagagtcgac ctgcaggcat gcaagcttga  12120
tatcaagctt atcgataatc aacctctgga ttacaaaatt tgtgaaagat tgactggtat  12180
tcttaactat gttgctcctt ttacgctatg tggatacgct gctttaatgc ctttgtatca  12240
tgctattgct tcccgtatgg ctttcatttt ctcctccttg tataaatcct ggttgctgtc  12300
tctttatgag gagttgtggc ccgttgtcag gcaacgtggc gtggtgtgca ctgtgtttgc  12360
tgacgcaacc cccactggtt ggggcattgc caccacctgt cagctccttt ccgggacttt  12420
cgctttcccc ctccctattg ccacggcgga actcatcgcc gcctgccttg cccgctgctg  12480
gacaggggct cggctgttgg gcactgacaa ttccgtggtg ttgtcgggga aatcatcgtc  12540
ctttccttgg ctgctcgcct gtgttgccac ctggattctg cgcgggacgt ccttctgcta  12600
cgtcccttcg gccctcaatc cagcggacct tccttcccgc ggcctgctgc cggctctgcg  12660
gcctcttccg cgtcttcgcc ttcgccctca gacgagtcgg atctcccttt gggccgcctc  12720
cccgcat                                                            12727
```

SEQ ID NO: 28 moltype = DNA length = 2712
FEATURE Location/Qualifiers
misc_feature 1..2712
note = synthetic polynucleotide
source 1..2712
mol_type = other DNA
organism = synthetic construct
SEQUENCE: 28
atgttcgaac ccaagaagaa gagaaaggtg ttcgaaacta gtgtgcccct gtatggcttc 60
acttccattt gtggccgacg gcctgaaatg gaagccgcgg tgtcaaccat accacggttt 120
ctgcagagct catcaggctc catgctggac ggacgctttg atccacagtc tgccgcacat 180
ttctttggag tctacgacgg ccacgggggc agccaggtcg ccaactactg cagggaaagg 240
atgcatttgg cacttgccga agagatcgcc aaagagaagc ccatgttgtg tgatggggat 300
acctggctgg agaagtggaa gaaagcgctt tttaactctt ttctgagagt ggattctgag 360
atagaatctg tcgcacccga gaccgtgggc agcacatccg tcgtagccgt agtgtttccc 420
tcccacatat tcgtcgccaa ctgcggcgac agtcgagccg tcctctgccg aggtaagacc 480
gccctgcctc tgagtgttga ccataagccc gaccgggagg atgaggccgc ccgaatcgag 540
gccgccggtg gaaaagtcat ccaatggaac ggcgcaagag tgttcggcgt gctggcgatg 600
tccaggagca ttggagaccg gtacctgaag cccagcataa tcccagatcc cgaagtgacc 660
gcagtcaaga gggtgaaaga ggacgattgt ctgatcctgg ctagcgatgg cgtatgggac 720
gtgatgactg atgaggaggc gtgtgaaatg gcccgcaagc gaatcctgct gtggcataaa 780
aaaaacgcag tcgcggggga cgcttctctt ctggcagacg aaaggcgcaa agaaggtaaa 840
gacccggctg ctatgagcgc cgccgaatat ctcagtaagc tggcaattca gcgagggtcc 900
aaagacaaca tttccgtggt cgtggtagac ctcaaaggcg gttccggcgg ttctagacca 960
ggcgaacgac cgtttcaatg ccggatatgt atgaggaact tctccgagga ggcaaacttg 1020
aggcgccaca cccgaacaca tacaggagaa aagccattcc aatgtcgaat ttgtatgcgc 1080
aatttttcag atcactcaag cctcaagcga cacctccgca cacatactgg ttcacagaag 1140
ccctttcagt gcaggatttg tatgcgcaac tttagccaat cagcgaacct tttgcggcac 1200
actagaacgc atacaggtga gaagcctttc cagtgtcgca tctgtatgcg gaacttcagc 1260
gaccccagtt cattgaagag gcatttgcga actcacaccg gttctcaaaa accttttcag 1320
tgccgaattt gtatgcgcaa cttcagccaa caaacaaatt tgacgagaca cacgcgcacg 1380
cacaccgggg aaaaaccgtt tcaatgtcga atctgcatgc gcaattttag cgatgcgaca 1440
caacttgtta ggcatctgcg cacacacttg cggggatccc cgaagaaaaa acggaaagtg 1500
acctgcaggg gaagcggagc tactaacttc agcctgctga agcaggctgg agacgtggag 1560
gagaaccctg gacctggtca ccatgatgag tttcccacca tggtgtttcc ttctgggcag 1620
atcagccagg cctcggcctt ggccccggcc cctccccaag tcctgcccca ggctccagcc 1680
cctgcccctg ctccagccat ggtatcagct ctggcccagg ccccagcccc tgtcccagtc 1740
ctagccccag gccctcctca ggctgtggcc ccacctgccc ccaagcccac ccaggctggg 1800
gaaggaacgc tgtcagaggc cctgctgcag ctgcagtttg atgatgaaga cctgggggcc 1860
ttgcttggca acagcacaga cccagctgtg ttcacagacc tggcatccgt cgacaactcc 1920
gagtttcagc agctgctgaa ccagggcata cctgtggccc cccacacaac tgagcccatg 1980
ctgatggagt accctgaggc tataactcgc ctagtgacag gggcccagag gccccccgac 2040
ccagctcctg ctccactggg ggccccgggg ctccccaatg gcctcctttc aggagatgaa 2100
gacttctcct ccattgcgga catggacttc tcagccctgc tgagtcagat cagctccggt 2160
ggtggcagcg gtcaattgac tcaagacgaa ttcacccaac tctcccaatc aatcgccgag 2220
ttccacacgt accaactcgg taacggccgt tgctcatctc tcctagctca gcgaatccac 2280
gcgccgccgg aaacagtatg gtccgtggtg agacgtttcg ataggccaca gatttacaaa 2340
cacttcatca aaagctgtaa cgtgagtgaa gatttcgaga tgcgagtggg atgcacgcgc 2400
gacgtgaacg tgataagtgg attaccggcg aatacgtctc gagagagatt agatctgttg 2460
gacgatgatc ggagagtgac tgggtttagt ataaccggtg gtgaacatag gctgaggaat 2520
tataaatcgg ttacgacggt tcatagattt gagaaagaag aagaagaaga aaggatctgg 2580
accgttgttt tggaatctta tgttgttgat gtaccggaag gtaattcgga ggaagatacg 2640
agattgtttg ctgatacggt tattagattg aatcttcaga aacttgcttc gatcactgaa 2700
gctatgaact aa 2712

SEQ ID NO: 29 moltype = DNA length = 2427
FEATURE Location/Qualifiers
misc_feature 1..2427
note = synthetic polynucleotide
source 1..2427
mol_type = other DNA
organism = synthetic construct
SEQUENCE: 29
atgttcgaac ccaagaagaa gagaaaggtg ttcgaaacta gtgtgcccct gtatggcttc 60
acttccattt gtggccgacg gcctgaaatg gaagccgcgg tgtcaaccat accacggttt 120
ctgcagagct catcaggctc catgctggac ggacgctttg atccacagtc tgccgcacat 180
ttctttggag tctacgacgg ccacgggggc agccaggtcg ccaactactg cagggaaagg 240
atgcatttgg cacttgccga agagatcgcc aaagagaagc ccatgttgtg tgatggggat 300
acctggctgg agaagtggaa gaaagcgctt tttaactctt ttctgagagt ggattctgag 360
atagaatctg tcgcacccga gaccgtgggc agcacatccg tcgtagccgt agtgtttccc 420
tcccacatat tcgtcgccaa ctgcggcgac agtcgagccg tcctctgccg aggtaagacc 480
gccctgcctc tgagtgttga ccataagccc gaccgggagg atgaggccgc ccgaatcgag 540
gccgccggtg gaaaagtcat ccaatggaac ggcgcaagag tgttcggcgt gctggcgatg 600
tccaggagca ttggagaccg gtacctgaag cccagcataa tcccagatcc cgaagtgacc 660
gcagtcaaga gggtgaaaga ggacgattgt ctgatcctgg ctagcgatgg cgtatgggac 720
gtgatgactg atgaggaggc gtgtgaaatg gcccgcaagc gaatcctgct gtggcataaa 780
aaaaacgcag tcgcggggga cgcttctctt ctggcagacg aaaggcgcaa agaaggtaaa 840
gacccggctg ctatgagcgc cgccgaatat ctcagtaagc tggcaattca gcgagggtcc 900

```
aaagacaaca tttccgtggt cgtggtagac ctcaaaggcg gttccggcgg ttctagacca  960
ggcgaacgac cgtttcaatg ccggatatgt atgaggaact tctccgagga ggcaaacttg  1020
aggcgccaca cccgaacaca tacaggagaa aagccattcc aatgtcgaat ttgtatgcgc  1080
aatttttcag atcactcaag cctcaagcga cacctccgca cacatactgg ttcacagaag  1140
ccctttcagt gcaggatttg tatgcgcaac tttagccaat cagcgaacct tttgcggcac  1200
actagaacgc atacaggtga gaagcctttc cagtgtcgca tctgtatgcg gaacttcagc  1260
gaccccagtt cattgaagag gcatttgcga actcacaccg gttctcaaaa accttttcag  1320
tgccgaattt gtatgcgcaa cttcagccaa caaacaaatt tgacgagaca cacgcgcacg  1380
cacaccgggg aaaaaccgtt tcaatgtcga atctgcatgc gcaattttag cgatgcgaca  1440
caacttgtta ggcatctgcg cacacacttg cggggatcca cctgcagggg aagcggagct  1500
actaacttca gcctgctgaa gcaggctgga gacgtggagg agaaccctgg acctggtcac  1560
catccgaaga aaaaacggaa agtggatgct aagtcactga ctgcctggtc ccggacactg  1620
gtgaccttca aggatgtgtt tgtggacttc accagggagg agtggaagct gctggacact  1680
gctcagcaga tcctgtacag aaatgtgatg ctggagaact ataagaacct ggtttccttg  1740
ggttatcagc ttactaagcc agatgtgatc ctccggttgg agaagggaga agagccctgg  1800
ctggtggaga gagaaattca ccaagagacc catcctgatt cagagactgc atttgaaatc  1860
aaatcatcag ttggtggtgg cagcggtcaa ttgactcaag acgaattcac ccaactctcc  1920
caatcaatcg ccgagttcca cacgtaccaa ctcggtaacg gccgttgctc atctctccta  1980
gctcagcgaa tccacgcgcc gccggaaaca gtatggtccg tggtgagacg tttcgatagg  2040
ccacagattt acaaacactt catcaaaagc tgtaacgtga gtgaagattt cgagatgcga  2100
gtgggatgca cgcgcgacgt gaacgtgata agtggattac cggcgaatac gtctcgagag  2160
agattagatc tgttggacga tgatcggaga gtgactgggt ttagtataac cggtggtgaa  2220
cataggctga ggaattataa atcggttacg acggttcata gatttgagaa agaagaagaa  2280
gaagaaagga tctggaccgt tgttttggaa tcttatgttg ttgatgtacc ggaaggtaat  2340
tcggaggaag atacgagatt gtttgctgat acggttatta gattgaatct tcagaaactt  2400
gcttcgatca ctgaagctat gaactaa                                      2427

SEQ ID NO: 30          moltype = DNA  length = 2079
FEATURE                Location/Qualifiers
misc_feature           1..2079
                       note = synthetic polynucleotide
source                 1..2079
                       mol_type = other DNA
                       organism = synthetic construct
SEQUENCE: 30
atgtctagac caggcgaacg accgtttcaa tgccggatat gtatgaggaa cttctcccag  60
aggtccagct tggtacggca cacccgaaca catacaggag aaaagccatt ccaatgtcga  120
atttgtatgc gcaatttttc agacaagtct gtgttggctc gacacctccg cacacatact  180
ggttcacaga agccctttca gtgcaggatt tgtatgcgca actttagcca acgctcatcc  240
ctggtaaggc acactagaac gcatacaggt gagaagcctt tccagtgtcg catctgtatg  300
cggaacttca gccagcggaa taacttgggc aggcatttgc gaactcacac cggttctcaa  360
aaaccttttc agtgccgaat ttgtatgcgc aacttcagca cccacgccgt attgacacga  420
cacacgcgca cgcacaccgg ggaaaaaccg tttcaatgtc gaatctgcat gcgcaatttt  480
agcgatagag ggaacctcac tcgacatctg cgcacacact tgcggggatc cacctgcagg  540
gatgagtttc ccaccatggt gtttccttct gggcagatca gccaggcctc ggccttggcc  600
ccggcccctc cccaagtcct gccccaggct ccagcccctg cccctgctcc agccatggta  660
tcagctctgg cccaggcccc agcccctgtc ccagtcctag ccccaggccc tcctcaggct  720
gtggccccac ctgcccccaa gcccacccag gctggggaag gaacgctgtc agaggccctg  780
ctgcagctgc agtttgatga tgaagacctg gggggccttgc ttggcaacag cacagaccca  840
gctgtgttca cagacctggc atccgtcgac aactccgagt ttcagcagct gctgaaccag  900
ggcatacctg tggcccccca cacaactgag cccatgctga tggagtaccc tgaggctata  960
actcgcctag tgacaggggc ccagaggccc cccgacccag ctcctgctcc actgggggcc  1020
ccggggctcc ccaatggcct cctttcagga gatgaagact tctcctccat tgcggacatg  1080
gacttctcag ccctgctgag tcagatcagc tcccaattgt gcgtacgcgg atcctctgct  1140
ggagacatga gagctgccaa cctttggcca agcccgctca tgatcaaacg ctctaagaag  1200
aacagcctgg ccttgtccct gacggccgac cagatggtca gtgccttgtt ggatgctgag  1260
ccccccatac tctattccga gtatgatcct accagaccct tcagtgaagc ttcgatgatg  1320
ggcttactga ccaacctggc agacagggag ctggttcaca tgatcaactg ggcgaagagg  1380
gtgccaggct ttgtggattt gaccctccat gatcaggtcc accttctaga atgtgcctgg  1440
ctagagatcc tgatgattgg tctcgtctgg cgctccatgg agcacccagt gaagctactg  1500
tttgctccta acttgctctt ggacaggaac cagggaaaat gtgtagaggg catggtggag  1560
atcttcgaca tgctgctggc tacatcatct cggttccgca tgatgaatct gcagggagag  1620
gagtttgtgt gcctcaaatc tattattttg cttaattctg gagtgtacac atttctgtcc  1680
agcaccctga agtctctgga agagaaggac catatccacc gagtcctgga caagatcaca  1740
gacactttga tccacctgat ggccaaggca ggcctgaccc tgcagcagca gcaccagcgg  1800
ctggcccagc tcctcctcat cctctcccac atcaggcaca tgagtaacaa aggcatggag  1860
catctgtaca gcatgaagtg caagaacgtg gtgcccctct atgacctgct gctggaggcg  1920
gcggacgccc accgcctaca tgcgcccact agccgtggag gggcatccgt ggaggagacg  1980
gaccaaagcc acttggccac tgcgggctct acttcatcgc attccttgca aaagtattac  2040
atcacggggg aggcagaggg tttccctgcc acagcttaa                         2079

SEQ ID NO: 31          moltype = DNA  length = 1818
FEATURE                Location/Qualifiers
misc_feature           1..1818
                       note = synthetic polynucleotide
source                 1..1818
                       mol_type = other DNA
                       organism = synthetic construct
SEQUENCE: 31
```

```
atggatgcta agtcactgac tgcctggtcc cggacactgg tgaccttcaa ggatgtgttt  60
gtggacttca ccagggagga gtggaagctg ctggacactg ctcagcagat cctgtacaga  120
aatgtgatgc tggagaacta taagaacctg gtttccttgg gttatcagct tactaagcca  180
gatgtgatcc tccggttgga gaagggagaa gagccctggc tggtggagag agaaattcac  240
caagagaccc atcctgattc agagactgca tttgaaatca aatcatcagt tctcgaggga  300
ggcggtggaa gcggcacctg caggtctaga ccaggcgaac gaccgtttca atgccggata  360
tgtatgagga acttctccca gaggtccagc ttggtacggc acacccgaac acatacagga  420
gaaaagccat tccaatgtcg aatttgtatg cgcaattttt cagacaagtc tgtgttggct  480
cgacacctcc gcacacatac tggttcacag aagccctttc agtgcaggat ttgtatgcgc  540
aactttagcc aacgctcatc cctggtaagg cacactagaa cgcatacagg tgagaagcct  600
ttccagtgtc gcatctgtat gcggaacttc agccagcgga ataacttggg caggcatttg  660
cgaactcaca ccggttctca aaaacctttt cagtgccgaa tttgtatgcg caacttcagc  720
acccacgccg tattgacacg acacacgcgc acgcacaccg gggaaaaacc gtttcaatgt  780
cgaatctgca tgcgcaattt tagcgataga gggaacctca ctcgacatct gcgcacacac  840
ttgcggggat cccaattgtg cgtacgcgga tcctctgctg gagacatgag agctgccaac  900
ctttggccaa gcccgctcat gatcaaacgc tctaagaaga acagcctggc cttgtccctg  960
acggccgacc agatggtcag tgccttgttg gatgctgagc cccccatact ctattccgag  1020
tatgatccta ccagaccctt cagtgaagct tcgatgatgg gcttactgac caacctggca  1080
gacagggagc tggttcacat gatcaactgg gcgaagaggg tgccaggctt tgtggatttg  1140
accctccatg atcaggtcca ccttctagaa tgtgcctggc tagagatcct gatgattggt  1200
ctcgtctggc gctccatgga gcacccagtg aagctactgt ttgctcctaa cttgctcttg  1260
gacaggaacc agggaaaatg tgtagagggc atggtggaga tcttcgacat gctgctggct  1320
acatcatctc ggttccgcat gatgaatctg cagggagagg agtttgtgtg cctcaaatct  1380
attattttgc ttaattctgg agtgtacaca tttctgtcca gcaccctgaa gtctctggaa  1440
gagaaggacc atatccaccg agtcctggac aagatcacag acactttgat ccacctgatg  1500
gccaaggcag gcctgaccct gcagcagcag caccagcggc tggcccagct cctcctcatc  1560
ctctcccaca tcaggcacat gagtaacaaa ggcatggagc atctgtacag catgaagtgc  1620
aagaacgtgg tgcccctcta tgacctgctg ctggaggcgg cggacgccca ccgcctacat  1680
gcgcccacta gccgtggagg ggcatccgtg gaggagacgg accaaagcca cttggccact  1740
gcgggctcta cttcatcgca ttccttgcaa aagtattaca tcacggggga ggcagagggt  1800
ttccctgcca cagcttaa                                                1818
```

```
SEQ ID NO: 32          moltype = DNA  length = 2115
FEATURE                Location/Qualifiers
misc_feature           1..2115
                       note = synthetic polynucleotide
source                 1..2115
                       mol_type = other DNA
                       organism = synthetic construct
SEQUENCE: 32
atgtctagac ccggagagcg cccattccag tgtcggattt gcatgcggaa cttttcgaga  60
agacacggcc tggacagaca tacccgtact catacaggtg aaaaaccctt tcagtgtcgg  120
atctgtatgc gaaatttctc cgaccacagc agcctgaaga gacatctacg tacccacacc  180
ggcagccaga agccatttca gtgtcggatc tgtatgcgga acttctccgt gagacacaac  240
ctgaccagac atctacgtac gcacaccgga gagaagccat tccaatgccg aatatgcatg  300
cgcaacttca gtgaccacag caacctgagc agacacctaa aaacccacac cggttcccag  360
aagccatttc agtgtcggat ctgtatgcgg aacttctccc agcgcagcag cctggtgaga  420
catctacgta cgcacaccgg agagaagcca ttccaatgcc gaatatgcat gcgcaacttc  480
agtgagagcg gccacctgaa gagacacctg cgtacgcacc tgaggggatc cacctgcagg  540
gactacaaag accatgacgg tgattataaa gatcatgaca tcgattacaa ggatgacgat  600
gacaagatgg cccccaagaa aaagaggaag gtgggcattc acggggtgcc gggtggactc  660
gagggaggcg gtggaagcgg cggtaccgag gacgtggtgt gctgccactc aatctacggc  720
aagaagaagg gtgatatcga cacctaccga tacataggct cttccgggac aggctgcgtg  780
gtcatagtgg gcaggatcgt cttgtccgga tccggcacta gtgcgcccat cacggcgtac  840
gcccagcaga cgagaggcct cctagggtgt ataatcacca gcctgactgg ccgggacaaa  900
aaccaagtgg agggtgaggt ccagatcgtg tcaactgcta cccaaacctt cctggcaacg  960
tgcatcaatg ggtatgctgg ggcagtctac cacggggccg gaacgaggac catcgcatca  1020
cccaagggtc ctgtcatcca gatgtatacc aatgtggacc aagaccttgt gggctggccc  1080
gctcctcaag gttcccgctc attgacaccc tgtacctgcg gctcctcgga cctttacctg  1140
gtcacgaggc acgccgatgt cattcccgtg cgccggcgag gtgatagcag ggtagcctg  1200
ctttcgcccc ggcccatttc ctacttgaaa ggctcctcgg ggggtccgct gttgtgcccc  1260
gcgggacacg ccgtgggcct attcagggcc gcggtgtgca cccgtggagt ggctaaagcg  1320
gtggacttta tccctgtgga gaacctagag acaaccatga gatccccggt gttcacggac  1380
aactcctctc caccagcagt caccctgacg cacccaatca ccaaaatcga tagggaggtt  1440
ctctaccagg agttcgatga gatggaagag tgctctcagc actatcccta cgatgtgccc  1500
gattacgctg gaggcggtgg aagcggcggt accgatgagt ttcccaccat ggtgtttcct  1560
tctgggcaga tcagccaggc ctcggccttg gccccggccc ctccccaagt cctgccccag  1620
gctccagccc ctgcccctgc tccagccatg gtatcagctc tggcccaggc cccagcccct  1680
gtcccagtcc tagccccagg ccctcctcag gctgtggccc cacctgcccc caagcccacc  1740
caggctgggg aaggaacgct gtcagaggcc ctgctgcagc tgcagtttga tgatgaagac  1800
ctgggggcct tgcttggcaa cagcacagac ccagctgtgt tcacagacct ggcatccgtc  1860
gacaactccg agtttcagca gctgctgaac cagggcatac ctgtggcccc ccacacaact  1920
gagcccatgc tgatggagta ccctgaggct ataactcgcc tagtgacagg ggcccagagg  1980
ccccccgacc cagctcctgc tccactgggg gccccggggc tccccaatgg cctcctttca  2040
ggagatgaag acttctcctc cattgcggac atggacttct cagccctgct gagtcagatc  2100
agctcccaat tgtaa                                                   2115
```

```
SEQ ID NO: 33          moltype = DNA  length = 1830
FEATURE                Location/Qualifiers
```

-continued

```
misc_feature             1..1830
                         note = synthetic polynucleotide
source                   1..1830
                         mol_type = other DNA
                         organism = synthetic construct
SEQUENCE: 33
atggatgcta agtcactgac tgcctggtcc cggacactgg tgaccttcaa ggatgtgttt  60
gtggacttca ccagggagga gtggaagctg ctggacactg ctcagcagat cctgtacaga  120
aatgtgatgc tggagaacta taagaacctg gtttccttgg gttatcagct tactaagcca  180
gatgtgatcc tccggttgga gaagggagaa gagccctggc tggtggagag agaaattcac  240
caagagaccc atcctgattc agagactgca tttgaaatca aatcatcagt tacctgcagg  300
gactacaaag accatgacgg tgattataaa gatcatgaca tcgattacaa ggatgacgat  360
gacaagatgg cccccaagaa aaagaggaag gtgggcattc acggggtgcc gggtggactc  420
gagggaggcg gtggaagcgg cggtaccgag gacgtggtgt gctgccactc aatctacggc  480
aagaagaagg gtgatatcga cacctaccga tacataggct cttccgggac aggctgcgtg  540
gtcatagtgg gcaggatcgt cttgtccgga tccggcacta gtgcgcccat cacggcgtac  600
gcccagcaga cgagaggcct cctagggtgt ataatcacca gcctgactgg ccgggacaaa  660
aaccaagtgg agggtgaggt ccagatcgtg tcaactgcta cccaaacctt cctggcaacg  720
tgcatcaatg ggtatgctg ggcagtctac cacggggccg gaacgaggac catcgcatca  780
cccaagggtc ctgtcatcca gatgtatacc aatgtggacc aagaccttgt gggctggccc  840
gctcctcaag gttcccgctc attgacaccc tgtacctgcg gctcctcgga cctttacctg  900
gtcacgaggc acgccgatgt cattcccgtg cgccggcgag gtgatagcag ggtagcctg  960
ctttcgcccc ggcccatttc ctacttgaaa ggctcctcgg ggggtccgct gttgtgcccc  1020
gcgggacacg ccgtgggcct attcagggcc gcggtgtgca cccgtggagt ggctaaagcg  1080
gtggacttta tccctgtgga gaacctagag acaaccatga gatccccggt gttcacggac  1140
aactcctctc caccagcagt caccctgacg cacccaatca ccaaaatcga tagggaggtt  1200
ctctaccagg agttcgatga gatggaagag tgctctcagc actatcccta cgatgtgccc  1260
gattacgctg gaggcggtgg aagcggcggt acctctagac ccggagagcg cccattccag  1320
tgtcggattt gcatgcggaa cttttcgaga agacacggcc tggacagaca tacccgtact  1380
catacaggtg aaaaaccctt tcagtgtcgg atctgtatgc gaaatttctc cgaccacagc  1440
agcctgaaga gacatctacg tacccacacc ggcagccaga agccatttca gtgtcggatc  1500
tgtatgcgga acttctccgt gagacacaac ctgaccagac atctacgtac gcacaccgga  1560
gagaagccat tccaatgccg aatatgcatg cgcaacttca gtgaccacag caacctgagc  1620
agacacctaa aaacccacac cggttcccag aagccatttc agtgtcggat ctgtatgcgg  1680
aacttctccc agcgcagcag cctggtgaga catctacgta cgcacaccgg agagaagcca  1740
ttccaatgcc gaatatgcat gcgcaacttc agtgagagcg gccacctgaa gagacacctg  1800
cgtacgcacc tgaggggatc ccaattgtaa                                   1830

SEQ ID NO: 34            moltype = DNA  length = 2997
FEATURE                  Location/Qualifiers
misc_feature             1..2997
                         note = synthetic polynucleotide
source                   1..2997
                         mol_type = other DNA
                         organism = synthetic construct
SEQUENCE: 34
atgtctagac caggcgaacg accgtttcaa tgccggatat gtatgaggaa cttctcccag  60
aggtccagct tggtacggca cacccgaaca catacaggag aaaagccatt ccaatgtcga  120
atttgtatgc gcaatttttc agacaagtct gtgttggctc gacacctccg cacacatact  180
ggttcacaga agccctttca gtgcaggatt tgtatgcgca actttagcca acgctcatcc  240
ctggtaaggc acactagaac gcatacaggt gagaagcctt tccagtgtcg catctgtatg  300
cggaacttca gccagcggaa taacttgggc aggcatttgc gaactcacac cggttctcaa  360
aaaccttttc agtgccgaat ttgtatgcgc aacttcagca cccacgccgt attgacacga  420
cacacgcgca cgcacaccgg ggaaaaaccg tttcaatgtc gaatctgcat gcgcaatttt  480
agcgatagag ggaacctcac tcgacatctg cgcacacact tgcggggatc cacctgcagg  540
gatgagtttc ccaccatggt gtttccttct gggcagatca gccaggcctc ggccttggcc  600
ccggcccctc cccaagtcct gccccaggct ccagcccctg cccctgctcc agccatggta  660
tcagctctgg cccaggcccc agcccctgtc ccagtcctag ccccaggccc tcctcaggct  720
gtggccccac ctgcccccaa gcccacccag gctggggaag gaacgctgtc agaggccctg  780
ctgcagctgc agtttgatga tgaagacctg gggccttgc ttggcaacag cacagaccca  840
gctgtgttca cagacctggc atccgtcgac aactccgagt ttcagcagct gctgaaccag  900
ggcatacctg tggcccccca cacaactgag cccatgctga tggagtaccc tgaggctata  960
actcgcctag tgacaggggc ccagaggccc cccgacccag ctcctgctcc actgggggcc  1020
ccggggctcc ccaatggcct cctttcagga gatgaagact tctcctccat tgcggacatg  1080
gacttctcag ccctgctgag tcagatcagc tcccaattgt gcgtacgcgg atcctctgct  1140
ggagacatga gagctgccaa cctttggcca agcccgctca tgatcaaacg ctctaagaag  1200
aacagcctgg ccttgtccct gacggccgac cagatggtca gtgccttgtt ggatgctgag  1260
ccccccatac tctattccga gtatgatcct accagaccct tcagtgaagc ttcgatgatg  1320
ggcttactga ccaacctggc agacagggag ctggttcaca tgatcaactg ggcgaagagg  1380
gtgccaggct ttgtggattt gaccctccat gatcaggtcc accttctaga atgtgcctgg  1440
ctagagatcc tgatgattgg tctcgtctgg cgctccatgg agcacccagt gaagctactg  1500
tttgctccta acttgctctt ggacaggaac cagggaaaat gtgtagaggg catggtggag  1560
atcttcgaca tgctgctggc tacatcatct cggttccgca tgatgaatct gcagggagag  1620
gagtttgtgt gcctcaaatc tattattttg cttaattctg gagtgtacac atttctgtcc  1680
agcaccctga agtctctgga agagaaggac catatccacc gagtcctgga caagatcaca  1740
gacactttga tccacctgat ggccaaggca ggcctgaccc tgcagcagca gcaccagcgg  1800
ctggcccagc tcctcctcat cctctcccac atcaggcaca tgagtaacaa aggcatggag  1860
catctgtaca gcatgaagtg caagaacgtg gtgcccctct atgacctgct gctggaggcg  1920
gcggacgccc accgcctaca tgcgcccact agccgtggag ggcatccgt ggaggagacg  1980
```

-continued

```
gaccaaagcc acttggccac tgcgggctct acttcatcgc attccttgca aaagtattac  2040
atcacggggg aggcagaggg tttccctgcc acagctcccg gggatgagat ggaagagtgc  2100
tctcagcact tacccggcgc cggcagtagt ggcgatatca tggattacaa ggatgacgac  2160
gataagggct cttccgggac aggctccgga tccggcacta gtgcgcccat cacggcgtac  2220
gcccagcaga cgagaggcct cctagggtgt ataatcacca gcctgactgg ccgggacaaa  2280
aaccaagtgg agggtgaggt ccagatcgtg tcaactgcta cccaaacctt cctggcaacg  2340
tgcatcaatg gggtatgctg ggcagtctac cacggggccg gaacgaggac catcgcatca  2400
cccaagggtc ctgtcatcca gatgtatacc aatgtggacc aagaccttgt gggctggccc  2460
gctcctcaag gttcccgctc attgacaccc tgtacctgcg gctcctcgga cctttacctg  2520
gtcacgaggc acgccgatgt cattcccgtg cgccggcgag gtgatagcag ggtagcctg   2580
ctttcgcccc ggcccatttc ctacttgaaa ggctcctctg gggtccgct gttgtgcccc   2640
gcgggacacg ccgtgggcct attcagggcc gcggtgtgca cccgtggagt ggctaaagcg  2700
gtggacttta tccctgtgga gaacctagag acaaccatga gatccccggt gttcacggac  2760
aactcctctc caccagcagt caccctgacg cacccaatca ccaaaatcga taccaaatac  2820
atcatgacat gcatgtcggc cgacctggag gtcgtcacga gcacctgggt gctcgttggc  2880
ggcgtcctgg ctgctctggc cgcgtattgc ctgtcaacag gctgcgtggt catagtgggc  2940
aggatcgtct tgtccgggaa gccggcaatt atacctgaca gggaggttct ctactaa     2997

SEQ ID NO: 35          moltype = DNA  length = 2994
FEATURE                Location/Qualifiers
misc_feature           1..2994
                       note = synthetic polynucleotide
source                 1..2994
                       mol_type = other DNA
                       organism = synthetic construct
SEQUENCE: 35
atggattaca aggatgacga cgataagggc tcttccggga caggctccgg atccggcact  60
agtgcgccca tcacggcgta cgcccagcag acgagaggcc tcctagggtg tataatcacc  120
agcctgactg gccgggacaa aaaccaagtg gagggtgagg tccagatcgt gtcaactgct  180
acccaaacct tcctggcaac gtgcatcaat ggggtatgct gggcagtcta ccacggggcc  240
ggaacgagga ccatcgcatc acccaagggt cctgtcatcc agatgtatac caatgtggac  300
caagaccttg tgggctggcc cgctcctcaa ggttcccgct cattgacacc ctgtacctgc  360
ggctcctcgg acctttacct ggtcacgagg cacgccgatg tcattcccgt gcgccggcga  420
ggtgatagca ggggtagcct gctttcgccc cggcccattt cctacttgaa aggctcctcg  480
gggggtccgc tgttgtgccc cgcgggacac gccgtgggcc tattcagggc cgcggtgtgc  540
acccgtggag tggctaaagc ggtggacttt atccctgtgg agaacctaga gacaaccatg  600
agatccccgg tgttcacgga caactcctct ccaccagcag tcaccctgac gcacccaatc  660
accaaaatcg ataccaaata catcatgaca tgcatgtcgg ccgacctgga ggtcgtcacg  720
agcacctggg tgctcgttgg cggcgtcctg gctgctctgg ccgcgtattg cctgtcaaca  780
ggctgcgtgg tcatagtggg caggatcgtc ttgtccggga agccggcagg cagtagcgga  840
agcagtatta tacctgacag ggaggttctc taccaggagt tcgaagatgt cgtgccatgc  900
tcaatgggct cgcccgggtc tagaccaggc gaacgaccgt ttcaatgccg gatatgtatg  960
aggaacttct cccagaggtc cagcttggta cggcacaccc gaacacatac aggagaaaag  1020
ccattccaat gtcgaatttg tatgcgcaat ttttcagaca agtctgtgtt ggctcgacac  1080
ctccgcacac atactggttc acagaagccc tttcagtgca ggatttgtat gcgcaacttt  1140
agccaacgct catccctggt aaggcacact agaacgcata caggtgagaa gcctttccag  1200
tgtcgcatct gtatgcggaa cttcagccag cggaataact tgggcaggca tttgcgaact  1260
cacaccggtt ctcaaaaacc ttttcagtgc cgaatttgta tgcgcaactt cagcacccac  1320
gccgtattga cacgacacac gcgcacgcac accggggaaa aaccgtttca atgtcgaatc  1380
tgcatgcgca attttagcga tagagggaac ctcactcgac atctgcgcac acacttgcgg  1440
ggatccacct gcagggatga gtttcccacc atggtgtttc cttctgggca gatcagccag  1500
gcctcggcct tggccccggc ccctccccaa gtcctgcccc aggctccagc ccctgcccct  1560
gctccagcca tggtatcagc tctggcccag gccccagccc ctgtcccagt cctagcccca  1620
ggccctcctc aggctgtggc cccacctgcc cccaagccca cccaggctgg ggaaggaacg  1680
ctgtcagagg ccctgctgca gctgcagttt gatgatgaag acctgggggc cttgcttggc  1740
aacagcacag acccagctgt gttcacagac ctggcatccg tcgacaactc cgagtttcag  1800
cagctgctga accagggcat acctgtggcc ccccacacaa ctgagcccat gctgatggag  1860
taccctgagg ctataactcg cctagtgaca ggggcccaga ggccccccga cccagctcct  1920
gctccactgg gggccccggg gctccccaat ggcctccttt caggagatga agacttctcc  1980
tccattgcgg acatggactt ctcagccctg ctgagtcaga tcagctccca attgtgcgta  2040
cgcggatcct ctgctggaga catgagagct gccaaccttt ggccaagccc gctcatgatc  2100
aaacgctcta agaagaacag cctggccttg tccctgacgg ccgaccagat ggtcagtgcc  2160
ttgttggatg ctgagccccc catactctat tccgagtatg atcctaccag acccttcagt  2220
gaagcttcga tgatgggctt actgaccaac ctggcagaca gggagctggt tcacatgatc  2280
aactgggcga agagggtgcc aggctttgtg gatttgaccc tccatgatca ggtccacctt  2340
ctagaatgtg cctggctaga gatcctgatg attggtctcg tctggcgctc catggagcac  2400
ccagtgaagc tactgtttgc tcctaacttg ctcttggaca ggaaccaggg aaaatgtgta  2460
gagggcatgg tggagatctt cgacatgctg ctggctacat catctcggtt ccgcatgatg  2520
aatctgcagg gagaggagtt tgtgtgcctc aaatctatta ttttgcttaa ttctggagtg  2580
tacacatttc tgtccagcac cctgaagtct ctggaagaga aggaccatat ccaccgagtc  2640
ctggacaaga tcacagacac tttgatccac ctgatggcca aggcaggcct gaccctgcag  2700
cagcagcacc agcggctggc ccagctcctc ctcatcctct cccacatcag gcacatgagt  2760
aacaaaggca tggagcatct gtacagcatg aagtgcaaga acgtggtgcc cctctatgac  2820
ctgctgctgg aggcggcgga cgcccaccgc ctacatgcgc ccactagccg tggaggggca  2880
tccgtggagg agacggacca aagccacttg gccactgcgg gctctacttc atcgcattcc  2940
ttgcaaaagt attacatcac gggggaggca gagggtttcc ctgccacagc ttaa        2994

SEQ ID NO: 36          moltype = DNA  length = 2187
FEATURE                Location/Qualifiers
```

```
misc_feature          1..2187
                      note = synthetic polynucleotide
source                1..2187
                      mol_type = other DNA
                      organism = synthetic construct
SEQUENCE: 36
atggactaca aagaccatga cggtgattat aaagatcatg acatcgatta caaggatgac  60
gatgacaaga tggcccccaa gaaaaagagg aaggtgggca ttcacggggt gccgggtgga  120
ctcgagggag gcggtggaag cggcggtacc gctagctcta gacccggaga gcgcccattc  180
cagtgtcgga tttgcatgcg gaacttttcg agaagacacg gcctggacag acatacccgt  240
actcatacag gtgaaaaacc ctttcagtgt cggatctgta tgcgaaattt ctccgaccac  300
agcagcctga agagacatct acgtacccac accggcagcc agaagccatt tcagtgtcgg  360
atctgtatgc ggaacttctc cgtgagacac aacctgacca gacatctacg tacgcacacc  420
ggagagaagc cattccaatg ccgaatatgc atgcgcaact tcagtgacca cagcaacctg  480
agcagacacc taaaaaccca caccggttcc cagaagccat ttcagtgtcg gatctgtatg  540
cggaacttct cccagcgcag cagcctggtg agacatctac gtacgcacac cggagagaag  600
ccattccaat gccgaatatg catgcgcaac ttcagtgaga gcggccacct gaagagacac  660
ctgcgtacgc acctgagggg atccacctgc agggatgagt ttcccaccat ggtgtttcct  720
tctgggcaga tcagccaggc ctcggccttg gccccggccc ctccccaagt cctgccccag  780
gctccagccc ctgcccctgc tccagccatg gtatcagctc tggcccaggc cccagcccct  840
gtcccagtcc tagccccagg ccctcctcag gctgtggccc cacctgcccc caagcccacc  900
caggctgggg aaggaacgct gtcagaggcc ctgctgcagc tgcagtttga tgatgaagac  960
ctgggggcct tgcttggcaa cagcacagac ccagctgtgt tcacagacct ggcatccgtc  1020
gacaactccg agtttcagca gctgctgaac cagggcatac ctgtggcccc ccacacaact  1080
gagcccatgc tgatggagta ccctgaggct ataactcgcc tagtgacagg ggcccagagg  1140
ccccccgacc cagctcctgc tccactgggg gccccggggc tccccaatgg cctcctttca  1200
ggagatgaag acttctcctc cattgcggac atggacttct cagccctgct gagtcagatc  1260
agctcccccg gggatgagat ggaagagtgc tctcagcact tacccggcgc cggcagtagt  1320
ggcgatatca tggattacaa ggatgacgac gataagggct cttccgggac aggctccgga  1380
tccggcacta gtgcgcccat cacggcgtac gcccagcaga cgagaggcct cctagggtgt  1440
ataatcacca gcctgactgg ccgggacaaa aaccaagtgg agggtgaggt ccagatcgtg  1500
tcaactgcta cccaaacctt cctggcaacg tgcatcaatg gggtatgctg ggcagtctac  1560
cacggggccg gaacgaggac catcgcatca cccaagggtc ctgtcatcca gatgtatacc  1620
aatgtggacc aagaccttgt gggctggccc gctcctcaag gttcccgctc attgacaccc  1680
tgtacctgcg gctcctcgga cctttacctg gtcacgaggc acgccgatgt cattcccgtg  1740
cgccggcgag gtgatagcag gggtagcctg ctttcgcccc ggcccatttc ctacttgaaa  1800
ggctcctctg gggtccgct gttgtgcccc gcgggacacg ccgtgggcct attcagggcc  1860
gcggtgtgca cccgtggagt ggctaaagcg gtggacttta tccctgtgga gaacctagag  1920
acaaccatga gatccccggt gttcacggac aactcctctc caccagcagt caccctgacg  1980
cacccaatca ccaaaatcga taccaaatac atcatgacat gcatgtcggc cgacctggag  2040
gtcgtcacga gcacctgggt gctcgttggc ggcgtcctgg ctgctctggc cgcgtattgc  2100
ctgtcaacag gctgcgtggt catagtgggc aggatcgtct tgtccgggaa gccggcaatt  2160
atacctgaca gggaggttct ctactaa                                      2187

SEQ ID NO: 37         moltype = DNA  length = 2637
FEATURE               Location/Qualifiers
misc_feature          1..2637
                      note = synthetic polynucleotide
source                1..2637
                      mol_type = other DNA
                      organism = synthetic construct
SEQUENCE: 37
atgctagcag tgtcagtgac atttgaagat gtggctgtgc tctttactcg ggacgagtgg  60
aagaagctgg atctgtctca gagaagcctg taccgtgagg tgatgctgga gaattacagc  120
aacctggcct ccatggcagg attcctgttt accaaaccaa aggtgatctc cctgttgcag  180
caaggagagg atccctgggg gggtagcggc agcggtagcg catgctctag accaggcgaa  240
cgaccgtttc aatgccggat atgtatgagg aacttctccc agaggtccag cttggtacgg  300
cacacccgaa cacatacagg agaaaagcca ttccaatgtc gaatttgtat gcgcaatttt  360
tcagacaagt ctgtgttggc tcgacacctc cgcacacata ctggttcaca gaagcccttt  420
cagtgcagga tttgtatgcg caactttagc caacgctcat ccctggtaag gcacactaga  480
acgcatacag gtgagaagcc tttccagtgt cgcatctgta tgcggaactt cagccagcgg  540
aataacttgg gcaggcattt gcgaactcac accggttctc aaaaaccttt tcagtgccga  600
atttgtatgc gcaacttcag cacccacgcc gtattgacac gacacacgcg cacgcacacc  660
ggggaaaaac cgtttcaatg tcgaatctgc atgcgcaatt ttagcgatag agggaacctc  720
actcgacatc tgcgcacaca cttgcgggga tcccaattgt gcgtacgcgg atcctctgct  780
ggagacatga gagctgccaa cctttggcca agcccgctca tgatcaaacg ctctaagaag  840
aacagcctgg ccttgtccct gacggccgac cagatggtca gtgccttgtt ggatgctgag  900
ccccccatac tctattccga gtatgatcct accagaccct tcagtgaagc ttcgatgatg  960
ggcttactga ccaacctggc agacagggag ctggttcaca tgatcaactg ggcgaagagg  1020
gtgccaggct ttgtggattt gaccctccat gatcaggtcc accttctaga atgtgcctgg  1080
ctagagatcc tgatgattgg tctcgtctgg cgctccatgg agcacccagt gaagctactg  1140
tttgctccta acttgctctt ggacaggaac cagggaaaat gtgtagaggg catggtggag  1200
atcttcgaca tgctgctggc tacatcatct cggttccgca tgatgaatct gcagggagag  1260
gagtttgtgt gcctcaaatc tattattttg cttaattctg gagtgtacac atttctgtcc  1320
agcaccctga agtctctgga agagaaggac catatccacc gagtcctgga caagatcaca  1380
gacactttga tccacctgat ggccaaggca ggcctgaccc tgcagcagca gcaccagcgg  1440
ctggcccagc tcctcctcat cctctcccac atcaggcaca tgagtaacaa aggcatggag  1500
catctgtaca gcatgaagtg caagaacgtg gtgcccctct atgacctgct gctggaggcg  1560
gcggacgccc accgcctaca tgcgcccact agccgtggag ggcatccgt ggaggagacg  1620
```

-continued

```
gaccaaagcc acttggccac tgcgggctct acttcatcgc attccttgca aaagtattac  1680
atcacggggg aggcagaggg tttccctgcc acagctcccg gggatgagat ggaagagtgc  1740
tctcagcact tacccggcgc cggcagtagt ggcgatatca tggattacaa ggatgacgac  1800
gataagggct cttccgggac aggctccgga tccggcacta gtgcgcccat cacggcgtac  1860
gcccagcaga cgagaggcct cctagggtgt ataatcacca gcctgactgg ccgggacaaa  1920
aaccaagtgg agggtgaggt ccagatcgtg tcaactgcta cccaaacctt cctggcaacg  1980
tgcatcaatg gggtatgctg ggcagtctac cacggggccg gaacgaggac catcgcatca  2040
cccaagggtc ctgtcatcca gatgtatacc aatgtggacc aagaccttgt gggctggccc  2100
gctcctcaag gttcccgctc attgacaccc tgtacctgcg gctcctcgga cctttacctg  2160
gtcacgaggc acgccgatgt cattcccgtg cgccggcgag gtgatagcag ggtagcctg   2220
ctttcgcccc ggcccatttc ctacttgaaa ggctcctctg gggtccgct gttgtgcccc   2280
gcgggacacg ccgtgggcct attcagggcc gcggtgtgca cccgtggagt ggctaaagcg  2340
gtggacttta tccctgtgga gaacctagag acaaccatga gatccccggt gttcacggac  2400
aactcctctc caccagcagt caccctgacg cacccaatca ccaaaatcga taccaaatac  2460
atcatgacat gcatgtcggc cgacctggag gtcgtcacga gcacctgggt gctcgttggc  2520
ggcgtcctgg ctgctctggc cgcgtattgc ctgtcaacag gctgcgtggt catagtgggc  2580
aggatcgtct tgtccgggaa gccggcaatt atacctgaca gggaggttct ctactaa     2637
```

```
SEQ ID NO: 38          moltype = DNA  length = 3012
FEATURE                Location/Qualifiers
misc_feature           1..3012
                       note = synthetic polynucleotide
source                 1..3012
                       mol_type = other DNA
                       organism = synthetic construct
SEQUENCE: 38
atgggaaaga aaaccaagcg gacagctgac agttcttctt cagaggatga ggaggagtat  60
gtcgtggaga aggtgctaga caggcgcgtg gttaagggac aagtggaata tctactgaag  120
tggaaaggct tttctgagga gcacaatact tgggaacctg agaaaaactt ggattgccct  180
gagctaattt ctgaatttat gaaaaagtat aagaagatga aggagggtga aaataataaa  240
cccagggaga agtcagaaag taacaagagg aaatccaatt tctcaaacag tgccgatgac  300
atcaaatcta aaaaaaagag agagcagagc aatgatatcg ctcggggctt tgagagagga  360
ctggaaccag aaaagatcat tgggcaaca gattcctgtg gtgatttaat gttcctaatg   420
aaatggaaag acacagatga agctgacctg gttcttgcaa aagaagctaa tgtgaaatgt  480
ccacaaattg tgatagcatt ttatgaagag agactgacat ggcatgcata tcctgaggat  540
gcggaaaaca aagagaaaga aacagcaaag agcgggggta gcggcagcgg tagcgcatgc  600
tctagaccag gcgaacgacc gtttcaatgc cggatatgta tgaggaactt ctcccagagg  660
tccagcttgg tacggcacac ccgaacacat acaggagaaa agccattcca atgtcgaatt  720
tgtatgcgca atttttcaga caagtctgtg ttggctcgac acctccgcac acatactggt  780
tcacagaagc cctttcagtg caggatttgt atgcgcaact ttagccaacg ctcatccctg  840
gtaaggcaca ctagaacgca tacaggtgag aagcctttcc agtgtcgcat ctgtatgcgg  900
aacttcagcc agcggaataa cttgggcagg catttgcgaa ctcacaccgg ttctcaaaaa  960
ccttttcagt gccgaatttg tatgcgcaac ttcagcaccc acgccgtatt gacacgacac  1020
acgcgcacgc acaccgggga aaaaccgttt caatgtcgaa tctgcatgcg caattttagc  1080
gatagaggga acctcactcg acatctgcgc acacacttgc ggggatccca attgtgcgta  1140
cgcggatcct ctgctggaga catgagagct gccaaccttt ggccaagccc gctcatgatc  1200
aaacgctcta agaagaacag cctggccttg tccctgacgg ccgaccagat ggtcagtgcc  1260
ttgttggatg ctgagccccc catactctat tccgagtatg atcctaccag accttcagt   1320
gaagcttcga tgatgggctt actgaccaac ctggcagaca gggagctggt tcacatgatc  1380
aactgggcga agagggtgcc aggctttgtg gatttgaccc tccatgatca ggtccacctt  1440
ctagaatgtg cctggctaga gatcctgatg attggtctcg tctggcgctc catggagcac  1500
ccagtgaagc tactgtttgc tcctaacttg ctcttggaca ggaaccaggg aaaatgtgta  1560
gagggcatgg tggagatctt cgacatgctg ctggctacat catctcggtt ccgcatgatg  1620
aatctgcagg gagaggagtt tgtgtgcctc aaatctatta ttttgcttaa ttctggagtg  1680
tacacatttc tgtccagcac cctgaagtct ctggaagaga aggaccatat ccaccgagtc  1740
ctggacaaga tcacagacac tttgatccac ctgatggcca aggcaggcct gaccctgcag  1800
cagcagcacc agcggctggc ccagctcctc ctcatcctct cccacatcag gcacatgagt  1860
aacaaaggca tggagcatct gtacagcatg aagtgcaaga acgtggtgcc cctctatgac  1920
ctgctgctgg aggcggcgga cgcccaccgc ctacatgcgc ccactagccg tggaggggca  1980
tccgtggagg agacggacca aagccacttg gccactgcgg gctctacttc atcgcattcc  2040
ttgcaaaagt attacatcac gggggaggca gagggtttcc ctgccacagc tcccggggat  2100
gagatggaag agtgctctca gcacttaccc ggcgccggca gtagtggcga tatcatggat  2160
tacaaggatg acgacgataa gggctcttcc gggacaggct ccggatccgg cactagtgcg  2220
cccatcacgg cgtacgccca gcagacgaga ggcctcctag ggtgtataat caccagcctg  2280
actggccggg acaaaaacca agtggagggt gaggtccaga tcgtgtcaac tgctacccaa  2340
accttcctgg caacgtgcat caatggggta tgctgggcag tctaccacgg ggccggaacg  2400
aggaccatcg catcacccaa gggtcctgtc atccagatgt ataccaatgt ggaccaagac  2460
cttgtgggct ggcccgctcc tcaaggttcc cgctcattga caccctgtac ctgcggctcc  2520
tcggaccttt acctggtcac gaggcacgcc gatgtcattc ccgtgcgccg gcgaggtgat  2580
agcaggggta gcctgctttc gccccggccc atttcctact tgaaaggctc ctctgggggt  2640
ccgctgttgt gccccgcggg acacgccgtg ggcctattca gggccgcggt gtgcacccgt  2700
ggagtggcta aagcggtgga ctttatccct gtggagaacc tagagacaac catgagatcc  2760
ccggtgttca cggacaactc ctctccacca gcagtcaccc tgacgcaccc aatcaccaaa  2820
atcgatacca aatacatcat gacatgcatg tcggccgacc tggaggtcgt cacgagcacc  2880
tgggtgctcg ttggcggcgt cctggctgct ctggccgcgt attgcctgtc aacaggctgc  2940
gtggtcatag tgggcaggat cgtcttgtcc gggaagccgg caattatacc tgacagggag  3000
gttctctact aa                                                     3012
```

```
SEQ ID NO: 39          moltype = DNA  length = 3762
```

-continued

```
FEATURE                Location/Qualifiers
misc_feature           1..3762
                       note = synthetic polynucleotide
source                 1..3762
                       mol_type = other DNA
                       organism = synthetic construct
SEQUENCE: 39
atgtccgaga gggaagtgtc gactgcgccg gcgggaacag acatgcccgc ggccaagaag  60
cagaagttga gcagcgacga gaacagcaac ccggacctct cgggagacga aaatgacgat  120
gctgtcagta ttgagagtgg cacaaacaca gaacgcccgg acacgcccac aaatacgcca  180
aatgcaccag gaaggaaaag ctggggaaag ggaaaatgga agtcaaagaa atgcaaatat  240
tctttcaaat gtgtgaacag cctcaaggaa gatcataacc agccattgtt tggagttcag  300
tttaactggc acagtaaaga aggagaccct ctggtgtttg caactgtggg aagcaacaga  360
gtaaccttat acgaatgcca ttcacagggg gagatacggt tattgcagtc ctatgtagat  420
gctgatgcag atgaaaactt ttacacttgt gcatggacct atgatagcaa caccagccac  480
cctctattag cagttgctgg atctagaggc attataagaa taattaatcc tataacaatg  540
cagtgtataa agcactatgt tggccatgga aatgctatca atgagctgaa attccaccca  600
cgagacccaa accttctcct gtcagtaagt aaagatcatg ctttacggtt atggaatatc  660
caaacagaca ctcttgtggc aatattcgga ggtgtggaag ggcacagaga tgaagttctg  720
agtgctgatt atgatctttt gggtgaaaaa ataatgtcct gtggtatgga tcactctctt  780
aaactgtgga gaatcaactc aaagaggatg atgaatgcaa ttaaggagtc ttatgattat  840
aacccaaaca aaactaacag gccatttatt tcccagaaaa tccactttcc tgacttttct  900
accagagaca tacataggaa ttatgttgat tgtgtgcgat ggttaggcga tttgatactt  960
tccaagtctt gtgaaaatgc cattgtatgc tggaaacctg gcaaaatgga ggatgatata  1020
gataaaatta aacctagtga gtctaatgtg actattcttg ggcgatttga ttacagccag  1080
tgtgacattt ggtacatgag gttttctatg gatttctggc aaaagatgct tgcattgggc  1140
aatcaggttg gcaaactgta tgtttgggat ttagaagtag aagatcctca taaagccaaa  1200
tgcacaacac tgacccatca taaatgtggc gcggctattc gacaaaccag tttcagtagg  1260
gatagcagca tcctcatagc tgtctgcgat gatgccagca tttggcgctg ggatcgactt  1320
cgagggggta gcggcagcgg tagcgcatgc tctagaccag gcgaacgacc gtttcaatgc  1380
cggatatgta tgaggaactt ctcccagagg tccagcttgg tacggcacac ccgaacacat  1440
acaggagaaa agccattcca atgtcgaatt tgtatgcgca atttttcaga caagtctgtg  1500
ttggctcgac acctccgcac acatactggt tcacagaagc cctttcagtg caggatttgt  1560
atgcgcaact ttagccaacg ctcatccctg gtaaggcaca ctagaacgca tacaggtgag  1620
aagcctttcc agtgtcgcat ctgtatgcgg aacttcagcc agcggaataa cttgggcagg  1680
catttgcgaa ctcacaccgg ttctcaaaaa ccttttcagt gccgaatttg tatgcgcaac  1740
ttcagcaccc acgccgtatt gacacgacac acgcgcacgc acaccgggga aaaaccgttt  1800
caatgtcgaa tctgcatgcg caattttagc gatagaggga acctcactcg acatctgcgc  1860
acacacttgc ggggatccca attgtgcgta cgcggatcct ctgctggaga catgagagct  1920
gccaaccttt ggccaagccc gctcatgatc aaacgctcta agaagaacag cctggccttg  1980
tccctgacgg ccgaccagat ggtcagtgcc ttgttggatg ctgagccccc catactctat  2040
tccgagtatg atcctaccag acccttcagt gaagcttcga tgatgggctt actgaccaac  2100
ctggcagaca gggagctggt tcacatgatc aactgggcga agagggtgcc aggctttgtg  2160
gatttgaccc tccatgatca ggtccacctt ctagaatgtg cctggctaga gatcctgatg  2220
attggtctcg tctggcgctc catggagcac ccagtgaagc tactgtttgc tcctaacttg  2280
ctcttggaca ggaaccaggg aaaatgtgta gagggcatgg tggagatctt cgacatgctg  2340
ctggctacat catctcggtt ccgcatgatg aatctgcagg gagaggagtt tgtgtgcctc  2400
aaatctatta ttttgcttaa ttctggagtg tacacatttc tgtccagcac cctgaagtct  2460
ctggaagaga aggaccatat ccaccgagtc ctggacaaga tcacagacac tttgatccac  2520
ctgatggcca aggcaggcct gaccctgcag cagcagcacc agcggctggc ccagctcctc  2580
ctcatcctct cccacatcag gcacatgagt aacaaaggca tggagcatct gtacagcatg  2640
aagtgcaaga acgtggtgcc cctctatgac ctgctgctgg aggcggcgga cgcccaccgc  2700
ctacatgcgc ccactagccg tggaggggca tccgtggagg agacggacca aagccacttg  2760
gccactgcgg gctctacttc atcgcattcc ttgcaaaagt attacatcac gggggaggca  2820
gagggtttcc ctgccacagc tcccggggat gagatggaag agtgctctca gcacttaccc  2880
ggcgccggca gtagtggcga tatcatggat tacaaggatg acgacgataa gggctcttcc  2940
gggacaggct ccggatccgg cactagtgcg cccatcacgg cgtacgccca gcagacgaga  3000
ggcctcctag ggtgtataat caccagcctg actggccggg acaaaaacca agtggagggt  3060
gaggtccaga tcgtgtcaac tgctacccaa accttcctgg caacgtgcat caatggggta  3120
tgctgggcag tctaccacgg ggccggaacg aggaccatcg catcacccaa gggtcctgtc  3180
atccagatgt ataccaatgt ggaccaagac cttgtgggct ggcccgctcc tcaaggttcc  3240
cgctcattga caccctgtac ctgcggctcc tcggaccttt acctggtcac gaggcacgcc  3300
gatgtcattc ccgtgcgccg gcgaggtgat agcaggggta gcctgctttc gccccggccc  3360
atttcctact tgaaaggctc ctctgggggt ccgctgttgt gccccgcggg acacgccgtg  3420
ggcctattca gggccgcggt gtgcacccgt ggagtggcta aagcggtgga ctttatccct  3480
gtggagaacc tagagacaac catgagatcc ccggtgttca cggacaactc ctctccacca  3540
gcagtcaccc tgacgcaccc aatcaccaaa atcgatacca aatacatcat gacatgcatg  3600
tcggccgacc tggaggtcgt cacgagcacc tgggtgctcg ttggcggcgt cctggctgct  3660
ctggccgcgt attgcctgtc aacaggctgc gtggtcatag tgggcaggat cgtcttgtcc  3720
gggaagccgg caattatacc tgacagggag gttctctact aa                    3762

SEQ ID NO: 40          moltype = AA  length = 903
FEATURE                Location/Qualifiers
REGION                 1..903
                       note = synthetic polypeptide
source                 1..903
                       mol_type = protein
                       organism = synthetic construct
SEQUENCE: 40
```

-continued

```
MFEPKKKRKV FETSVPLYGF TSICGRRPEM EAAVSTIPRF LQSSSGSMLD GRFDPQSAAH  60
FFGVYDGHGG SQVANYCRER MHLALAEEIA KEKPMLCDGD TWLEKWKKAL FNSFLRVDSE  120
IESVAPETVG STSVVAVVFP SHIFVANCGD SRAVLCRGKT ALPLSVDHKP DREDEAARIE  180
AAGGKVIQWN GARVFGVLAM SRSIGDRYLK PSIIPDPEVT AVKRVKEDDC LILASDGVWD  240
VMTDEEACEM ARKRILLWHK KNAVAGDASL LADERRKEGK DPAAMSAAEY LSKLAIQRGS  300
KDNISVVVVD LKGGSGGSRP GERPFQCRIC MRNFSEEANL RRHTRTHTGE KPFQCRICMR  360
NFSDHSSLKR HLRTHTGSQK PFQCRICMRN FSQSANLLRH TRTHTGEKPF QCRICMRNFS  420
DPSSLKRHLR THTGSQKPFQ CRICMRNFSQ QTNLTRHTRT HTGEKPFQCR ICMRNFSDAT  480
QLVRHLRTHL RGSPKKKRKV TCRGSGATNF SLLKQAGDVE ENPGPGHHDE FPTMVFPSGQ  540
ISQASALAPA PPQVLPQAPA PAPAPAMVSA LAQAPAPVPV LAPGPPQAVA PPAPKPTQAG  600
EGTLSEALLQ LQFDDEDLGA LLGNSTDPAV FTDLASVDNS EFQQLLNQGI PVAPHTTEPM  660
LMEYPEAITR LVTGAQRPPD PAPAPLGAPG LPNGLLSGDE DFSSIADMDF SALLSQISSG  720
GGSGQLTQDE FTQLSQSIAE FHTYQLGNGR CSSLLAQRIH APPETVWSVV RRFDRPQIYK  780
HFIKSCNVSE DFEMRVGCTR DVNVISGLPA NTSRERLDLL DDDRRVTGFS ITGGEHRLRN  840
YKSVTTVHRF EKEEEEERIW TVVLESYVVD VPEGNSEEDT RLFADTVIRL NLQKLASITE  900
AMN                                                                903

SEQ ID NO: 41          moltype = AA  length = 808
FEATURE                Location/Qualifiers
REGION                 1..808
                       note = synthetic polypeptide
source                 1..808
                       mol_type = protein
                       organism = synthetic construct
SEQUENCE: 41
MFEPKKKRKV FETSVPLYGF TSICGRRPEM EAAVSTIPRF LQSSSGSMLD GRFDPQSAAH  60
FFGVYDGHGG SQVANYCRER MHLALAEEIA KEKPMLCDGD TWLEKWKKAL FNSFLRVDSE  120
IESVAPETVG STSVVAVVFP SHIFVANCGD SRAVLCRGKT ALPLSVDHKP DREDEAARIE  180
AAGGKVIQWN GARVFGVLAM SRSIGDRYLK PSIIPDPEVT AVKRVKEDDC LILASDGVWD  240
VMTDEEACEM ARKRILLWHK KNAVAGDASL LADERRKEGK DPAAMSAAEY LSKLAIQRGS  300
KDNISVVVVD LKGGSGGSRP GERPFQCRIC MRNFSEEANL RRHTRTHTGE KPFQCRICMR  360
NFSDHSSLKR HLRTHTGSQK PFQCRICMRN FSQSANLLRH TRTHTGEKPF QCRICMRNFS  420
DPSSLKRHLR THTGSQKPFQ CRICMRNFSQ QTNLTRHTRT HTGEKPFQCR ICMRNFSDAT  480
QLVRHLRTHL RGSTCRGSGA TNFSLLKQAG DVEENPGPGH HPKKKRKVDA KSLTAWSRTL  540
VTFKDVFVDF TREEWKLLDT AQQILYRNVM LENYKNLVSL GYQLTKPDVI LRLEKGEEPW  600
LVEREIHQET HPDSETAFEI KSSVGGGSGQ LTQDEFTQLS QSIAEFHTYQ LGNGRCSSLL  660
AQRIHAPPET VWSVVRRFDR PQIYKHFIKS CNVSEDFEMR VGCTRDVNVI SGLPANTSRE  720
RLDLLDDDRR VTGFSITGGE HRLRNYKSVT TVHRFEKEEE EERIWTVVLE SYVVDVPEGN  780
SEEDTRLFAD TVIRLNLQKL ASITEAMN                                     808

SEQ ID NO: 42          moltype = AA  length = 692
FEATURE                Location/Qualifiers
REGION                 1..692
                       note = synthetic polypeptide
source                 1..692
                       mol_type = protein
                       organism = synthetic construct
SEQUENCE: 42
MSRPGERPFQ CRICMRNFSQ RSSLVRHTRT HTGEKPFQCR ICMRNFSDKS VLARHLRTHT  60
GSQKPFQCRI CMRNFSQRSS LVRHTRTHTG EKPFQCRICM RNFSQRNNLG RHLRTHTGSQ  120
KPFQCRICMR NFSTHAVLTR HTRTHTGEKP FQCRICMRNF SDRGNLTRHL RTHLRGSTCR  180
DEFPTMVFPS GQISQASALA PAPPQVLPQA PAPAPAPAMV SALAQAPAPV PVLAPGPPQA  240
VAPPAPKPTQ AGEGTLSEAL LQLQFDDEDL GALLGNSTDP AVFTDLASVD NSEFQQLLNQ  300
GIPVAPHTTE PMLMEYPEAI TRLVTGAQRP PDPAPAPLGA PGLPNGLLSG DEDFSSIADM  360
DFSALLSQIS SQLCVRGSSA GDMRAANLWP SPLMIKRSKK NSLALSLTAD QMVSALLDAE  420
PPILYSEYDP TRPFSEASMM GLLTNLADRE LVHMINWAKR VPGFVDLTLH DQVHLLECAW  480
LEILMIGLVW RSMEHPVKLL FAPNLLLDRN QGKCVEGMVE IFDMLLATSS RFRMMNLQGE  540
EFVCLKSIIL LNSGVYTFLS STLKSLEEKD HIHRVLDKIT DTLIHLMAKA GLTLQQQHQR  600
LAQLLLILSH IRHMSNKGME HLYSMKCKNV VPLYDLLLEA ADAHRLHAPT SRGGASVEET  660
DQSHLATAGS TSSHSLQKYY ITGEAEGFPA TA                                692

SEQ ID NO: 43          moltype = AA  length = 605
FEATURE                Location/Qualifiers
REGION                 1..605
                       note = synthetic polypeptide
source                 1..605
                       mol_type = protein
                       organism = synthetic construct
SEQUENCE: 43
MDAKSLTAWS RTLVTFKDVF VDFTREEWKL LDTAQQILYR NVMLENYKNL VSLGYQLTKP  60
DVILRLEKGE EPWLVEREIH QETHPDSETA FEIKSSVLEG GGGSGTCRSR PGERPFQCRI  120
CMRNFSQRSS LVRHTRTHTG EKPFQCRICM RNFSDKSVLA RHLRTHTGSQ KPFQCRICMR  180
NFSQRSSLVR HTRTHTGEKP FQCRICMRNF SQRNNLGRHL RTHTGSQKPF QCRICMRNFS  240
THAVLTRHTR THTGEKPFQC RICMRNFSDR GNLTRHLRTH LRGSQLCVRG SSAGDMRAAN  300
LWPSPLMIKR SKKNSLALSL TADQMVSALL DAEPPILYSE YDPTRPFSEA SMMGLLTNLA  360
DRELVHMINW AKRVPGFVDL TLHDQVHLLE CAWLEILMIG LVWRSMEHPV KLLFAPNLLL  420
DRNQGKCVEG MVEIFDMLLA TSSRFRMMNL QGEEFVCLKS IILLNSGVYT FLSSTLKSLE  480
EKDHIHRVLD KITDTLIHLM AKAGLTLQQQ HQRLAQLLLI LSHIRHMSNK GMEHLYSMKC  540
KNVVPLYDLL LEAADAHRLH APTSRGGASV EETDQSHLAT AGSTSSHSLQ KYYITGEAEG  600
```

```
FPATA                                                              605

SEQ ID NO: 44          moltype = AA  length = 704
FEATURE                Location/Qualifiers
REGION                 1..704
                       note = synthetic polypeptide
source                 1..704
                       mol_type = protein
                       organism = synthetic construct
SEQUENCE: 44
MSRPGERPFQ CRICMRNFSR RHGLDRHTRT HTGEKPFQCR ICMRNFSDHS SLKRHLRTHT  60
GSQKPFQCRI CMRNFSVRHN LTRHLRTHTG EKPFQCRICM RNFSDHSNLS RHLKTHTGSQ  120
KPFQCRICMR NFSQRSSLVR HLRTHTGEKP FQCRICMRNF SESGHLKRHL RTHLRGSTCR  180
DYKDHDGDYK DHDIDYKDDD DKMAPKKKRK VGIHGVPGGL EGGGGSGGTE DVVCCHSIYG  240
KKKGDIDTYR YIGSSGTGCV VIVGRIVLSG SGTSAPITAY AQQTRGLLGC IITSLTGRDK  300
NQVEGEVQIV STATQTFLAT CINGVCWAVY HGAGTRTIAS PKGPVIQMYT NVDQDLVGWP  360
APQGSRSLTP CTCGSSDLYL VTRHADVIPV RRRGDSRGSL LSPRPISYLK GSSGGPLLCP  420
AGHAVGLFRA AVCTRGVAKA VDFIPVENLE TTMRSPVFTD NSSPPAVTLT HPITKIDREV  480
LYQEFDEMEE CSQHYPYDVP DYAGGGGSGG TDEFPTMVFP SGQISQASAL APAPPQVLPQ  540
APAPAPAPAM VSALAQAPAP VPVLAPGPPQ AVAPPAPKPT QAGEGTLSEA LLQLQFDDED  600
LGALLGNSTD PAVFTDLASV DNSEFQQLLN QGIPVAPHTT EPMLMEYPEA ITRLVTGAQR  660
PPDPAPAPLG APGLPNGLLS GDEDFSSIAD MDFSALLSQI SSQL                   704

SEQ ID NO: 45          moltype = AA  length = 609
FEATURE                Location/Qualifiers
REGION                 1..609
                       note = synthetic polypeptide
source                 1..609
                       mol_type = protein
                       organism = synthetic construct
SEQUENCE: 45
MDAKSLTAWS RTLVTFKDVF VDFTREEWKL LDTAQQILYR NVMLENYKNL VSLGYQLTKP  60
DVILRLEKGE EPWLVEREIH QETHPDSETA FEIKSSVTCR DYKDHDGDYK DHDIDYKDDD  120
DKMAPKKKRK VGIHGVPGGL EGGGGSGGTE DVVCCHSIYG KKKGDIDTYR YIGSSGTGCV  180
VIVGRIVLSG SGTSAPITAY AQQTRGLLGC IITSLTGRDK NQVEGEVQIV STATQTFLAT  240
CINGVCWAVY HGAGTRTIAS PKGPVIQMYT NVDQDLVGWP APQGSRSLTP CTCGSSDLYL  300
VTRHADVIPV RRRGDSRGSL LSPRPISYLK GSSGGPLLCP AGHAVGLFRA AVCTRGVAKA  360
VDFIPVENLE TTMRSPVFTD NSSPPAVTLT HPITKIDREV LYQEFDEMEE CSQHYPYDVP  420
DYAGGGGSGG TSRPGERPFQ CRICMRNFSR RHGLDRHTRT HTGEKPFQCR ICMRNFSDHS  480
SLKRHLRTHT GSQKPFQCRI CMRNFSVRHN LTRHLRTHTG EKPFQCRICM RNFSDHSNLS  540
RHLKTHTGSQ KPFQCRICMR NFSQRSSLVR HLRTHTGEKP FQCRICMRNF SESGHLKRHL  600
RTHLRGSQL                                                          609

SEQ ID NO: 46          moltype = AA  length = 998
FEATURE                Location/Qualifiers
REGION                 1..998
                       note = synthetic polypeptide
source                 1..998
                       mol_type = protein
                       organism = synthetic construct
SEQUENCE: 46
MSRPGERPFQ CRICMRNFSQ RSSLVRHTRT HTGEKPFQCR ICMRNFSDKS VLARHLRTHT  60
GSQKPFQCRI CMRNFSQRSS LVRHTRTHTG EKPFQCRICM RNFSQRNNLG RHLRTHTGSQ  120
KPFQCRICMR NFSTHAVLTR HTRTHTGEKP FQCRICMRNF SDRGNLTRHL RTHLRGSTCR  180
DEFPTMVFPS GQISQASALA PAPPQVLPQA PAPAPAPAMV SALAQAPAPV PVLAPGPPQA  240
VAPPAPKPTQ AGEGTLSEAL LQLQFDDEDL GALLGNSTDP AVFTDLASVD NSEFQQLLNQ  300
GIPVAPHTTE PMLMEYPEAI TRLVTGAQRP PDPAPAPLGA PGLPNGLLSG DEDFSSIADM  360
DFSALLSQIS SQLCVRGSSA GDMRAANLWP SPLMIKRSKK NSLALSLTAD QMVSALLDAE  420
PPILYSEYDP TRPFSEASMM GLLTNLADRE LVHMINWAKR VPGFVDLTLH DQVHLLECAW  480
LEILMIGLVW RSMEHPVKLL FAPNLLLDRN QGKCVEGMVE IFDMLLATSS RFRMMNLQGE  540
EFVCLKSIIL LNSGVYTFLS STLKSLEEKD HIHRVLDKIT DTLIHLMAKA GLTLQQQHQR  600
LAQLLLILSH IRHMSNKGME HLYSMKCKNV VPLYDLLLEA ADAHRLHAPT SRGGASVEET  660
DQSHLATAGS TSSHSLQKYY ITGEAEGFPA TAPGDEMEEC SQHLPGAGSS GDIMDYKDDD  720
DKGSSGTGSG SGTSAPITAY AQQTRGLLGC IITSLTGRDK NQVEGEVQIV STATQTFLAT  780
CINGVCWAVY HGAGTRTIAS PKGPVIQMYT NVDQDLVGWP APQGSRSLTP CTCGSSDLYL  840
VTRHADVIPV RRRGDSRGSL LSPRPISYLK GSSGGPLLCP AGHAVGLFRA AVCTRGVAKA  900
VDFIPVENLE TTMRSPVFTD NSSPPAVTLT HPITKIDTKY IMTCMSADLE VVTSTWVLVG  960
GVLAALAAYC LSTGCVVIVG RIVLSGKPAI IPDREVLY                          998

SEQ ID NO: 47          moltype = AA  length = 997
FEATURE                Location/Qualifiers
REGION                 1..997
                       note = synthetic polypeptide
source                 1..997
                       mol_type = protein
                       organism = synthetic construct
SEQUENCE: 47
MDYKDDDDKG SSGTGSGSGT SAPITAYAQQ TRGLLGCIIT SLTGRDKNQV EGEVQIVSTA  60
TQTFLATCIN GVCWAVYHGA GTRTIASPKG PVIQMYTNVD QDLVGWPAPQ GSRSLTPCTC  120
```

```
GSSDLYLVTR HADVIPVRRR GDSRGSLLSP RPISYLKGSS GGPLLCPAGH AVGLFRAAVC  180
TRGVAKAVDF IPVENLETTM RSPVFTDNSS PPAVTLTHPI TKIDTKYIMT CMSADLEVVT  240
STWVLVGGVL AALAAYCLST GCVVIVGRIV LSGKPAGSSG SSIIPDREVL YQEFEDVVPC  300
SMGSPGSRPG ERPFQCRICM RNFSQRSSLV RHTRTHTGEK PFQCRICMRN FSDKSVLARH  360
LRTHTGSQKP FQCRICMRNF SQRSSLVRHT RTHTGEKPFQ CRICMRNFSQ RNNLGRHLRT  420
HTGSQKPFQC RICMRNFSTH AVLTRHTRTH TGEKPFQCRI CMRNFSDRGN LTRHLRTHLR  480
GSTCRDEFPT MVFPSGQISQ ASALAPAPPQ VLPQAPAPAP APAMVSALAQ APAPVPVLAP  540
GPPQAVAPPA PKPTQAGEGT LSEALLQLQF DDEDLGALLG NSTDPAVFTD LASVDNSEFQ  600
QLLNQGIPVA PHTTEPMLME YPEAITRLVT GAQRPPDPAP APLGAPGLPN GLLSGDEDFS  660
SIADMDFSAL LSQISSQLCV RGSSAGDMRA ANLWPSPLMI KRSKKNSLAL SLTADQMVSA  720
LLDAEPPILY SEYDPTRPFS EASMMGLLTN LADRELVHMI NWAKRVPGFV DLTLHDQVHL  780
LECAWLEILM IGLVWRSMEH PVKLLFAPNL LLDRNQGKCV EGMVEIFDML LATSSRFRMM  840
NLQGEEFVCL KSIILLNSGV YTFLSSTLKS LEEKDHIHRV LDKITDTLIH LMAKAGLTLQ  900
QQHQRLAQLL LILSHIRHMS NKGMEHLYSM KCKNVVPLYD LLLEAADAHR LHAPTSRGGA  960
SVEETDQSHL ATAGSTSSHS LQKYYITGEA EGFPATA                          997

SEQ ID NO: 48          moltype = AA  length = 728
FEATURE                Location/Qualifiers
REGION                 1..728
                       note = synthetic polypeptide
source                 1..728
                       mol_type = protein
                       organism = synthetic construct
SEQUENCE: 48
MDYKDHDGDY KDHDIDYKDD DDKMAPKKKR KVGIHGVPGG LEGGGGSGGT ASSRPGERPF  60
QCRICMRNFS RRHGLDRHTR THTGEKPFQC RICMRNFSDH SSLKRHLRTH TGSQKPFQCR  120
ICMRNFSVRH NLTRHLRTHT GEKPFQCRIC MRNFSDHSNL SRHLKTHTGS QKPFQCRICM  180
RNFSQRSSLV RHLRTHTGEK PFQCRICMRN FSESGHLKRH LRTHLRGSTC RDEFPTMVFP  240
SGQISQASAL APAPPQVLPQ APAPAPAPAM VSALAQAPAP VPVLAPGPPQ AVAPPAPKPT  300
QAGEGTLSEA LLQLQFDDED LGALLGNSTD PAVFTDLASV DNSEFQQLLN QGIPVAPHTT  360
EPMLMEYPEA ITRLVTGAQR PPDPAPAPLG APGLPNGLLS GDEDFSSIAD MDFSALLSQI  420
SSPGDEMEEC SQHLPGAGSS GDIMDYKDDD DKGSSGTGSG SGTSAPITAY AQQTRGLLGC  480
IITSLTGRDK NQVEGEVQIV STATQTFLAT CINGVCWAVY HGAGTRTIAS PKGPVIQMYT  540
NVDQDLVGWP APQGSRSLTP CTCGSSDLYL VTRHADVIPV RRRGDSRGSL LSPRPISYLK  600
GSSGGPLLCP AGHAVGLFRA AVCTRGVAKA VDFIPVENLE TTMRSPVFTD NSSPPAVTLT  660
HPITKIDTKY IMTCMSADLE VVTSTWVLVG GVLAALAAYC LSTGCVVIVG RIVLSGKPAI  720
IPDREVLY                                                          728

SEQ ID NO: 49          moltype = AA  length = 878
FEATURE                Location/Qualifiers
REGION                 1..878
                       note = synthetic polypeptide
source                 1..878
                       mol_type = protein
                       organism = synthetic construct
SEQUENCE: 49
MLAVSVTFED VAVLFTRDEW KKLDLSQRSL YREVMLENYS NLASMAGFLF TKPKVISLLQ  60
QGEDPWGGSG SGSACSRPGE RPFQCRICMR NFSQRSSLVR HTRTHTGEKP FQCRICMRNF  120
SDKSVLARHL RTHTGSQKPF QCRICMRNFS QRSSLVRHTR THTGEKPFQC RICMRNFSQR  180
NNLGRHLRTH TGSQKPFQCR ICMRNFSTHA VLTRHTRTHT GEKPFQCRIC MRNFSDRGNL  240
TRHLRTHLRG SQLCVRGSSA GDMRAANLWP SPLMIKRSKK NSLALSLTAD QMVSALLDAE  300
PPILYSEYDP TRPFSEASMM GLLTNLADRE LVHMINWAKR VPGFVDLTLH DQVHLLECAW  360
LEILMIGLVW RSMEHPVKLL FAPNLLLDRN QGKCVEGMVE IFDMLLATSS RFRMMNLQGE  420
EFVCLKSIIL LNSGVYTFLS STLKSLEEKD HIHRVLDKIT DTLIHLMAKA GLTLQQQHQR  480
LAQLLLILSH IRHMSNKGME HLYSMKCKNV VPLYDLLLEA ADAHRLHAPT SRGGASVEET  540
DQSHLATAGS TSSHSLQKYY ITGEAEGFPA TAPGDEMEEC SQHLPGAGSS GDIMDYKDDD  600
DKGSSGTGSG SGTSAPITAY AQQTRGLLGC IITSLTGRDK NQVEGEVQIV STATQTFLAT  660
CINGVCWAVY HGAGTRTIAS PKGPVIQMYT NVDQDLVGWP APQGSRSLTP CTCGSSDLYL  720
VTRHADVIPV RRRGDSRGSL LSPRPISYLK GSSGGPLLCP AGHAVGLFRA AVCTRGVAKA  780
VDFIPVENLE TTMRSPVFTD NSSPPAVTLT HPITKIDTKY IMTCMSADLE VVTSTWVLVG  840
GVLAALAAYC LSTGCVVIVG RIVLSGKPAI IPDREVLY                         878

SEQ ID NO: 50          moltype = AA  length = 1003
FEATURE                Location/Qualifiers
REGION                 1..1003
                       note = synthetic polypeptide
source                 1..1003
                       mol_type = protein
                       organism = synthetic construct
SEQUENCE: 50
MGKKTKRTAD SSSSEDEEEY VVEKVLDRRV VKGQVEYLLK WKGFSEEHNT WEPEKNLDCP  60
ELISEFMKKY KKMKEGENNK PREKSESNKR KSNFSNSADD IKSKKKREQS NDIARGFERG  120
LEPEKIIGAT DSCGDLMFLM KWKDTDEADL VLAKEANVKC PQIVIAFYEE RLTWHAYPED  180
AENKEKETAK SGGSGSGSAC SRPGERPFQC RICMRNFSQR SSLVRHTRTH TGEKPFQCRI  240
CMRNFSDKSV LARHLRTHTG SQKPFQCRIC MRNFSQRSSL VRHTRTHTGE KPFQCRICMR  300
NFSQRNNLGR HLRTHTGSQK PFQCRICMRN FSTHAVLTRH TRTHTGEKPF QCRICMRNFS  360
DRGNLTRHLR THLRGSQLCV RGSSAGDMRA ANLWPSPLMI KRSKKNSLAL SLTADQMVSA  420
LLDAEPPILY SEYDPTRPFS EASMMGLLTN LADRELVHMI NWAKRVPGFV DLTLHDQVHL  480
LECAWLEILM IGLVWRSMEH PVKLLFAPNL LLDRNQGKCV EGMVEIFDML LATSSRFRMM  540
```

-continued

```
NLQGEEFVCL KSIILLNSGV YTFLSSTLKS LEEKDHIHRV LDKITDTLIH LMAKAGLTLQ  600
QQHQRLAQLL LILSHIRHMS NKGMEHLYSM KCKNVVPLYD LLLEAADAHR LHAPTSRGGA  660
SVEETDQSHL ATAGSTSSHS LQKYYITGEA EGFPATAPGD EMEECSQHLP GAGSSGDIMD  720
YKDDDDKGSS GTGSGSGTSA PITAYAQQTR GLLGCIITSL TGRDKNQVEG EVQIVSTATQ  780
TFLATCINGV CWAVYHGAGT RTIASPKGPV IQMYTNVDQD LVGWPAPQGS RSLTPCTCGS  840
SDLYLVTRHA DVIPVRRRGD SRGSLLSPRP ISYLKGSSGG PLLCPAGHAV GLFRAAVCTR  900
GVAKAVDFIP VENLETTMRS PVFTDNSSPP AVTLTHPITK IDTKYIMTCM SADLEVVTST  960
WVLVGGVLAA LAAYCLSTGC VVIVGRIVLS GKPAIIPDRE VLY                   1003

SEQ ID NO: 51           moltype = AA  length = 1253
FEATURE                 Location/Qualifiers
REGION                  1..1253
                        note = synthetic polypeptide
source                  1..1253
                        mol_type = protein
                        organism = synthetic construct
SEQUENCE: 51
MSEREVSTAP AGTDMPAAKK QKLSSDENSN PDLSGDENDD AVSIESGTNT ERPDTPTNTP  60
NAPGRKSWGK GKWKSKKCKY SFKCVNSLKE DHNQPLFGVQ FNWHSKEGDP LVFATVGSNR  120
VTLYECHSQG EIRLLQSYVD ADADENFYTC AWTYDSNTSH PLLAVAGSRG IIRIINPITM  180
QCIKHYVGHG NAINELKFHP RDPNLLLSVS KDHALRLWNI QTDTLVAIFG GVEGHRDEVL  240
SADYDLLGEK IMSCGMDHSL KLWRINSKRM MNAIKESYDY NPNKTNRPFI SQKIHFPDFS  300
TRDIHRNYVD CVRWLGDLIL SKSCENAIVC WKPGKMEDDI DKIKPSESNV TILGRFDYSQ  360
CDIWYMRFSM DFWQKMLALG NQVGKLYVWD LEVEDPHKAK CTTLTHHKCG AAIRQTSFSR  420
DSSILIAVCD DASIWRWDRL RGGSGSGSAC SRPGERPFQC RICMRNFSQR SSLVRHTRTH  480
TGEKPFQCRI CMRNFSDKSV LARHLRTHTG SQKPFQCRIC MRNFSQRSSL VRHTRTHTGE  540
KPFQCRICMR NFSQRNNLGR HLRTHTGSQK PFQCRICMRN FSTHAVLTRH TRTHTGEKPF  600
QCRICMRNFS DRGNLTRHLR THLRGSQLCV RGSSAGDMRA ANLWPSPLMI KRSKKNSLAL  660
SLTADQMVSA LLDAEPPILY SEYDPTRPFS EASMMGLLTN LADRELVHMI NWAKRVPGFV  720
DLTLHDQVHL LECAWLEILM IGLVWRSMEH PVKLLFAPNL LLDRNQGKCV EGMVEIFDML  780
LATSSRFRMM NLQGEEFVCL KSIILLNSGV YTFLSSTLKS LEEKDHIHRV LDKITDTLIH  840
LMAKAGLTLQ QQHQRLAQLL LILSHIRHMS NKGMEHLYSM KCKNVVPLYD LLLEAADAHR  900
LHAPTSRGGA SVEETDQSHL ATAGSTSSHS LQKYYITGEA EGFPATAPGD EMEECSQHLP  960
GAGSSGDIMD YKDDDDKGSS GTGSGSGTSA PITAYAQQTR GLLGCIITSL TGRDKNQVEG  1020
EVQIVSTATQ TFLATCINGV CWAVYHGAGT RTIASPKGPV IQMYTNVDQD LVGWPAPQGS  1080
RSLTPCTCGS SDLYLVTRHA DVIPVRRRGD SRGSLLSPRP ISYLKGSSGG PLLCPAGHAV  1140
GLFRAAVCTR GVAKAVDFIP VENLETTMRS PVFTDNSSPP AVTLTHPITK IDTKYIMTCM  1200
SADLEVVTST WVLVGGVLAA LAAYCLSTGC VVIVGRIVLS GKPAIIPDRE VLY        1253

SEQ ID NO: 52           moltype = DNA  length = 9439
FEATURE                 Location/Qualifiers
misc_feature            1..9439
                        note = synthetic vector
source                  1..9439
                        mol_type = other DNA
                        organism = synthetic construct
SEQUENCE: 52
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
```

-continued

```
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
```

```
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttcgtcgaag tcgaagtcga cctcccgtct cagtaaaggt cgtcgaagtc  7860
gaagtcgacc aatcggactg ccttcgtacg tcgaagtcga agtcgaccgt atcagtcgcc  7920
tcggaacgtc gaagtcgaag tcgaccattc gtaagaggct cactctccct tacacggagt  7980
ggataactag ttaggcgtgt acggtgggag gcctatataa gcagagctcg tttagtgaac  8040
cgtcagatcg cctggaacgc gtaccggtgt cgccaccatg gtgagcaagg gcgaggagga  8100
taacatggcc atcatcaagg agttcatgcg cttcaaggtg cacatggagg gctccgtgaa  8160
cggccacgag ttcgagatcg agggcgaggg cgagggccgc ccctacgagg gcacccagac  8220
cgccaagctg aaggtgacca agggtggccc cctgcccttc gcctgggaca tcctgtcccc  8280
tcagttcatg tacggctcca aggcctacgt gaagcacccc gccgacatcc ccgactactt  8340
gaagctgtcc ttccccgagg gcttcaagtg ggagcgcgtg atgaacttcg aggacggcgg  8400
cgtggtgacc gtgacccagg actcctccct gcaggacggc gagttcatct acaaggtgaa  8460
gctgcgcggc accaacttcc cctccgacgg ccccgtaatg cagaagaaga ccatgggctg  8520
gcaggcctcc tccgagcgga tgtaccccga ggacggcgcc ctgaagggcg agatcaagca  8580
gaggctgaag ctgaaggacg gcggccacta cgacgctgag gtcaagacca cctacaaggc  8640
caagaagccc gtgcagctgc ccggcgccta caacgtcaac atcaagttgg acatcacctc  8700
ccacaacgag gactacacca tcgtggaaca gtacgaacgc gccgagggcc gccactccac  8760
cggcggcatg gacgagctgt acaagtaaag cggccgcgac tctagagtcg acctgcaggc  8820
atgcaagctt gatatcaagc ttatcgataa tcaacctctg gattacaaaa tttgtgaaag  8880
attgactggt attcttaact atgttgctcc ttttacgcta tgtggatacg ctgctttaat  8940
gcctttgtat catgctattg cttcccgtat ggctttcatt ttctcctcct tgtataaatc  9000
ctggttgctg tctctttatg aggagttgtg gcccgttgtc aggcaacgtg gcgtggtgtg  9060
cactgtgttt gctgacgcaa cccccactgg ttggggcatt gccaccacct gtcagctcct  9120
ttccgggact ttcgctttcc ccctccctat tgccacggcg gaactcatcg ccgcctgcct  9180
tgcccgctgc tggacagggg ctcggctgtt gggcactgac aattccgtgg tgttgtcggg  9240
gaaatcatcg tcctttcctt ggctgctcgc ctgtgttgcc acctggattc tgcgcgggac  9300
gtccttctgc tacgtccctt cggccctcaa tccagcggac cttccttccc gcggcctgct  9360
gccggctctg cggcctcttc cgcgtcttcg ccttcgccct cagacgagtc ggatctccct  9420
ttgggccgcc tccccgcat                                                 9439
```

```
SEQ ID NO: 53          moltype = DNA  length = 9439
FEATURE                Location/Qualifiers
misc_feature           1..9439
                       note = synthetic vector
source                 1..9439
                       mol_type = other DNA
                       organism = synthetic construct
SEQUENCE: 53
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
```

-continued

```
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
```

```
tgtgactctg gtaactagag atccctcaga ccctttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtggaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttagacgtcg aagtagccgt agtcccgtct cagtaaaggt agacgtcgaa  7860
gtagccgtag aatcggactg ccttcgtaag acgtcgaagt agccgtaggt atcagtcgcc  7920
tcggaaagac gtcgaagtag ccgtagattc gtaagaggct cactctccct tacacggagt  7980
ggataactag ttaggcgtgt acggtgggag gcctatataa gcagagctcg tttagtgaac  8040
cgtcagatcg cctggaacgc gtaccggtgt cgccaccatg gtgagcaagg gcgaggagga  8100
taacatggcc atcatcaagg agttcatgcg cttcaaggtg cacatggagg gctccgtgaa  8160
cggccacgag ttcgagatcg agggcgaggg cgagggccgc ccctacgagg gcacccagac  8220
cgccaagctg aaggtgacca agggtggccc cctgcccttc gcctgggaca tcctgtcccc  8280
tcagttcatg tacggctcca aggcctacgt gaagcacccc gccgacatcc ccgactactt  8340
gaagctgtcc ttccccgagg gcttcaagtg ggagcgcgtg atgaacttcg aggacggcgg  8400
cgtggtgacc gtgacccagg actcctccct gcaggacggc gagttcatct acaaggtgaa  8460
gctgcgcggc accaacttcc cctccgacgg ccccgtaatg cagaagaaga ccatgggctg  8520
gcaggcctcc tccgagcgga tgtaccccga ggacggcgcc ctgaagggcg agatcaagca  8580
gaggctgaag ctgaaggacg gcggccacta cgacgctgag gtcaagacca cctacaaggc  8640
caagaagccc gtgcagctgc ccggcgccta caacgtcaac atcaagttgg acatcacctc  8700
ccacaacgag gactacacca tcgtggaaca gtacgaacgc gccgagggcc gccactccac  8760
cggcggcatg gacgagctgt acaagtaaag cggccgcgac tctagagtcg acctgcaggc  8820
atgcaagctt gatatcaagc ttatcgataa tcaacctctg gattacaaaa tttgtgaaag  8880
attgactggt attcttaact atgttgctcc ttttacgcta tgtggatacg ctgctttaat  8940
gcctttgtat catgctattg cttcccgtat ggctttcatt ttctcctcct tgtataaatc  9000
ctggttgctg tctctttatg aggagttgtg gcccgttgtc aggcaacgtg gcgtggtgtg  9060
cactgtgttt gctgacgcaa cccccactgg ttggggcatt gccaccacct gtcagctcct  9120
ttccgggact ttcgctttcc ccctccctat tgccacggcg gaactcatcg ccgcctgcct  9180
tgcccgctgc tggacagggg ctcggctgtt gggcactgac aattccgtgg tgttgtcggg  9240
gaaatcatcg tcctttcctt ggctgctcgc ctgtgttgcc acctggattc tgcgcgggac  9300
gtccttctgc tacgtccctt cggccctcaa tccagcggac cttccttccc gcggcctgct  9360
gccggctctg cggcctcttc cgcgtcttcg ccttcgccct cagacgagtc ggatctccct  9420
ttgggccgcc tccccgcat                                               9439
```

```
SEQ ID NO: 54          moltype = DNA  length = 9439
FEATURE                Location/Qualifiers
misc_feature           1..9439
                       note = synthetic vector
source                 1..9439
                       mol_type = other DNA
                       organism = synthetic construct
SEQUENCE: 54
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga ccctttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
```

-continued

```
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
```

```
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttcggcgtag ccgatgtcgc gctcccgtct cagtaaaggt cggcgtagcc  7860
gatgtcgcgc aatcggactg ccttcgtacg gcgtagccga tgtcgcgcgt atcagtcgcc  7920
tcggaacggc gtagccgatg tcgcgcattc gtaagaggct cactctccct tacacggagt  7980
ggataactag ttaggcgtgt acggtgggag gcctatataa gcagagctcg tttagtgaac  8040
cgtcagatcg cctggaacgc gtaccggtgt cgccaccatg gtgagcaagg gcgaggagga  8100
taacatggcc atcatcaagg agttcatgcg cttcaaggtg cacatggagg gctccgtgaa  8160
cggccacgag ttcgagatcg agggcgaggg cgagggccgc ccctacgagg gcacccagac  8220
cgccaagctg aaggtgacca agggtggccc cctgcccttc gcctgggaca tcctgtcccc  8280
tcagttcatg tacggctcca aggcctacgt gaagcacccc gccgacatcc ccgactactt  8340
gaagctgtcc ttccccgagg gcttcaagtg ggagcgcgtg atgaacttcg aggacggcgg  8400
cgtggtgacc gtgacccagg actcctccct gcaggacggc gagttcatct acaaggtgaa  8460
gctgcgcggc accaacttcc cctccgacgg ccccgtaatg cagaagaaga ccatgggctg  8520
gcaggcctcc tccgagcgga tgtaccccga ggacggcgcc ctgaagggcg agatcaagca  8580
gaggctgaag ctgaaggacg gcggccacta cgacgctgag gtcaagacca cctacaaggc  8640
caagaagccc gtgcagctgc ccggcgccta caacgtcaac atcaagttgg acatcacctc  8700
ccacaacgag gactacacca tcgtggaaca gtacgaacgc gccgagggcc gccactccac  8760
cggcggcatg gacgagctgt acaagtaaag cggccgcgac tctagagtcg acctgcaggc  8820
atgcaagctt gatatcaagc ttatcgataa tcaacctctg gattacaaaa tttgtgaaag  8880
attgactggt attcttaact atgttgctcc ttttacgcta tgtggatacg ctgctttaat  8940
gcctttgtat catgctattg cttcccgtat ggctttcatt ttctcctcct tgtataaatc  9000
ctggttgctg tctctttatg aggagttgtg gcccgttgtc aggcaacgtg gcgtggtgtg  9060
cactgtgttt gctgacgcaa cccccactgg ttggggcatt gccaccacct gtcagctcct  9120
ttccgggact ttcgctttcc ccctccctat tgccacggcg gaactcatcg ccgcctgcct  9180
tgcccgctgc tggacagggg ctcggctgtt gggcactgac aattccgtgg tgttgtcggg  9240
gaaatcatcg tcctttcctt ggctgctcgc ctgtgttgcc acctggattc tgcgcgggac  9300
gtccttctgc tacgtccctt cggccctcaa tccagcggac cttccttccc gcggcctgct  9360
gccggctctg cggcctcttc cgcgtcttcg ccttcgccct cagacgagtc ggatctccct  9420
ttgggccgcc tccccgcat                                               9439
```

```
SEQ ID NO: 55           moltype = DNA  length = 10091
FEATURE                 Location/Qualifiers
misc_feature            1..10091
                        note = synthetic vector
source                  1..10091
                        mol_type = other DNA
                        organism = synthetic construct
SEQUENCE: 55
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
```

-continued

```
atccctcaga ccctttagt cagtgtggaa aatctctagc agcatctaga attaattccg 360
tgtattctat agtgtcacct aaatcgtatg tgtatgatac ataaggttat gtattaattg 420
tagccgcgtt ctaacgacaa tatgtacaag cctaattgtg tagcatctgg cttactgaag 480
cagaccctat catctctctc gtaaactgcc gtcagagtcg gtttggttgg acgaaccttc 540
tgagtttctg gtaacgccgt cccgcacccg gaaatggtca gcgaaccaat cagcagggtc 600
atcgctagcc agatcctcta cgccggacgc atcgtggccg gcatcaccgg cgccacaggt 660
gcggttgctg gcgcctatat cgccgacatc accgatgggg aagatcgggc tcgccacttc 720
gggctcatga gcgcttgttt cggcgtgggt atggtggcag gccccgtggc cgggggactg 780
ttgggcgcca tctccttgca tgcaccattc cttgcggcgg cggtgctcaa cggcctcaac 840
ctactactgg gctgcttcct aatgcaggag tcgcataagg gagagcgtcg aatggtgcac 900
tctcagtaca atctgctctg atgccgcata gttaagccag ccccgacacc cgccaacacc 960
cgctgacgcg ccctgacggg cttgtctgct cccggcatcc gcttacagac aagctgtgac 1020
cgtctccggg agctgcatgt gtcagaggtt ttcaccgtca tcaccgaaac gcgcgagacg 1080
aaagggcctc gtgatacgcc tatttttata ggttaatgtc atgataataa tggtttctta 1140
gacgtcaggt ggcacttttc ggggaaatgt gcgcggaacc cctatttgtt tatttttcta 1200
aatacattca aatatgtatc cgctcatgag acaataaccc tgataaatgc ttcaataata 1260
ttgaaaaagg aagagtatga gtattcaaca tttccgtgtc gcccttattc ccttttttgc 1320
ggcattttgc cttcctgttt ttgctcaccc agaaacgctg gtgaaagtaa aagatgctga 1380
agatcagttg ggtgcacgag tgggttacat cgaactggat ctcaacagcg gtaagatcct 1440
tgagagtttt cgccccgaag aacgttttcc aatgatgagc acttttaaag ttctgctatg 1500
tggcgcggta ttatcccgta ttgacgccgg gcaagagcaa ctcggtcgcc gcatacacta 1560
ttctcagaat gacttggttg agtactcacc agtcacagaa aagcatctta cggatggcat 1620
gacagtaaga gaattatgca gtgctgccat aaccatgagt gataacactg cggccaactt 1680
acttctgaca acgatcggag gaccgaagga gctaaccgct tttttgcaca acatggggga 1740
tcatgtaact cgccttgatc gttgggaacc ggagctgaat gaagccatac caaacgacga 1800
gcgtgacacc acgatgcctg tagcaatggc aacaacgttg cgcaaactat taactggcga 1860
actacttact ctagcttccc ggcaacaatt aatagactgg atggaggcgg ataaagttgc 1920
aggaccactt ctgcgctcgg cccttccggc tggctggttt attgctgata aatctggagc 1980
cggtgagcgt gggtctcgcg gtatcattgc agcactgggg ccagatggta agccctcccg 2040
tatcgtagtt atctacacga cggggagtca ggcaactatg gatgaacgaa atagacagat 2100
cgctgagata ggtgcctcac tgattaagca ttggtaactg tcagaccaag tttactcata 2160
tatactttag attgatttaa aacttcattt ttaatttaaa aggatctagg tgaagatcct 2220
ttttgataat ctcatgacca aaatccctta acgtgagttt tcgttccact gagcgtcaga 2280
ccccgtagaa aagatcaaag gatcttcttg agatcctttt tttctgcgcg taatctgctg 2340
cttgcaaaca aaaaaaccac cgctaccagc ggtggtttgt ttgccggatc aagagctacc 2400
aactcttttt ccgaaggtaa ctggcttcag cagagcgcag ataccaaata ctgtctttct 2460
agtgtagccg tagttaggcc accacttcaa gaactctgta gcaccgccta catacctcgc 2520
tctgctaatc ctgttaccag tggctgctgc cagtggcgat aagtcgtgtc ttaccgggtt 2580
ggactcaaga cgatagttac cggataaggc gcagcggtcg ggctgaacgg ggggttcgtg 2640
cacacagccc agcttggagc gaacgaccta caccgaactg agatacctac agcgtgagct 2700
atgagaaagc gccacgcttc ccgaagggag aaaggcggac aggtatccgg taagcggcag 2760
ggtcggaaca ggagagcgca cgagggagct tccaggggga aacgcctggt atctttatag 2820
tcctgtcggg tttcgccacc tctgacttga gcgtcgattt ttgtgatgct cgtcaggggg 2880
gcggagccta tggaaaaacg ccagcaacgc ggccttttta cggttcctgg ccttttgctg 2940
gccttttgct cacatgttct ttcctgcgtt atcccctgat tctgtggata accgtattac 3000
cgcctttgag tgagctgata ccgctcgccg cagccgaacg accgagcgca gcgagtcagt 3060
gagcgaggaa gcggaagagc gcccaatacg caaaccgcct ctccccgcgc gttggccgat 3120
tcattaatgc agctgtggaa tgtgtgtcag ttagggtgtg gaaagtcccc aggctcccca 3180
gcaggcagaa gtatgcaaag catgcatctc aattagtcag caaccaggtg tggaaagtcc 3240
ccaggctccc cagcaggcag aagtatgcaa agcatgcatc tcaattagtc agcaaccata 3300
gtcccgcccc taactccgcc catcccgccc ctaactccgc ccagttccgc ccattctccg 3360
ccccatggct gactaatttt ttttatttat gcagaggccg aggccgcctc ggcctctgag 3420
ctattccaga agtagtgagg aggctttttt ggaggcctag gcttttgcaa aaagcttgga 3480
cacaagacag gcttgcgaga tatgtttgag aataccactt tatcccgcgt cagggagagg 3540
cagtgcgtaa aaagacgcgg actcatgtga aatactggtt tttagtgcgc cagatctcta 3600
taatctcgcg caacctattt tcccctcgaa cactttttaa gccgtagata aacaggctgg 3660
gacacttcac atgagcgaaa aatacatcgt cacctgggac atgttgcaga tccatgcacg 3720
taaactcgca agccgactga tgccttctga acaatggaaa ggcattattg ccgtaagccg 3780
tggcggtctg taccgggtgc gttactggcg cgtgaactgg gtattcgtca tgtcgatacc 3840
gtttgtattt ccagctacga tcacgacaac cagcgcgagc ttaaagtgct gaaacgcgca 3900
gaaggcgatg gcgaaggctt catcgttatt gatgacctgg tggataccgg tggtactgcg 3960
gttgcgattc gtgaaatgta tccaaaagcg cactttgtca ccatcttcgc aaaaccggct 4020
ggtcgtccgc tggttgatga ctatgttgtt gatatcccgc aagatacctg gattgaacag 4080
ccgtgggata tgggcgtcgt attcgtcccg ccaatctccg gtcgctaatc ttttcaacgc 4140
ctggcactgc cgggcgttgt tctttttaac ttcaggcggg ttacaatagt ttccagtaag 4200
tattctggag gctgcatcca tgacacaggc aaacctgagc gaaaccctgt tcaaaccccg 4260
ctttaaacat cctgaaacct cgacgctagt ccgccgcttt aatcacggcg cacaaccgcc 4320
tgtgcagtcg gcccttgatg gtaaaaccat ccctcactgg tatcgcatga ttaaccgtct 4380
gatgtggatc tggcgcggca ttgacccacg cgaaatcctc gacgtccagg cacgtattgt 4440
gatgagcgat gccgaacgta ccgacgatga tttatacgat acggtgattg gctaccgtgg 4500
cggcaactgg atttatgagt gggccccgga tctttgtgaa ggaaccttac ttctgtggtg 4560
tgacataatt ggacaaacta cctacagaga tttaaagctc taaggtaaat ataaaatttt 4620
taagtgtata atgtgttaaa ctactgattc taattgtttg tgtattttag attccaacct 4680
atggaactga tgaatgggag cagtggtgga atgcctttaa tgaggaaaac ctgttttgct 4740
cagaagaaat gccatctagt gatgatgagg ctactgctga ctctcaacat tctactcctc 4800
caaaaaagaa gagaaaggta gaagacccca aggactttcc ttcagaattg ctaagttttt 4860
tgagtcatgc tgtgtttagt aatagaactc ttgcttgctt tgctatttac accacaaagg 4920
aaaaagctgc actgctatac aagaaaatta tggaaaaata ttctgtaacc tttataagta 4980
ggcataacag ttataatcat aacatactgt tttttcttac tccacacagg catagagtgt 5040
```

-continued

```
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttcgtcgaag tcgaagtcga cctcccgtct cagtaaaggt cgtcgaagtc  7860
gaagtcgacc aatcggactg ccttcgtacg tcgaagtcga agtcgaccgt atcagtcgcc  7920
tcggaacgtc gaagtcgaag tcgaccattc gtaagaggct cactctccct tacacggagt  7980
ggataactag tgttgacatt gattattgac tagttattaa tagtaatcaa ttacggggtc  8040
attagttcat agcccatata tggagttccg cgttacataa cttacggtaa atggcccgcc  8100
tggctgaccg cccaacgacc cccgcccatt gacgtcaata atgacgtatg ttcccatagt  8160
aacgccaata gggactttcc attgacgtca atgggtggag tatttacggt aaactgccca  8220
cttggcagta catcaagtgt atcatatgcc aagtacgccc cctattgacg tcaatgacgg  8280
taaatggccc gcctggcatt atgcccagta catgacctta tgggactttc ctacttggca  8340
gtacatctac gtattagtca tcgctattac catggtgatg cggttttggc agtacatcaa  8400
tgggcgtgga tagcggtttg actcacgggg atttccaagt ctccacccca ttgacgtcaa  8460
tgggagtttg ttttggcacc aaaatcaacg ggactttcca aaatgtcgta acaactccgc  8520
cccattgacg caaatgggcg gtaggcgtgt acggtgggag gtctatataa gcagagctca  8580
cgcgtaccgg tgtcgccacc atggtgagca agggcgagga ggataacatg gccatcatca  8640
aggagttcat gcgcttcaag gtgcacatgg agggctccgt gaacggccac gagttcgaga  8700
tcgagggcga gggcgagggc cgcccctacg agggcaccca gaccgccaag ctgaaggtga  8760
ccaagggtgg cccccctgccc ttcgcctggg acatcctgtc ccctcagttc atgtacggct  8820
ccaaggccta cgtgaagcac cccgccgaca tccccgacta cttgaagctg tccttccccg  8880
agggcttcaa gtgggagcgc gtgatgaact tcgaggacgg cggcgtggtg accgtgaccc  8940
aggactcctc cctgcaggac ggcgagttca tctacaaggt gaagctgcgc ggcaccaact  9000
tcccctccga cggccccgta atgcagaaga agaccatggg ctggcaggcc tcctccgagc  9060
ggatgtaccc cgaggacggc gccctgaagg gcgagatcaa gcagaggctg aagctgaagg  9120
acggcggcca ctacgacgct gaggtcaaga ccacctacaa ggccaagaag cccgtgcagc  9180
tgcccggcgc ctacaacgtc aacatcaagt tggacatcac ctcccacaac gaggactaca  9240
ccatcgtgga acagtacgaa cgcgccgagg gccgccactc caccggcggc atggacgagc  9300
tgtacaagaa gcttagccat ggcttcccgc cggaggtgga ggagcaggat gatggcacgc  9360
tgcccatgtc ttgtgcccag gagagcggga tggaccgtca ccctgcagcc tgtgcttctg  9420
ctaggatcaa tgtgtagtaa agcggccgcg actctagagt cgacctgcag gcatgcaagc  9480
ttgatatcaa gcttatcgat aatcaacctc tggattacaa aatttgtgaa agattgactg  9540
gtattcttaa ctatgttgct ccttttacgc tatgtggata cgctgcttta atgcctttgt  9600
atcatgctat tgcttcccgt atggctttca ttttctcctc cttgtataaa tcctggttgc  9660
tgtctcttta tgaggagttg tggcccgttg tcaggcaacg tggcgtggtg tgcactgtgt  9720
ttgctgacgc aacccccact ggttggggca ttgccaccac ctgtcagctc ctttccggga  9780
```

```
ctttcgcttt ccccctccct attgccacgg cggaactcat cgccgcctgc cttgcccgct  9840
gctggacagg ggctcggctg ttgggcactg acaattccgt ggtgttgtcg gggaaatcat  9900
cgtcctttcc ttggctgctc gcctgtgttg ccacctggat tctgcgcggg acgtccttct  9960
gctacgtccc ttcggccctc aatccagcgg accttccttc ccgcggcctg ctgccggctc  10020
tgcggcctct tccgcgtctt cgccttcgcc ctcagacgag tcggatctcc ctttgggccg  10080
cctccccgca t                                                      10091

SEQ ID NO: 56           moltype = DNA  length = 10091
FEATURE                 Location/Qualifiers
misc_feature            1..10091
                        note = synthetic vector
source                  1..10091
                        mol_type = other DNA
                        organism = synthetic construct
SEQUENCE: 56
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc cctttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
```

-continued

```
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtggaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttagacgtcg aagtagccgt agtcccgtct cagtaaaggt agacgtcgaa  7860
gtagccgtag aatcggactg ccttcgtaag acgtcgaagt agccgtaggt atcagtcgcc  7920
tcggaaagac gtcgaagtag ccgtagattc gtaagaggct cactctccct tacacggagt  7980
ggataactag tgttgacatt gattattgac tagttattaa tagtaatcaa ttacggggtc  8040
attagttcat agcccatata tggagttccg cgttacataa cttacggtaa atggcccgcc  8100
tggctgaccg cccaacgacc cccgcccatt gacgtcaata atgacgtatg ttcccatagt  8160
aacgccaata gggactttcc attgacgtca atgggtggag tatttacggt aaactgccca  8220
cttggcagta catcaagtgt atcatatgcc aagtacgccc cctattgacg tcaatgacgg  8280
taaatggccc gcctggcatt atgcccagta catgacctta tgggactttc ctacttggca  8340
gtacatctac gtattagtca tcgctattac catggtgatg cggttttggc agtacatcaa  8400
tgggcgtgga tagcggtttg actcacgggg atttccaagt ctccacccca ttgacgtcaa  8460
tgggagtttg ttttggcacc aaaatcaacg ggactttcca aaatgtcgta acaactccgc  8520
cccattgacg caaatgggcg gtaggcgtgt acggtgggag gtctatataa gcagagctca  8580
```

```
cgcgtaccgg tgtcgccacc atggtgagca agggcgagga ggataacatg gccatcatca  8640
aggagttcat gcgcttcaag gtgcacatgg agggctccgt gaacggccac gagttcgaga  8700
tcgagggcga gggcgagggc cgcccctacg agggcaccca gaccgccaag ctgaaggtga  8760
ccaagggtgg cccccctgccc ttcgcctggg acatcctgtc ccctcagttc atgtacggct  8820
ccaaggccta cgtgaagcac cccgccgaca tccccgacta cttgaagctg tccttccccg  8880
agggcttcaa gtgggagcgc gtgatgaact tcgaggacgg cggcgtggtg accgtgaccc  8940
aggactcctc cctgcaggac ggcgagttca tctacaaggt gaagctgcgc ggcaccaact  9000
tcccctccga cggccccgta atgcagaaga agaccatggg ctggcaggcc tcctccgagc  9060
ggatgtaccc cgaggacggc gccctgaagg gcgagatcaa gcagaggctg aagctgaagg  9120
acggcggcca ctacgacgct gaggtcaaga ccacctacaa ggccaagaag cccgtgcagc  9180
tgcccggcgc ctacaacgtc aacatcaagt tggacatcac ctcccacaac gaggactaca  9240
ccatcgtgga acagtacgaa cgcgccgagg gccgccactc caccggcggc atggacgagc  9300
tgtacaagaa gcttagccat ggcttcccgc cggaggtgga ggagcaggat gatggcacgc  9360
tgcccatgtc ttgtgcccag gagagcggga tggaccgtca ccctgcagcc tgtgcttctg  9420
ctaggatcaa tgtgtagtaa agcggccgcg actctagagt cgacctgcag gcatgcaagc  9480
ttgatatcaa gcttatcgat aatcaacctc tggattacaa aatttgtgaa agattgactg  9540
gtattcttaa ctatgttgct ccttttacgc tatgtggata cgctgcttta atgcctttgt  9600
atcatgctat tgcttcccgt atggctttca ttttctcctc cttgtataaa tcctggttgc  9660
tgtctcttta tgaggagttg tggcccgttg tcaggcaacg tggcgtggtg tgcactgtgt  9720
ttgctgacgc aacccccact ggttggggca ttgccaccac ctgtcagctc ctttccggga  9780
ctttcgcttt ccccctccct attgccacgg cggaactcat cgccgcctgc cttgcccgct  9840
gctggacagg ggctcggctg ttgggcactg acaattccgt ggtgttgtcg gggaaatcat  9900
cgtcctttcc ttggctgctc gcctgtgttg ccacctggat tctgcgcggg acgtccttct  9960
gctacgtccc ttcggccctc aatccagcgg accttccttc ccgcggcctg ctgccggctc  10020
tgcggcctct tccgcgtctt cgccttcgcc ctcagacgag tcggatctcc ctttgggccg  10080
cctccccgca t                                                  10091
```

```
SEQ ID NO: 57          moltype = DNA  length = 10091
FEATURE                Location/Qualifiers
misc_feature           1..10091
                       note = synthetic vector
source                 1..10091
                       mol_type = other DNA
                       organism = synthetic construct
SEQUENCE: 57
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc cctttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatgggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtcttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
```

-continued

```
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtggaaaga tacctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
```

```
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttcggcgtag ccgatgtcgc gctcccgtct cagtaaaggt cggcgtagcc  7860
gatgtcgcgc aatcggactg ccttcgtacg gcgtagccga tgtcgcgcgt atcagtcgcc  7920
tcggaacggc gtagccgatg tcgcgcattc gtaagaggct cactctccct tacacggagt  7980
ggataactag tgttgacatt gattattgac tagttattaa tagtaatcaa ttacggggtc  8040
attagttcat agcccatata tggagttccg cgttacataa cttacggtaa atggcccgcc  8100
tggctgaccg cccaacgacc cccgcccatt gacgtcaata atgacgtatg ttcccatagt  8160
aacgccaata gggactttcc attgacgtca atgggtggag tatttacggt aaactgccca  8220
cttggcagta catcaagtgt atcatatgcc aagtacgccc cctattgacg tcaatgacgg  8280
taaatggccc gcctggcatt atgcccagta catgacctta tgggactttc ctacttggca  8340
gtacatctac gtattagtca tcgctattac catggtgatg cggttttggc agtacatcaa  8400
tgggcgtgga tagcggtttg actcacgggg atttccaagt ctccacccca ttgacgtcaa  8460
tgggagtttg ttttggcacc aaaatcaacg ggactttcca aaatgtcgta acaactccgc  8520
cccattgacg caaatgggcg gtaggcgtgt acggtgggag gtctatataa gcagagctca  8580
cgcgtaccgg tgtcgccacc atggtgagca agggcgagga ggataacatg gccatcatca  8640
aggagttcat gcgcttcaag gtgcacatgg agggctccgt gaacggccac gagttcgaga  8700
tcgagggcga gggcgagggc cgcccctacg agggcaccca gaccgccaag ctgaaggtga  8760
ccaagggtgg cccctgccc ttcgcctggg acatcctgtc ccctcagttc atgtacggct  8820
ccaaggccta cgtgaagcac cccgccgaca tccccgacta cttgaagctg tccttccccg  8880
agggcttcaa gtgggagcgc gtgatgaact tcgaggacgg cggcgtggtg accgtgaccc  8940
aggactcctc cctgcaggac ggcgagttca tctacaaggt gaagctgcgc ggcaccaact  9000
tcccctccga cggccccgta atgcagaaga agaccatggg ctggcaggcc tcctccgagc  9060
ggatgtaccc cgaggacggc gccctgaagg gcgagatcaa gcagaggctg aagctgaagg  9120
acggcggcca ctacgacgct gaggtcaaga ccacctacaa ggccaagaag cccgtgcagc  9180
tgcccggcgc ctacaacgtc aacatcaagt tggacatcac ctcccacaac gaggactaca  9240
ccatcgtgga acagtacgaa cgcgccgagg gccgccactc caccggcggc atggacgagc  9300
tgtacaagaa gcttagccat ggcttcccgc cggaggtgga ggagcaggat gatggcacgc  9360
tgcccatgtc ttgtgcccag gagagcggga tggaccgtca ccctgcagcc tgtgcttctg  9420
ctaggatcaa tgtgtagtaa agcggccgcg actctagagt cgacctgcag gcatgcaagc  9480
ttgatatcaa gcttatcgat aatcaacctc tggattacaa aatttgtgaa agattgactg  9540
gtattcttaa ctatgttgct ccttttacgc tatgtggata cgctgcttta atgcctttgt  9600
atcatgctat tgcttcccgt atggctttca ttttctcctc cttgtataaa tcctggttgc  9660
tgtctcttta tgaggagttg tggcccgttg tcaggcaacg tggcgtggtg tgcactgtgt  9720
ttgctgacgc aacccccact ggttggggca ttgccaccac ctgtcagctc ctttccggga  9780
ctttcgcttt ccccctccct attgccacgg cggaactcat cgccgcctgc cttgcccgct  9840
gctggacagg ggctcggctg ttgggcactg acaattccgt ggtgttgtcg gggaaatcat  9900
cgtcctttcc ttggctgctc gcctgtgttg ccacctggat tctgcgcggg acgtccttct  9960
gctacgtccc ttcggccctc aatccagcgg accttccttc ccgcggcctg ctgccggctc  10020
tgcggcctct tccgcgtctt cgccttcgcc ctcagacgag tcggatctcc ctttgggccg  10080
cctccccgca t                                                     10091
```

```
SEQ ID NO: 58            moltype = DNA  length = 9868
FEATURE                  Location/Qualifiers
misc_feature             1..9868
                         note = synthetic vector
source                   1..9868
                         mol_type = other DNA
                         organism = synthetic construct
SEQUENCE: 58
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
```

-continued

```
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
```

```
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttcgtcgaag tcgaagtcga cctcccgtct cagtaaaggt cgtcgaagtc  7860
gaagtcgacc aatcggactg ccttcgtacg tcgaagtcga agtcgaccgt atcagtcgcc  7920
tcggaacgtc gaagtcgaag tcgaccattc gtaagaggct cactctccct tacacggagt  7980
ggataactag tccgataaaa taaaagattt tatttagtct ccagaaaaag gggggaatga  8040
aagaccccac ctgtaggtta tggcaagcta gctgcagtaa cgccattatt gcaaggcatg  8100
gaaaaatacc aaaccaagaa tagagaagtt cagatcaagg gcgggtacat gaaaatagct  8160
aacgtagggc caaacaggat atctgcggtg agcagtttcg gccccggccc ggggccaaga  8220
acagatggtc accgcagttt cggccccggc ccgaggccaa gagcagatgg tccccagata  8280
tggcccaacc ctcagcagtt tcttaagacc catcagatgt ttccaggctc ccccaaggac  8340
ctgaaatgac cctgcgcctt atttgaatta accaatcagc ctgcttctcg cttctgttcg  8400
cgcgcttctg cttcccgagc tctataaaag agctcacaac ccctcactcg gcgcgccagt  8460
cctccgacag actgagtcgc ccgggacgcg taccggtgtc gccaccatgg tgagcaaggg  8520
cgaggaggat aacatggcca tcatcaagga gttcatgcgc ttcaaggtgc acatggaggg  8580
ctccgtgaac ggccacgagt tcgagatcga gggcgagggc gagggccgcc cctacgaggg  8640
cacccagacc gccaagctga aggtgaccaa gggtggcccc ctgcccttcg cctgggacat  8700
cctgtcccct cagttcatgt acggctccaa ggcctacgtg aagcaccccg ccgacatccc  8760
cgactacttg aagctgtcct tccccgaggg cttcaagtgg gagcgcgtga tgaacttcga  8820
ggacggcggc gtggtgaccg tgacccagga ctcctccctg caggacggcg agttcatcta  8880
caaggtgaag ctgcgcggca ccaacttccc ctccgacggc cccgtaatgc agaagaagac  8940
catgggctgg caggcctcct ccgagcggat gtaccccgag gacggcgccc tgaagggcga  9000
gatcaagcag aggctgaagc tgaaggacgg cggccactac gacgctgagg tcaagaccac  9060
ctacaaggcc aagaagcccg tgcagctgcc cggcgcctac aacgtcaaca tcaagttgga  9120
catcacctcc cacaacgagg actacaccat cgtggaacag tacgaacgcg ccgagggccg  9180
ccactccacc ggcggcatgg acgagctgta caagtaaagc ggccgcgact ctagagtcga  9240
cctgcaggca tgcaagcttg atatcaagct tatcgataat caacctctgg attacaaaat  9300
ttgtgaaaga ttgactggta ttcttaacta tgttgctcct tttacgctat gtggatacgc  9360
tgctttaatg cctttgtatc atgctattgc ttcccgtatg gctttcattt tctcctcctt  9420
gtataaatcc tggttgctgt ctctttatga ggagttgtgg cccgttgtca ggcaacgtgg  9480
cgtggtgtgc actgtgtttg ctgacgcaac ccccactggt tggggcattg ccaccacctg  9540
tcagctcctt tccgggactt tcgctttccc cctccctatt gccacggcgg aactcatcgc  9600
cgcctgcctt gcccgctgct ggacaggggc tcggctgttg ggcactgaca attccgtggt  9660
gttgtcgggg aaatcatcgt cctttccttg gctgctcgcc tgtgttgcca cctggattct  9720
gcgcgggacg tccttctgct acgtcccttc ggccctcaat ccagcggacc ttccttcccg  9780
cggcctgctg ccggctctgc ggcctcttcc gcgtcttcgc cttcgccctc agacgagtcg  9840
gatctccctt tgggccgcct ccccgcat                                    9868
```

```
SEQ ID NO: 59           moltype = DNA  length = 9868
FEATURE                 Location/Qualifiers
misc_feature            1..9868
                        note = synthetic vector
source                  1..9868
                        mol_type = other DNA
                        organism = synthetic construct
SEQUENCE: 59
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
```

-continued

```
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc cctttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tcccccctgaa cctgaaacat  5220
```

-continued

```
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttagacgtcg aagtagccgt agtcccgtct cagtaaaggt agacgtcgaa  7860
gtagccgtag aatcggactg ccttcgtaag acgtcgaagt agccgtaggt atcagtcgcc  7920
tcggaaagac gtcgaagtag ccgtagattc gtaagaggct cactctccct tacacggagt  7980
ggataactag tccgataaaa taaaagattt tatttagtct ccagaaaaag gggggaatga  8040
aagaccccac ctgtaggtta tggcaagcta gctgcagtaa cgccattatt gcaaggcatg  8100
gaaaaatacc aaaccaagaa tagagaagtt cagatcaagg gcgggtacat gaaaatagct  8160
aacgtagggc caaacaggat atctgcggtg agcagtttcg gccccggccc ggggccaaga  8220
acagatggtc accgcagttt cggccccggc ccgaggccaa gagcagatgg tccccagata  8280
tggcccaacc ctcagcagtt tcttaagacc catcagatgt ttccaggctc ccccaaggac  8340
ctgaaatgac cctgcgcctt atttgaatta accaatcagc ctgcttctcg cttctgttcg  8400
cgcgcttctg cttcccgagc tctataaaag agctcacaac ccctcactcg gcgcgccagt  8460
cctccgacag actgagtcgc ccgggacgcg taccggtgtc gccaccatgg tgagcaaggg  8520
cgaggaggat aacatggcca tcatcaagga gttcatgcgc ttcaaggtgc acatggaggg  8580
ctccgtgaac ggccacgagt tcgagatcga gggcgagggc gagggccgcc cctacgaggg  8640
cacccagacc gccaagctga aggtgaccaa gggtggcccc ctgcccttcg cctgggacat  8700
cctgtcccct cagttcatgt acggctccaa ggcctacgtg aagcaccccg ccgacatccc  8760
cgactacttg aagctgtcct tccccgaggg cttcaagtgg gagcgcgtga tgaacttcga  8820
ggacggcggc gtggtgaccg tgacccagga ctcctccctg caggacggcg agttcatcta  8880
caaggtgaag ctgcgcggca ccaacttccc ctccgacggc cccgtaatgc agaagaagac  8940
catgggctgg caggcctcct ccgagcggat gtaccccgag gacggcgccc tgaagggcga  9000
gatcaagcag aggctgaagc tgaaggacgg cggccactac gacgctgagg tcaagaccac  9060
ctacaaggcc aagaagcccg tgcagctgcc cggcgcctac aacgtcaaca tcaagttgga  9120
catcacctcc cacaacgagg actacaccat cgtggaacag tacgaacgcg ccgagggccg  9180
ccactccacc ggcggcatgg acgagctgta caagtaaagc ggccgcgact ctagagtcga  9240
cctgcaggca tgcaagcttg atatcaagct tatcgataat caacctctgg attacaaaat  9300
ttgtgaaaga ttgactggta ttcttaacta tgttgctcct tttacgctat gtggatacgc  9360
tgctttaatg cctttgtatc atgctattgc ttcccgtatg gctttcattt tctcctcctt  9420
gtataaatcc tggttgctgt ctctttatga ggagttgtgg cccgttgtca ggcaacgtgg  9480
cgtggtgtgc actgtgtttg ctgacgcaac ccccactggt tggggcattg ccaccacctg  9540
tcagctcctt tccgggactt tcgctttccc cctccctatt gccacggcgg aactcatcgc  9600
cgcctgcctt gcccgctgct ggacaggggc tcggctgttg ggcactgaca attccgtggt  9660
gttgtcgggg aaatcatcgt cctttccttg gctgctcgcc tgtgttgcca cctggattct  9720
gcgcgggacg tccttctgct acgtcccttc ggccctcaat ccagcggacc ttccttcccg  9780
cggcctgctg ccggctctgc ggcctcttcc gcgtcttcgc cttcgccctc agacgagtcg  9840
gatctccctt tgggccgcct ccccgcat                                    9868
```

```
SEQ ID NO: 60          moltype = DNA  length = 9868
FEATURE                Location/Qualifiers
misc_feature           1..9868
                       note = synthetic vector
source                 1..9868
                       mol_type = other DNA
                       organism = synthetic construct
SEQUENCE: 60
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc cctttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
```

-continued

```
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttcggcgtag ccgatgtcgc gctcccgtct cagtaaaggt cggcgtagcc  7860
gatgtcgcgc aatcggactg ccttcgtacg gcgtagccga tgtcgcgcgt atcagtcgcc  7920
tcggaacggc gtagccgatg tcgcgcattc gtaagaggct cactctccct tacacggagt  7980
ggataactag tccgataaaa taaaagattt tatttagtct ccagaaaaag gggggaatga  8040
aagaccccac ctgtaggtta tggcaagcta gctgcagtaa cgccattatt gcaaggcatg  8100
gaaaaatacc aaaccaagaa tagagaagtt cagatcaagg gcgggtacat gaaaatagct  8160
aacgtagggc caaacaggat atctgcggtg agcagtttcg gccccggccc ggggccaaga  8220
acagatggtc accgcagttt cggcccccggc ccgaggccaa gagcagatgg tccccagata  8280
tggcccaacc ctcagcagtt tcttaagacc catcagatgt ttccaggctc cccccaaggac  8340
ctgaaatgac cctgcgcctt atttgaatta accaatcagc ctgcttctcg cttctgttcg  8400
cgcgcttctg cttcccgagc tctataaaag agctcacaac ccctcactcg gcgcgccagt  8460
cctccgacag actgagtcgc ccgggacgcg taccggtgtc gccaccatgg tgagcaaggg  8520
cgaggaggat aacatggcca tcatcaagga gttcatgcgc ttcaaggtgc acatggaggg  8580
ctccgtgaac ggccacgagt tcgagatcga gggcgagggc gagggccgcc cctacgaggg  8640
cacccagacc gccaagctga aggtgaccaa gggtggcccc ctgcccttcg cctgggacat  8700
cctgtcccct cagttcatgt acggctccaa ggcctacgtg aagcaccccg ccgacatccc  8760
cgactacttg aagctgtcct tccccgaggg cttcaagtgg gagcgcgtga tgaacttcga  8820
ggacggcggc gtggtgaccg tgacccagga ctcctccctg caggacggcg agttcatcta  8880
caaggtgaag ctgcgcggca ccaacttccc ctccgacggc cccgtaatgc agaagaagac  8940
catgggctgg caggcctcct ccgagcggat gtaccccgag gacggcgccc tgaagggcga  9000
```

```
gatcaagcag aggctgaagc tgaaggacgg cggccactac gacgctgagg tcaagaccac  9060
ctacaaggcc aagaagcccg tgcagctgcc cggcgcctac aacgtcaaca tcaagttgga  9120
catcacctcc cacaacgagg actacaccat cgtggaacag tacgaacgcg ccgagggccg  9180
ccactccacc ggcggcatgg acgagctgta caagtaaagc ggccgcgact ctagagtcga  9240
cctgcaggca tgcaagcttg atatcaagct tatcgataat caacctctgg attacaaaat  9300
ttgtgaaaga ttgactggta ttcttaacta tgttgctcct tttacgctat gtggatacgc  9360
tgctttaatg cctttgtatc atgctattgc ttcccgtatg gctttcattt tctcctcctt  9420
gtataaatcc tggttgctgt ctctttatga ggagttgtgg cccgttgtca ggcaacgtgg  9480
cgtggtgtgc actgtgtttg ctgacgcaac ccccactggt tggggcattg ccaccacctg  9540
tcagctcctt tccgggactt tcgctttccc cctccctatt gccacggcgg aactcatcgc  9600
cgcctgcctt gcccgctgct ggacaggggc tcggctgttg ggcactgaca attccgtggt  9660
gttgtcgggg aaatcatcgt cctttccttg gctgctcgcc tgtgttgcca cctggattct  9720
gcgcgggacg tccttctgct acgtcccttc ggccctcaat ccagcggacc ttccttcccg  9780
cggcctgctg ccggctctgc ggcctcttcc gcgtcttcgc cttcgccctc agacgagtcg  9840
gatctccctt tgggccgcct ccccgcat                                    9868

SEQ ID NO: 61          moltype = DNA  length = 11090
FEATURE                Location/Qualifiers
misc_feature           1..11090
                       note = synthetic vector
source                 1..11090
                       mol_type = other DNA
                       organism = synthetic construct
SEQUENCE: 61
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtcttcct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
```

-continued

```
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcgtcgacc gggtttcgta acaatcgcat  7800
gaggattcgc aacgccttcg gcgtagccga tgtcgcgctc ccgtctcagt aaaggtcggc  7860
gtagccgatg tcgcgcaatc ggactgcctt cgtacggcgt agccgatgtc gcgcgtatca  7920
gtcgcctcgg aacggcgtag ccgatgtcgc gcattcgtaa gaggctcact ctcccttaca  7980
cggagtggat aactagtttc gcatattaag gtgacgcgtg tggcctcgaa caccgagcga  8040
```

```
ccctgcagcg acccgcttaa ggatccaccg gtcgccacca cacatacaca gaaatggcct  8100
taccagtgac cgccttgctc ctgccgctgg ccttgctgct ccacgccgcc aggccggaca  8160
tccagatgac acagactaca tcctccctgt ctgcctctct gggagacaga gtcaccatca  8220
gttgcagggc aagtcaggac attagtaaat atttaaattg gtatcagcag aaaccagatg  8280
gaactgttaa actcctgatc taccatacat caagattaca ctcaggagtc ccatcaaggt  8340
tcagtggcag tgggtctgga acagattatt ctctcaccat tagcaacctg gagcaagaag  8400
atattgccac ttacttttgc caacagggta atacgcttcc gtacacgttc ggaggcggca  8460
ccaagctgga gatcacaggt ggcggtggct cgggcggtgg tgggtcgggt ggcggcggat  8520
ctgaggtgaa actgcaggag tcaggacctg gcctggtggc gccctcacag agcctgtccg  8580
tcacatgcac tgtctcaggg gtctcattac ccgactatgg tgtaagctgg attcgccagc  8640
ctccacgaaa gggtctggag tggctgggag taatatgggg tagtgaaacc acatactata  8700
attcagctct caaatccaga ctgaccatca tcaaggacaa ctccaagagc caagttttct  8760
taaaaatgaa cagtctgcaa actgatgaca cagccattta ctactgtgcc aaacattatt  8820
actacggtgg tagctatgct atggactact ggggccaagg aacctcagtc accgtctcct  8880
cagaacaaaa actcatctca gaagaagatc tgaatggggc cgcaaccacg acgccagcgc  8940
cgcgaccacc aacaccggcg cccaccatcg cgttgcagcc cctgtccctg cgcccagagg  9000
cgtgccggcc agcggcgggg ggcgcagtgc acacgagggg gctggacttc gcctgtgatt  9060
tttgggtgct ggtggtggtt ggtggagtcc tggcttgcta tagcttgcta gtaacagtgg  9120
cctttattat tttctgggtg aggagtaaga ggagcaggct cctgcacagt gactacatga  9180
acatgactcc ccgccgcccc gggcccaccc gcaagcatta ccagccctat gccccaccac  9240
gcgacttcgc agcctatcgc tccaaacggg gcagaaagaa actcctgtat atattcaaac  9300
aaccatttat gagaccagta caaactactc aagaggaaga tggctgtagc tgccgatttc  9360
cagaagaaga agaaggagga tgtgaactga gagtgaagtt cagcaggagc gcagacgccc  9420
ccgcgtacaa gcagggccag aaccagctct ataacgagct caatctagga cgaagagagg  9480
agtacgatgt tttggacaag agacgtggcc gggaccctga gatgggggga aagccgagaa  9540
ggaagaaccc tcaggaaggc ctgtacaatg aactgcagaa agataagatg gcggaggcct  9600
acagtgagat tgggatgaaa ggcgagcgcc ggaggggcaa ggggcacgat ggcctttacc  9660
agggtctcag tacagccacc aaggacacct acgacgccct tcacatgcag gccctgcccc  9720
ctcgcggcat ggtgagcaag ggcgaggagg ataacatggc catcatcaag gagttcatgc  9780
gcttcaaggt gcacatggag ggctccgtga acggccacga gttcgagatc gagggcgagg  9840
gcgagggccg cccctacgag ggcacccaga ccgccaagct gaaggtgacc aagggtggcc  9900
ccctgccctt cgcctgggac atcctgtccc ctcagttcat gtacggctcc aaggcctacg  9960
tgaagcaccc cgccgacatc cccgactact tgaagctgtc cttccccgag ggcttcaagt  10020
gggagcgcgt gatgaacttc gaggacggcg gcgtggtgac cgtgacccag gactcctccc  10080
tgcaggacgg cgagttcatc tacaaggtga agctgcgcgg caccaacttc ccctccgacg  10140
gccccgtaat gcagaagaag accatgggct gggaggcctc ctccgagcgg atgtaccccg  10200
aggacggcgc cctgaagggc gagatcaagc agaggctgaa gctgaaggac ggcggccact  10260
acgacgctga ggtcaagacc acctacaagg ccaagaagcc cgtgcagctg cccggcgcct  10320
acaacgtcaa catcaagttg gacatcacct cccacaacga ggactacacc atcgtggaac  10380
agtacgaacg cgccgagggc cgccactcca ccggcggcat ggacgagctg tacaagtaaa  10440
gcggccgcga ctctagagtc gacctgcagg catgcaagct tgatatcaag cttatcgata  10500
atcaacctct ggattacaaa atttgtgaaa gattgactgg tattcttaac tatgttgctc  10560
cttttacgct atgtggatac gctgctttaa tgcctttgta tcatgctatt gcttcccgta  10620
tggctttcat tttctcctcc ttgtataaat cctggttgct gtctctttat gaggagttgt  10680
ggcccgttgt caggcaacgt ggcgtggtgt gcactgtgtt tgctgacgca acccccactg  10740
gttggggcat tgccaccacc tgtcagctcc tttccgggac tttcgctttc cccctcccta  10800
ttgccacggc ggaactcatc gccgcctgcc ttgcccgctg ctggacaggg gctcggctgt  10860
tgggcactga caattccgtg gtgttgtcgg ggaaatcatc gtcctttcct tggctgctcg  10920
cctgtgttgc cacctggatt ctgcgcggga cgtccttctg ctacgtccct tcggccctca  10980
atccagcgga ccttccttcc cgcggcctgc tgccggctct gcggcctctt ccgcgtcttc  11040
gccttcgccc tcagacgagt cggatctccc tttgggccgc ctccccgcat             11090
```

```
SEQ ID NO: 62          moltype = DNA  length = 10333
FEATURE                Location/Qualifiers
misc_feature           1..10333
                       note = synthetic vector
source                 1..10333
                       mol_type = other DNA
                       organism = synthetic construct
SEQUENCE: 62
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
```

-continued

```
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
gatgagcgat gccgaacgta ccgacgatga tttatacgat acggtgattg gctaccgtgg  4500
cggcaactgg atttatgagt gggcccccga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
```

-continued

```
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttccgggttt cgtaacaatc gcatgaggat  7800
tcgcaacgcc ttagacgtcg aagtagccgt agtcccgtct cagtaaaggt agacgtcgaa  7860
gtagccgtag aatcggactg ccttcgtaag acgtcgaagt agccgtaggt atcagtcgcc  7920
tcggaaagac gtcgaagtag ccgtagattc gtaagaggct cactctccct tacacggagt  7980
ggataactag ttaggcgtgt acggtgggag gcctatataa gcagagctcg tttagtgaac  8040
cgtcagatcg cctggaacgc gtaccggtgt cgccaccatg ggtctcacct cccaactgct  8100
tccccctctg ttcttcctgc tagcatgtgc cggcaacttt gtccacggac acaagtgcga  8160
tatcacctta caggagatca tcaaaacttt gaacagcctc acagagcaga agactctgtg  8220
caccgagttg accgtaacag acatctttgc tgcctccaag aacacaactg agaaggaaac  8280
cttctgcagg gctgcgactg tgctccggca gttctacagc caccatgaga aggacactcg  8340
ctgcctgggt gcgactgcac agcagttcca caggcacaag cagctgatcc gattcctgaa  8400
acggctcgac aggaacctct ggggcctggc gggcttgaat tcctgtcctg tgaaggaagc  8460
caaccagagt acgttggaaa acttcttgga aaggctaaag acgatcatga gagagaaata  8520
ttcaaagtgt tcgagcctcg agggcggcgg agagggcaga ggaagtcttc taacatgcgg  8580
tgacgtggag gagaatcccg gccctaggat gcttctcctg gtgacaagcc ttctgctctg  8640
tgagttacca cacccagcat tcctcctgat cccacgcaaa gtgtgtaacg gaataggtat  8700
tggtgaattt aaagactcac tctccataaa tgctacgaat attaaacact tcaaaaactg  8760
cacctccatc agtggcgatc tccacatcct gccggtggca tttaggggtg actccttcac  8820
acatactcct cctctggatc cacaggaact ggatattctg aaaaccgtaa aggaaatcac  8880
agggtttttg ctgattcagg cttggcctga aaacaggacg gacctccatg cctttgagaa  8940
cctagaaatc atacgcggca ggaccaagca acatggtcag ttttctcttg cagtcgtcag  9000
cctgaacata acatccttgg gattacgctc cctcaaggag ataagtgatg gagatgtgat  9060
aatttcagga aacaaaaatt tgtgctatgc aaatacaata aactggaaaa aactgtttgg  9120
gacctccggt cagaaaacca aaattataag caacagaggt gaaaacagct gcaaggccac  9180
aggccaggtc tgccatgcct tgtgctcccc cgagggctgc tggggcccgg agcccaggga  9240
ctgcgtctct tgccggaatg tcagccgagg cagggaatgc gtggacaagt gcaaccttct  9300
ggagggtgag ccaagggagt ttgtggagaa ctctgagtgc atacagtgcc acccagagtg  9360
cctgcctcag gccatgaaca tcacctgcac aggacgggga ccagacaact gtatccagtg  9420
tgcccactac attgacggcc cccactgcgt caagacctgc ccggcaggag tcatgggaga  9480
aaacaacacc ctggtctgga agtacgcaga cgccggccat gtgtgccacc tgtgccatcc  9540
aaactgcacc tacggatgca ctgggccagg tcttgaaggc tgtccaacga atgggcctaa  9600
gatcccgtcc atcgccactg ggatggtggg ggccctcctc ttgctgctgg tggtggccct  9660
ggggatcggc ctcttcatgt gaagcggccg cgactctaga gtcgacctgc aggcatgcaa  9720
gcttgatatc aagcttatcg ataatcaacc tctggattac aaaatttgtg aaagattgac  9780
tggtattctt aactatgttg ctccttttac gctatgtgga tacgctgctt taatgccttt  9840
gtatcatgct attgcttccc gtatggcttt cattttctcc tccttgtata aatcctggtt  9900
gctgtctctt tatgaggagt tgtggcccgt tgtcaggcaa cgtggcgtgg tgtgcactgt  9960
gtttgctgac gcaaccccca ctggttgggg cattgccacc acctgtcagc tcctttccgg  10020
gactttcgct ttccccctcc ctattgccac ggcggaactc atcgccgcct gccttgcccg  10080
ctgctggaca ggggctcggc tgttgggcac tgacaattcc gtggtgttgt cggggaaatc  10140
atcgtccttt ccttggctgc tcgcctgtgt tgccacctgg attctgcgcg ggacgtcctt  10200
ctgctacgtc ccttcggccc tcaatccagc ggaccttcct tcccgcggcc tgctgccggc  10260
tctgcggcct cttccgcgtc ttcgccttcg ccctcagacg agtcggatct ccctttgggc  10320
cgcctccccg cat                                                     10333
```

```
SEQ ID NO: 63           moltype = DNA  length = 9281
FEATURE                 Location/Qualifiers
misc_feature            1..9281
```

```
                         note = synthetic vector
source                   1..9281
                         mol_type = other DNA
                         organism = synthetic construct
SEQUENCE: 63
cgataccgtc gacctcgagg gaattaattc gagctcggta cctttaagac caatgactta  60
caaggcagct gtagatctta gccacttttt aaaagaaaag gggggactgg aagggctaat  120
tcactcccaa cgaagacaag atctgctttt tgcttgtact gggtctctct ggttagacca  180
gatctgagcc tgggagctct ctggctaact agggaaccca ctgcttaagc ctcaataaag  240
cttgccttga gtgcttcaag tagtgtgtgc ccgtctgttg tgtgactctg gtaactagag  300
atccctcaga cccttttagt cagtgtggaa aatctctagc agcatctaga attaattccg  360
tgtattctat agtgtcacct aaatcgtatg tgtatgatac ataaggttat gtattaattg  420
tagccgcgtt ctaacgacaa tatgtacaag cctaattgtg tagcatctgg cttactgaag  480
cagaccctat catctctctc gtaaactgcc gtcagagtcg gtttggttgg acgaaccttc  540
tgagtttctg gtaacgccgt cccgcacccg gaaatggtca gcgaaccaat cagcagggtc  600
atcgctagcc agatcctcta cgccggacgc atcgtggccg gcatcaccgg cgccacaggt  660
gcggttgctg gcgcctatat cgccgacatc accgatgggg aagatcgggc tcgccacttc  720
gggctcatga gcgcttgttt cggcgtgggt atggtggcag gccccgtggc cgggggactg  780
ttgggcgcca tctccttgca tgcaccattc cttgcggcgg cggtgctcaa cggcctcaac  840
ctactactgg gctgcttcct aatgcaggag tcgcataagg gagagcgtcg aatggtgcac  900
tctcagtaca atctgctctg atgccgcata gttaagccag ccccgacacc cgccaacacc  960
cgctgacgcg ccctgacggg cttgtctgct cccggcatcc gcttacagac aagctgtgac  1020
cgtctccggg agctgcatgt gtcagaggtt ttcaccgtca tcaccgaaac gcgcgagacg  1080
aaagggcctc gtgatacgcc tatttttata ggttaatgtc atgataataa tggtttctta  1140
gacgtcaggt ggcacttttc ggggaaatgt gcgcggaacc cctatttgtt tatttttcta  1200
aatacattca aatatgtatc cgctcatgag acaataaccc tgataaatgc ttcaataata  1260
ttgaaaaagg aagagtatga gtattcaaca tttccgtgtc gcccttattc ccttttttgc  1320
ggcattttgc cttcctgttt ttgctcaccc agaaacgctg gtgaaagtaa aagatgctga  1380
agatcagttg ggtgcacgag tgggttacat cgaactggat ctcaacagcg gtaagatcct  1440
tgagagtttt cgccccgaag aacgttttcc aatgatgagc acttttaaag ttctgctatg  1500
tggcgcggta ttatcccgta ttgacgccgg gcaagagcaa ctcggtcgcc gcatacacta  1560
ttctcagaat gacttggttg agtactcacc agtcacagaa aagcatctta cggatggcat  1620
gacagtaaga gaattatgca gtgctgccat aaccatgagt gataacactg cggccaactt  1680
acttctgaca acgatcggag gaccgaagga gctaaccgct tttttgcaca acatggggga  1740
tcatgtaact cgccttgatc gttgggaacc ggagctgaat gaagccatac caaacgacga  1800
gcgtgacacc acgatgcctg tagcaatggc aacaacgttg cgcaaactat taactggcga  1860
actacttact ctagcttccc ggcaacaatt aatagactgg atggaggcgg ataaagttgc  1920
aggaccactt ctgcgctcgg cccttccggc tggctggttt attgctgata aatctggagc  1980
cggtgagcgt gggtctcgcg gtatcattgc agcactgggg ccagatggta agccctcccg  2040
tatcgtagtt atctacacga cggggagtca ggcaactatg gatgaacgaa atagacagat  2100
cgctgagata ggtgcctcac tgattaagca ttggtaactg tcagaccaag tttactcata  2160
tatactttag attgatttaa aacttcattt ttaatttaaa aggatctagg tgaagatcct  2220
ttttgataat ctcatgacca aaatccctta acgtgagttt tcgttccact gagcgtcaga  2280
ccccgtagaa aagatcaaag gatcttcttg agatcctttt tttctgcgcg taatctgctg  2340
cttgcaaaca aaaaaaccac cgctaccagc ggtggtttgt ttgccggatc aagagctacc  2400
aactcttttt ccgaaggtaa ctggcttcag cagagcgcag ataccaaata ctgtctttct  2460
agtgtagccg tagttaggcc accacttcaa gaactctgta gcaccgccta catacctcgc  2520
tctgctaatc ctgttaccag tggctgctgc cagtggcgat aagtcgtgtc ttaccgggtt  2580
ggactcaaga cgatagttac cggataaggc gcagcggtcg ggctgaacgg ggggttcgtg  2640
cacacagccc agcttggagc gaacgaccta caccgaactg agatacctac agcgtgagct  2700
atgagaaagc gccacgcttc ccgaagggag aaaggcggac aggtatccgg taagcggcag  2760
ggtcggaaca ggagagcgca cgagggagct tccaggggga aacgcctggt atctttatag  2820
tcctgtcggg tttcgccacc tctgacttga gcgtcgattt ttgtgatgct cgtcaggggg  2880
gcggagccta tggaaaaacg ccagcaacgc ggccttttta cggttcctgg ccttttgctg  2940
gccttttgct cacatgttct ttcctgcgtt atcccctgat tctgtggata accgtattac  3000
cgcctttgag tgagctgata ccgctcgccg cagccgaacg accgagcgca gcgagtcagt  3060
gagcgaggaa gcggaagagc gcccaatacg caaaccgcct ctccccgcgc gttggccgat  3120
tcattaatgc agctgtggaa tgtgtgtcag ttagggtgtg gaaagtcccc aggctcccca  3180
gcaggcagaa gtatgcaaag catgcatctc aattagtcag caaccaggtg tggaaagtcc  3240
ccaggctccc cagcaggcag aagtatgcaa agcatgcatc tcaattagtc agcaaccata  3300
gtcccgcccc taactccgcc catcccgccc ctaactccgc ccagttccgc ccattctccg  3360
ccccatggct gactaatttt ttttatttat gcagaggccg aggccgcctc ggcctctgag  3420
ctattccaga agtagtgagg aggctttttt ggaggcctag gcttttgcaa aaagcttgga  3480
cacaagacag gcttgcgaga tatgtttgag aataccactt tatcccgcgt cagggagagg  3540
cagtgcgtaa aaagacgcgg actcatgtga aatactggtt tttagtgcgc cagatctcta  3600
taatctcgcg caacctattt tcccctcgaa cactttttaa gccgtagata aacaggctgg  3660
gacacttcac atgagcgaaa aatacatcgt cacctgggac atgttgcaga tccatgcacg  3720
taaactcgca agccgactga tgccttctga acaatggaaa ggcattattg ccgtaagccg  3780
tggcggtctg taccgggtgc gttactggcg cgtgaactgg gtattcgtca tgtcgatacc  3840
gtttgtattt ccagctacga tcacgacaac cagcgcgagc ttaaagtgct gaaacgcgca  3900
gaaggcgatg gcgaaggctt catcgttatt gatgacctgg tggataccgg tggtactgcg  3960
gttgcgattc gtgaaatgta tccaaaagcg cactttgtca ccatcttcgc aaaaccggct  4020
ggtcgtccgc tggttgatga ctatgttgtt gatatcccgc aagatacctg gattgaacag  4080
ccgtgggata tgggcgtcgt attcgtcccg ccaatctccg gtcgctaatc ttttcaacgc  4140
ctggcactgc cgggcgttgt tctttttaac ttcaggcggg ttacaatagt ttccagtaag  4200
tattctggag gctgcatcca tgacacaggc aaacctgagc gaaaccctgt tcaaaccccg  4260
ctttaaacat cctgaaacct cgacgctagt ccgccgcttt aatcacggcg cacaaccgcc  4320
tgtgcagtcg gcccttgatg gtaaaaccat ccctcactgg tatcgcatga ttaaccgtct  4380
gatgtggatc tggcgcggca ttgacccacg cgaaatcctc gacgtccagg cacgtattgt  4440
```

-continued

```
gatgagcgat gccgaacgta ccgacgatga tttatacgat acggtgattg gctaccgtgg  4500
cggcaactgg atttatgagt gggccccgga tctttgtgaa ggaaccttac ttctgtggtg  4560
tgacataatt ggacaaacta cctacagaga tttaaagctc taaggtaaat ataaaatttt  4620
taagtgtata atgtgttaaa ctactgattc taattgtttg tgtattttag attccaacct  4680
atggaactga tgaatgggag cagtggtgga atgcctttaa tgaggaaaac ctgttttgct  4740
cagaagaaat gccatctagt gatgatgagg ctactgctga ctctcaacat tctactcctc  4800
caaaaaagaa gagaaaggta gaagacccca aggactttcc ttcagaattg ctaagttttt  4860
tgagtcatgc tgtgtttagt aatagaactc ttgcttgctt tgctatttac accacaaagg  4920
aaaaagctgc actgctatac aagaaaatta tggaaaaata ttctgtaacc tttataagta  4980
ggcataacag ttataatcat aacatactgt tttttcttac tccacacagg catagagtgt  5040
ctgctattaa taactatgct caaaaattgt gtacctttag ctttttaatt tgtaaagggg  5100
ttaataagga atatttgatg tatagtgcct tgactagaga tcataatcag ccataccaca  5160
tttgtagagg ttttacttgc tttaaaaaac ctcccacacc tccccctgaa cctgaaacat  5220
aaaatgaatg caattgttgt tgttaacttg tttattgcag cttataatgg ttacaaataa  5280
agcaatagca tcacaaattt cacaaataaa gcattttttt cactgcattc tagttgtggt  5340
ttgtccaaac tcatcaatgt atcttatcat gtctggatca actggataac tcaagctaac  5400
caaaatcatc ccaaacttcc caccccatac cctattacca ctgccaatta cctagtggtt  5460
tcatttactc taaacctgtg attcctctga attattttca ttttaaagaa attgtatttg  5520
ttaaatatgt actacaaact tagtagttgg aagggctaat tcactcccaa agaagacaag  5580
atatccttga tctgtggatc taccacacac aaggctactt ccctgattag cagaactaca  5640
caccagggcc aggggtcaga tatccactga cctttggatg gtgctacaag ctagtaccag  5700
ttgagccaga taaggtagaa gaggccaata aaggagagaa caccagcttg ttacaccctg  5760
tgagcctgca tgggatggat gacccggaga gagaagtgtt agagtggagg tttgacagcc  5820
gcctagcatt tcatcacgtg gcccgagagc tgcatccgga gtacttcaag aactgctgat  5880
atcgagcttg ctacaaggga ctttccgctg gggactttcc agggaggcgt ggcctgggcg  5940
ggactgggga gtggcgagcc ctcagatcct gcatataagc agctgctttt tgcctgtact  6000
gggtctctct ggttagacca gatctgagcc tgggagctct ctggctaact agggaaccca  6060
ctgcttaagc ctcaataaag cttgccttga gtgcttcaag tagtgtgtgc ccgtctgttg  6120
tgtgactctg gtaactagag atccctcaga cccttttagt cagtgtggaa aatctctagc  6180
agtggcgccc gaacagggac ttgaaagcga aagggaaacc agaggagctc tctcgacgca  6240
ggactcggct tgctgaagcg cgcacggcaa gaggcgaggg gcggcgactg gtgagtacgc  6300
caaaaatttt gactagcgga ggctagaagg agagagatgg gtgcgagagc gtcagtatta  6360
agcgggggag aattagatcg cgatgggaaa aaattcggtt aaggccaggg ggaaagaaaa  6420
aatataaatt aaaacatata gtatgggcaa gcagggagct agaacgattc gcagttaatc  6480
ctggcctgtt agaaacatca gaaggctgta gacaaatact gggacagcta caaccatccc  6540
ttcagacagg atcagaagaa cttagatcat tatataatac agtagcaacc ctctattgtg  6600
tgcatcaaag gatagagata aaagacacca aggaagcttt agacaagata gaggaagagc  6660
aaaacaaaag taagaccacc gcacagcaag cggccggccg ctgatcttca gacctggagg  6720
aggagatatg agggacaatt ggagaagtga attatataaa tataaagtag taaaaattga  6780
accattagga gtagcaccca ccaaggcaaa gagaagagtg gtgcagagag aaaaaagagc  6840
agtgggaata ggagctttgt tccttgggtt cttgggagca gcaggaagca ctatgggcgc  6900
agcgtcaatg acgctgacgg tacaggccag acaattattg tctggtatag tgcagcagca  6960
gaacaatttg ctgagggcta ttgaggcgca acagcatctg ttgcaactca cagtctgggg  7020
catcaagcag ctccaggcaa gaatcctggc tgtgaaagat acctaaagga tcaacagctc  7080
ctggggattt ggggttgctc tggaaaactc atttgcacca ctgctgtgcc ttggaatgct  7140
agttggagta ataaatctct ggaacagatt tggaatcaca cgacctggat ggagtgggac  7200
agagaaatta acaattacac aagcttaata cactccttaa ttgaagaatc gcaaaaccag  7260
caagaaaaga atgaacaaga attattggaa ttagataaat gggcaagttt gtggaattgg  7320
tttaacataa caaattggct gtggtatata aaattattca taatgatagt aggaggcttg  7380
gtaggtttaa gaatagtttt tgctgtactt tctatagtga atagagttag gcagggatat  7440
tcaccattat cgtttcagac ccacctccca accccgaggg gacccgacag gcccgaagga  7500
atagaagaag aaggtggaga gagagacaga gacagatcca ttcgattagt gaacggatct  7560
cgacggtatc gccaaatggc agtattcatc cacaatttta aaagaaaagg ggggattggg  7620
gggtacagtg caggggaaag aatagtagac ataatagcaa cagacataca aactaaagaa  7680
ttacaaaaac aaattacaaa aattcaaaat tttcgggttt attacaggga cagcagagat  7740
ccagtttgga tcgataagct tgatatcgaa ttcgtcgacc gggtttcgta acaatcgcat  7800
gaggattcgc aacgccttcg gcgtagccga tgtcgcgctc ccgtctcagt aaaggtcggc  7860
gtagccgatg tcgcgcaatc ggactgcctt cgtacggcgt agccgatgtc gcgcgtatca  7920
gtcgcctcgg aacggcgtag ccgatgtcgc gcattcgtaa gaggctcact ctcccttaca  7980
cggagtggat aactagtttc gcatattaag gtgacgcgtg tggcctcgaa caccgagcga  8040
ccctgcagcg acccgcttaa ggatccaccg gtcgccacca cacatacaca gaaatgcact  8100
catctgctct cctttgctgt ctcgtgctcc tgactggagt acgcgcgtca cccggtcaag  8160
ggacacaaag cgaaaactcc tgtacgcatt ttccgggcaa cctccctaat atgcttcgcg  8220
acttgcgaga tgcattttcc agggtgaaga ccttcttcca gatgaaggac cagttggata  8280
atcttctcct caaggagtct cttttggagg acttcaaggg ctacctggga tgtcaagccc  8340
ttagcgaaat gattcagttt tatcttgaag aggtcatgcc gcaagctgag aaccaggacc  8400
ccgacataaa agcccatgtg aactccctcg gcgagaattt gaagacgctg agacttagat  8460
tgagaagatg tcatagattt ctcccatgtg agaataagtc caaggctgtc gagcaggtta  8520
agaatgcttt caataagttg caggaaaaag gaatctataa ggcaatgagc gagtttgaca  8580
tctttattaa ctacattgag gcttatatga ctatgaaaat tagaaactaa agcggccgcg  8640
actctagagt cgacctgcag gcatgcaagc ttgatatcaa gcttatcgat aatcaacctc  8700
tggattacaa aatttgtgaa agattgactg gtattcttaa ctatgttgct ccttttacgc  8760
tatgtggata cgctgcttta atgcctttgt atcatgctat tgcttcccgt atggctttca  8820
ttttctcctc cttgtataaa tcctggttgc tgtctcttta tgaggagttg tggcccgttg  8880
tcaggcaacg tggcgtggtg tgcactgtgt ttgctgacgc aacccccact ggttggggca  8940
ttgccaccac ctgtcagctc ctttccggga ctttcgcttt ccccctccct attgccacgg  9000
cggaactcat cgccgcctgc cttgcccgct gctggacagg ggctcggctg ttgggcactg  9060
acaattccgt ggtgttgtcg gggaaatcat cgtcctttcc ttggctgctc gcctgtgttg  9120
ccacctggat tctgcgcggg acgtccttct gctacgtccc ttcggccctc aatccagcgg  9180
```

```
accttccttc ccgcggcctg ctgccggctc tgcggcctct tccgcgtctt cgccttcgcc  9240
ctcagacgag tcggatctcc ctttgggccg cctccccgca t                      9281

SEQ ID NO: 64           moltype = DNA  length = 11931
FEATURE                 Location/Qualifiers
misc_feature            1..11931
                        note = synthetic vector
source                  1..11931
                        mol_type = other DNA
                        organism = synthetic construct
SEQUENCE: 64
tctcgcgcaa cctattttcc cctcgaacac tttttaagcc gtagataaac aggctgggac  60
acttcacatg agcgaaaaat acatcgtcac ctgggacatg ttgcagatcc atgcacgtaa  120
actcgcaagc cgactgatgc cttctgaaca atggaaaggc attattgccg taagccgtgg  180
cggtctgtac cgggtgcgtt actggcgcgt gaactgggta ttcgtcatgt cgataccgtt  240
tgtatttcca gctacgatca cgacaaccag cgcgagctta aagtgctgaa acgcgcagaa  300
ggcgatggcg aaggcttcat cgttattgat gacctggtgg ataccggtgg tactgcggtt  360
gcgattcgtg aaatgtatcc aaaagcgcac tttgtcacca tcttcgcaaa accggctggt  420
cgtccgctgg ttgatgacta tgttgttgat atcccgcaag atacctggat tgaacagccg  480
tgggatatgg gcgtcgtatt cgtcccgcca atctccggtc gctaatcttt tcaacgcctg  540
gcactgccgg gcgttgttct ttttaacttc aggcgggtta caatagtttc cagtaagtat  600
tctggaggct gcatccatga cacaggcaaa cctgagcgaa accctgttca aaccccgctt  660
taaacatcct gaaacctcga cgctagtccg ccgctttaat cacggcgcac aaccgcctgt  720
gcagtcggcc cttgatggta aaaccatccc tcactggtat cgcatgatta accgtctgat  780
gtggatctgg cgcggcattg acccacgcga aatcctcgac gtccaggcac gtattgtgat  840
gagcgatgcc gaacgtaccg acgatgattt atacgatacg gtgattggct accgtggcgg  900
caactggatt tatgagtggg ccccggatct ttgtgaagga accttacttc tgtggtgtga  960
cataattgga caaactacct acagagattt aaagctctaa ggtaaatata aaatttttaa  1020
gtgtataatg tgttaaacta ctgattctaa ttgtttgtgt attttagatt ccaacctatg  1080
gaactgatga atgggagcag tggtggaatg cctttaatga ggaaaacctg ttttgctcag  1140
aagaaatgcc atctagtgat gatgaggcta ctgctgactc tcaacattct actcctccaa  1200
aaaagaagag aaaggtagaa gaccccaagg actttccttc agaattgcta agttttttga  1260
gtcatgctgt gtttagtaat agaactcttg cttgctttgc tatttacacc acaaaggaaa  1320
aagctgcact gctatacaag aaaattatgg aaaaatattc tgtaaccttt ataagtaggc  1380
ataacagtta taatcataac atactgtttt ttcttactcc acacaggcat agagtgtctg  1440
ctattaataa ctatgctcaa aaattgtgta cctttagctt tttaatttgt aaaggggtta  1500
ataaggaata tttgatgtat agtgccttga ctagagatca taatcagcca taccacattt  1560
gtagaggttt tacttgcttt aaaaaacctc ccacacctcc ccctgaacct gaaacataaa  1620
atgaatgcaa ttgttgttgt taacttgttt attgcagctt ataatggtta caaataaagc  1680
aatagcatca caaatttcac aaataaagca tttttttcac tgcattctag ttgtggtttg  1740
tccaaactca tcaatgtatc ttatcatgtc tggatcaact ggataactca agctaaccaa  1800
aatcatccca aacttcccac cccataccct attaccactg ccaattacct agtggtttca  1860
tttactctaa acctgtgatt cctctgaatt attttcattt taaagaaatt gtatttgtta  1920
aatatgtact acaaacttag tagttggaag ggctaattca ctcccaaaga agacaagata  1980
tccttgatct gtggatctac cacacacaag gctacttccc tgattagcag aactacacac  2040
cagggccagg ggtcagatat ccactgacct ttggatggtg ctacaagcta gtaccagttg  2100
agccagataa ggtagaagag gccaataaag gagagaacac cagcttgtta caccctgtga  2160
gcctgcatgg gatggatgac ccggagagag aagtgttaga gtggaggttt gacagccgcc  2220
tagcatttca tcacgtggcc cgagagctgc atccggagta cttcaagaac tgctgatatc  2280
gagcttgcta caagggactt tccgctgggg actttccagg gaggcgtggc ctgggcggga  2340
ctggggagtg gcgagccctc agatcctgca tataagcagc tgctttttgc ctgtactggg  2400
tctctctggt tagaccagat ctgagcctgg gagctctctg gctaactagg gaacccactg  2460
cttaagcctc aataaagctt gccttgagtg cttcaagtag tgtgtgcccg tctgttgtgt  2520
gactctggta actagagatc cctcagaccc ttttagtcag tgtggaaaat ctctagcagt  2580
ggcgcccgaa cagggacttg aaagcgaaag ggaaaccaga ggagctctct cgacgcagga  2640
ctcggcttgc tgaagcgcgc acggcaagag gcgaggggcg gcgactggtg agtacgccaa  2700
aaattttgac tagcggaggc tagaaggaga gagatgggtg cgagagcgtc agtattaagc  2760
gggggagaat tagatcgcga tgggaaaaaa ttcggttaag gccaggggga aagaaaaaat  2820
ataaattaaa acatatagta tgggcaagca gggagctaga acgattcgca gttaatcctg  2880
gcctgttaga aacatcagaa ggctgtagac aaatactggg acagctacaa ccatcccttc  2940
agacaggatc agaagaactt agatcattat ataatacagt agcaaccctc tattgtgtgc  3000
atcaaaggat agagataaaa gacaccaagg aagctttaga caagatagag gaagagcaaa  3060
acaaaagtaa gaccaccgca cagcaagcgg ccggccgctg atcttcagac ctggaggagg  3120
agatatgagg gacaattgga gaagtgaatt atataaatat aaagtagtaa aaattgaacc  3180
attaggagta gcacccacca aggcaaagag aagagtggtg cagagagaaa aaagagcagt  3240
gggaatagga gctttgttcc ttgggttctt gggagcagca ggaagcacta tgggcgcagc  3300
gtcaatgacg ctgacggtac aggccagaca attattgtct ggtatagtgc agcagcagaa  3360
caatttgctg agggctattg aggcgcaaca gcatctgttg caactcacag tctggggcat  3420
caagcagctc caggcaagaa tcctggctgt ggaaagatac ctaaaggatc aacagctcct  3480
gggatttggg gttgctctgg aaaactcatt tgcaccactg ctgtgccttg gaatgctagt  3540
tggagtaata aatctctgga acagatttgg aatcacacga cctggatgga gtgggacaga  3600
gaaattaaca attacacaag cttaatacac tccttaattg aagaatcgca aaaccagcaa  3660
gaaaagaatg aacaagaatt attggaatta gataaatggg caagtttgtg gaattggttt  3720
aacataacaa attggctgtg gtatataaaa ttattcataa tgatagtagg aggcttggta  3780
ggtttaagaa tagtttttgc tgtactttct atagtgaata gagttaggca gggatattca  3840
ccattatcgt ttcagaccca cctcccaacc ccgaggggac ccgacaggcc cgaaggaata  3900
gaagaagaag gtggagagag agacagagac agatccattc gattagtgaa cggatctcga  3960
cggtatcgcc aaatggcagt attcatccac aattttaaaa gaaaaggggg gattgggggg  4020
tacagtgcag gggaaagaat agtagacata atagcaacag acatacaaac taaagaatta  4080
```

-continued

```
caaaaacaaa ttacaaaaat tcaaaatttt cgggtttatt acagggacag cagagatcca  4140
gtttggatcg ataagcttga tatcgaattc ctgcagcctt agtttctaat tttcatagtc  4200
atataagcct caatgtagtt aataaagatg tcaaactcgc tcattgcctt atagattcct  4260
ttttcctgca acttattgaa agcattctta acctgctcga cagccttgga cttattctca  4320
catgggagaa atctatgaca tcttctcaat ctaagtctca gcgtcttcaa attctcgccg  4380
agggagttca catgggcttt tatgtcgggg tcctggttct cagcttgcgg catgacctct  4440
tcaagataaa actgaatcat ttcgctaagg gcttgacatc ccaggtagcc cttgaagtcc  4500
tccaaaagag actccttgag gagaagatta tccaactggt ccttcatctg gaagaaggtc  4560
ttcaccctgg aaaatgcatc tcgcaagtcg cgaagcatat tagggaggtt gcccggaaaa  4620
tgcgtacagg agttttcgct ttgtgtccct tgaccgggtg acgcgcgtac tccagtcagg  4680
agcacgagac agcaaaggag agcagatgag tgcatttctg tgtatgtgtg gtggcgaccg  4740
gtggatcctt aagcgggtcg ctgcagggtc gctcggtgtt cgaggccaca cgcgtcacct  4800
taatatgcga aactagttat ccactccgtg taagggagag tgagcctctt acgaatgcgc  4860
gacatcggct acgccgttcc gaggcgactg atacgcgcga catcggctac gccgtacgaa  4920
ggcagtccga ttgcgcgaca tcggctacgc cgacctttac tgagacggga gcgcgacatc  4980
ggctacgccg aaggcgttgc gaatcctcat gcgattgtta cgaaacccgc cgataaaata  5040
aaagatttta tttagtctcc agaaaaaggg gggaatgaaa gaccccacct gtaggtttgg  5100
caagctagct gcagtaacgc cattttgcaa ggcatggaaa aataccaaac caagaataga  5160
gaagttcaga tcaagggcgg gtacatgaaa atagctaacg ttgggccaaa caggatatct  5220
gcggtgagca gtttcggccc cggcccgggg ccaagaacag atggtcaccg cagtttcggc  5280
cccggcccga ggccaagaac agatggtccc cagatatggc ccaaccctca gcagtttctt  5340
aagacccatc agatgtttcc aggctccccc aaggacctga aatgaccctg cgccttattt  5400
gaattaacca atcagcctgc ttctcgcttc tgttcgcgcg cttctgcttc ccgagctcta  5460
taaaagagct cacaacccct cactcggcgc gccagtcctc cgacagactg agtcgcccgg  5520
gggggatctg gagctctcga gaattctcac gcgtgccgcc accatgtcta gacccggaga  5580
gcgcccattc cagtgtcgga tttgcatgcg gaacttttcg agaagacacg gcctggacag  5640
acatacccgt actcatacag gtgaaaaacc ctttcagtgt cggatctgta tgcgaaattt  5700
ctccgaccac agcagcctga agagacatct acgtacccac accggcagcc agaagccatt  5760
tcagtgtcgg atctgtatgc ggaacttctc cgtgagacac aacctgacca gacatctacg  5820
tacgcacacc ggagagaagc cattccaatg ccgaatatgc atgcgcaact tcagtgacca  5880
cagcaacctg agcagacacc taaaaaccca caccggttcc cagaagccat ttcagtgtcg  5940
gatctgtatg cggaacttct cccagcgcag cagcctggtg agacatctac gtacgcacac  6000
cggagagaag ccattccaat gccgaatatg catgcgcaac ttcagtgaga gcggccacct  6060
gaagagacac ctgcgtacgc acctgagggg atccacctgc agggactaca aagaccatga  6120
cggtgattat aaagatcatg acatcgatta caaggatgac gatgacaaga tggcccccaa  6180
gaaaaagagg aaggtgggca ttcacggggt gccgggtgga ctcgagggag gcggtggaag  6240
cggcggtacc gaggacgtgg tgtgctgcca ctcaatctac ggcaagaaga agggtgatat  6300
cgacacctac cgatacatag gctcttccgg gacaggctgc gtggtcatag tgggcaggat  6360
cgtcttgtcc ggatccggca ctagtgcgcc catcacggcg tacgcccagc agacgagagg  6420
cctcctaggg tgtataatca ccagcctgac tggccgggac aaaaaccaag tggagggtga  6480
ggtccagatc gtgtcaactg ctacccaaac cttcctggca acgtgcatca atggggtatg  6540
ctgggcagtc taccacgggg ccggaacgag gaccatcgca tcacccaagg gtcctgtcat  6600
ccagatgtat accaatgtgg accaagacct tgtgggctgg cccgctcctc aaggttcccg  6660
ctcattgaca ccctgtacct gcggctcctc ggacctttac ctggtcacga ggcacgccga  6720
tgtcattccc gtgcgccggc gaggtgatag caggggtagc ctgctttcgc cccggcccat  6780
ttcctacttg aaaggctcct cgggggtccc gctgttgtgc ccccgcggac acgccgtggg  6840
cctattcagg gccgcggtgt gcacccgtgg agtggctaaa gcggtggact ttatccctgt  6900
ggagaaccta gagacaacca tgagatcccc ggtgttcacg gacaactcct ctccaccagc  6960
agtcaccctg acgcacccaa tcaccaaaat cgatagggag gttctctacc aggagttcga  7020
tgagatggaa gagtgctctc agcactatcc ctacgatgtg cccgattacg ctggaggcgg  7080
tggaagcggc ggtaccgatg agtttcccac catggtgttt ccttctgggc agatcagcca  7140
ggcctcggcc ttggccccgg cccctcccca agtcctgccc caggctccag cccctgcccc  7200
tgctccagcc atggtatcag ctctggccca ggccccagcc cctgtcccag tcctagcccc  7260
aggccctcct caggctgtgg ccccacctgc ccccaagccc acccaggctg gggaaggaac  7320
gctgtcagag gccctgctgc agctgcagtt tgatgatgaa gacctggggg ccttgcttgg  7380
caacagcaca gacccagctg tgttcacaga cctggcatcc gtcgacaact ccgagtttca  7440
gcagctgctg aaccagggca tacctgtggc cccccacaca actgagccca tgctgatgga  7500
gtaccctgag gctataactc gcctagtgac aggggcccag aggcccccccg acccagctcc  7560
tgctccactg gggccccggg ggctccccaa tggcctcctt tcaggagatg aagacttctc  7620
ctccattgcg gacatggact tctcagccct gctgagtcag atcagctccc aattgtaagc  7680
ggccgcgact ctagagtcga cctgcaggca tgcaagcttg atatcaagct tatcgataat  7740
caacctctgg attacaaaat ttgtgaaaga ttgactggta ttcttaacta tgttgctcct  7800
tttacgctat gtggatacgc tgctttaatg cctttgtatc atgctattgc ttcccgtatg  7860
gctttcattt tctcctcctt gtataaatcc tggttgctgt ctctttatga ggagttgtgg  7920
cccgttgtca ggcaacgtgg cgtggtgtgc actgtgtttg ctgacgcaac ccccactggt  7980
tggggcattg ccaccacctg tcagctcctt tccgggactt tcgctttccc cctccctatt  8040
gccacggcgg aactcatcgc cgcctgcctt gcccgctgct ggacaggggc tcggctgttg  8100
ggcactgaca attccgtggt gttgtcgggg aaatcatcgt cctttccttg gctgctcgcc  8160
tgtgttgcca cctggattct gcgcgggacg tccttctgct acgtcccttc ggccctcaat  8220
ccagcggacc ttccttcccg cggcctgctg ccggctctgc ggcctcttcc gcgtcttcgc  8280
cttcgccctc agacgagtcg gatctccctt tgggccgcct ccccgcatcg ataccgtcga  8340
cctcgaggga attaattcga gctcggtacc tttaagacca atgacttaca aggcagctgt  8400
agatcttagc cactttttaa aagaaaaggg gggactggaa gggctaattc actcccaacg  8460
aagacaagat ctgctttttg cttgtactgg gtctctctgg ttagaccaga tctgagcctg  8520
ggagctctct ggctaactag ggaacccact gcttaagcct caataaagct tgccttgagt  8580
gcttcaagta gtgtgtgccc gtctgttgtg tgactctggt aactagagat ccctcagacc  8640
cttttagtca gtgtggaaaa tctctagcag catctagaat taattccgtg tattctatag  8700
tgtcacctaa atcgtatgtg tatgatacat aaggttatgt attaattgta gccgcgttct  8760
aacgacaata tgtacaagcc taattgtgta gcatctggct tactgaagca gaccctatca  8820
```

```
tctctctcgt aaactgccgt cagagtcggt ttggttggac gaaccttctg agtttctggt  8880
aacgccgtcc cgcacccgga aatggtcagc gaaccaatca gcagggtcat cgctagccag  8940
atcctctacg ccggacgcat cgtggccggc atcaccggcg ccacaggtgc ggttgctggc  9000
gcctatatcg ccgacatcac cgatggggaa gatcgggctc gccacttcgg gctcatgagc  9060
gcttgtttcg gcgtgggtat ggtggcaggc cccgtggccg ggggactgtt gggcgccatc  9120
tccttgcatg caccattcct tgcggcggcg gtgctcaacg gcctcaacct actactgggc  9180
tgcttcctaa tgcaggagtc gcataaggga gagcgtcgaa tggtgcactc tcagtacaat  9240
ctgctctgat gccgcatagt taagccagcc ccgacacccg ccaacacccg ctgacgcgcc  9300
ctgacgggct tgtctgctcc cggcatccgc ttacagacaa gctgtgaccg tctccgggag  9360
ctgcatgtgt cagaggtttt caccgtcatc accgaaacgc gcgagacgaa agggcctcgt  9420
gatacgccta tttttatagg ttaatgtcat gataataatg gtttcttaga cgtcaggtgg  9480
cacttttcgg ggaaatgtgc gcggaacccc tatttgttta tttttctaaa tacattcaaa  9540
tatgtatccg ctcatgagac aataaccctg ataaatgctt caataatatt gaaaaaggaa  9600
gagtatgagt attcaacatt tccgtgtcgc ccttattccc ttttttgcgg cattttgcct  9660
tcctgttttt gctcacccag aaacgctggt gaaagtaaaa gatgctgaag atcagttggg  9720
tgcacgagtg ggttacatcg aactggatct caacagcggt aagatccttg agagttttcg  9780
ccccgaagaa cgttttccaa tgatgagcac ttttaaagtt ctgctatgtg gcgcggtatt  9840
atcccgtatt gacgccgggc aagagcaact cggtcgccgc atacactatt ctcagaatga  9900
cttggttgag tactcaccag tcacagaaaa gcatcttacg gatggcatga cagtaagaga  9960
attatgcagt gctgccataa ccatgagtga taacactgcg gccaacttac ttctgacaac  10020
gatcggagga ccgaaggagc taaccgcttt tttgcacaac atgggggatc atgtaactcg  10080
ccttgatcgt tgggaaccgg agctgaatga agccatacca aacgacgagc gtgacaccac  10140
gatgcctgta gcaatggcaa caacgttgcg caaactatta actggcgaac tacttactct  10200
agcttcccgg caacaattaa tagactggat ggaggcggat aaagttgcag gaccacttct  10260
gcgctcggcc cttccggctg gctggtttat tgctgataaa tctggagccg gtgagcgtgg  10320
gtctcgcggt atcattgcag cactggggcc agatggtaag ccctcccgta tcgtagttat  10380
ctacacgacg gggagtcagg caactatgga tgaacgaaat agacagatcg ctgagatagg  10440
tgcctcactg attaagcatt ggtaactgtc agaccaagtt tactcatata tactttagat  10500
tgatttaaaa cttcattttt aatttaaaag gatctaggtg aagatccttt ttgataatct  10560
catgaccaaa atcccttaac gtgagttttc gttccactga gcgtcagacc ccgtagaaaa  10620
gatcaaagga tcttcttgag atcctttttt tctgcgcgta atctgctgct tgcaaacaaa  10680
aaaaccaccg ctaccagcgg tggtttgttt gccggatcaa gagctaccaa ctctttttcc  10740
gaaggtaact ggcttcagca gagcgcagat accaaatact gtctttctag tgtagccgta  10800
gttaggccac cacttcaaga actctgtagc accgcctaca tacctcgctc tgctaatcct  10860
gttaccagtg gctgctgcca gtggcgataa gtcgtgtctt accgggttgg actcaagacg  10920
atagttaccg gataaggcgc agcggtcggg ctgaacgggg ggttcgtgca cacagcccag  10980
cttggagcga acgacctaca ccgaactgag atacctacag cgtgagctat gagaaagcgc  11040
cacgcttccc gaagggagaa aggcggacag gtatccggta agcggcaggg tcggaacagg  11100
agagcgcacg agggagcttc caggggggaaa cgcctggtat ctttatagtc ctgtcgggtt  11160
tcgccacctc tgacttgagc gtcgattttt gtgatgctcg tcaggggggc ggagcctatg  11220
gaaaaacgcc agcaacgcgg cctttttacg gttcctggcc ttttgctggc cttttgctca  11280
catgttcttt cctgcgttat cccctgattc tgtggataac cgtattaccg cctttgagtg  11340
agctgatacc gctcgccgca gccgaacgac cgagcgcagc gagtcagtga gcgaggaagc  11400
ggaagagcgc ccaatacgca aaccgcctct ccccgcgcgt tggccgattc attaatgcag  11460
ctgtggaatg tgtgtcagtt agggtgtgga aagtccccag gctccccagc aggcagaagt  11520
atgcaaagca tgcatctcaa ttagtcagca accaggtgtg gaaagtcccc aggctcccca  11580
gcaggcagaa gtatgcaaag catgcatctc aattagtcag caaccatagt cccgccccta  11640
actccgccca tcccgcccct aactccgccc agttccgccc attctccgcc ccatggctga  11700
ctaatttttt ttatttatgc agaggccgag gccgcctcgg cctctgagct attccagaag  11760
tagtgaggag gcttttttgg aggcctaggc ttttgcaaaa agcttggaca caagacaggc  11820
ttgcgagata tgtttgagaa taccacttta tcccgcgtca gggagaggca gtgcgtaaaa  11880
agacgcggac tcatgtgaaa tactggtttt tagtgcgcca gatctctata a           11931

SEQ ID NO: 65          moltype = AA  length = 7
FEATURE                Location/Qualifiers
REGION                 1..7
                       note = synthetic polypeptide
source                 1..7
                       mol_type = protein
                       organism = synthetic construct
SEQUENCE: 65
PKKKRKV                                                            7

SEQ ID NO: 66          moltype = AA  length = 298
FEATURE                Location/Qualifiers
REGION                 1..298
                       note = synthetic polypeptide
source                 1..298
                       mol_type = protein
                       organism = synthetic construct
SEQUENCE: 66
VPLYGFTSIC GRRPEMEAAV STIPRFLQSS SGSMLDGRFD PQSAAHFFGV YDGHGGSQVA  60
NYCRERMHLA LAEEIAKEKP MLCDGDTWLE KWKKALFNSF LRVDSEIESV APETVGSTSV  120
VAVVFPSHIF VANCGDSRAV LCRGKTALPL SVDHKPDRED EAARIEAAGG KVIQWNGARV  180
FGVLAMSRSI GDRYLKPSII PDPEVTAVKR VKEDDCLILA SDGVWDVMTD EEACEMARKR  240
ILLWHKKNAV AGDASLLADE RRKEGKDPAA MSAAEYLSKL AIQRGSKDNI SVVVVDLK    298

SEQ ID NO: 67          moltype = AA  length = 5
FEATURE                Location/Qualifiers
```

```
REGION                  1..5
                        note = synthetic polypeptide
source                  1..5
                        mol_type = protein
                        organism = synthetic construct
SEQUENCE: 67
GGSGG                                                             5

SEQ ID NO: 68           moltype = AA  length = 22
FEATURE                 Location/Qualifiers
REGION                  1..22
                        note = synthetic polypeptide
source                  1..22
                        mol_type = protein
                        organism = synthetic construct
SEQUENCE: 68
GSGATNFSLL KQAGDVEENP GP                                          22

SEQ ID NO: 69           moltype = AA  length = 191
FEATURE                 Location/Qualifiers
REGION                  1..191
                        note = synthetic polypeptide
source                  1..191
                        mol_type = protein
                        organism = synthetic construct
SEQUENCE: 69
DEFPTMVFPS GQISQASALA PAPPQVLPQA PAPAPAPAMV SALAQAPAPV PVLAPGPPQA  60
VAPPAPKPTQ AGEGTLSEAL LQLQFDDEDL GALLGNSTDP AVFTDLASVD NSEFQQLLNQ  120
GIPVAPHTTE PMLMEYPEAI TRLVTGAQRP PDPAPAPLGA PGLPNGLLSG DEDFSSIADM  180
DFSALLSQIS S                                                      191

SEQ ID NO: 70           moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 70
GGGSG                                                             5

SEQ ID NO: 71           moltype = AA  length = 177
FEATURE                 Location/Qualifiers
REGION                  1..177
                        note = synthetic polypeptide
source                  1..177
                        mol_type = protein
                        organism = synthetic construct
SEQUENCE: 71
TQDEFTQLSQ SIAEFHTYQL GNGRCSSLLA QRIHAPPETV WSVVRRFDRP QIYKHFIKSC  60
NVSEDFEMRV GCTRDVNVIS GLPANTSRER LDLLDDDRRV TGFSITGGEH RLRNYKSVTT  120
VHRFEKEEEE ERIWTVVLES YVVDVPEGNS EEDTRLFADT VIRLNLQKLA SITEAMN     177

SEQ ID NO: 72           moltype = AA  length = 96
FEATURE                 Location/Qualifiers
REGION                  1..96
                        note = synthetic polypeptide
source                  1..96
                        mol_type = protein
                        organism = synthetic construct
SEQUENCE: 72
DAKSLTAWSR TLVTFKDVFV DFTREEWKLL DTAQQILYRN VMLENYKNLV SLGYQLTKPD  60
VILRLEKGEE PWLVEREIHQ ETHPDSETAF EIKSSV                           96

SEQ ID NO: 73           moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 73
CVRGS                                                             5

SEQ ID NO: 74           moltype = AA  length = 314
FEATURE                 Location/Qualifiers
REGION                  1..314
                        note = synthetic polypeptide
source                  1..314
```

-continued

```
                      mol_type = protein
                      organism = synthetic construct
SEQUENCE: 74
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATA                                                   314

SEQ ID NO: 75         moltype = AA  length = 6
FEATURE               Location/Qualifiers
REGION                1..6
                      note = synthetic polypeptide
source                1..6
                      mol_type = protein
                      organism = synthetic construct
SEQUENCE: 75
GGGGSG                                                            6

SEQ ID NO: 76         moltype = AA  length = 176
FEATURE               Location/Qualifiers
REGION                1..176
                      note = synthetic polypeptide
REGION                19..25
                      note = misc_feature - Xaa can be any naturally occurring
                       amino acid
REGION                47..53
                      note = misc_feature - Xaa can be any naturally occurring
                       amino acid
REGION                76..82
                      note = misc_feature - Xaa can be any naturally occurring
                       amino acid
REGION                104..110
                      note = misc_feature - Xaa can be any naturally occurring
                       amino acid
REGION                133..139
                      note = misc_feature - Xaa can be any naturally occurring
                       amino acid
REGION                161..167
                      note = misc_feature - Xaa can be any naturally occurring
                       amino acid
source                1..176
                      mol_type = protein
                      organism = synthetic construct
SEQUENCE: 76
SRPGERPFQC RICMRNFSXX XXXXXHTRTH TGEKPFQCRI CMRNFSXXXX XXXHLRTHTG  60
SQKPFQCRIC MRNFSXXXXX XXHLRTHTGE KPFQCRICMR NFSXXXXXXX HLKTHTGSQK  120
PFQCRICMRN FSXXXXXXXH LRTHTGEKPF QCRICMRNFS XXXXXXXHLR THLRGS      176

SEQ ID NO: 77         moltype = AA  length = 39
FEATURE               Location/Qualifiers
REGION                1..39
                      note = synthetic polypeptide
source                1..39
                      mol_type = protein
                      organism = synthetic construct
SEQUENCE: 77
DYKDHDGDYK DHDIDYKDDD DKMAPKKKRK VGIHGVPGG                        39

SEQ ID NO: 78         moltype = AA  length = 10
FEATURE               Location/Qualifiers
REGION                1..10
                      note = synthetic polypeptide
source                1..10
                      mol_type = protein
                      organism = synthetic construct
SEQUENCE: 78
EDVVCCHSIY                                                        10

SEQ ID NO: 79         moltype = AA  length = 8
FEATURE               Location/Qualifiers
REGION                1..8
                      note = synthetic polypeptide
source                1..8
                      mol_type = protein
                      organism = synthetic construct
SEQUENCE: 79
HSIYGKKK                                                          8
```

```
SEQ ID NO: 80           moltype = AA  length = 6
FEATURE                 Location/Qualifiers
REGION                  1..6
                        note = synthetic polypeptide
source                  1..6
                        mol_type = protein
                        organism = synthetic construct
SEQUENCE: 80
DTYRYI                                                              6

SEQ ID NO: 81           moltype = AA  length = 13
FEATURE                 Location/Qualifiers
REGION                  1..13
                        note = synthetic polypeptide
source                  1..13
                        mol_type = protein
                        organism = synthetic construct
SEQUENCE: 81
GCVVIVGRIV LSG                                                      13

SEQ ID NO: 82           moltype = AA  length = 189
FEATURE                 Location/Qualifiers
REGION                  1..189
                        note = synthetic polypeptide
source                  1..189
                        mol_type = protein
                        organism = synthetic construct
SEQUENCE: 82
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180
SPVFTDNSS                                                           189

SEQ ID NO: 83           moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 83
LYQEFDEMEE CSQH                                                     14

SEQ ID NO: 84           moltype = AA  length = 9
FEATURE                 Location/Qualifiers
REGION                  1..9
                        note = synthetic polypeptide
source                  1..9
                        mol_type = protein
                        organism = synthetic construct
SEQUENCE: 84
YPYDVPDYA                                                           9

SEQ ID NO: 85           moltype = AA  length = 241
FEATURE                 Location/Qualifiers
REGION                  1..241
                        note = synthetic polypeptide
source                  1..241
                        mol_type = protein
                        organism = synthetic construct
SEQUENCE: 85
GKKKGDIDTY RYIGSSGTGC VVIVGRIVLS GSGTSAPITA YAQQTRGLLG CIITSLTGRD  60
KNQVEGEVQI VSTATQTFLA TCINGVCWAV YHGAGTRTIA SPKGPVIQMY TNVDQDLVGW  120
PAPQGSRSLT PCTCGSSDLY LVTRHADVIP VRRRGDSRGS LLSPRPISYL KGSSGGPLLC  180
PAGHAVGLFR AAVCTRGVAK AVDFIPVENL ETTMRSPVFT DNSSPPAVTL THPITKIDRE  240
V                                                                   241

SEQ ID NO: 86           moltype = AA  length = 304
FEATURE                 Location/Qualifiers
REGION                  1..304
                        note = synthetic polypeptide
source                  1..304
                        mol_type = protein
                        organism = synthetic construct
SEQUENCE: 86
DEMEECSQHL PGAGSSGDIM DYKDDDDKGS SGTGSGSGTS APITAYAQQT RGLLGCIITS  60
LTGRDKNQVE GEVQIVSTAT QTFLATCING VCWAVYHGAG TRTIASPKGP VIQMYTNVDQ  120
DLVGWPAPQG SRSLTPCTCG SSDLYLVTRH ADVIPVRRRG DSRGSLLSPR PISYLKGSSG  180
```

```
GPLLCPAGHA VGLFRAAVCT RGVAKAVDFI PVENLETTMR SPVFTDNSSP PAVTLTHPIT  240
KIDTKYIMTC MSADLEVVTS TWVLVGGVLA ALAAYCLSTG CVVIVGRIVL SGKPAIIPDR  300
EVLY                                                               304

SEQ ID NO: 87          moltype = AA  length = 10
FEATURE                Location/Qualifiers
REGION                 1..10
                       note = synthetic polypeptide
source                 1..10
                       mol_type = protein
                       organism = synthetic construct
SEQUENCE: 87
DEMEECSQHL                                                         10

SEQ ID NO: 88          moltype = AA  length = 10
FEATURE                Location/Qualifiers
REGION                 1..10
                       note = synthetic polypeptide
source                 1..10
                       mol_type = protein
                       organism = synthetic construct
SEQUENCE: 88
PGAGSSGDIM                                                         10

SEQ ID NO: 89          moltype = AA  length = 8
FEATURE                Location/Qualifiers
REGION                 1..8
                       note = synthetic polypeptide
source                 1..8
                       mol_type = protein
                       organism = synthetic construct
SEQUENCE: 89
DYKDDDDK                                                           8

SEQ ID NO: 90          moltype = AA  length = 12
FEATURE                Location/Qualifiers
REGION                 1..12
                       note = synthetic polypeptide
source                 1..12
                       mol_type = protein
                       organism = synthetic construct
SEQUENCE: 90
GSSGTGSGSG TS                                                      12

SEQ ID NO: 91          moltype = AA  length = 186
FEATURE                Location/Qualifiers
REGION                 1..186
                       note = synthetic polypeptide
source                 1..186
                       mol_type = protein
                       organism = synthetic construct
SEQUENCE: 91
APITAYAQQT RGLLGCIITS LTGRDKNQVE GEVQIVSTAT QTFLATCING VCWAVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180
SPVFTD                                                             186

SEQ ID NO: 92          moltype = AA  length = 33
FEATURE                Location/Qualifiers
REGION                 1..33
                       note = synthetic polypeptide
source                 1..33
                       mol_type = protein
                       organism = synthetic construct
SEQUENCE: 92
NSSPPAVTLT HPITKIDTKY IMTCMSADLE VVT                               33

SEQ ID NO: 93          moltype = AA  length = 45
FEATURE                Location/Qualifiers
REGION                 1..45
                       note = synthetic polypeptide
source                 1..45
                       mol_type = protein
                       organism = synthetic construct
SEQUENCE: 93
STWVLVGGVL AALAAYCLST GCVVIVGRIV LSGKPAIIPD REVLY                  45

SEQ ID NO: 94          moltype = AA  length = 297
FEATURE                Location/Qualifiers
```

```
REGION                1..297
                      note = synthetic polypeptide
source                1..297
                      mol_type = protein
                      organism = synthetic construct
SEQUENCE: 94
DYKDDDDKGS SGTGSGSGTS APITAYAQQT RGLLGCIITS LTGRDKNQVE GEVQIVSTAT  60
QTFLATCING VCWAVYHGAG TRTIASPKGP VIQMYTNVDQ DLVGWPAPQG SRSLTPCTCG  120
SSDLYLVTRH ADVIPVRRRG DSRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAIIPDR EVLYQEFEDV VPCSMGS     297

SEQ ID NO: 95         moltype = AA  length = 303
FEATURE               Location/Qualifiers
REGION                1..303
                      note = synthetic polypeptide
source                1..303
                      mol_type = protein
                      organism = synthetic construct
SEQUENCE: 95
DYKDDDDKGS SGTGSGSGTS APITAYAQQT RGLLGCIITS LTGRDKNQVE GEVQIVSTAT  60
QTFLATCING VCWAVYHGAG TRTIASPKGP VIQMYTNVDQ DLVGWPAPQG SRSLTPCTCG  120
SSDLYLVTRH ADVIPVRRRG DSRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAGSSGS SIIPDREVLY QEFEDVVPCS  300
MGS                                                                303

SEQ ID NO: 96         moltype = AA  length = 51
FEATURE               Location/Qualifiers
REGION                1..51
                      note = synthetic polypeptide
source                1..51
                      mol_type = protein
                      organism = synthetic construct
SEQUENCE: 96
STWVLVGGVL AALAAYCLST GCVVIVGRIV LSGKPAGSSG SSIIPDREVL Y           51

SEQ ID NO: 97         moltype = AA  length = 65
FEATURE               Location/Qualifiers
REGION                1..65
                      note = synthetic polypeptide
source                1..65
                      mol_type = protein
                      organism = synthetic construct
SEQUENCE: 97
LAVSVTFEDV AVLFTRDEWK KLDLSQRSLY REVMLENYSN LASMAGFLFT KPKVISLLQQ  60
GEDPW                                                             65

SEQ ID NO: 98         moltype = AA  length = 190
FEATURE               Location/Qualifiers
REGION                1..190
                      note = synthetic polypeptide
source                1..190
                      mol_type = protein
                      organism = synthetic construct
SEQUENCE: 98
GKKTKRTADS SSSEDEEEYV VEKVLDRRVV KGQVEYLLKW KGFSEEHNTW EPEKNLDCPE  60
LISEFMKKYK KMKEGENNKP REKSESNKRK SNFSNSADDI KSKKKREQSN DIARGFERGL  120
EPEKIIGATD SCGDLMFLMK WKDTDEADLV LAKEANVKCP QIVIAFYEER LTWHAYPEDA  180
ENKEKETAKS                                                         190

SEQ ID NO: 99         moltype = AA  length = 440
FEATURE               Location/Qualifiers
REGION                1..440
                      note = synthetic polypeptide
source                1..440
                      mol_type = protein
                      organism = synthetic construct
SEQUENCE: 99
SEREVSTAPA GTDMPAAKKQ KLSSDENSNP DLSGDENDDA VSIESGTNTE RPDTPTNTPN  60
APGRKSWGKG KWKSKKCKYS FKCVNSLKED HNQPLFGVQF NWHSKEGDPL VFATVGSNRV  120
TLYECHSQGE IRLLQSYVDA DADENFYTCA WTYDSNTSHP LLAVAGSRGI IRIINPITMQ  180
CIKHYVGHGN AINELKFHPR DPNLLLSVSK DHALRLWNIQ TDTLVAIFGG VEGHRDEVLS  240
ADYDLLGEKI MSCGMDHSLK LWRINSKRMM NAIKESYDYN PNKTNRPFIS QKIHFPDFST  300
RDIHRNYVDC VRWLGDLILS KSCENAIVCW KPGKMEDDID KIKPSESNVT ILGRFDYSQC  360
DIWYMRFSMD FWQKMLALGN QVGKLYVWDL EVEDPHKAKC TTLTHHKCGA AIRQTSFSRD  420
SSILIAVCDD ASIWRWDRLR                                              440

SEQ ID NO: 100        moltype = AA  length = 9
```

-continued

```
FEATURE                Location/Qualifiers
REGION                 1..9
                       note = synthetic polypeptide
source                 1..9
                       mol_type = protein
                       organism = synthetic construct
SEQUENCE: 100
GGSGSGSAC                                                    9

SEQ ID NO: 101         moltype = AA  length = 172
FEATURE                Location/Qualifiers
REGION                 1..172
                       note = synthetic polypeptide
REGION                 17..23
                       note = misc_feature - Xaa can be any naturally occurring
                        amino acid
REGION                 45..51
                       note = misc_feature - Xaa can be any naturally occurring
                        amino acid
REGION                 74..80
                       note = misc_feature - Xaa can be any naturally occurring
                        amino acid
REGION                 102..108
                       note = misc_feature - Xaa can be any naturally occurring
                        amino acid
REGION                 131..137
                       note = misc_feature - Xaa can be any naturally occurring
                        amino acid
REGION                 159..165
                       note = misc_feature - Xaa can be any naturally occurring
                        amino acid
source                 1..172
                       mol_type = protein
                       organism = synthetic construct
SEQUENCE: 101
PGERPFQCRI CMRNFSXXXX XXXHTRTHTG EKPFQCRICM RNFSXXXXXX XHLRTHTGSQ  60
KPFQCRICMR NFSXXXXXXX HLRTHTGEKP FQCRICMRNF SXXXXXXXHL KTHTGSQKPF  120
QCRICMRNFS XXXXXXXHLR THTGEKPFQC RICMRNFSXX XXXXXHLRTH LR          172

SEQ ID NO: 102         moltype = AA  length = 265
FEATURE                Location/Qualifiers
REGION                 1..265
                       note = synthetic polypeptide
source                 1..265
                       mol_type = protein
                       organism = synthetic construct
SEQUENCE: 102
EDVVCCHSIY GKKKGDIDTY RYIGSSGTGC VVIVGRIVLS GSGTSAPITA YAQQTRGLLG  60
CIITSLTGRD KNQVEGEVQI VSTATQTFLA TCINGVCWAV YHGAGTRTIA SPKGPVIQMY  120
TNVDQDLVGW PAPQGSRSLT PCTCGSSDLY LVTRHADVIP VRRRGDSRGS LLSPRPISYL  180
KGSSGGPLLC PAGHAVGLFR AAVCTRGVAK AVDFIPVENL ETTMRSPVFT DNSSPPAVTL  240
THPITKIDRE VLYQEFDEME ECSQH                                        265

SEQ ID NO: 103         moltype = AA  length = 9
FEATURE                Location/Qualifiers
REGION                 1..9
                       note = synthetic polypeptide
source                 1..9
                       mol_type = protein
                       organism = synthetic construct
SEQUENCE: 103
LEGGGGSGG                                                    9

SEQ ID NO: 104         moltype = AA  length = 8
FEATURE                Location/Qualifiers
REGION                 1..8
                       note = synthetic polypeptide
source                 1..8
                       mol_type = protein
                       organism = synthetic construct
SEQUENCE: 104
GGGGSGGT                                                     8

SEQ ID NO: 105         moltype = AA  length = 15
FEATURE                Location/Qualifiers
REGION                 1..15
                       note = synthetic polypeptide
source                 1..15
                       mol_type = protein
```

```
                        organism = synthetic construct
SEQUENCE: 105
NSSPPAVTLT HPITK                                                   15

SEQ ID NO: 106          moltype = AA  length = 63
FEATURE                 Location/Qualifiers
REGION                  1..63
                        note = synthetic polypeptide
source                  1..63
                        mol_type = protein
                        organism = synthetic construct
SEQUENCE: 106
IDTKYIMTCM SADLEVVTST WVLVGGVLAA LAAYCLSTGC VVIVGRIVLS GKPAIIPDRE  60
VLY                                                                63

SEQ ID NO: 107          moltype = AA  length = 305
FEATURE                 Location/Qualifiers
REGION                  1..305
                        note = synthetic polypeptide
source                  1..305
                        mol_type = protein
                        organism = synthetic construct
SEQUENCE: 107
PLYGFTSICG RRPEMEDAVS TIPRFLQSSS GSMLDGRFDP QSAAHFFGVY DGHGGSQVAN  60
YCRERMHLAL AEEIAKEKPM LCDGDTWLEK WKKALFNSFL RVDSEIGSVA PETVGSTSVV  120
AVVFPSHIFV ANCGDSRAVL CRGKTALPLS VDHKPDREDE AARIEAAGGK VIQWNGARVF  180
GVLAMSRSIG DRYLKPSIIP DPEVTAVKRV KEDDCLILAS DGVWDVMTDE EACEMARKRI  240
LLWHKKNAVA GDASLLADER RKEGKDPAAM SAAEYLSKLA IQRGSKDNIS VVVVDLKDYK  300
DDDDK                                                              305

SEQ ID NO: 108          moltype = AA  length = 188
FEATURE                 Location/Qualifiers
REGION                  1..188
                        note = synthetic polypeptide
source                  1..188
                        mol_type = protein
                        organism = synthetic construct
SEQUENCE: 108
APTQDEFTQL SQSIAEFHTY QLGNGRCSSL LAQRIHAPPE TVWSVVRRFD RPQIYKHFIK  60
SCNVSEDFEM RVGCTRDVNV ISGLPANTSR ERLDLLDDDR RVTGFSITGG EHRLRNYKSV  120
TTVHRFEKEE EEERIWTVVL ESYVVDVPEG NSEEDTRLFA DTVIRLNLQK LASITEAMNY  180
PYDVPDYA                                                           188

SEQ ID NO: 109          moltype = AA  length = 109
FEATURE                 Location/Qualifiers
REGION                  1..109
                        note = synthetic polypeptide
source                  1..109
                        mol_type = protein
                        organism = synthetic construct
SEQUENCE: 109
SRGVQVETIS PGDGRTFPKR GQTCVVHYTG MLEDGKKFDS SRDRNKPFKF MLGKQEVIRG  60
WEEGVAQMSV GQRAKLTISP DYAYGATGHP GIIPPHATLV FDVELLKLE              109

SEQ ID NO: 110          moltype = AA  length = 92
FEATURE                 Location/Qualifiers
REGION                  1..92
                        note = synthetic polypeptide
source                  1..92
                        mol_type = protein
                        organism = synthetic construct
SEQUENCE: 110
ILWHEMWHEG LEEASRLYFG ERNVKGMFEV LEPLHAMMER GPQTLKETSF NQAYGRDLME  60
AQEWCRKYMK SGNVKDLLQA WDLYYHVFRR IS                                92

SEQ ID NO: 111          moltype = AA  length = 92
FEATURE                 Location/Qualifiers
REGION                  1..92
                        note = synthetic polypeptide
source                  1..92
                        mol_type = protein
                        organism = synthetic construct
SEQUENCE: 111
MKRDHHHHHH QDKKTMMMNE EDDGNGMDEL LAVLGYKVRS SEMADVAQKL EQLEVMMSNV  60
QEDDLSQLAT ETVHYNPAEL YTWLDSMLTD LN                                92

SEQ ID NO: 112          moltype = AA  length = 345
FEATURE                 Location/Qualifiers
REGION                  1..345
```

```
                         note = synthetic polypeptide
source                   1..345
                         mol_type = protein
                         organism = synthetic construct
SEQUENCE: 112
MAASDEVNLI ESRTVVPLNT WVLISNFKVA YNILRRPDGT FNRHLAEYLD RKVTANANPV  60
DGVFSFDVLI DRRINLLSRV YRPAYADQEQ PPSILDLEKP VDGDIVPVIL FFHGGSFAHS  120
SANSAIYDTL CRRLVGLCKC VVVSVNYRRA PENPYPCAYD DGWIALNWVN SRSWLKSKKD  180
SKVHIFLAGD SSGGNIAHNV ALRAGESGID VLGNILLNPM FGGNERTESE KSLDGKYFVT  240
VRDRDWYWKA FLPEGEDREH PACNPFSPRG KSLEGVSFPK SLVVVAGLDL IRDWQLAYAE  300
GLKKAGQEVK LMHLEKATVG FYLLPNNNHF HNVMDEISAF VNAEC                  345

SEQ ID NO: 113           moltype = AA  length = 150
FEATURE                  Location/Qualifiers
REGION                   1..150
                         note = synthetic polypeptide
source                   1..150
                         mol_type = protein
                         organism = synthetic construct
SEQUENCE: 113
HTLYAPGGYD IMGYLDQIGN RPNPQVELGP VDTSCALILC DLKQKDTPIV YASEAFLYMT  60
GYSNAEVLGR NCRFLQSPDG MVKPKSTRKY VDSNTINTMR KAIDRNAEVQ VEVVNFKKNG  120
QRFVNFLTMI PVRDETGEYR YSMGFQCETE                                   150

SEQ ID NO: 114           moltype = AA  length = 150
FEATURE                  Location/Qualifiers
REGION                   1..150
                         note = synthetic polypeptide
source                   1..150
                         mol_type = protein
                         organism = synthetic construct
SEQUENCE: 114
HTLYAPGGYD IMGYLRQIRN RPNPQVELGP VDTSCALILC DLKQKDTPIV YASEAFLYMT  60
GYSNAEVLGR NCRFLQSPDG MVKPKSTRKY VDSNTINTMR KAIDRNAEVQ VEVVNFKKNG  120
QRFVNFLTMI PVRDETGEYR YSMGFQCETE                                   150

SEQ ID NO: 115           moltype = AA  length = 171
FEATURE                  Location/Qualifiers
REGION                   1..171
                         note = synthetic polypeptide
source                   1..171
                         mol_type = protein
                         organism = synthetic construct
SEQUENCE: 115
MNGAIGGDLL LNFPDMSVLE RQRAHLKYLN PTFDSPLAGF FADSSMITGG EMDSYLSTAG  60
LNLPMMYGET TVEGDSRLSI SPETTLGTGN FKKRKFDTET KDCNEKKKKM TMNRDDLVEE  120
GEEEKSKITE QNNGSTKSIK KMKHKAKKEE NNFSNDSSKV TKELEKTDYI H            171

SEQ ID NO: 116           moltype = AA  length = 612
FEATURE                  Location/Qualifiers
REGION                   1..612
                         note = synthetic polypeptide
source                   1..612
                         mol_type = protein
                         organism = synthetic construct
SEQUENCE: 116
MKMDKKTIVW FRRDLRIEDN PALAAAAHEG SVFPVFIWCP EEEGQFYPGR ASRWWMKQSL  60
AHLSQSLKAL GSDLTLIKTH NTISAILDCI RVTGATKVVF NHLYDPVSLV RDHTVKEKLV  120
ERGISVQSYN GDLLYEPWEI YCEKGKPFTS FNSYWKKCLD MSIESVMLPP PWRLMPITAA  180
AEAIWACSIE ELGLENEAEK PSNALLTRAW SPGWSNADKL LNEFIEKQLI DYAKNSKKVV  240
GNSTSLLSPY LHFGEISVRH VFQCARMKQI IWARDKNSEG EESADLFLRG IGLREYSRYI  300
CFNFPFTHEQ SLLSHLRFFP WDADVDKFKA WRQGRTGYPL VDAGMRELWA TGWMHNRIRV  360
IVSSFAVKFL LLPWKWGMKY FWDTLLDADL ECDILGWQYI SGSIPDGHEL DRLDNPALQG  420
AKYDPEGEYI RQWLPELARL PTEWIHHPWD APLTVLKASG VELGTNYAKP IVDIDTAREL  480
LAKAISRTRE AQIMIGAAPD EIVADSFEAL GANTIKEPGL CPSVSSNDQQ VPSAVRYNGS  540
KRVKPEEEEE RDMKKSRGFD ERELFSTAES SSSSSVFFVS QSCSLASEGK NLEGIQDSSD  600
QITTSLGKNG CK                                                      612

SEQ ID NO: 117           moltype = AA  length = 551
FEATURE                  Location/Qualifiers
REGION                   1..551
                         note = synthetic polypeptide
source                   1..551
                         mol_type = protein
                         organism = synthetic construct
SEQUENCE: 117
MDELFPLIFP AEPAQASGPY VEIIEQPKQR GMRFRYKCEG RSAGSIPGER STDTTKTHPT  60
IKINGYTGPG TVRISLVTKD PPHRPHPHEL VGKDCRDGFY EAELCPDRCI HSFQNLGIQC  120
VKKRDLEQAI SQRIQTNNNP FQVPIEEQRG DYDLNAVRLC FQVTVRDPSG RPLRLPPVLS  180
```

```
HPIFDNRAPN TAELKICRVN RNSGSCLGGD EIFLLCDKVQ KEDIEVYFTG PGWEARGSFS  240
QADVHRQVAI VFRTPPYADP SLQAPVRVSM QLRRPSDREL SEPMEFQYLP DTDDRHRIEE  300
KRKRTYETFK SIMKKSPFSG PTDPRPPPRR IAVPSRSSAS VPKPAPQPYP FTSSLSTINY  360
DEFPTMVFPS GQISQASALA PAPPQVLPQA PAPAPAPAMV SALAQAPAPV PVLAPGPPQA  420
VAPPAPKPTQ AGEGTLSEAL LQLQFDDEDL GALLGNSTDP AVFTDLASVD NSEFQQLLNQ  480
GIPVAPHTTE PMLMEYPEAI TRLVTGAQRP PDPAPAPLGA PGLPNGLLSG DEDFSSIADM  540
DFSALLSQIS S                                                      551

SEQ ID NO: 118          moltype = AA  length = 261
FEATURE                 Location/Qualifiers
REGION                  1..261
                        note = synthetic polypeptide
source                  1..261
                        mol_type = protein
                        organism = synthetic construct
SEQUENCE: 118
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT LSEALLQLQF DDEDLGALLG NSTDPAVFTD  180
LASVDNSEFQ QLLNQGIPVA PHTTEPMLME YPEAITRLVT GAQRPPDPAP APLGAPGLPN  240
GLLSGDEDFS SIADMDFSAL L                                           261

SEQ ID NO: 119          moltype = AA  length = 112
FEATURE                 Location/Qualifiers
REGION                  1..112
                        note = synthetic polypeptide
source                  1..112
                        mol_type = protein
                        organism = synthetic construct
SEQUENCE: 119
SLSEALLQLQ FDDEDLGALL GNSTDPAVFT DLASVDNSEF QQLLNQGIPV APHTTEPMLM  60
EYPEAITRLV TGAQRPPDPA PAPLGAPGLP NGLLSGDEDF SSIADMDFSA LL          112

SEQ ID NO: 120          moltype = AA  length = 162
FEATURE                 Location/Qualifiers
REGION                  1..162
                        note = synthetic polypeptide
source                  1..162
                        mol_type = protein
                        organism = synthetic construct
SEQUENCE: 120
SVLPQAPAPA PAPAMVSALA QAPAPVPVLA PGPPQAVAPP APKPTQAGEG TLSEALLQLQ  60
FDDEDLGALL GNSTDPAVFT DLASVDNSEF QQLLNQGIPV APHTTEPMLM EYPEAITRLV  120
TGAQRPPDPA PAPLGAPGLP NGLLSGDEDF SSIADMDFSA LL                    162

SEQ ID NO: 121          moltype = AA  length = 62
FEATURE                 Location/Qualifiers
REGION                  1..62
                        note = synthetic polypeptide
source                  1..62
                        mol_type = protein
                        organism = synthetic construct
SEQUENCE: 121
SPHTTEPMLM EYPEAITRLV TGAQRPPDPA PAPLGAPGLP NGLLSGDEDF SSIADMDFSA  60
LL                                                                62

SEQ ID NO: 122          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 122
DEANLRR                                                           7

SEQ ID NO: 123          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 123
DPSVLKR                                                           7

SEQ ID NO: 124          moltype = AA  length = 7
FEATURE                 Location/Qualifiers
REGION                  1..7
```

```
                          note = synthetic polypeptide
source                    1..7
                          mol_type = protein
                          organism = synthetic construct
SEQUENCE: 124
QSANLLR                                                                 7

SEQ ID NO: 125            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 125
DPSSLKR                                                                 7

SEQ ID NO: 126            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 126
QQTNLTR                                                                 7

SEQ ID NO: 127            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 127
DATQLVR                                                                 7

SEQ ID NO: 128            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 128
ERRSLAR                                                                 7

SEQ ID NO: 129            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 129
EEANLRR                                                                 7

SEQ ID NO: 130            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 130
DHSSLKR                                                                 7

SEQ ID NO: 131            moltype = AA  length = 7
FEATURE                   Location/Qualifiers
REGION                    1..7
                          note = synthetic polypeptide
source                    1..7
                          mol_type = protein
                          organism = synthetic construct
SEQUENCE: 131
QRSSLVR                                                                 7

SEQ ID NO: 132            moltype = AA  length = 7
FEATURE                   Location/Qualifiers
```

```
REGION                1..7
                      note = synthetic polypeptide
source                1..7
                      mol_type = protein
                      organism = synthetic construct
SEQUENCE: 132
DMGNLGR                                                                   7

SEQ ID NO: 133        moltype = AA  length = 7
FEATURE               Location/Qualifiers
REGION                1..7
                      note = synthetic polypeptide
source                1..7
                      mol_type = protein
                      organism = synthetic construct
SEQUENCE: 133
RSHDLTR                                                                   7

SEQ ID NO: 134        moltype = AA  length = 7
FEATURE               Location/Qualifiers
REGION                1..7
                      note = synthetic polypeptide
source                1..7
                      mol_type = protein
                      organism = synthetic construct
SEQUENCE: 134
HKSSLTR                                                                   7

SEQ ID NO: 135        moltype = AA  length = 7
FEATURE               Location/Qualifiers
REGION                1..7
                      note = synthetic polypeptide
source                1..7
                      mol_type = protein
                      organism = synthetic construct
SEQUENCE: 135
DSSNLRR                                                                   7

SEQ ID NO: 136        moltype = AA  length = 7
FEATURE               Location/Qualifiers
REGION                1..7
                      note = synthetic polypeptide
source                1..7
                      mol_type = protein
                      organism = synthetic construct
SEQUENCE: 136
DQGNLIR                                                                   7

SEQ ID NO: 137        moltype = AA  length = 7
FEATURE               Location/Qualifiers
REGION                1..7
                      note = synthetic polypeptide
source                1..7
                      mol_type = protein
                      organism = synthetic construct
SEQUENCE: 137
QKQALTR                                                                   7

SEQ ID NO: 138        moltype = AA  length = 7
FEATURE               Location/Qualifiers
REGION                1..7
                      note = synthetic polypeptide
source                1..7
                      mol_type = protein
                      organism = synthetic construct
SEQUENCE: 138
DRGNLTR                                                                   7

SEQ ID NO: 139        moltype = AA  length = 7
FEATURE               Location/Qualifiers
REGION                1..7
                      note = synthetic polypeptide
source                1..7
                      mol_type = protein
                      organism = synthetic construct
SEQUENCE: 139
RSHDLTV                                                                   7

SEQ ID NO: 140        moltype = AA  length = 7
```

-continued

```
FEATURE              Location/Qualifiers
REGION               1..7
                     note = synthetic polypeptide
source               1..7
                     mol_type = protein
                     organism = synthetic construct
SEQUENCE: 140
DKSVLAR                                                        7

SEQ ID NO: 141       moltype = AA  length = 7
FEATURE              Location/Qualifiers
REGION               1..7
                     note = synthetic polypeptide
source               1..7
                     mol_type = protein
                     organism = synthetic construct
SEQUENCE: 141
QTNNLGR                                                        7

SEQ ID NO: 142       moltype = AA  length = 7
FEATURE              Location/Qualifiers
REGION               1..7
                     note = synthetic polypeptide
source               1..7
                     mol_type = protein
                     organism = synthetic construct
SEQUENCE: 142
THAVLTR                                                        7

SEQ ID NO: 143       moltype = AA  length = 7
FEATURE              Location/Qualifiers
REGION               1..7
                     note = synthetic polypeptide
source               1..7
                     mol_type = protein
                     organism = synthetic construct
SEQUENCE: 143
TKSLLAR                                                        7

SEQ ID NO: 144       moltype = AA  length = 7
FEATURE              Location/Qualifiers
REGION               1..7
                     note = synthetic polypeptide
source               1..7
                     mol_type = protein
                     organism = synthetic construct
SEQUENCE: 144
QKQALDR                                                        7

SEQ ID NO: 145       moltype = AA  length = 7
FEATURE              Location/Qualifiers
REGION               1..7
                     note = synthetic polypeptide
source               1..7
                     mol_type = protein
                     organism = synthetic construct
SEQUENCE: 145
DTSVLNR                                                        7

SEQ ID NO: 146       moltype = AA  length = 7
FEATURE              Location/Qualifiers
REGION               1..7
                     note = synthetic polypeptide
source               1..7
                     mol_type = protein
                     organism = synthetic construct
SEQUENCE: 146
QGTSLAR                                                        7

SEQ ID NO: 147       moltype = AA  length = 7
FEATURE              Location/Qualifiers
REGION               1..7
                     note = synthetic polypeptide
source               1..7
                     mol_type = protein
                     organism = synthetic construct
SEQUENCE: 147
VRHNLTR                                                        7
```

```
SEQ ID NO: 148          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 148
EKQNLAR                                                                 7

SEQ ID NO: 149          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 149
DPSNLRR                                                                 7

SEQ ID NO: 150          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 150
DHSNLSR                                                                 7

SEQ ID NO: 151          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 151
QSTSLQR                                                                 7

SEQ ID NO: 152          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 152
NMSNLTR                                                                 7

SEQ ID NO: 153          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 153
DRSVLRR                                                                 7

SEQ ID NO: 154          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 154
LQENLTR                                                                 7

SEQ ID NO: 155          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 155
DRSSLRR                                                                 7
```

```
SEQ ID NO: 156          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 156
QSGTLHR                                                            7

SEQ ID NO: 157          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 157
QLANLAR                                                            7

SEQ ID NO: 158          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 158
DQTTLRR                                                            7

SEQ ID NO: 159          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 159
DPSNLAR                                                            7

SEQ ID NO: 160          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 160
QGGNLAL                                                            7

SEQ ID NO: 161          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 161
RADMLRR                                                            7

SEQ ID NO: 162          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 162
QKANLGV                                                            7

SEQ ID NO: 163          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 163
```

```
RLDMLAR                                                    7

SEQ ID NO: 164         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 164
QRGNLNM                                                    7

SEQ ID NO: 165         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 165
RPQELRR                                                    7

SEQ ID NO: 166         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 166
RQDNLGR                                                    7

SEQ ID NO: 167         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 167
DGGNLGR                                                    7

SEQ ID NO: 168         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 168
QQGNLQL                                                    7

SEQ ID NO: 169         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 169
RRQELTR                                                    7

SEQ ID NO: 170         moltype = AA  length = 7
FEATURE                Location/Qualifiers
REGION                 1..7
                       note = synthetic polypeptide
source                 1..7
                       mol_type = protein
                       organism = synthetic construct
SEQUENCE: 170
QASNLTR                                                    7

SEQ ID NO: 171         moltype = AA  length = 7
FEATURE                Location/Qualifiers
REGION                 1..7
                       note = synthetic polypeptide
source                 1..7
                       mol_type = protein
                       organism = synthetic construct
```

```
SEQUENCE: 171
RAHNLLL                                                             7

SEQ ID NO: 172          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 172
QSTTLKR                                                             7

SEQ ID NO: 173          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 173
QGTTLKR                                                             7

SEQ ID NO: 174          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 174
QRSNLAR                                                             7

SEQ ID NO: 175          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 175
RRHGLDR                                                             7

SEQ ID NO: 176          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 176
ESGHLKR                                                             7

SEQ ID NO: 177          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 177
QLSNLTR                                                             7

SEQ ID NO: 178          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 178
DRSSLKR                                                             7

SEQ ID NO: 179          moltype = AA  length = 7
FEATURE                 Location/Qualifiers
REGION                  1..7
                        note = synthetic polypeptide
source                  1..7
                        mol_type = protein
```

```
                        organism = synthetic construct
SEQUENCE: 179
VRHSLTR                                                                     7

SEQ ID NO: 180          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 180
ESGALRR                                                                     7

SEQ ID NO: 181          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 181
cgtcgaagtc gaagtcgacc                                                       20

SEQ ID NO: 182          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 182
ggacgacgtt acggacgtac                                                       20

SEQ ID NO: 183          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 183
agacgtcgaa gtagccgtag                                                       20

SEQ ID NO: 184          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 184
ggacgacgcc gatgtagaag                                                       20

SEQ ID NO: 185          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 185
tgaagcagtc gacgccgaag                                                       20

SEQ ID NO: 186          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 186
ggacgacgcg gtctaagaag                                                       20

SEQ ID NO: 187          moltype = DNA  length = 20
FEATURE                 Location/Qualifiers
misc_feature            1..20
                        note = synthetic polynucleotide
source                  1..20
```

```
                        mol_type = other DNA
                        organism = synthetic construct
SEQUENCE: 187
cgacgaggtc gcataagtag                                                20

SEQ ID NO: 188          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 188
agacgcagta taggtcgaac                                                20

SEQ ID NO: 189          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 189
agacgcagta taggacgacg                                                20

SEQ ID NO: 190          moltype = DNA  length = 20
FEATURE                 Location/Qualifiers
misc_feature            1..20
                        note = synthetic polynucleotide
source                  1..20
                        mol_type = other DNA
                        organism = synthetic construct
SEQUENCE: 190
cggcgtagcc gatgtcgcgc                                                20

SEQ ID NO: 191          moltype = DNA  length = 19
FEATURE                 Location/Qualifiers
misc_feature            1..19
                        note = synthetic polynucleotide
source                  1..19
                        mol_type = other DNA
                        organism = synthetic construct
SEQUENCE: 191
ggtcgttgcg gtagtcgaa                                                 19

SEQ ID NO: 192          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 192
QRNNLGR                                                              7

SEQ ID NO: 193          moltype = AA  length = 200
FEATURE                 Location/Qualifiers
REGION                  1..200
                        note = synthetic polypeptide
source                  1..200
                        mol_type = protein
                        organism = synthetic construct
SEQUENCE: 193
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT LSEALLQLQF DDEDLGALLG NSTDPAVFTD  180
LASVDNSEFQ QLLNQGIPVA                                                200

SEQ ID NO: 194          moltype = AA  length = 150
FEATURE                 Location/Qualifiers
REGION                  1..150
                        note = synthetic polypeptide
source                  1..150
                        mol_type = protein
                        organism = synthetic construct
SEQUENCE: 194
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ VLPQAPAPAP APAMVSALAQ  120
APAPVPVLAP GPPQAVAPPA PKPTQAGEGT                                     150
```

```
SEQ ID NO: 195         moltype = AA  length = 100
FEATURE                Location/Qualifiers
REGION                 1..100
                       note = synthetic polypeptide
source                 1..100
                       mol_type = protein
                       organism = synthetic construct
SEQUENCE: 195
SQYLPDTDDR HRIEEKRKRT YETFKSIMKK SPFSGPTDPR PPPRRIAVPS RSSASVPKPA  60
PQPYPFTSSL STINYDEFPT MVFPSGQISQ ASALAPAPPQ                        100

SEQ ID NO: 196         moltype = AA  length = 101
FEATURE                Location/Qualifiers
REGION                 1..101
                       note = synthetic polypeptide
source                 1..101
                       mol_type = protein
                       organism = synthetic construct
SEQUENCE: 196
SRSSASVPKP APQPYPFTSS LSTINYDEFP TMVFPSGQIS QASALAPAPP QVLPQAPAPA  60
PAPAMVSALA QAPAPVPVLA PGPPQAVAPP APKPTQAGEG T                      101

SEQ ID NO: 197         moltype = AA  length = 119
FEATURE                Location/Qualifiers
REGION                 1..119
                       note = synthetic polypeptide
source                 1..119
                       mol_type = protein
                       organism = synthetic construct
SEQUENCE: 197
PTQAGEGTLS EALLQLQFDD EDLGALLGNS TDPAVFTDLA SVDNSEFQQL LNQGIPVAPH  60
TTEPMLMEYP EAITRLVTGA QRPPDPAPAP LGAPGLPNGL LSGDEDFSSI ADMDFSALL   119

SEQ ID NO: 198         moltype = AA  length = 190
FEATURE                Location/Qualifiers
REGION                 1..190
                       note = synthetic polypeptide
source                 1..190
                       mol_type = protein
                       organism = synthetic construct
SEQUENCE: 198
RDSREGMFLP KPEAGSAISD VFEGREVCQP KRIRPFHPPG SPWANRPLPA SLAPTPTGPV  60
HEPVGSLTPA PVPQPLDPAP AVTPEASHLL EDPDEETSQA VKALREMADT VIPQKEEAAI  120
CGQMDLSHPP PRGHLDELTT TLESMTEDLN LDSPLTPELN EILDTFLNDE CLLHAMHIST  180
GLSIFDTSLF                                                         190

SEQ ID NO: 199         moltype = AA  length = 116
FEATURE                Location/Qualifiers
REGION                 1..116
                       note = synthetic polypeptide
source                 1..116
                       mol_type = protein
                       organism = synthetic construct
SEQUENCE: 199
PLDPAPAVTP EASHLLEDPD EETSQAVKAL REMADTVIPQ KEEAAICGQM DLSHPPPRGH  60
LDELTTTLES MTEDLNLDSP LTPELNEILD TFLNDECLLH AMHISTGLSI FDTSLF      116

SEQ ID NO: 200         moltype = AA  length = 66
FEATURE                Location/Qualifiers
REGION                 1..66
                       note = synthetic polypeptide
source                 1..66
                       mol_type = protein
                       organism = synthetic construct
SEQUENCE: 200
DLSHPPPRGH LDELTTTLES MTEDLNLDSP LTPELNEILD TFLNDECLLH AMHISTGLSI  60
FDTSLF                                                             66

SEQ ID NO: 201         moltype = AA  length = 126
FEATURE                Location/Qualifiers
REGION                 1..126
                       note = synthetic polypeptide
source                 1..126
                       mol_type = protein
                       organism = synthetic construct
SEQUENCE: 201
SSLAPTPTGP VHEPVGSLTP APVPQPLDPA PAVTPEASHL LEDPDEETSQ AVKALREMAD  60
TVIPQKEEAA ICGQMDLSHP PPRGHLDELT TTLESMTEDL NLDSPLTPEL NEILDTFLND  120
```

-continued

```
ECLLHA                                                            126

SEQ ID NO: 202          moltype = AA  length = 101
FEATURE                 Location/Qualifiers
REGION                  1..101
                        note = synthetic polypeptide
source                  1..101
                        mol_type = protein
                        organism = synthetic construct
SEQUENCE: 202
PLDPAPAVTP EASHLLEDPD EETSQAVKAL REMADTVIPQ KEEAAICGQM DLSHPPPRGH  60
LDELTTTLES MTEDLNLDSP LTPELNEILD TFLNDECLLH A                     101

SEQ ID NO: 203          moltype = AA  length = 76
FEATURE                 Location/Qualifiers
REGION                  1..76
                        note = synthetic polypeptide
source                  1..76
                        mol_type = protein
                        organism = synthetic construct
SEQUENCE: 203
SVKALREMAD TVIPQKEEAA ICGQMDLSHP PPRGHLDELT TTLESMTEDL NLDSPLTPEL  60
NEILDTFLND ECLLHA                                                 76

SEQ ID NO: 204          moltype = AA  length = 51
FEATURE                 Location/Qualifiers
REGION                  1..51
                        note = synthetic polypeptide
source                  1..51
                        mol_type = protein
                        organism = synthetic construct
SEQUENCE: 204
DLSHPPPRGH LDELTTTLES MTEDLNLDSP LTPELNEILD TFLNDECLLH A           51

SEQ ID NO: 205          moltype = AA  length = 316
FEATURE                 Location/Qualifiers
REGION                  1..316
                        note = synthetic polypeptide
source                  1..316
                        mol_type = protein
                        organism = synthetic construct
SEQUENCE: 205
GRADALDDFD LDMLGSDALD DFDLDMLGSD ALDDFDLDML GSDALDDFDL DMLINSRSSG  60
SPKKKRKVGS GGGSGGSGSV LPQAPAPAPA PAMVSALAQA PAPVPVLAPG PPQAVAPPAP  120
KPTQAGEGTL SEALLQLQFD DEDLGALLGN STDPAVFTDL ASVDNSEFQQ LLNQGIPVAP  180
HTTEPMLMEY PEAITRLVTG AQRPPDPAPA PLGAPGLPNG LLSGDEDFSS IADMDFSALL  240
SGGGSGGSGS DLSHPPPRGH LDELTTTLES MTEDLNLDSP LTPELNEILD TFLNDECLLH  300
AMHISTGLSI FDTSLF                                                 316

SEQ ID NO: 206          moltype = AA  length = 526
FEATURE                 Location/Qualifiers
REGION                  1..526
                        note = synthetic polypeptide
source                  1..526
                        mol_type = protein
                        organism = synthetic construct
SEQUENCE: 206
GRADALDDFD LDMLGSDALD DFDLDMLGSD ALDDFDLDML GSDALDDFDL DMLINSRSSG  60
SPKKKRKVGS QYLPDTDDRH RIEEKRKRTY ETFKSIMKKS PFSGPTDPRP PPRRIAVPSR  120
SSASVPKPAP QPYPFTSSLS TINYDEFPTM VFPSGQISQA SALAPAPPQV LPQAPAPAPA  180
PAMVSALAQA PAPVPVLAPG PPQAVAPPAP KPTQAGEGTL SEALLQLQFD DEDLGALLGN  240
STDPAVFTDL ASVDNSEFQQ LLNQGIPVAP HTTEPMLMEY PEAITRLVTG AQRPPDPAPA  300
PLGAPGLPNG LLSGDEDFSS IADMDFSALL GSGSGSRDSR EGMFLPKPEA GSAISDVFEG  360
REVCQPKRIR PFHPPGSPWA NRPLPASLAP TPTGPVHEPV GSLTPAPVPQ PLDPAPAVTP  420
EASHLLEDPD EETSQAVKAL REMADTVIPQ KEEAAICGQM DLSHPPPRGH LDELTTTLES  480
MTEDLNLDSP LTPELNEILD TFLNDECLLH AMHISTGLSI FDTSLF                526

SEQ ID NO: 207          moltype = AA  length = 11
FEATURE                 Location/Qualifiers
REGION                  1..11
                        note = synthetic polypeptide
source                  1..11
                        mol_type = protein
                        organism = synthetic construct
SEQUENCE: 207
DALDDFDLDM L                                                      11

SEQ ID NO: 208          moltype = AA  length = 53
FEATURE                 Location/Qualifiers
```

```
REGION                  1..53
                        note = synthetic polypeptide
source                  1..53
                        mol_type = protein
                        organism = synthetic construct
SEQUENCE: 208
GRADALDDFD LDMLGSDALD DFDLDMLGSD ALDDFDLDML GSDALDDFDL DML         53

SEQ ID NO: 209          moltype = AA  length = 2414
FEATURE                 Location/Qualifiers
REGION                  1..2414
                        note = synthetic polypeptide
source                  1..2414
                        mol_type = protein
                        organism = synthetic construct
SEQUENCE: 209
MAENVVEPGP PSAKRPKLSS PALSASASDG TDFGSLFDLE HDLPDELINS TELGLTNGGD  60
INQLQTSLGM VQDAASKHKQ LSELLRSGSS PNLNMGVGGP GQVMASQAQQ SSPGLGLINS  120
MVKSPMTQAG LTSPNMGMGT SGPNQGPTQS TGMMNSPVNQ PAMGMNTGMN AGMNPGMLAA  180
GNGQGIMPNQ VMNGSIGAGR GRQNMQYPNP GMGSAGNLLT EPLQQGSPQM GGQTGLRGPQ  240
PLKMGMMNNP NPYGSPYTQN PGQQIGASGL GLQIQTKTVL SNNLSPFAMD KKAVPGGGMP  300
NMGQQPAPQV QQPGLVTPVA QGMGSGAHTA DPEKRKLIQQ QLVLLLHAHK CQRREQANGE  360
VRQCNLPHCR TMKNVLNHMT HCQSGKSCQV AHCASSRQII SHWKNCTRHD CPVCLPLKNA  420
GDKRNQQPIL TGAPVGLGNP SSLGVGQQSA PNLSTVSQID PSSIERAYAA LGLPYQVNQM  480
PTQPQVQAKN QQNQQPGQSP QGMRPMSNMS ASPMGVNGGV GVQTPSLLSD SMLHSAINSQ  540
NPMMSENASV PSLGPMPTAA QPSTTGIRKQ WHEDITQDLR NHLVHKLVQA IFPTPDPAAL  600
KDRRMENLVA YARKVEGDMY ESANNRAEYY HLLAEKIYKI QKELEEKRRT RLQKQNMLPN  660
AAGMVPVSMN PGPNMGQPQP GMTSNGPLPD PSMIRGSVPN QMMPRITPQS GLNQFGQMSM  720
AQPPIVPRQT PPLQHHGQLA QPGALNPPMG YGPRMQQPSN QGQFLPQTQF PSQGMNVTNI  780
PLAPSSGQAP VSQAQMSSSS CPVNSPIMPP GSQGSHIHCP QLPQPALHQN SPSPVPSRTP  840
TPHHTPPSIG AQQPPATTIP APVPTPPAMP PGPQSQALHP PPRQTPTPPT TQLPQQVQPS  900
LPAAPSADQP QQQPRSQQST AASVPTPTAP LLPPQPATPL SQPAVSIEGQ VSNPPSTSST  960
EVNSQAIAEK QPSQEVKMEA KMEVDQPEPA DTQPEDISES KVEDCKMEST ETEERSTELK  1020
TEIKEEEDQP STSATQSSPA PGQSKKKIFK PEELRQALMP TLEALYRQDP ESLPFRQPVD  1080
PQLLGIPDYF DIVKSPMDLS TIKRKLDTGQ YQEPWQYVDD IWLMFNNAWL YNRKTSRVYK  1140
YCSKLSEVFE QEIDPVMQSL GYCCGRKLEF SPQTLCCYGK QLCTIPRDAT YYSYQNRYHF  1200
CEKCFNEIQG ESVSLGDDPS QPQTTINKEQ FSKRKNDTLD PELFVECTEC GRKMHQICVL  1260
HHEIIWPAGF VCDGCLKKSA RTRKENKFSA KRLPSTRLGT FLENRVNDFL RRQNHPESGE  1320
VTVRVVHASD KTVEVKPGMK ARFVDSGEMA ESFPYRTKAL FAFEEIDGVD LCFFGMHVQE  1380
YGSDCPPPNQ RRVYISYLDS VHFFRPKCLR TAVYHEILIG YLEYVKKLGY TTGHIWACPP  1440
SEGDDYIFHC HPPDQKIPKP KRLQEWYKKM LDKAVSERIV HDYKDIFKQA TEDRLTSAKE  1500
LPYFEGDFWP NVLEESIKEL EQEEEERKRE ENTSNESTDV TKGDSKNAKK KNNKKTSKNK  1560
SSLSRGNKKK PGMPNVSNDL SQKLYATMEK HKEVFFVIRL IAGPAANSLP PIVDPDPLIP  1620
CDLMDGRDAF LTLARDKHLE FSSLRRAQWS TMCMLVELHT QSQDRFVYTC NECKHHVETR  1680
WHCTVCEDYD LCITCYNTKN HDHKMEKLGL GLDDESNNQQ AAATQSPGDS RRLSIQRCIQ  1740
SLVHACQCRN ANCSLPSCQK MKRVVQHTKG CKRKTNGGCP ICKQLIALCC YHAKHCQENK  1800
CPVPFCLNIK QKLRQQQLQH RLQQAQMLRR RMASMQRTGV VGQQQGLPSP TPATPTTPTG  1860
QQPTTPQTPQ PTSQPQPTPP NSMPPYLPRT QAAGPVSQGK AAGQVTPPTP PQTAQPPLPG  1920
PPPAAVEMAM QIQRAAETQR QMAHVQIFQR PIQHQMPPMT PMAPMGMNPP PMTRGPSGHL  1980
EPGMGPTGMQ QQPPWSQGGL PQPQQLQSGM PRPAMMSVAQ HGQPLNMAPQ PGLGQVGISP  2040
LKPGTVSQQA LQNLLRTLRS PSSPLQQQQV LSILHANPQL LAAFIKQRAA KYANSNPQPI  2100
PGQPGMPQGQ PGLQPPTMPG QQGVHSNPAM QNMNPMQAGV QRAGLPQQQP QQQLQPPMGG  2160
MSPQAQQMNM NHNTMPSQFR DILRRQQMMQ QQQQQGAGPG IGPGMANHNQ FQQPQGVGYP  2220
PQQQQRMQHH MQQMQQGNMG QIGQLPQALG AEAGASLQAY QQRLLQQQMG SPVQPNPMSP  2280
QQHMLPNQAQ SPHLQGQQIP NSLSNQVRSP QPVPSPRPQS QPPHSSPSPR MQPQPSPHHV  2340
SPQTSSPHPG LVAAQANPME QGHFASPDQN SMLSQLASNP GMANLHGASA TDLGLSTDNS  2400
DLNSNLSQST LDIH                                                    2414

SEQ ID NO: 210          moltype = AA  length = 617
FEATURE                 Location/Qualifiers
REGION                  1..617
                        note = synthetic polypeptide
source                  1..617
                        mol_type = protein
                        organism = synthetic construct
SEQUENCE: 210
IFKPEELRQA LMPTLEALYR QDPESLPFRQ PVDPQLLGIP DYFDIVKSPM DLSTIKRKLD  60
TGQYQEPWQY VDDIWLMFNN AWLYNRKTSR VYKYCSKLSE VFEQEIDPVM QSLGYCCGRK  120
LEFSPQTLCC YGKQLCTIPR DATYYSYQNR YHFCEKCFNE IQGESVSLGD DPSQPQTTIN  180
KEQFSKRKND TLDPELFVEC TECGRKMHQI CVLHHEIIWP AGFVCDGCLK KSARTRKENK  240
FSAKRLPSTR LGTFLENRVN DFLRRQNHPE SGEVTVRVVH ASDKTVEVKP GMKARFVDSG  300
EMAESFPYRT KALFAFEEID GVDLCFFGMH VQEYGSDCPP PNQRRVYISY LDSVHFFRPK  360
CLRTAVYHEI LIGYLEYVKK LGYTTGHIWA CPPSEGDDYI FHCHPPDQKI PKPKRLQEWY  420
KKMLDKAVSE RIVHDYKDIF KQATEDRLTS AKELPYFEGD FWPNVLEESI KELEQEEEER  480
KREENTSNES TDVTKGDSKN AKKKNNKKTS KNKSSLSRGN KKKPGMPNVS NDLSQKLYAT  540
MEKHKEVFFV IRLIAGPAAN SLPPIVDPDP LIPCDLMDGR DAFLTLARDK HLEFSSLRRA  600
QWSTMCMLVE LHTQSQD                                                 617

SEQ ID NO: 211          moltype = AA  length = 308
```

-continued

```
FEATURE                Location/Qualifiers
REGION                 1..308
                       note = synthetic polypeptide
source                 1..308
                       mol_type = protein
                       organism = synthetic construct
SEQUENCE: 211
VNKFLRRQNH PEAGEVFVRV VASSDKTVEV KPGMKSRFVD SGEMSESFPY RTKALFAFEE  60
IDGVDVCFFG MHVQEYGSDC PPPNTRRVYI SYLDSIHFFR PRCLRTAVYH EILIGYLEYV  120
KKLGYVTGHI WACPPSEGDD YIFHCHPPDQ KIPKPKRLQE WYKKMLDKAF AERIIHDYKD  180
IFKQATEDRL TSAKELPYFE GDFWPNVLEE SIKELEQEEE ERKKEESTAA SETTEGSQGD  240
SKNAKKKNNK KTNKNKSSIS RANKKKPSMP NVSNDLSQKL YATMEKHKEV FFVIHLHAGP  300
VINTLPPI                                                          308

SEQ ID NO: 212         moltype = AA  length = 314
FEATURE                Location/Qualifiers
REGION                 1..314
                       note = synthetic polypeptide
source                 1..314
                       mol_type = protein
                       organism = synthetic construct
SEQUENCE: 212
VNNFLKKKEA GAGEVHIRVV SSSDKCVEVK PGMRRRFVEQ GEMMNEFPYR AKALFAFEEV  60
DGIDVCFFGM HVQEYGSECP APNTRRVYIA YLDSVHFFRP RQYRTAVYHE ILLGYMDYVK  120
QLGYTMAHIW ACPPSEGDDY IFHCHPTDQK IPKPKRLQEW YKKMLDKGMI ERIIQDYKDI  180
LKQAMEDKLG SAAELPYFEG DFWPNVLEES IKELDQEEEE KRKQAEAAEA AAAANLFSIE  240
ENEVSGDGKK KGQKKAKKSN KSKAAQRKNS KKSNEHQSGN DLSTKIYATM EKHKEVFFVI  300
RLHSAQSAAS LAPI                                                   314

SEQ ID NO: 213         moltype = AA  length = 634
FEATURE                Location/Qualifiers
REGION                 1..634
                       note = synthetic polypeptide
source                 1..634
                       mol_type = protein
                       organism = synthetic construct
SEQUENCE: 213
NGKYSDPWEY VDDVWLMFDN AWLYNRKTSR VYRYCTKLSE VFEAEIDPVM QALGYCCGRK  60
YTFNPQVLCC YGKQLCTIPR DAKYYSYQNR YTYCQKCFND IQGDTVTLGD DPLQSQTQIK  120
KDQFKEMKND HLELEPFVNC QECGRKQHQI CVLWLDSIWP GGFVCDNCLK KKNSKRKENK  180
FNAKRLPTTK LGVYIETRVN NFLKKKEAGA GEVHIRVVSS SDKCVEVKPG MRRRFVEQGE  240
MMNEFPYRAK ALFAFEEVDG IDVCFFGMHV QEYGSECPAP NTRRVYIAYL DSVHFFRPRQ  300
YRTAVYHEIL LGYMDYVKQL GYTMAHIWAC PPSEGDDYIF HCHPTDQKIP KPKRLQEWYK  360
KMLDKGMIER IIQDYKDILK QAMEDKLGSA AELPYFEGDF WPNVLEESIK ELDQEEEEKR  420
KQAEAAEAAA AANLFSIEEN EVSGDGKKKG QKKAKKSNKS KAAQRKNSKK SNEHQSGNDL  480
STKIYATMEK HKEVFFVIRL HSAQSAASLA PIQDPDPLLT CDLMDGRDAF LTLARDKHFE  540
FSSLRRAQFS TLSMLYELHN QGQDKFVYTC NHCKTAVETR YHCTVCDDFD LCIVCKEKVG  600
HQHKMEKLGF DIDDGSALAD HKQANPQEAR KQSI                             634

SEQ ID NO: 214         moltype = AA  length = 382
FEATURE                Location/Qualifiers
REGION                 1..382
                       note = synthetic polypeptide
source                 1..382
                       mol_type = protein
                       organism = synthetic construct
SEQUENCE: 214
MDAKSLTAWS RTLVTFKDVF VDFTREEWKL LDTAQQIVYR NVMLENYKNL VSLGYQLTKP  60
DVILRLEKGE EPWLVSGGGS GGSGSSPKKK RKVEASVQVK RVLEKSPGKL LVKMPFQASP  120
GGKGEGGGAT TSAQVMVIKR PGRKRKAEAD PQAIPKKRGR KPGSVVAAAA AEAKKKAVKE  180
SSIRSVQETV LPIKKRKTRE TVSIEVKEVV KPLLVSTLGE KSGKGLKTCK SPGRKSKESS  240
PKGRSSSASS PPKKEHHHHH HHAESPKAPM PLLPPPPPPE PQSSEDPISP PEPQDLSSSI  300
CKEEKMPRAG SLESDGCPKE PAKTQPMVAA AATTTTTTTT TVAEKYKHRG EGERKDIVSS  360
SMPRPNREEP VDSRTPVTER VS                                          382

SEQ ID NO: 215         moltype = AA  length = 74
FEATURE                Location/Qualifiers
REGION                 1..74
                       note = synthetic polypeptide
source                 1..74
                       mol_type = protein
                       organism = synthetic construct
SEQUENCE: 215
DAKSLTAWSR TLVTFKDVFV DFTREEWKLL DTAQQIVYRN VMLENYKNLV SLGYQLTKPD  60
VILRLEKGEE PWLV                                                   74

SEQ ID NO: 216         moltype = AA  length = 296
FEATURE                Location/Qualifiers
REGION                 1..296
```

-continued

```
                        note = synthetic polypeptide
source                  1..296
                        mol_type = protein
                        organism = synthetic construct
SEQUENCE: 216
PKKKRKVEAS VQVKRVLEKS PGKLLVKMPF QASPGGKGEG GGATTSAQVM VIKRPGRKRK  60
AEADPQAIPK KRGRKPGSVV AAAAAEAKKK AVKESSIRSV QETVLPIKKR KTRETVSIEV  120
KEVVKPLLVS TLGEKSGKGL KTCKSPGRKS KESSPKGRSS SASSPPKKEH HHHHHHAESP  180
KAPMPLLPPP PPPEPQSSED PISPPEPQDL SSSICKEEKM PRAGSLESDG CPKEPAKTQP  240
MVAAAATTTT TTTTTVAEKY KHRGEGERKD IVSSSMPRPN REEPVDSRTP VTERVS      296

SEQ ID NO: 217          moltype = AA  length = 792
FEATURE                 Location/Qualifiers
REGION                  1..792
                        note = synthetic polypeptide
source                  1..792
                        mol_type = protein
                        organism = synthetic construct
SEQUENCE: 217
MKGDTRHLNG EEDAGGREDS ILVNGACSDQ SSDSPPILEA IRTPEIRGRR SSSRLSKREV  60
SSLLSYTQDL TGDGDGEDGD GSDTPVMPKL FRETRTRSES PAVRTRNNNS VSSRERHRPS  120
PRSTRGRQGR NHVDESPVEF PATRSLRRRA TASAGTPWPS PPSSYLTIDL TDDTEDTHGT  180
PQSSSTPYAR LAQDSQQGGM ESPQVEADSG DGDSSEYQDG KEFGIGDLVW GKIKGFSWWP  240
AMVVSWKATS KRQAMSGMRW VQWFGDGKFS EVSADKLVAL GLFSQHFNLA TFNKLVSYRK  300
AMYHALEKAR VRAGKTFPSS PGDSLEDQLK PMLEWAHGGF KPTGIEGLKP NNTQPENKTR  360
RRTADDSATS DYCPAPKRLK TNCYNNGKDR GDEDQSREQM ASDVANNKSS LEDGCLSCGR  420
KNPVSFHPLF EGGLCQTCRD RFLELFYMYD DDGYQSYCTV CCEGRELLLC SNTSCCRCFC  480
VECLEVLVGT GTAAEAKLQE PWSCYMCLPQ RCHGVLRRRK DWNVRLQAFF TSDTGLEYEA  540
PKLYPAIPAA RRRPIRVLSL FDGIATGYLV LKELGIKVGK YVASEVCEES IAVGTVKHEG  600
NIKYVNDVRN ITKKNIEEWG PFDLVIGGSP CNDLSNVNPA RKGLYEGTGR LFFEFYHLLN  660
YSRPKEGDDR PFFWMFENVV AMKVGDKRDI SRFLECNPVM IDAIKVSAAH RARYFWGNLP  720
GMNRPVIASK NDKLELQDCL EYNRIAKDLW LSCALHRRVQ HGPWCPPEAA GKVLERACHP  780
TPLRPSEGLL CM                                                     792

SEQ ID NO: 218          moltype = AA  length = 1084
FEATURE                 Location/Qualifiers
REGION                  1..1084
                        note = synthetic polypeptide
source                  1..1084
                        mol_type = protein
                        organism = synthetic construct
SEQUENCE: 218
MSSQSHPDGL SGRDQPVELL NPARVNHMPS TVDVATALPL QVAPSAVPMD LRLDHQFSLP  60
VAEPALREQQ LQQELLALKQ KQQIQRQILI AEFQRQHEQL SRQHEAQLHE HIKQQQEMLA  120
MKHQQELLEH QRKLERHRQE QELEKQHREQ KLQQLKNKEK GKESAVASTE VKMKLQEFVL  180
NKKKALAHRN LNHCISSDPR YWYGKTQHSS LDQSSPPQSG VSTSYNHPVL GMYDAKDDFP  240
LRKTASEPNL KLRSRLKQKV AERRSSPLLR RKDGPVVTAL KKRPLDVTDS ACSSAPGSGP  300
SSPNNSSGSV SAENGIAPAV PSIPAETSLA HRLVAREGSA APLPLYTSPS LPNITLGLPA  360
TGPSAGTAGQ QDTERLTLPA LQQRLSLFPG THLTPYLSTS PLERDGGAAH SPLLQHMVLL  420
EQPPAQAPLV TGLGALPLHA QSLVGADRVS PSIHKLRQHR PLGRTQSAPL PQNAQALQHL  480
VIQQQHQQFL EKHKQQFQQQ QLQMNKIIPK PSEPARQPES HPEETEEELR EHQALLDEPY  540
LDRLPGQKEA HAQAGVQVKQ EPIESDEEEA EPPREVEPGQ RQPSEQELLF RQQALLLEQQ  600
RIHQLRNYQA SMEAAGIPVS FGGHRPLSRA QSSPASATFP VSVQEPPTKP RFTTGLVYDT  660
LMLKHQCTCG SSSSHPEHAG RIQSIWSRLQ ETGLRGKCEC IRGRKATLEE LQTVHSEAHT  720
LLYGTNPLNR QKLDSKKLLG SLASVFVRLP CGGVGVDSDT IWNEVHSAGA ARLAVGCVVE  780
LVFKVATGEL KNGFAVVRPP GHHAEESTPM GFCYFNSVAV AAKLLQQRLS VSKILIVDWD  840
VHHGNGTQQA FYSDPSVLYM SLHRYDDGNF FPGSGAPDEV GTGPGVGFNV NMAFTGGLDP  900
PMGDAEYLAA FRTVVMPIAS EFAPDVVLVS SGFDAVEGHP TPLGGYNLSA RCFGYLTKQL  960
MGLAGGRIVL ALEGGHDLTA ICDASEACVS ALLGNELDPL PEKVLQQRPN ANAVRSMEKV  1020
MEIHSKYWRC LQRTTSTAGR SLIEAQTCEN EEAETVTAMA SLSVGVKPAE KRPDEEPMEE  1080
EPPL                                                              1084

SEQ ID NO: 219          moltype = AA  length = 31
FEATURE                 Location/Qualifiers
REGION                  1..31
                        note = synthetic polypeptide
REGION                  1..3
                        note = misc_feature - Xaa can be any naturally occurring
                         amino acid
REGION                  5..9
                        note = misc_feature - Xaa can be any naturally occurring
                         amino acid
REGION                  11..23
                        note = misc_feature - Xaa can be any naturally occurring
                         amino acid
REGION                  25..30
                        note = misc_feature - Xaa can be any naturally occurring
                         amino acid
source                  1..31
```

```
                        mol_type = protein
                        organism = synthetic construct
SEQUENCE: 219
XXXCXXXXXC XXXXXXXXXX XXXHXXXXXX H                                   31

SEQ ID NO: 220          moltype = AA  length = 23
FEATURE                 Location/Qualifiers
REGION                  1..23
                        note = synthetic polypeptide
REGION                  1..3
                        note = misc_feature - Xaa can be any naturally occurring
                         amino acid
REGION                  5..6
                        note = misc_feature - Xaa can be any naturally occurring
                         amino acid
REGION                  8..18
                        note = misc_feature - Xaa can be any naturally occurring
                         amino acid
REGION                  20..22
                        note = misc_feature - Xaa can be any naturally occurring
                         amino acid
source                  1..23
                        mol_type = protein
                        organism = synthetic construct
SEQUENCE: 220
XXXCXXCXXX XXXXXXXXHX XXH                                            23

SEQ ID NO: 221          moltype = AA  length = 85
FEATURE                 Location/Qualifiers
REGION                  1..85
                        note = synthetic polypeptide
REGION                  16..22
                        note = misc_feature - Xaa can be any naturally occurring
                         amino acid
REGION                  44..50
                        note = misc_feature - Xaa can be any naturally occurring
                         amino acid
REGION                  72..78
                        note = misc_feature - Xaa can be any naturally occurring
                         amino acid
source                  1..85
                        mol_type = protein
                        organism = synthetic construct
SEQUENCE: 221
GERPFQCRIC MANFSXXXXX XXHTRTHTGE KPFQCRICMA NFSXXXXXXX HLRTHTGEKP  60
FQCRICMANF SXXXXXXXHL KTHLR                                          85

SEQ ID NO: 222          moltype = AA  length = 85
FEATURE                 Location/Qualifiers
REGION                  1..85
                        note = synthetic polypeptide
REGION                  16..22
                        note = misc_feature - Xaa can be any naturally occurring
                         amino acid
REGION                  44..50
                        note = misc_feature - Xaa can be any naturally occurring
                         amino acid
REGION                  72..78
                        note = misc_feature - Xaa can be any naturally occurring
                         amino acid
source                  1..85
                        mol_type = protein
                        organism = synthetic construct
SEQUENCE: 222
GEAPFQCRIC MANFSXXXXX XXHTRTHTGE KPFQCRICMA NFSXXXXXXX HLRTHTGEKP  60
FQCRICMANF SXXXXXXXHL KTHLR                                          85

SEQ ID NO: 223          moltype = AA  length = 85
FEATURE                 Location/Qualifiers
REGION                  1..85
                        note = synthetic polypeptide
source                  1..85
                        mol_type = protein
                        organism = synthetic construct
SEQUENCE: 223
GERPFQCRIC MANFSGRQAL DRHTRTHTGE KPFQCRICMA NFSDKANLTR HLRTHTGEKP  60
FQCRICMANF SQRNNLGRHL KTHLR                                          85

SEQ ID NO: 224          moltype = AA  length = 85
```

```
FEATURE                Location/Qualifiers
REGION                 1..85
                       note = synthetic polypeptide
source                 1..85
                       mol_type = protein
                       organism = synthetic construct
SEQUENCE: 224
GEAPFQCRIC MANFSRQDRL DRHTRTHTGE KPFQCRICMA NFSQKEHLAG HLRTHTGEKP  60
FQCRICMANF SRRDNLNRHL KTHLR                                       85

SEQ ID NO: 225         moltype = AA  length = 85
FEATURE                Location/Qualifiers
REGION                 1..85
                       note = synthetic polypeptide
source                 1..85
                       mol_type = protein
                       organism = synthetic construct
SEQUENCE: 225
GERPFQCRIC MANFSRQDRL DRHTRTHTGE KPFQCRICMA NFSQKEHLAG HLRTHTGEKP  60
FQCRICMANF SRRDNLNRHL KTHLR                                       85

SEQ ID NO: 226         moltype = AA  length = 85
FEATURE                Location/Qualifiers
REGION                 1..85
                       note = synthetic polypeptide
source                 1..85
                       mol_type = protein
                       organism = synthetic construct
SEQUENCE: 226
GEAPFQCRIC MANFSTGQIL DRHTRTHTGE KPFQCRICMA NFSVAHSLKR HLRTHTGEKP  60
FQCRICMANF SDPSNLRRHL KTHLR                                       85

SEQ ID NO: 227         moltype = AA  length = 85
FEATURE                Location/Qualifiers
REGION                 1..85
                       note = synthetic polypeptide
source                 1..85
                       mol_type = protein
                       organism = synthetic construct
SEQUENCE: 227
GERPFQCRIC MANFSTGQIL DRHTRTHTGE KPFQCRICMA NFSVAHSLKR HLRTHTGEKP  60
FQCRICMANF SDPSNLRRHL KTHLR                                       85

SEQ ID NO: 228         moltype = AA  length = 85
FEATURE                Location/Qualifiers
REGION                 1..85
                       note = synthetic polypeptide
source                 1..85
                       mol_type = protein
                       organism = synthetic construct
SEQUENCE: 228
GERPFQCRIC MRNFSRQSNL SRHTRTHTGE KPFQCRICMR NFSRNEHLVL HLRTHTGEKP  60
FQCRICMRNF SQKTGLRVHL KTHLR                                       85

SEQ ID NO: 229         moltype = DNA  length = 11
FEATURE                Location/Qualifiers
misc_feature           1..11
                       note = synthetic polynucleotide
source                 1..11
                       mol_type = other DNA
                       organism = synthetic construct
SEQUENCE: 229
cgaagacgct g                                                      11

SEQ ID NO: 230         moltype = DNA  length = 11
FEATURE                Location/Qualifiers
misc_feature           1..11
                       note = synthetic polynucleotide
source                 1..11
                       mol_type = other DNA
                       organism = synthetic construct
SEQUENCE: 230
agagtgagga c                                                      11

SEQ ID NO: 231         moltype = DNA  length = 11
FEATURE                Location/Qualifiers
misc_feature           1..11
                       note = synthetic polynucleotide
source                 1..11
```

```
                        mol_type = other DNA
                        organism = synthetic construct
SEQUENCE: 231
acagtgagga c                                                    11

SEQ ID NO: 232          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 232
atagtgagga c                                                    11

SEQ ID NO: 233          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 233
agacgctgct c                                                    11

SEQ ID NO: 234          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 234
tgacgctgct t                                                    11

SEQ ID NO: 235          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 235
agacggtgct c                                                    11

SEQ ID NO: 236          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 236
acacgctgct c                                                    11

SEQ ID NO: 237          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 237
agacgctact c                                                    11

SEQ ID NO: 238          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 238
agacgctgct a                                                    11

SEQ ID NO: 239          moltype = DNA  length = 11
FEATURE                 Location/Qualifiers
misc_feature            1..11
                        note = synthetic polynucleotide
```

```
source                  1..11
                        mol_type = other DNA
                        organism = synthetic construct
SEQUENCE: 239
agactctgct c                                                              11

SEQ ID NO: 240          moltype = DNA  length = 11
FEATURE                 Location/Qualifiers
misc_feature            1..11
                        note = synthetic polynucleotide
source                  1..11
                        mol_type = other DNA
                        organism = synthetic construct
SEQUENCE: 240
attatgggag a                                                              11

SEQ ID NO: 241          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 241
APITAYAQQT RGLLGCIITS LTGRDKNQVE GEVQIVSTAT QTFLATCING VCWTVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVAKAVDFI PVENLETTMR  180

SEQ ID NO: 242          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 242
APITAYSQQT RGLLGCIITS LTGRDKNQVE GEVQVVSTAT QSFLATCVNG VCWTVYHGAG  60
SKTLAGPKGP ITQMYTNVDQ DLVGWQAPPG ARSLTPCTCG SSDLYLVTRH ADVIPVRRRG  120
DSRGSLLSPR PVSYLKGSSG GPLLCPSGHA VGIFRAAVCT RGVAKAVDFV PVESMETTMR  180

SEQ ID NO: 243          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 243
APITAYAQQT RGLLGTIVVS MTGRDKTEQA GEIQVLSTVT QSFLGTSISG VLWTVYHGAG  60
NKTLAGSRGP VTQMYSSAEG DLVGWPSPPG TKSLEPCTCG AVDLYLVTRN ADVIPARRRG  120
DKRGALLSPR PLSTLKGSSG GPVLCPRGHA VGVFRAAVCS RGVAKSIDFI PVETLDIVTR  180

SEQ ID NO: 244          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 244
APITAYAQQT RGLLGTIVTS LTGRDKNVVT GEVQVLSTAT QTFLGTTVGG VIWTVYHGAG  60
SRTLAGAKHP ALQMYTNVDQ DLVGWPAPPG AKSLEPCACG SSDLYLVTRD ADVIPARRRG  120
DSTASLLSPR PLACLKGSSG GPVMCPSGHV AGIFRAAVCT RGVAKSLQFI PVETLSTQAR  180

SEQ ID NO: 245          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 245
APITAYAQQT RGLFSTIVTS LTGRDTNENC GEVQVLSTAT QSFLGTAVNG VMWTVYHGAG  60
AKTISGPKGP VNQMYTNVDQ DLVGWPAPPG VRSLAPCTCG SADLYLVTRH ADVIPVRRRG  120
DTRGALLSPR PISILKGSSG GPLLCPMGHR AGIFRAAVCT RGVAKAVDFV PVESLETTMR  180

SEQ ID NO: 246          moltype = AA  length = 180
FEATURE                 Location/Qualifiers
REGION                  1..180
```

-continued

```
                        note = synthetic polypeptide
source                  1..180
                        mol_type = protein
                        organism = synthetic construct
SEQUENCE: 246
APITAYAQQT RGVLGAIVLS LTGRDKNEAE GEVQFLSTAT QTFLGICING VMWTLFHGAG  60
SKTLAGPKGP VVQMYTNVDK DLVGWPSPPG KGSLTRCTCG SADLYLVTRH ADVIPARRRG  120
DTRASLLSPR PISYLKGSSG GPIMCPSGHV VGVFRAAVCT RGVAKALEFV PVENLETTMR  180

SEQ ID NO: 247          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 247
APITAYAQQT RGLVGTIVTS LTGRDKNEAE GEVQVVSTAT QSFLATTING VLWTVYHGAG  60
SKNLAGPKGP VCQMYTNVDQ DLVGWPAPLG ARSLAPCTCG SSDLYLVTRG ADVIPARRRG  120
DTRAALLSPR PISTLKGSSG GPLMCPSGHV VGLFRAAVCT RGVAKALDFI PVENMDTTMR  180

SEQ ID NO: 248          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 248
APISAYAQQT RGLISTLVVS LTGRDKNETA GEVQVLSTST QTFLGTNVGG VMWGPYHGAG  60
TRTVAGRGGP VLQMYTSVSD DLVGWPAPPG SKSLEPCSCG SADLYLVTRN ADVLPLRRKG  120
DGTASLLSPR PVSSLKGSSG GPVLCPQSHC VGIFRAAVCT RGVAKAVQFV PIEKMQVAQR  180

SEQ ID NO: 249          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 249
APITAYAQQT RGLLGCIITS LTGRDKNQVE GEVQIVSTAT QTFLATCING VCWTVYHGAG  60
TRTIASPKGP VIQMYTNVDQ DLVGWPAPQG SRSLTPCTCG SSDLYLVTRH ADVIPVRRRG  120
DSRGSLLSPR PISYLKGSSG GPLLCPAGHA VGLFRAAVCT RGVTKAVDFI PVENLETTMR  180

SEQ ID NO: 250          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 250
APITAYSQQT RGLLGCIITS LTGRDKNQVE GEVQVVSTAT QSFLATCVNG VCWTVYHGAG  60
SKTLAAPKGP ITQMYTNVDQ DLVGWPKPPG ARSLTPCTCG SSDLYLVTRH ADVIPVRRRG  120
DSRGSLLSPR PVSYLKGSSG GPLLCPFGHA VGIFRAAVCT RGVAKAVDFV PVESMETTMR  180

SEQ ID NO: 251          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 251
APITAYAQQT RGLLGTIVVS MTGRDKTEQA GEIQVLSTVT QSFLGTTISG VLWTVYHGAG  60
NKTLAGSRGP VTQMYSSAEG DLVGWPSPPG TKSLEPCTCG AVDLYLVTRN ADVIPARRRG  120
DKRGALLSPR PLSTLKGSSG GPVLCPRGHA VGVFRAAVCS RGVAKSIDFI PVETLDIVTR  180

SEQ ID NO: 252          moltype = AA  length = 182
FEATURE                 Location/Qualifiers
REGION                  1..182
                        note = synthetic polypeptide
source                  1..182
                        mol_type = protein
                        organism = synthetic construct
SEQUENCE: 252
APITAYTQQT RGLLGAIVVS LTGRDKNEQA GQVQVLSSVT QTFLGTSISG VLWTVYHGAG  60
NKTLAGPKGP VTQMYTSAEG DLVGWPSPPG TKSLDPCTCG AVDLYLVTRN ADVIPVRRKD  120
```

-continued

```
DRRGALLSPR PLSTLKGSSG GPVLCSRGHA VGLFRAAVSY NTFGVAKSID FIPVESLDVA  180
TR                                                                182

SEQ ID NO: 253          moltype = AA  length = 180
FEATURE                 Location/Qualifiers
REGION                  1..180
                        note = synthetic polypeptide
source                  1..180
                        mol_type = protein
                        organism = synthetic construct
SEQUENCE: 253
APITAYAQQT RGLLGTIVTS LTGRDKNVVT GEVQVLSTAT QTFLGTTVGG VIWTVYHGAG  60
SRTLAGAKHP ALQMYTNVDQ DLVGWPAPPG AKSLEPCACG SSDLYLVTRD ADVIPARRRG  120
DSTASLLSPR PLACLKGSSG GPVMCPSGHV AGIFRAAVCT RGVAKSLQFI PVETLSTQAR  180

SEQ ID NO: 254          moltype = AA  length = 186
FEATURE                 Location/Qualifiers
REGION                  1..186
                        note = synthetic polypeptide
source                  1..186
                        mol_type = protein
                        organism = synthetic construct
SEQUENCE: 254
APITAYAQQT RGLLGCIITS LTGRDKNQVE GEVQIMSTAT QTFLATCING VCWAVYHGAG  60
TRTIASPKGP VIQMYTNVDQ DLVGWPAPQG SRSLTPCTCG SSDLYLVTRH ADVIPVRRRG  120
DGRGSLLSPR PISYLKGSSG GPLLCPAGHA VGLFRAAVCT RGVAKAVDFI PVENLETTMR  180
SPVFTD                                                            186

SEQ ID NO: 255          moltype = AA  length = 186
FEATURE                 Location/Qualifiers
REGION                  1..186
                        note = synthetic polypeptide
source                  1..186
                        mol_type = protein
                        organism = synthetic construct
SEQUENCE: 255
APITAYAQQT RGLLGCIITS LTGRDKNQVE GEVQIVSTAT QTLLATCING VCWAVYHGAG  60
TRTIASPKGP VIQMYTNVDK DLVGWPAPQG SRSLTPCTCG SSDLYLVTRH ADVIPVRRRG  120
DRRGSLLSPR PISYLKGSSG GPLLCPAGHA VGLFRAAVCT RGVAKAVYFI PVENLETTMR  180
SPVFTD                                                            186

SEQ ID NO: 256          moltype = AA  length = 12
FEATURE                 Location/Qualifiers
REGION                  1..12
                        note = synthetic polypeptide
source                  1..12
                        mol_type = protein
                        organism = synthetic construct
SEQUENCE: 256
GSVVIVGRII LS                                                     12

SEQ ID NO: 257          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 257
GCVVIVGRIV LSGK                                                   14

SEQ ID NO: 258          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 258
GCVCIIGRLH INQR                                                   14

SEQ ID NO: 259          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 259
```

```
GCVVIVGHIE LEGK                                                   14

SEQ ID NO: 260          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 260
GSVVIVGRVV LSGQ                                                   14

SEQ ID NO: 261          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 261
GSVAIVGRII LSGR                                                   14

SEQ ID NO: 262          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 262
GCVVICGRIV TSGK                                                   14

SEQ ID NO: 263          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 263
GSVVVVGRVV LGSN                                                   14

SEQ ID NO: 264          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 264
STWVLVGGVL AALAAYCLST GCVVIVGRIV LSGKPAIIPD REVLYQEFDE MEEC       54

SEQ ID NO: 265          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 265
STWVLVGGVL AALAAYCLST GCVVIVGRVV LSGKPAIIPD REVLYREFDE MEEC       54

SEQ ID NO: 266          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 266
STWVLVGGVL AALAAYCLST GCVVIVGRIV LSGRPAIIPD REVLYREFDE MEEC       54

SEQ ID NO: 267          moltype = AA  length = 54
FEATURE                 Location/Qualifiers
REGION                  1..54
                        note = synthetic polypeptide
source                  1..54
                        mol_type = protein
                        organism = synthetic construct
```

```
SEQUENCE: 267
STWVLVGGVL AALAAYCLTT GSVVIVGRII LSGRPAIVPD RELLYQEFDE MEEC        54

SEQ ID NO: 268          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 268
STWVLVGGVL AALAAYCLTT GSVVIVGRII LSGRPAIIPD RELLYQEFDE MEEC        54

SEQ ID NO: 269          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 269
STWVLVGGVL AALAAYCLTT GSVVIVGRII LSGKPAVVPD RELLYQEFDE MEEC        54

SEQ ID NO: 270          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 270
STWVLVGGVL AALAAYCLTT GSVVIVGRII LSGRPAVIPD RELLYREFDE MEEC        54

SEQ ID NO: 271          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 271
STWVLAGGVL AAVAAYCLAT GCVCIIGRLH VNQRAVVAPD KEVLYEAFDE MEEC        54

SEQ ID NO: 272          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 272
STWVLAGGVL AAVAAYCLAT GCVSIIGRLH INGRAVVAPD KEVLYEAFDE MEEC        54

SEQ ID NO: 273          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 273
SSWVLAGGVL AAVAAYCLAT GCISIIGRLH LNDRVVVAPD KEILYEAFDE MEEC        54

SEQ ID NO: 274          moltype = AA  length = 54
FEATURE                 Location/Qualifiers
REGION                  1..54
                        note = synthetic polypeptide
source                  1..54
                        mol_type = protein
                        organism = synthetic construct
SEQUENCE: 274
STWVLAGGVL AAVAAYCLAT GCVSIIGRLH LNDQVVVTPD KEILYEAFDE MEEC        54

SEQ ID NO: 275          moltype = AA  length = 54
FEATURE                 Location/Qualifiers
REGION                  1..54
                        note = synthetic polypeptide
source                  1..54
                        mol_type = protein
```

```
                          organism = synthetic construct
SEQUENCE: 275
STWVLLGGVL AALAAYCLSV GCVVIVGHIE LEGKPALVPD KEVLYQQYDE MEEC        54

SEQ ID NO: 276            moltype = AA  length = 54
FEATURE                   Location/Qualifiers
REGION                    1..54
                          note = synthetic polypeptide
source                    1..54
                          mol_type = protein
                          organism = synthetic construct
SEQUENCE: 276
STWVLLGGVL AAVAAYCLSV GCVVIVGHIE LGGKPALVPD KEVLYQQYDE MEEC        54

SEQ ID NO: 277            moltype = AA  length = 4
FEATURE                   Location/Qualifiers
REGION                    1..4
                          note = synthetic polypeptide
source                    1..4
                          mol_type = protein
                          organism = synthetic construct
SEQUENCE: 277
SGTS                                                               4

SEQ ID NO: 278            moltype = AA  length = 4
FEATURE                   Location/Qualifiers
REGION                    1..4
                          note = synthetic polypeptide
source                    1..4
                          mol_type = protein
                          organism = synthetic construct
SEQUENCE: 278
GSGS                                                               4

SEQ ID NO: 279            moltype = AA  length = 13
FEATURE                   Location/Qualifiers
REGION                    1..13
                          note = synthetic polypeptide
source                    1..13
                          mol_type = protein
                          organism = synthetic construct
SEQUENCE: 279
QEFEDVVPCS MGS                                                     13

SEQ ID NO: 280            moltype = AA  length = 9
FEATURE                   Location/Qualifiers
REGION                    1..9
                          note = synthetic polypeptide
source                    1..9
                          mol_type = protein
                          organism = synthetic construct
SEQUENCE: 280
EDVVCCHSI                                                          9

SEQ ID NO: 281            moltype = AA  length = 9
FEATURE                   Location/Qualifiers
REGION                    1..9
                          note = synthetic polypeptide
source                    1..9
                          mol_type = protein
                          organism = synthetic construct
SEQUENCE: 281
DEMEECSQH                                                          9

SEQ ID NO: 282            moltype = AA  length = 20
FEATURE                   Location/Qualifiers
REGION                    1..20
                          note = synthetic polypeptide
source                    1..20
                          mol_type = protein
                          organism = synthetic construct
SEQUENCE: 282
CMSADLEVVT STWVLVGGVL                                              20

SEQ ID NO: 283            moltype = AA  length = 20
FEATURE                   Location/Qualifiers
REGION                    1..20
                          note = synthetic polypeptide
source                    1..20
```

```
                        mol_type = protein
                        organism = synthetic construct
SEQUENCE: 283
CMSADLEVVT STWVLVGGVL                                                20

SEQ ID NO: 284          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 284
CMQADLEVMT STWVLAGGVL                                                20

SEQ ID NO: 285          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 285
CMQADLEIMT SSWVLAGGVL                                                20

SEQ ID NO: 286          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 286
CMSADLEVTT STWVLLGGVL                                                20

SEQ ID NO: 287          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 287
YQEFDEMEEC SQHLPYIEQG                                                20

SEQ ID NO: 288          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 288
YQEFDEMEEC ASHLPYIEQG                                                20

SEQ ID NO: 289          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 289
YEAFDEMEEC ASRAALIEEG                                                20

SEQ ID NO: 290          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 290
YEAFDEMEEC ASKAALIEEG                                                20

SEQ ID NO: 291          moltype = AA  length = 20
FEATURE                 Location/Qualifiers
REGION                  1..20
                        note = synthetic polypeptide
```

```
source                  1..20
                        mol_type = protein
                        organism = synthetic construct
SEQUENCE: 291
YQQYDEMEEC SQAAPYIEQA                                                20

SEQ ID NO: 292          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 292
WISSECTTPC SGSWLRDVWD                                                20

SEQ ID NO: 293          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 293
WINEDCSTPC SGSWLRDVWD                                                20

SEQ ID NO: 294          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 294
WITEDCPIPC SGSWLRDVWD                                                20

SEQ ID NO: 295          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 295
WITEDCPVPC SGSWLQDIWD                                                20

SEQ ID NO: 296          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 296
WINEDYPSPC SDDWLRTIWD                                                20

SEQ ID NO: 297          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 297
GADTEDVVCC SMSYSWTGAL                                                20

SEQ ID NO: 298          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 298
EEASEDVVCC SMSYTWTGAL                                                20

SEQ ID NO: 299          moltype = AA  length = 20
FEATURE                 Location/Qualifiers
REGION                  1..20
```

```
                        note = synthetic polypeptide
source                  1..20
                        mol_type = protein
                        organism = synthetic construct
SEQUENCE: 299
SEEDDSVVCC SMSYSWTGAL                                             20

SEQ ID NO: 300          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 300
SDQEDSVICC SMSYSWTGAL                                             20

SEQ ID NO: 301          moltype = AA  length = 20
FEATURE                 Location/Qualifiers
REGION                  1..20
                        note = synthetic polypeptide
source                  1..20
                        mol_type = protein
                        organism = synthetic construct
SEQUENCE: 301
DSEEQSVVCC SMSYSWTGAL                                             20

SEQ ID NO: 302          moltype = AA  length = 11
FEATURE                 Location/Qualifiers
REGION                  1..11
                        note = synthetic polypeptide
source                  1..11
                        mol_type = protein
                        organism = synthetic construct
SEQUENCE: 302
NSSPPAVTLT H                                                      11

SEQ ID NO: 303          moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 303
GGSGG                                                             5

SEQ ID NO: 304          moltype = AA  length = 221
FEATURE                 Location/Qualifiers
REGION                  1..221
                        note = synthetic polypeptide
source                  1..221
                        mol_type = protein
                        organism = synthetic construct
SEQUENCE: 304
TGCVVIVGRI VLSGSGTSAP ITAYAQQTRG LLGCIITSLT GRDKNQVEGE VQIVSTATQT  60
FLATCINGVC WAVYHGAGTR TIASPKGPVI QMYTNVDQDL VGWPAPQGSR SLTPCTCGSS  120
DLYLVTRHAD VIPVRRRGDS RGSLLSPRPI SYLKGSSGGP LLCPAGHAVG LFRAAVCTRG  180
VAKAVDFIPV ENLETTMRSP VFTDNSSPPA VTLTHGGSGG S                     221

SEQ ID NO: 305          moltype = AA  length = 221
FEATURE                 Location/Qualifiers
REGION                  1..221
                        note = synthetic polypeptide
source                  1..221
                        mol_type = protein
                        organism = synthetic construct
SEQUENCE: 305
TGCVVIVGRI VLSGSGTSAP ITAYAQQTRG LLGCIITSLT GRDKNQVEGE VQIMSTATQT  60
FLATCINGVC WAVYHGAGTR TIASPKGPVI QMYTNVDQDL VGWPAPQGSR SLTPCTCGSS  120
DLYLVTRHAD VIPVRRRGDG RGSLLSPRPI SYLKGSSGGP LLCPAGHAVG LFRAAVCTRG  180
VAKAVDFIPV ENLETTMRSP VFTDNSSPPA VTLTHGGSGG S                     221

SEQ ID NO: 306          moltype = AA  length = 221
FEATURE                 Location/Qualifiers
REGION                  1..221
                        note = synthetic polypeptide
source                  1..221
                        mol_type = protein
```

```
                        organism = synthetic construct
SEQUENCE: 306
TGCVVIVGRI VLSGSGTSAP ITAYAQQTRG LLGCIITSLT GRDKNQVEGE VQIVSTATQT  60
LLATCINGVC WAVYHGAGTR TIASPKGPVI QMYTNVDKDL VGWPAPQGSR SLTPCTCGSS  120
DLYLVTRHAD VIPVRRRGDR RGSLLSPRPI SYLKGSSGGP LLCPAGHAVG LFRAAVCTRG  180
VAKAVYFIPV ENLETTMRSP VFTDNSSPPA VTLTHGGSGG S                     221

SEQ ID NO: 307          moltype = AA  length = 182
FEATURE                 Location/Qualifiers
REGION                  1..182
                        note = synthetic polypeptide
source                  1..182
                        mol_type = protein
                        organism = synthetic construct
SEQUENCE: 307
MAPITAYAQQ TRGLLGCIIT SLTGRDKNQV EGEVQIVSTA AQTFLATCIN GVCWTVYHGA  60
GTRTIASPKG PVIQMYTNVD KDLVGWPAPQ GSRSLTPCTC GSSDLYLVTR HADVIPVRRR  120
GDSRGSLLSP RPISYLKGSS GGPLLCPAGH AVGIFRAAVC TRGVAKAVDF IPVESLETTM  180
RS                                                                182

SEQ ID NO: 308          moltype = AA  length = 195
FEATURE                 Location/Qualifiers
REGION                  1..195
                        note = synthetic polypeptide
source                  1..195
                        mol_type = protein
                        organism = synthetic construct
SEQUENCE: 308
MKKKGSVVIV GRIVLNGAYA QQTRGLLGCI ITSLTGRDKN QVEGEVQIVS TAAQTFLATC  60
INGVCWTVYH GAGTRTIASP KGPVIQMYTN VDKDLVGWPA PQGSRSLTPC TCGSSDLYLV  120
TRHADVIPVR RRGDSRGSLL SPRPISYLKG SSGGPLLCPA GHAVGIFRAA VCTRGVAKAV  180
DFIPVESLET TMRSP                                                  195

SEQ ID NO: 309          moltype = AA  length = 195
FEATURE                 Location/Qualifiers
REGION                  1..195
                        note = synthetic polypeptide
source                  1..195
                        mol_type = protein
                        organism = synthetic construct
SEQUENCE: 309
MKKKGSVVIV GRIVLNGAYA QQTRGEEGCQ ETSQTGRDKN QVEGEVQIVS TAAQTFLATC  60
INGVCWTVYH GAGTRTIASP KGPVIQMYTN VDKDLVGWPA PQGSRSLTPC TCGSSDLYLV  120
TRHADVIPVR RRGDSRGSLL SPRPISYLKG SSGGPLLCPA GHAVGIFRAA VCTRGVAKAV  180
DFIPVESLET TMRSP                                                  195

SEQ ID NO: 310          moltype = AA  length = 197
FEATURE                 Location/Qualifiers
REGION                  1..197
                        note = synthetic polypeptide
source                  1..197
                        mol_type = protein
                        organism = synthetic construct
SEQUENCE: 310
MKKKGSVVIV GRINLSGDTA YAQQTRGEEG CQETSQTGRD KNQVEGEVQI VSTAAQTFLA  60
TCINGVCWTV YHGAGTRTIA SPKGPVIQMY TNVDKDLVGW PAPQGSRSLT PCTCGSSDLY  120
LVTRHADVIP VRRRGDSRGS LLSPRPISYL KGSSGGPLLC PAGHAVGIFR AAVCTRGVAK  180
AVDFIPVESL ETTMRSP                                                197

SEQ ID NO: 311          moltype = AA  length = 197
FEATURE                 Location/Qualifiers
REGION                  1..197
                        note = synthetic polypeptide
source                  1..197
                        mol_type = protein
                        organism = synthetic construct
SEQUENCE: 311
MKKKGSVVIV GRINLSGDTA YAQQTRGEEG CQETSQTGRD KNQVEGEVQI VSTATQTFLA  60
TCINGVCWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVCTRGVAK  180
AVDFIPVESL ETTMRSP                                                197

SEQ ID NO: 312          moltype = AA  length = 197
FEATURE                 Location/Qualifiers
REGION                  1..197
                        note = synthetic polypeptide
source                  1..197
                        mol_type = protein
                        organism = synthetic construct
```

```
SEQUENCE: 312
MKKKGSVVIV GRINLSGDTA YAQQTRGEEG CQETSQTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 313         moltype = AA  length = 197
FEATURE                Location/Qualifiers
REGION                 1..197
                       note = synthetic polypeptide
source                 1..197
                       mol_type = protein
                       organism = synthetic construct
SEQUENCE: 313
MKKKGSVVIV GRINLSGDTA YAQQTRGEQG CQKTSHTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 314         moltype = AA  length = 197
FEATURE                Location/Qualifiers
REGION                 1..197
                       note = synthetic polypeptide
source                 1..197
                       mol_type = protein
                       organism = synthetic construct
SEQUENCE: 314
MKKKGSVVIV GRINLSGDTA YAQQTRGEQG TQKTSHTGRD KNQVEGEVQI VSTATQTFLA  60
TSINGVLWTV YHGAGTRTIA SPKGPVTQMY TNVDKDLVGW QAPQGSRSLT PCTCGSSDLY  120
LVTRHADVIP VRRRGDSRGS LLSPRPISYL KGSSGGPLLC PAGHAVGIFR AAVSTRGVAK  180
AVDFIPVESL ETTMRSP                                                197

SEQ ID NO: 315         moltype = AA  length = 196
FEATURE                Location/Qualifiers
REGION                 1..196
                       note = synthetic polypeptide
source                 1..196
                       mol_type = protein
                       organism = synthetic construct
SEQUENCE: 315
KKKGSVVIVG RINLSGDTAY AQQTRGEEGC QETSQTGRDK NQVEGEVQIV STATQTFLAT  60
SINGVLWTVY HGAGTRTIAS PKGPVTQMYT NVDKDLVGWQ APQGSRSLTP CTCGSSDLYL  120
VTRHADVIPV RRRGDSRGSL LSPRPISYLK GSAGGPLLCP AGHAVGIFRA AVSTRGVAKA  180
VDFIPVESLE TTMRSP                                                 196

SEQ ID NO: 316         moltype = AA  length = 21
FEATURE                Location/Qualifiers
REGION                 1..21
                       note = synthetic polypeptide
source                 1..21
                       mol_type = protein
                       organism = synthetic construct
SEQUENCE: 316
GELDELVYLL DGPGYDPIHS D                                           21

SEQ ID NO: 317         moltype = AA  length = 158
FEATURE                Location/Qualifiers
REGION                 1..158
                       note = synthetic polypeptide
source                 1..158
                       mol_type = protein
                       organism = synthetic construct
SEQUENCE: 317
ISLIAALAVD YVIGMENAMP WNLPADLAWF KRNTLNKPVI MGRHTWESIG RPLPGRKNII  60
LSSQPSTDDR VTWVKSVDEA IAACGDVPEI MVIGGGRVIE QFLPKAQKLY LTHIDAEVEG  120
DTHFPDYEPD DWESVFSEFH DADAQNSHSY CFEILERR                         158

SEQ ID NO: 318         moltype = AA  length = 107
FEATURE                Location/Qualifiers
REGION                 1..107
                       note = synthetic polypeptide
source                 1..107
                       mol_type = protein
                       organism = synthetic construct
SEQUENCE: 318
GVQVETISPG DGRTFPKRGQ TCVVHYTGML EDGKKFDSSR DRNKPFKFML GKQEVIRGWE  60
EGVAQMSVGQ RAKLTISPDY AYGATGHPGI IPPHATLVFD VELLKLE               107

SEQ ID NO: 319         moltype = AA  length = 19
```

```
FEATURE                Location/Qualifiers
REGION                 1..19
                       note = synthetic polypeptide
source                 1..19
                       mol_type = protein
                       organism = synthetic construct
SEQUENCE: 319
TRGVEEVAEG VVLLRRRGN                                               19

SEQ ID NO: 320         moltype = AA  length = 229
FEATURE                Location/Qualifiers
REGION                 1..229
                       note = synthetic polypeptide
source                 1..229
                       mol_type = protein
                       organism = synthetic construct
SEQUENCE: 320
MMGSVELNLR ETELCLGLPG GDTVAPVTGN KRGFSETVDL KLNLNNEPAN KEGSTTHDVV  60
TFDSKEKSAC PKDPAKPPAK AQVVGWPPVR SYRKNVMVSC QKSSGGPEAA AFVKVSMDGA  120
PYLRKIDLRM YKSYDELSNA LSNMFSSFTM GKHGGEEGMI DFMNERKLMD LVNSWDYVPS  180
YEDKDGDWML VGDVPWPMFV DTCKRLRLMK GSDAIGLAPR AMEKCKSRA             229

SEQ ID NO: 321         moltype = AA  length = 68
FEATURE                Location/Qualifiers
REGION                 1..68
                       note = synthetic polypeptide
source                 1..68
                       mol_type = protein
                       organism = synthetic construct
SEQUENCE: 321
KEKSACPKDP AKPPAKAQVV GWPPVRSYRK NVMVSCQKSS GGPEAAAFVK VSMDGAPYLR  60
KIDLRMYK                                                           68

SEQ ID NO: 322         moltype = AA  length = 42
FEATURE                Location/Qualifiers
REGION                 1..42
                       note = synthetic polypeptide
source                 1..42
                       mol_type = protein
                       organism = synthetic construct
SEQUENCE: 322
PITKIDTKYI MTCMSADLEV VTSTWVLVGG VLAALAAYCL ST                     42

SEQ ID NO: 323         moltype = AA  length = 6
FEATURE                Location/Qualifiers
REGION                 1..6
                       note = synthetic polypeptide
source                 1..6
                       mol_type = protein
                       organism = synthetic construct
SEQUENCE: 323
GSSGSS                                                             6

SEQ ID NO: 324         moltype = AA  length = 304
FEATURE                Location/Qualifiers
REGION                 1..304
                       note = synthetic polypeptide
source                 1..304
                       mol_type = protein
                       organism = synthetic construct
SEQUENCE: 324
DEMEECSQHL PGAGSSGDIM DYKDDDDKGS SGTGSGSGTS APITAYAQQT RGLLGCIITS  60
LTGRDKNQVE GEVQIMSTAT QTFLATCING VCWAVYHGAG TRTIASPKGP VIQMYTNVDQ  120
DLVGWPAPQG SRSLTPCTCG SSDLYLVTRH ADVIPVRRRG DGRGSLLSPR PISYLKGSSG  180
GPLLCPAGHA VGLFRAAVCT RGVAKAVDFI PVENLETTMR SPVFTDNSSP PAVTLTHPIT  240
KIDTKYIMTC MSADLEVVTS TWVLVGGVLA ALAAYCLSTG CVVIVGRIVL SGKPAIIPDR  300
EVLY                                                               304

SEQ ID NO: 325         moltype = AA  length = 297
FEATURE                Location/Qualifiers
REGION                 1..297
                       note = synthetic polypeptide
source                 1..297
                       mol_type = protein
                       organism = synthetic construct
SEQUENCE: 325
DYKDDDDKGS SGTGSGSGTS APITAYAQQT RGLLGCIITS LTGRDKNQVE GEVQIMSTAT  60
QTFLATCING VCWAVYHGAG TRTIASPKGP VIQMYTNVDQ DLVGWPAPQG SRSLTPCTCG  120
SSDLYLVTRH ADVIPVRRRG DGRGSLLSPR PISYLKGSSG GPLLCPAGHA VGLFRAAVCT  180
```

-continued

```
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAIIPDR EVLYQEFEDV VPCSMGS     297

SEQ ID NO: 326         moltype = AA  length = 303
FEATURE                Location/Qualifiers
REGION                 1..303
                       note = synthetic polypeptide
source                 1..303
                       mol_type = protein
                       organism = synthetic construct
SEQUENCE: 326
DYKDDDDKGS SGTGSGSGTS APITAYAQQT RGLLGCIITS LTGRDKNQVE GEVQIMSTAT  60
QTFLATCING VCWAVYHGAG TRTIASPKGP VIQMYTNVDQ DLVGWPAPQG SRSLTPCTCG  120
SSDLYLVTRH ADVIPVRRRG DGRGSLLSPR PISYLKGSSG GPLLCPAGHA VGLFRAAVCT  180
RGVAKAVDFI PVENLETTMR SPVFTDNSSP PAVTLTHPIT KIDTKYIMTC MSADLEVVTS  240
TWVLVGGVLA ALAAYCLSTG CVVIVGRIVL SGKPAGSSGS SIIPDREVLY QEFEDVVPCS  300
MGS                                                               303

SEQ ID NO: 327         moltype = AA  length = 304
FEATURE                Location/Qualifiers
REGION                 1..304
                       note = synthetic polypeptide
source                 1..304
                       mol_type = protein
                       organism = synthetic construct
SEQUENCE: 327
DEMEECSQHL PGAGSSGDIM DYKDDDDKGS SGTGSGSGTS APITAYAQQT RGLLGCIITS  60
LTGRDKNQVE GEVQIVSTAT QTLLATCING VCWAVYHGAG TRTIASPKGP VIQMYTNVDK  120
DLVGWPAPQG SRSLTPCTCG SSDLYLVTRH ADVIPVRRRG DRRGSLLSPR PISYLKGSSG  180
GPLLCPAGHA VGLFRAAVCT RGVAKAVYFI PVENLETTMR SPVFTDNSSP PAVTLTHPIT  240
KIDTKYIMTC MSADLEVVTS TWVLVGGVLA ALAAYCLSTG CVVIVGRIVL SGKPAIIPDR  300
EVLY                                                              304

SEQ ID NO: 328         moltype = AA  length = 297
FEATURE                Location/Qualifiers
REGION                 1..297
                       note = synthetic polypeptide
source                 1..297
                       mol_type = protein
                       organism = synthetic construct
SEQUENCE: 328
DYKDDDDKGS SGTGSGSGTS APITAYAQQT RGLLGCIITS LTGRDKNQVE GEVQIVSTAT  60
QTLLATCING VCWAVYHGAG TRTIASPKGP VIQMYTNVDK DLVGWPAPQG SRSLTPCTCG  120
SSDLYLVTRH ADVIPVRRRG DRRGSLLSPR PISYLKGSSG GPLLCPAGHA VGLFRAAVCT  180
RGVAKAVYFI PVENLETTMR SPVFTDNSSP PAVTLTHPIT KIDTKYIMTC MSADLEVVTS  240
TWVLVGGVLA ALAAYCLSTG CVVIVGRIVL SGKPAIIPDR EVLYQEFEDV VPCSMGS     297

SEQ ID NO: 329         moltype = AA  length = 303
FEATURE                Location/Qualifiers
REGION                 1..303
                       note = synthetic polypeptide
source                 1..303
                       mol_type = protein
                       organism = synthetic construct
SEQUENCE: 329
DYKDDDDKGS SGTGSGSGTS APITAYAQQT RGLLGCIITS LTGRDKNQVE GEVQIVSTAT  60
QTLLATCING VCWAVYHGAG TRTIASPKGP VIQMYTNVDK DLVGWPAPQG SRSLTPCTCG  120
SSDLYLVTRH ADVIPVRRRG DRRGSLLSPR PISYLKGSSG GPLLCPAGHA VGLFRAAVCT  180
RGVAKAVYFI PVENLETTMR SPVFTDNSSP PAVTLTHPIT KIDTKYIMTC MSADLEVVTS  240
TWVLVGGVLA ALAAYCLSTG CVVIVGRIVL SGKPAGSSGS SIIPDREVLY QEFEDVVPCS  300
MGS                                                               303

SEQ ID NO: 330         moltype = AA  length = 224
FEATURE                Location/Qualifiers
REGION                 1..224
                       note = synthetic polypeptide
source                 1..224
                       mol_type = protein
                       organism = synthetic construct
SEQUENCE: 330
MSVIKPDMKI KLRMEGAVNG HPFAIEGVGL GKPFEGKQSM DLKVKEGGPL PFAYDILTTV  60
FCYGNRVFAK YPENIVDYFK QSFPEGYSWE RSMNYEDGGI CNATNDITLD GDCYIYEIRF  120
DGVNFPANGP VMQKRTVKWE PSTEKLYVRD GVLKGDVNMA LSLEGGGHYR CDFKTTYKAK  180
KVVQLPDYHF VDHHIEIKSH DKDYSNVNLH EHAEAHSELP RQAK                  224

SEQ ID NO: 331         moltype = AA  length = 224
FEATURE                Location/Qualifiers
REGION                 1..224
                       note = synthetic polypeptide
```

-continued

```
source                  1..224
                        mol_type = protein
                        organism = synthetic construct
SEQUENCE: 331
MSVIKPDMKI KLRMEGAVNG HPFAIEGVGL GKPFEGKQSM DLKVKEGGPL PFAYDILTTV  60
FCYGNRVFAK YPENIVDYFK QSFPEGYSWE RSMNYEDGGI CNATNDITLD GDCYIYEIRF  120
DGVNFPANGP VMQKRTVKWE PSTENLYVRD GVLKGDVNMA LSLEGGGHYR CDFKTTYKAK  180
KVVQLPDYHF VDHHIEIKSH DKDYSNVNLH EHAEAHSELP RQAK                  224

SEQ ID NO: 332          moltype = AA  length = 224
FEATURE                 Location/Qualifiers
REGION                  1..224
                        note = synthetic polypeptide
source                  1..224
                        mol_type = protein
                        organism = synthetic construct
SEQUENCE: 332
MSVIKPDMKI KLRMEGAVNG HPFAIEGVGL GKPFEGKQSM DLKVKEGGPL PFAYDILTMA  60
FCYGNRVFAK YPENIVDYFK QSFPEGYSWE RSMHYEDGGS CNATNDITLD GDCYIYEIRF  120
DGVNFPANGP VMQKRTVKWE RSTENLYVRD GVLKSDGNYA LSLEGGGHYR CDFKTTYKAK  180
KVVQLPDYHS VDHHIEIKSH DKDYSNVNLH EHAEAHSELP RQAN                  224

SEQ ID NO: 333          moltype = AA  length = 236
FEATURE                 Location/Qualifiers
REGION                  1..236
                        note = synthetic polypeptide
source                  1..236
                        mol_type = protein
                        organism = synthetic construct
SEQUENCE: 333
MVSKGEENNM AIIKEFMRFK VHMEGSVNGH EFEIEGEGEG RPYEAFQTAK LKVTKGGPLP  60
FAWDILSPQF MYGSKVYIKH PADIPDYFKL SFPEGFRWER VMNFEDGGII HVNQDSSLQD  120
GVFIYKVKLR GTNFPSDGPV MQKKTMGWEA SEERMYPEDG AHKAEIKKRL KLKDGGHYAA  180
EVKTTYKAKK PVQLPGAYIV DIKLDIVSHN EDYTIVEQYE RAEGRHSTGG MDELYK      236

SEQ ID NO: 334          moltype = AA  length = 595
FEATURE                 Location/Qualifiers
REGION                  1..595
                        note = synthetic polypeptide
source                  1..595
                        mol_type = protein
                        organism = synthetic construct
SEQUENCE: 334
MTMTLHTKAS GMALLHQIQG NELEPLNRPQ LKIPLERPLG EVYLDSSKPA VYNYPEGAAY  60
EFNAAAAANA QVYGQTGLPY GPGSEAAAFG SNGLGGFPPL NSVSPSPLML LHPPPQLSPF  120
LQPHGQQVPY YLENEPSGYT VREAGPPAFY RPNSDNRRQG GRERLASTND KGSMAMESAK  180
ETRYCAVCND YASGYHYGVW SCEGCKAFFK RSIQGHNDYM CPATNQCTID KNRRKSCQAC  240
RLRKCYEVGM MKGGIRKDRR GGRMLKHKRQ RDDGEGRGEV GSAGDMRAAN LWPSPLMIKR  300
SKKNSLALSL TADQMVSALL DAEPPILYSE YDPTRPFSEA SMMGLLTNLA DRELVHMINW  360
AKRVPGFVDL TLHDQVHLLE CAWLEILMIG LVWRSMEHPG KLLFAPNLLL DRNQGKCVEG  420
MVEIFDMLLA TSSRFRMMNL QGEEFVCLKS IILLNSGVYT FLSSTLKSLE EKDHIHRVLD  480
KITDTLIHLM AKAGLTLQQQ HQRLAQLLLI LSHIRHMSNK GMEHLYSMKC KNVVPLYDLL  540
LEMLDAHRLH APTSRGGASV EETDQSHLAT AGSTSSHSLQ KYYITGEAEG FPATV       595

SEQ ID NO: 335          moltype = AA  length = 314
FEATURE                 Location/Qualifiers
REGION                  1..314
                        note = synthetic polypeptide
source                  1..314
                        mol_type = protein
                        organism = synthetic construct
SEQUENCE: 335
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPGK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKR  240
MEHLYSMKCK NVVPLYDLLL EMLDAHRLHA PTSRGGASVE ETDQSHLATA GSTSSHSLQK  300
YYITGEAEGF PATV                                                   314

SEQ ID NO: 336          moltype = AA  length = 314
FEATURE                 Location/Qualifiers
REGION                  1..314
                        note = synthetic polypeptide
source                  1..314
                        mol_type = protein
                        organism = synthetic construct
SEQUENCE: 336
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPGK  120
```

```
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDLLL EAADAHRLHA PTSRGGASVE ETDQSHLATA GSTSSHSLQK  300
YYITGEAEGF PATA                                                   314

SEQ ID NO: 337         moltype = AA  length = 314
FEATURE                Location/Qualifiers
REGION                 1..314
                       note = synthetic polypeptide
source                 1..314
                       mol_type = protein
                       organism = synthetic construct
SEQUENCE: 337
SAGDMRAANL WPSPLMIKRS KKNSLALSLT ADQMVSALLD AEPPILYSEY DPTRPFSEAS  60
MMGLLTNLAD RELVHMINWA KRVPGFVDLT LHDQVHLLEC AWLEILMIGL VWRSMEHPVK  120
LLFAPNLLLD RNQGKCVEGM VEIFDMLLAT SSRFRMMNLQ GEEFVCLKSI ILLNSGVYTF  180
LSSTLKSLEE KDHIHRVLDK ITDTLIHLMA KAGLTLQQQH QRLAQLLLIL SHIRHMSNKG  240
MEHLYSMKCK NVVPLYDAAL EMLDAHRLHA PTSRGGASVE ETDQSHLATA GSTSSHSLQK  300
YYITGEAEGF PATV                                                   314

SEQ ID NO: 338         moltype = AA  length = 306
FEATURE                Location/Qualifiers
REGION                 1..306
                       note = synthetic polypeptide
source                 1..306
                       mol_type = protein
                       organism = synthetic construct
SEQUENCE: 338
PPQIEEACEL PECQVDAGNK VCNLQCNNHA CGWDGGDCSL NFNDPWKNCT QSLQCWKYFS  60
DGHCDSQCNS AGCLFDGFDC QLTEGQCNPL YDQYCKDHFS DGHCDQGCNS AECEWDGLDC  120
AEHVPERLAA GTLVLVVLLP PDQLRNNSFH FLRELSHVLH TNVVFKRDAQ GQQMIFPYYG  180
HEEELRKHPI KRSTVGWATS SLLPGTSGGR QRRELDPMDI RGSIVYLEID NRQCVQSSSQ  240
CFQSATDVAA FLGALASLGS LNIPYKIEAV KSEPVEPPLP SQLHLMYVAA AAFVLLFFVG  300
CGVLLS                                                            306

SEQ ID NO: 339         moltype = AA  length = 358
FEATURE                Location/Qualifiers
REGION                 1..358
                       note = synthetic polypeptide
source                 1..358
                       mol_type = protein
                       organism = synthetic construct
SEQUENCE: 339
PCVGSNPCYN QGTCEPTSEN PFYRCLCPAK FNGLLCHILD YSFTGGAGRD IPPPQIEEAC  60
ELPECQVDAG NKVCNLQCNN HACGWDGGDC SLNFNDPWKN CTQSLQCWKY FSDGHCDSQC  120
NSAGCLFDGF DCQLTEGQCN PLYDQYCKDH FSDGHCDQGC NSAECEWDGL DCAEHVPERL  180
AAGTLVLVVL LPPDQLRNNS FHFLRELSHV LHTNVVFKRD AQGQQMIFPY YGHEEELRKH  240
PIKRSTVGWA TSSLLPGTSG GRQRRELDPM DIRGSIVYLE IDNRQCVQSS SQCFQSATDV  300
AAFLGALASL GSLNIPYKIE AVKSEPVEPP LPSQLHLMYV AAAAFVLLFF VGCGVLLS    358

SEQ ID NO: 340         moltype = AA  length = 4
FEATURE                Location/Qualifiers
REGION                 1..4
                       note = synthetic polypeptide
source                 1..4
                       mol_type = protein
                       organism = synthetic construct
SEQUENCE: 340
PGER                                                              4

SEQ ID NO: 341         moltype = AA  length = 5
FEATURE                Location/Qualifiers
REGION                 1..5
                       note = synthetic polypeptide
source                 1..5
                       mol_type = protein
                       organism = synthetic construct
SEQUENCE: 341
TGSQK                                                             5

SEQ ID NO: 342         moltype = AA  length = 5
FEATURE                Location/Qualifiers
REGION                 1..5
                       note = synthetic polypeptide
source                 1..5
                       mol_type = protein
                       organism = synthetic construct
SEQUENCE: 342
TGEKP                                                             5
```

```
SEQ ID NO: 343          moltype = AA  length = 4
FEATURE                 Location/Qualifiers
REGION                  1..4
                        note = synthetic polypeptide
source                  1..4
                        mol_type = protein
                        organism = synthetic construct
SEQUENCE: 343
THLR                                                            4

SEQ ID NO: 344          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 344
TGGGEKP                                                         7

SEQ ID NO: 345          moltype = AA  length = 55
FEATURE                 Location/Qualifiers
REGION                  1..55
                        note = synthetic polypeptide
source                  1..55
                        mol_type = protein
                        organism = synthetic construct
SEQUENCE: 345
FHYDRNNIAV GADESVVKEA HREVINSSTE GLLLNIDKDI RKILSGYIVE IEDTE     55

SEQ ID NO: 346          moltype = AA  length = 7
FEATURE                 Location/Qualifiers
REGION                  1..7
                        note = synthetic polypeptide
source                  1..7
                        mol_type = protein
                        organism = synthetic construct
SEQUENCE: 346
VEIEDTE                                                         7

SEQ ID NO: 347          moltype = AA  length = 18
FEATURE                 Location/Qualifiers
REGION                  1..18
                        note = synthetic polypeptide
source                  1..18
                        mol_type = protein
                        organism = synthetic construct
SEQUENCE: 347
KDIRKILSGY IVEIEDTE                                             18

SEQ ID NO: 348          moltype = AA  length = 28
FEATURE                 Location/Qualifiers
REGION                  1..28
                        note = synthetic polypeptide
source                  1..28
                        mol_type = protein
                        organism = synthetic construct
SEQUENCE: 348
STEGLLLNID KDIRKILSGY IVEIEDTE                                  28

SEQ ID NO: 349          moltype = AA  length = 14
FEATURE                 Location/Qualifiers
REGION                  1..14
                        note = synthetic polypeptide
source                  1..14
                        mol_type = protein
                        organism = synthetic construct
SEQUENCE: 349
EVKQENRLLN ESES                                                 14

SEQ ID NO: 350          moltype = AA  length = 46
FEATURE                 Location/Qualifiers
REGION                  1..46
                        note = synthetic polypeptide
source                  1..46
                        mol_type = protein
                        organism = synthetic construct
SEQUENCE: 350
```

-continued

```
VGADESVVKE AHREVINSST EGLLLNIDKD IRKILSGYIV EIEDTE                46

SEQ ID NO: 351          moltype = AA  length = 24
FEATURE                 Location/Qualifiers
REGION                  1..24
                        note = synthetic polypeptide
source                  1..24
                        mol_type = protein
                        organism = synthetic construct
SEQUENCE: 351
GGSGGSGGSG GSGGSGGSGG SGGS                                        24

SEQ ID NO: 352          moltype = AA  length = 40
FEATURE                 Location/Qualifiers
REGION                  1..40
                        note = synthetic polypeptide
source                  1..40
                        mol_type = protein
                        organism = synthetic construct
SEQUENCE: 352
GGGGSGGGGS GGGGSGGGGS GGGGSGGGGS GGGGSGGGGS                       40

SEQ ID NO: 353          moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 353
GGGGS                                                             5

SEQ ID NO: 354          moltype = AA  length = 6
FEATURE                 Location/Qualifiers
REGION                  1..6
                        note = synthetic polypeptide
source                  1..6
                        mol_type = protein
                        organism = synthetic construct
SEQUENCE: 354
GGSGGS                                                            6

SEQ ID NO: 355          moltype = AA  length = 16
FEATURE                 Location/Qualifiers
REGION                  1..16
                        note = synthetic polypeptide
source                  1..16
                        mol_type = protein
                        organism = synthetic construct
SEQUENCE: 355
GSGSGSGSGS GSGSGS                                                 16

SEQ ID NO: 356          moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 356
TGSKP                                                             5

SEQ ID NO: 357          moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 357
TGQKP                                                             5

SEQ ID NO: 358          moltype = AA  length = 5
FEATURE                 Location/Qualifiers
REGION                  1..5
                        note = synthetic polypeptide
source                  1..5
                        mol_type = protein
                        organism = synthetic construct
```

```
SEQUENCE: 358
TGGKP                                                             5

SEQ ID NO: 359         moltype = AA  length = 6
FEATURE                Location/Qualifiers
REGION                 1..6
                       note = synthetic polypeptide
source                 1..6
                       mol_type = protein
                       organism = synthetic construct
SEQUENCE: 359
TGSQKP                                                            6

SEQ ID NO: 360         moltype = AA  length = 21
FEATURE                Location/Qualifiers
REGION                 1..21
                       note = synthetic polypeptide
source                 1..21
                       mol_type = protein
                       organism = synthetic construct
SEQUENCE: 360
GSGEGRGSLL TCGDVEENPG P                                           21

SEQ ID NO: 361         moltype = AA  length = 23
FEATURE                Location/Qualifiers
REGION                 1..23
                       note = synthetic polypeptide
source                 1..23
                       mol_type = protein
                       organism = synthetic construct
SEQUENCE: 361
GSGQCTNYAL LKLAGDVESN PGP                                         23

SEQ ID NO: 362         moltype = AA  length = 25
FEATURE                Location/Qualifiers
REGION                 1..25
                       note = synthetic polypeptide
source                 1..25
                       mol_type = protein
                       organism = synthetic construct
SEQUENCE: 362
GSGVKQTLNF DLLKLAGDVE SNPGP                                       25

SEQ ID NO: 363         moltype = DNA  length = 494
FEATURE                Location/Qualifiers
misc_feature           1..494
                       note = synthetic polynucleotide
source                 1..494
                       mol_type = other DNA
                       organism = synthetic construct
SEQUENCE: 363
ccgataaaat aaaagatttt atttagtctc cagaaaaagg ggggaatgaa agaccccacc  60
tgtaggttat ggcaagctag ctgcagtaac gccattattg caaggcatgg aaaaatacca  120
aaccaagaat agagaagttc agatcaaggg cgggtacatg aaaatagcta acgtagggcc  180
aaacaggata tctgcggtga gcagtttcgg ccccggcccg gggccaagaa cagatggtca  240
ccgcagtttc ggccccggcc cgaggccaag agcagatggt ccccagatat ggcccaaccc  300
tcagcagttt cttaagaccc atcagatgtt tccaggctcc cccaaggacc tgaaatgacc  360
ctgcgcctta tttgaattaa ccaatcagcc tgcttctcgc ttctgttcgc gcgcttctgc  420
ttcccgagct ctataaaaga gctcacaacc cctcactcgg cgcgccagtc ctccgacaga  480
ctgagtcgcc cggg                                                   494

SEQ ID NO: 364         moltype = DNA  length = 588
FEATURE                Location/Qualifiers
misc_feature           1..588
                       note = synthetic polynucleotide
source                 1..588
                       mol_type = other DNA
                       organism = synthetic construct
SEQUENCE: 364
gttgacattg attattgact agttattaat agtaatcaat tacggggtca ttagttcata  60
gcccatatat ggagttccgc gttacataac ttacggtaaa tggcccgcct ggctgaccgc  120
ccaacgaccc ccgcccattg acgtcaataa tgacgtatgt tcccatagta acgccaatag  180
ggactttcca ttgacgtcaa tgggtggagt atttacggta aactgcccac ttggcagtac  240
atcaagtgta tcatatgcca agtacgcccc ctattgacgt caatgacggt aaatggcccg  300
cctggcatta tgcccagtac atgaccttat gggactttcc tacttggcag tacatctacg  360
tattagtcat cgctattacc atggtgatgc ggttttggca gtacatcaat gggcgtggat  420
agcggtttga ctcacgggga tttccaagtc tccaccccat tgacgtcaat gggagtttgt  480
tttggcacca aaatcaacgg gactttccaa aatgtcgtaa caactccgcc ccattgacgc  540
aaatgggcgg taggcgtgta cggtgggagg tctatataag cagagctc              588
```

```
SEQ ID NO: 365         moltype = DNA  length = 65
FEATURE                Location/Qualifiers
misc_feature           1..65
                       note = synthetic polynucleotide
source                 1..65
                       mol_type = other DNA
                       organism = synthetic construct
SEQUENCE: 365
taggcgtgta cggtgggagg cctatataag cagagctcgt ttagtgaacc gtcagatcgc  60
ctgga                                                              65

SEQ ID NO: 366         moltype = DNA  length = 63
FEATURE                Location/Qualifiers
misc_feature           1..63
                       note = synthetic polynucleotide
source                 1..63
                       mol_type = other DNA
                       organism = synthetic construct
SEQUENCE: 366
ttcgcatatt aaggtgacgc gtgtggcctc gaacaccgag cgaccctgca gcgacccgct  60
taa                                                                63

SEQ ID NO: 367         moltype = DNA  length = 180
FEATURE                Location/Qualifiers
misc_feature           1..180
                       note = synthetic polynucleotide
source                 1..180
                       mol_type = other DNA
                       organism = synthetic construct
SEQUENCE: 367
cgccaaatgg cagtattcat ccacaatttt aaaagaaaag gggggattgg ggggtacagt  60
gcaggggaaa gaatagtaga cataatagca acagacatac aaactaaaga attacaaaaa  120
caaattacaa aaattcaaaa ttttcgggtt tattacaggg acagcagaga tccagtttgg  180

SEQ ID NO: 368         moltype = DNA  length = 592
FEATURE                Location/Qualifiers
misc_feature           1..592
                       note = synthetic polynucleotide
source                 1..592
                       mol_type = other DNA
                       organism = synthetic construct
SEQUENCE: 368
taatcaacct ctggattaca aaatttgtga aagattgact ggtattctta actatgttgc  60
tccttttacg ctatgtggat acgctgcttt aatgcctttg tatcatgcta ttgcttcccg  120
tatggctttc attttctcct ccttgtataa atcctggttg ctgtctcttt atgaggagtt  180
gtggcccgtt gtcaggcaac gtggcgtggt gtgcactgtg tttgctgacg caacccccac  240
tggttggggc attgccacca cctgtcagct cctttccggg actttcgctt tccccctccc  300
tattgccacg gcggaactca tcgccgcctg ccttgcccgc tgctggacag gggctcggct  360
gttgggcact gacaattccg tggtgttgtc ggggaaatca tcgtcctttc cttggctgct  420
cgcctgtgtt gccacctgga ttctgcgcgg gacgtccttc tgctacgtcc cttcggccct  480
caatccagcg gaccttcctt cccgcggcct gctgccggct ctgcggcctc ttccgcgtct  540
tcgccttcgc cctcagacga gtcggatctc cctttgggcc gcctccccgc at          592

SEQ ID NO: 369         moltype = DNA  length = 636
FEATURE                Location/Qualifiers
misc_feature           1..636
                       note = synthetic polynucleotide
source                 1..636
                       mol_type = other DNA
                       organism = synthetic construct
SEQUENCE: 369
gttggaaggg ctaattcact cccaaagaag acaagatatc cttgatctgt ggatctacca  60
cacacaaggc tacttccctg attagcagaa ctacacacca gggccagggg tcagatatcc  120
actgaccttt ggatggtgct acaagctagt accagttgag ccagataagg tagaagaggc  180
caataaagga gagaacacca gcttgttaca ccctgtgagc ctgcatggga tggatgaccc  240
ggagagagaa gtgttagagt ggaggtttga cagccgccta gcatttcatc acgtggcccg  300
agagctgcat ccggagtact tcaagaactg ctgatatcga gcttgctaca agggactttc  360
cgctggggac tttccaggga ggcgtggcct gggcgggact ggggagtggc gagccctcag  420
atcctgcata taagcagctg ctttttgcct gtactgggtc tctctggtta gaccagatct  480
gagcctggga gctctctggc taactaggga acccactgct taagcctcaa taaagcttgc  540
cttgagtgct tcaagtagtg tgtgcccgtc tgttgtgtga ctctggtaac tagagatccc  600
tcagaccctt ttagtcagtg tggaaaatct ctagca                            636

SEQ ID NO: 370         moltype = DNA  length = 236
FEATURE                Location/Qualifiers
misc_feature           1..236
                       note = synthetic polynucleotide
source                 1..236
```

```
                        mol_type = other DNA
                        organism = synthetic construct
SEQUENCE: 370
actggaaggg ctaattcact cccaacgaag acaagatctg ctttttgctt gtactgggtc  60
tctctggtta gaccagatct gagcctggga gctctctggc taactaggga acccactgct  120
taagcctcaa taaagcttgc cttgagtgct tcaagtagtg tgtgcccgtc tgttgtgtga  180
ctctggtaac tagagatccc tcagaccctt ttagtcagtg tggaaaatct ctagca      236

SEQ ID NO: 371          moltype = DNA  length = 205
FEATURE                 Location/Qualifiers
misc_feature            1..205
                        note = synthetic polynucleotide
source                  1..205
                        mol_type = other DNA
                        organism = synthetic construct
SEQUENCE: 371
tccttgggtt cttgggagca gcaggaagca ctatgggcgc agcgtcaatg acgctgacgg  60
tacaggccag acaattattg tctggtatag tgcagcagca gaacaatttg ctgagggcta  120
ttgaggcgca acagcatctg ttgcaactca cagtctgggg catcaagcag ctccaggcaa  180
gaatcctggc tgtgaaagat accta                                        205

SEQ ID NO: 372          moltype = AA  length = 235
FEATURE                 Location/Qualifiers
REGION                  1..235
                        note = synthetic polypeptide
source                  1..235
                        mol_type = protein
                        organism = synthetic construct
SEQUENCE: 372
VSKGEEDNMA IIKEFMRFKV HMEGSVNGHE FEIEGEGEGR PYEGTQTAKL KVTKGGPLPF  60
AWDILSPQFM YGSKAYVKHP ADIPDYLKLS FPEGFKWERV MNFEDGGVVT VTQDSSLQDG  120
EFIYKVKLRG TNFPSDGPVM QKKTMGWQAS SERMYPEDGA LKGEIKQRLK LKDGGHYDAE  180
VKTTYKAKKP VQLPGAYNVN IKLDITSHNE DYTIVEQYER AEGRHSTGGM DELYK       235

SEQ ID NO: 373          moltype = AA  length = 544
FEATURE                 Location/Qualifiers
REGION                  1..544
                        note = synthetic polypeptide
source                  1..544
                        mol_type = protein
                        organism = synthetic construct
SEQUENCE: 373
ALPVTALLLP LALLLHAARP DIQMTQTTSS LSASLGDRVT ISCRASQDIS KYLNWYQQKP  60
DGTVKLLIYH TSRLHSGVPS RFSGSGSGTD YSLTISNLEQ EDIATYFCQQ GNTLPYTFGG  120
GTKLEITGGG GSGGGGSGGG GSEVKLQESG PGLVAPSQSL SVTCTVSGVS LPDYGVSWIR  180
QPPRKGLEWL GVIWGSETTY YNSALKSRLT IIKDNSKSQV FLKMNSLQTD DTAIYYCAKH  240
YYYGGSYAMD YWGQGTSVTV SSEQKLISEE DLNGAATTTP APRPPTPAPT IALQPLSLRP  300
EACRPAAGGA VHTRGLDFAC DFWVLVVVGG VLACYSLLVT VAFIIFWVRS KRSRLLHSDY  360
MNMTPRRPGP TRKHYQPYAP PRDFAAYRSK RGRKKLLYIF KQPFMRPVQT TQEEDGCSCR  420
FPEEEEGGCE LRVKFSRSAD APAYKQGQNQ LYNELNLGRR EEYDVLDKRR GRDPEMGGKP  480
RRKNPQEGLY NELQKDKMAE AYSEIGMKGE RRRGKGHDGL YQGLSTATKD TYDALHMQAL  540
PPRG                                                               544

SEQ ID NO: 374          moltype = AA  length = 153
FEATURE                 Location/Qualifiers
REGION                  1..153
                        note = synthetic polypeptide
source                  1..153
                        mol_type = protein
                        organism = synthetic construct
SEQUENCE: 374
MGLTSQLLPP LFFLLACAGN FVHGHKCDIT LQEIIKTLNS LTEQKTLCTE LTVTDIFAAS  60
KNTTEKETFC RAATVLRQFY SHHEKDTRCL GATAQQFHRH KQLIRFLKRL DRNLWGLAGL  120
NSCPVKEANQ STLENFLERL KTIMREKYSK CSS                               153

SEQ ID NO: 375          moltype = AA  length = 177
FEATURE                 Location/Qualifiers
REGION                  1..177
                        note = synthetic polypeptide
source                  1..177
                        mol_type = protein
                        organism = synthetic construct
SEQUENCE: 375
HSSALLCCLV LLTGVRASPG QGTQSENSCT HFPGNLPNML RDLRDAFSRV KTFFQMKDQL  60
DNLLLKESLL EDFKGYLGCQ ALSEMIQFYL EEVMPQAENQ DPDIKAHVNS LGENLKTLRL  120
RLRRCHRFLP CENKSKAVEQ VKNAFNKLQE KGIYKAMSEF DIFINYIEAY MTMKIRN     177

SEQ ID NO: 376          moltype = AA  length = 335
FEATURE                 Location/Qualifiers
```

-continued

```
REGION                 1..335
                       note = synthetic polypeptide
source                 1..335
                       mol_type = protein
                       organism = synthetic construct
SEQUENCE: 376
RKVCNGIGIG EFKDSLSINA TNIKHFKNCT SISGDLHILP VAFRGDSFTH TPPLDPQELD  60
ILKTVKEITG FLLIQAWPEN RTDLHAFENL EIIRGRTKQH GQFSLAVVSL NITSLGLRSL  120
KEISDGDVII SGNKNLCYAN TINWKKLFGT SGQKTKIISN RGENSCKATG QVCHALCSPE  180
GCWGPEPRDC VSCRNVSRGR ECVDKCNLLE GEPREFVENS ECIQCHPECL PQAMNITCTG  240
RGPDNCIQCA HYIDGPHCVK TCPAGVMGEN NTLVWKYADA GHVCHLCHPN CTYGCTGPGL  300
EGCPTNGPKI PSIATGMVGA LLLLLVVALG IGLFM                            335

SEQ ID NO: 377         moltype = AA  length = 176
FEATURE                Location/Qualifiers
REGION                 1..176
                       note = synthetic polypeptide
REGION                 19..25
                       note = misc_feature - Xaa can be any naturally occurring
                        amino acid
REGION                 47..53
                       note = misc_feature - Xaa can be any naturally occurring
                        amino acid
REGION                 76..82
                       note = misc_feature - Xaa can be any naturally occurring
                        amino acid
REGION                 104..110
                       note = misc_feature - Xaa can be any naturally occurring
                        amino acid
REGION                 133..139
                       note = misc_feature - Xaa can be any naturally occurring
                        amino acid
REGION                 161..167
                       note = misc_feature - Xaa can be any naturally occurring
                        amino acid
source                 1..176
                       mol_type = protein
                       organism = synthetic construct
SEQUENCE: 377
SRPGERPFQC RICMRNFSXX XXXXXHTRTH TGEKPFQCRI CMRNFSXXXX XXXHLRTHTG  60
SQKPFQCRIC MRNFSXXXXX XXHTRTHTGE KPFQCRICMR NFSXXXXXXX HLRTHTGSQK  120
PFQCRICMRN FSXXXXXXXH TRTHTGEKPF QCRICMRNFS XXXXXXXHLR THLRGS      176

SEQ ID NO: 378         moltype = AA  length = 606
FEATURE                Location/Qualifiers
REGION                 1..606
                       note = synthetic polypeptide
REGION                 128..134
                       note = misc_feature - Xaa can be any naturally occurring
                        amino acid
REGION                 156..162
                       note = misc_feature - Xaa can be any naturally occurring
                        amino acid
REGION                 185..191
                       note = misc_feature - Xaa can be any naturally occurring
                        amino acid
REGION                 213..219
                       note = misc_feature - Xaa can be any naturally occurring
                        amino acid
REGION                 242..248
                       note = misc_feature - Xaa can be any naturally occurring
                        amino acid
REGION                 270..276
                       note = misc_feature - Xaa can be any naturally occurring
                        amino acid
source                 1..606
                       mol_type = protein
                       organism = synthetic construct
SEQUENCE: 378
MDAKSLTAWS RTLVTFKDVF VDFTREEWKL LDTAQQILYR NVMLENYKNL VSLGYQLTKP  60
DVILRLEKGE EPWLVEREIH QETHPDSETA FEIKSSVLEG GGGSGGTCRS RPGERPFQCR  120
ICMRNFSXXX XXXXHTRTHT GEKPFQCRIC MRNFSXXXXX XXHLRTHTGS QKPFQCRICM  180
RNFSXXXXXX XHLRTHTGEK PFQCRICMRN FSXXXXXXXH LKTHTGSQKP FQCRICMRNF  240
SXXXXXXXHL RTHTGEKPFQ CRICMRNFSX XXXXXXHLRT HLRGSQLCVR GSSAGDMRAA  300
NLWPSPLMIK RSKKNSLALS LTADQMVSAL LDAEPPILYS EYDPTRPFSE ASMMGLLTNL  360
ADRELVHMIN WAKRVPGFVD LTLHDQVHLL ECAWLEILMI GLVWRSMEHP VKLLFAPNLL  420
LDRNQGKCVE GMVEIFDMLL ATSSRFRMMN LQGEEFVCLK SIILLNSGVY TFLSSTLKSL  480
EEKDHIHRVL DKITDTLIHL MAKAGLTLQQ QHQRLAQLLL ILSHIRHMSN KGMEHLYSMK  540
CKNVVPLYDL LLEAADAHRL HAPTSRGGAS VEETDQSHLA TAGSTSSHSL QKYYITGEAE  600
```

-continued

```
GFPATA                                                          606

SEQ ID NO: 379          moltype = AA  length = 991
FEATURE                 Location/Qualifiers
REGION                  1..991
                        note = synthetic polypeptide
REGION                  319..325
                        note = misc_feature - Xaa can be any naturally occurring
                         amino acid
REGION                  347..353
                        note = misc_feature - Xaa can be any naturally occurring
                         amino acid
REGION                  376..382
                        note = misc_feature - Xaa can be any naturally occurring
                         amino acid
REGION                  404..410
                        note = misc_feature - Xaa can be any naturally occurring
                         amino acid
REGION                  433..439
                        note = misc_feature - Xaa can be any naturally occurring
                         amino acid
REGION                  461..467
                        note = misc_feature - Xaa can be any naturally occurring
                         amino acid
source                  1..991
                        mol_type = protein
                        organism = synthetic construct
SEQUENCE: 379
MDYKDDDDKG SSGTGSGSGT SAPITAYAQQ TRGLLGCIIT SLTGRDKNQV EGEVQIVSTA  60
TQTFLATCIN GVCWAVYHGA GTRTIASPKG PVIQMYTNVD QDLVGWPAPQ GSRSLTPCTC  120
GSSDLYLVTR HADVIPVRRR GDSRGSLLSP RPISYLKGSS GGPLLCPAGH AVGLFRAAVC  180
TRGVAKAVDF IPVENLETTM RSPVFTDNSS PPAVTLTHPI TKIDTKYIMT CMSADLEVVT  240
STWVLVGGVL AALAAYCLST GCVVIVGRIV LSGKPAIIPD REVLYQEFED VVPCSMGSPG  300
SRPGERPFQC RICMRNFSXX XXXXXHTRTH TGEKPFQCRI CMRNFSXXXX XXXHLRTHTG  360
SQKPFQCRIC MRNFSXXXXX XXHLRTHTGE KPFQCRICMR NFSXXXXXXX HLKTHTGSQK  420
PFQCRICMRN FSXXXXXXXH LRTHTGEKPF QCRICMRNFS XXXXXXXHLR THLRGSTCRD  480
EFPTMVFPSG QISQASALAP APPQVLPQAP APAPAPAMVS ALAQAPAPVP VLAPGPPQAV  540
APPAPKPTQA GEGTLSEALL QLQFDDEDLG ALLGNSTDPA VFTDLASVDN SEFQQLLNQG  600
IPVAPHTTEP MLMEYPEAIT RLVTGAQRPP DPAPAPLGAP GLPNGLLSGD EDFSSIADMD  660
FSALLSQISS QLCVRGSSAG DMRAANLWPS PLMIKRSKKN SLALSLTADQ MVSALLDAEP  720
PILYSEYDPT RPFSEASMMG LLTNLADREL VHMINWAKRV PGFVDLTLHD QVHLLECAWL  780
EILMIGLVWR SMEHPVKLLF APNLLLDRNQ GKCVEGMVEI FDMLLATSSR FRMMNLQGEE  840
FVCLKSIILL NSGVYTFLSS TLKSLEEKDH IHRVLDKITD TLIHLMAKAG LTLQQQHQRL  900
AQLLLILSHI RHMSNKGMEH LYSMKCKNVV PLYDLLLEAA DAHRLHAPTS RGGASVEETD  960
QSHLATAGST SSHSLQKYYI TGEAEGFPAT A                              991

SEQ ID NO: 380          moltype = AA  length = 172
FEATURE                 Location/Qualifiers
REGION                  1..172
                        note = synthetic polypeptide
REGION                  17..23
                        note = misc_feature - Xaa can be any naturally occurring
                         amino acid
REGION                  45..51
                        note = misc_feature - Xaa can be any naturally occurring
                         amino acid
REGION                  74..80
                        note = misc_feature - Xaa can be any naturally occurring
                         amino acid
REGION                  102..108
                        note = misc_feature - Xaa can be any naturally occurring
                         amino acid
REGION                  131..137
                        note = misc_feature - Xaa can be any naturally occurring
                         amino acid
REGION                  159..165
                        note = misc_feature - Xaa can be any naturally occurring
                         amino acid
source                  1..172
                        mol_type = protein
                        organism = synthetic construct
SEQUENCE: 380
PGERPFQCRI CMRNFSXXXX XXXHTRTHTG EKPFQCRICM RNFSXXXXXX XHLRTHTGSQ  60
KPFQCRICMR NFSXXXXXXX HTRTHTGEKP FQCRICMRNF SXXXXXXXHL RTHTGSQKPF  120
QCRICMRNFS XXXXXXXHTR THTGEKPFQC RICMRNFSXX XXXXXHLRTH LR          172
```